(12) United States Patent
Saiah et al.

(10) Patent No.: US 10,980,784 B2
(45) Date of Patent: Apr. 20, 2021

(54) RAPAMYCIN ANALOGS AND USES THEREOF

(71) Applicant: Navitor Pharmaceuticals, Inc., Cambridge, MA (US)

(72) Inventors: Eddine Saiah, Brookline, MA (US); David John O'Neill, Arlington, MA (US); Seong Woo Anthony Kang, Somerville, MA (US)

(73) Assignee: NAVITOR PHARMACEUTICALS, INC., Cambridge, MA (US)

( * ) Notice: Subject to any disclaimer, the term of this patent is extended or adjusted under 35 U.S.C. 154(b) by 2 days.

(21) Appl. No.: 16/443,298

(22) Filed: Jun. 17, 2019

(65) Prior Publication Data

US 2019/0388401 A1 Dec. 26, 2019

Related U.S. Application Data

(60) Provisional application No. 62/685,666, filed on Jun. 15, 2018.

(51) Int. Cl.
*C07D 498/18* (2006.01)
*A61K 31/436* (2006.01)
*A61P 13/12* (2006.01)
*A61P 3/10* (2006.01)
*C07D 405/06* (2006.01)

(52) U.S. Cl.
CPC ............. *A61K 31/436* (2013.01); *A61P 3/10* (2018.01); *A61P 13/12* (2018.01); *C07D 405/06* (2013.01); *C07D 498/18* (2013.01)

(58) Field of Classification Search
CPC ............................ C07D 405/06; C07D 498/18
See application file for complete search history.

(56) References Cited

U.S. PATENT DOCUMENTS

| | | | |
|---|---|---|---|
| 5,362,735 A | 11/1994 | Luengo | |
| 5,639,600 A | 6/1997 | McGrath et al. | |
| 7,087,648 B1 | 8/2006 | McGrath | |
| 7,390,799 B2 | 6/2008 | Bruncko et al. | |
| 8,138,347 B2 | 3/2012 | Knight et al. | |
| 2010/0305093 A1 | 12/2010 | Anand et al. | |
| 2019/0031683 A1 | 1/2019 | Saiah et al. | |

FOREIGN PATENT DOCUMENTS

| WO | WO 95/14023 | * | 5/1995 |
|---|---|---|---|
| WO | WO 95/16691 | * | 6/1995 |
| WO | WO-2001042246 A2 | | 6/2001 |
| WO | WO-2002088112 A1 | | 11/2002 |
| WO | WO-2003063794 A2 | | 8/2003 |
| WO | WO-2004019973 A1 | | 3/2004 |
| WO | WO-2004089925 A1 | | 10/2004 |
| WO | WO-2004106328 A1 | | 12/2004 |
| WO | WO-2005007623 A2 | | 1/2005 |
| WO | WO-2005113554 A2 | | 12/2005 |
| WO | WO-2006078846 A1 | | 7/2006 |
| WO | WO-2006122806 A2 | | 11/2006 |
| WO | WO-2007016176 A2 | | 2/2007 |
| WO | WO-2007044729 A2 | | 4/2007 |
| WO | WO-2007044813 A1 | | 4/2007 |
| WO | WO-2007053452 A1 | | 5/2007 |
| WO | WO-2007061737 A2 | | 5/2007 |
| WO | WO-2007070514 A1 | | 6/2007 |
| WO | WO-2007084786 A1 | | 7/2007 |
| WO | WO-2007129161 A2 | | 11/2007 |
| WO | WO-2007133249 A2 | | 11/2007 |
| WO | WO-2007136940 A2 | | 11/2007 |
| WO | WO-2008014446 A2 | | 1/2008 |
| WO | WO-2008032162 A1 | | 3/2008 |
| WO | WO-2008039218 A2 | | 4/2008 |
| WO | WO-2008070740 A1 | | 6/2008 |
| WO | WO-2008109943 A1 | | 9/2008 |
| WO | WO-2009114512 A1 | | 9/2009 |
| WO | WO-2009143313 A1 | | 11/2009 |
| WO | WO-2009153597 A2 | | 12/2009 |
| WO | WO-2010062571 A1 | | 6/2010 |
| WO | WO-2010106211 A1 | | 9/2010 |
| WO | WO-2010110685 A2 | | 9/2010 |
| WO | WO-2010114484 A1 | | 10/2010 |
| WO | WO-2011090760 A1 | | 7/2011 |
| WO | WO-2012007926 A1 | | 1/2012 |
| WO | WO-2012097039 A1 | | 7/2012 |
| WO | WO-2015051043 A1 | | 4/2015 |
| WO | WO-2017044720 A1 | | 3/2017 |

OTHER PUBLICATIONS

Liberles. Proceedings of the National Academy of Sciences of the United States of America, 1997, 94(15), 7825-7830 (Year: 1997).*
Alvero et al., "Targeting the mitochondria activates two independent cell death pathways in ovarian cancer stem cells," Molecular Cancer Therapeutics, vol. 10, No. 8, Aug. 2011 (pp. 1385-1393).
Apsel et al., "Targeted polypharmacology: discovery of dual inhibitors of tyrosine and phosphoinositide kinases," Nature Chemical Biology, vol. 4, No. 11, Nov. 2008 (pp. 691-699).
Awad et al., "Altered TFEB-mediated lysosomal biogenesis in Gaucher disease iPSC-derived neuronal cells," Human Molecular Genetics, vol. 24, No. 20, Oct. 2015 (pp. 5775-5788).
Berge et al., "Pharmaceutical Salts", J. Pharmaceutical Sciences, vol. 66, No. 1, Jan. 1977 (pp. 1-19).
Bonne et al., "Emery-Dreifuss muscular dystrophy, laminopathies, and other nuclear envelopathies," Handbook of Clinical Neurology, vol. 113, 2013 (pp. 1367-1376).
Chang et al., "Novel Phosphoinositide 3-Kinase/mTOR Dual Inhibitor, NVP-BGT226, Displays Potent Growth-Inhibitory Activity against Human Head and Neck Cancer Cells In Vitro and In Vivo," Clinical Cancer Research, vol. 17, No. 22, Nov. 2011 (pp. 7116-7126).

(Continued)

*Primary Examiner* — Noble E Jarrell

(74) *Attorney, Agent, or Firm* — Andrea L. C. Reid; Dechert LLP; Todd K. Macklin

(57) ABSTRACT

The present invention provides compounds, compositions thereof, and methods of using the same.

4 Claims, 52 Drawing Sheets

(56) References Cited

OTHER PUBLICATIONS

Chen et al., "Rapamycin ameliorates kidney fibrosis by inhibiting the activation of mTOR signaling in interstitial macrophages and myofibroblasts," PLoS One, vol. 7, No. 3, Mar. 2012 (p. E33626).
Choo et al., "Rapamycin differentially inhibits S6Ks and 4E-BP1 to mediate cell-type-specific repression of mRNA translation," Proceedings of the National Academy of Sciences, vol. 105, No. 45, Nov. 2008 (pp. 17414-17419).
Cortes et al., "Polyglutamine-expanded androgen receptor interferes with TFEB to elicit autophagy defects in SBMA," Nature Neuroscience, vol. 17, No. 9, Sep. 2014 (pp. 1180-1189).
Decressac et al., "TFEB-mediated autophagy rescues midbrain dopamine neurons from a-synuclein toxicity," Proceedings of the National Academy of Sciences, USA, vol. 110, No. 19, May 2013 (pp. E1817-E1826).
Di Paolo et al., "Chronic Inhibition of Mammalian Target of Rapamycin Signaling Downregulates Insulin Receptor Substrates 1 and 2 and AKT Activation: A Crossroad between Cancer and Diabetes?" JASN, vol. 17, No. 8, 2006 (pp. 2236-2244).
Di Rosa et al., "Autophagy in Diabetic Retinopathy," Curr. Neuropharmacol., vol. 14, No. 8, 2016 (pp. 810-825).
Eleftheriadis et al., "Differential effects of the two amino acid sensing systems, the GCN2 kinase and the mTOR complex 1, on primary human alloreactive CD4+ T-cells," Int. J. Mol. Med., vol. 37, No. 5, 2016, (pp. 1412-1420).
Feldman et al., "Active-Site Inhibitors of mTOR Target Rapamycin-Resistant Outputs of mTORC1 and mTORC2," PLoS One, vol. 7, No. 2, Feb. 2009 (13 pages).
Fok et al., "Combined treatment of rapamycin and dietary restriction has a larger effect on the transcriptome and metabolome of liver," Aging Cell, vol. 13, No. 2, Apr. 2014 (pp. 311-319).
Franz et al., "Molecular Therapies for Tuberous Sclerosis and Neurofibromatosis," Current Neurology and Neuroscience Reports, vol. 12, No. 3, Jun. 2012 (pp. 294-301).
Fujii, S., et al., "Insufficient autophagy promotes bronchial epithelial cell senescence in chronic obstructive pulmonary disease," Oncoimmunology, vol. 1, No. 5, Aug. 24, 2012 (pp. 630-641).
Garcia-Martinez et al., "Ku-0063794 is a specific inhibitor of the mammalian target of rapamycin (mTOR)," Biochemical Journal, vol. 421, No. 1, Jun. 2009 (pp. 29-42).
Grinfeld et al., "Acid Catalyzed Functionalization of Rapamycin," Tet. Lett., vol. 35, No. 37, 1994 (pp. 6835-6838).
Gross et al., "Abstract 4484: AR-mTOR-26—A potent, selective mTORC 1/2 kinase inhibitor for the treatment of malignancy," 101st Annual Meeting of the American Association of Cancer Research (AACR), Apr. 17-21, 2010, Washington, D.C. (2 pages).
Guertin et al., "Defining the Role of mTOR in Cancer", Cancer Cell, vol. 12, No. 1, Jul. 10, 2007 (pp. 9-22).
Gupta et al., "Identification of Selective Inhibitors of Cancer Stem Cells by High-Throughput Screening," Cell, vol. 138, No. 4, Aug. 2009 (pp. 645-659).
Howell et al., "A growing role for mTOR in promoting anabolic metabolism," Biochemical Society Transactions, vol. 41, No. 4, Aug. 2013 (pp. 906-912).
Hua et al., "Rapamycin inhibition of eosinophil differentiation attenuates allergic airway inflammation in mice," Respirology, vol. 20, No. 7, Oct. 2015 (pp. 1055-1065).
Ilagen et al., "Emerging role of mTOR in the response to cancer therapeutics," Trends Cancer, vol. 2, No. 5, May 2016 (pp. 241-251).
International Search Report and Written Opinion issued by the United States Patent and Trademark Office as International Searching Authority for International Application No. PCT/US2019/037507 dated Nov. 13, 2019 (19 pages).
Jacinto et al., "Mammalian TOR complex 2 controls the actin cytoskeleton and is rapamycin insensitive," Nature Cell Biology, vol. 6, No. 11, Nov. 2004 (pp. 1122-1128).
Jiang et al., "Rheb/mTORC1 Signaling Promotes Kidney Fibroblast Activation and Fibrosis," Journal of the American Society of Nephrology, vol. 24, No. 7, Jul. 2013 (pp. 1114-1126).
Johnson et al., "MTOR inhibition alleviates mitochondrial disease in a mouse model of Leigh syndrome," Science, vol. 342, No. 6165, 2013 (pp. 1524-1528).
Kaeberlin, "mTOR Inhibition: From Aging to Autism and Beyond," Scientifica, vol. 2013, 2013 (Article ID 849186).
Kashiyama et al., "Antitumor Activity and Induction of TP53-Dependent Apoptosis toward Ovarian Clear Cell Adenocarcinoma by the Dual PI3K/mTOR Inhibitor DS-7423," PLoS One, vol. 9, No. 2, Feb. 2014 (12 pages).
Kennedy et al., "The Mechanistic Target of Rapamycin: The Grand ConducTOR of Metabolism and Aging," Cell Metab., vol. 23, No. 6, Jun. 4, 2016 (pp. 990-1003).
Kim et al., "Nutrient Regulation of the mTOR Complex 1 Signaling Pathway," Molecules and Cells, vol. 35, No. 6, Jun. 2013 (pp. 463-473).
Kolosova et al., "Prevention of age-related macular degeneration-like retinopathy by rapamycin in rats," Am. J. Path., vol. 181, No. 2, 2012 (pp. 472-477).
Laberge et al., "MTOR regulates the pro-tumorigenic senescence-associated secretory phenotype by promoting IL1A translation," Nature Cell Biology, vol. 17, No. 8, Aug. 2015 (pp. 1049-1061).
Lamming et al., "Rapamycin-induced insulin resistance is mediated by mTORC2 loss and uncoupled from longevity," Science, vol. 335, Mar. 2012 (pp. 1638-1643).
Laplante et al., "mTOR signaling in growth control and disease," Cell, vol. 149, No. 2, Apr. 2012 (pp. 274-293).
Lee et al., "Abstract C270: in vitro and in vivo antitumor activity of DCBC10901, a potent PI3K/mTORC1/mTORC2 inhibitor," Molecular Cancer Therapeutics, vol. 12, No. 11 (Supp), Nov. 2013 (2 pages).
Li et al., "Rapamycin: One Drug, Many Effects," Cell Met., vol. 19, No. 3, Mar. 4, 2014 (pp. 373-379).
Liu et al., "Characterization of Torin2, an ATP-competitive inhibitor of mTOR, ATM, and ATR," Cancer Research, vol. 73, No. 8, Apr. 2013 (pp. 2574-2586).
Liu et al., "Kinome-wide Selectivity Profiling of ATP-competitive Mammalian Target of Rapamycin (mTOR) Inhibitors and Characterization of Their Binding Kinetics," Journal of Biological Chemistry, vol. 287, No. 13, Mar. 2012 (pp. 9742-9752).
Liu et al., "Rapamycin reduces renal hypoxia, interstitial inflammation and fibrosis in a rat model of unilateral ureteral obstruction," Clinical and Investigative Medicine, vol. 37, No. 3, Jun. 2014 (pp. E142-E-153).
Luengo et al., "Structure-activity studies of rapamycin analogs: evidence that the C-7 methoxy group is part of the effector domain and positioned at the FKBP12-FRAP interface," Chemistry and Biology, vol. 2, No. 7, Jul. 1995 (pp. 471-481).
Ma et al., "Rapamycin reduced pulmonary vascular remodelling by inhibiting cell proliferation via Akt/mTOR signalling pathway downregulation in the carotid artery-jugular vein shunt pulmonary hypertension rat model," Interact. Cardiovasc. Thorac. Surg., vol. 25, No. 2, Aug. 1, 2017 (pp. 206-211).
Mannick et al., "mTOR inhibition improves immune function in the elderly," Science Translational Medicine, vol. 6, No. 268, Dec. 24, 2014 (pp. 268ra179).
Mannick et al., "TORC1 inhibition enhances immune function and reduces infections in the elderly," Sci. Trans. Med., vol. 10, No. 449, Jul. 11, 2018, eaaq1564 (10 pages).
Medina et al., "Transcriptional Activation of Lysosomal Exocytosis Promotes Cellular Clearance," Developmental Cell, vol. 21, No. 3, Sep. 2011 (pp. 421-430).
Mercer et al., "Exploration of a potent PI3 kinase/mTOR inhibitor as a novel anti-fibrotic agent in IPF," Thorax, vol. 71, No. 8, Aug. 2016 (pp. 701-711).
Miller et al., "322 Poster mTORC1/mTORC2 selective inhibitors: Identification and characterization of novel small molecules with anti-tumor activity," European Journal of Cancer Supplements, vol. 6, No. 12, Oct. 2008 (pp. 102-103).
Mitra et al., "Dual mTOR Inhibition Is Required to Prevent TGF-β-Mediated Fibrosis: Implications for Scleroderma," Journal of Investigative Dermatology, vol. 135, No. 11, Nov. 2015 (pp. 2873-2876).

(56) References Cited

OTHER PUBLICATIONS

Mori et al., "The mTOR pathway is highly activated in diabetic nephropathy and rapamycin has a strong therapeutic potential," Biochem. Res. Commun., vol. 384, No. 4, Jul. 10, 2009 (pp. 471-475).
Nacarelli et al., "Mitochondrial stress induces cellular senescence in an mTORC1-dependent manner," Free Radical Biology and Medicine, vol. 95, Jun. 2016 (pp. 133-154).
Navarro et al., "Targeting Tumor Mitochondrial Metabolism Overcomes Resistance to Antiangiogenics," Cell Reports, vol. 15, No. 12, Jun. 2016 (pp. 2705-2718).
Okamoto et al., "The Neuroprotective Effect of Rapamycin as a Modulator of the mTOR-NF-?B Axis during Retinal Inflammation", PLOS ONE, vol. 11, No. 1, 2016, e0146517.
Pal et al., "mTOR: A Potential Therapeutic Target in Osteoarthritis?" Drugs R&D, vol. 15, No. 1, Mar. 2015 (pp. 27-36).
Pastore et al, "Gene transfer of master autophagy regulator TFEB results in clearance of toxic protein and correction of hepatic disease in alpha-1-anti-trypsin deficiency," EMBO Molecular Medicine, vol. 5, No. 3, Mar. 2013 (pp. 397-412).
Patel et al., "Autophagy in Idiopathic Pulmonary Fibrosis," PLoS One, vol. 7, No. 7, Jul. 2012 (pp. E41394).
Pereira et al., "mTOR inhibition with rapamycin causes impaired insulin signalling and glucose uptake in human subcutaneous and omental adipocytes," Mol Cell Endocrinol., vol. 355, No. 1, May 15, 2012 (pp. 96-105).
Polito et al., "Selective clearance of aberrant tau proteins and rescue of neurotoxicity by transcription factor EB," EMBO Molecular Medicine, vol. 6, No. 9, Sep. 2014 (pp. 1142-1160).
Porter et al., "Autophagic dysregulation in glaucomatous trabecular meshwork cells," Biochim. Biophys. Acta., vol. 1852, No. 3, Mar. 2015 (pp. 379-385).
PubChem, Compound Summary for CID 23376689, (1R,9S,12S,1 5R,16E,18R,21R,23S,24Z,26E,28E,30S,32S,35R)-1,18-Dihydroxy-12-[(2R)-1-[(1S,3R,4R)-4-hydroxy-3-methoxycyclohexyl]propan-2-yl]-19-methoxy-15,17,21,23,29,35-hexamethyl-30-pent-2-ynoxy-11,36-dioxa-4-azatricyclo[30.3.1.04.9]hexatriaconta-16,24,26,28-tetraene-2,3,10,14,20-pentone, Dec. 5, 2007 (4 pages).
Puri et al., "Autophagy modulation as a potential therapeutic target for liver diseases," Journal of Clinical and Experimental Hepatology, vol. 4, No. 1, Mar. 2014 (pp. 51-59).
Ramos et al., "Rapamycin Reverses Elevated mTORC1 Signaling in Lamin A/C-Deficient Mice, Rescues Cardiac and Skeletal Muscle Function, and Extends Survival," Science Translational Medicine, vol. 4, No. 144, Jul. 2012 (pp. 144ra103).
Sarbassov et al., "Prolonged rapamycin treatment inhibits mTORC2 assembly and Akt/PKB," Molecular Cell, vol. 22, No. 2, Apr. 2006 (pp. 159-168).
Sarbassov et al., "Rictor, a novel binding partner of mTOR, defines a rapamycin-insensitive and raptor-independent pathway that regulates the cytoskeleton," Current Biology, vol. 14, No. 14, Jul. 2004 (pp. 1296-1302).
Sardiello, "Transcription factor EB: from master coordinator of lysosomal pathways to candidate therapeutic target in degenerative storage diseases," Annals of the New York Academy of Sciences, vol. 1371, No. 1, 2016 (pp. 3-14).
Sciarretta et al., "New Insights Into the Role of mTOR Signaling in the Cardiovascular System," Circ. Res., vol. 122, No. 3, Feb. 2, 2018 (pp. 489-505).
Shum et al., "Pharmacological inhibition of S6K1 increases glucose metabolism and Akt signalling in vitro and in diet-induced obese mice," Diabetologia, vol. 59, No. 3, Mar. 2016 (pp. 592-603).
Spampanato et al., "Transcription factor EB (TFEB) is a new therapeutic target for Pompe disease," EMBO Molecular Medicine, vol. 5, No. 5, May 2013 (pp. 691-706).
Syed et al., "Keloid disease can be inhibited by antagonizing excessive mTOR signaling with a novel dual TORC1/2 inhibitor," The American Journal of Pathology, vol. 181, No. 5, Nov. 2012 (pp. 1642-1658).
Taveira-DaSilva et al., "Clinical features, epidemiology, and therapy of lymphangioleiomyomatosis," Journal of Clinical Epidemiology, vol. 7, Apr. 2015 (pp. 249-257).
Thoreen et al., "An ATP-competitive mammalian target of rapamycin inhibitor reveals rapamycin-resistant functions of mTORC1," Journal of Biological Chemistry, vol. 284, No. 12, Mar. 2009 (pp. 8023-8032).
Torres et al., "Prospects for mTOR inhibitor use in patients with polycystic kidney disease and hamartomatous diseases," Clin. J. Am. Soc. Nephrol., vol. 5, No. 7, Jul. 2010 (pp. 1312-1329).
Tsunemi et al., "PGC-1a rescues Huntington's disease proteotoxicity by preventing oxidative stress and promoting TFEB function," Science Translational Medicine, vol. 4, No. 142, Jul. 2012 (pp. 142ra97).
Varin et al., "Dual mTORC1/2 inhibition induces anti-proliferative effect in NF1-associated plexiform neurofibroma and malignant peripheral nerve sheath tumor cells," Oncotarget, vol. 7, No. 24, Jan. 2016 (pp. 35753-35767).
Wallace et al., "Abstract B267: AR-mTOR-1: A potent, selcecitve mTORC 1/2 kinase inhibitor for the treatment of malignancy," AACR, International Conference: Molecular Targets and Cancer Therapeutics, Nov. 15-19, 2009, Boston, Massachusetts (2 pages).
Wander et al., "Next-generation mTOR inhibitors in clinical oncology: how pathway complexity informs therapeutic strategy," The Journal of Clinical Investigation, vol. 121, Apr. 2011 (pp. 1231-1241).
Wu et al., "Rapamycin attenuates unilateral ureteral obstruction-induced renal fibrosis," Kidney International, vol. 69, No. 11, Jun. 2006 (pp. 2029-2036).
Yano et al., "Clinical impact of myocardial mTORC1 activation in nonischemic dilated cardiomyopathy," Journal of Molecular and Cellular Cardiology, vol. 91, Feb. 2016 (pp. 6-9).
Yu et al., "Biochemical, Cellular, and In vivo Activity of Novel ATP-Competitive and Selective Inhibitors of the Mammalian Target of Rapamycin," Cancer Research, vol. 69, No. 15,Aug. 2009 (pp. 6232-6240).
Yu et al., "Rapamycin and Dietary Restriction Induce Metabolically Distinctive Changes in Mouse Liver," Journals of Gerontology: Biological Sciences, vol. 70, No. 4, Apr. 2015 (pp. 410-420).
Zhao et al., "mTOR pathway activation in age-related retinal disease," Aging, vol. 3, No. 4, Apr. 2011 (pp. 346-347).
Zschiedrich et al., "Targeting mTOR Signaling Can Prevent the Progression of FSGS," J. Am. Soc. Nephrol., vol. 28, No. 7, Jul. 2017 (pp. 2144-2157).

* cited by examiner

RAPAMYCIN ANALOGS AND USES THEREOF

CROSS-REFERENCE TO RELATED APPLICATIONS

This application claims the benefit of U.S. Provisional App. No 62/685,666 filed on Jun. 15, 2018, the content of which is hereby incorporated by reference.

TECHNICAL FIELD OF THE INVENTION

The present invention relates to compounds and methods useful for modulating mTORC1 activity. The invention also provides pharmaceutically acceptable compositions comprising provided compounds of the present invention and methods of using such compositions in the treatment of various disorders.

BACKGROUND OF THE INVENTION mTOR complex 1 (mTORC1) positively regulates cell growth and proliferation by promoting many anabolic processes, including biosynthesis of proteins, lipids and organelles, and by limiting catabolic processes such as autophagy. Much of the knowledge about mTORC1 function comes from the use of the bacterial macrolide rapamycin. Upon entering the cell, rapamycin binds to FK506-binding protein of 12 kDa (FKBP12) and interacts with the FKBP12-rapamycin binding domain (FRB) of mTOR, thus inhibiting mTORC1 functions (Guertin, D. A. & Sabatini, D. M. Cancer Cell 12(1): 9-22 (2007)). In contrast to its effect on mTORC1, FKBP12-rapamycin cannot physically interact with or acutely inhibit mTOR complex 2 (mTORC2) (Janinto, E. et al., Nat. Cell Bio., 6(11): 1122-8 (2004); Sarbassov, D. D. et al., Curr. Biol. 14(14): 1296-302 (2004)). On the basis of these observations, mTORC1 and mTORC2 have been respectively characterized as the rapamycin-sensitive and rapamycin-insensitive complexes. However, this paradigm might not be entirely accurate, as chronic rapamycin treatment can, in some cases, inhibit mTORC2 activity by blocking its assembly (Sarbassov, D. D. et al., Mol. Cell, 22(2): 159-68 (2006)). In addition, recent reports suggest that important mTORC1 functions are resistant to inhibition by rapamycin (Choo, A. Y. et al., Proc. Natl. Acad. Sci., 105(45): 17414-9 (2008); Feldman, M. E. et al., PLoS Biol., 7(2):e38 (2009); Garcia-Martinez, J. M. et al., Biochem J., 421(1): 29-42 (2009); Thoreen, C. C. et al., J. Biol. Chem., 284(12): 8023-32 (2009)). Therefore, selective inhibition of mTORC1 would enable the treatment of diseases that involve dysregulation of protein synthesis and cellular metabolism. Furthermore, this detailed understanding of regulating mTORC1 activation pathways will permit the discovery of new strategies for regulating abnormal disease processes by modulating mTORC1 activity across its spectrum of function.

Many diseases are associated with abnormal cellular responses triggered by events as described above. These diseases include, but are not limited to, autoimmune diseases, inflammatory diseases, bone diseases, metabolic diseases, neurological and neurodegenerative diseases, cancer, cardiovascular diseases, allergies and asthma, Alzheimer's disease, and hormone-related diseases.

The mechanistic target of rapamycin complex 1 (mTORC1) is a master growth regulator that senses diverse environmental cues, such as growth factors, cellular stresses, and nutrient and energy levels. When activated, mTORC1 phosphorylates substrates that potentiate anabolic processes, such as mRNA translation and lipid synthesis, and limits catabolic ones, such as autophagy. mTORC1 dysregulation occurs in a broad spectrum of diseases, including diabetes, epilepsy, neurodegeneration, immune response, suppressed skeletal muscle growth, and cancer among others (Howell, J. J. et al., Biochem. Soc. Trans., 41: 906-12 (2013); Kim, S. G. et al., Molecular and cells, 35(6): 463-73 (2013); Laplante, M. & Sabatini, D. M., Cell, 149(2): 274-93 (2012)).

Rapamycin was initially discovered as an antifungal metabolite produced by *Streptomyces hygroscopicus* from a soil sample of Easter Island. Subsequently, rapamycin was found to possess immunosuppressive and antiproliferative properties in mammalian cells, spurring an interest in identifying the mode of action of rapamycin. Rapamycin was shown to be a potent inhibitor of S6K1 phosphorylation. Concurrently, the target of rapamycin (TOR) was identified in yeast and animal cells. Rapamycin forms a gain-of-function complex with the 12 kDa FK506-binding protein (FKBP12), and this complex binds and specifically acts as an allosteric inhibitor of mammalian TOR (mTOR, also known as mechanistic TOR) complex 1 (mTORC1).

Biochemical and genetic analysis of mTOR has demonstrated that it is present in two functionally distinct complexes. The core components of mTORC1 consist of mTOR, mammalian lethal with sec-13 protein 8 (mLST8), and regulatory-associated protein of TOR (Raptor). Additional components include DEP-domain-containing mTOR-interacting protein (DEPTOR) and Proline-rich Akt substrate 40 kDa (PRAS40).

The mTOR complex 2 (mTORC2) core is composed of mTOR, rapamycin insensitive companion of mTOR (Rictor), stress-activated protein kinase-interacting protein 1 (mSIN1), and mLST8. Protein observed with rictor 1/2 (protor 1/2) and DEPTOR are additional regulatory components. S6 kinase 1 (S6K1) and eukaryotic inhibition factor eIF4E binding protein 1 (4E-BP1) are two well-characterized substrates of mTORC1 while AKT is a well characterized substrate of mTORC2 (Li, J. et al., Cell Met., 19(3): 373-9 (2014)).

Because FKBP12-rapamycin does not bind to mTORC2, rapamycin was initially thought to inhibit only mTORC1 (Sarbassov, D .D. et al., Curr. Biol., 14(14): 1296-302 (2004)). However, in 2006 it was shown that rapamycin suppresses the assembly and function of mTORC2 and inhibits pAkt (Sarbassov, D.D. et al., Molecular Cell, 22(2): 159-68 (2006)). The effects of rapamycin on the phosphorylation of S473 of Akt (an mTORC2 substrate) and of T389 of S6K1 (an mTORC1 substrate) were compared in multiple cell lines. In PC3, HEK-293T, HeLa, and H460 cells, 1 or 24 hour treatments with rapamycin inhibited S6K1 phosphorylation, consistent with inhibition of mTORC1. Selective inhibition of S6K1 by rapamycin should lead to an increase in Akt phosphorylation, and, indeed, this is what is reported in HeLa cells. However, in PC3 cells, the drug strongly decreased Akt phosphorylation suggesting that rapamycin is not selective in this cell line. Partial inhibition of pAKT is observed in HEK-293T cells. In about one third of the cell lines, rapamycin caused a strong or partial inhibition of Akt phosphorylation, while the drug either did not affect or increased Akt phosphorylation in the others. The inhibition of pAKT after 24 hours is also observed in primary and non-transformed cell lines including endothelial and muscle cells. Rapamycin was also shown to inhibit pAkt in vivo, as mice treated daily for 1 week with the drug had decreased Akt phosphorylation in the thymus, adipose tissue, heart, and lung. These findings demonstrated that inhibition of Akt phosphorylation by rapamycin is common and occurs in normal cell lines, cancer cell lines as well as in vivo.

It was concluded by Sarbassov et al. that rapamycin and its analogs (CCI 779, RAD001 also known as Everolimus, AP23573) can inhibit mTORC2 function in certain cell lines and tissues. Rapamycin-mediated inhibition of Akt may help explain the side effects of the drug. For example, rapamycin strongly inhibits Akt phosphorylation in adipose tissue, a tissue type in which insulin-stimulated Akt activity plays an important role in suppressing lipolysis. Inhibition of Akt by rapamycin in adipocytes may allow lipolysis to remain high even in the presence of insulin, resulting in the accumulation of free fatty acids in the plasma that can be used by the liver to generate triglycerides, providing a molecular mechanism for the hyperlipidemia commonly seen in patients treated with rapamycin.

Pereira et al. (Mol Cell Endocrinol., 355(1): 96-105 (2012)) explored rapamycin effects on glucose uptake and insulin signaling proteins in adipocytes obtained via fat biopsies in human donors. At therapeutic concentration (0.01 µM) rapamycin reduced AKT (PKB) Ser473 phosphorylation and reduced glucose uptake in human adipocytes through impaired insulin signaling.

Lamming et al. (Science., 335(6076): 1638-1643 (2012)) demonstrated that rapamycin disrupted mTORC2 in vivo and that mTORC2 was required for the insulin-mediated suppression of hepatic gluconeogenesis.

Similar results were shown in human. Di Paolo et al. published similar findings in human (JASN, 17(8): 2236-2244 (2006)). The main objective of their study was to ascertain the effect of chronic exposure to rapamycin on AKT activation, in view of its crucial role in the regulation of cell growth and survival, as well as in the cell response to nutrients and growth factors. They found that mTOR inhibition was associated with a marked downregulation of basal and insulin-induced AKT phosphorylation. AKT is responsible primarily for many of the metabolic actions of insulin and they concluded therefore that the depression of AKT activation significantly correlated with the increase of insulin resistance in renal transplant recipients.

Kennedy et al. reviewed recently the role of mTORC1 and mTORC2 in metabolism and aging (Cell Metab., 23(6): 990-1003 (2016)).

It has been surprisingly found that provided compounds inhibit mTORC1, but do not impact mTORC2 (as measured by their impact on pAKT) over extended periods of time (e.g., 8 hours, 24 hours, 30 hours, and 48 hours). This novel activity is predicated on the presence of a sufficiently large group at the C-7 position of rapamycin and its analogs. Small substitutions at this position such as OMe, as seen in rapamycin, OEt, OBn do not confer selectivity over mTORC2 at 24 hours. Medium length groups, such as OCH$_2$CH$_2$OH or OCH$_2$CH$_2$CH$_2$OH show partial selectivity over mTORC2 at 24 hours, but still show some level of inhibition. In comparison, larger groups, such as those of the present invention (e.g., 1-19), provide a marked selectivity over mTORC2 as measured by the impact of pAKT.

The location of this substitution is also critical to the observed selectivity. Introduction of larger substitutions at position 43 for example does not lead to this unique selectivity profile claimed in this application.

For the purpose of clarity, the structure of Rapamycin is reproduced below with the C-7 and C-43 positions noted.

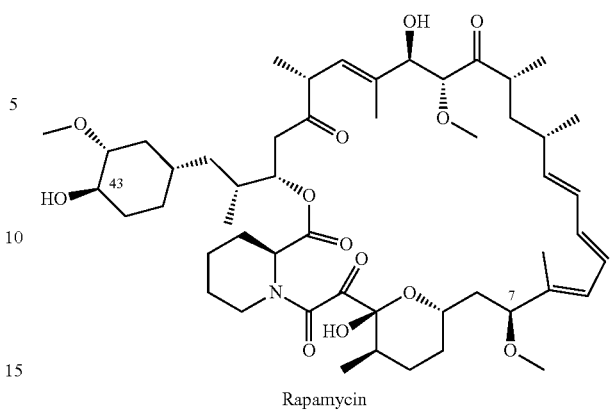

Rapamycin

In some embodiments, the present invention provides novel rapamycin analogues that are potent mTORC1 inhibitors as measured by pS6K. Unlike Rapamycin and Everolimus, these compounds do not inhibit pAKT at longer time points (e.g., 24 hours and 48 hours). These compounds also show improved solubility and improved pharmacokinetics comparing to Rapamycin.

The activity of a compound utilized in this invention as an inhibitor of mTORC1, may be assayed in vitro, in vivo or in a cell line. In vitro assays include assays that determine the inhibition of mTORC1. Detailed conditions for assaying a compound utilized in this invention as an inhibitor of mTORC1 are well known to one of ordinary skill in the art. Such methods are described in detail by Liu et al., Cancer Research, 73(8): 2574-86 (2013) and Liu et al., J. Biological Chemistry 287(13): 9742-52 (2012).

SUMMARY OF THE INVENTION

It has now been found that compounds of this invention, and pharmaceutically acceptable compositions thereof, are effective as inhibitors mTORC1 inhibitors. Such compounds have the general Formula I:

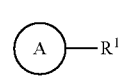

I or a pharmaceutically acceptable salt thereof, wherein Ring A and R$^1$ are as defined and described herein.

Compounds of the present invention, and pharmaceutically acceptable compositions thereof, are useful for treating a variety of diseases, disorders or conditions, associated with mTORC1. Such diseases, disorders, or conditions include those described herein.

Significantly, the compounds of the present invention do not inhibit mTORC2, as demonstrated by the lack of Akt phosphorylation inhibition.

Figure 18:
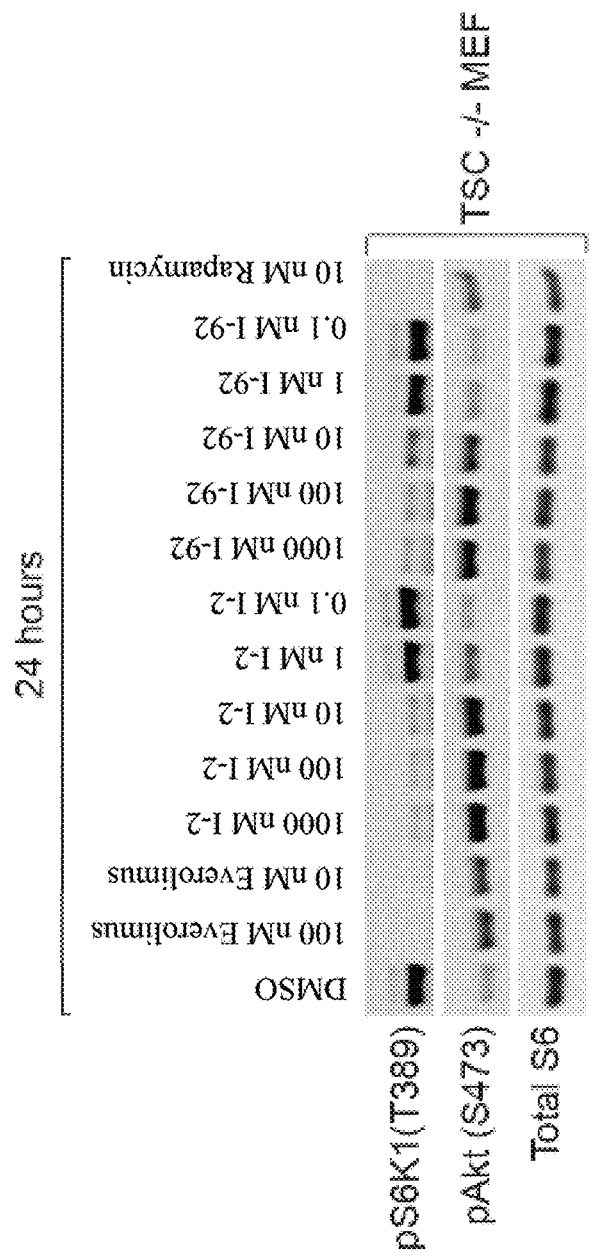

FIG. 18 shows a Western blot performed after treating TSC −/− MEF cells with everolimus, rapamycin, or compounds of the present invention (I-2 and I-92) for 24 hours. Staining indicates strong inhibition of the mTORC1 pathway for everolimus, rapamycin, and I-2, and a moderate concentration dependent inhibition of the mTORC1 pathway for I-92.

Figure 19:
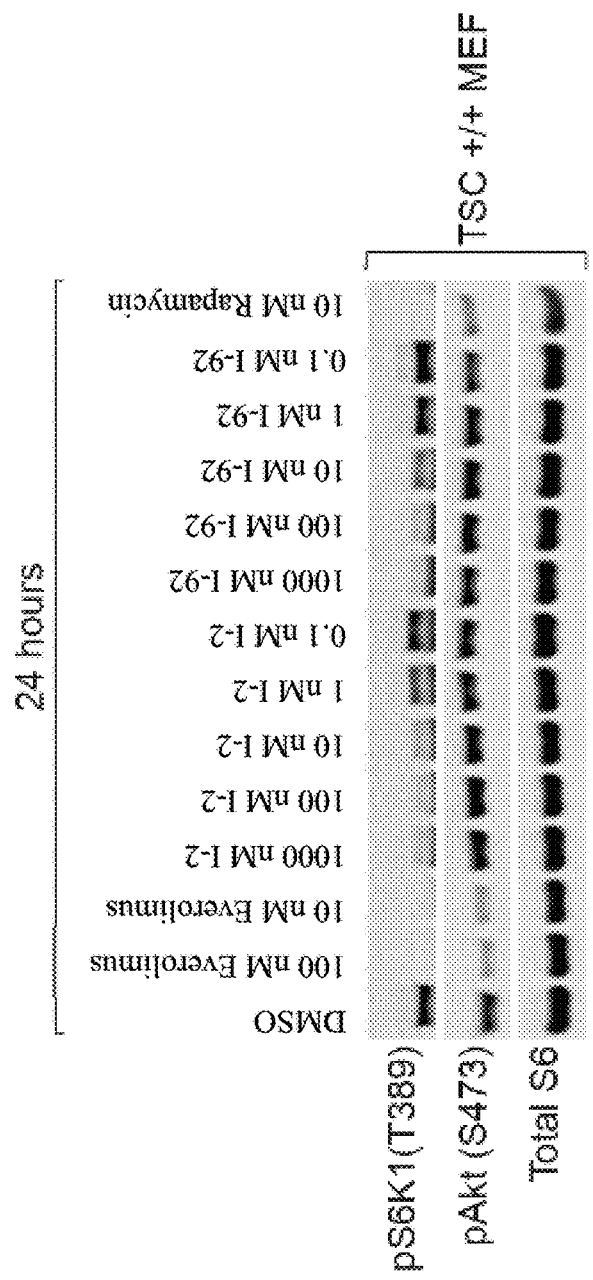

FIG. 19 shows a Western blot performed after treating TSC +/+ MEF cells with everolimus, rapamycin, or compounds of the present invention (I-2 and I-92) for 24 hours. Staining indicates strong inhibition of the mTORC1 pathway for everolimus, rapamycin, and moderate concentration dependent inhibition of the mTORC1 pathway for I-2 and I-92. Significantly, the compounds of the present invention do not inhibit mTORC2, as demonstrated by the lack of Akt phosphorylation inhibition.

Figure 20:
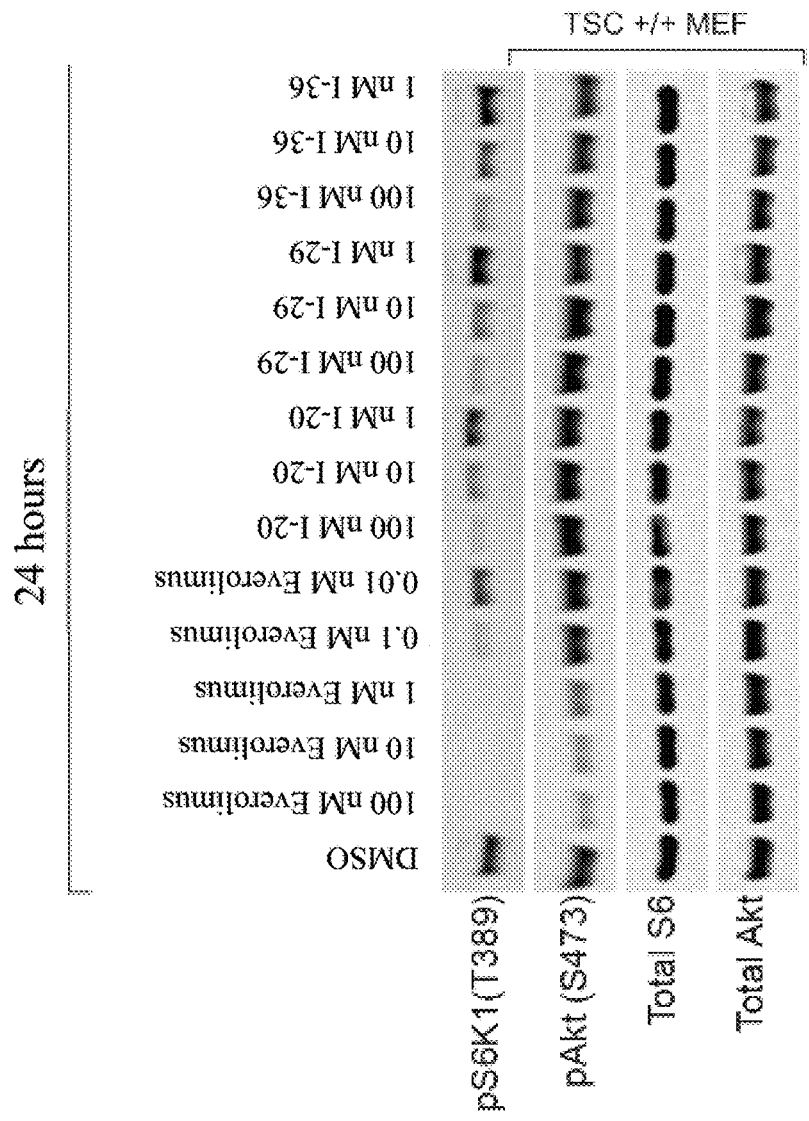

FIG. 20 shows a Western blot performed after treating TSC +/+ MEF cells with everolimus, or compounds of the present invention (I-20, I-29 and I-36) for 24 hours. Staining indicates strong inhibition of the mTORC1 pathway for everolimus, and moderate concentration dependent inhibition of the mTORC1 pathway for I-20, I-29, and I-36. Significantly, the compounds of the present invention do not inhibit mTORC2, as demonstrated by the lack of Akt phosphorylation inhibition.

Figure 21:
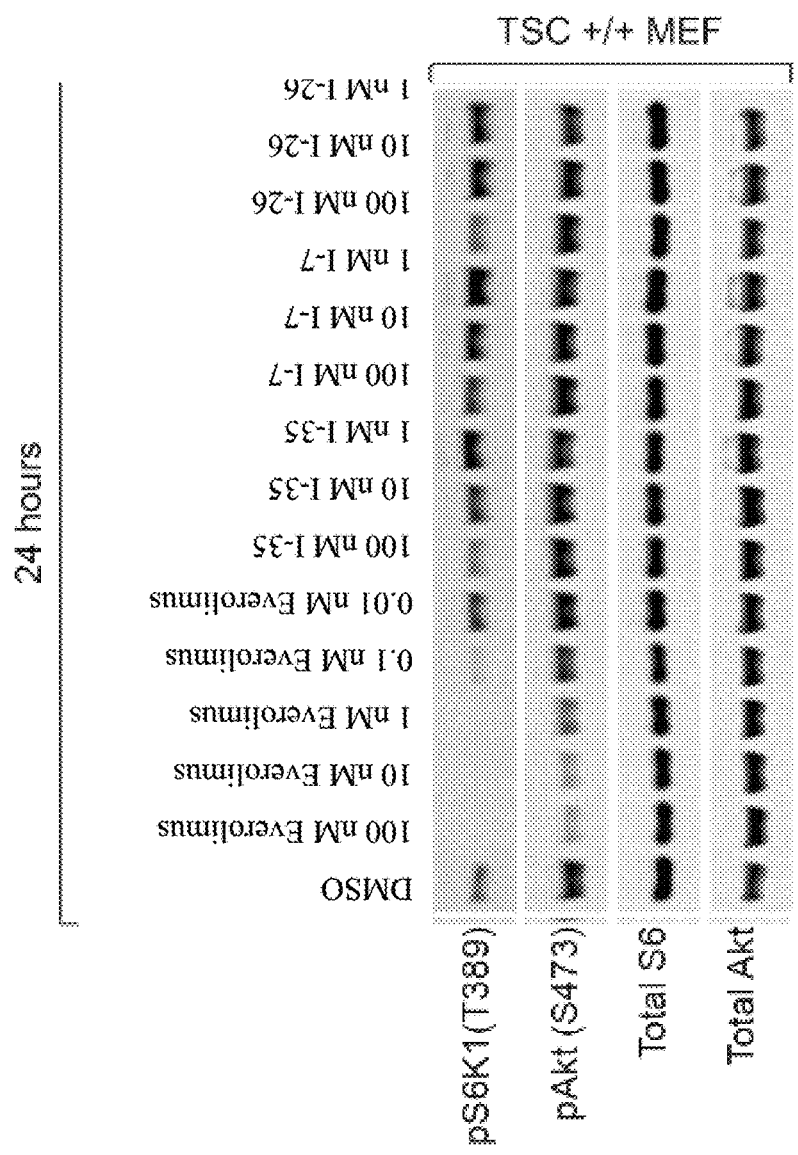

FIG. 21 shows a Western blot performed after treating TSC +/+ MEF cells with everolimus, or compounds of the present invention (I-35, I-7 and I-26) for 24 hours. Staining indicates strong inhibition of the mTORC1 pathway for everolimus, and modest concentration dependent inhibition of the mTORC1 pathway for I-35, I-7, and I-26. Significantly, the compounds of the present invention do not inhibit mTORC2, as demonstrated by the lack of Akt phosphorylation inhibition.

Figure 22:
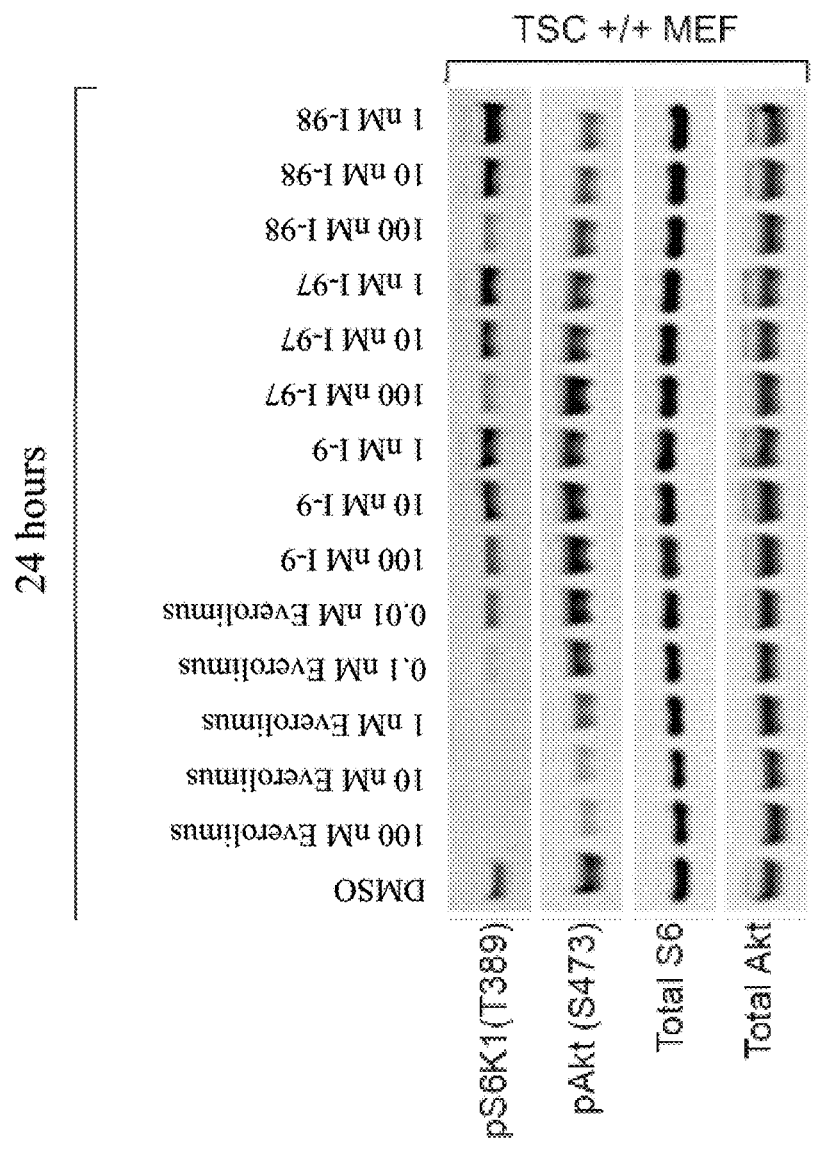

FIG. 22 shows a Western blot performed after treating TSC +/+ MEF cells with everolimus, or compounds of the present invention (I-9, I-97 and I-98) for 24 hours. Staining indicates strong inhibition of the mTORC1 pathway for everolimus, modest concentration dependent inhibition of the mTORC1 pathway for I-9, I-97, and I-98. Significantly, the compounds of the present invention do not inhibit mTORC2, as demonstrated by the lack of Akt phosphorylation inhibition.

Figure 23:
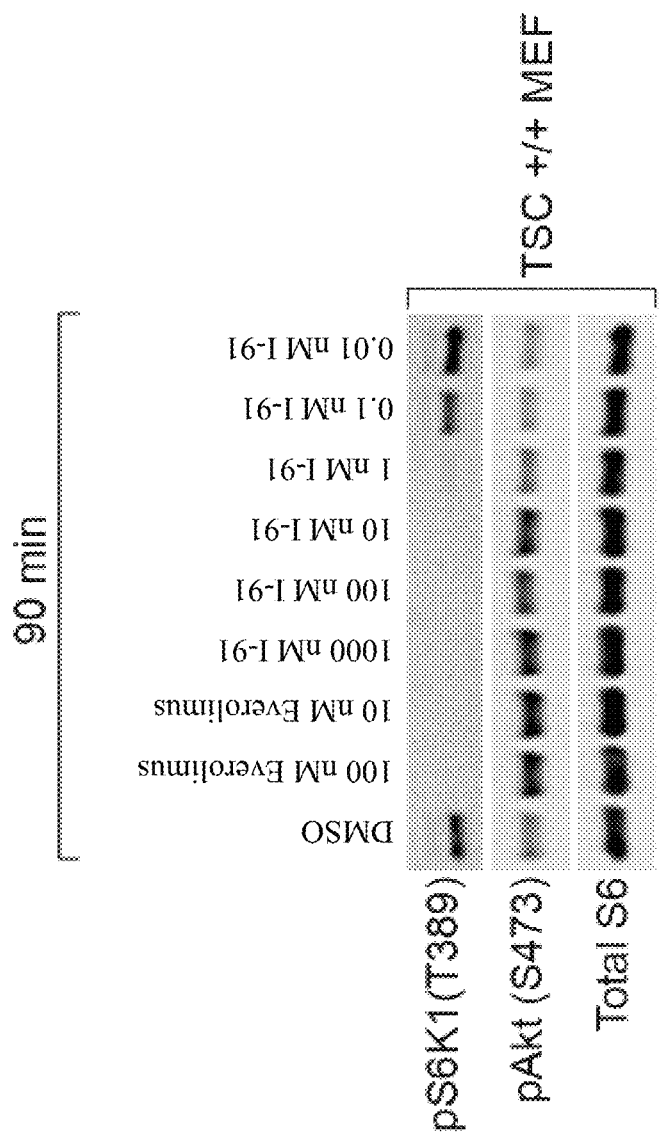

FIG. 23 shows a Western blot performed after treating TSC +/+ MEF cells with everolimus, or a compounds of the present invention (I-91) for 90 minutes. Staining indicates strong inhibition of the mTORC1 pathway for rapamycin and I-91. Interestingly, I-91 exhibits some inhibition of mTORC2, as demonstrated by Akt phosphorylation inhibition.

Figure 24:
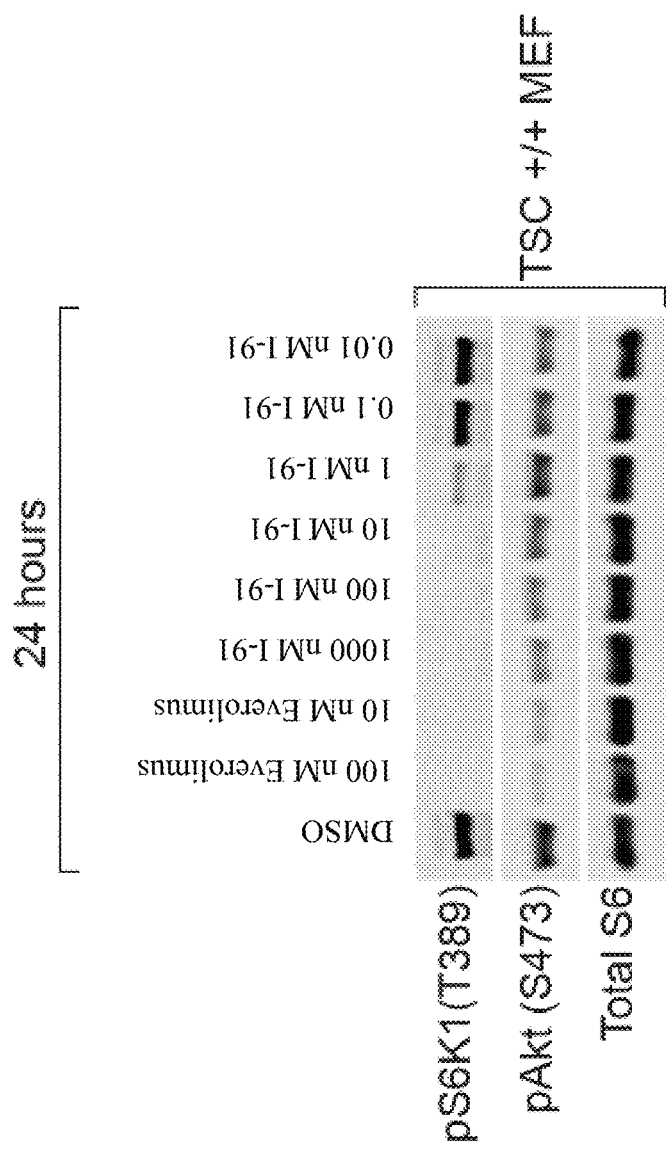

FIG. 24 shows a Western blot performed after treating TSC +/+ MEF cells with everolimus, or a compounds of the present invention (I-91) for 24 hours. Staining indicates strong inhibition of the mTORC1 pathway for rapamycin and I-91. Interestingly, I-91 exhibits some inhibition of mTORC2, as demonstrated by Akt phosphorylation inhibition.

Figure 25:
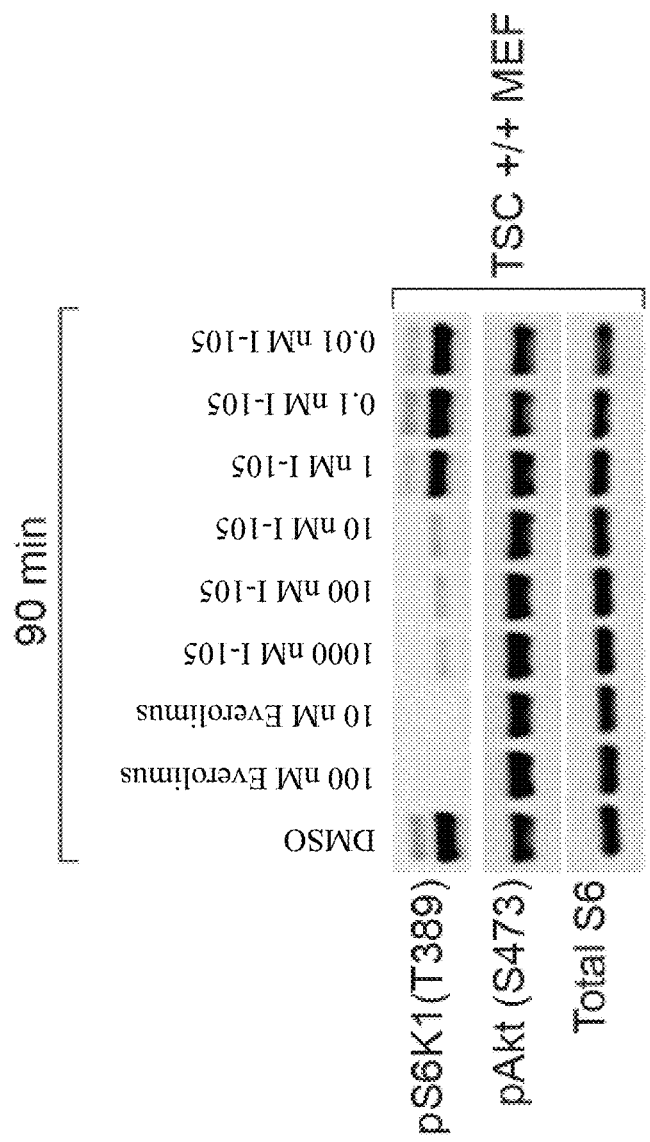

FIG. 25 shows a Western blot performed after treating TSC +/+ MEF cells with everolimus, or a compounds of the present invention (I-105) for 90 minutes. Staining indicates strong inhibition of the mTORC1 pathway for rapamycin and I-105. Significantly, the compound of the present invention does not inhibit mTORC2, as demonstrated by the lack of Akt phosphorylation inhibition.

Figure 26:
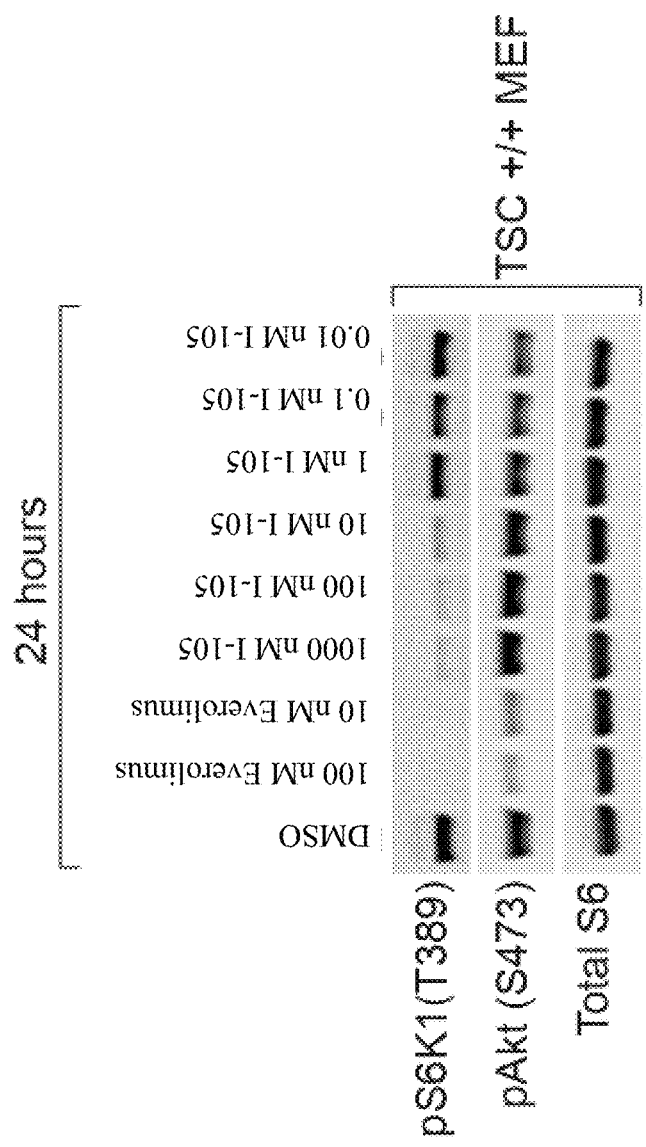

FIG. 26 shows a Western blot performed after treating TSC +/+ MEF cells with everolimus, or a compounds of the present invention (I-105) for 24 hours. Staining indicates strong inhibition of the mTORC1 pathway for rapamycin and I-105. Significantly, the compound of the present invention does not inhibit mTORC2, as demonstrated by the lack of Akt phosphorylation inhibition.

Figure 27:
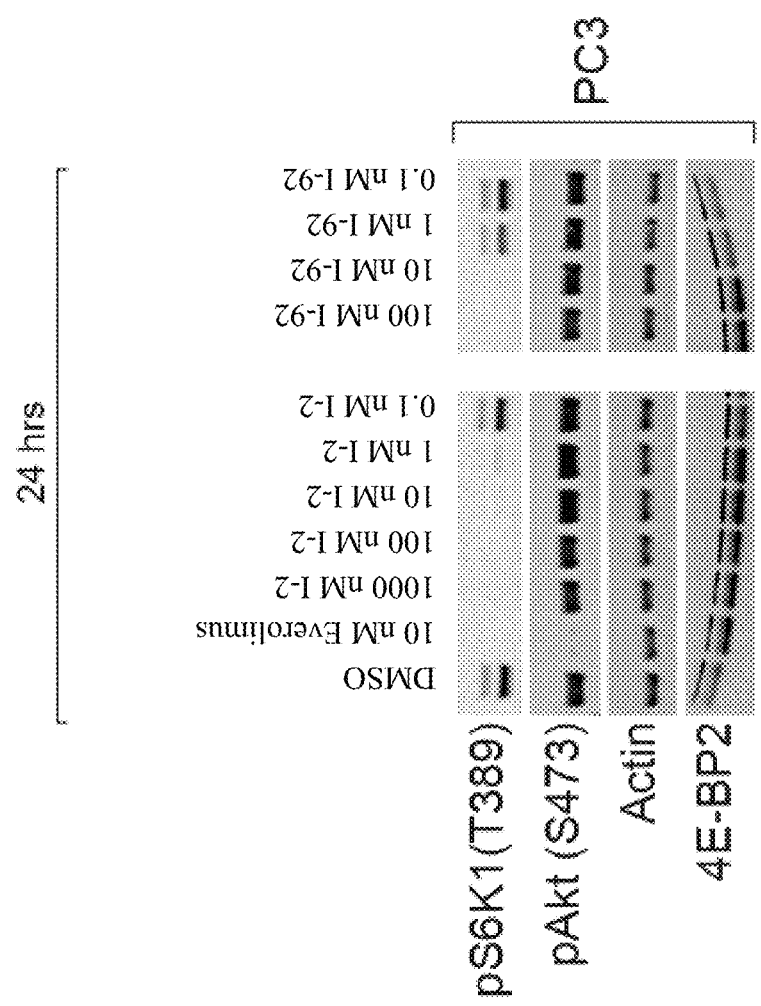

FIG. 27 shows two Western blots performed after treating PC3 cells with everolimus or compounds of the present invention (I-2 and I-92) for 24 hours. Staining indicates strong inhibition of the mTORC1 pathway for each compound tested and no inhibition of 4E-BP1 phosphorylation. Significantly, the compounds of the present invention do not inhibit mTORC2, as demonstrated by the lack of Akt phosphorylation inhibition.

Figure 28:
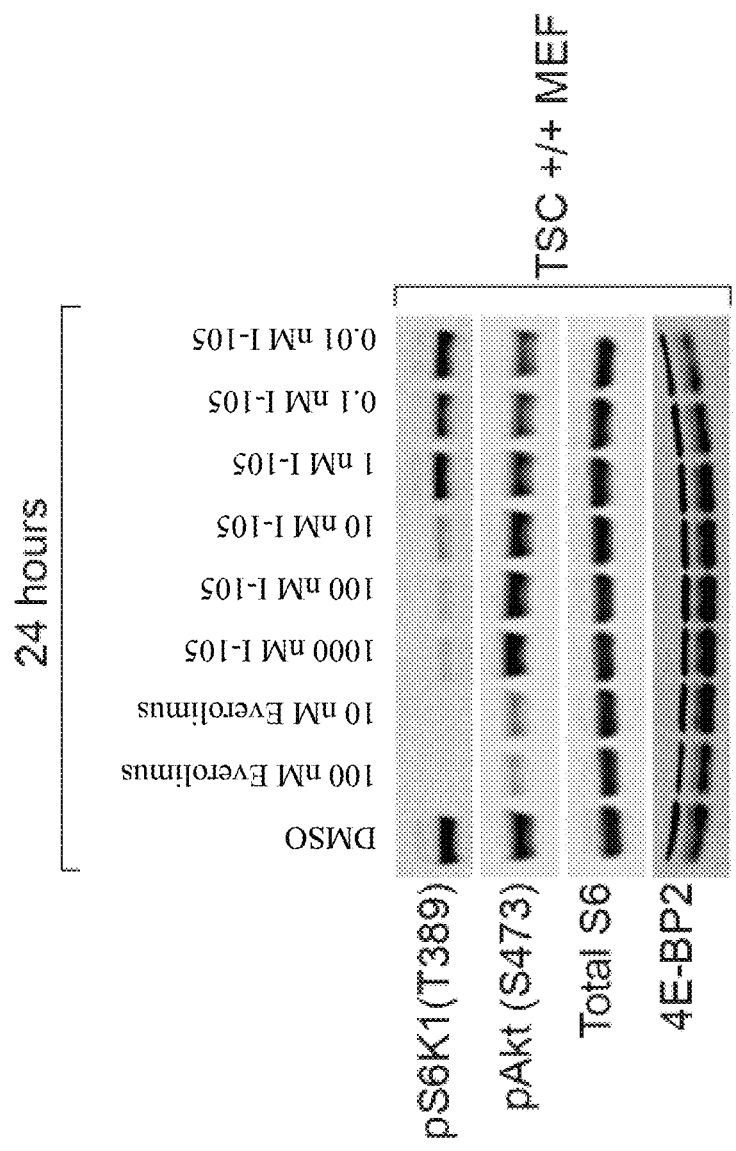

FIG. 28 shows a Western blot performed after treating TSC +/+ MEF cells with everolimus or a compound of the present invention (I-105) for 24 hours. Staining indicates strong inhibition of the mTORC1 pathway for each compound tested and no inhibition of 4E-BP1 phosphorylation. Significantly, the compounds of the present invention do not inhibit mTORC2, as demonstrated by the lack of Akt phosphorylation inhibition.

Figure 29:
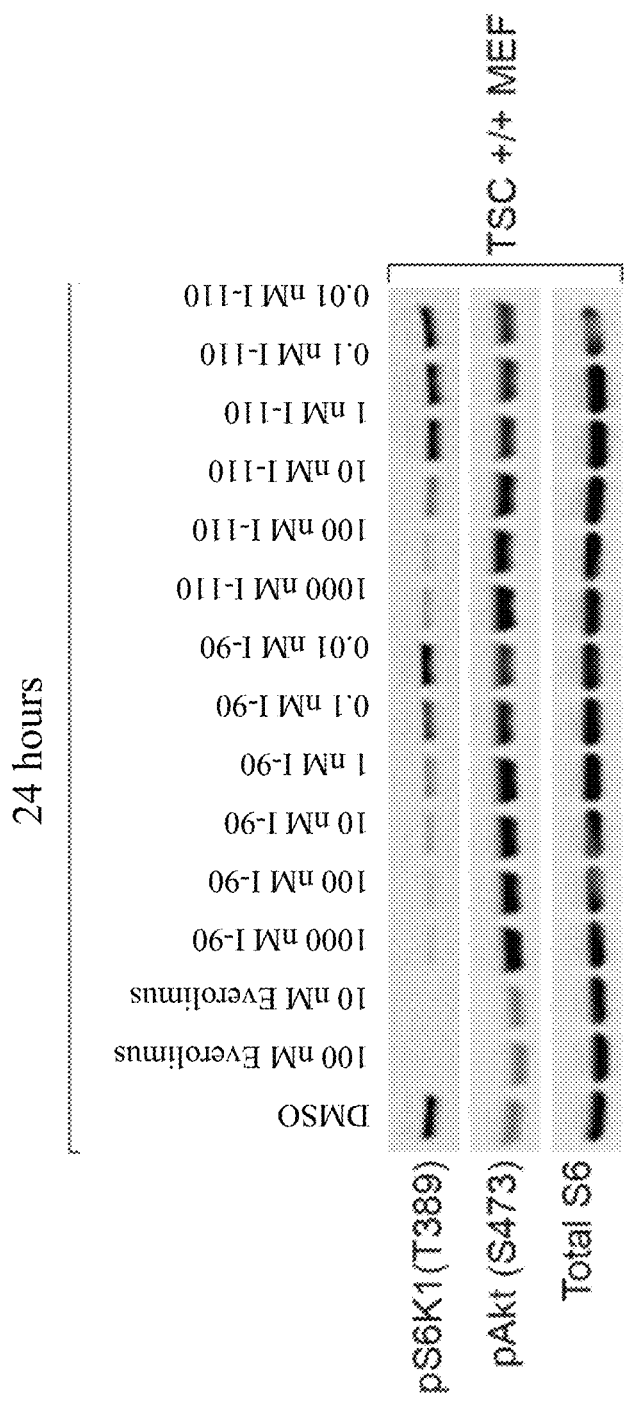

FIG. 29 shows a Western blot performed after treating TSC +/+ MEF cells with everolimus or compounds of the present invention (I-90 and I-110) for 24 hours. Staining indicates strong inhibition of the mTORC1 pathway for everolimus and I-90, and moderate concentration dependent inhibition of the mTORC1 pathway for I-110. Significantly, the compounds of the present invention do not inhibit mTORC2, as demonstrated by the lack of Akt phosphorylation inhibition.

Figure 30:
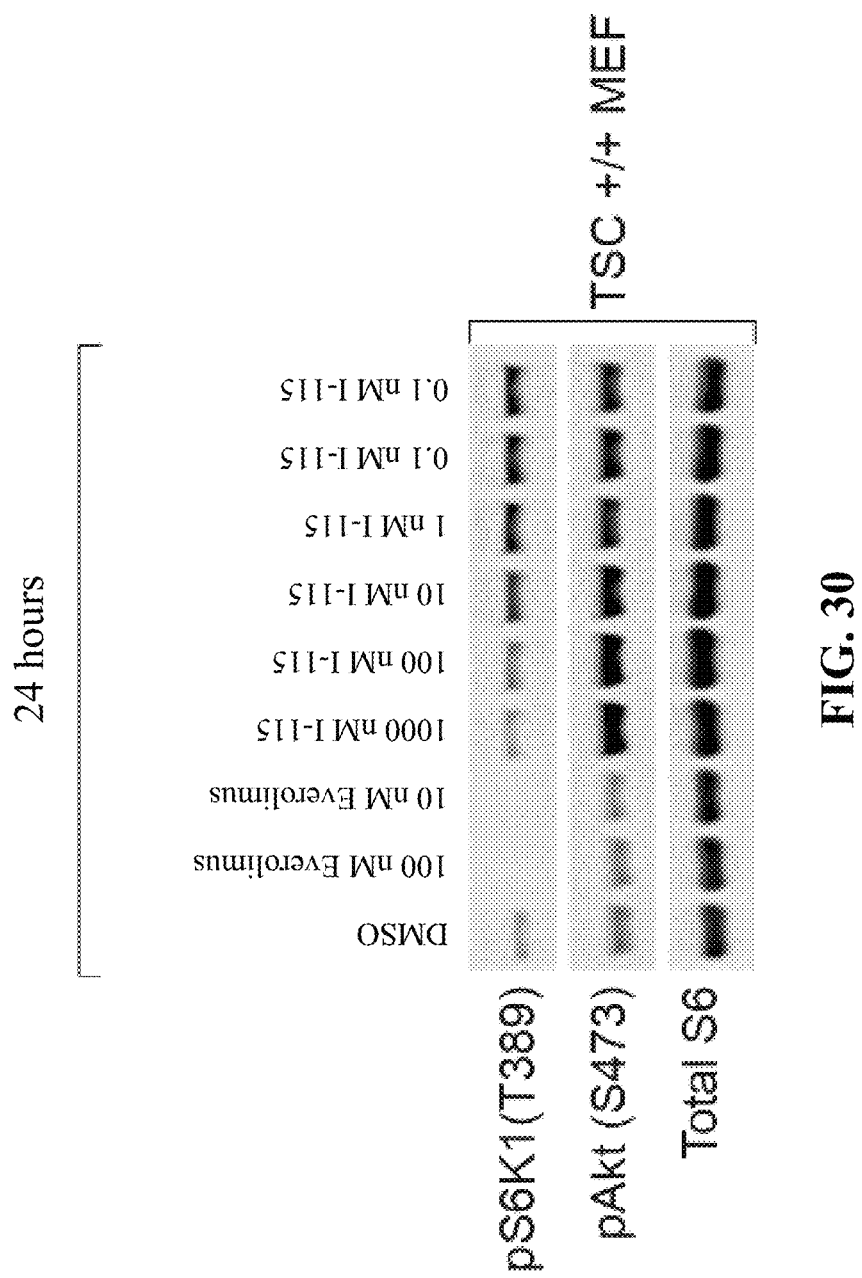

FIG. 30 shows a Western blot performed after treating TSC +/+ MEF cells with everolimus or a compound of the present invention (I-115) for 24 hours. Staining indicates strong inhibition of the mTORC1 pathway for everolimus and moderate concentration dependent inhibition of the mTORC1 pathway for I-115. Significantly, the compound of the present invention does not inhibit mTORC2, as demonstrated by the lack of Akt phosphorylation inhibition.

Figure 31:
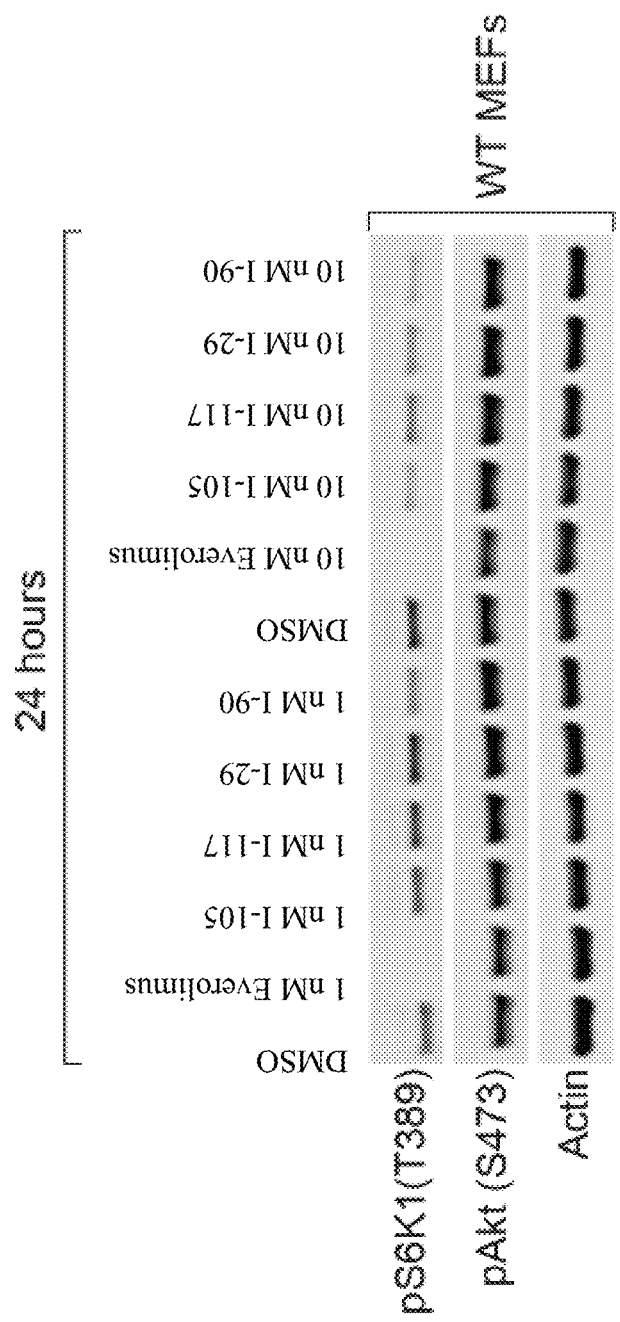

FIG. 31 shows a Western blot performed after treating wild-type MEF cells with everolimus or compounds of the present invention (I-105, I-117, I-29, and I-90) for 24 hours. Staining indicates strong inhibition of the mTORC1 pathway for everolimus, and moderate inhibition of the mTORC1 pathway for I-105, I-117, I-29, and I-90. Significantly, the compounds of the present invention do not inhibit mTORC2, as demonstrated by the lack of Akt phosphorylation inhibition.

Figure 32:
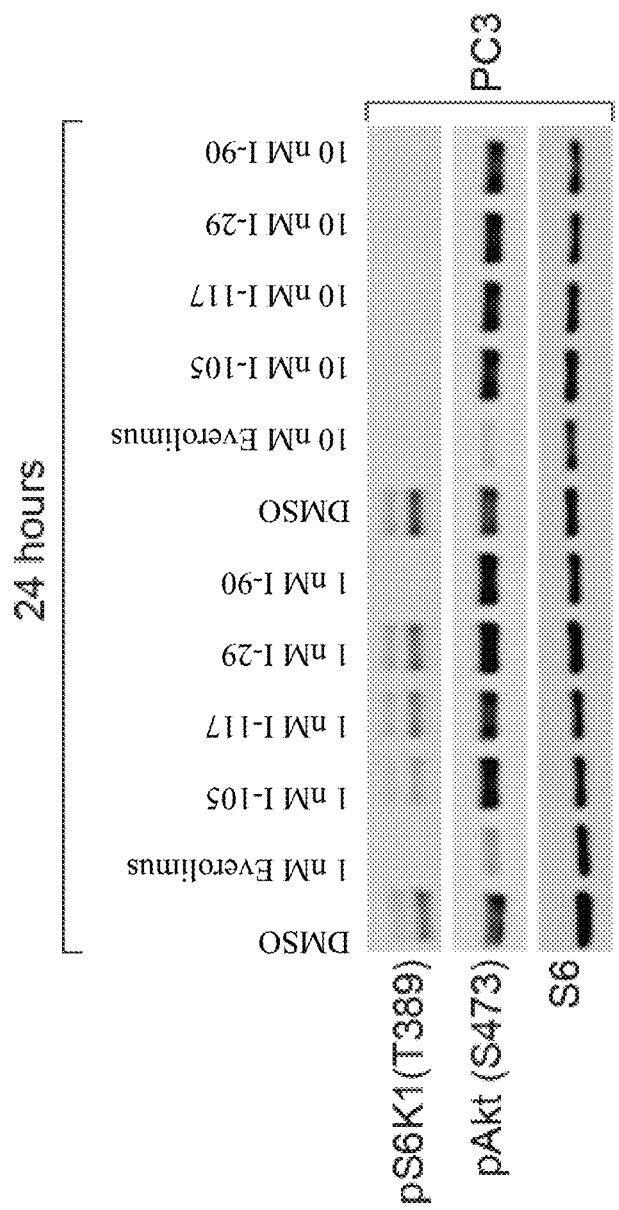

FIG. 32 shows a Western blot performed after treating wild-type MEF cells with everolimus or compounds of the present invention (I-105, I-117, I-29, and I-90) for 24 hours. Staining indicates strong inhibition of the mTORC1 pathway for each compound tested. Significantly, the compounds of the present invention do not inhibit mTORC2, as demonstrated by the lack of Akt phosphorylation inhibition.

Figure 33:
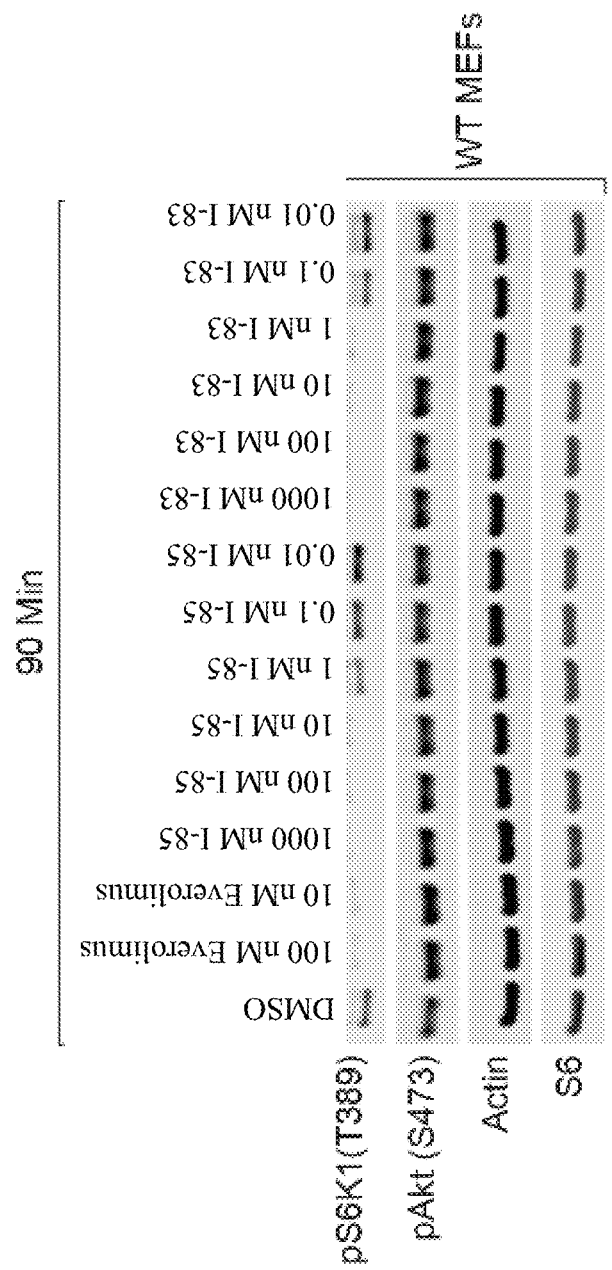

FIG. 33 shows a Western blot performed after treating wild-type MEF cells with everolimus or compounds of the present invention (I-85 and I-83) for 90 minutes. Staining indicates strong inhibition of the mTORC1 pathway for each compound tested. Significantly, the compounds of the present invention do not inhibit mTORC2, as demonstrated by the lack of Akt phosphorylation inhibition.

Figure 34:
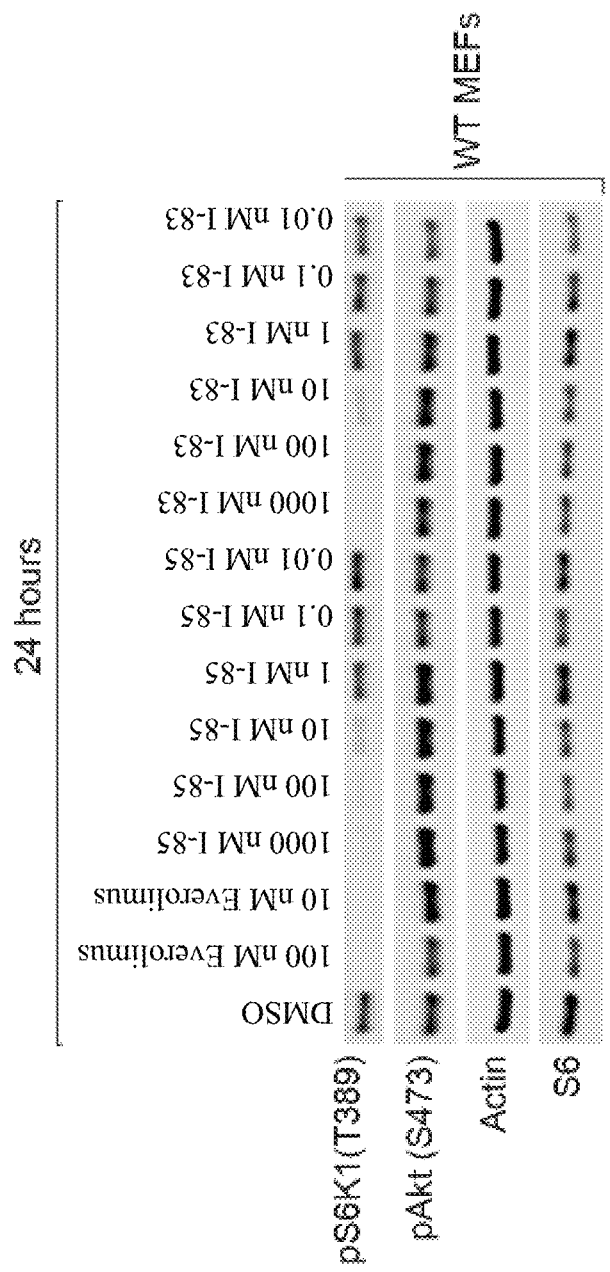

FIG. 34 shows a Western blot performed after treating wild-type MEF cells with everolimus or compounds of the present invention (I-85 and I-83) for 24 hours. Staining indicates strong inhibition of the mTORC1 pathway for each compound tested. Significantly, the compounds of the present invention do not inhibit mTORC2, as demonstrated by the lack of Akt phosphorylation inhibition.

Figure 35:
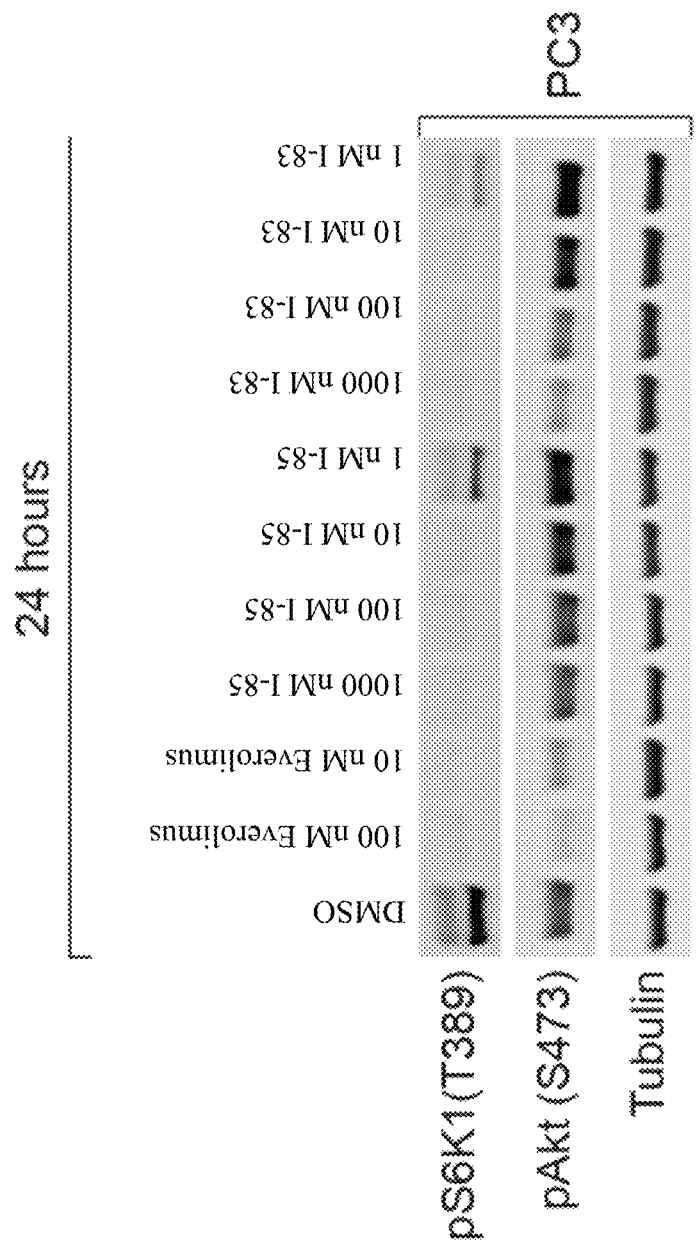

FIG. 35 shows a Western blot performed after treating PC3 cells with everolimus or compounds of the present invention (I-85 and I-83) for 24 hours. Staining indicates strong inhibition of the mTORC1 pathway for each compound tested.

Figure 36:
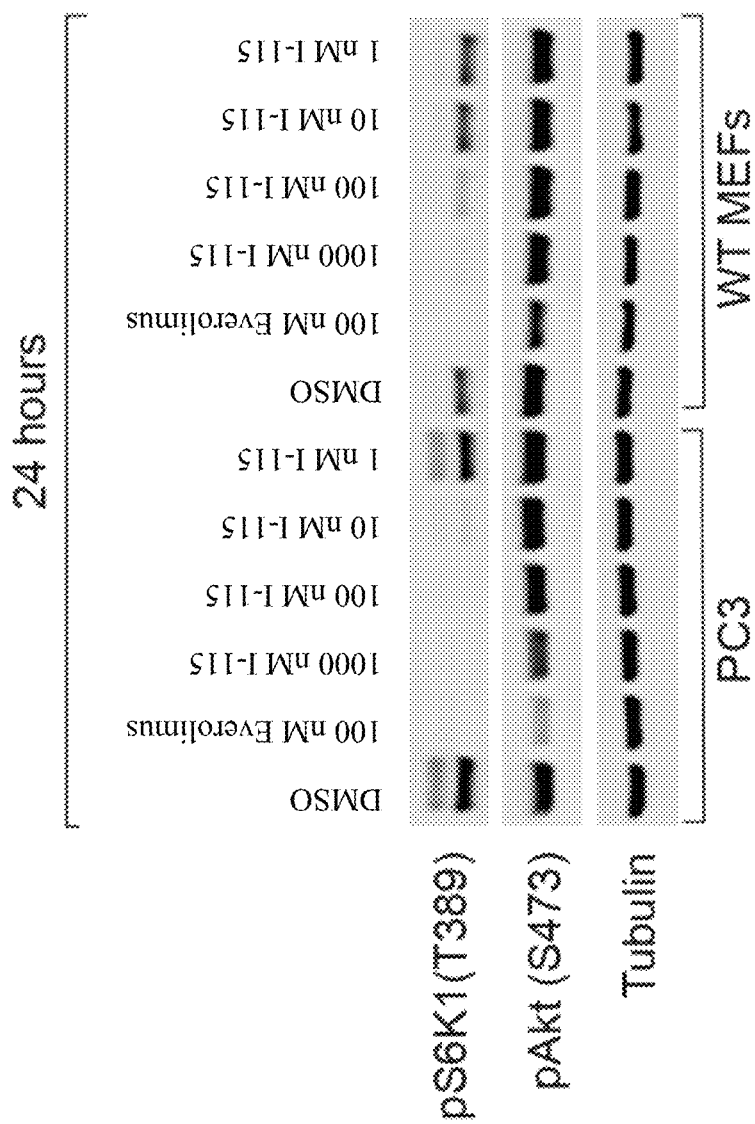

FIG. 36 shows a Western blot performed after treating PC3 cells and wild-type MEF cells with everolimus or a compound of the present invention (I-115) for 24 hours. Staining indicates strong inhibition of the mTORC1 pathway for each compound tested in the PC3 cells, strong inhibition of the mTORC1 pathway for everolimus in WT MEF cells, and moderate concentration dependent inhibition of the mTORC1 pathway for I-115 in WT MEF cells. Significantly, the compound of the present invention does not inhibit mTORC2, as demonstrated by the lack of Akt phosphorylation inhibition.

Figure 37:
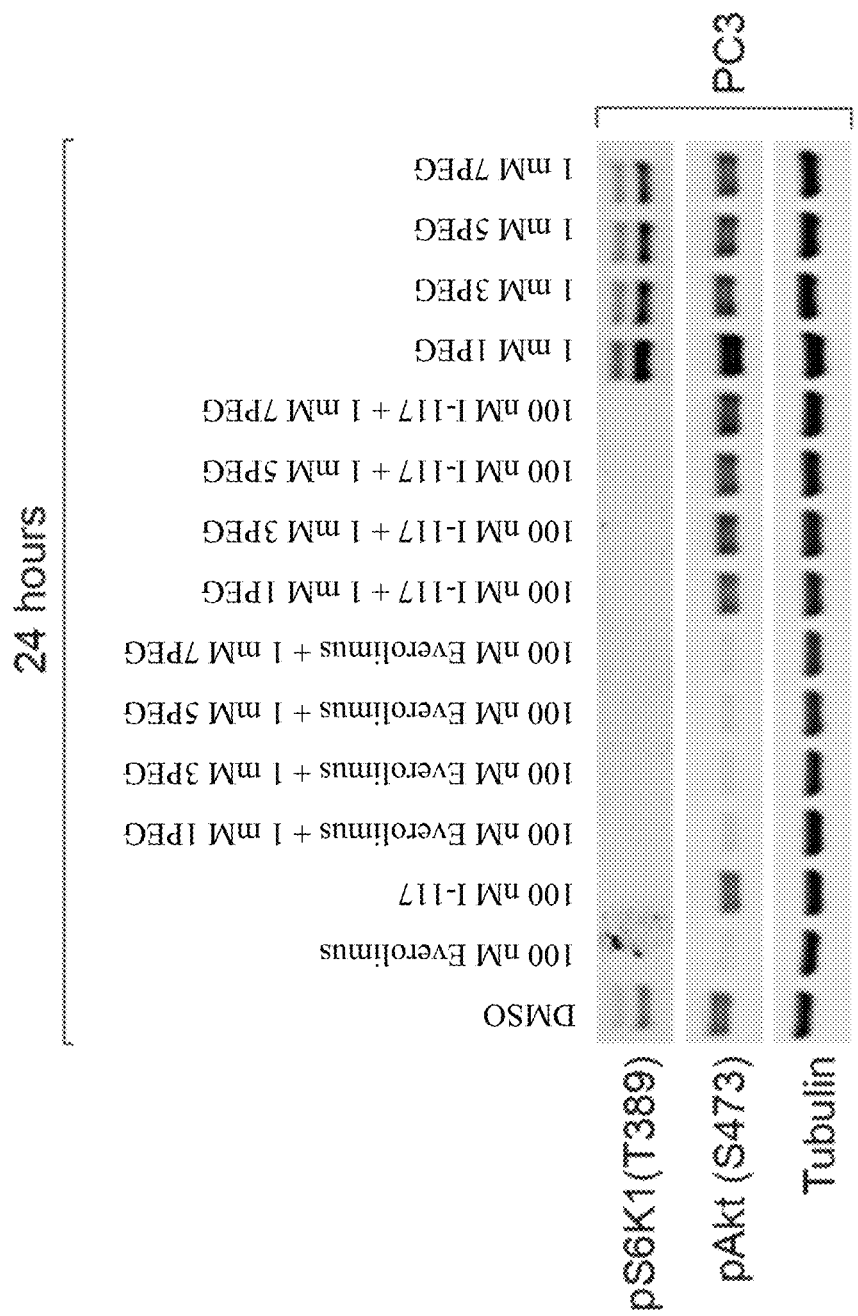

FIG. 37 shows a Western blot performed after treating PC3 cells with everolimus, a compound of the present invention (I-117), short PEGs, everolimus in combination with a short PEG, or I-117 in combination with a short PEG, for 24 hours. Staining indicates strong inhibition of the mTORC1 pathway for everolimus and I-117, alone and in combination with a short PEG. The short PEGs did not alone show inhibition of mTORC1 or mTORC2. Significantly, the compound of the present invention does not inhibit mTORC2, either alone or in combination with a short PEG, as demonstrated by the lack of Akt phosphorylation inhibition.

Figure 38:
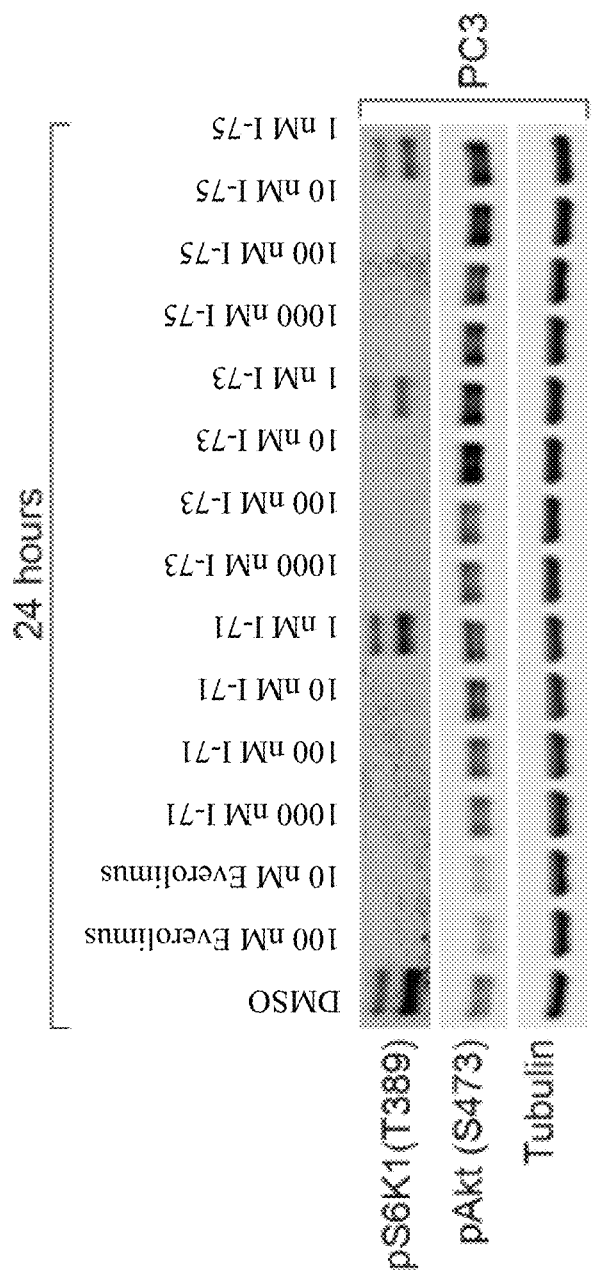

FIG. 38 shows a Western blot performed after treating PC3 cells with everolimus or compounds of the present invention (I-71, I-73 and I-75) for 24 hours. Staining indicates strong inhibition of the mTORC1 pathway for all compounds tested. Significantly, the compounds of the present invention do not inhibit mTORC2, as demonstrated by the lack of Akt phosphorylation inhibition.

Figure 39:
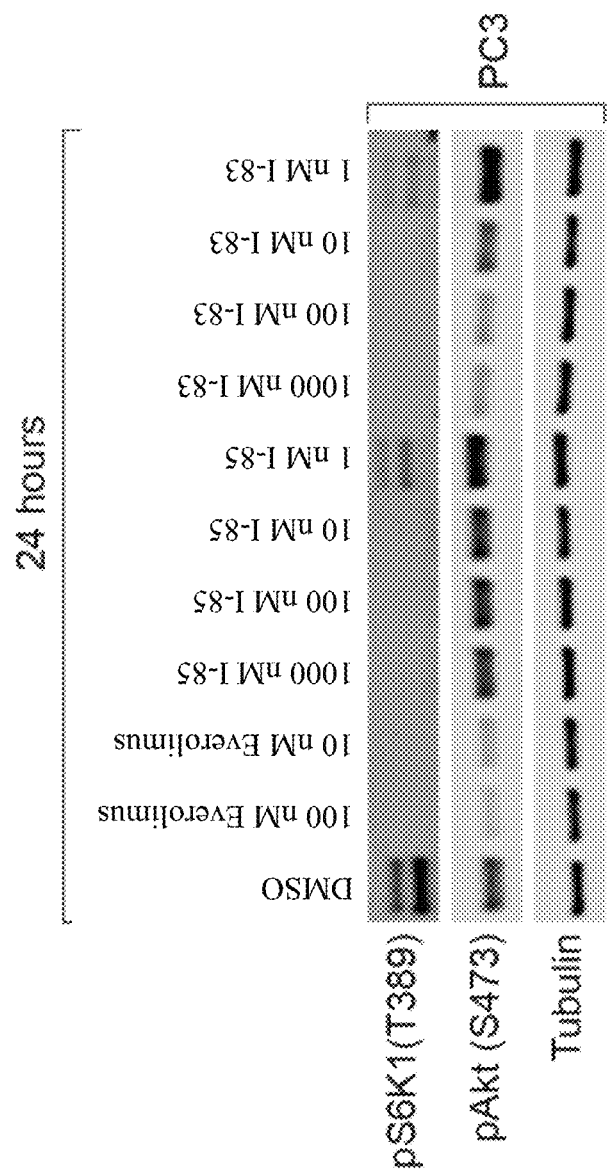

FIG. 39 shows a Western blot performed after treating PC3 cells with everolimus or compounds of the present invention (I-85 and I-83) for 24 hours. Staining indicates strong inhibition of the mTORC1 pathway for all compounds tested. Significantly, the compounds of the present invention do not inhibit mTORC2, as demonstrated by the lack of Akt phosphorylation inhibition.

Figure 40:
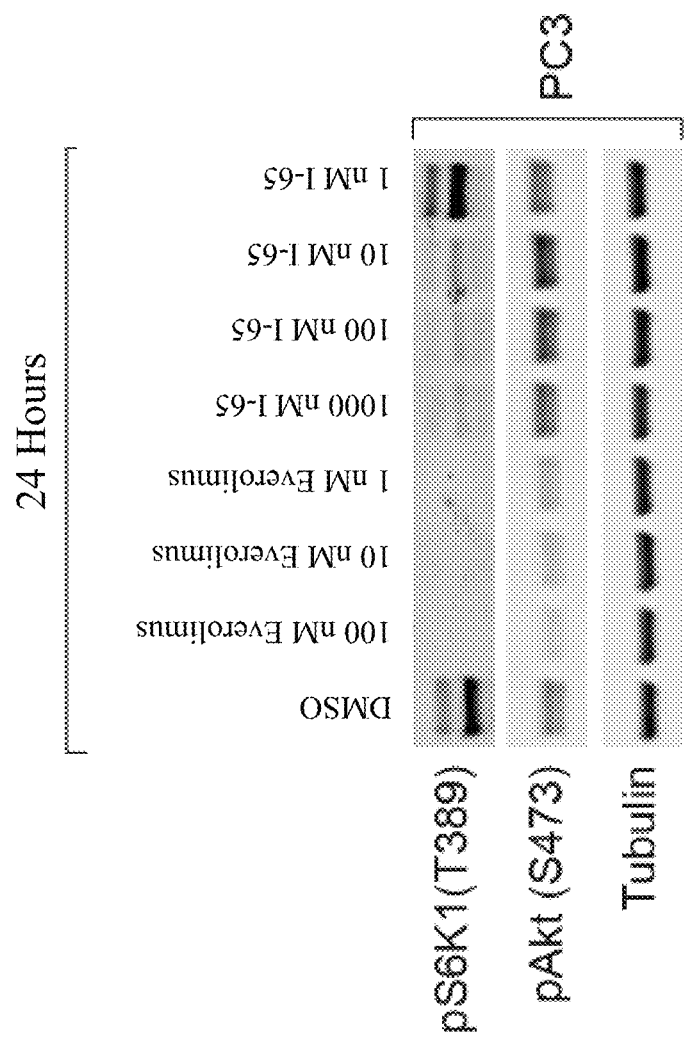

FIG. 40 shows a Western blot performed after treating PC3 cells with everolimus or a compounds of the present invention (I-65) for 24 hours. Staining indicates strong inhibition of the mTORC1 pathway for both compounds tested. Significantly, the compound of the present invention does not inhibit mTORC2, as demonstrated by the lack of Akt phosphorylation inhibition.

Figure 41:
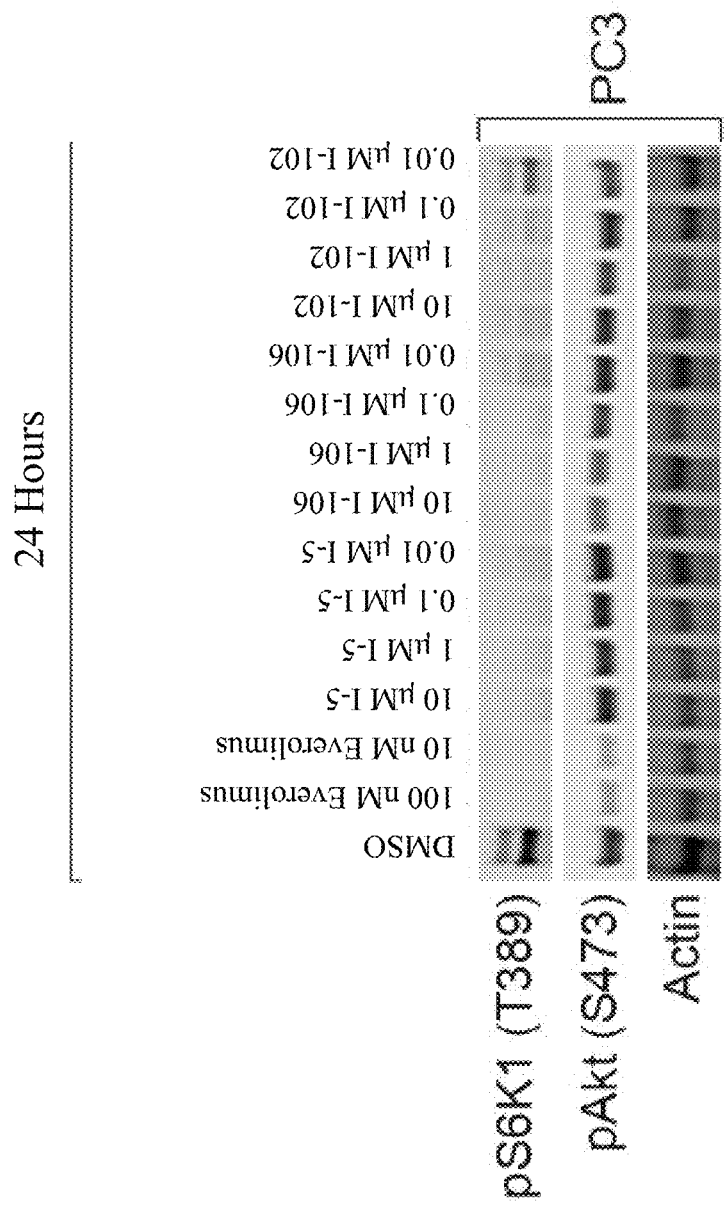

FIG. 41 shows a Western blot performed after treating PC3 cells with everolimus or compounds of the present invention (I-5, I-106 and I-102) for 24 hours. Staining indicates strong inhibition of the mTORC1 pathway for all compounds tested. Significantly, the compounds of the present invention do not inhibit mTORC2, as demonstrated by the lack of Akt phosphorylation inhibition.

Figure 42:
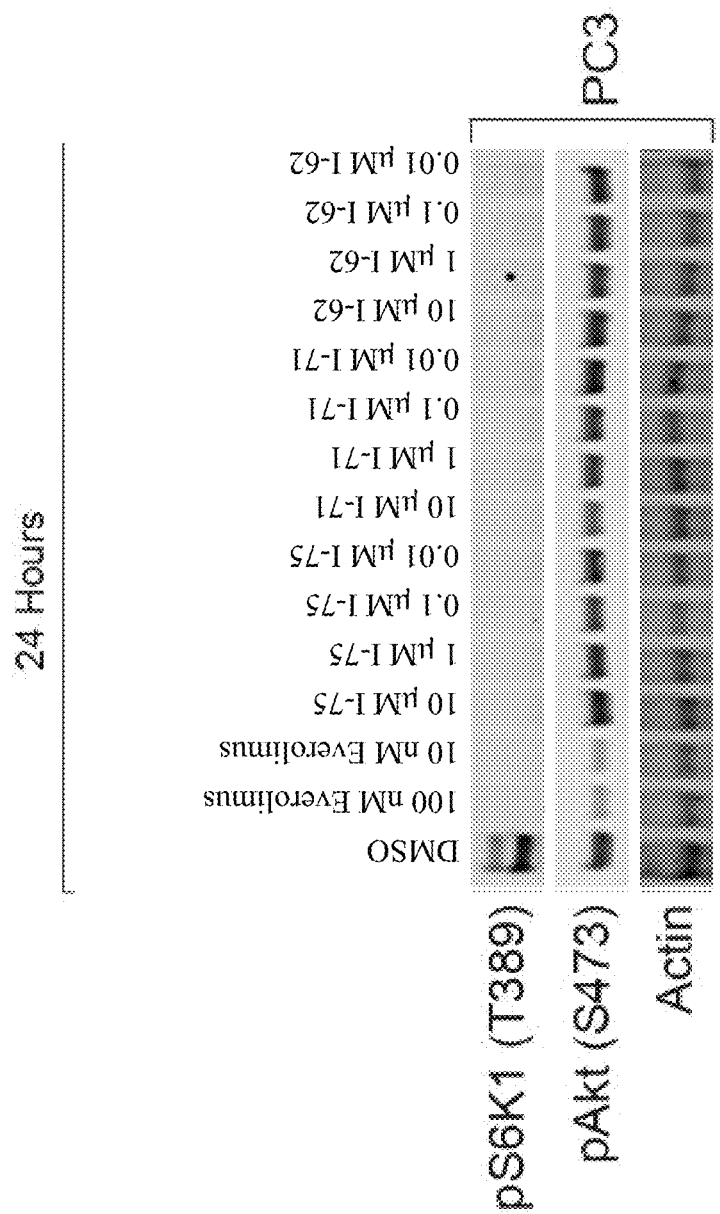

FIG. 42 shows a Western blot performed after treating PC3 cells with everolimus or compounds of the present invention (I-75, I-71 and I-62) for 24 hours. Staining indicates strong inhibition of the mTORC1 pathway for all compounds tested. Significantly, the compounds of the present invention do not inhibit mTORC2, as demonstrated by the lack of Akt phosphorylation inhibition.

Figure 43:
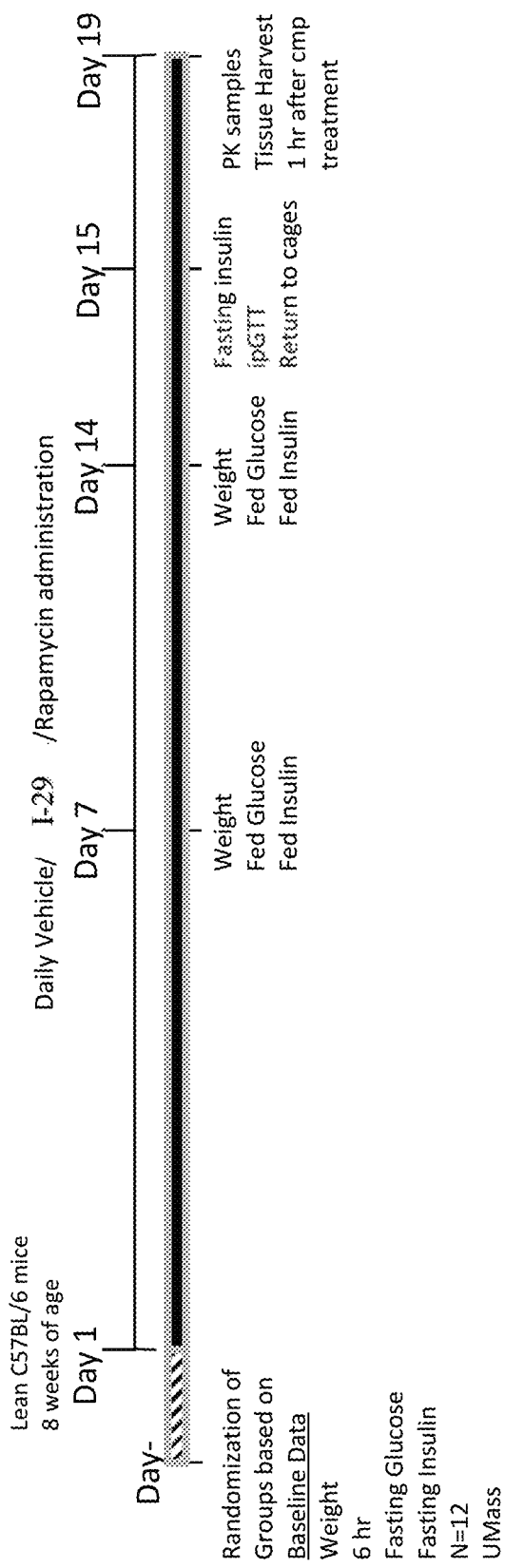

FIG. 43 shows the time course for a glucose tolerance and insulin sensitivity test in lean C57B1/6 mice.

Figure 44:
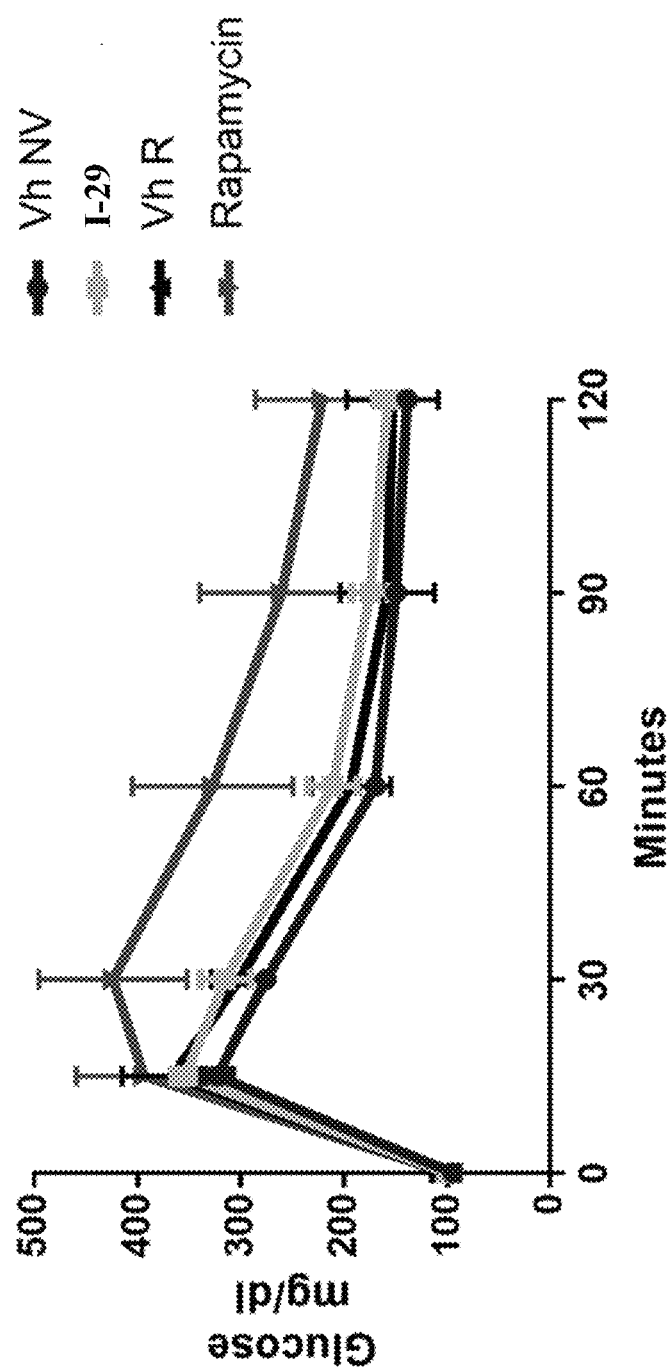

FIG. 44 shows the results of an intraperitoneal glucose tolerance test in lean C57B1/6 mice during chronic treatment with rapamycin, I-29 or vehicle. *P<0.001; **P<0.0001; one-ANOVA and all bars indicate mean and SD.

Figure 45:
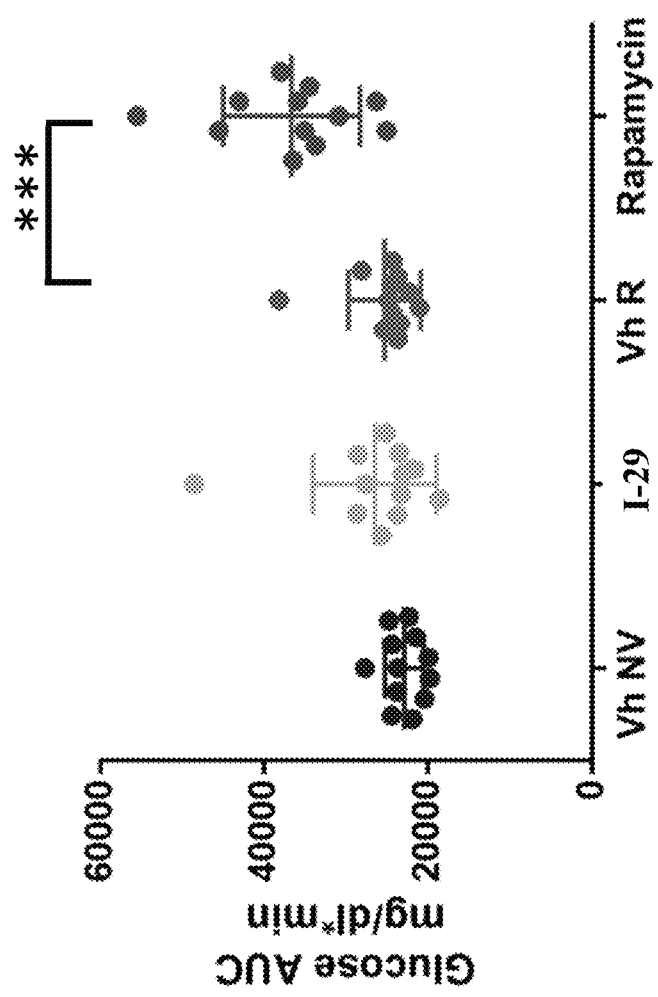

FIG. 45 shows the area under the curve (AUC) for glucose clearance in lean C57B1/6 mice during chronic treatment with rapamycin, I-29 or vehicle. ***P<0.001; T-test and all bars indicate mean and SD.

Figure 46:
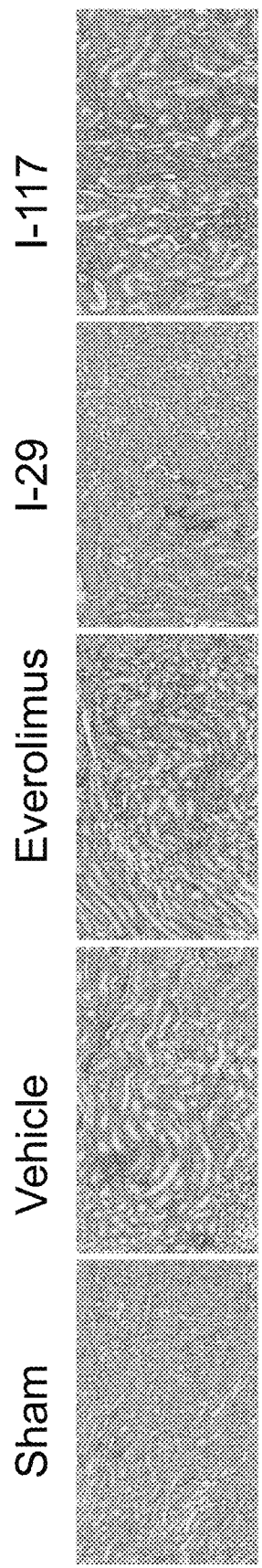

FIG. 46 shows Sirius red staining of kidney tissue from an AKI/CKD mouse model.

Figure 47:
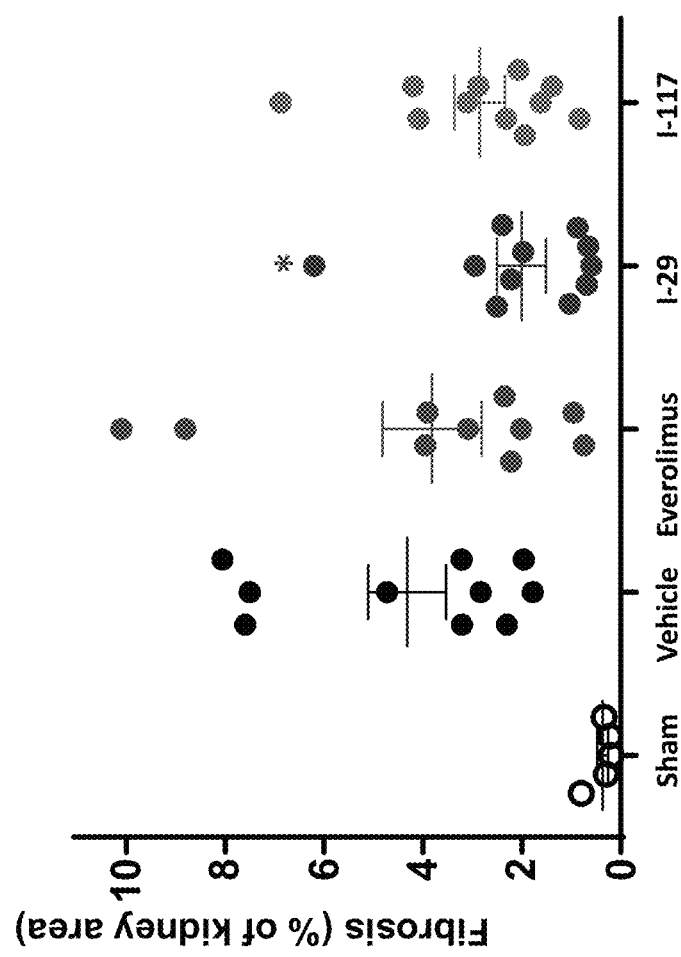

FIG. 47 shows the percent area of kidney tissue fibrosis in an AKI/CKD mouse model following treatment with everolimus, I-29, I-117, or vehicle. *P=0.02 compared with vehicle, t-test.

Figure 48:
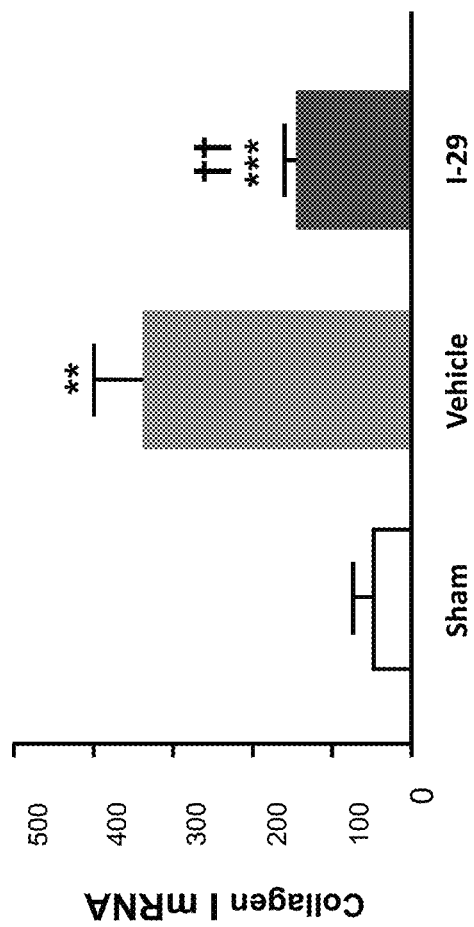

FIG. 48 shows the collagen I mRNA expression in an AKI/CKD mouse model following treatment with vehicle or I-29. P<0.01, *P<0.001 vs. sham; ††P<0.01 vs. vehicle.

Figure 49:
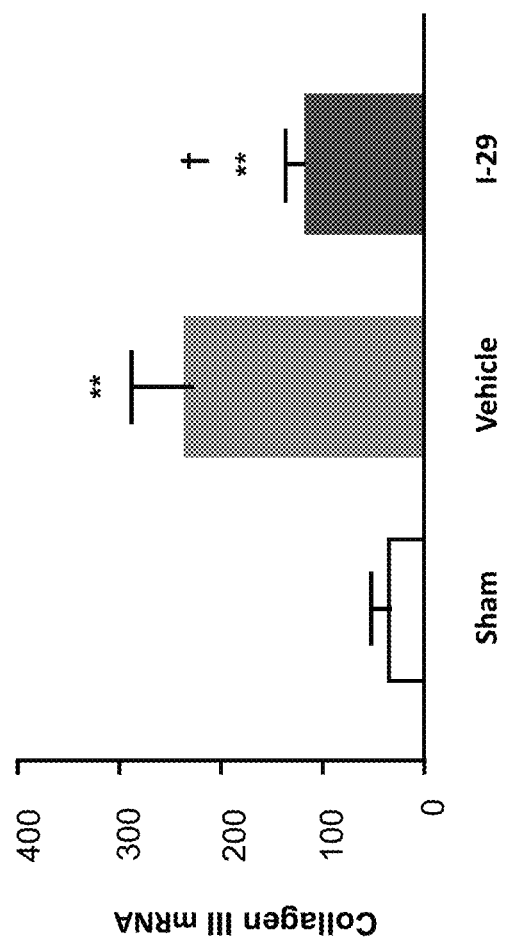

FIG. 49 shows the collagen III mRNA expression in an AKI/CKD mouse model following treatment with vehicle or I-29. **P<0.01 vs. sham; †P<0.05 vs. vehicle.

Figure 50:
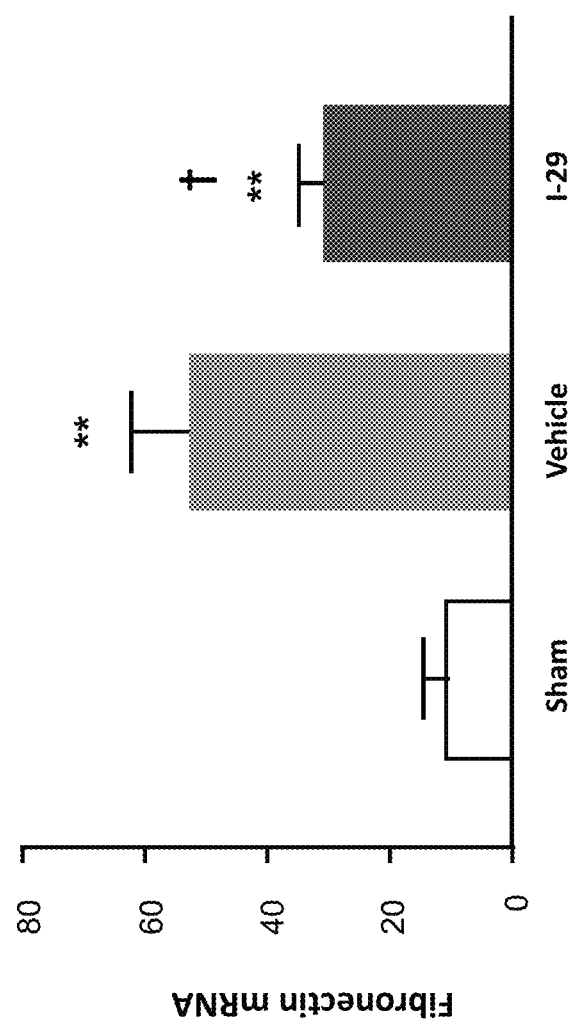

FIG. 50 shows the fibronectin mRNA expression in an AKI/CKD mouse model following treatment with vehicle or I-29. **P<0.01 vs. sham; †P<0.05 vs. vehicle.

Figure 51:
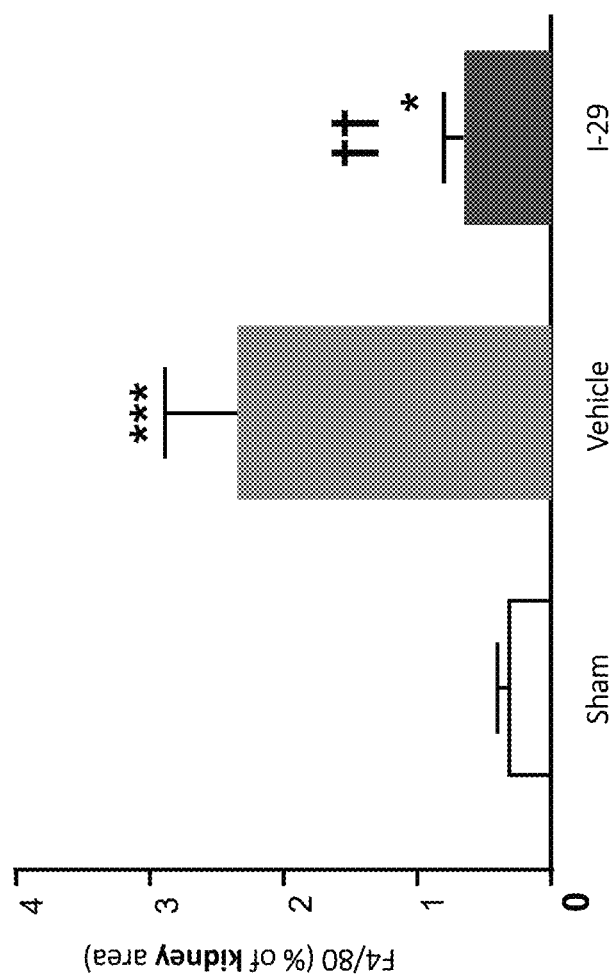

FIG. 51 shows the area of kidney tissue infiltrated by macrophages in an AKI/CKD mouse model following treatment with vehicle or I-29. *P<0.05, ***P<0.001 vs. sham; ††P<0.05 vs. vehicle.

Figure 52:
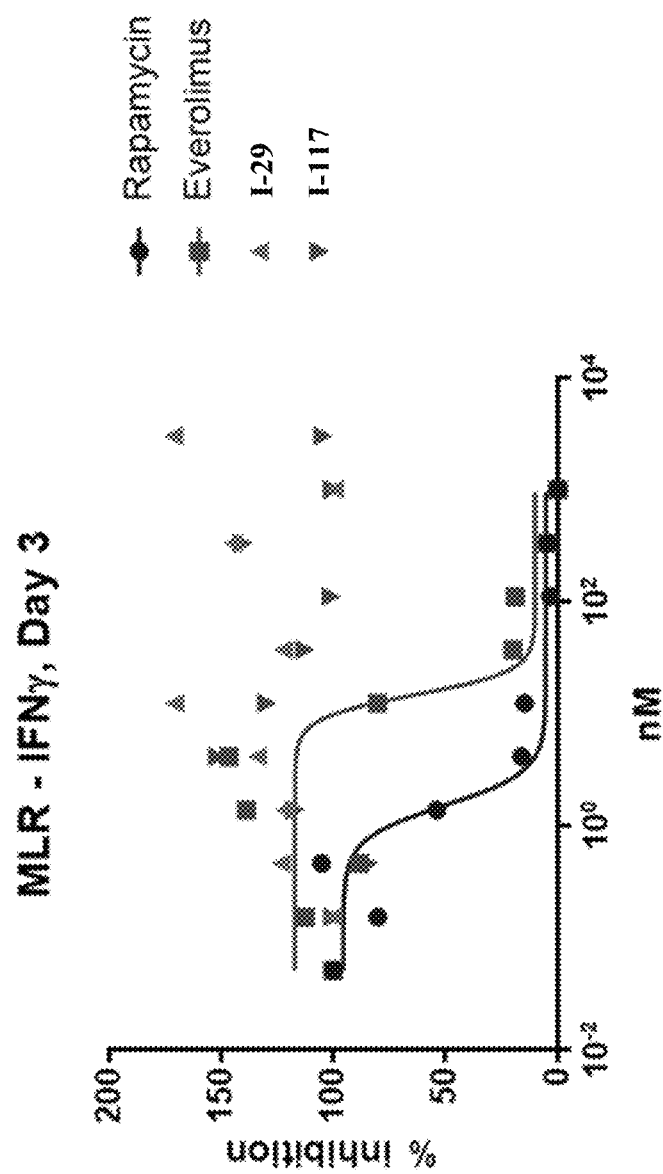

FIG. 52 shows the percent inhibition of IFN-γ production in an allogeneic MLR assay following treatment with rapamycin, everolimus, I-29, or I-117.

DETAILED DESCRIPTION OF CERTAIN EMBODIMENTS

1. General Description of Certain Embodiments of the Invention:

In certain embodiments, the present invention provides a compound of Formula I:

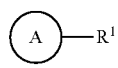

or a pharmaceutically acceptable salt thereof, wherein:

Ring A is a monovalent derivative of rapamycin or an analog a rapalog) thereof;

wherein $R^1$ is attached thereto at the C-7 hydroxyl position of the rapamycin, or analog thereof;

$R^1$ is an optionally substituted straight or branched saturated or unsaturated monovalent $C_{3-30}$ hydrocarbon chain wherein one or more methylene units of $R^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or —P(O)(R)$_2$, or a 6-18 membered saturated or partially unsaturated heterocyclic ring having 1-6 heteroatoms independently selected from nitrogen, oxygen, or sulfur; or $R^1$ is selected from Formula P-0:

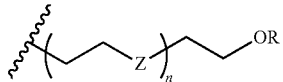
P-0 wherein:

⌇ indicates the attachment point to Ring A;

each Z is independently —O—, —S—, —NR—, or —SO$_2$—;

n is from about 2 to about 300; and each R is independently hydrogen or an optionally substituted $C_{1-6}$ aliphatic group.

In some embodiments, the present invention provides a compound of Formula I other than those selected from:

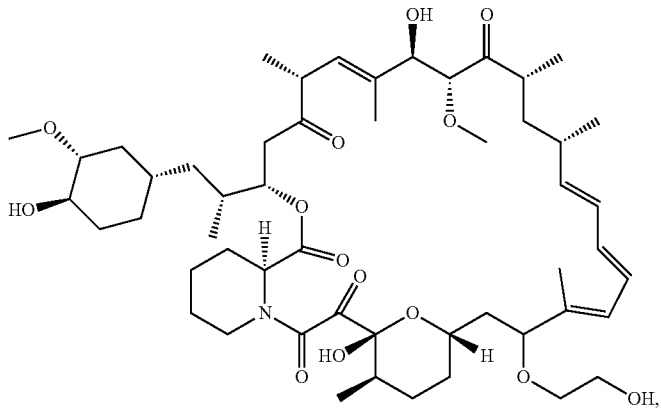

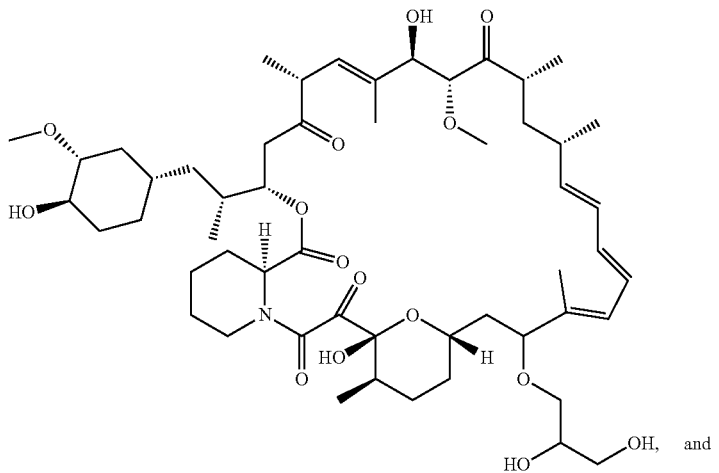
and

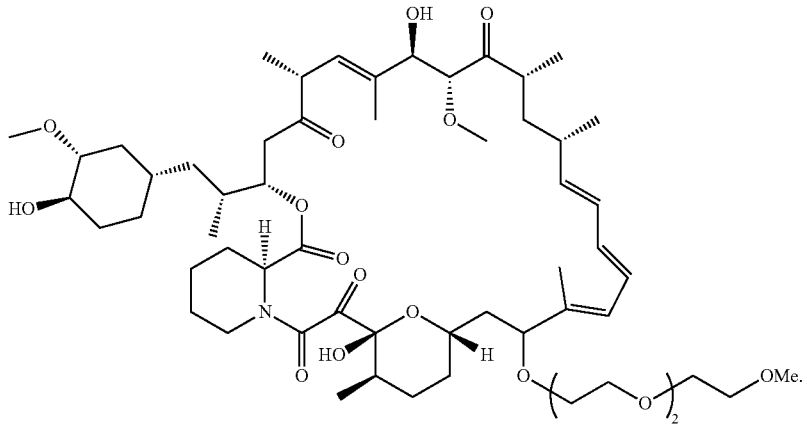

2. Compounds and Definitions:

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroaryl" used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5-to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; $-CH=CHPh$, which may be substituted with $R°$; $-(CH_2)_{0-4}O(CH_2)_{0-1}$-pyridyl which may be substituted with $R°$; $-NO_2$; $-CN$; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(CH_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-SC(S)SR°$, $-(CH_2)_{0-4}OC(O)NR°_2$; $-C(O)N(OR°)R°$; $-C(O)C(O)R°$; $-C(O)CH_2C(O)R°$; $-C(NOR°)R°$; $-(CH_2)_{0-4}SSR°$, $-(CH_2)_{0-4}S(O)_2R°$; $-(CH_2)_{0-4}S(O)_2OR°$; $-(CH_2)_{0-4}OS(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched)alkylene)$O-N(R°)_2$; or $-(C_{1-4}$ straight or branched alkylene)$C(O)O-N(R°)_2$, wherein each $R°$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R°$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R°$ (or the ring formed by taking two independent occurrences of $R°$ together with their intervening atoms), are independently halogen, $-(CH_2)_{0-2}R^\bullet$, $-haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R°$ include $=O$ and $=S$.

Suitable divalent substituents on a saturated carbon atom of an "optionally substituted" group include the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^1$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each Rt is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —R•, —(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The terms "measurable affinity" and "measurably inhibit," as used herein, means a measurable change in mTORC1 activity between a sample comprising a compound of the present invention, or composition thereof, and mTORC1, and an equivalent sample comprising mTORC1 in the absence of said compound, or composition thereof.

3. Description of Exemplary Embodiments:

As described above, in certain embodiments, the present invention provides a compound of Formula I:

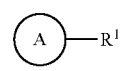

I or a pharmaceutically acceptable salt thereof, wherein:

Ring A is a monovalent derivative of rapamycin or an analog (i.e., a rapalog) thereof wherein R$^1$ is attached thereto at the C-7 hydroxyl position of the rapamycin, or analog thereof; and R$^1$ is an optionally substituted straight or branched saturated or unsaturated monovalent C$_{3-30}$ hydrocarbon chain wherein one or more methylene units of R$^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or —P(O)(R)$_2$; or a 6-18 membered saturated or partially unsaturated heterocyclic ring having 1-6 heteroatoms independently selected from nitrogen, oxygen, or sulfur; or R$^1$ is selected from Formula P-0:

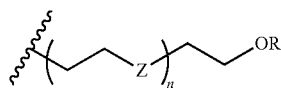

P-0 wherein:

⸺ indicates the attachment point to Ring A;

each Z is independently —O—, —S—, —NR—, or —SO$_2$—;

n is from about 2 to about 300; and each R is independently hydrogen or an optionally substituted C$_{1-6}$ aliphatic group.

It will be appreciated that the term "rapamycin", and structures thereof, recited throughout the specification is intended to encompass rapamycin and analogs thereof.

For the purpose of clarity, provided Formula II is reproduced below with the R$^1$ moiety depicted attached at the C-7 hydroxyl position. Accordingly, the present invention provides a compound of Formula II:

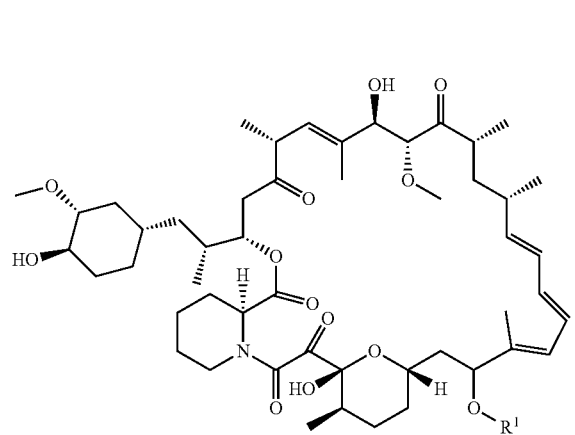

II or a pharmaceutically acceptable salt thereof, wherein:
$R^1$ is an optionally substituted straight or branched saturated or unsaturated monovalent $C_{3-30}$ hydrocarbon chain wherein one or more methylene units of $R^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, —S(O)$_2$—, or —P(O)(R)$_2$; or a 6-18 membered saturated or partially unsaturated heterocyclic ring having 1-6 heteroatoms independently selected from nitrogen, oxygen, or sulfur; or
$R^1$ is selected from Formula P-0:

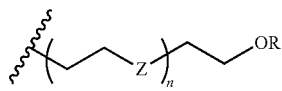

P-0 wherein:
⸾ indicates the attachment point to the C-7 hydroxyl position;
each Z is independently —O—, —S—, —NR—, or —SO$_2$—;
n is from about 2 to about 300; and
each R is independently hydrogen or an optionally substituted $C_{1-6}$ aliphatic group.
In some embodiments, the present invention provides a compound of Formula II-a or II-b:

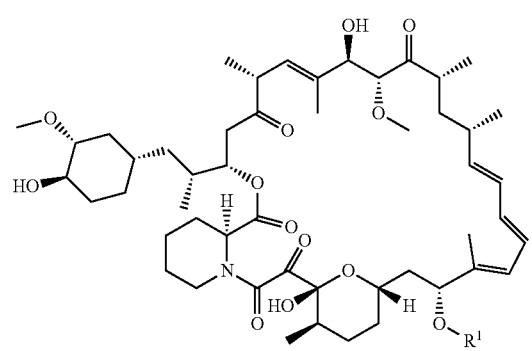

II-a

, or

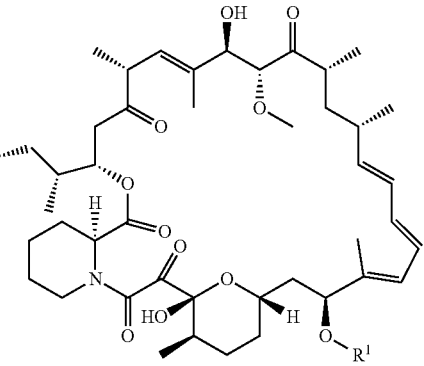

II-b

, or a pharmaceutically acceptable salt thereof, wherein each of $R^1$ is as defined above and described herein in classes and subclasses.

It will be appreciated that the term "rapamycin", and structure thereof, recited throught the specification is intended to encompass rapamycin and analogs thereof. Accordingly, in certain embodiments Ring A is Rapamycin. In some embodiments, Ring A is Everolimus. In some Embodiments, Ring A is Temsirolimus. In some embodiments, Ring A is Ridaforolimus. In some embodiments, Ring A is Umirolimus.

The above recited analogs of rapamycin (i.e., rapalogs) are for exemplification and not intended to limit the current invention.

As defined above, $R^1$ is an optionally substituted straight or branched saturated or unsaturated monovalent $C_{3-30}$ hydrocarbon chain wherein one or more methylene units of $R^1$ are optionally and independently replaced by —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)—, or —S(O)$_2$—, or a 6-18 saturated or partially unsaturated heterocyclic ring having 1-6 heteroatoms independently selected from nitrogen, oxygen, or sulfur.

In certain embodiments, $R^1$ is an optionally substituted straight or branched saturated or unsaturated monovalent $C_{3-30}$ hydrocarbon chain wherein one or more methylene units of $R^1$ are optionally and independently replaced by —N(R)—, —N(R)C(O)—, —C(O)N(R)—, -N(R)S(O)$_2$—, —S(O)$_2$N(R)—, —O—, —C(O)—, —OC(O)—, —C(O)O—, —S—, —S(O)—, —S(O)$_2$—, or —P(O)(R)$_2$. In some embodiments, $R^1$ is an optionally substituted branched saturated monovalent hydrocarbon chain wherein one or more methylene units of $R^1$ are optionally and independently replaced by —N(R)—, —N(R)C(O)—, —C(O)N(R) -N(R)S(O)$_2$—, —S(O)$_2$N(R) —O—, —C(O)—, —OC(O)—, —C(O)O—, —S—, —S(O)—, —S(O)$_2$—, or —P(O)(R)$_2$. In some embodiments, $R^1$ is an optionally substituted straight unsaturated monovalent hydrocarbon chain wherein one or more methylene units of $R^1$ are optionally and independently replaced by -N(R) —N(R)C(O)—, —C(O)N(R)—, —N(R)S(O)$_2$—, —S(O)$_2$N(R) —O—, —C(O)—, —OC(O)—, —C(O)O—S—, —S(O)—, —S(O)$_2$—, or —P(O)(R)$_2$. In some embodiments, $R^1$ is an optionally substituted branched unsaturated monovalent hydrocarbon chain wherein one or more methylene units of $R^1$ are optionally and independently replaced by —N(R)—, —N(R)C(O)—, —C(O)N(R)—, —N(R)S(O)$_2$—, —S(O)$_2$N(R) —O—, —C(O)—, —OC(O)—, —C(O)O—, —S—, —S(O)—, —S(O)$_2$—, or —P(O)(R)$_2$. In some embodiments, R$^1$ is an optionally substituted straight saturated monovalent hydrocarbon chain wherein one or more methylene units of R$^1$ are optionally and independently replaced by —O—.

In some embodiments, R$^1$ is

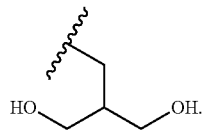

In some embodiments, R$^1$ is

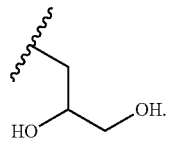 [SMILES: *CC(O)CO]

In some embodiments, R$^1$ is

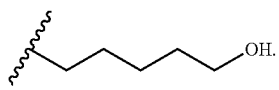 [SMILES: *CCCCCO]

In some embodiments, R$^1$ is

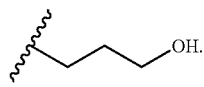

In some embodiments, R$^1$ is

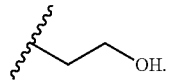 [SMILES: *CCO]

In some embodiments, R$^1$ is

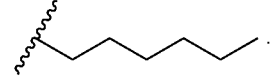 [SMILES: *CCCCCC]

In some embodiments, R$^1$ is

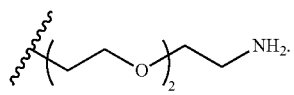

In some embodiments, R$^1$ is

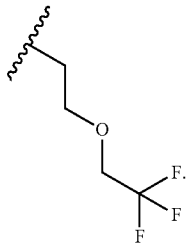 [SMILES: *CCOCC(F)(F)F]

In some embodiments, R$^1$ is

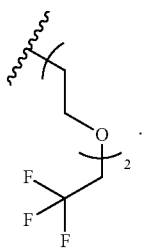

In some embodiments, R$^1$ is

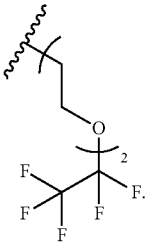

In some embodiments, R$^1$ is

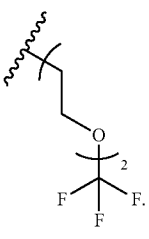

In some embodiments, R$^1$ is

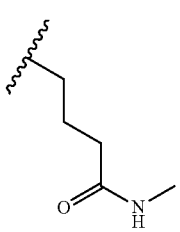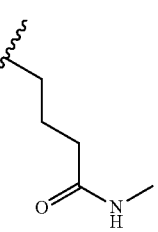

In some embodiments, $R^1$ is
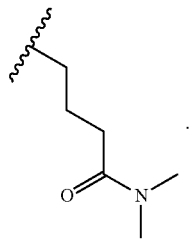 [SMILES: *CCCC(=O)N(C)C]
In some embodiments, $R^1$ is
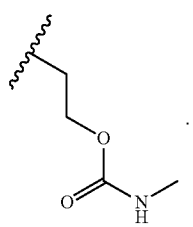 [SMILES: *CCOC(=O)NC]
In some embodiments, $R^1$ is
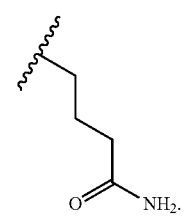 [SMILES: *CCCC(N)=O]
In some embodiments, $R^1$ is
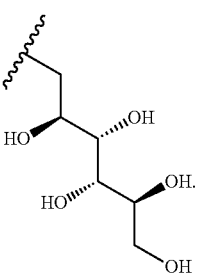 [SMILES: *C[C@H](O)[C@H](O)[C@@H](O)[C@@H](O)CO]
In some embodiments, $R^1$ is
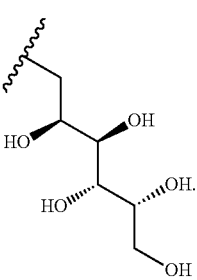 [SMILES: *C[C@H](O)[C@@H](O)[C@@H](O)[C@H](O)CO]
In some embodiments, $R^1$ is
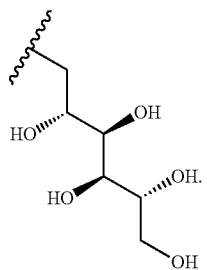 [SMILES: *C[C@@H](O)[C@@H](O)[C@H](O)[C@H](O)CO]
In some embodiments, $R^1$ is
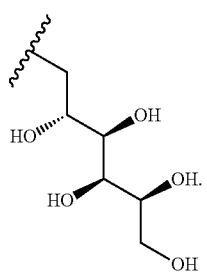 [SMILES: *C[C@@H](O)[C@@H](O)[C@H](O)[C@@H](O)CO]
In some embodiments, $R^1$ is
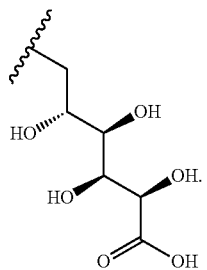 [SMILES: *C[C@@H](O)[C@@H](O)[C@H](O)[C@@H](O)C(=O)O]
In some embodiments, $R^1$ is
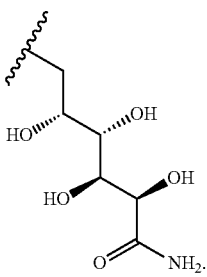 [SMILES: *C[C@@H](O)[C@H](O)[C@H](O)[C@@H](O)C(N)=O]
In some embodiments, $R^1$ is
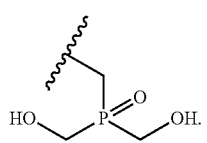

In some embodiments, $R^1$ is of Formula P-0:

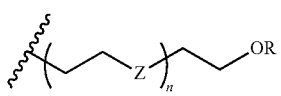

wherein:

⌇ indicates the attachment point to Ring A;

each Z is independently —O—, —S—, —NR—, or —SO$_2$—;

n is from about 2 to about 300; and each R is independently hydrogen, or an optionally substituted $C_{1-6}$ aliphatic group.

In some embodiemnts, n is from about 2 to about 10; from about 10 to about 20; from about 20 to about 30; from about 30 to about 40; from about 40 to about 50; from about 50 to about 60; from about 60 to about 70; from about 70 to about 80; from about 80 to about 90; from about 90 to about 100; from about 110 to about 120; from about 120 to about 130; from about 140 to about 150; from about 150 to about 160; from about 170 to about 180; from about 180 to about 190; from about 190 to about 200; from 200 to about 210; from about 210 to about 220; from about 220 to about 230; from about 230 to about 240; from about 240 to about 250; from about 250 to about 260; from about 260 to about 270; from about 270 to about 280; from about 280 to about 290; or from about 290 to about 300.

In some embodiments $R^1$ is

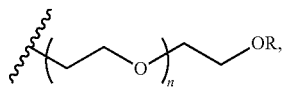

wherein n and R are as described herein.

In some embodiments $R^1$ is

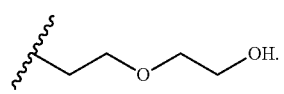 [SMILES: *CCOCCO]

In some embodiments $R^1$ is

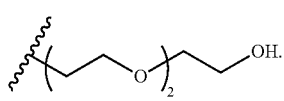

In some embodiments $R^1$ is

In some embodiments $R^1$ is

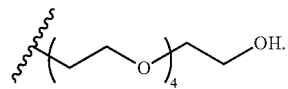

In some embodiments $R^1$ is

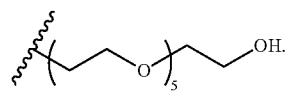

In some embodiments $R^1$ is

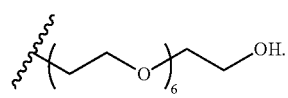

In some embodiments $R^1$ is

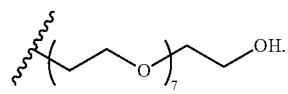

In some embodiments $R^1$ is

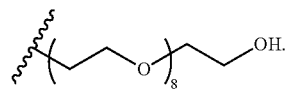

In some embodiments $R^1$ is

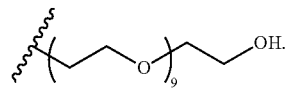

In some embodiments $R^1$ is

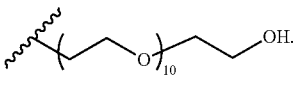

In some embodiments $R^1$ is

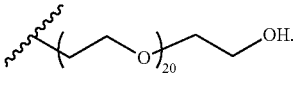

In some embodiments $R^1$ is

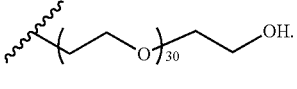

In some embodiments R¹ is

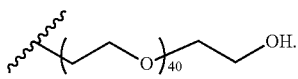

In some embodiments R¹ is

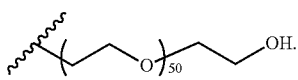

In some embodiments R¹ is

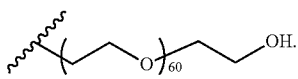

In some embodiments R¹ is

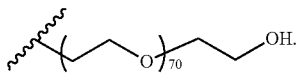

In some embodiments R¹ is

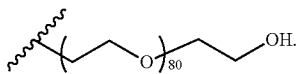

In some embodiments R¹ is

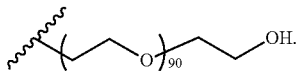

In some embodiments R¹ is

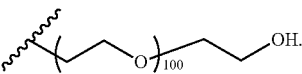

In some embodiments R¹ is

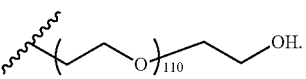

In some embodiments R¹ is

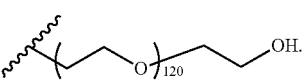

In some embodiments R¹ is

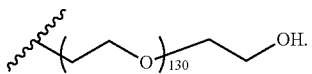

In some embodiments R¹ is

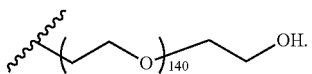

In some embodiments R¹ is

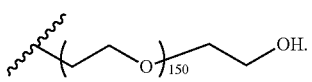

In some embodiments R¹ is

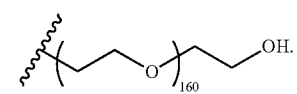

In some embodiments R¹ is

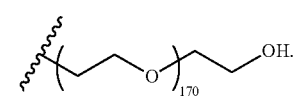

In some embodiments R¹ is

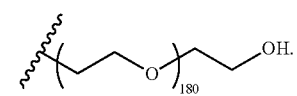

In some embodiments R¹ is

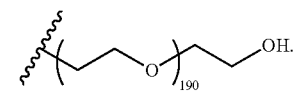

In some embodiments R¹ is

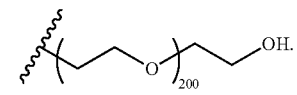

In some embodiments R¹ is

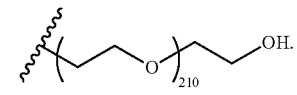

In some embodiments R¹ is

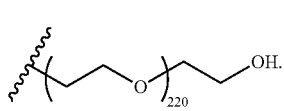

In some embodiments R¹ is

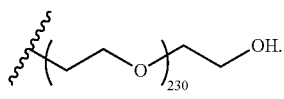

In some embodiments R¹ is

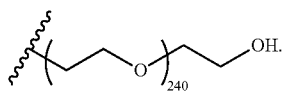

In some embodiments R¹ is

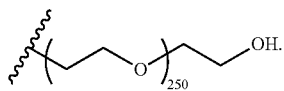

In some embodiments R¹ is

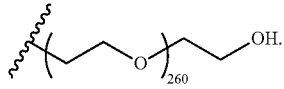

In some embodiments R¹ is

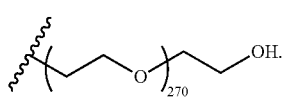

In some embodiments R¹ is

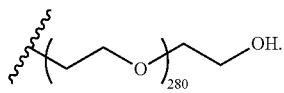

In some embodiments R¹ is

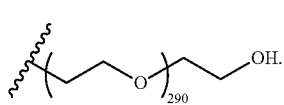

In some embodiments R¹ is

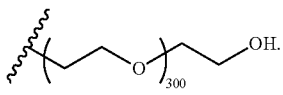

In some embodiments R¹ is

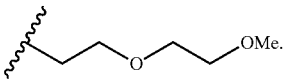 [SMILES: *CCOCCOC]

In some embodiments R¹ is

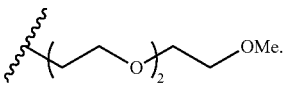

In some embodiments R¹ is

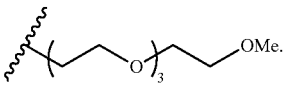

In some embodiments R¹ is

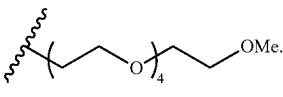

In some embodiments R¹ is

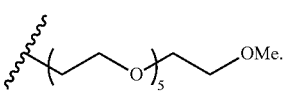

In some embodiments R¹ is

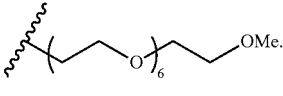

In some embodiments R¹ is

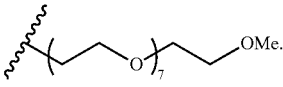

In some embodiments R¹ is

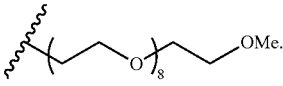

In some embodiments R¹ is


In some embodiments R¹ is


In some embodiments R¹ is

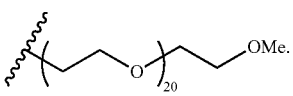

In some embodiments R¹ is

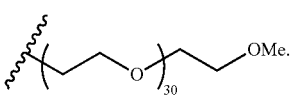

In some embodiments R¹ is

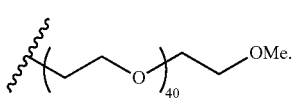

In some embodiments R¹ is

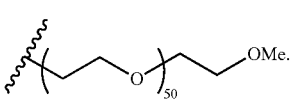

In some embodiments R¹ is

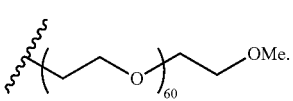

In some embodiments R¹ is

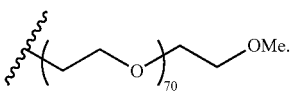

In some embodiments R¹ is

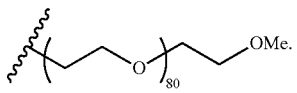

In some embodiments R¹ is

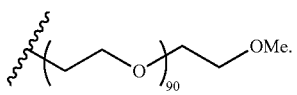

In some embodiments R¹ is

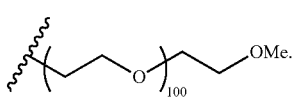

In some embodiments R¹ is

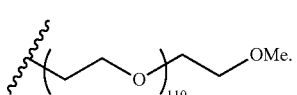

In some embodiments R¹ is

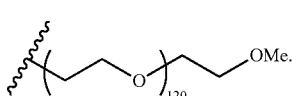

In some embodiments R¹ is

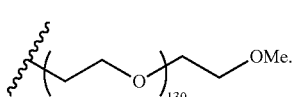

In some embodiments R¹ is

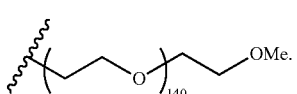

In some embodiments R¹ is

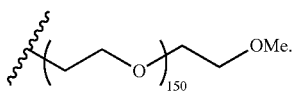

In some embodiments R¹ is

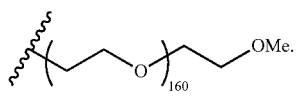

In some embodiments R¹ is

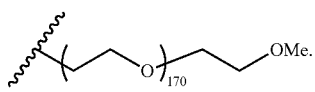

In some embodiments R¹ is

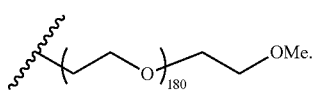

In some embodiments R¹ is

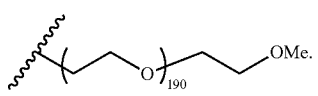

In some embodiments R¹ is

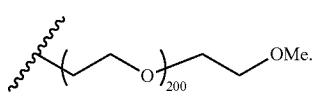

In some embodiments R¹ is

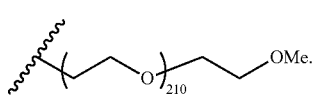

In some embodiments R¹ is

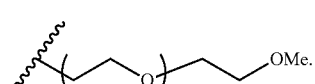

In some embodiments R¹ is

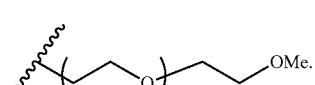

In some embodiments R¹ is

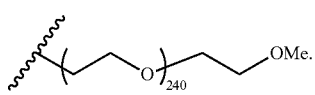

In some embodiments R¹ is

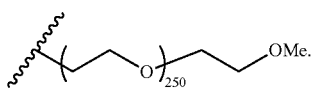

In some embodiments R¹ is

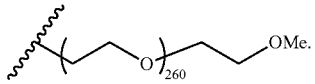

In some embodiments R¹ is

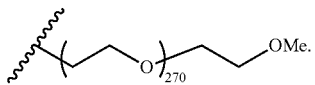

In some embodiments R¹ is

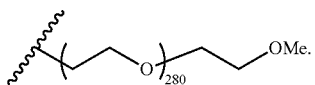

In some embodiments R¹ is

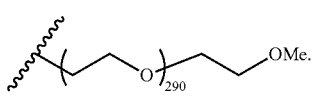

In some embodiments R¹ is

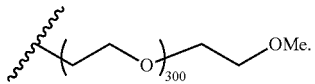

In some embodiments R¹ is

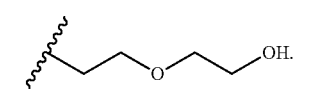 [SMILES: *CCOCCO]

In some embodiments R¹ is

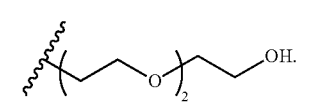

In some embodiments R[1] is
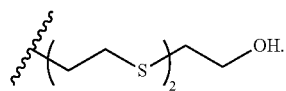
In some embodiments R[1] is
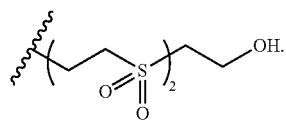
In some embodiments R[1] is
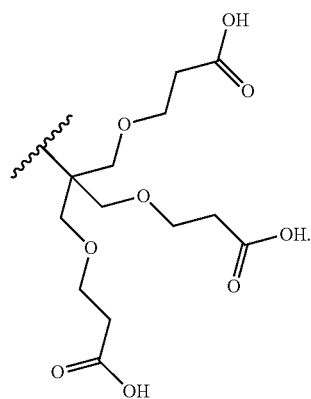 [SMILES: *C(COCCC(=O)O)(COCCC(=O)O)COCCC(=O)O]
In some embodiments R[1] is
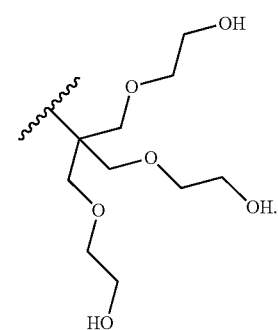 [SMILES: *C(COCCO)(COCCO)COCCO]
In some embodiments R[1] is
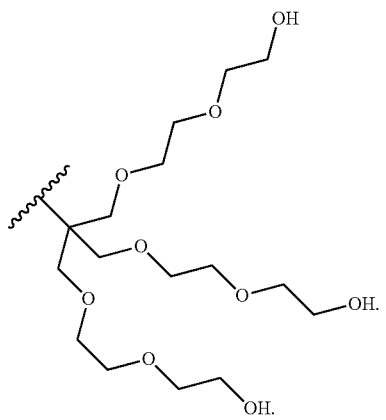 [SMILES: *C(COCCOCCO)(COCCOCCO)COCCOCCO]
In some embodiments R[1] is
[structure with three cyanoethyl ether arms]
In some embodiments R[1] is
[structure with two hydroxyethyl-PEG arms]
In some embodiments R[1] is
[structure with two hydroxyethyl ether arms]

In some embodiments, $R^1$ is

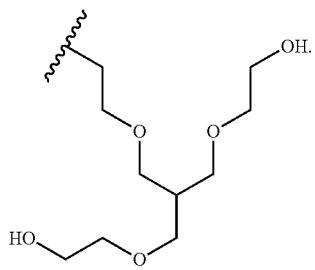

In some embodiments $R^1$ is

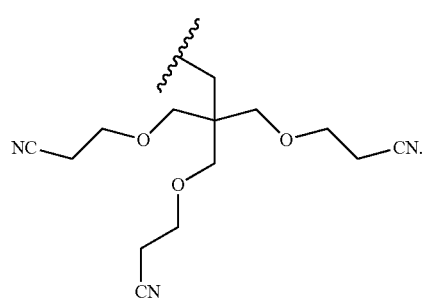 [SMILES: *CC(COCCC#N)(COCCC#N)COCCC#N]

In some embodiments $R^1$ is

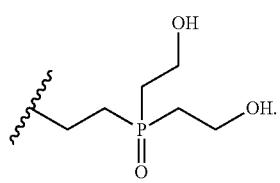 [SMILES: *CCP(=O)(CCO)CCO]

In certain embodiments, $R^1$ is a 6-18 membered saturated or partially unsaturated heterocyclic ring having 1-6 heteroatoms independently selected from nitrogen, oxygen, or sulfur.

In some embodiments $R^1$ is

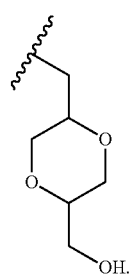 [SMILES: *CC1COC(CO)CO1]

In some embodiments $R^1$ is

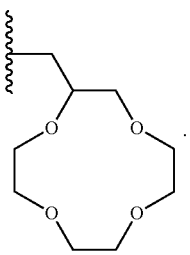 [SMILES: *CC1COCCOCCOCCO1]

In some embodiments $R^1$ is

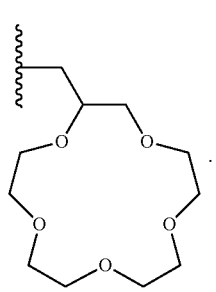 [SMILES: *CC1COCCOCCOCCOCCO1]

In some embodiments $R^1$ is

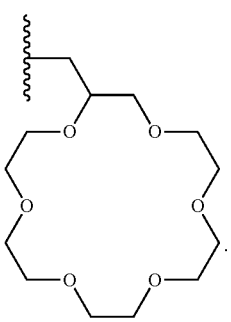 [SMILES: *CC1COCCOCCOCCOCCOCCO1]

In some embodiments, $R^1$ is selected from those depicted in Table 1, below.

In certain embodiments, R is independently hydrogen or an optionally substituted group selected from $C_{1-6}$ aliphatic.

In some embodiments, R is hydrogen. In some embodiments, R is methyl. In some embodiments, R is ethyl. In some embodiments, R is propyl. In some embodiments, R is

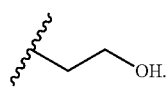 [SMILES: *CCO]

In some embodiments, R is selected from those depicted in Table 1, below.

In some embodiments, the present invention provides a compound of Formula III:

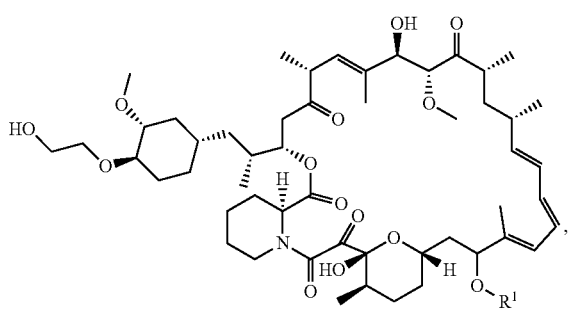

or a pharmaceutically acceptable salt thereof, wherein: $R^1$ is as described herein.

In some embodiments, the present invention provides a compound of Formula III-a or III-b:

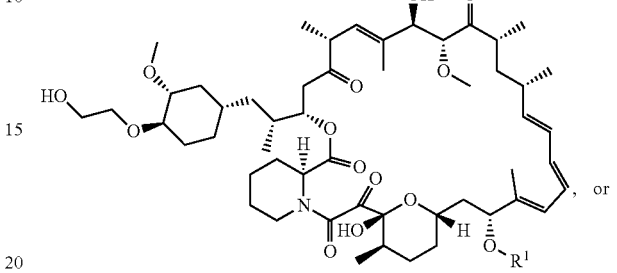

or a pharmaceutically acceptable salt thereof, wherein: $R^1$ is as described herein.

In some embodiments, the present invention provides a compound of Formula IV:

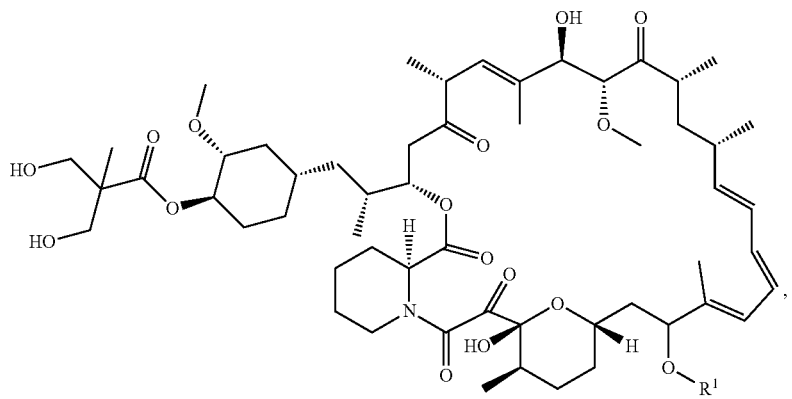

or a pharmaceutically acceptable salt thereof, wherein:
$R^1$ is as described herein.

In some embodiments, the present invention provides a compound of Formula IV-a or IV-b:

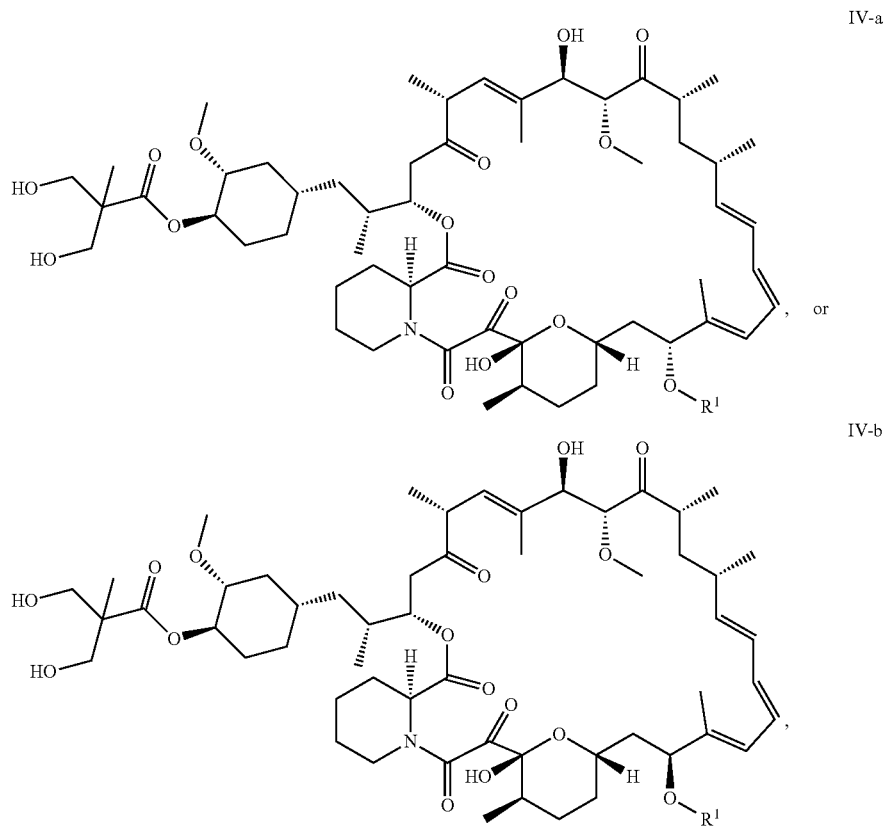

or a pharmaceutically acceptable salt thereof, wherein:
$R^1$ is as described herein.

In some embodiments, the present invention provides a compound of Formula VI:

In some embodiments, the present invention provides a compound of Formula V-a or V-b:

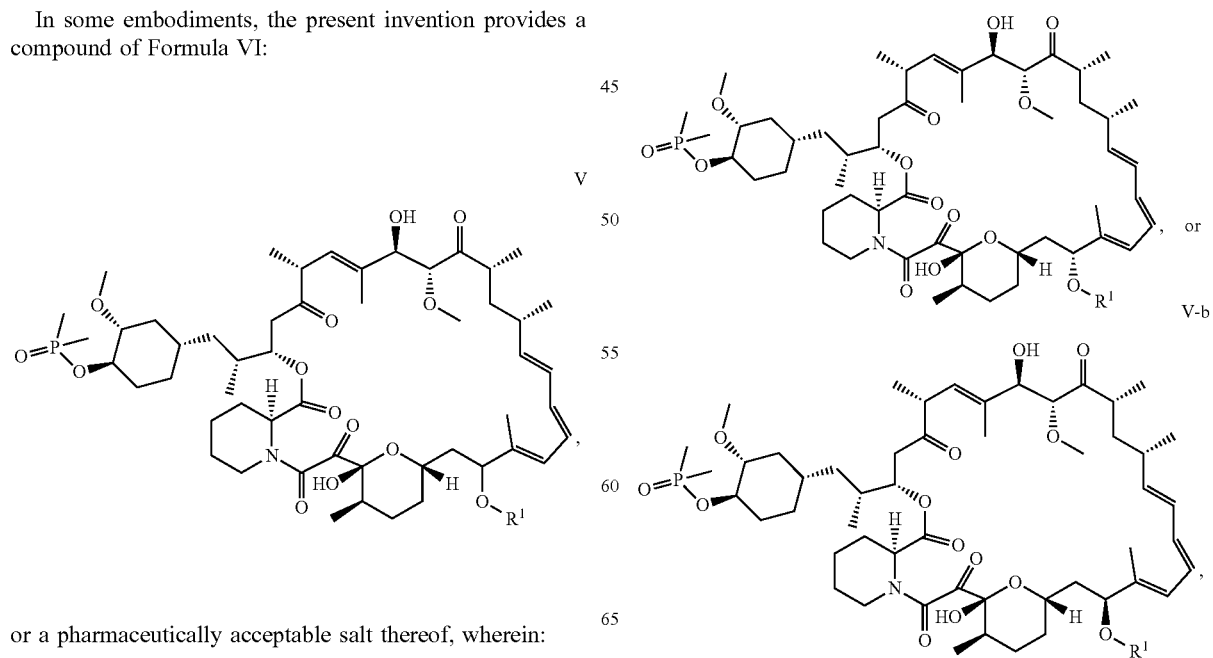

or a pharmaceutically acceptable salt thereof, wherein:
$R^1$ is as described herein.

or a pharmaceutically acceptable salt thereof, wherein:
$R^1$ is as described herein.
In some embodiments, the present invention provides a compound of Formula VI:
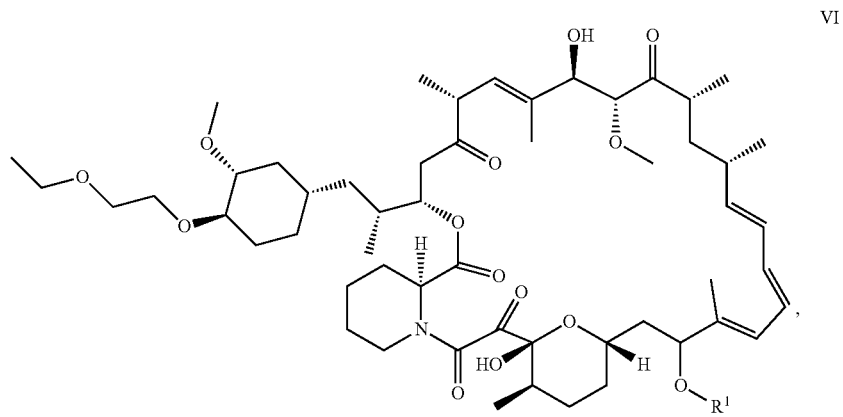
or a pharmaceutically acceptable salt thereof, wherein:
$R^1$ is as described herein.
In some embodiments, the present invention provides a compound of Formula VI-a or VI-b:

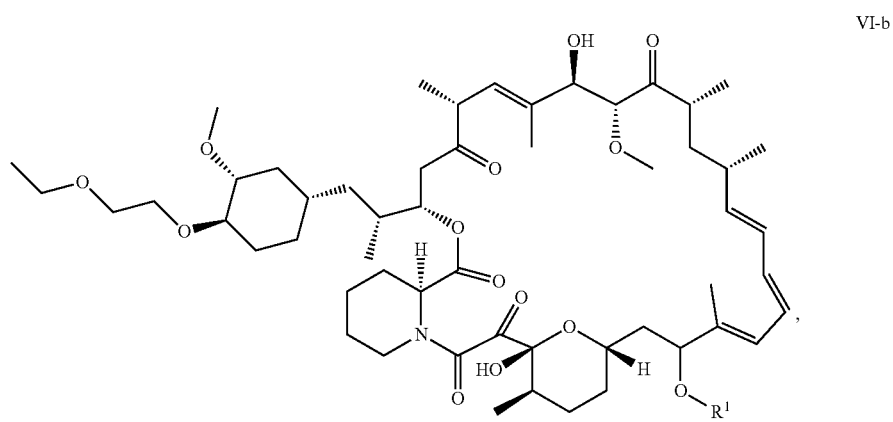

or a pharmaceutically acceptable salt thereof, wherein:
R¹ is as described herein.
In some embodiments, the present invention provides a compound of Formula VII:
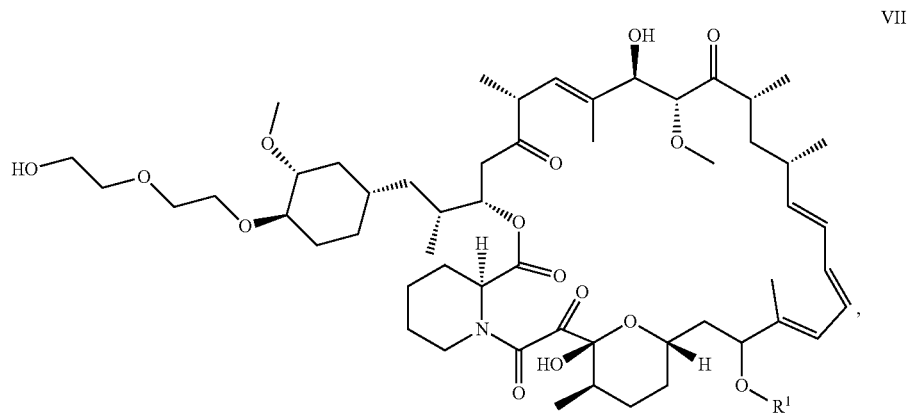
VII
or a pharmaceutically acceptable salt thereof, wherein:
R¹ is as described herein.
In some embodiments, the present invention provides a compound of Formula VII-a or VII-b:
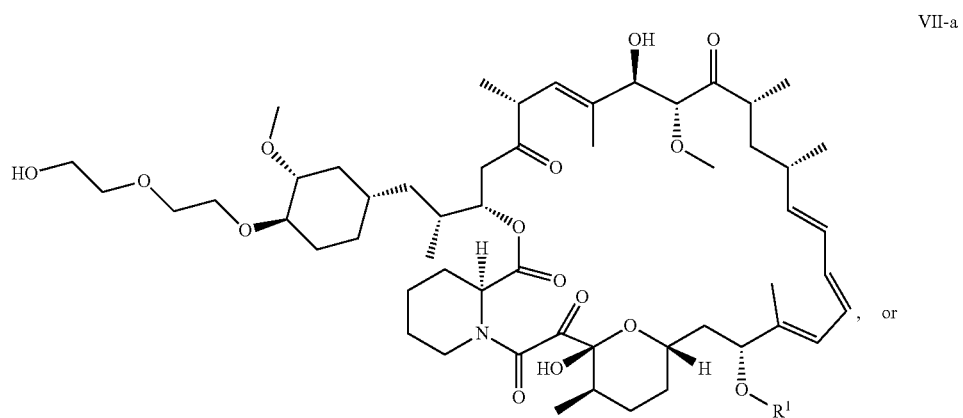
VII-a
, or
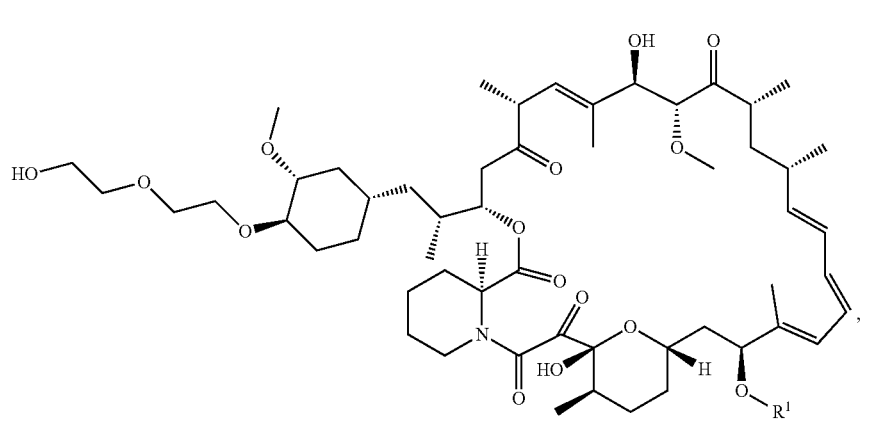
VII-b
, or a pharmaceutically acceptable salt thereof, wherein:
R¹ is as described herein.
In some embodiments, the present invention provides a compound of Formula VIII:
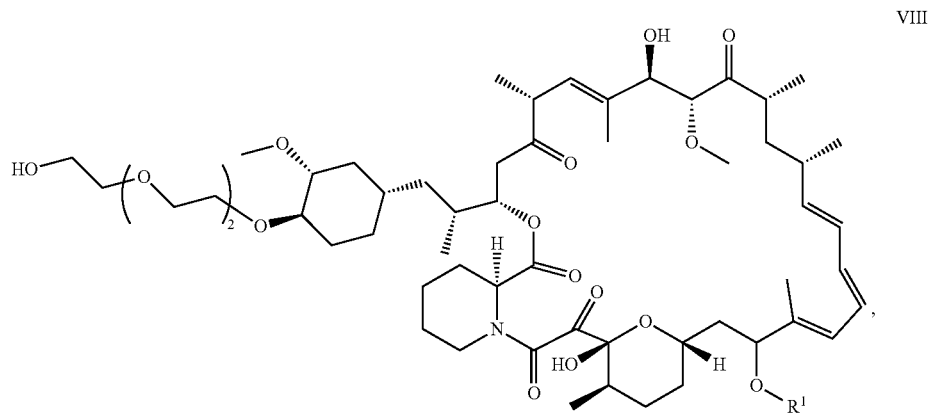
VIII
or a pharmaceutically acceptable salt thereof, wherein:
R¹ is as described herein.
In some embodiments, the present invention provides a compound of Formula VIII-a or VIII-b:

VIII-a
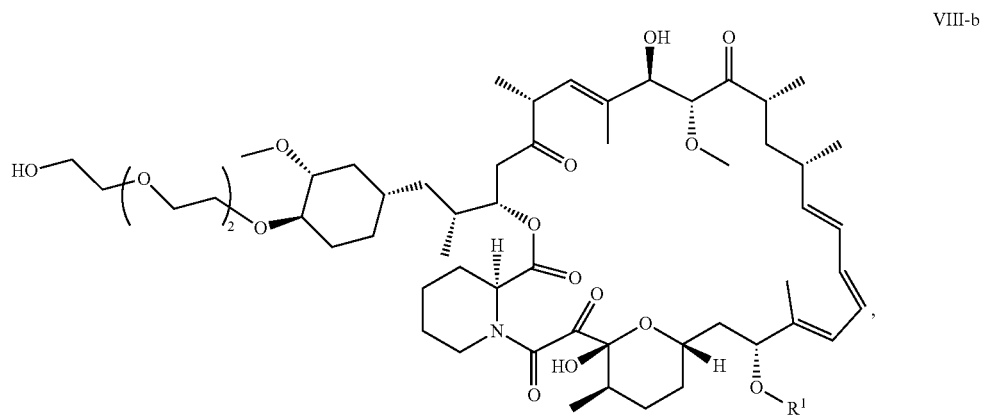
VIII-b or a pharmaceutically acceptable salt thereof, wherein:
R¹ is as described herein.
In some embodiments, the present invention provides a compound of Formula IX-a, IX-b, IX-c, IX-d, IX-e, IX-f, or IX-g:
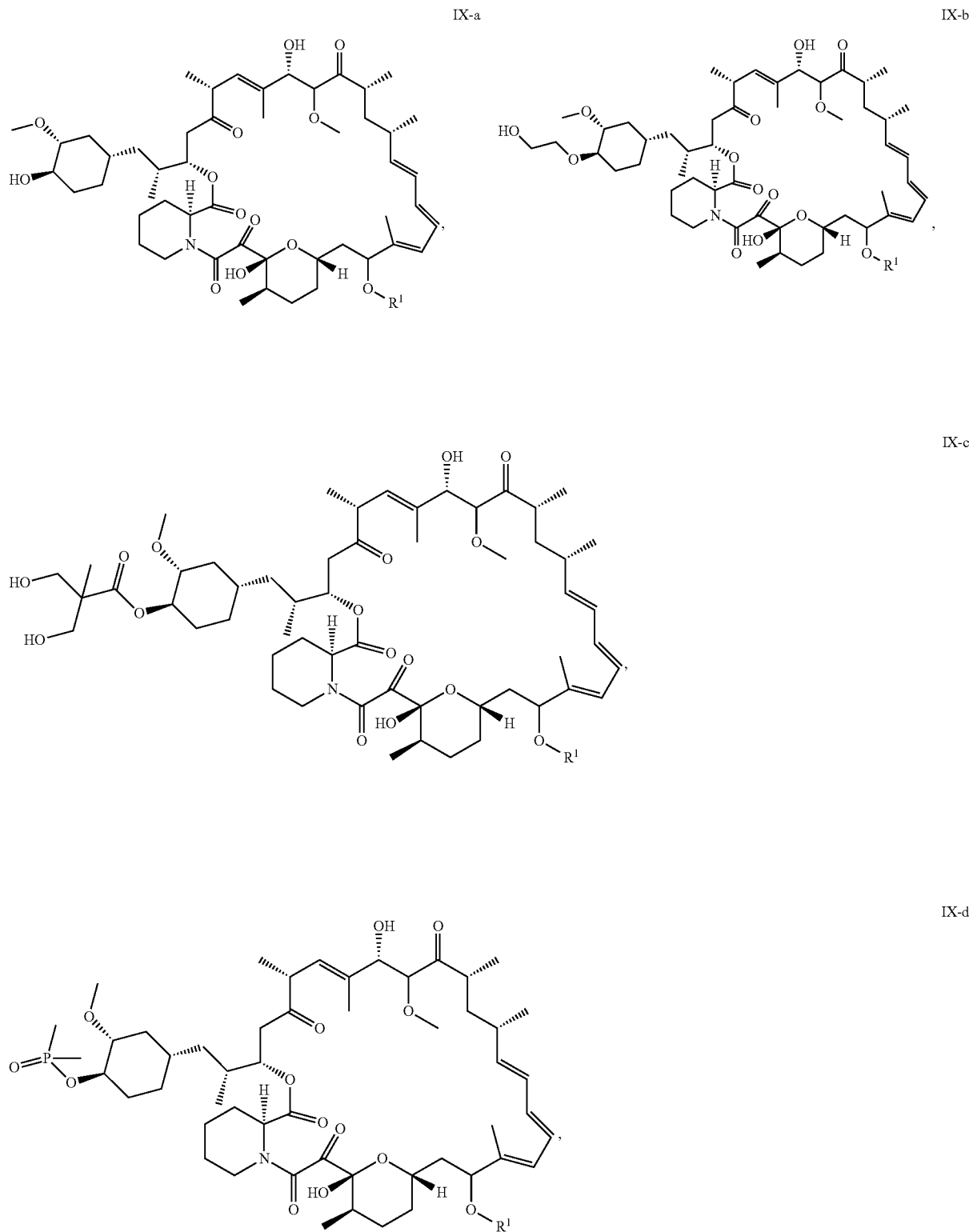

-continued
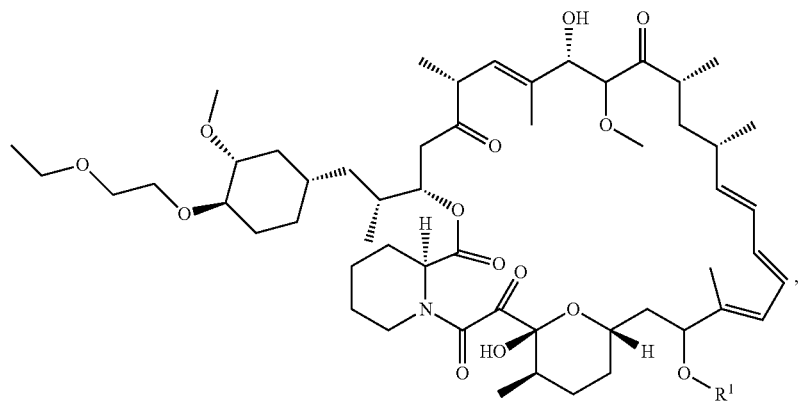
IX-e
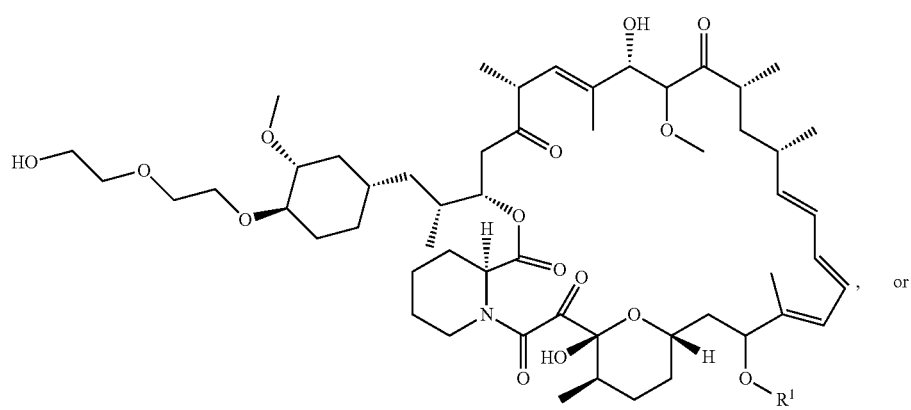
IX-f
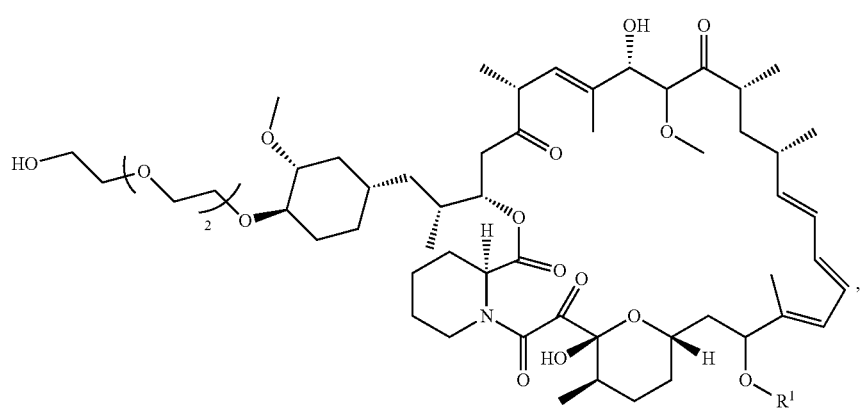
IX-g or a pharmaceutically acceptable salt thereof, wherein:
R¹ is as described herein.
In some embodiments, the present invention provides a compound of Formula X-a, X-b, X-c, X-d, X-e, X-f, or X-g:
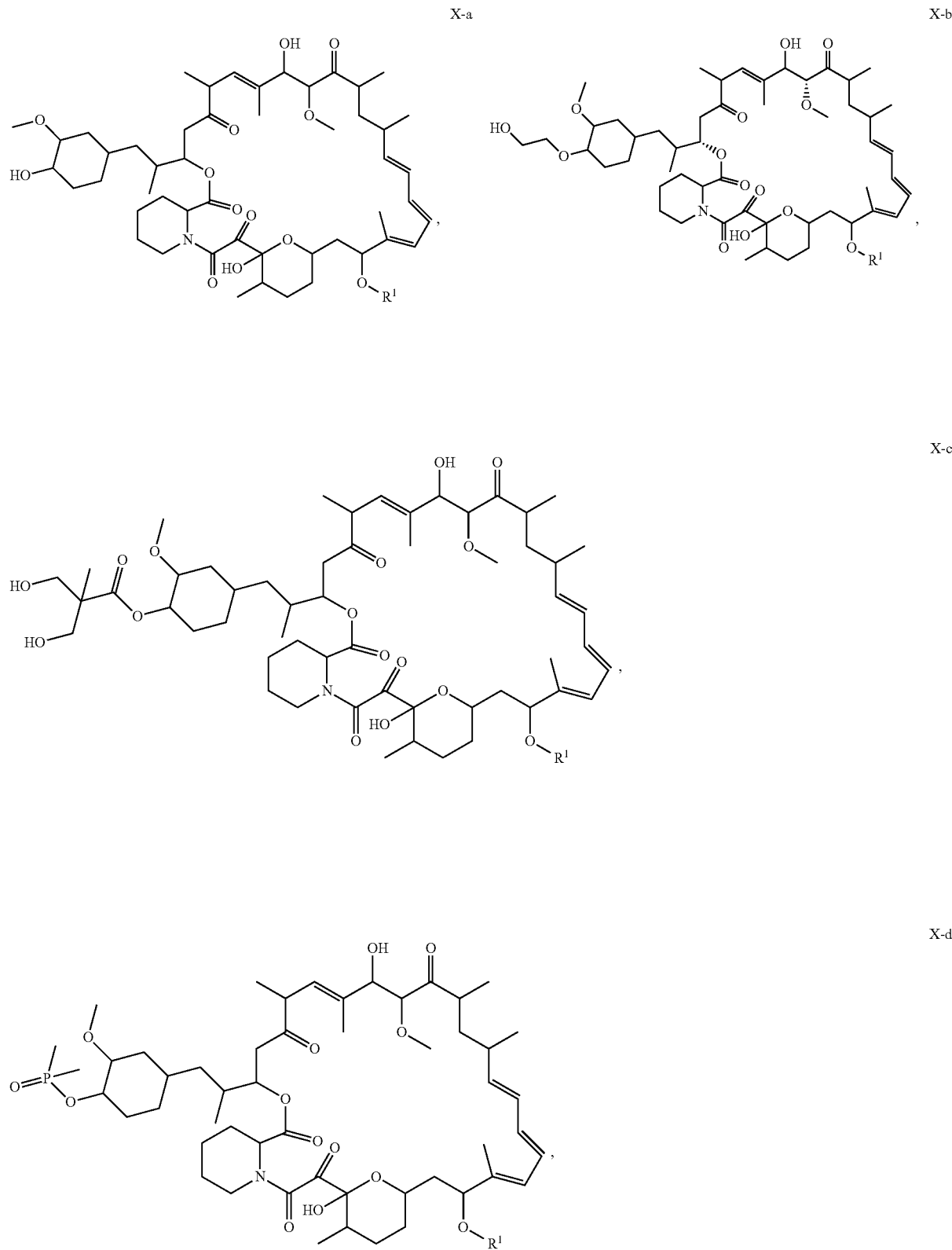

-continued
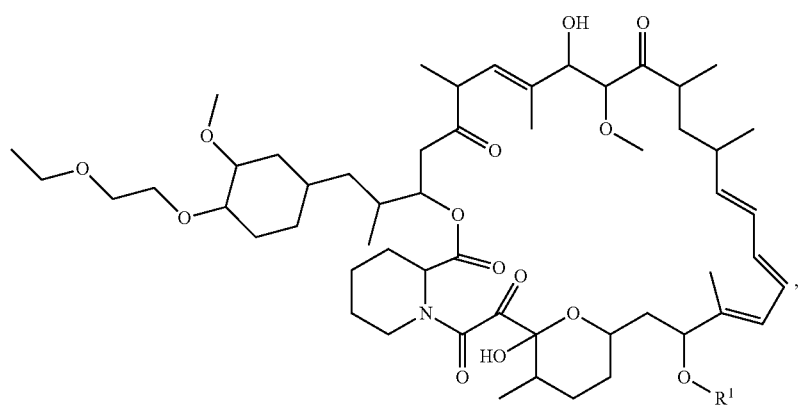
X-e
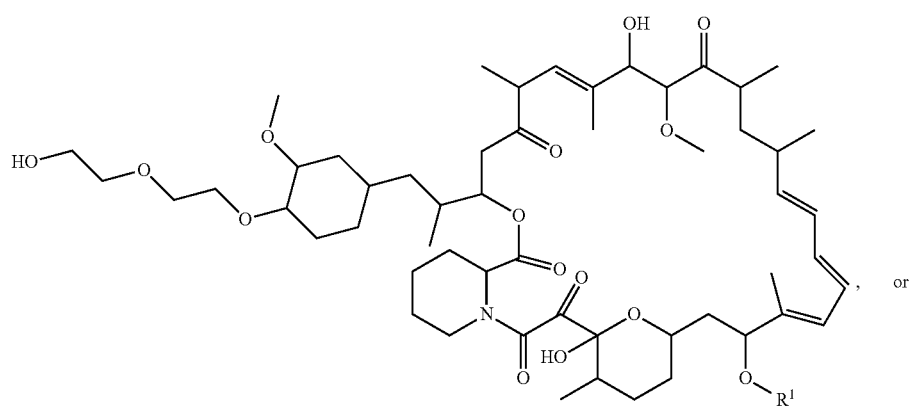
X-f
, or
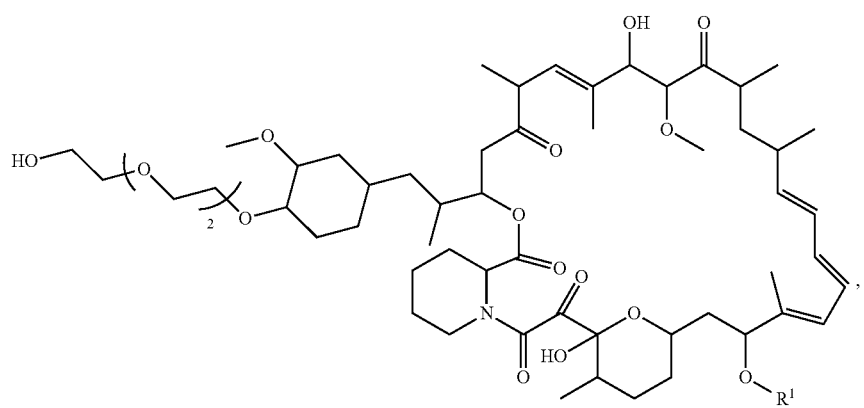
X-g or a pharmaceutically acceptable salt thereof, wherein:
R¹ is as described herein.
In some embodiments, the present invention provides a compound of Formula XI-a, XI-b, XI-c, XI-d, XI-e, XI-f, or XI-g:
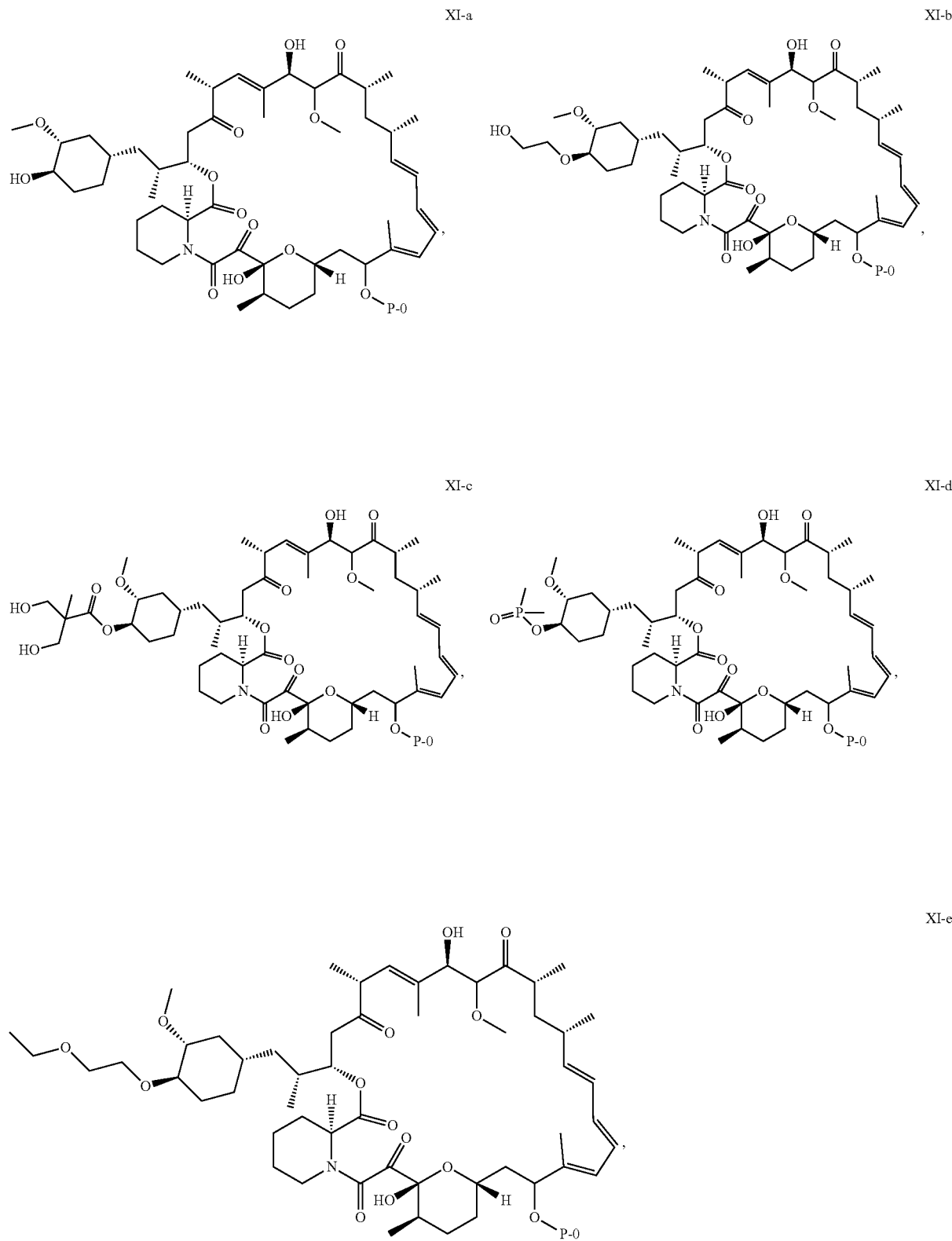

-continued
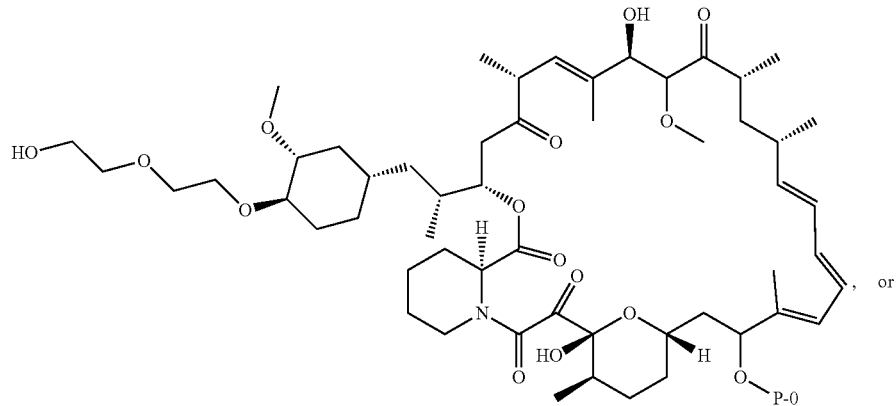
XI-f
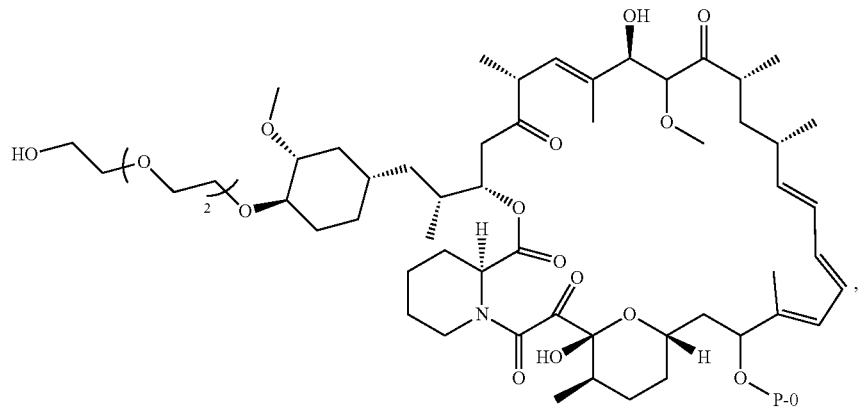
XI-g
or a pharmaceutically acceptable salt thereof, wherein:
P-0 is as described herein.
In some embodiments, the present invention provides a compound of Formula XII:
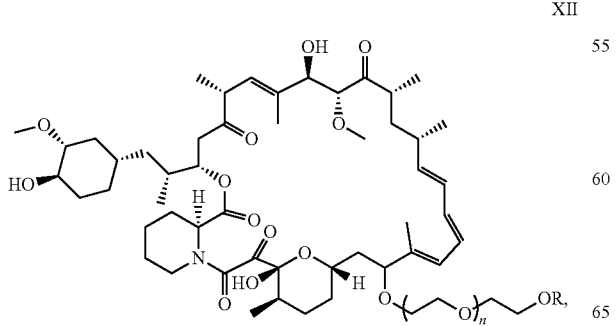
XII or a pharmaceutically acceptable salt thereof, wherein:
R and n are as described herein.
In some embodiments, the present invention provides a compound of Formulae XII-a or XII-b:
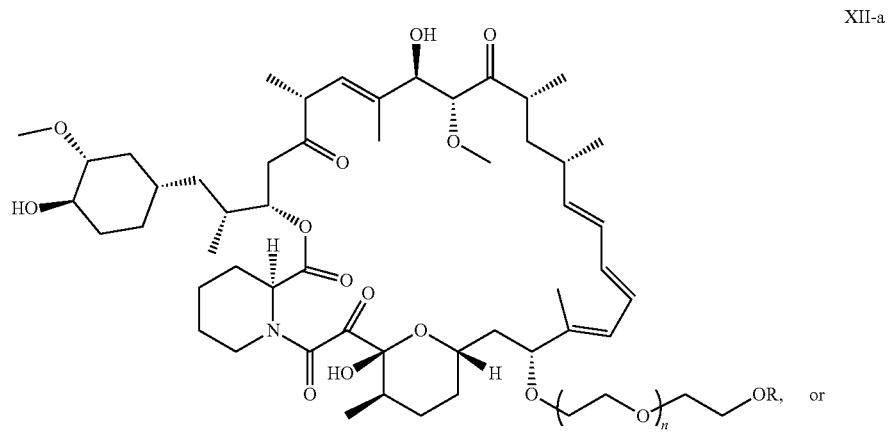
XII-a
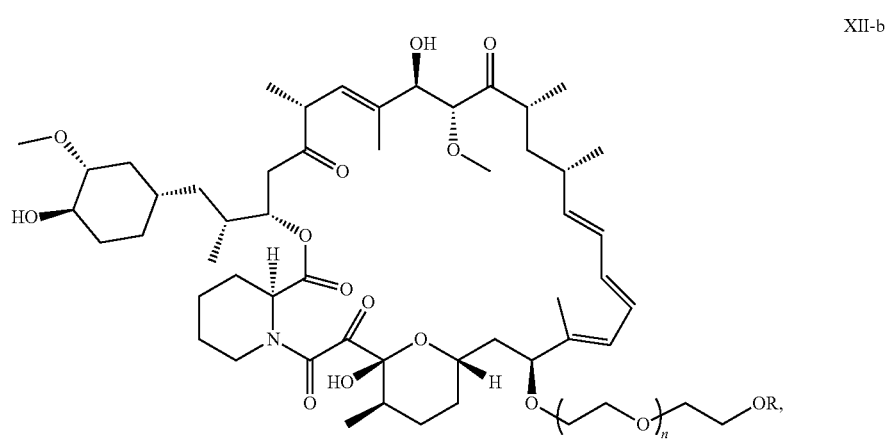
XII-b
or a pharmaceutically acceptable salt thereof, wherein:
R and n are as described herein.
In some embodiments, the present invention provides a compound of Formula XIII:
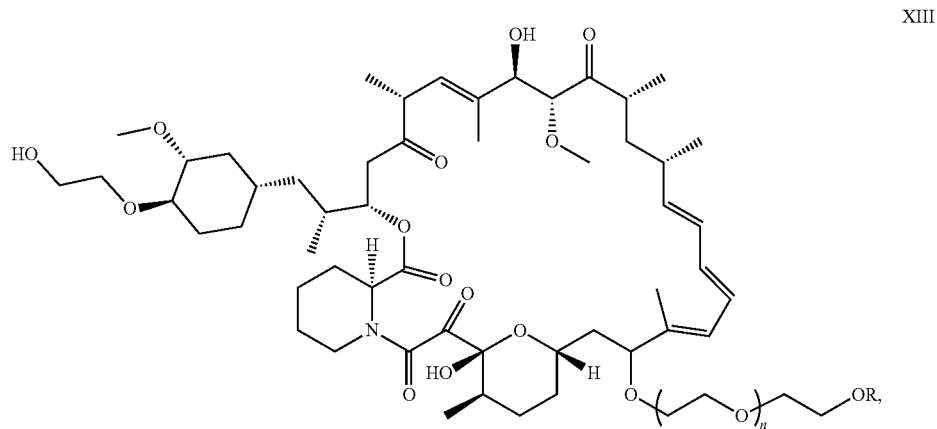
XIII le;.5qor a pharmaceutically acceptable salt thereof, wherein:
R and n are as described herein.

In some embodiments, the present invention provides a compound of Formula XIII-a or XIII-b:

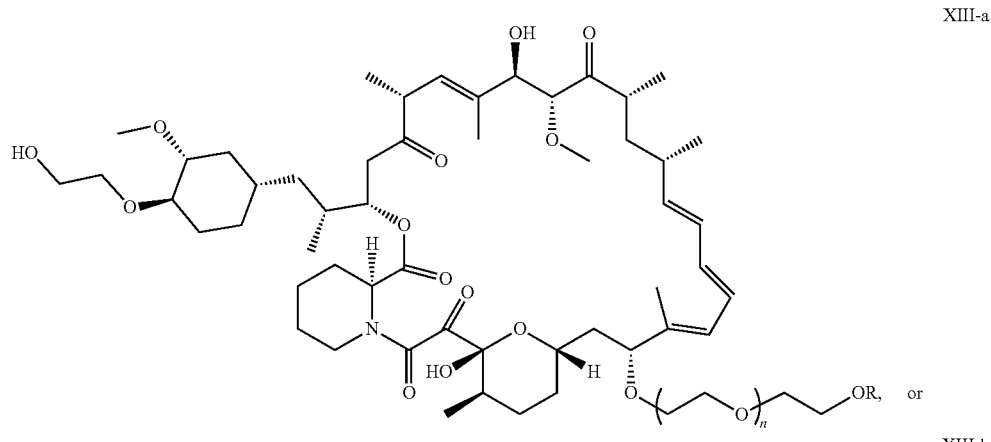

XIII-a

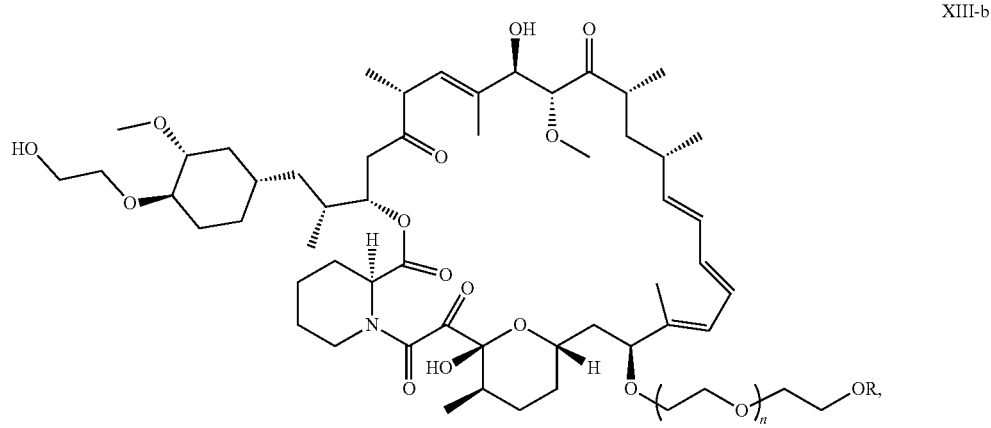

XIII-b or a pharmaceutically acceptable salt thereof, wherein:
R and n are as described herein.

In some embodiments, the present invention provides a compound of Formula XIV:

In some embodiments, the present invention provides a compound of Formula XIV-a or XIV-b:

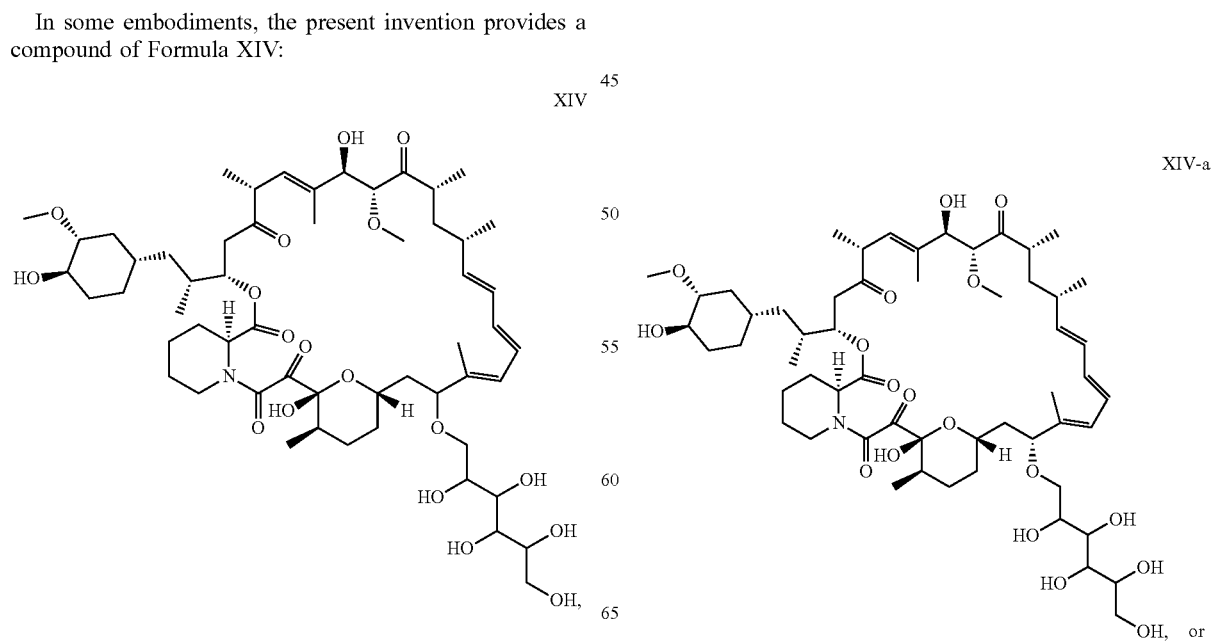

or a pharmaceutically acceptable salt thereof.

-continued
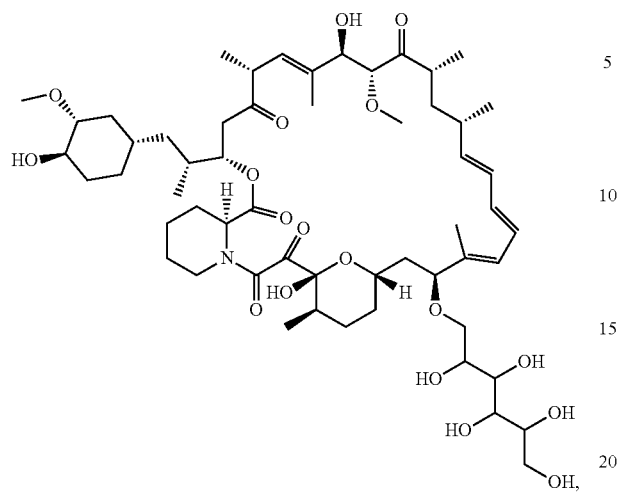
or a pharmaceutically acceptable salt thereof.
In some embodiments, the present invention provides a compound of Formula XV:
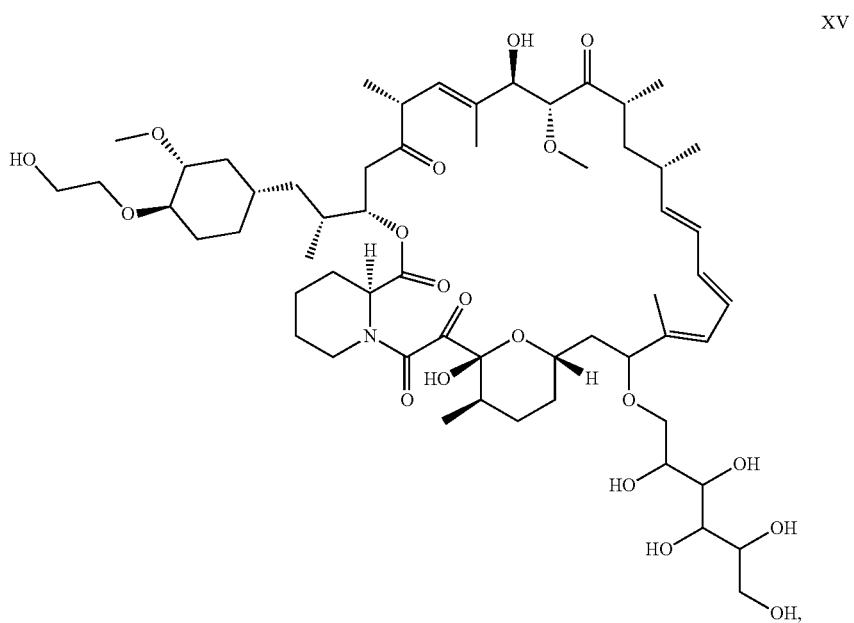 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC(O)C(O)C(O)C(O)CO)C[C@@H]3CC[C@@H](C)[C@@](O)(O3)C(=O)C(=O)N3CCCC[C@H]3C(=O)O2)CC[C@H]1OCCO]
or a pharmaceutically acceptable salt thereof.

In some embodiments, the present invention provides a compound of Formula XV-a or XV-b:

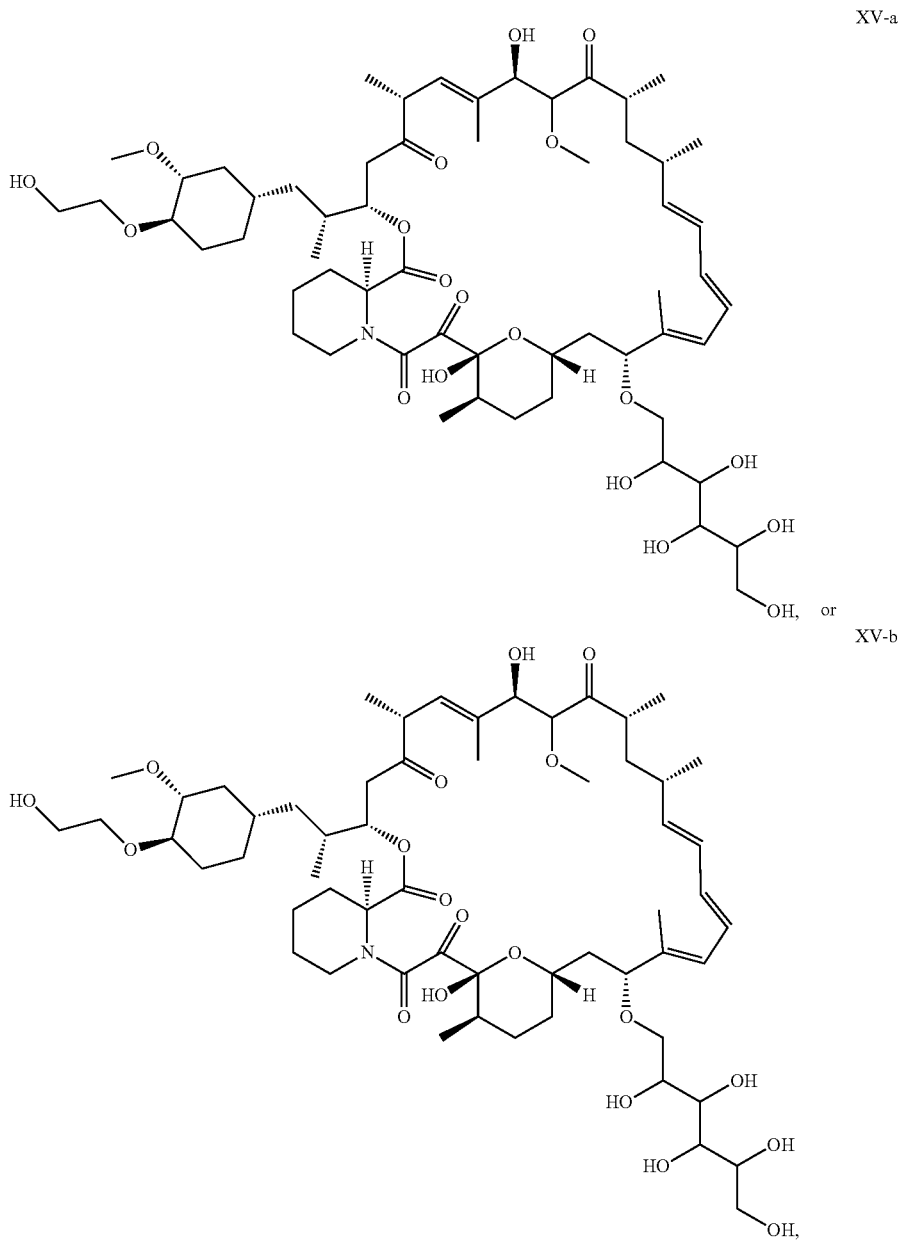

or a pharmaceutically acceptable salt thereof

Rapamycin is marketed under the brand name Rapamune® (generic name, sirolimus) and is well known for its antiproliferative and immunosuppressive activity. Rapamycin is FDA approved for the prevention of transplant rejection and for coating stents to prevent restenosis. Aside from the documented benefits of rapamycin, it is well known that rapamycin is associated with a number of serious side effects. Such side effects include diabetes-like symptoms of decreased glucose tolerance and lowering of insulin sensitivity. In addition, it has been reported that rapamycin activates the Akt signaling pathway (including activation of Akt and ERK) thereby increasing a patient's risk of cancer.

As used herein the phrase "rapamycin alone" is intended to compare a compound of the present invention with rapamycin, or an analog thereof, as alternatives.

In some embodiments, a provided compound of Formula I, II, III, IV, V, VI, VII, VIII, XII, XIII, XIV, or XV is more efficatious than rapamycin alone. In some embodiments, a provided compound of Formula II-a, III-a, IV-a, V-a, VI-a, VII-a, VIII-a, XII-a, XIII-a, XIV-a, or XV-a is more efficatious than rapamycin alone. In some embodiments, a provided compound of Formula II-b, IV-b, V-b, VI-b, VII-b, VIII-b, XII-b, XIII-b, XIV-b, or XV-b is more efficatious than rapamycin alone.

In some embodiments, a provided compound of Formula IX-a, IX-b, IX-c, IX-d, IX-e, IX-f, or IX-g is more efficatious than rapamycin alone.

In some embodiments, a provided compound of Formula X-a, X-b, X-c, X-d, X-e, X-f, or X-g is more efficacious than rapamycin alone.

In some embodiments, a provided compound of Formula XI-a, XI-b, XI-c, XI-d, XI-e, XI-f, or XI-g is more efficacious than rapamycin alone.

In some embodiments, a provided compound of Formula II-a or II-b is more efficacious than rapamycin alone. In some embodiments, a provided compound of Formula III-a or III-b is more efficacious than rapamycin alone. In some embodiments, a provided compound of Formula IV-a or IV-b is more efficacious than rapamycin alone. In some embodiments, a provided compound of Formula V-a or V-b is more efficacious than rapamycin alone. In some embodiments, a provided compound of Formula VI-a or VI-b is more efficacious than rapamycin alone. In some embodiments, a provided compound of Formula VII-a or VII-b is more efficacious than rapamycin alone. In some embodiments, a provided compound of Formula VIII-a or VIII-b is more efficacious than rapamycin alone. In some embodiments, a provided compound of Formula XII-a or XII-b is more efficacious than rapamycin alone. In some embodiments, a provided compound of Formula XIII-a or XIII-b is more efficacious than rapamycin alone. In some embodiments, a provided compound of Formula XIV-a or XIV-b is more efficacious than rapamycin alone. In some embodiments, a provided compound of Formula XV-a or XV-b is more efficacious than rapamycin alone.

In some embodiments, a provided compound of Formula I, II, III, IV, V, VI, VII, VIII, XII, XIII, XIV, or XV when administered to a patient, results in fewer and/or lesser severity of side effects than when rapamycin is administered.

In some embodiments, a provided compound of Formula IX-a, IX-b, IX-c, IX-d, IX-e, IX-f, or IX-g when administered to a patient, results in fewer and/or lesser severity of side effects than when rapamycin is administered.

In some embodiments, a provided compound of Formula X-a, X-b, X-c, X-d, X-e, X-f, or X-g when administered to a patient, results in fewer and/or lesser severity of side effects than when rapamycin is administered.

In some embodiments, a provided compound of Formula XI-a, XI-b, XI-c, XI-d, XI-e, XI-f, or XI-g when administered to a patient, results in fewer and/or lesser severity of side effects than when rapamycin is administered.

Exemplary compounds of the invention are set forth in Table 1, below.

TABLE 1

Exemplary Compounds

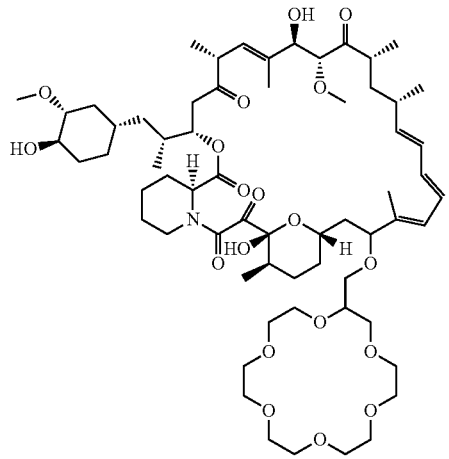 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC3COCCOCCOCCOCCOCCO3)C[C@@H]3CC[C@@H](C)[C@@](O)(O3)C(=O)C(=O)N3CCCC[C@H]3C(=O)O2)CC[C@H]1O]

I-1

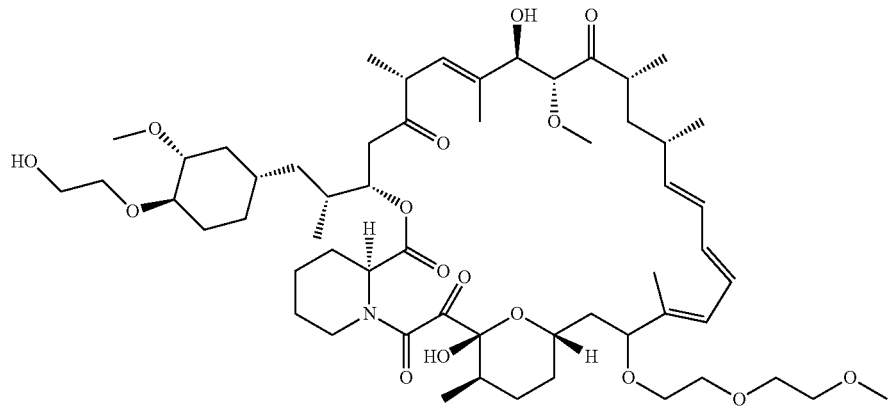 [SMILES: COCCOCCOC1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

I-2

TABLE 1-continued
Exemplary Compounds
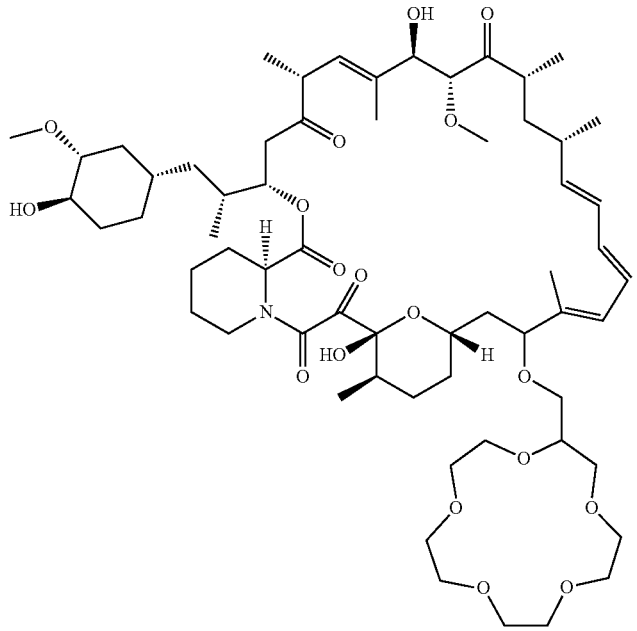 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC3COCCOCCOCCOCCO3)C[C@@H]3CC[C@@H](C)[C@@](O)(O3)C(=O)C(=O)N3CCCC[C@H]3C(=O)O2)CC[C@H]1O]
I-3
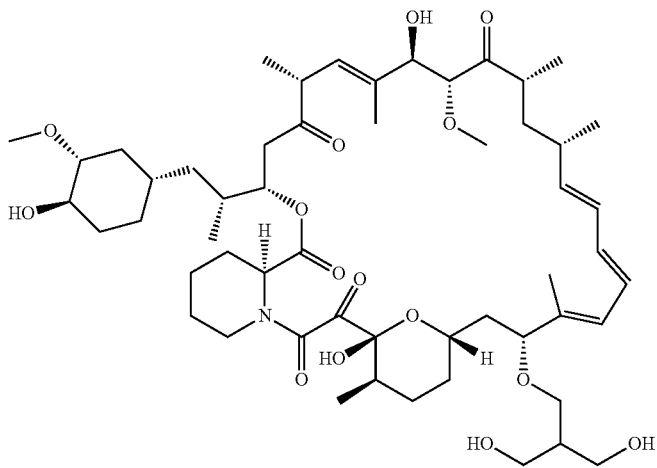 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCC(CO)CO)C[C@@H]3CC[C@@H](C)[C@@](O)(O3)C(=O)C(=O)N3CCCC[C@H]3C(=O)O2)CC[C@H]1O]
I-4
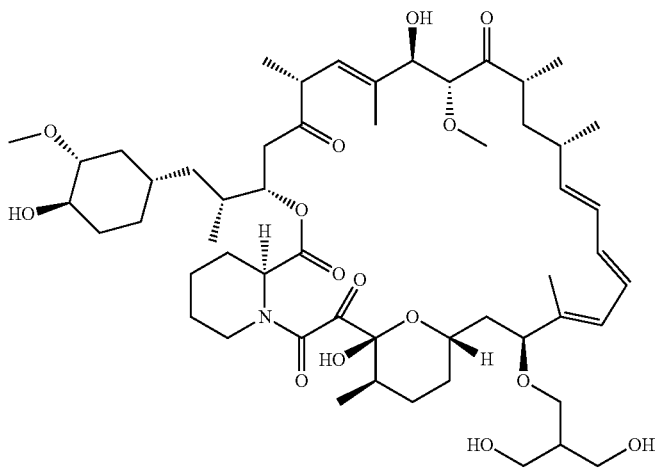 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCC(CO)CO)C[C@@H]3CC[C@@H](C)[C@@](O)(O3)C(=O)C(=O)N3CCCC[C@H]3C(=O)O2)CC[C@H]1O]
I-5

TABLE 1-continued
Exemplary Compounds
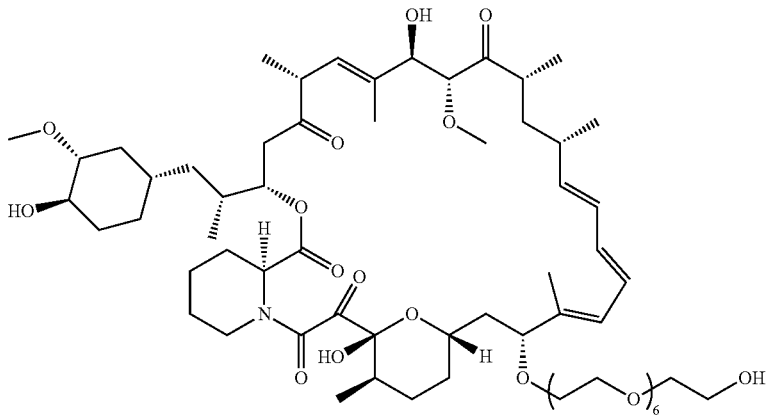
I-6
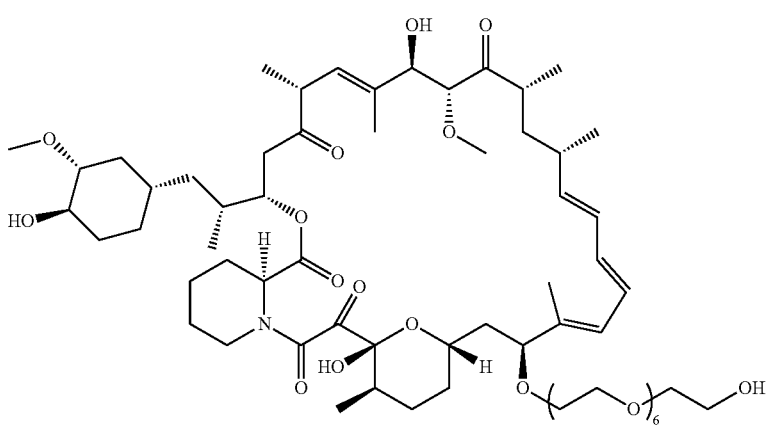
I-7
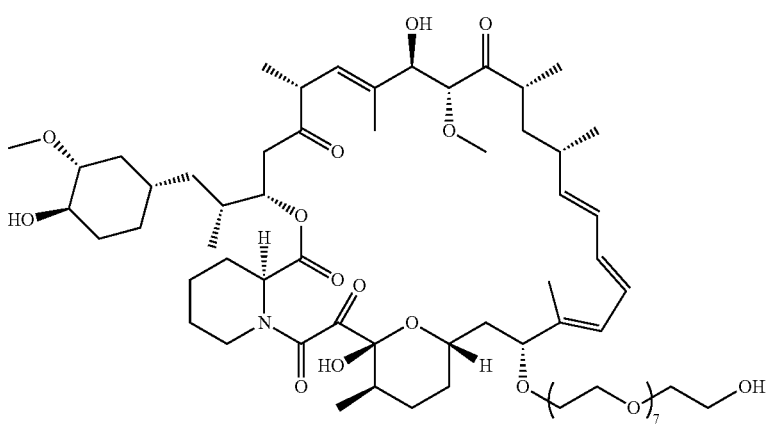
I-8

TABLE 1-continued
Exemplary Compounds
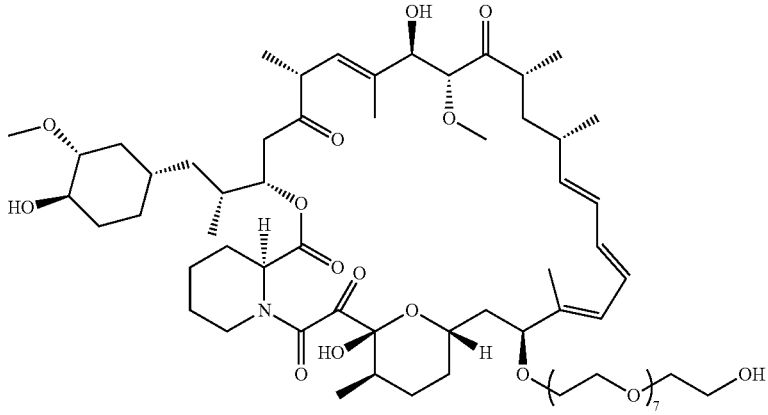
I-9
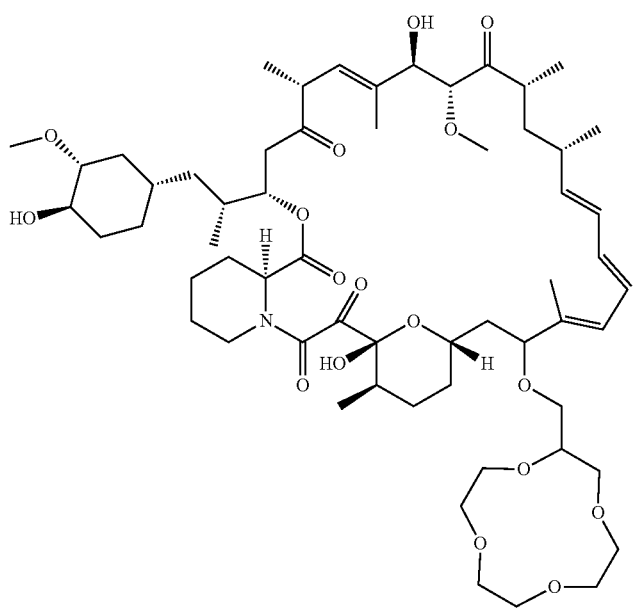
I-10
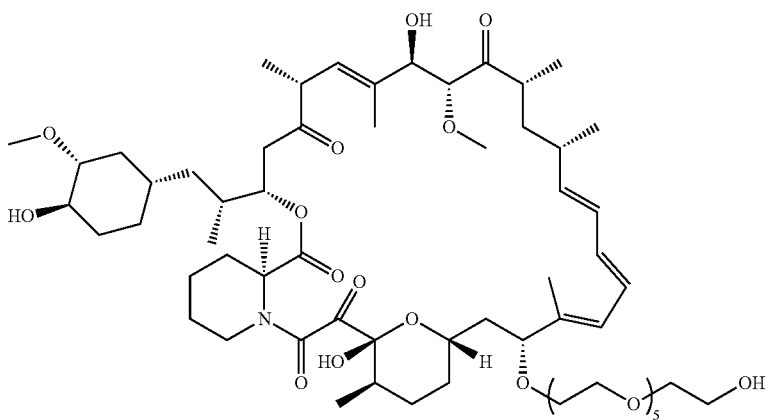
I-11

TABLE 1-continued
Exemplary Compounds
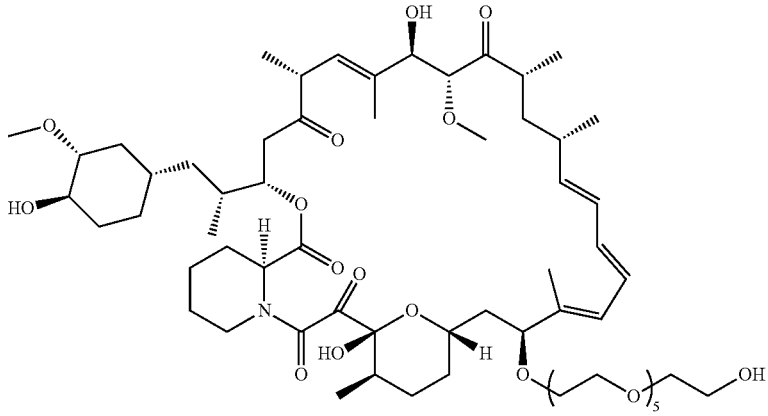
I-12
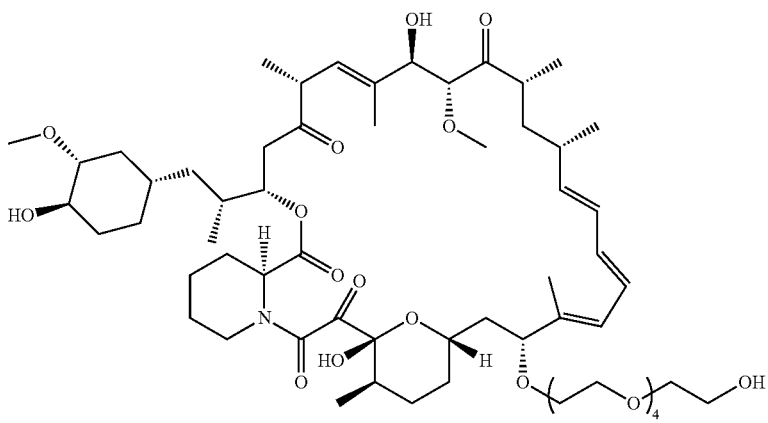
I-13
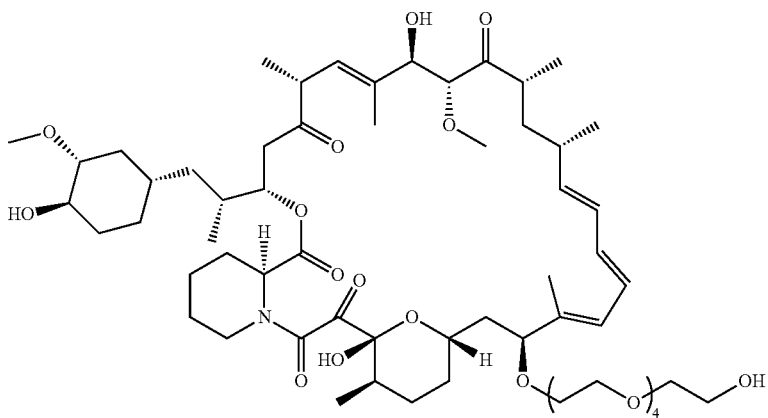
I-14

TABLE 1-continued
Exemplary Compounds
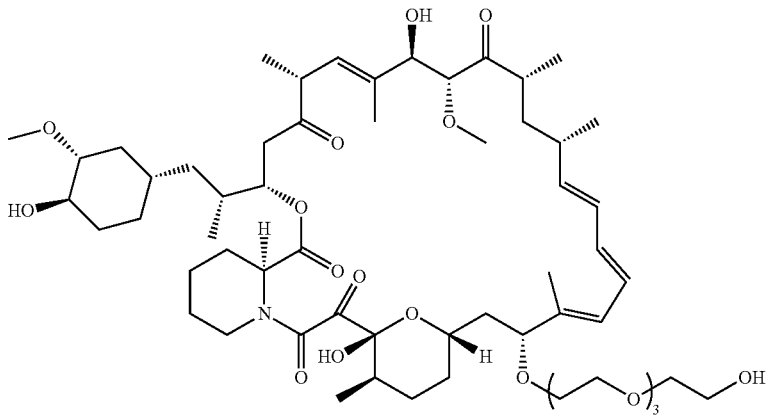
I-15
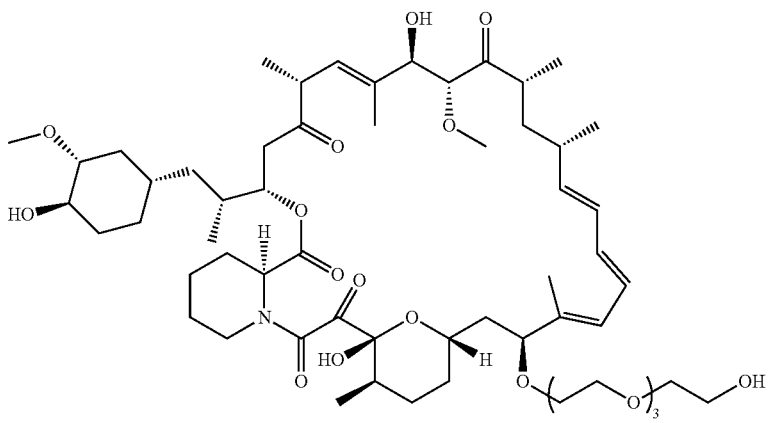
I-16
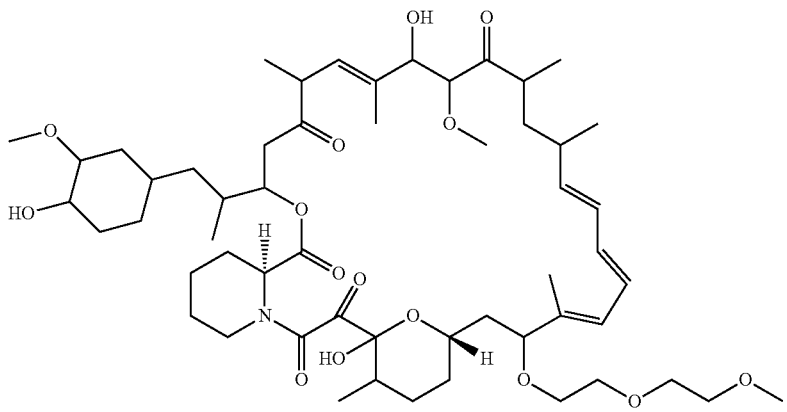
I-17

TABLE 1-continued
Exemplary Compounds
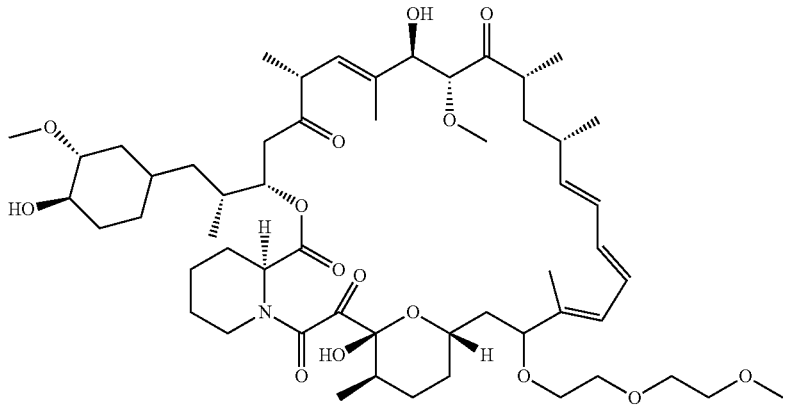
I-18
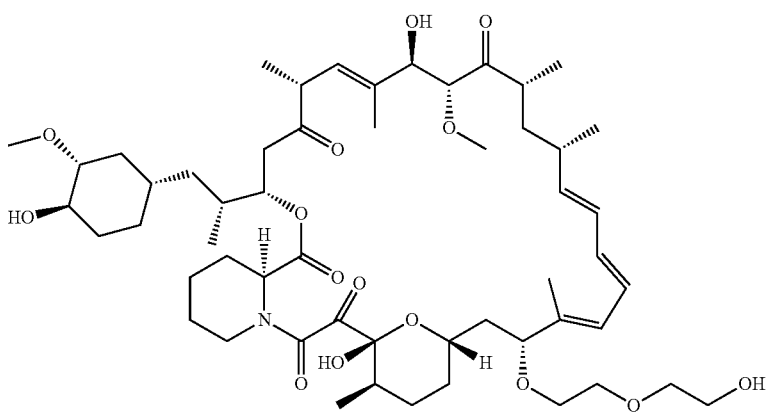
I-19
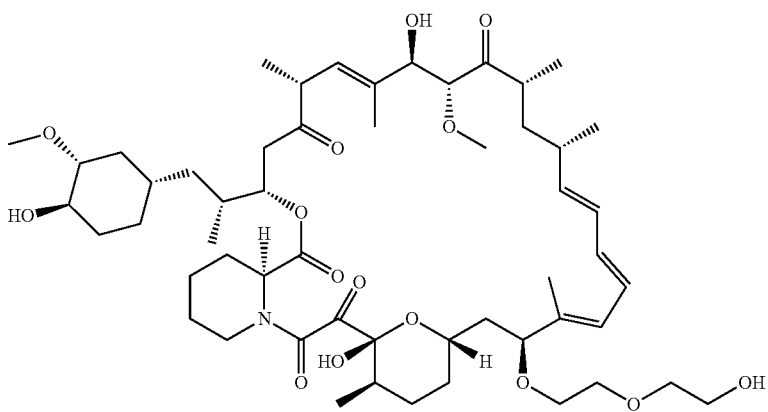 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCO)C[C@@H]3CC[C@@H](C)[C@@](O)(O3)C(=O)C(=O)N3CCCC[C@H]3C(=O)O2)CC[C@H]1O]
I-20

TABLE 1-continued
Exemplary Compounds
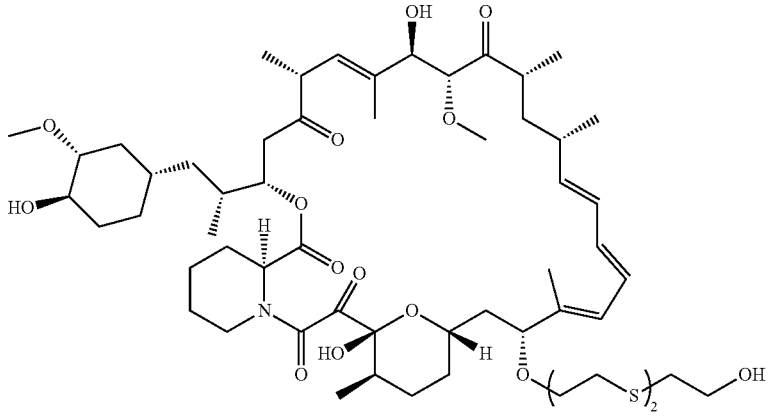
I-21
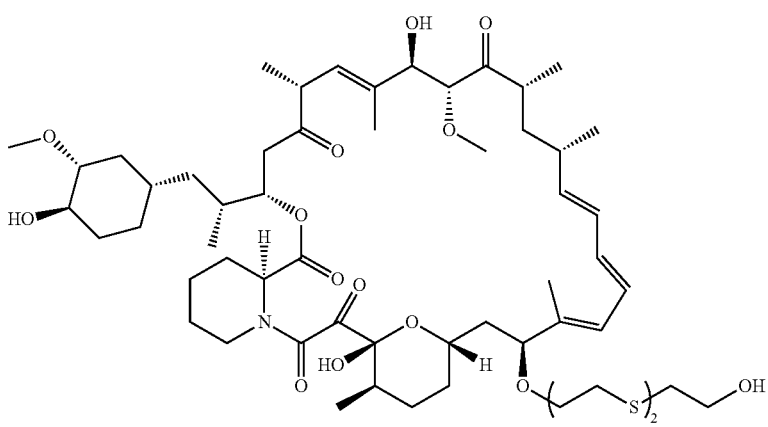
I-22
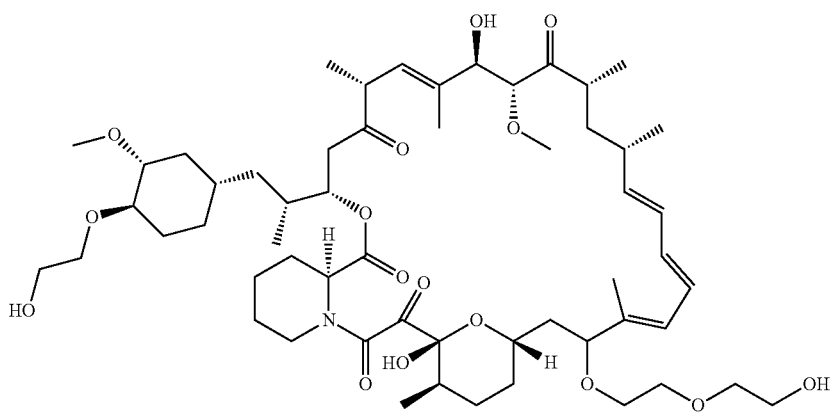 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCO)C[C@@H]3CC[C@@H](C)[C@@](O)(O3)C(=O)C(=O)N3CCCC[C@H]3C(=O)O2)CC[C@H]1OCCO]
I-23

TABLE 1-continued
Exemplary Compounds
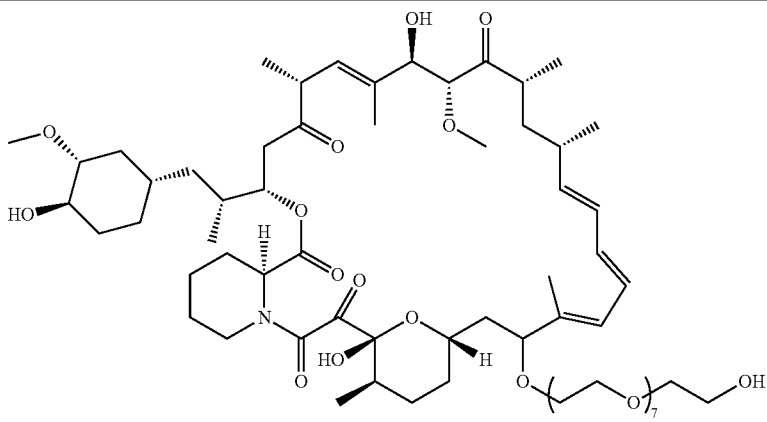
I-24
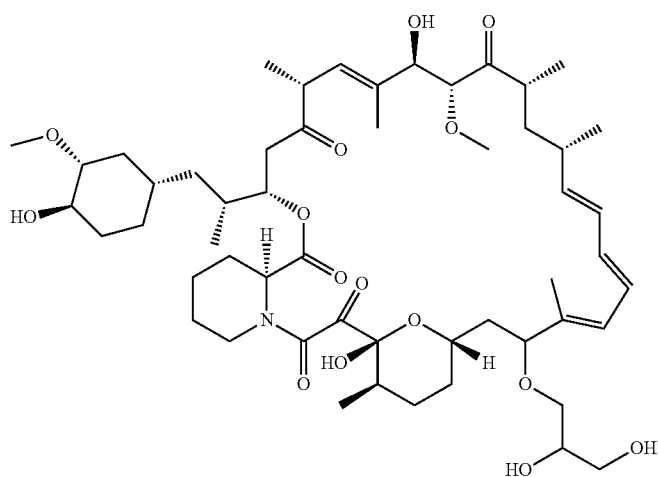
I-25
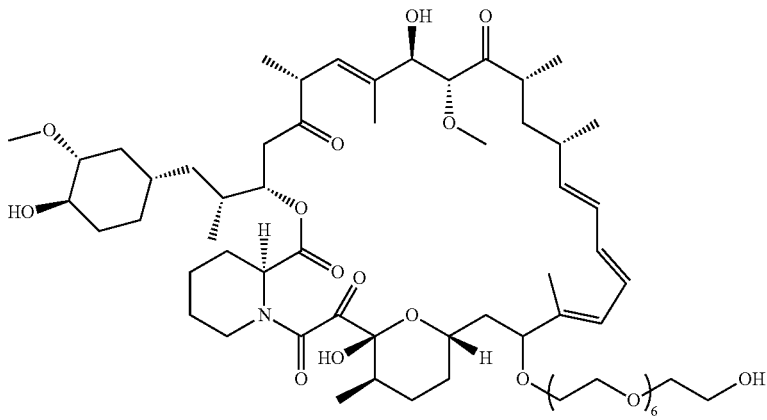
I-26

TABLE 1-continued
Exemplary Compounds
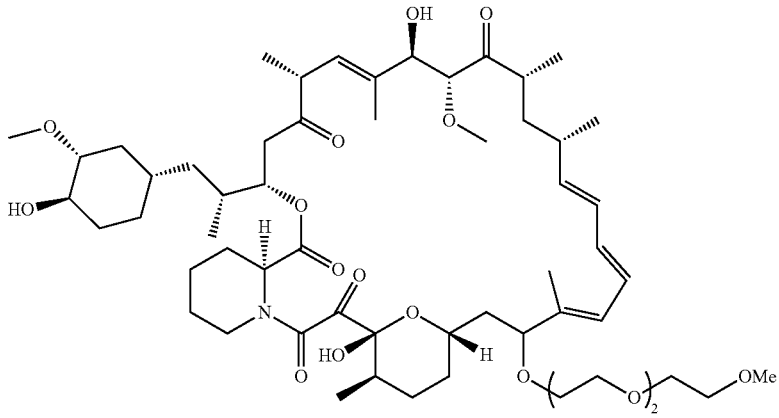
I-27
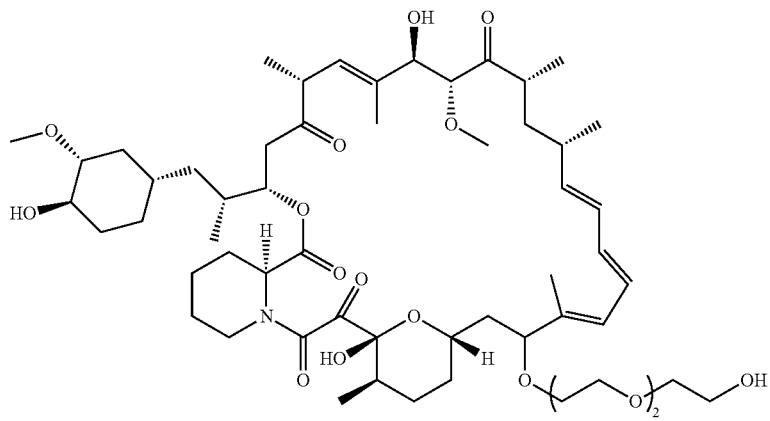
I-28
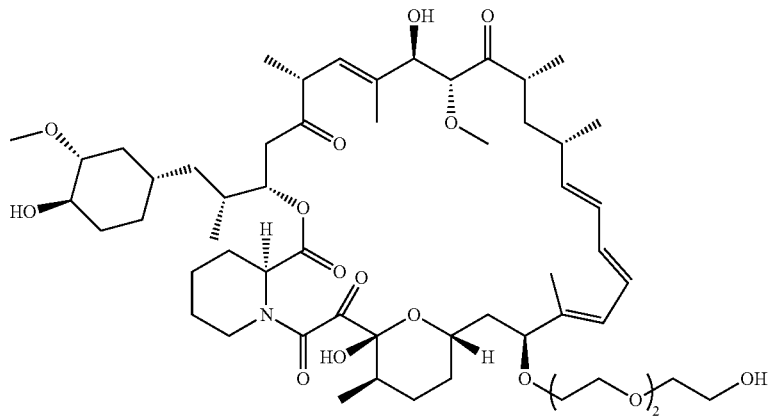
I-29

TABLE 1-continued
Exemplary Compounds
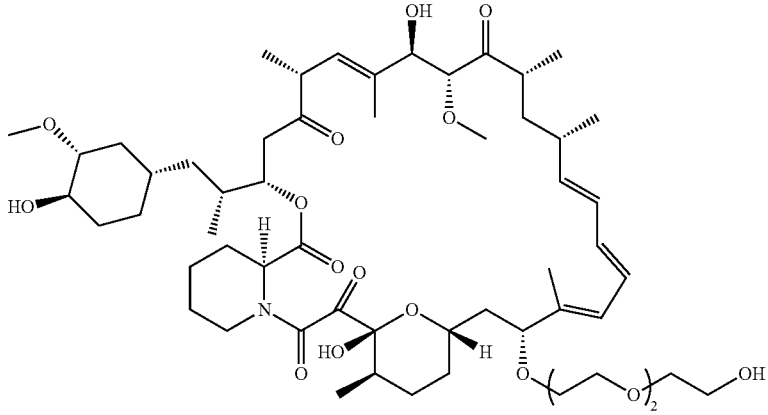
I-30
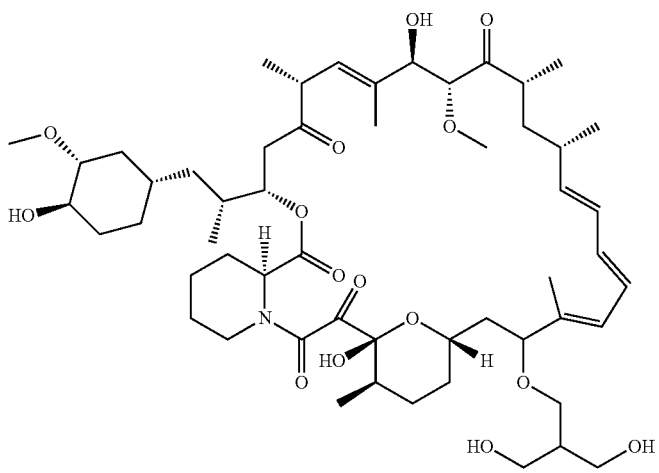 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC(CO)CO)C[C@@H]3CC[C@@H](C)[C@@](O)(O3)C(=O)C(=O)N3CCCC[C@H]3C(=O)O2)CC[C@H]1O]
I-31
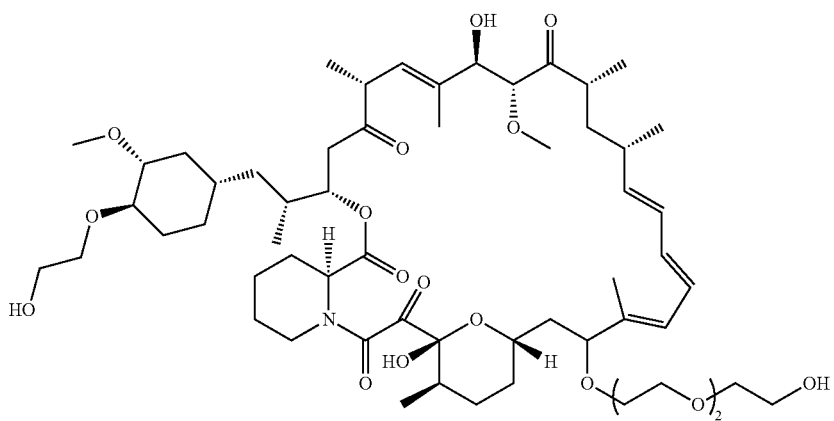
I-32

TABLE 1-continued
Exemplary Compounds
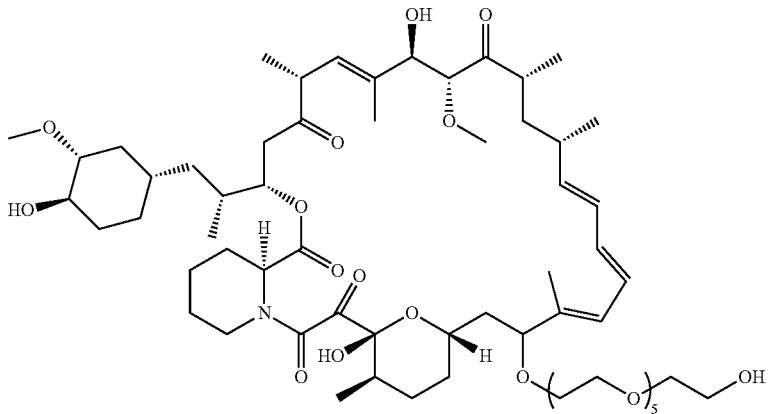
I-33
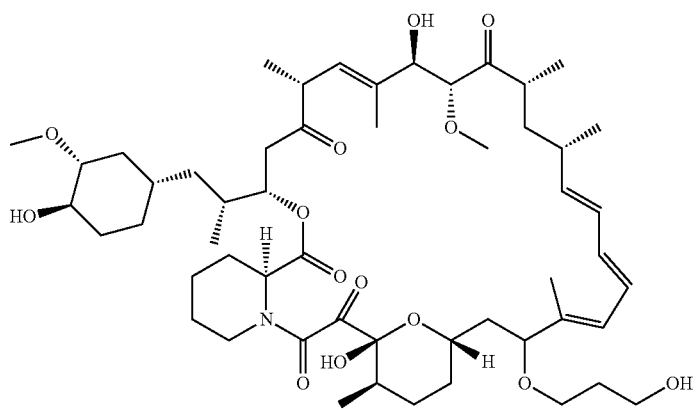 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCO)C[C@@H]3CC[C@@H](C)[C@@](O)(O3)C(=O)C(=O)N3CCCC[C@H]3C(=O)O2)CC[C@H]1O]
I-34
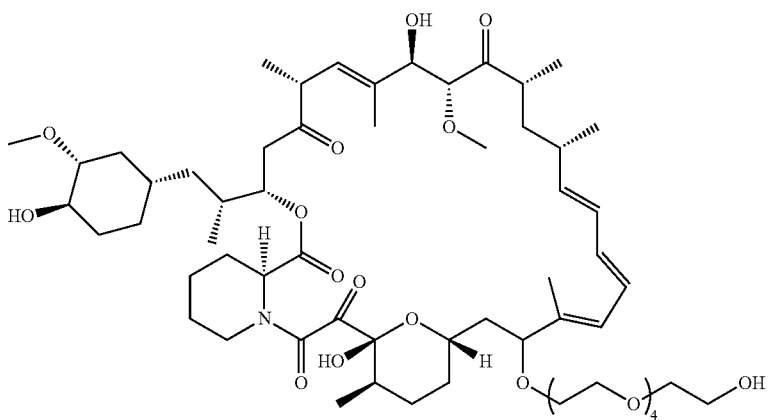
I-35

TABLE 1-continued
Exemplary Compounds
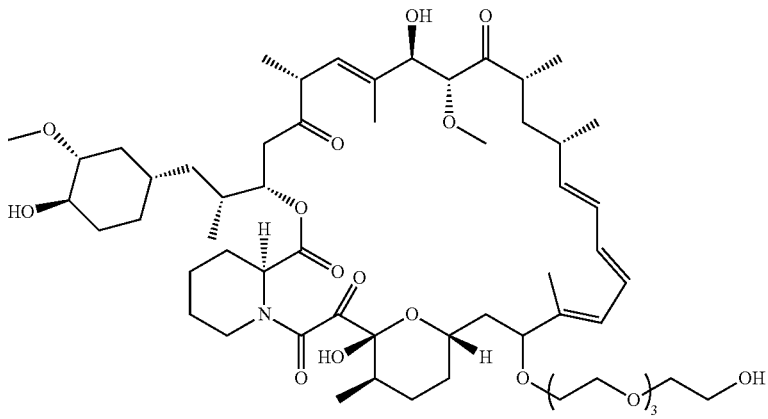
I-36
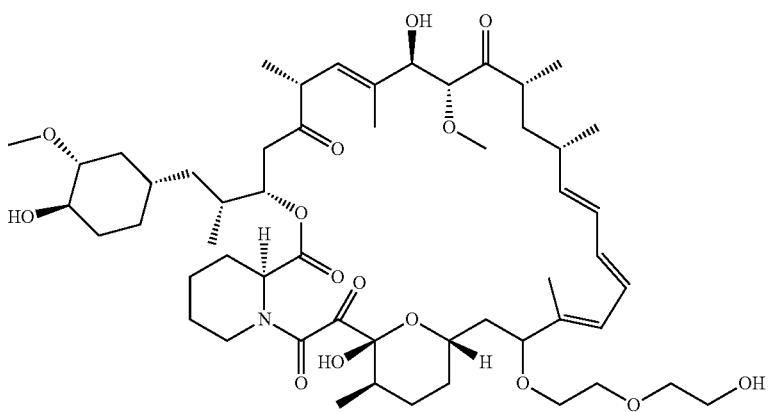 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCO)C[C@@H]3CC[C@@H](C)[C@@](O)(O3)C(=O)C(=O)N3CCCC[C@H]3C(=O)O2)CC[C@H]1O]
I-37
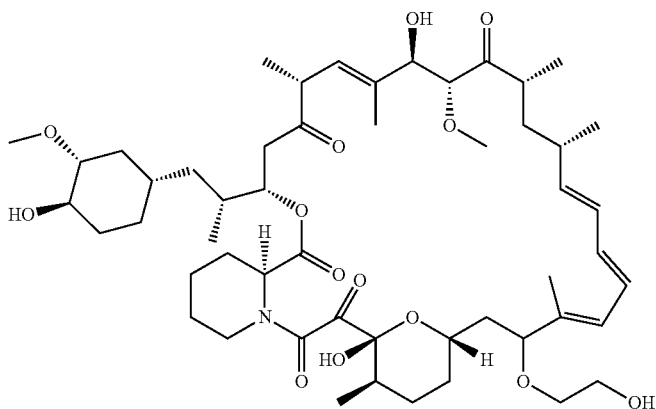 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCO)C[C@@H]3CC[C@@H](C)[C@@](O)(O3)C(=O)C(=O)N3CCCC[C@H]3C(=O)O2)CC[C@H]1O]
I-38

TABLE 1-continued

Exemplary Compounds

I-39

I-41

I-42

TABLE 1-continued
Exemplary Compounds
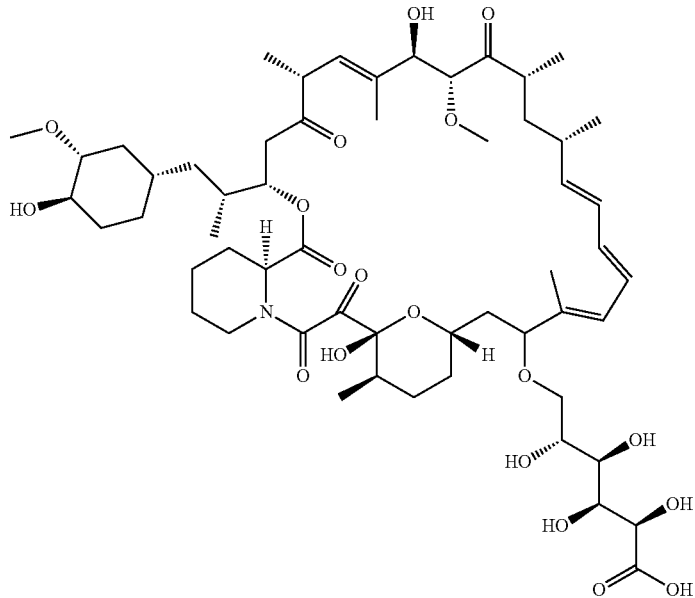 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC[C@@H](O)[C@@H](O)[C@H](O)[C@@H](O)C(=O)O)C[C@@H]3CC[C@@H](C)[C@@](O)(O3)C(=O)C(=O)N3CCCC[C@H]3C(=O)O2)CC[C@H]1O]
I-44
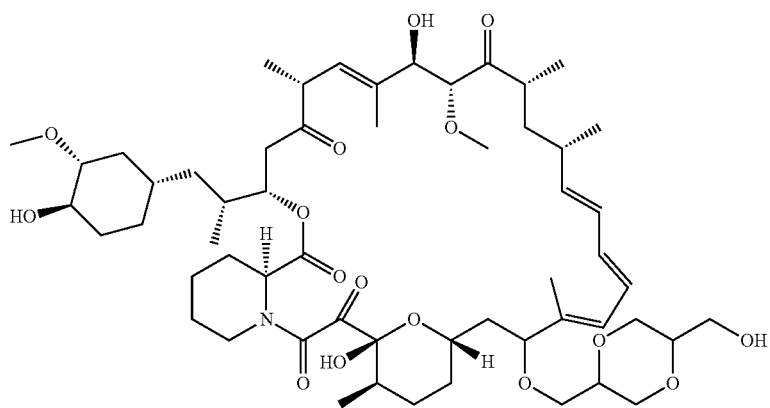 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC3COC(CO)CO3)C[C@@H]3CC[C@@H](C)[C@@](O)(O3)C(=O)C(=O)N3CCCC[C@H]3C(=O)O2)CC[C@H]1O]
I-45
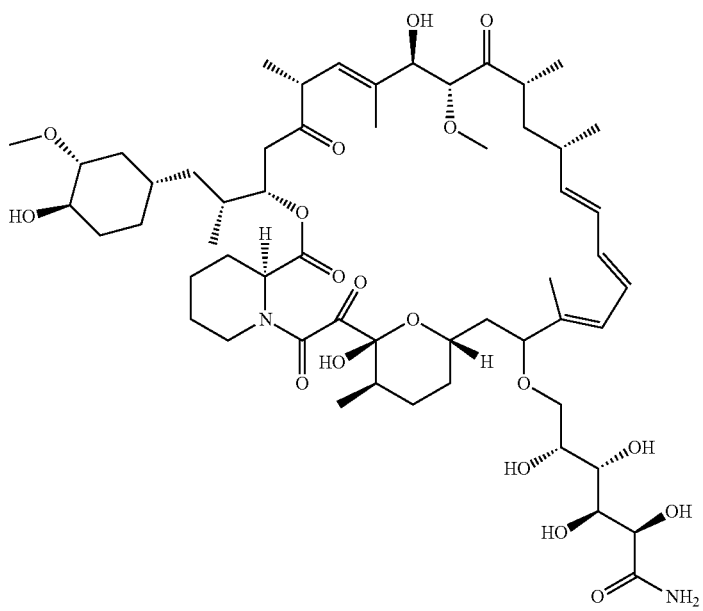 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC[C@@H](O)[C@H](O)[C@H](O)[C@@H](O)C(N)=O)C[C@@H]3CC[C@@H](C)[C@@](O)(O3)C(=O)C(=O)N3CCCC[C@H]3C(=O)O2)CC[C@H]1O]
I-47

TABLE 1-continued
Exemplary Compounds
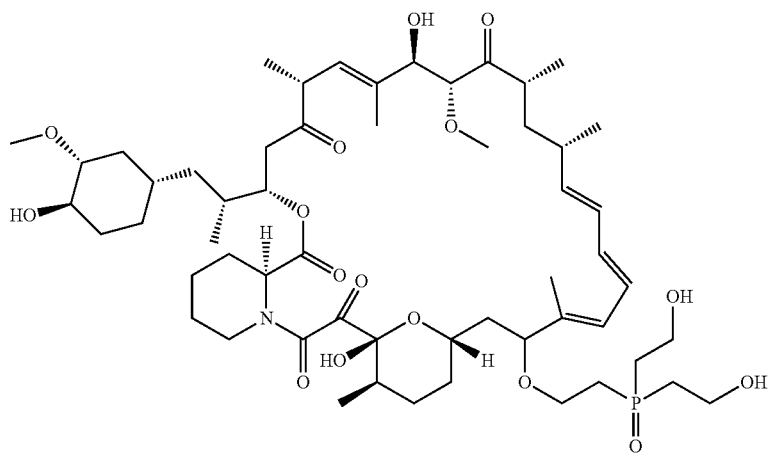 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCP(=O)(CCO)CCO)C[C@@H]3CC[C@@H](C)[C@@](O)(O3)C(=O)C(=O)N3CCCC[C@H]3C(=O)O2)CC[C@H]1O]
I-48
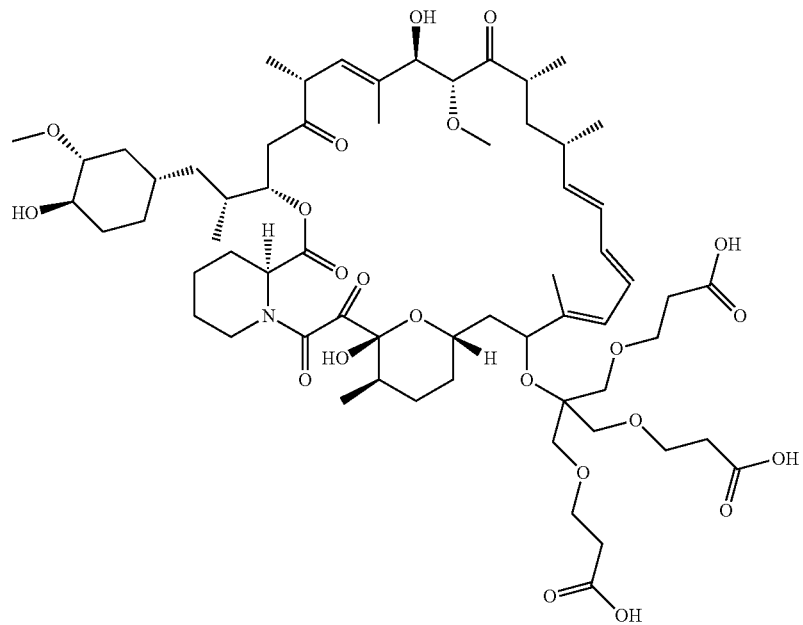 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCC(=O)O)(COCCC(=O)O)COCCC(=O)O)C[C@@H]3CC[C@@H](C)[C@@](O)(O3)C(=O)C(=O)N3CCCC[C@H]3C(=O)O2)CC[C@H]1O]
I-49

TABLE 1-continued
Exemplary Compounds
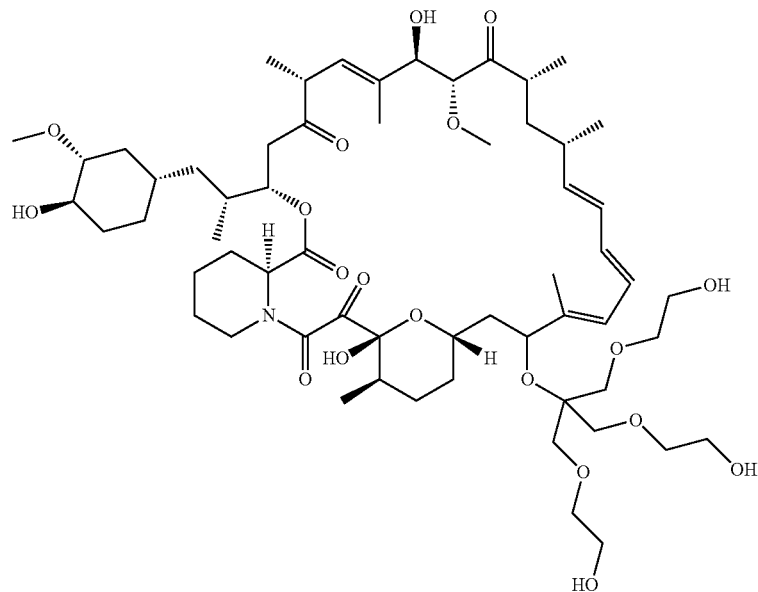 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCO)(COCCO)COCCO)C[C@@H]3CC[C@@H](C)[C@@](O)(O3)C(=O)C(=O)N3CCCC[C@H]3C(=O)O2)CC[C@H]1O]
I-50
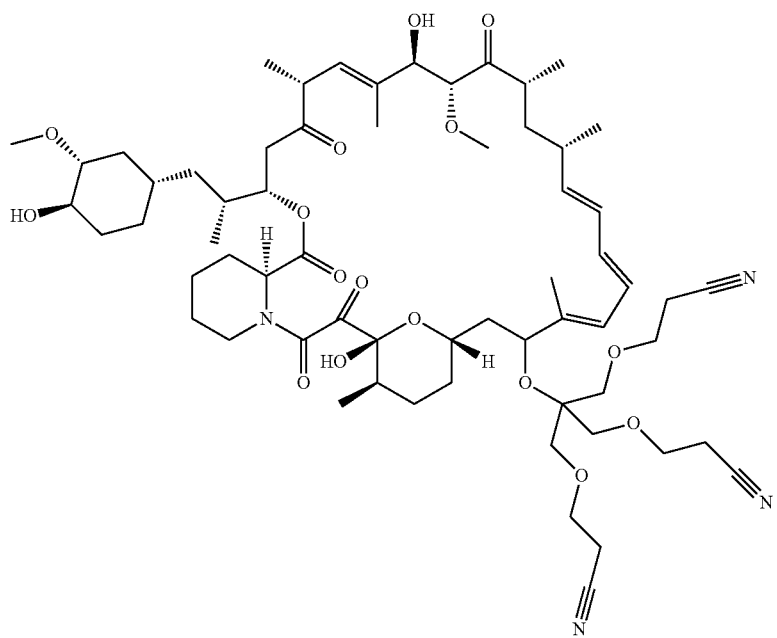 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCC#N)(COCCC#N)COCCC#N)C[C@@H]3CC[C@@H](C)[C@@](O)(O3)C(=O)C(=O)N3CCCC[C@H]3C(=O)O2)CC[C@H]1O]
I-51

TABLE 1-continued
Exemplary Compounds
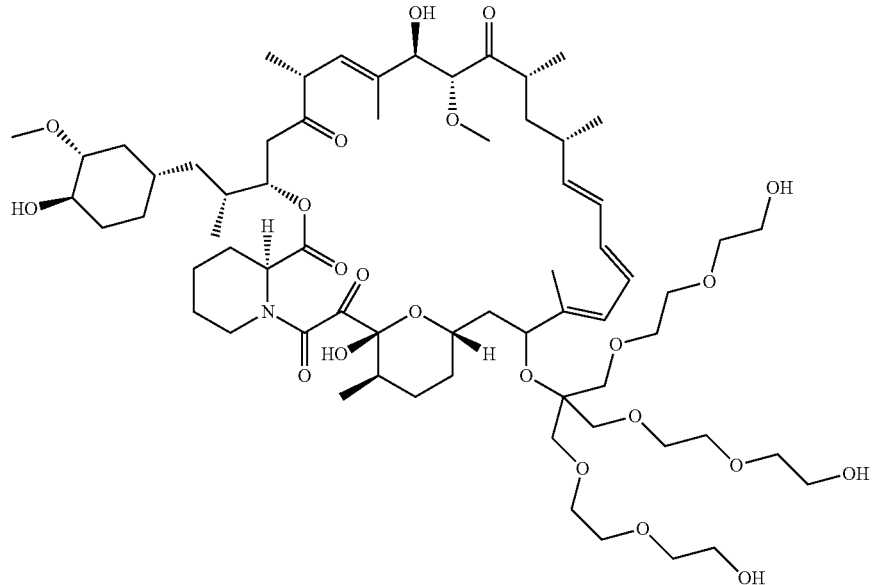 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCOCCO)(COCCOCCO)COCCOCCO)C[C@@H]3CC[C@@H](C)[C@@](O)(O3)C(=O)C(=O)N3CCCC[C@H]3C(=O)O2)CC[C@H]1O]
I-52
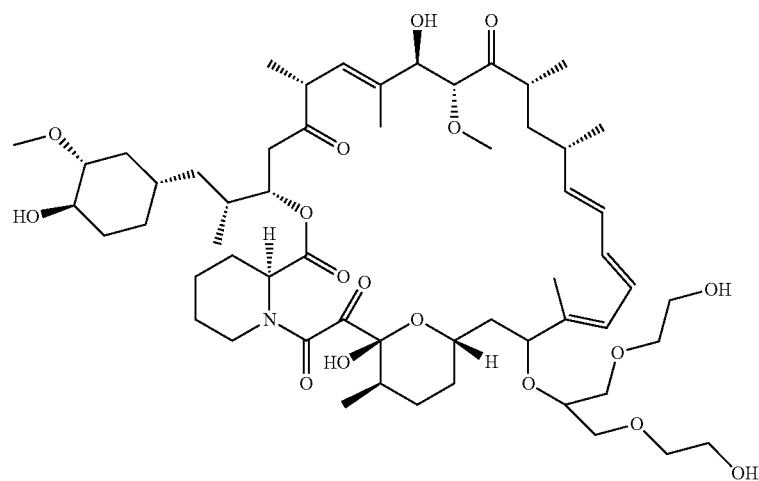 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCO)COCCO)C[C@@H]3CC[C@@H](C)[C@@](O)(O3)C(=O)C(=O)N3CCCC[C@H]3C(=O)O2)CC[C@H]1O]
I-53
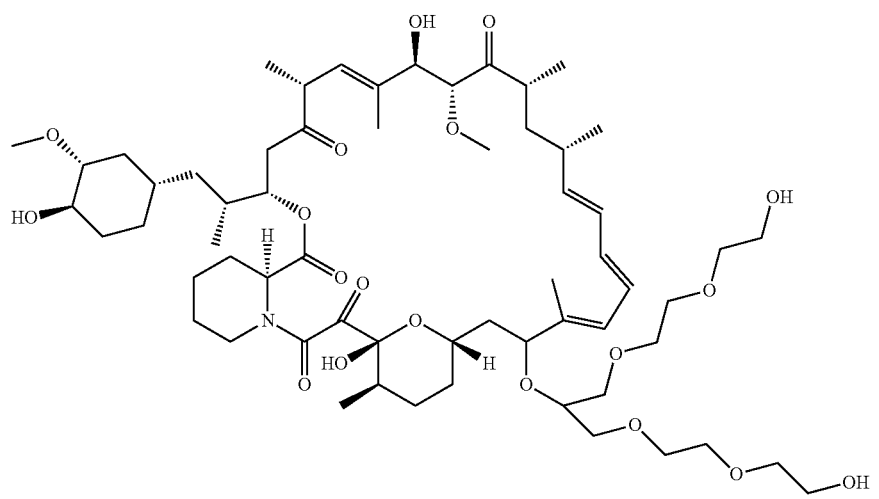 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC(COCCOCCO)COCCOCCO)C[C@@H]3CC[C@@H](C)[C@@](O)(O3)C(=O)C(=O)N3CCCC[C@H]3C(=O)O2)CC[C@H]1O]
I-54

TABLE 1-continued
Exemplary Compounds
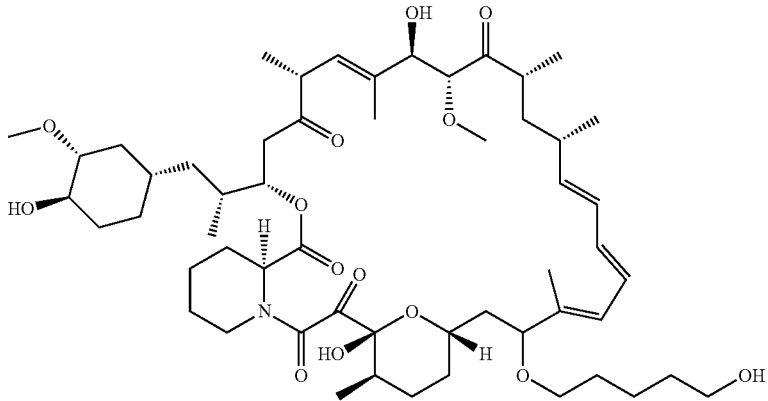 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCCCO)C[C@@H]3CC[C@@H](C)[C@@](O)(O3)C(=O)C(=O)N3CCCC[C@H]3C(=O)O2)CC[C@H]1O]
I-55
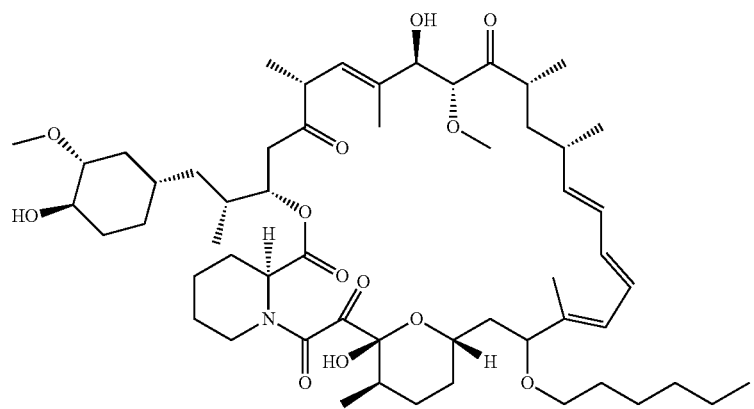 [SMILES: CCCCCCOC1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]
I-56
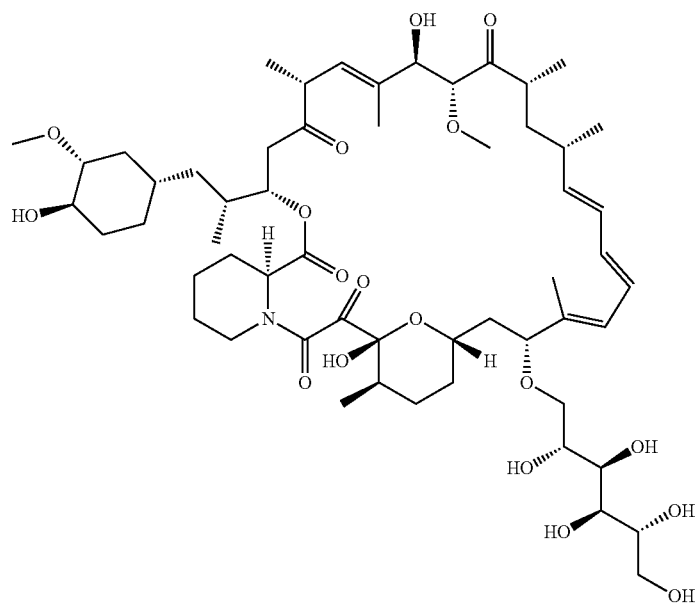 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OC[C@@H](O)[C@@H](O)[C@H](O)[C@H](O)CO)C[C@@H]3CC[C@@H](C)[C@@](O)(O3)C(=O)C(=O)N3CCCC[C@H]3C(=O)O2)CC[C@H]1O]
I-57

TABLE 1-continued
Exemplary Compounds
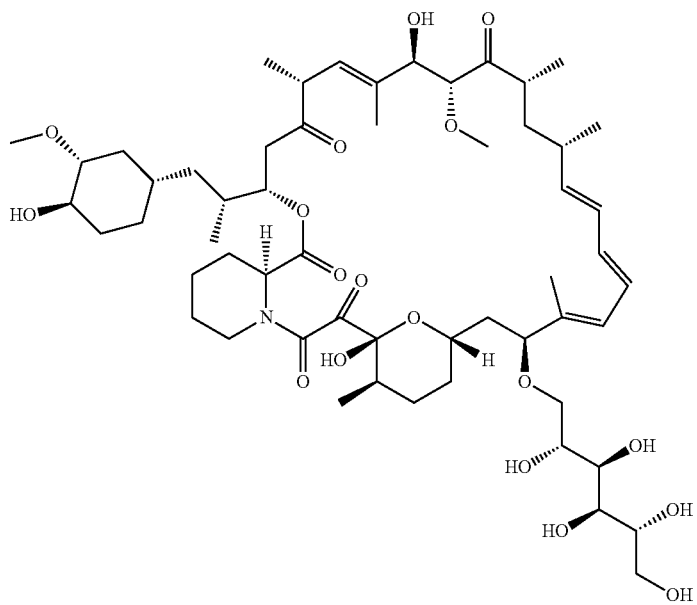 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OC[C@@H](O)[C@@H](O)[C@H](O)[C@H](O)CO)C[C@@H]3CC[C@@H](C)[C@@](O)(O3)C(=O)C(=O)N3CCCC[C@H]3C(=O)O2)CC[C@H]1O]
I-58
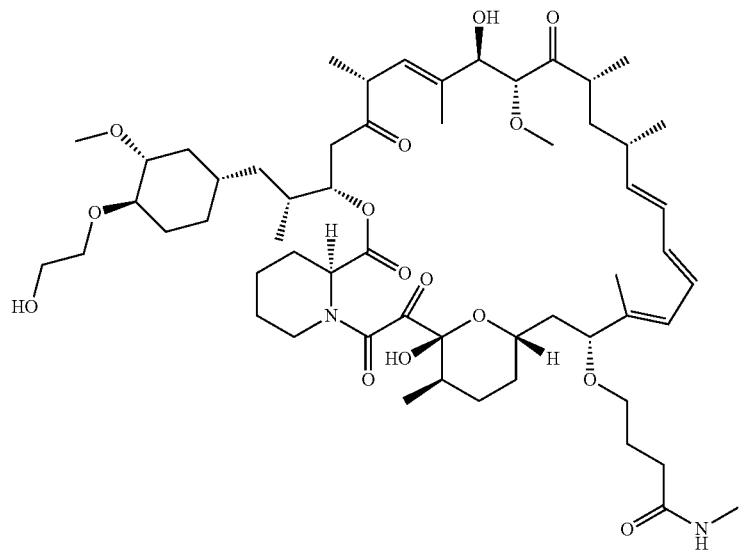
I-59

TABLE 1-continued
Exemplary Compounds
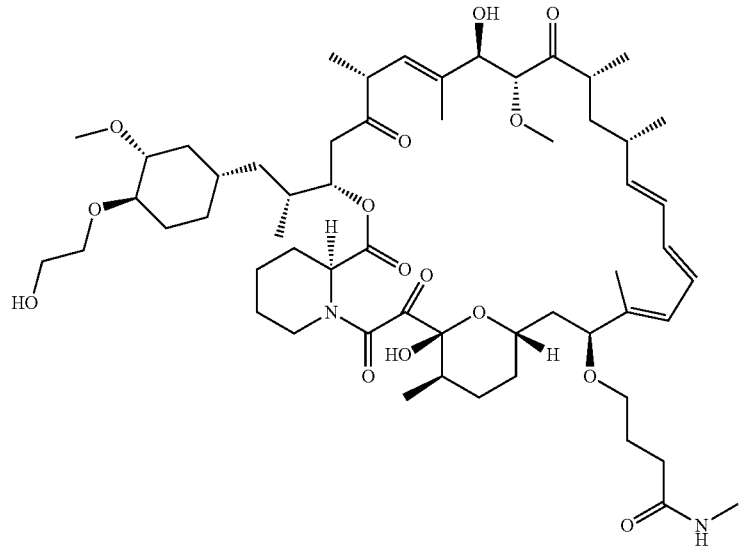 [SMILES: CNC(=O)CCCO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
I-60
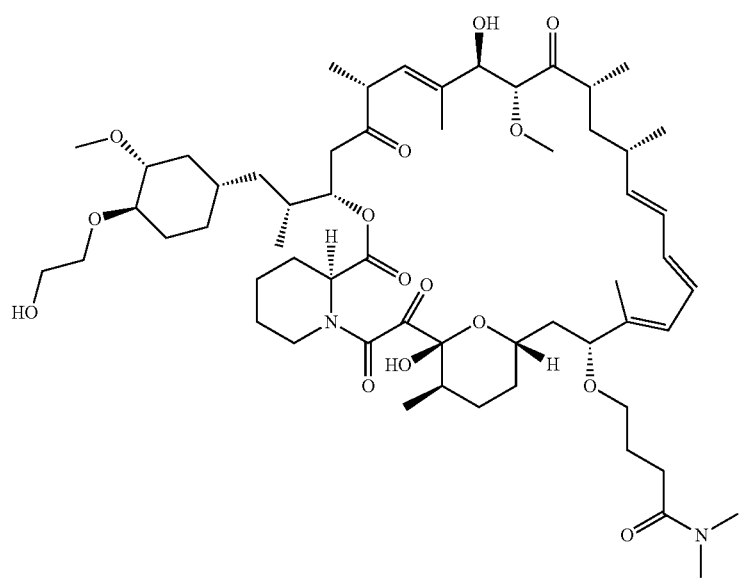
I-61

TABLE 1-continued
Exemplary Compounds
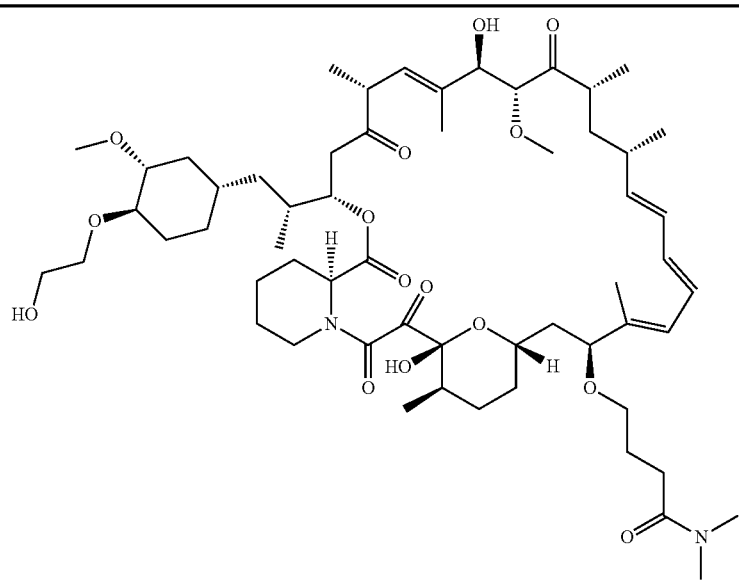
I-62
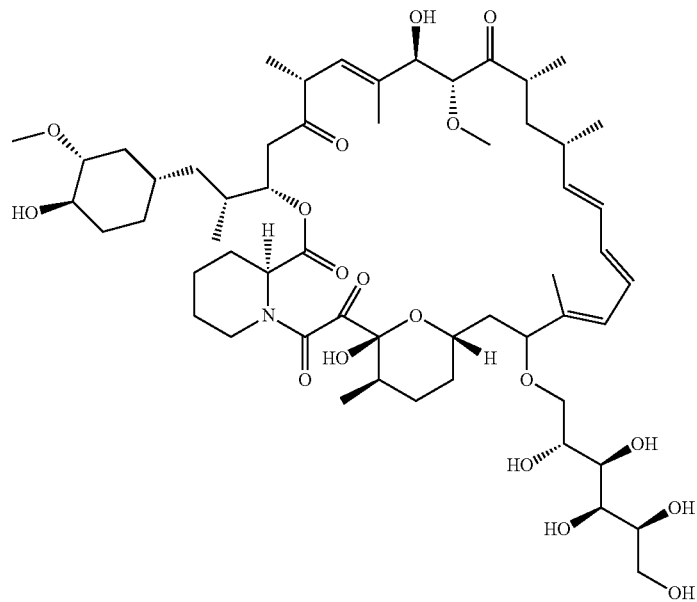 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC[C@@H](O)[C@@H](O)[C@H](O)[C@@H](O)CO)C[C@@H]3CC[C@@H](C)[C@@](O)(O3)C(=O)C(=O)N3CCCC[C@H]3C(=O)O2)CC[C@H]1O]
I-63

TABLE 1-continued
Exemplary Compounds
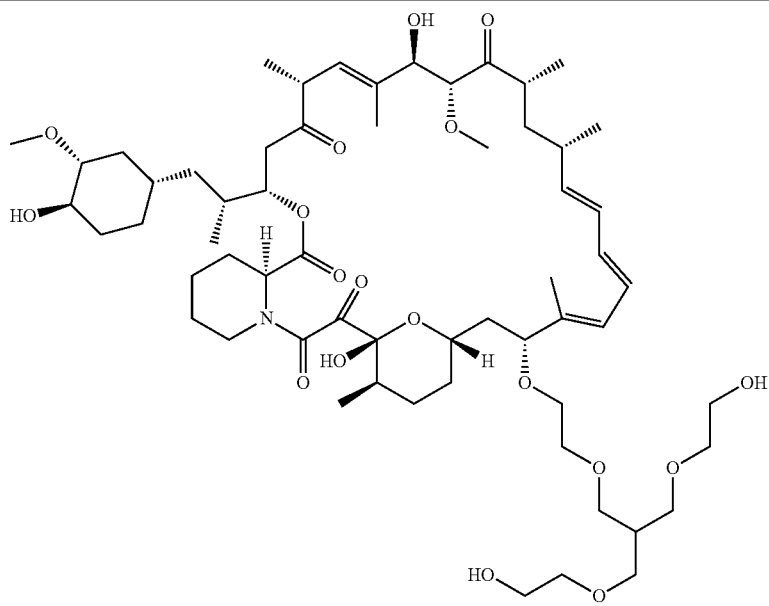
I-64
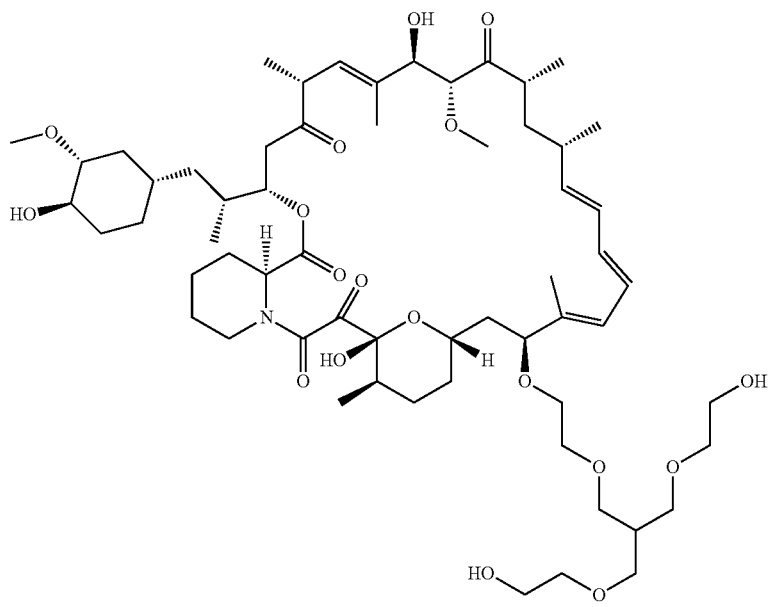 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCC(COCCO)COCCO)C[C@@H]3CC[C@@H](C)[C@@](O)(O3)C(=O)C(=O)N3CCCC[C@H]3C(=O)O2)CC[C@H]1O]
I-65

TABLE 1-continued
Exemplary Compounds
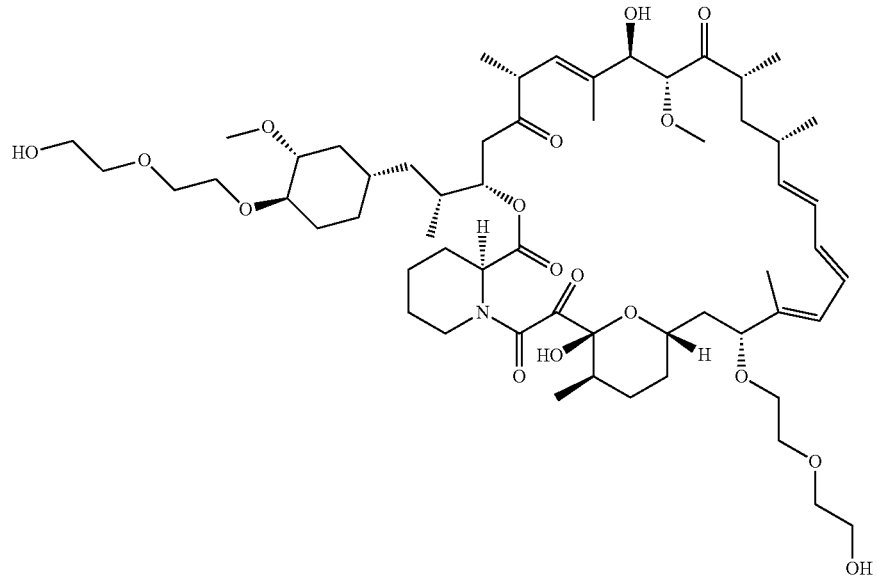 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOCCO)C[C@@H]3CC[C@@H](C)[C@@](O)(O3)C(=O)C(=O)N3CCCC[C@H]3C(=O)O2)CC[C@H]1OCCOCCO]
I-66
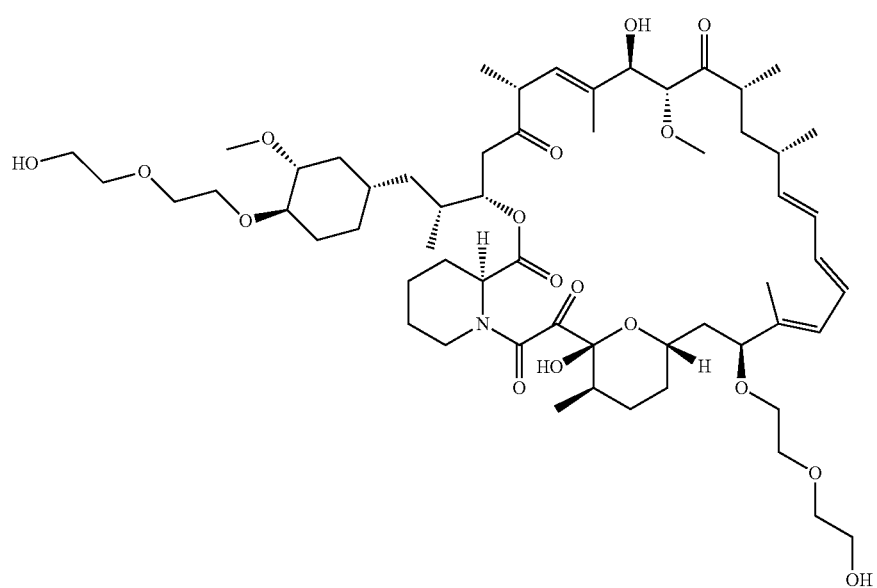 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCO)C[C@@H]3CC[C@@H](C)[C@@](O)(O3)C(=O)C(=O)N3CCCC[C@H]3C(=O)O2)CC[C@H]1OCCOCCO]
I-67

TABLE 1-continued
Exemplary Compounds
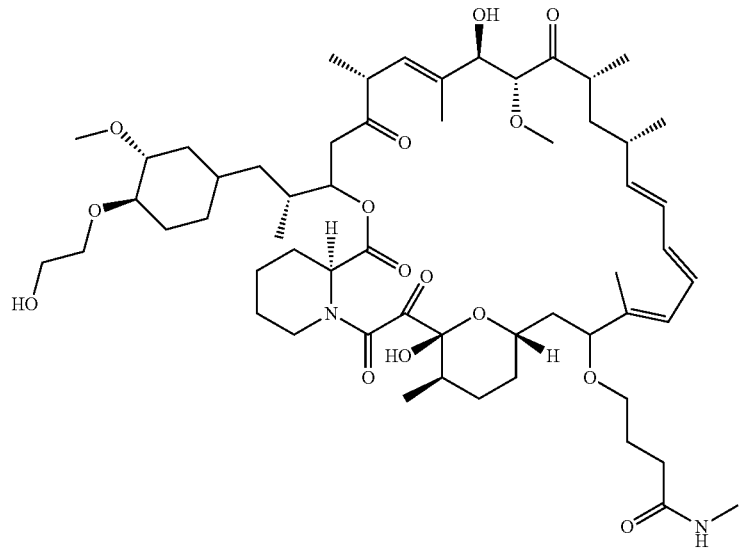 [SMILES: CNC(=O)CCCOC1C[C@@H]2CC[C@@H](C)[C@@](O)(O2)C(=O)C(=O)N2CCCC[C@H]2C(=O)OC([C@H](C)CC2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
I-68
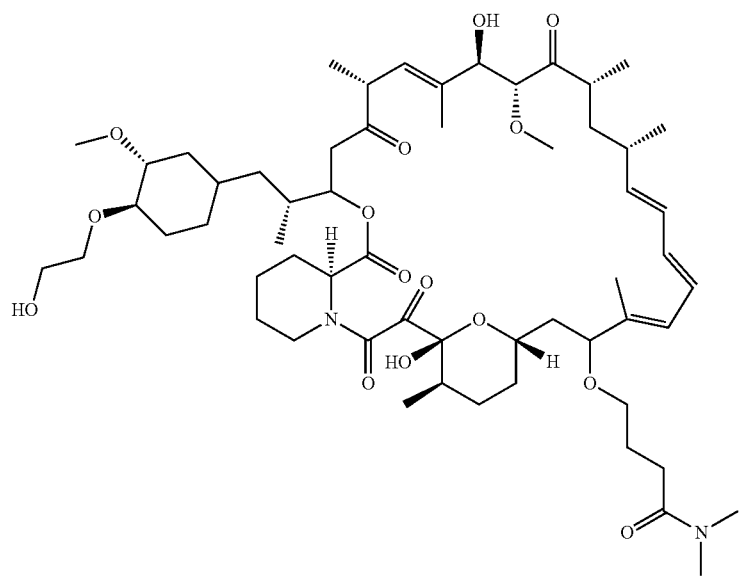 [SMILES: CO[C@@H]1CC(C[C@@H](C)C2CC(=O)[C@H](C)/C=C(\C)[C@@H](O)[C@@H](OC)C(=O)[C@H](C)C[C@H](C)/C=C/C=C/C=C(\C)C(OCCCC(=O)N(C)C)C[C@@H]3CC[C@@H](C)[C@@](O)(O3)C(=O)C(=O)N3CCCC[C@H]3C(=O)O2)CC[C@H]1OCCO]
I-69

TABLE 1-continued
Exemplary Compounds
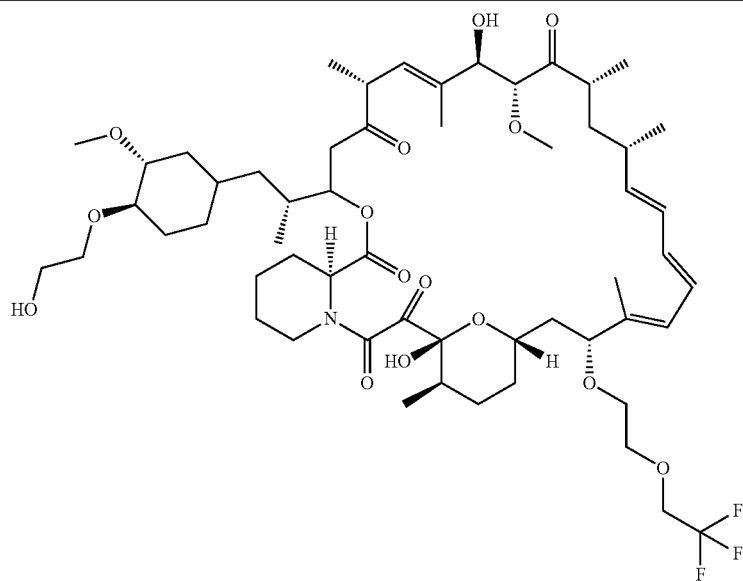
I-70
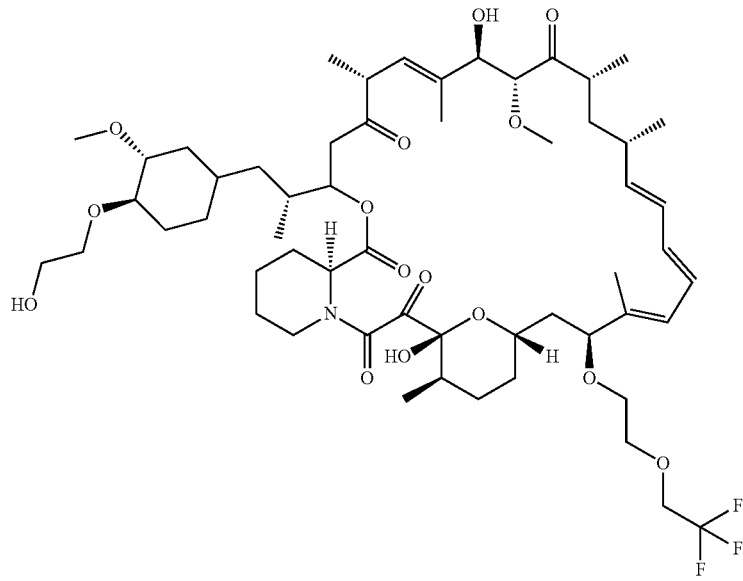 [SMILES: CO[C@@H]1CC(C[C@@H](C)C2CC(=O)[C@H](C)/C=C(\C)[C@@H](O)[C@@H](OC)C(=O)[C@H](C)C[C@H](C)/C=C/C=C/C=C(\C)[C@@H](OCCOCC(F)(F)F)C[C@@H]3CC[C@@H](C)[C@@](O)(O3)C(=O)C(=O)N3CCCC[C@H]3C(=O)O2)CC[C@H]1OCCO]
I-71

TABLE 1-continued
Exemplary Compounds
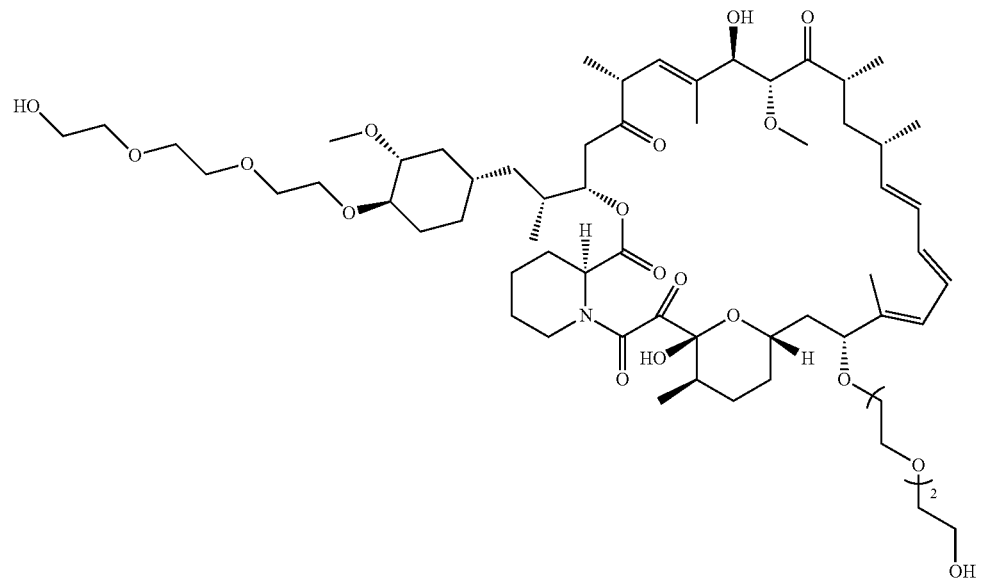
I-72
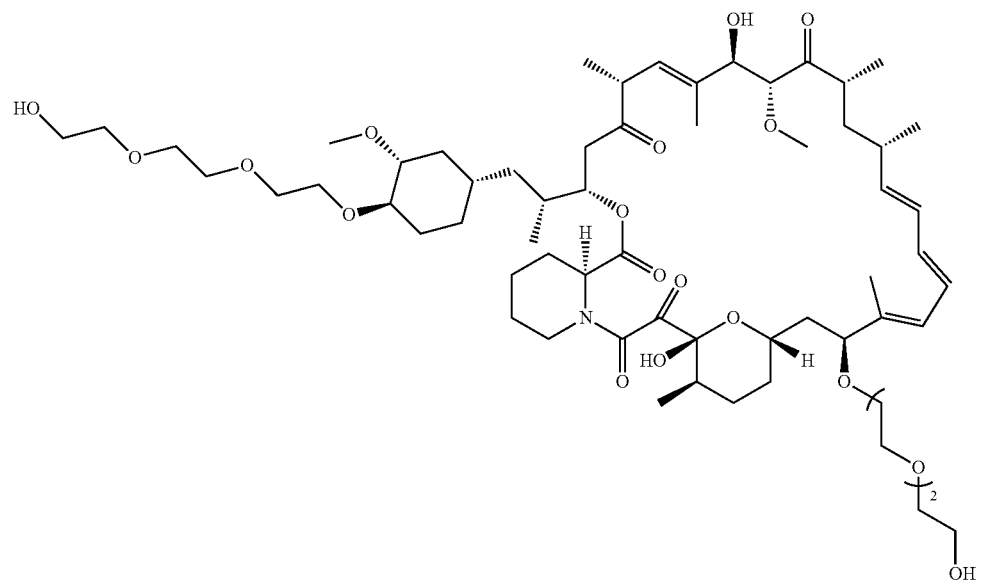
I-73

TABLE 1-continued
Exemplary Compounds
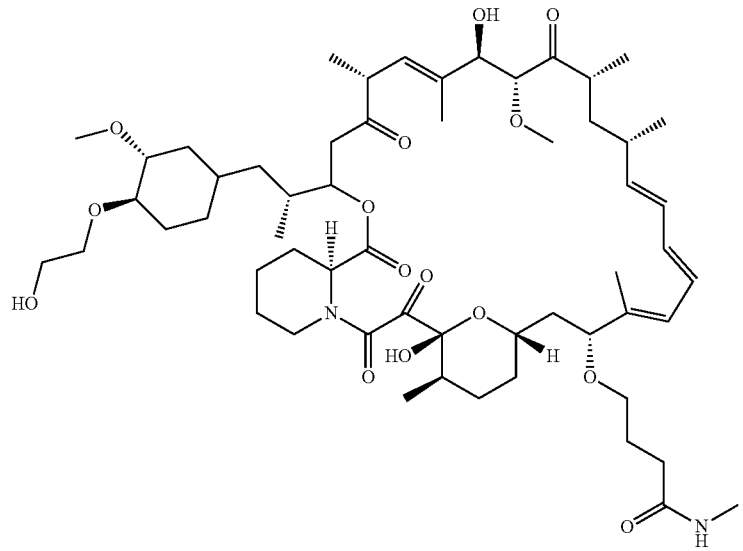
I-74
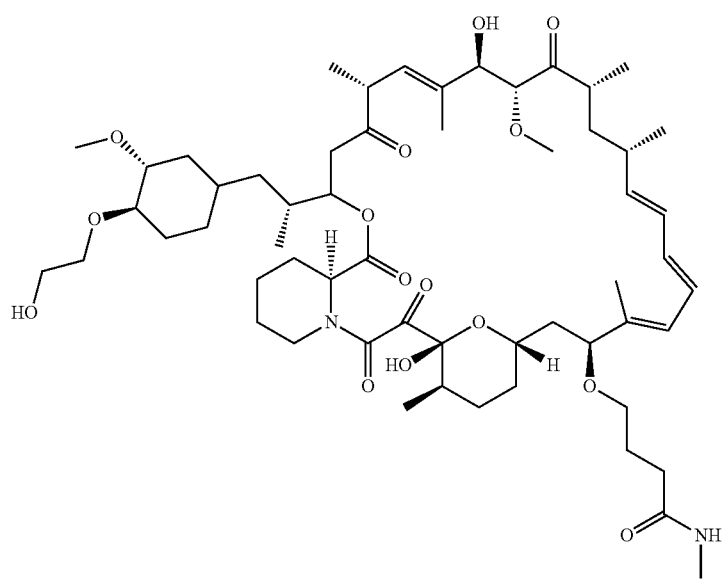 [SMILES: CNC(=O)CCCO[C@H]1C[C@@H]2CC[C@@H](C)[C@@](O)(O2)C(=O)C(=O)N2CCCC[C@H]2C(=O)OC([C@H](C)CC2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]
I-75

TABLE 1-continued
Exemplary Compounds
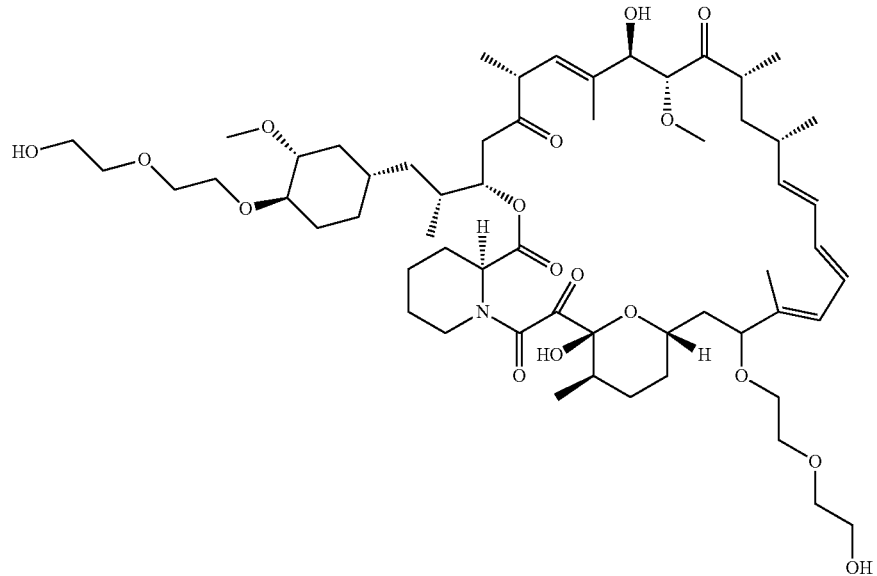
I-76
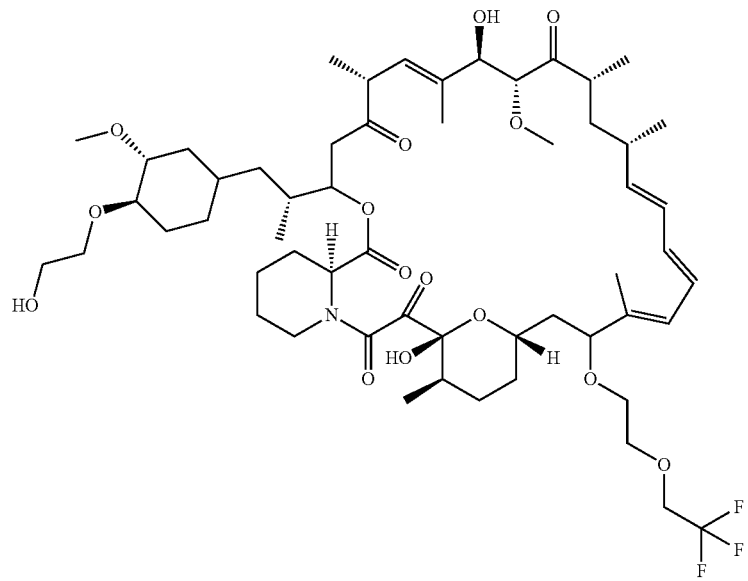 [SMILES: CO[C@@H]1CC(C[C@@H](C)C2CC(=O)[C@H](C)/C=C(\C)[C@@H](O)[C@@H](OC)C(=O)[C@H](C)C[C@H](C)/C=C/C=C/C=C(\C)C(OCCOCC(F)(F)F)C[C@@H]3CC[C@@H](C)[C@@](O)(O3)C(=O)C(=O)N3CCCC[C@H]3C(=O)O2)CC[C@H]1OCCO]
I-77

TABLE 1-continued
Exemplary Compounds
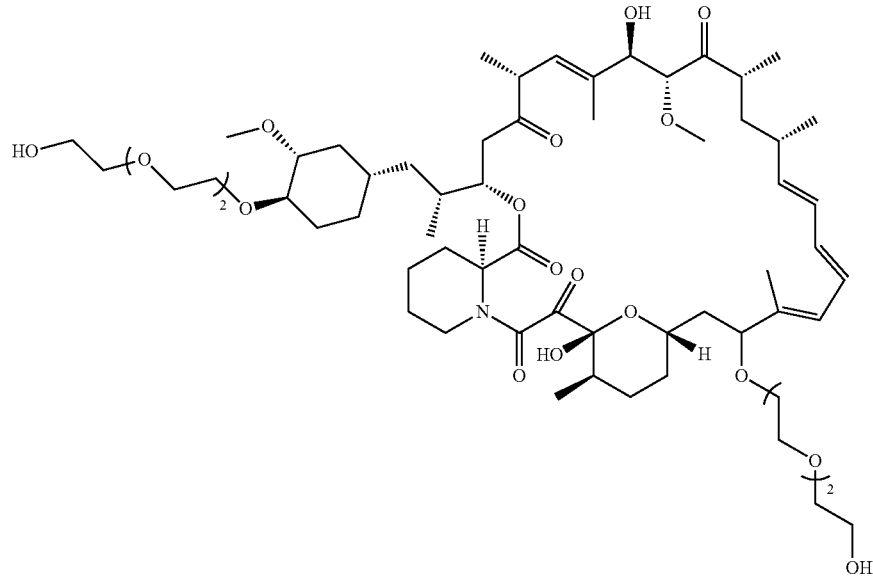
I-78
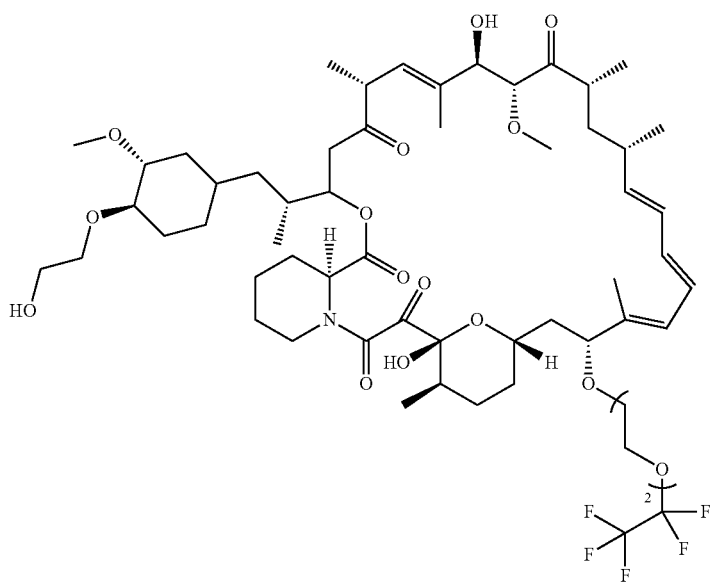
I-79

TABLE 1-continued
Exemplary Compounds
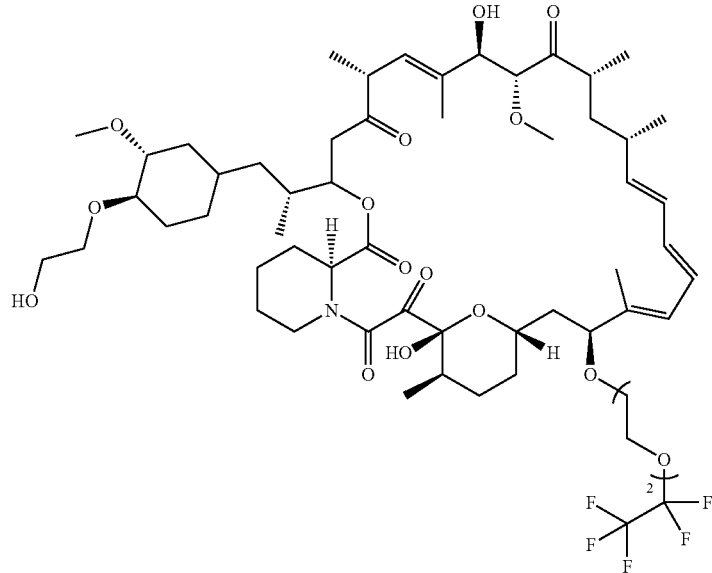
I-80
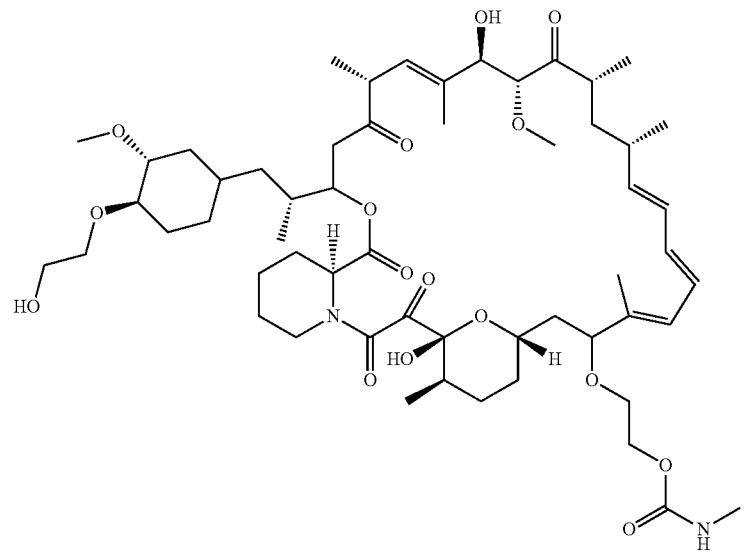
I-81

TABLE 1-continued
Exemplary Compounds
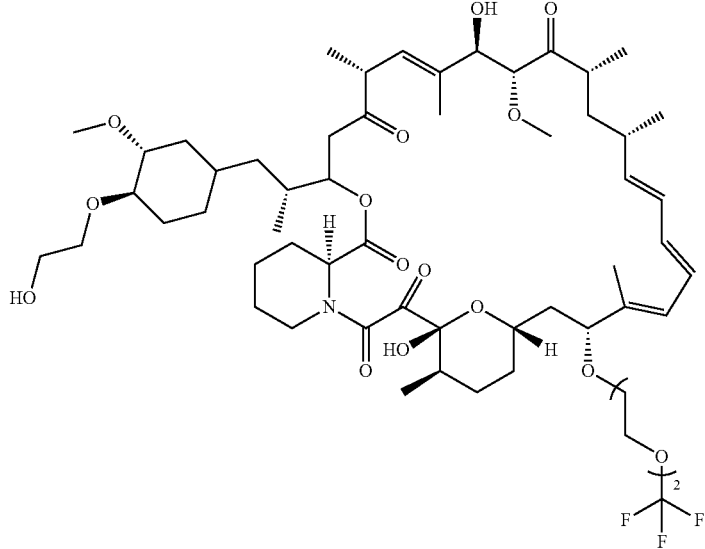
I-82
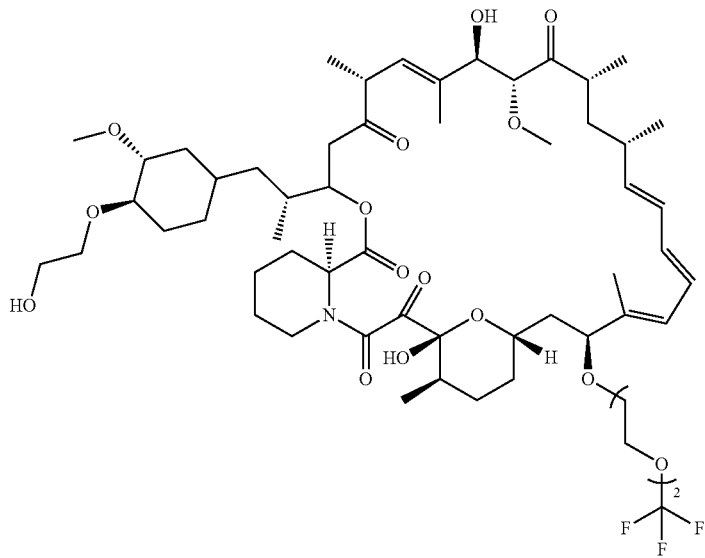
I-83

TABLE 1-continued
Exemplary Compounds
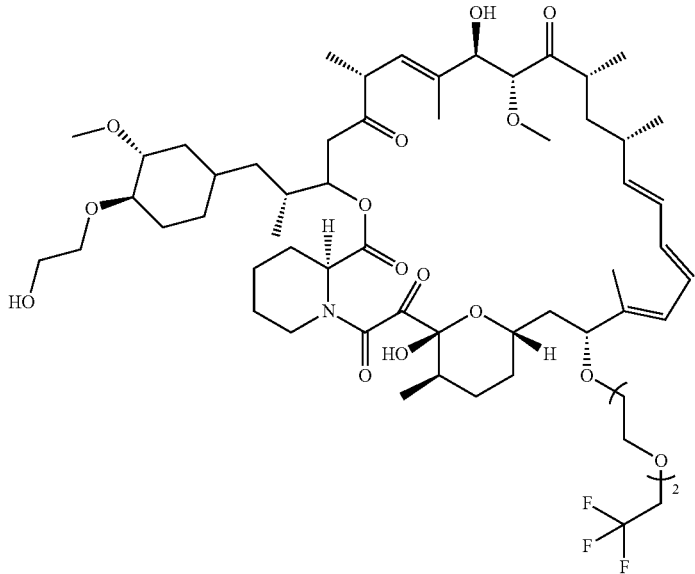
I-84
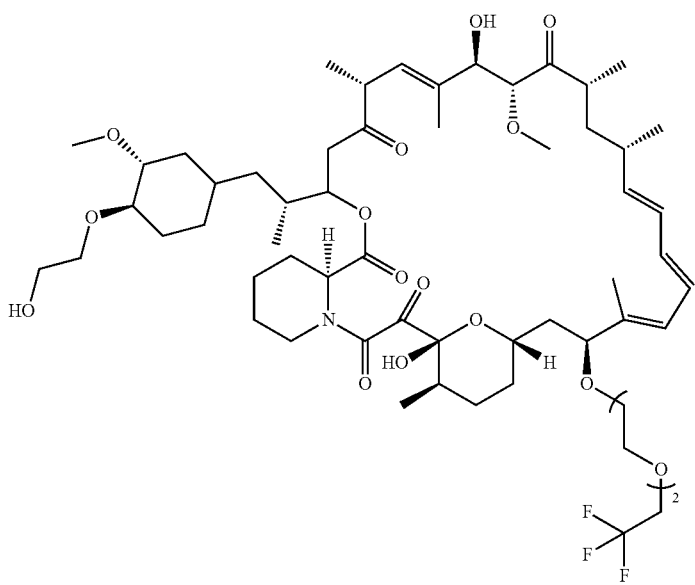
I-85

TABLE 1-continued
Exemplary Compounds
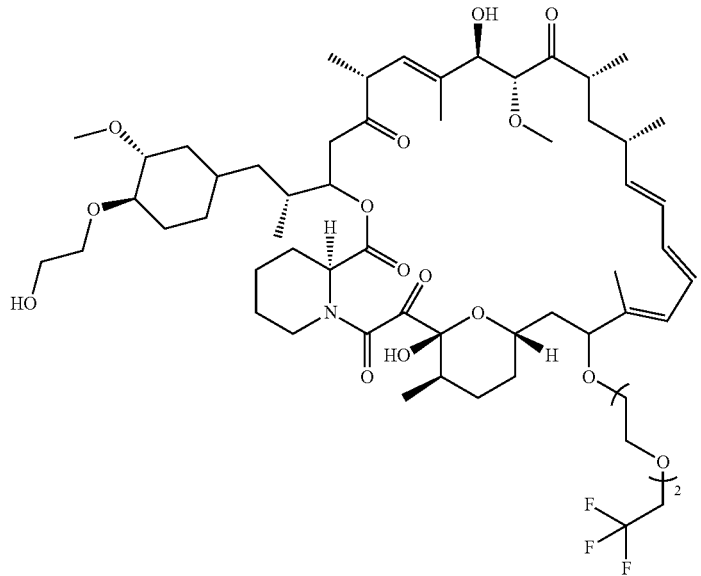
I-86
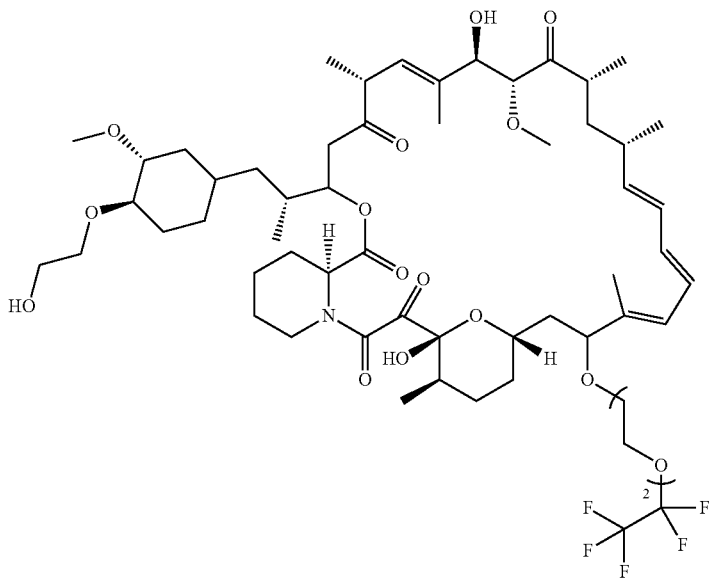
I-87

TABLE 1-continued
Exemplary Compounds
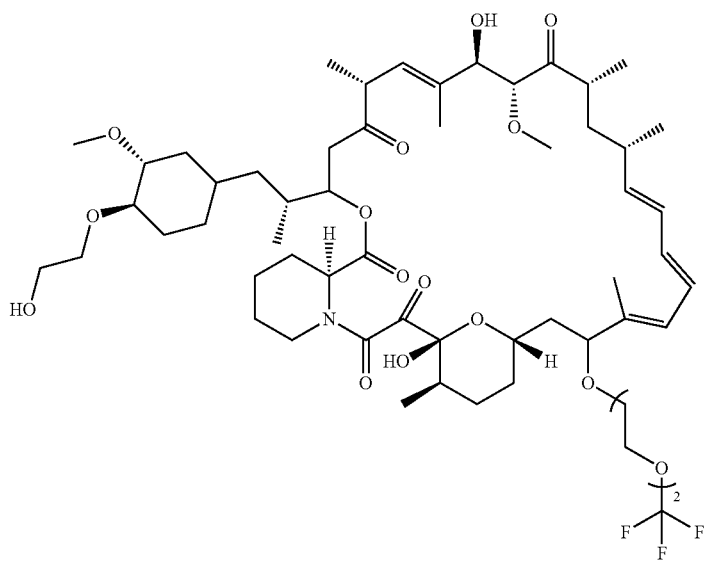
I-88
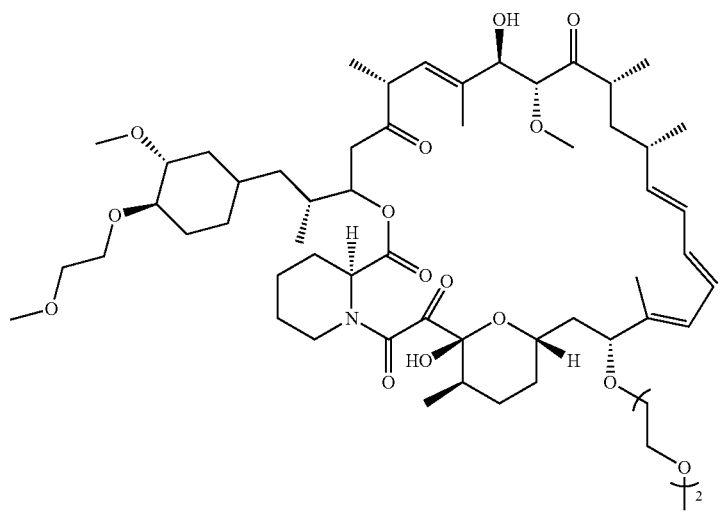
I-89
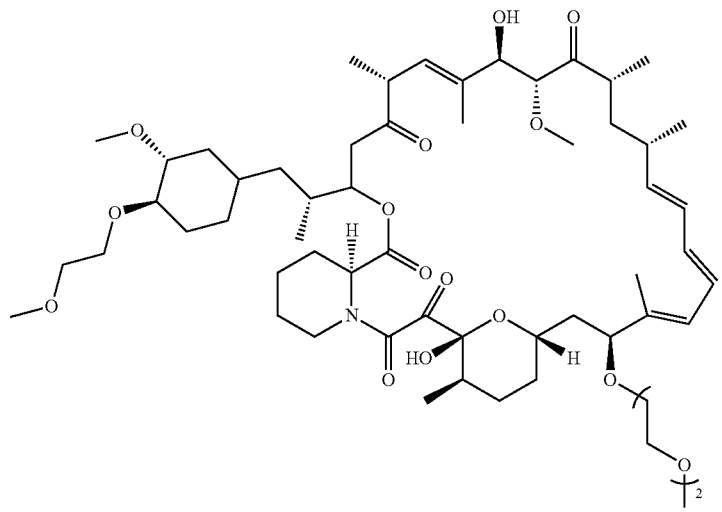
I-90

TABLE 1-continued
Exemplary Compounds
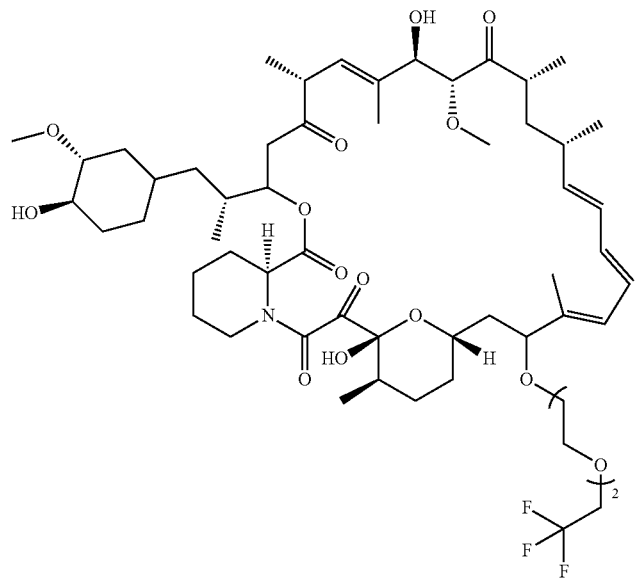
I-91
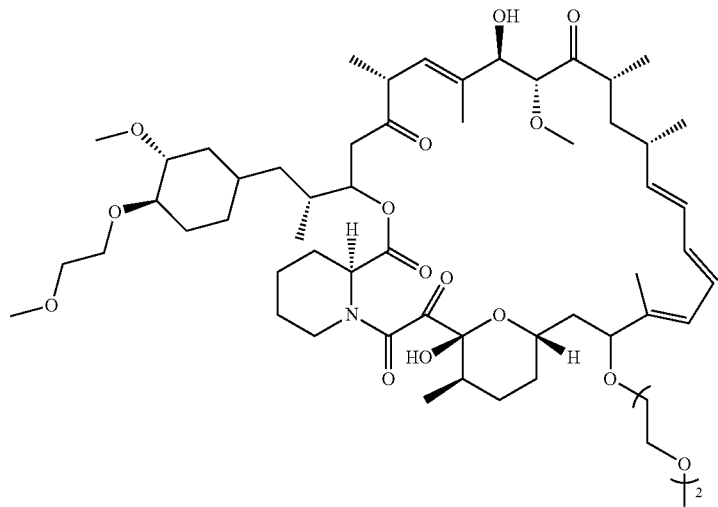
I-92

TABLE 1-continued
Exemplary Compounds
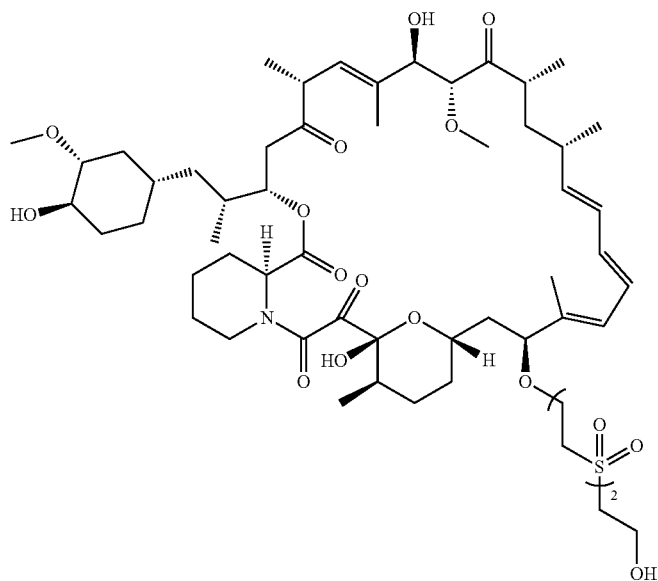
I-95
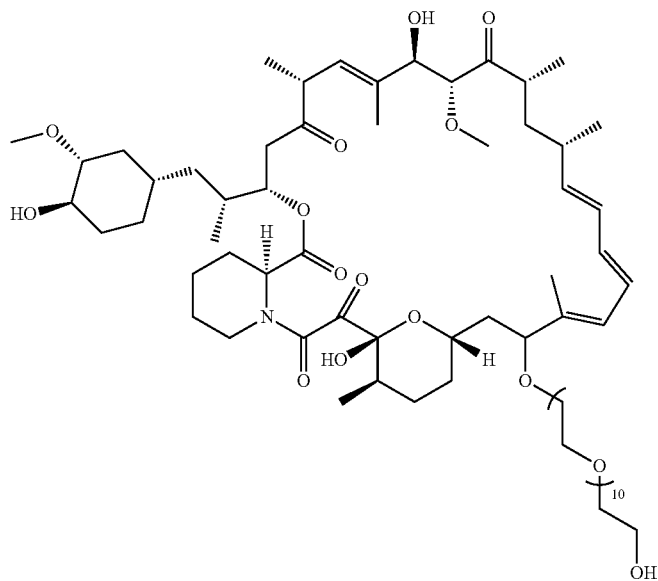
I-96

TABLE 1-continued
Exemplary Compounds
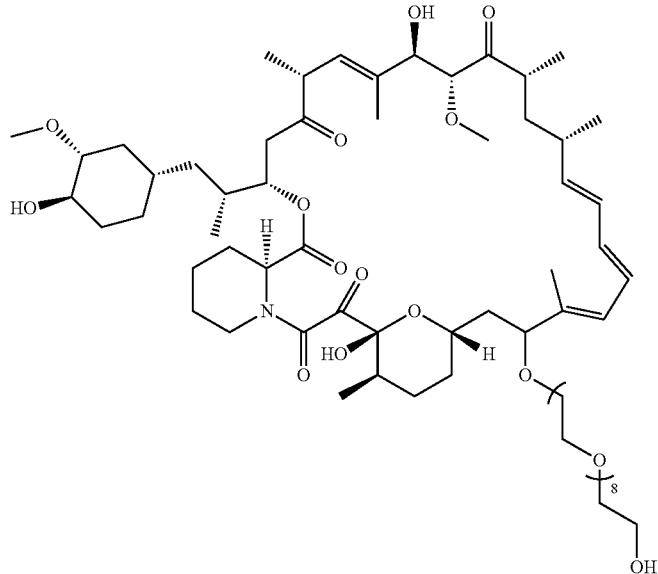
I-97
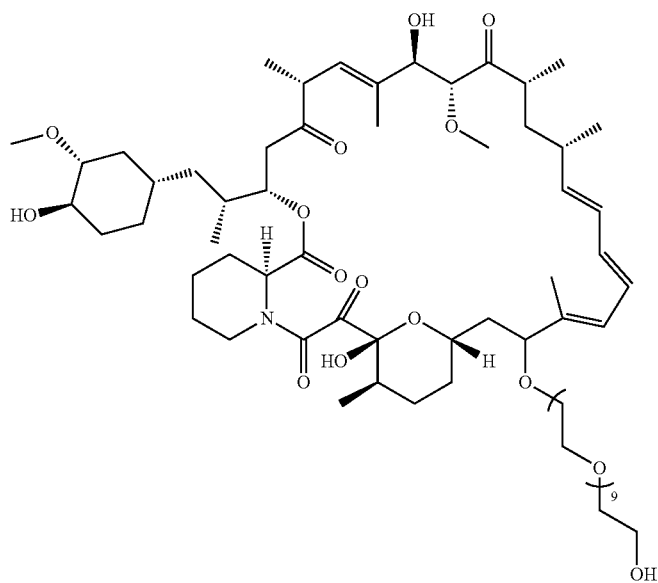
I-98

TABLE 1-continued
Exemplary Compounds
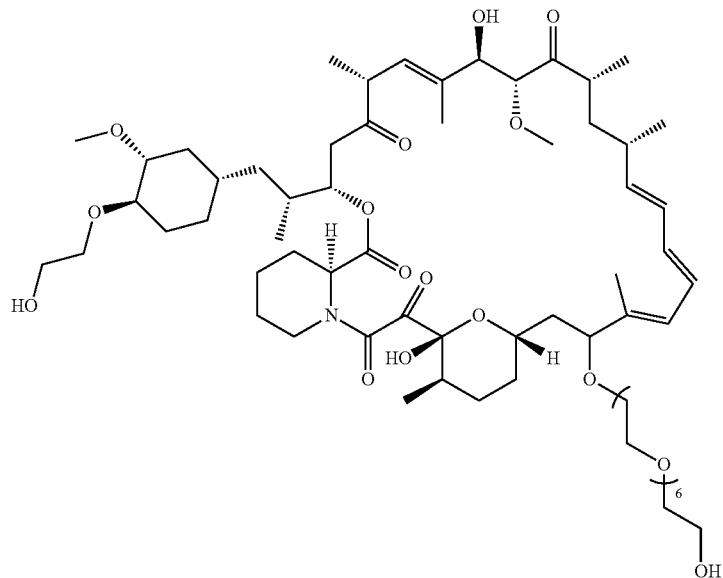
I-99
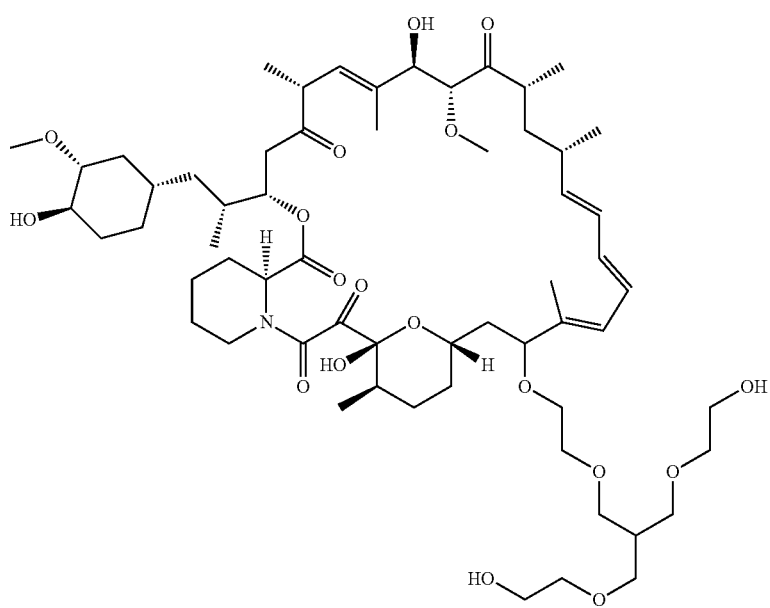 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCC(COCCO)COCCO)C[C@@H]3CC[C@@H](C)[C@@](O)(O3)C(=O)C(=O)N3CCCC[C@H]3C(=O)O2)CC[C@H]1O]
I-100

TABLE 1-continued
Exemplary Compounds
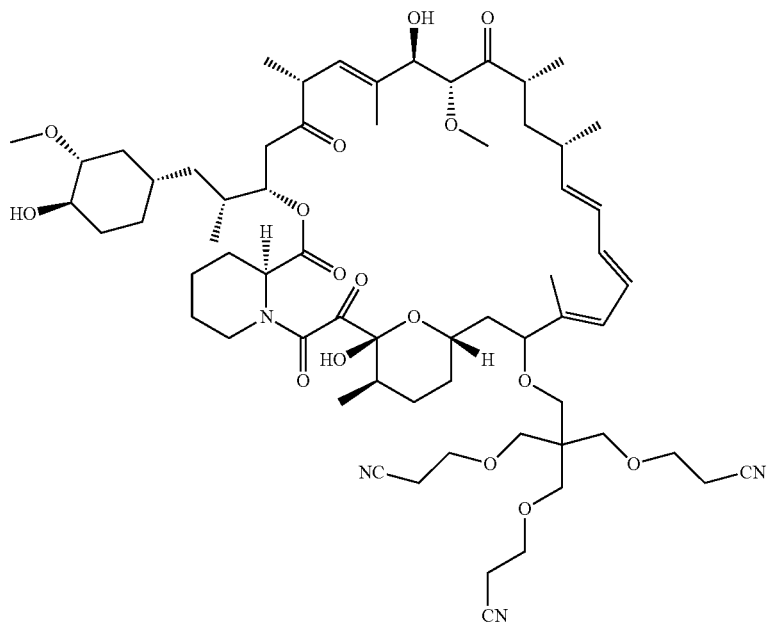 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCC(COCCC#N)(COCCC#N)COCCC#N)C[C@@H]3CC[C@@H](C)[C@@](O)(O3)C(=O)C(=O)N3CCCC[C@H]3C(=O)O2)CC[C@H]1O]
I-101
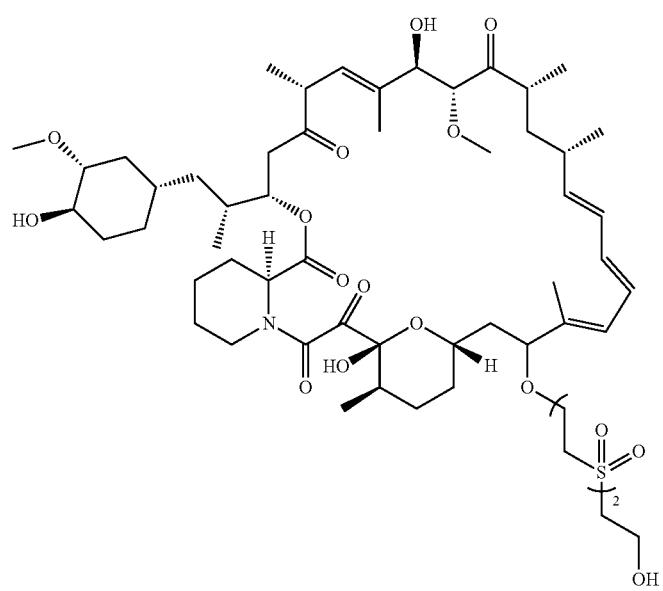
I-102

TABLE 1-continued
Exemplary Compounds
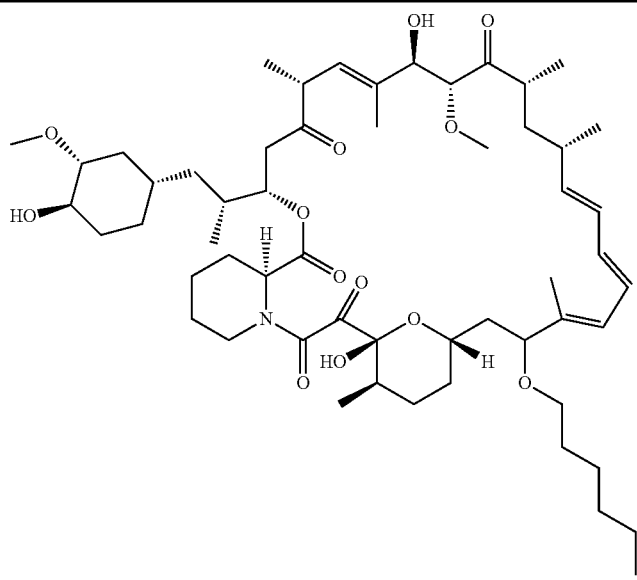
I-103
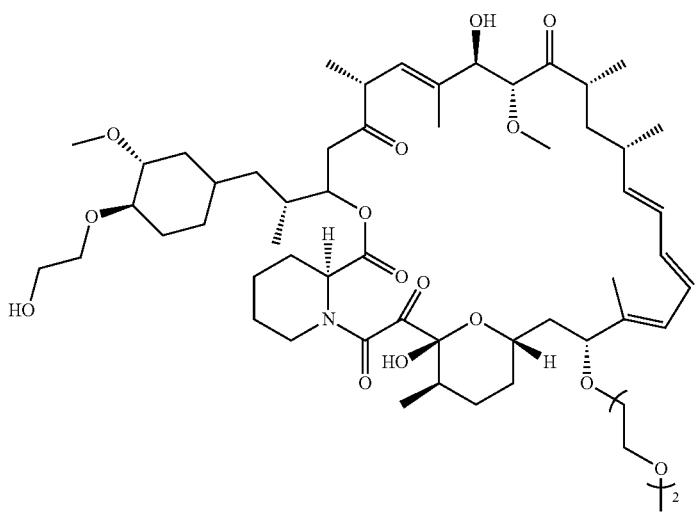
I-104
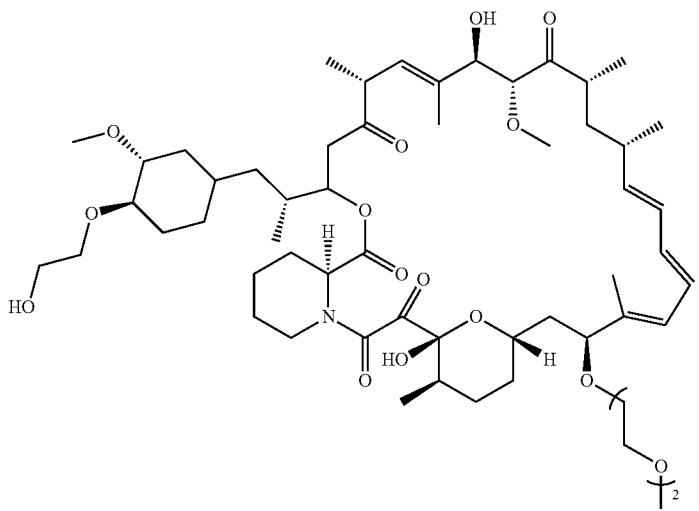
I-105

TABLE 1-continued
Exemplary Compounds
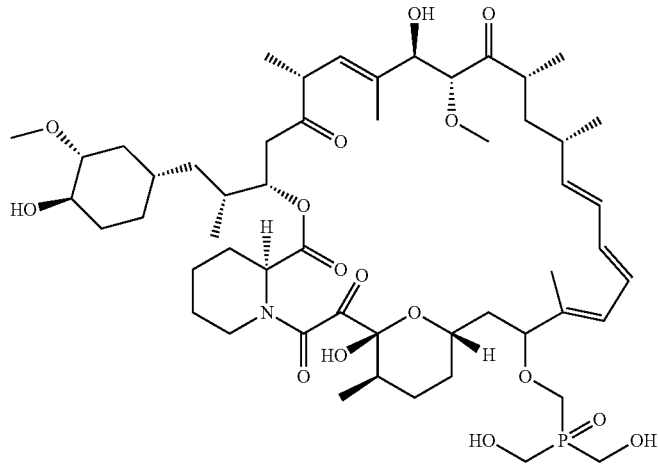 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCP(=O)(CO)CO)C[C@@H]3CC[C@@H](C)[C@@](O)(O3)C(=O)C(=O)N3CCCC[C@H]3C(=O)O2)CC[C@H]1O]
I-106
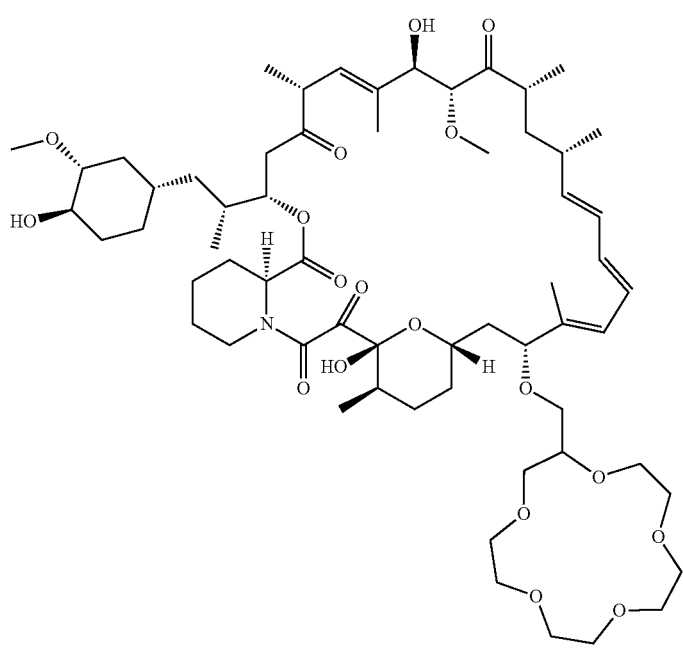 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCC3COCCOCCOCCOCCO3)C[C@@H]3CC[C@@H](C)[C@@](O)(O3)C(=O)C(=O)N3CCCC[C@H]3C(=O)O2)CC[C@H]1O]
I-107

TABLE 1-continued
Exemplary Compounds
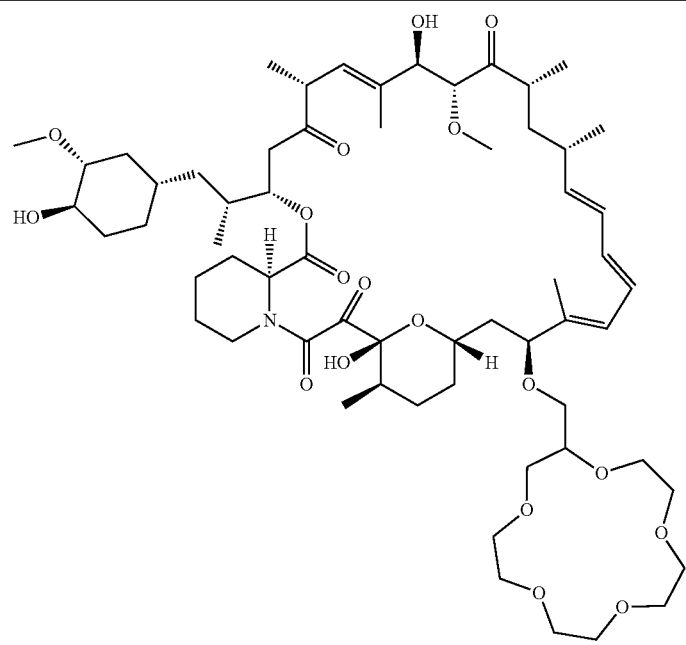
I-108
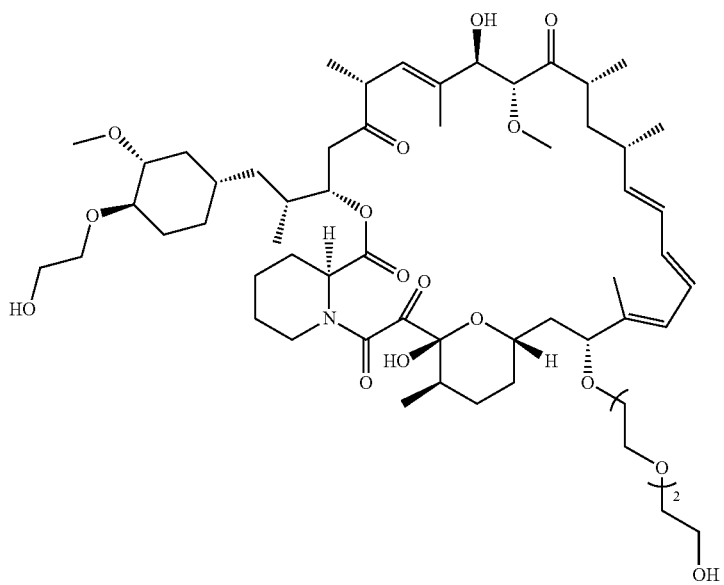
I-109

TABLE 1-continued
Exemplary Compounds
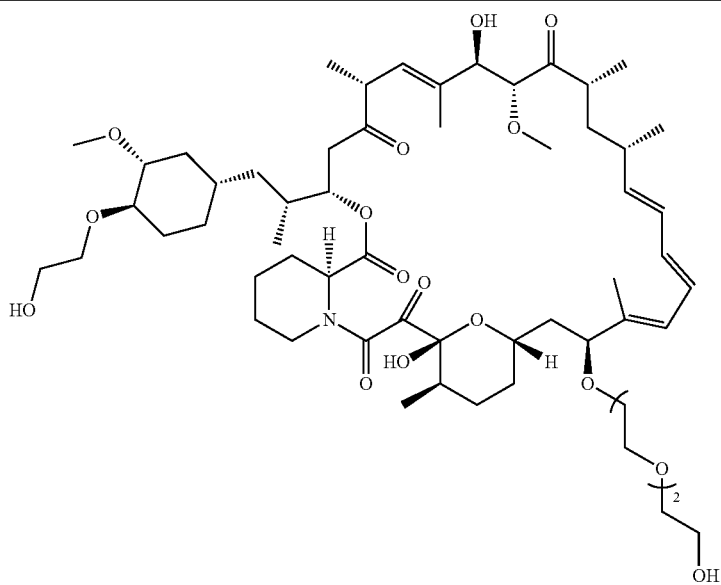
I-110
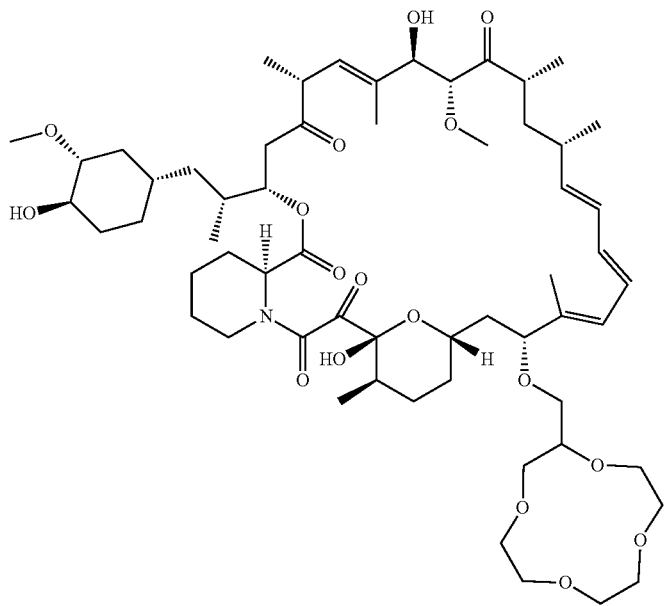 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCC3COCCOCCOCCO3)C[C@@H]3CC[C@@H](C)[C@@](O)(O3)C(=O)C(=O)N3CCCC[C@H]3C(=O)O2)CC[C@H]1O]
I-111

TABLE 1-continued
Exemplary Compounds
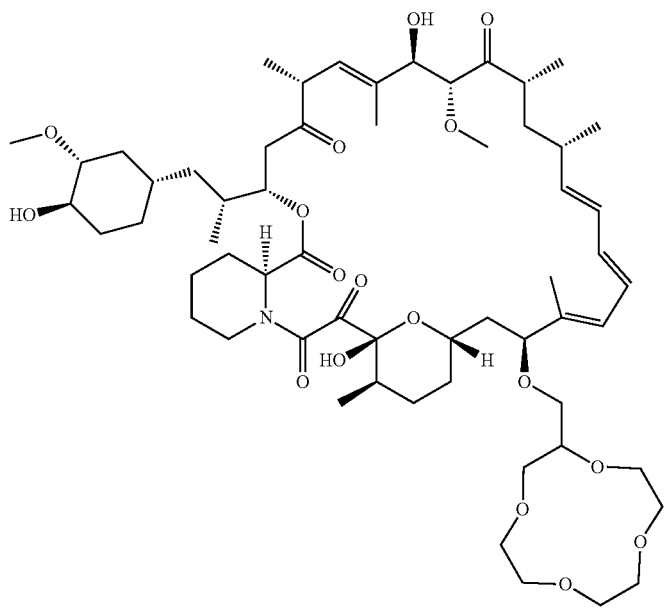 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCC3COCCOCCOCCO3)C[C@@H]3CC[C@@H](C)[C@@](O)(O3)C(=O)C(=O)N3CCCC[C@H]3C(=O)O2)CC[C@H]1O]
I-112
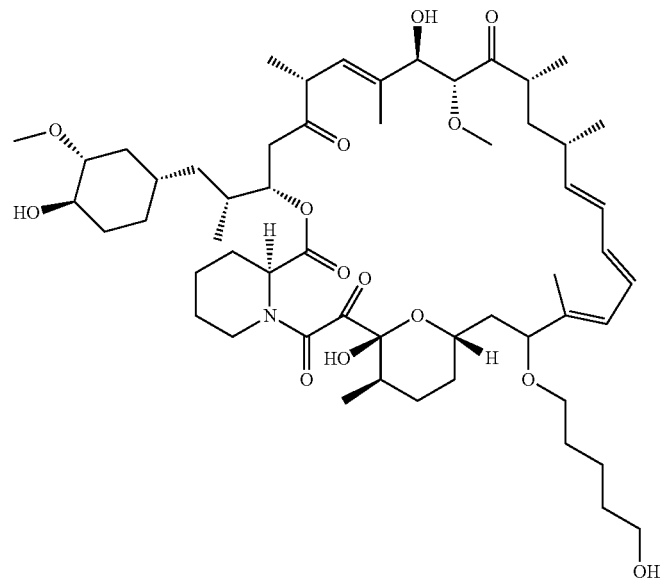 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCCCO)C[C@@H]3CC[C@@H](C)[C@@](O)(O3)C(=O)C(=O)N3CCCC[C@H]3C(=O)O2)CC[C@H]1O]
I-113

TABLE 1-continued
Exemplary Compounds
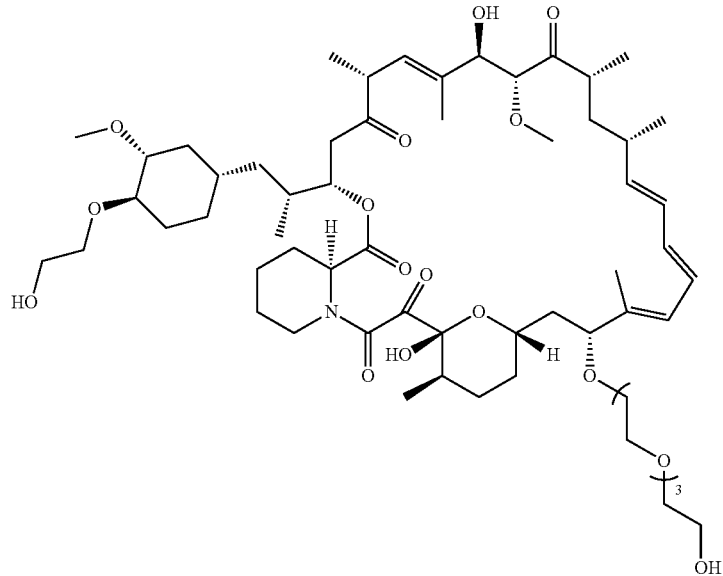
I-114
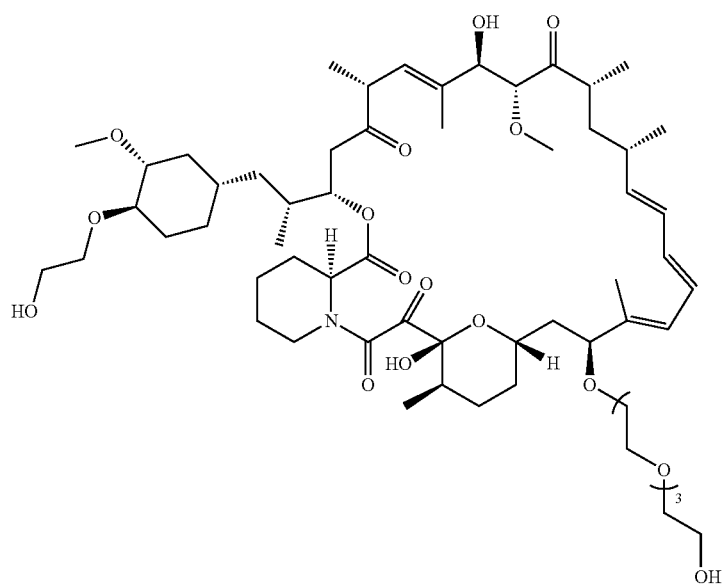
I-115

TABLE 1-continued
Exemplary Compounds
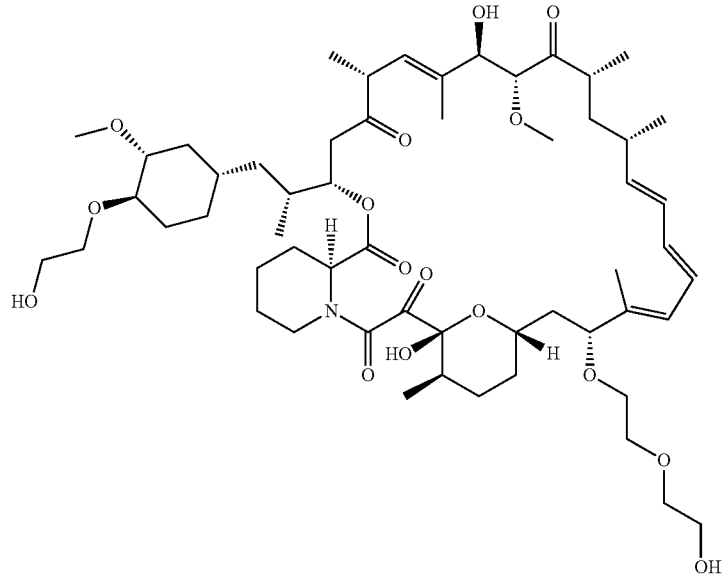 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOCCO)C[C@@H]3CC[C@@H](C)[C@@](O)(O3)C(=O)C(=O)N3CCCC[C@H]3C(=O)O2)CC[C@H]1OCCO]
I-116
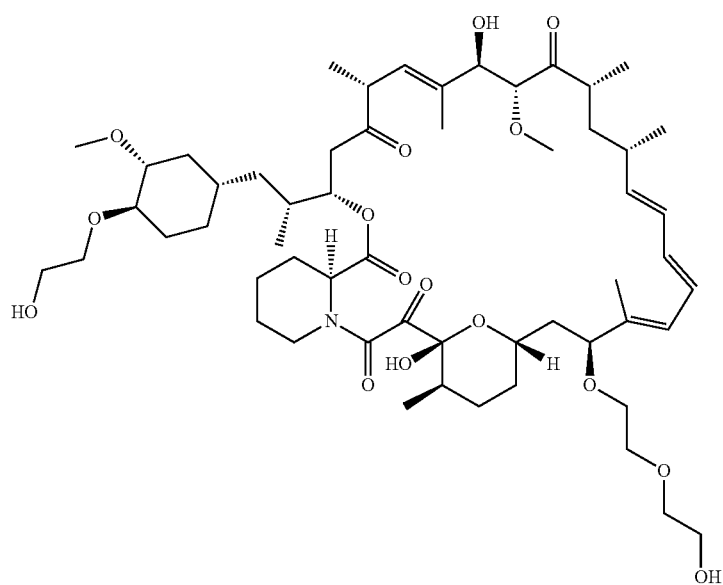 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCO)C[C@@H]3CC[C@@H](C)[C@@](O)(O3)C(=O)C(=O)N3CCCC[C@H]3C(=O)O2)CC[C@H]1OCCO]
I-117

TABLE 1-continued
Exemplary Compounds
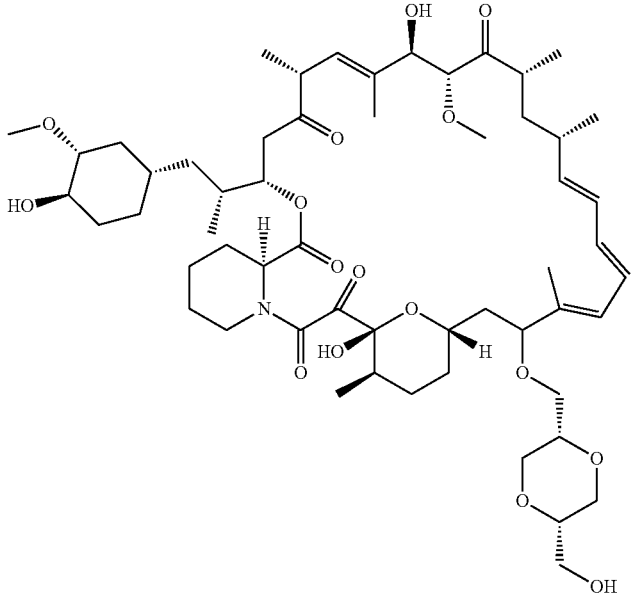 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OC[C@H]3CO[C@@H](CO)CO3)C[C@@H]3CC[C@@H](C)[C@@](O)(O3)C(=O)C(=O)N3CCCC[C@H]3C(=O)O2)CC[C@H]1O]
I-118
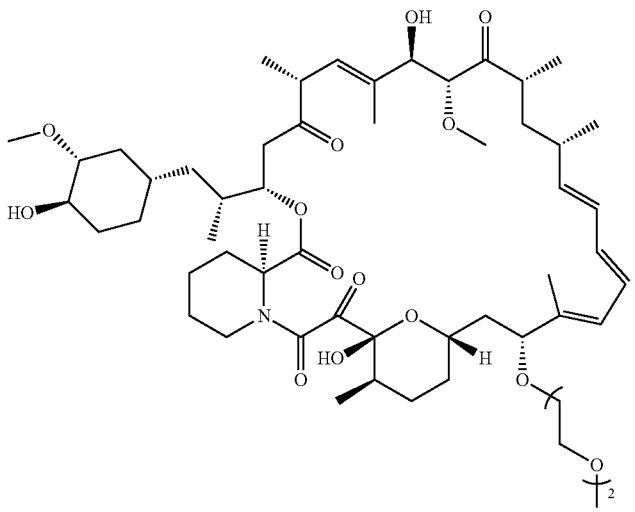
I-119
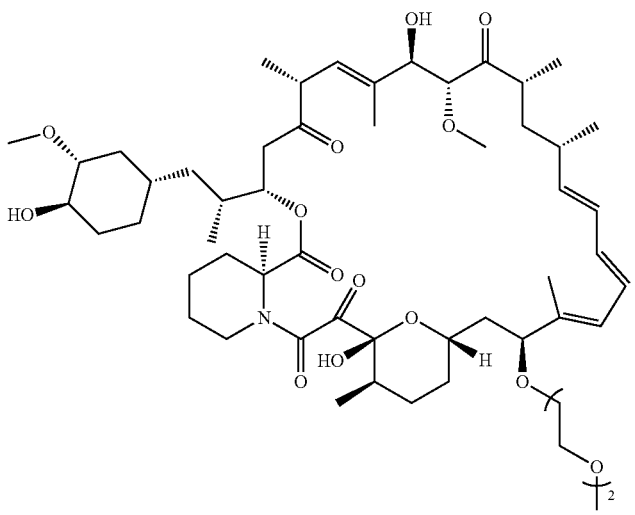
I-120

TABLE 1-continued
Exemplary Compounds
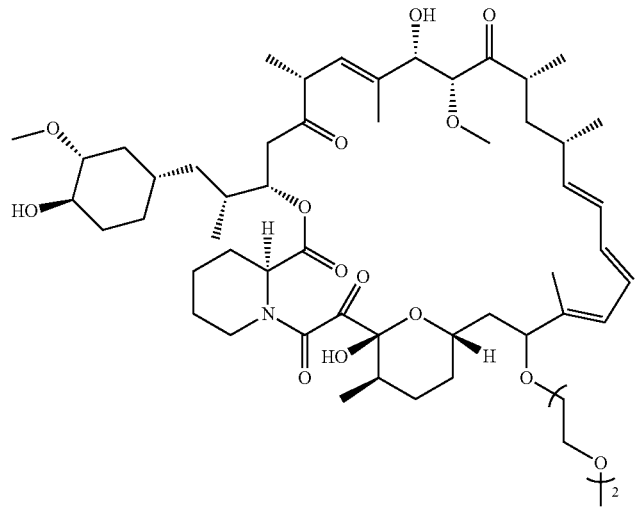
I-121
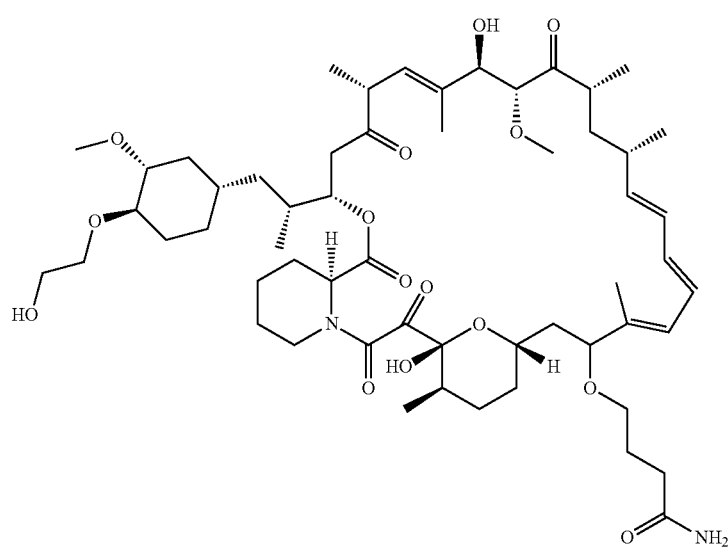 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCCC(N)=O)C[C@@H]3CC[C@@H](C)[C@@](O)(O3)C(=O)C(=O)N3CCCC[C@H]3C(=O)O2)CC[C@H]1OCCO]
I-123

TABLE 1-continued
Exemplary Compounds
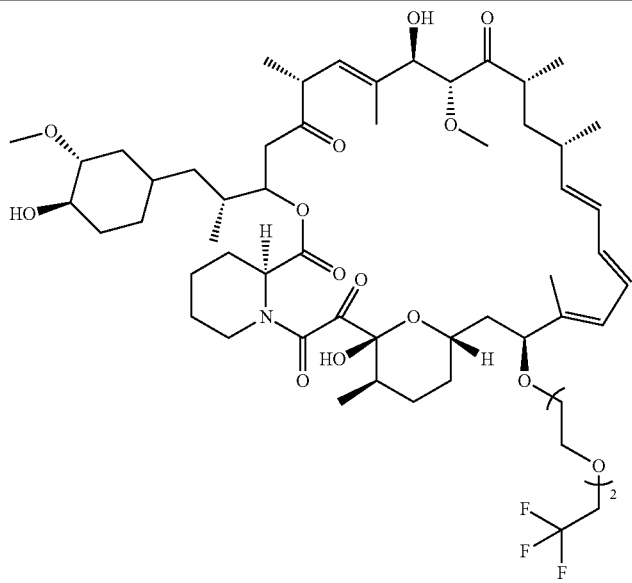
I-125
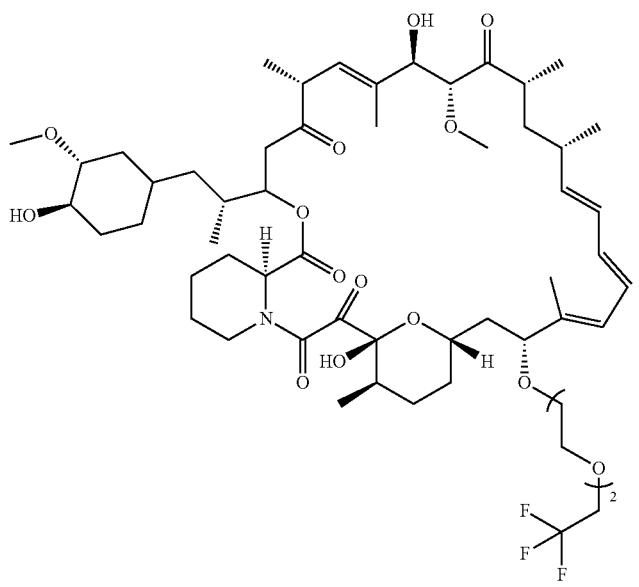
I-126
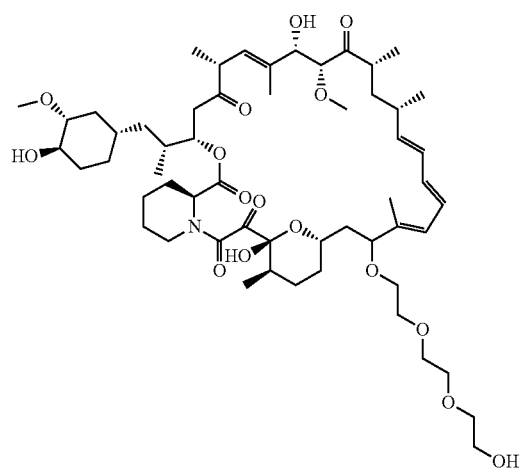
I-127

TABLE 1-continued

Exemplary Compounds

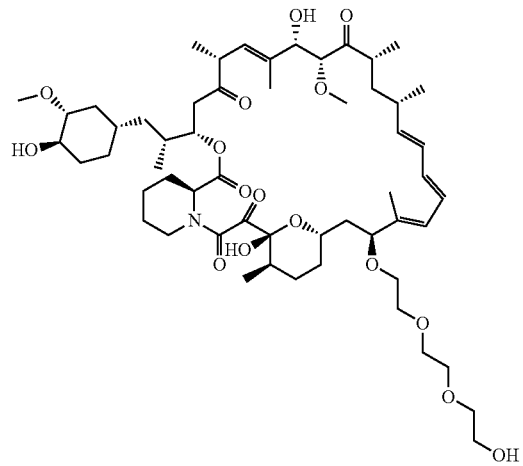

I-128

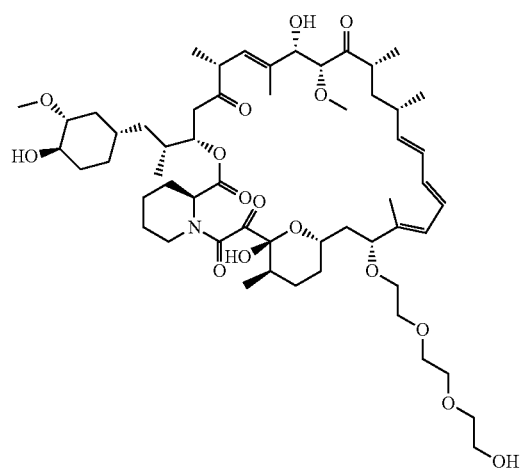 [SMILES: CO[C@@H]1C[C@H](C[C@@H](C)[C@@H]2CC(=O)[C@H](C)/C=C(\C)[C@H](O)[C@@H](OC)C(=O)[C@H](C)C[C@H](C)/C=C/C=C/C=C(\C)C(OCCOCCOCCO)C[C@@H]3CC[C@@H](C)[C@@](O)(O3)C(=O)C(=O)N3CCCC[C@H]3C(=O)O2)CC[C@H]1O]

I-129

In some embodiments, the present invention provides a compound set forth in Table 1, above, or a pharmaceutically acceptable salt thereof. It will be appreciated that the present invention also provides a compound set forth in Table 1, above, as a racemic mixture at the C7 position, or a pharmaceutically acceptable salt thereof. Further, it will be appreciated that compounds set forth in Table 1, above, as racemic mixtures at the C7 hydroxyl position may be separated into diastereomers by various methods, e.g., chiral chromatography.

4. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit mTORC1, in a biological sample or in a patient. In certain embodiments, the amount of compound in compositions of this invention is such that is effective to measurably inhibit mTORC1, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non- toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of mTORC1 and are therefore useful for treating one or more disorders associated with activity of mTORC1. Thus, in certain embodiments, the present invention provides a method for treating an mTORC1-mediated disorder comprising the step of administering to a patient in need thereof a compound of the present invention, or pharmaceutically acceptable composition thereof As used herein, the terms "mTORC1-mediated" disorders, diseases, and/or conditions as used herein means any disease or other deleterious condition in which mTORC1, is known to play a role. Accordingly, another embodiment of the present invention relates to treating or lessening the severity of one or more diseases in which mTORC1 is known to play a role. In certain embodiments, an mTORC1-mediated disorder, disease, and/or condition is selected from those described by Matt Kaeberlin, Scientifica, vol. 2013, Article ID 849186.

The methods described herein include methods for the treatment of cancer in a subject. As used in this context, to "treat" means to ameliorate or improve at least one symptom or clinical parameter of the cancer. For example, a treatment can result in a reduction in tumor size or growth rate. A treatment need not cure the cancer or cause remission 100% of the time, in all subjects.

As used herein, the term "cancer" refers to cells having the capacity for autonomous growth, i.e., an abnormal state or condition characterized by rapidly proliferating cell growth. The term is meant to include all types of cancerous growths or oncogenic processes, metastatic tissues or malignantly transformed cells, tissues, or organs, irrespective of histopathologic type or stage of invasiveness. The term "tumor" as used herein refers to cancerous cells, e.g., a mass of cancer cells.

Cancers that can be treated or diagnoses using the methods described herein include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

In some embodiments, the methods described herein are used for treating or diagnosing a carcinoma in a subject. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. In some embodiments, the cancer is renal carcinoma or melanoma. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

In some embodiments, the cancers that are treated by the methods described herein are cancers that have increased levels of mTORC1 or an increased expression or activity of a mTORC1 relative to normal tissues or to other cancers of the same tissues; methods known in the art and described herein can be used to identify those cancers. In some embodiments, the methods include obtaining a sample comprising cells of the cancer, determining the mTORC1 activity in the sample, and administering a treatment as described herein (e.g., a provided inhibitor of mTORC1). In some embodiments, the cancer is one that is shown herein to have increased levels of mTORC1 activity.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by inhibiting mTORC1 activity. Cellular proliferative disorders described herein include, e.g., cancer, obesity, and proliferation-dependent diseases. Such disorders may be diagnosed using methods known in the art.

Cancer

Cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). In some embodiments, the cancer is melanoma or breast cancer.

Fibrotic Diseases

Idiopathic Pulmonary Fibrosis (IPF). The PI3K pathway is activated in fibrotic foci, the cardinal lesions in IPF. mTOR kinase inhibitor GSK2126458 reduces PI3K pathway signaling and functional responses in IPF-derived lung fibroblasts and mTOR inhibition reduces collagen expression in models of IPF patients. In the bleomycin model of pulmonary fibrosis, rapamycin treatment is antifibrotic, and rapamycin also decreases expression of α-smooth muscle actin and fibronectin by fibroblasts in vitro.

In some embodiments, the method of inhibiting mTORC1 activity is used to treat idiopathic pulmonary fibrosis (IPF) (see Mercer, P. F. et al., Thorax., 71(8): 701-11 (2016); Patel, A. S., et al., PLoS One, 7(7): e41394 (2012)) Accordingly, in some embodiments, the present invention provides a method of treating idiopathic pulmonary fibrosis (IPF), in a patient in need thereof, comprising the step of administering to said patient a provided compound or pharmaceutically acceptable salt thereof Kidney Fibrosis. mTORC1 is activated in myofibroblasts, a major pathogenic cell type in kidney fibrosis. Inhibition of mTOR with rapamycin in a murine model of kidney fibrosis (UUO), attenuated expression of markers of fibrosis and tubulointerstitial damage.

In some embodiments, the method of inhibiting mTORC1 activity is used to treat kidney fibrosis (see Jiang, L., et al., J Am Soc Nephrol, 24(7): 1114-26 (2013); Wu, M. J. et al., Kidney International, 69(11): 2029-36 (2006); Chen, G. et al., PLoS One, 7(3): e33626 (2012); Liu, C. F. et al., Clin Invest Med, 37(34): E142-53 (2014)). Accordingly, in some embodiments, the present invention provides a method of treating kidney fibrosis, in a patient in need thereof, comprising the step of administering to said patient a provided compound or pharmaceutically acceptable salt thereof.

In some embodiments, the method of inhibiting mTORC1 activity is used to treat scleroderma (see Mitra, A., et al., J Invest Dermatol. 135(11): 2873-6 (2015)). Accordingly, in some embodiments, the present invention provides a method of treating scleroderma, in a patient in need thereof, comprising the step of administering to said patient a provided compound or pharmaceutically acceptable salt thereof.

In some embodiments, the method of inhibiting mTORC1 activity is used to treat hypertrophic scarring and keloid disease (see Syed, F., et al., Am J Pathol. 181(5): 1642-58 (2012)). Accordingly, in some embodiments, the present invention provides a method of treating hypertrophic scarring and keloid disease, in a patient in need thereof, comprising the step of administering to said patient a provided compound or pharmaceutically acceptable salt thereof.

In some embodiments, the method of inhibiting mTORC1 activity is used to treat cardiac fibrosis (see Yano, T., et al., JMol Cell Cardiol. 91: 6-9 (2016)). Accordingly, in some embodiments, the present invention provides a method of treating cardiac fibrosis, in a patient in need thereof, comprising the step of administering to said patient a provided compound or pharmaceutically acceptable salt thereof.

Other Proliferative Diseases

Other proliferative diseases include, e.g., obesity, benign prostatic hyperplasia, psoriasis, abnormal keratinization, lymphoproliferative disorders (e.g., a disorder in which there is abnormal proliferation of cells of the lymphatic system), chronic rheumatoid arthritis, arteriosclerosis, restenosis, and diabetic retinopathy. Proliferative diseases that are hereby incorporated by reference include those described in U.S. Pat. Nos. 5,639,600 and 7,087,648.

Other Disorders

Other disorders include lysosomal storage diseases, including, but not limited to, Pompe disease, Gaucher disease, mucopolysaccharidosis, multiple sulfatase deficiency; neurodegenerative diseases such as Parkinson's disease, Alzheimer's disease, Huntington's disease, alpha1-anti-trypsin deficiency, and spinal bulbar muscular atrophy.

In some embodiments, the method of inhibiting mTORC1 activity is used to treat asthma (see Hua, W., et al., Respirology, 20(7): 1055-65 (2015)). Accordingly, in some embodiments, the present invention provides a method of treating asthma, in a patient in need thereof, comprising the step of administering to said patient a provided compound or pharmaceutically acceptable salt thereof.

In some embodiments, the method of inhibiting mTORC1 activity is used to treat a lysosomal storage disease (see Sardiello, M., Annals of the New York Academy of Sciences, 1371(1): 3-14 (2016); Awad, O., et al., Hum Mol Genet. 24(20): 5775-88 (2015); Spampanato, C., et al., EMBO Mol Med., 5(5): 691-706 (2013); Medina, D.L., et al., Dev Cell., 21(3): 421-30 (2011)). Accordingly, in some embodiments, the present invention provides a method of treating a lysosomal storage disease, in a patient in need thereof, comprising the step of administering to said patient a provided compound or pharmaceutically acceptable salt thereof In some embodiments, the method of inhibiting mTORC1 activity is used to treat Parkinson's disease (see Decressac, M., et al., Proc Natl Acad Sci U S A., 110(19):E1817-26 (2013)). Accordingly, in some embodiments, the present invention provides a method of treating Parkinson's disease, in a patient in need thereof, comprising the step of administering to said patient a provided compound or pharmaceutically acceptable salt thereof.

In some embodiments, the method of inhibiting mTORC1 activity is used to treat Alzheimer's disease (see Polito, V.A., et al., EMBO Mol Med. 6(9):1142-60 (2014)). Accordingly, in some embodiments, the present invention provides a method of treating Alzheimer's disease, in a patient in need thereof, comprising the step of administering to said patient a provided compound or pharmaceutically acceptable salt thereof.

In some embodiments, the method of inhibiting mTORC1 activity is used to treat Huntington's disease (see Tsunemi, T., et al., Sci Transl Med., 4(142): 142ra97 (2012)). Accordingly, in some embodiments, the present invention provides a method of treating Huntington's disease, in a patient in need thereof, comprising the step of administering to said patient a provided compound or pharmaceutically acceptable salt thereof.

In some embodiments, the method of inhibiting mTORC1 activity is used to treat alpha-1-anti-trypsin deficiency (see Pastore, N. et al., EMBO Mol Med., 5(3): 397-412 (2013)). Accordingly, in some embodiments, the present invention provides a method of treating alpha1-anti-trypsin deficiency, in a patient in need thereof, comprising the step of administering to said patient a provided compound or pharmaceutically acceptable salt thereof.

In some embodiments, the method of inhibiting mTORC1 activity is used to treat spinal bulbar muscular atrophy (see Cortes, C. J., et al., Nat Neurosci., 17(9): 1180-9 (2014)). Accordingly, in some embodiments, the present invention provides a method of treating spinal bulbar muscular atrophy, in a patient in need thereof, comprising the step of administering to said patient a provided compound or pharmaceutically acceptable salt thereof.

In some embodiments, a compound of the present invention binds to FKBP12 to form a complex. In some embodiments, the complex between a compound of the present invention and FKBP12 interacts with the FK506-rapamycin binding domain of mTOR.

In some embodiments, a compound of the present invention binds FKBP12 and interferes with protein-protein interaction between FRAP and FKBP12. In some embodiments, the $R^1$ group of a compound of the present invention interacts with both FRAP and FKBP12.

The present invention provides compounds that are inhibitors of mTORC1 activity and were shown to selectively inhibit mTORC1 over mTORC2 as measured by pS6K inhibition (a measure of mTORC1 activity) and pAKT activation (a measure of mTORC2 activity). In some embodiments, a provided compound inhibits mTORC1 selectively over mTORC2. In some embodiments, a provided compound does not measurably inhibit mTORC2. In some embodiments, a provided compound has a pAKT activation $IC_{50}$ of >10 µM. In some embodiments, a provided compound inhibits mTORC1 with >10-fold selectivity over mTORC2. In some embodiments, a provided compound inhibits mTORC1 with >20-fold selectivity over mTORC2. In some embodiments, a provided compound inhibits mTORC1 with >50-fold selectivity over mTORC2. In some embodiments, a provided compound inhibits mTORC1 with >100-fold selectivity over mTORC2. In some embodiments, a provided compound inhibits mTORC1 with >150-fold selectivity over mTORC2. In some embodiments, a provided compound inhibits mTORC1 with >200-fold selectivity over mTORC2. In some embodiments, a provided compound inhibits mTORC1 with >500-fold selectivity over mTORC2. In some embodiments, a provided compound inhibits mTORC1 with >1,000-fold selectivity over mTORC2.

In some embodiments, a provided compound inhibits mTORC1 selectively over mTORC2 after chronic treatment or exposure. In some embodiments, a provided compound inhibits mTORC1 selectively over mTORC2 after about 24 hours of treatment or exposure. In some embodiments, a provided compound inhibits mTORC1 selectively over mTORC2 after about 36 hours of treatment or exposure. In some embodiments, a provided compound inhibits mTORC1 selectively over mTORC2 after about 48 hours of treatment or exposure. In some embodiments, a provided compound inhibits mTORC1 selectively over mTORC2 after about 72 hours of treatment or exposure. In some embodiments, a provided compound inhibits mTORC1 selectively over mTORC2 after about 96 hours of treatment or exposure. In some embodiments, a provided compound inhibits mTORC1 selectively over mTORC2 after about 120 hours of treatment or exposure. In some embodiments, a provided compound inhibits mTORC1 selectively over mTORC2 after about 144 hours of treatment or exposure. In some embodiments, a provided compound inhibits mTORC1 selectively over mTORC2 after about one week of treatment or exposure. In some embodiments, a provided compound inhibits mTORC1 selectively over mTORC2 after more than about one week of treatment or exposure.

In some embodiments, a provided compound is less immunosuppressive than existing rapalogs. In some embodiments, a provided compound is less immunosuppressive than rapamycin. In some embodiments, a provided compound is less immunosuppressive than everolimus. In some embodiments, a provided compound is less immunosuppressive than temsirolimus. In some embodiments, a provided compound is less immunosuppressive than ridaforolimus. In some embodiments, a provided compound is less immunosuppressive than umirolimus.

In some embodiments, a provided compound suppresses interferon gamma (IFN-γ) production less than rapalogs. In some embodiments, a provided compound suppresses IFN-γ production less than rapamycin. In some embodiments, a provided compound suppresses IFN-γ production less than everolimus. In some embodiments, a provided compound suppresses IFN-γ production less than temsirolimus. In some embodiments, a provided compound suppresses IFN-γ production less than ridaforolimus. In some embodiments, a provided compound suppresses IFN-γ production less than umirolimus.

In some embodiments, a provided compound decreases the expression of fibrosis biomarkers in tissue that has been damaged. In some embodiments, a provided compound decreases the expression of collagen I (COL1A2) in tissue that has been damaged. In some embodiments, a provided compound decreases the expression of collagen III (COL3A1) in tissue that has been damaged. In some embodiments, a provided compound decreases the expression of fibronectin (FN1) in tissue that has been damaged.

In some embodiments, a provided compound decreases the propensity of immune cells from infiltrating damaged tissue. In some embodiments, a provided compound decreases the propensity of macrophage cells from infiltrating damaged tissue.

In some embodiments, a provided compound induces less glucose tolerance than rapalogs. In some embodiments, a provided compound induces less glucose tolerance than rapamycin. In some embodiments, a provided compound induces less glucose tolerance than everolimus. In some embodiments, a provided compound induces less glucose tolerance than temsirolimus. In some embodiments, a provided compound induces less glucose tolerance than ridaforolimus. In some embodiments, a provided compound induces less glucose tolerance than umirolimus. In some embodiments, a provided compound does not induce glucose tolerance significantly more than a placebo or vehicle alone.

Accordingly, in some embodiments, the present invention provides a method of treating a disorder associate with mTORC1 comprising administering to patient a compound that inhibits mTORC1 wherein said compound does not inhibit mTORC2. Such compounds may be employed for indications where rapamycin and rapalogs demonstrated a benefit either in animal models or in a human disease setting. Such indications include:

Treatment of Metabolic Disease (Obesity and Insulin Resistance in Type 2 Diabetes). Inhibition of mTORC1 pathway leads to extension of life span in yeast, fly and mouse, and caloric restriction improves longevity and insulin sensitivity. The underlying mechanism has been proposed to function by regulation of mTORC1 activation. Rapamycin-induced insulin resistance has been shown to be mediated by inhibition of mTORC2 and selective mTORC1 inhibitor is predicted to improve insulin sensitivity and glucose homeostasis.

In some embodiments, the method of inhibiting mTORC1 activity is used to treat metabolic disease (obesity and insulin resistance in type 2 diabetes) (see Yu, Z., et al., J Gerontol A Biol Sci Med Sci, 70(4), 410-20 (2015); Fok, W. C., et al., Aging Cell 13 (2): 311-9 (2014); Shum, M., et al., Diabetologia, 59(3):592-603 (2016); Lamming, D. W., et al., Science 335(6076): 1638-43 (2012)). Accordingly, in some embodiments, the present invention provides a method of treating metabolic disease (obesity and insulin resistance in type 2 diabetes), in a patient in need thereof, comprising the step of administering to said patient a provided compound or pharmaceutically acceptable salt thereof.

Neurofibromatosis. Neurofibromatosis type 1 (NF1) is caused by mutations in the NF1 gene. Its protein product, neurofibromin, functions as a tumor suppressor and ultimately produces constitutive upregulation of mTOR. mTOR inhibitors have been shown to reduce tumor size and induce anti-proliferative effect in NF1-associated plexiform neurofibroma.

In some embodiments, the method of inhibiting mTORC1 activity is used to treat neurofibromatosis (see Franz, D.N., et al., Curr Neurol Neurosci Rep., 12(3): 294-301 (2012); Varin, J., et al., Oncotarget., 7: 35753-67 (2016)). Accordingly, in some embodiments, the present invention provides a method of treating neurofibromatosis, in a patient in need thereof, comprising the step of administering to said patient a provided compound or pharmaceutically acceptable salt thereof.

Cardiomyopathy and skeletal muscle dystrophy, Emery-Dreifuss muscular dystrophy model (LMNA$^{-/-}$). Mutations in LMNA result in several human diseases including limb-girdle muscular dystrophy (LGMD1B), Emery-Dreifuss muscular dystrophy (EDMD2/3), dilated cardiomyopathy (DCM) and conduction-system disease (CMD1A), lipodystrophy, Charcot-Marie-Tooth disease, and Hutchinson-Gilford progeria syndrome (HGPS). Lmna$^{-/-}$ mice have elevated mTORC1 activity and short-term treatment with rapamycin in Lmna$^{-/-}$ mice results in reduced mTORC1 signaling, improved cardiac and skeletal muscle function and enhanced survival by ~50%.

In some embodiments, the method of inhibiting mTORC1 activity is used to treat cardiomyopathy and skeletal muscle dystrophy (see Ramos, F., et al., Sci Transl Med., 4(144): 144ra103 (2012); Bonne, G. & Quijano-Roy, S., Handb Clin Neurol., 113: 1367-76 (2013)). Accordingly, in some embodiments, the present invention provides a method of treating cardiomyopathy and skeletal muscle dystrophy, in a patient in need thereof, comprising the step of administering to said patient a provided compound or pharmaceutically acceptable salt thereof.

Leigh syndrome. Ndufs4 knockout (KO) mice are used as a model of Leigh syndrome and exhibit hyperactivation of mTORC1 and metabolic defects. Treatment of Ndufs4 KO mice with rapamycin extended lifespan, improve metabolic and neurological defect associated with this disease.

In some embodiments, the method of inhibiting mTORC1 activity is used to treat Leigh syndrome (see Johnson, S. C., et al., Science, 342(6165): 1524-8 (2013)). Accordingly, in some embodiments, the present invention provides a method of treating Leigh syndrome, in a patient in need thereof, comprising the step of administering to said patient a provided compound or pharmaceutically acceptable salt thereof.

Oncology. Inhibition of mTOR with rapalogs has been shown to have antitumor activity in murine cancer models and in cancer patients. Examples of sensitive cancer types include, but are not limited to, hepatocellular carcinoma, breast cancers, mantle cell lymphomas, lung carcinoma, tuberous sclerosis and lymphangioleiomyomatosis.

In some embodiments, the method of inhibiting mTORC1 activity is used to treat cancer and oncologic disorders (see Hagan, E. & manning, B.D., Trends Cancer, 2(5): 241-51 (2016)). Accordingly, in some embodiments, the present invention provides a method of treating cancer and oncologic disorders, in a patient in need thereof, comprising the step of administering to said patient a provided compound or pharmaceutically acceptable salt thereof.

Non-alcoholic steatohepatitis (NASH). The present invention provides inhibitors that induce autophagy to clear degraded cytoplasmic proteins, and NASH disease is characterized by lipid deposits, inflammation and fibrosis in the liver. The inhibition of mTORC1 pathway induce autophagy and down regulate SREBP-1 to decrease lipid biosynthesis to reduce lipid storage.

In some embodiments, the method of inhibiting mTORC1 activity is used to treat non-alcoholic steatohepatitis (NASH) (see Puri, P. & Chandra, A., J Clin Exp Hepatol, 4(1): 51-9 (2014)). Accordingly, in some embodiments, the present invention provides a method of treating non-alcoholic steatohepatitis (NASH), in a patient in need thereof, comprising the step of administering to said patient a provided compound or pharmaceutically acceptable salt thereof.

Tuberous sclerosis (TSC) and lymphangioleiomyomatosis (LAM). Failure in the regulation of mTOR is critical to the pathogenesis of the inherited disorder tuberous sclerosis complex (TSC) and the related lung disease, lymphangioleiomyomatosis (LAM). Both diseases are caused by mutations of TSC1 or TSC2 leading to inappropriate activity of signaling downstream of mTORC1. TSC patients develop nonmalignant tumors in many organs, including the brain, while LAM patients, mostly women, accumulate abnormal, muscle-like cells in certain organs or tissues, especially the lungs, lymph nodes, and kidneys. The rapalogs, everolimus and sirolimus, are currently approved for the treatment of both TSC and LAM, respectively, by the U.S. FDA.

In some embodiments, the method of inhibiting mTORC1 activity is used to treat tuberous sclerosis and lymphangioleiomyomatosis (see Wander, S. A., et al., J. Clin. Invest., 121(4): 1231-41 (2011); Taveira-DaSilva, A. M. & Moss, J., J. Clin Epidemiol., 7: 249-57 (2015)). Accordingly, in some embodiments, the present invention provides a method of treating tuberous sclerosis and lymphangioleiomyomatosis, in a patient in need thereof, comprising the step of administering to said patient a provided compound or pharmaceutically acceptable salt thereof.

Senescence and diseases of aging. Rapamycin suppresses the mammalian TORC1 complex, which regulates translation, and extends lifespan in diverse species, including mice. Rapamycin was shown to inhibit the pro-inflammatory phenotype of senescent cells. As senescent cells accumulate with age, the senescence-associated secretory phenotype (SASP) can disrupt tissues and contribute to age-related pathologies, including cancer. Inhibition of mTOR suppressed the secretion of inflammatory cytokines by senescent cells. Rapamycin reduced cytokine levels including IL6 and suppressed translation of the membrane-bound cytokine IL1A. Reduced IL1A diminishes NF-κB transcriptional activity, which controls the SASP. Thus, mTORC1 inhibitors might ameliorate age-related pathologies, including late-life cancer, by suppressing senescence-associated inflammation.

In some embodiments, the method of inhibiting mTORC1 activity is used to treat senescence and diseases of aging (see Laberge, R. M., et al., Nature Cell Biology, 17(8): 1049-61 (2015); Nacarelli, T., et al., Free Radic Biol Med., 95: 133-54 (2016)). Accordingly, in some embodiments, the present invention provides a method of treating senescence and diseases of aging, in a patient in need thereof, comprising the step of administering to said patient a provided compound or pharmaceutically acceptable salt thereof.

Diabetic nephropathy and kidney-related complications of type 1 diabetes and type 2 diabetes. Diabetic nephropathy is a kidney complication of type-1 and type-2 diabetes, affecting up to nearly 40% of people with diabetes. High levels of glucose force the kidneys work excessively to filter blood, resulting in kidney damage. Studies suggest that the mTOR pathway is highly activated in patients with diabetic neuropathy and may play a role in the pathological changes and renal dysfunction due to chronic high glucose. Further, mTOR inhibition may attenuate hyperinsulinemia.

In some embodiments, the method of inhibiting mTORC1 activity is used to treat diabetic nephropathy or kidney-related complications of type 1 diabetes and type 2 diabetes (see Mori, H., et al., Biochem. Res. Commun. 384(4): 471-5 (2009)). Accordingly, in some embodiments, the present invention provides a method of treating diabetic nephropathy or kidney-related complications of type 1 diabetes and type 2 diabetes in a patient in need thereof, comprising the step of administering to said patient a provided compound or pharmaceutically acceptable salt thereof.

Polycystic kidney disease. Polycystic kidney disease (PKD) is characterized by the development and accumulation of destructive kidney cysts that eventually result in kidney failure. PKD may be autosomal dominant (ADPKD) or recessive (ARPKD). Dysfunctional mTOR signaling pathway has been observed in ADPKD and ARPKD. Thus, normalization of the mTORC1 pathway may ameliorate the development of cysts and progression of the disease.

In some embodiments, the method of inhibiting mTORC1 activity is used to treat PKD (see Torres, V. E., et al., Clin. J. Am. Soc. Nephrol. 5(7): 1312-29 (2010)). Accordingly, in some embodiments, the present invention provides a method of treating PKD in a patient in need thereof, comprising the step of administering to said patient a provided compound or pharmaceutically acceptable salt thereof. In some embodiments, PKD is autosomal dominate. In some embodiments, PKD is autosomal recessive.

Focal Segmental Glomerulosclerosis (FSGS) and other diseases associated with sclerosis of the kidney. FSGS is the most common primary glomerular disorder causing end-stage renal disease (ESRD) in the United States. As the disease progresses there is a mismatch of podocyte cells in Bowman's capsule and the surface area of the glomerular basement membrane they cover. Studies have shown that podocyte size control is regulated by mTOR and that mTOR activation contributes to disease progression. Further, constitutive mTORC1 activation has been shown to cause FSGS-like lesions in mouse knockdown experiments. Thus, mTORC1 inhibition might ameliorate (FSGS) or other diseases associated with sclerosis of the kidney by normalizing or increasing autophagic activity.

In some embodiments, the method of inhibiting mTORC1 activity is used to treat FSGS or other diseases associated with sclerosis of the kidney (see Zschiedrich, S. et al., J. Am. Soc. Nephrol. 28(7): 2144-57 (2017)). Accordingly, in some embodiments, the present invention provides a method of treating FSGS or other diseases associated with sclerosis of the kidney in a patient in need thereof, comprising the step of administering to said patient a provided compound or pharmaceutically acceptable salt thereof.

Age-Related Macular Degeneration. Age-related macular degeneration (AMD) is a leading cause of blindness characterized by the death of photoreceptors in the macula. Possible mechanisms of AMD progression include oxidative stress leading to deposits of proteins and dysfunctional organelles, leading to retinal pigment epithelium hypertrophy, dedifferentiation, and eventual atrophy. mTOR is implicated in the dedifferentiation of the retinal pigment epithelium. Thus, mTORC1 inhibition may ameliorate AMD by blocking hypertrophy and dedifferentiation.

In some embodiments, the method of inhibiting mTORC1 activity is used to treat age-related macular degeneration (see Kolosova, N. G., et al., Am. J. Path. 181(2): 472-7 (2012) and Zhen, C. & Vollrath, D., Aging 3(4): 346-47 (2011)). Accordingly, in some embodiments, the present invention provides a method of treating age-related macular degeneration in a patient in need thereof, comprising the step of administering to said patient a provided compound or pharmaceutically acceptable salt thereof.

Diabetic Macular Edema. Diabetic macular edema (DME) is a leading cause of blindness in persons with diabetes, affecting approximately 35% of people with diabetes. Studies suggest that the pathogenesis of DME is an inflammatory disease involving various cytokines and chemokines. Chronic inflammatory and oxidative stress may contribute to the progression of DME. Thus, inhibition of mTORC1 may ameliorate DME symptoms and progression by decreasing the inflammatory response.

In some embodiments, the method of inhibiting mTORC1 activity is used to treat DME (see Okamoto, T., et al., PLOS ONE, (11)(1): e0146517, https://doi.org/10.1371/journal.pone.0146517 (2016)). Accordingly, in some embodiments, the present invention provides a method of treating DME in a patient in need thereof, comprising the step of administering to said patient a provided compound or pharmaceutically acceptable salt thereof.

Diabetic retinopathy. Diabetic retinopathy (DR) is a common eye disease accounting for ~5% of blindness in adults and is associated with chronic hyperglycemia and defects of insulin signaling pathways. DR patients suffer persistent injury to retinal blood vessels and neurons by inflammation, reactive oxygen species and endoplasmic reticulum stress caused by chronic hyperglycemia. Significantly, rapamycin has been shown to block the action of insulin-induced hypoxia-inducible factor-1 (HIF-1) and retinal cell senescence, and induces autophagy, and could be beneficial in promoting apoptosis of nascent blood vessels and preventing angiogenesis. Thus, inhibition of mTORC1 may ameliorate DR symptoms and progression by decreasing inflammation and inhibiting pathogenic signaling pathways.

In some embodiments, the method of inhibiting mTORC1 activity is used to treat DR (see Di Rosa, M., et al., Curr. Neuropharmacol. 14(8): 810-25 (2016)). Accordingly, in some embodiments, the present invention provides a method of treating DR in a patient in need thereof, comprising the step of administering to said patient a provided compound or pharmaceutically acceptable salt thereof.

Glaucoma. Glaucoma is a common optic neuropathy associated with aging and elevated intraocular pressure, and is the leading cause of irreversible blindness. Studies suggest that mTOR dependent dysregulation of autophagocytosis may be a factor in the progression of the disease. Thus, inhibition of mTORC1 may slow the progression or ameliorate glaucoma by normalizing or increasing autophagy.

In some embodiments, the method of inhibiting mTORC1 activity is used to treat glaucoma (see Porter, K., et al., Biochim. Biophys. Acta. 1852(3): 379-85 (2014)). Accordingly, in some embodiments, the present invention provides a method of treating glaucoma in a patient in need thereof, comprising the step of administering to said patient a provided compound or pharmaceutically acceptable salt thereof.

Restoring immune function. mTORC1 inhibition has been shown to reduce the expression of programmed death-1 (PD-1) receptor in $CD4^+$ and $CD8^+$ T lymphocytes, promoting T-cell signaling. Thus, mTORC1 inhibition may restore immune function by improving the adaptive immune response.

In some embodiments, the method of inhibiting mTORC1 activity is used to restore immune function (see Mannick, J. B., et al., Sci. Trans. Med. 6(268): ppra179 (2014)). Accordingly, in some embodiments, the present invention provides a method of restoring immune function in a patient in need thereof, comprising the step of administering to said patient a provided compound or pharmaceutically acceptable salt thereof.

Treatment of respiratory and/or urinary tract infections. mTORC1 inhibition may reduce infections by upregulation of antiviral gene expression and response. Thus, mTORC1 inhibition may enhance the ability of a patient's immune system to defend against respiratory and/or urinary tract infections.

In some embodiments, the method of inhibiting mTORC1 activity is used to treat respiratory and/or urinary tract infections. (see Mannick, J. B., et al., Sci. Trans. Med. 10(449): eaaq1564 (2018)). Accordingly, in some embodiments, the present invention provides a method of restoring immune function in a patient in need thereof, comprising the step of administering to said patient a provided compound or pharmaceutically acceptable salt thereof.

Heart failure. mTORC1 activity is essential for cardiac hypertrophy in response to stress but can lead to cardiac derangements as a result of cardiac remodeling following infarction. Inhibition of mTORC1 reduces cardiac remodeling and heart failure in response to pressure overload. Thus, inhibition of mTORC1 may decrease heart failure in patients who have suffered damage to the myocardium.

In some embodiments, the method of inhibiting mTORC1 activity is used to treat heart failure (see Sciarretta, S. et al., Circ. Res. 122(3): 489-505 (2018)). Accordingly, in some embodiments, the present invention provides a method of treating heart failure in a patient in need thereof, comprising the step of administering to said patient a provided compound or pharmaceutically acceptable salt thereof.

Osteoarthritis. Osteoarthritis (OA) is a chronic degenerative disease resulting in loss of cartilage and joint inflammation. mTOR may play a significant role in collagen homeostasis and turnover and remodeling of cartilage. Thus, inhibition of mTORC1 may slow the progression or ameliorate osteoarthritis symptoms by normalizing cartilage turnover.

In some embodiments, the method of inhibiting mTORC1 activity is used to treat osteoarthritis (see Pal, B., et al., Drugs R&D, 15(1): 27-36 (2017))). Accordingly, in some embodiments, the present invention provides a method of treating osteoarthritis in a patient in need thereof, comprising the step of administering to said patient a provided compound or pharmaceutically acceptable salt thereof.

Pulmonary arterial hypertension. Pulmonary arterial hypertension (PAH) is a progressive, fatal disease associated with increases pulmonary vascular resistance. Pulmonary arterial smooth muscle cell proliferation and migration are implicated in the progressing of arterial wall thickening, exacerbating vasoconstriction. Thus, inhibition of mTORC1 may alleviate PAH by reducing vascular remodeling.

In some embodiments, the method of inhibiting mTORC1 activity is used to treat PAH (see Ma, X., et al., Interact. Cardiovasc. Thorac. Surg. 25(2): 206-11 (2017)). Accordingly, in some embodiments, the present invention provides a method of treating PAH is a patient in need thereof, comprising the step of administering to said patient a provided compound or pharmaceutically acceptable salt thereof.

Chronic Obstructive Pulmonary Disease. Reduced autophagy results in the accumulation of proteins and other cellular materials that accelerate cellular senescence in patients with chronic obstructive pulmonary disease (COPD). Thus, inhibition of mTORC1 may slow the progression or ameliorate COPD symptoms by normalizing or increasing autophagy.

In some embodiments, the method of inhibiting mTORC1 activity is used to treat COPD (see Fujii, S., et al., Oncoimmunology 1(5): 630-41 (2012)). Accordingly, in some embodiments, the present invention provides a method of treating COPD in a patient in need thereof, comprising the step of administering to said patient a provided compound or pharmaceutically acceptable salt thereof.

Additional therapeutic indications where mTORC inhibition may be beneficial are: cardiovascular disease (acute coronary syndrome), coronary occlusions with eluting stents, polycystic kidney disease, and kidney disease associated with cyst formation or cystogenesis), neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis.

In some embodiments, the method of inhibiting mTORC1 activity is used to treat cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma associated with TSC1/2 mutations, breast cancer, hepatocellular cancer, leukemia, glioma, adenoid cystic carcinoma, senescence, autism, and vascular rheumatoid arthritis.

Accordingly, in some embodiments, the present invention provides a method of treating cardiovascular disease (acute coronary syndrome), coronary occlusions with eluting stents, polycystic kidney disease, neurofibromatosis, epilepsy assoc. with TSC1 and/or TSC2 mutations, polycystic liver, pachyonychia congenital, fragile x syndrome, Friedrich ataxia, Peutz-Jeghers syndrome, eye disease including neovascular age-related macular degeneration, uveitis, diabetic macular edema, fibroblast growth including pulmonary fibrosis, renal insufficiency/fibrosis, metabolic syndrome, diseases of the immune system including immune senescence, lupus nephritis, chronic immune thrombocytopenia, multiple sclerosis, cancer including lymphoma, tumors associated with TSC1/2 mutations, angiomyolipoma assoc. with TSC1/2 mutations, breast cancer, hepatocellular cancer, leukemia, glioma, adenoid cystic carcinoma, senescence, autism, and vascular rheumatoid arthritis, in a patient in need thereof, comprising the step of administering to said patient a provided compound or pharmaceutically acceptable salt thereof.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body.

Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The term "biological sample", as used herein, includes, without limitation, cell cultures or extracts thereof biopsied material obtained from a mammal or extracts thereof and blood, saliva, urine, feces, semen, tears, or other body fluids or extracts thereof In other embodiments, the present invention provides a method for treating a disorder mediated by mTORC1 in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from Astra7eneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g., in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™ Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g., under the trademark Carboplat™. Oxaliplatin can be administered, e.g., in the form as it is marketed, e.g., under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g., BCR-Abl kinase) and mutants, such as compounds which target decrease or inhibit the activity of c-Abl family members and their gene fusion products, such as an N-phenyl-2- pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802), navitoclax (and analogs thereof, see U.S. Pat. No. 7,390,799), NH-1 (Shenayng Pharmaceutical University), obatoclax (and analogs thereof, see WO 2004/106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO 2008/039218 and WO 2011/090760, the entirety of which are incorporated herein by reference.

Further examples of SYK inhibitory compounds, and conditions treatable by such compounds in combination with compounds of this invention can be found in WO 2003/063794, WO 2005/007623, and WO 2006/078846, the entirety of which are incorporated herein by reference.

Further examples of PI3K inhibitory compounds, and conditions treatable by such compounds in combination with compounds of this invention can be found in WO 2004/019973, WO 2004/089925, WO 2007/016176, U.S. Pat. No. 8,138,347, WO 2002/088112, WO 2007/084786, WO 2007/129161, WO 2006/122806, WO 2005/113554, and WO 2007/044729 the entirety of which are incorporated herein by reference.

Further examples of JAK inhibitory compounds, and conditions treatable by such compounds in combination with compounds of this invention can be found in WO 2009/114512, WO 2008/109943, WO 2007/053452, WO 2000/142246, and WO 2007/070514, the entirety of which are incorporated herein by reference.

Further anti-angiogenic compounds include compounds having another mechanism for their activity, e.g., unrelated to protein or lipid kinase inhibition, e.g., thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are, e.g., inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid-™Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g., hydroxamate peptidomimetic inhibitor batimastat and its orally bioavailable analogue marimastat (BB-2516), prinomastat (AG3340), metastat (NSC 683551) BMS-279251 , BAY 12-9566, TAA211 , MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™) rituximab (Rittman®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-aminolmethyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art (see Hellman, Principles of Radiation Therapy, Cancer, in Principles and Practice of Oncology, Devita et al., Eds., 4$^{th}$ Edition, Vol. 1, pp. 248-275 (1993)).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocortisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g., Patents International (e.g., IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the additional therapeutic agent administered in combination with a compound of the present invention is another mTOR inhibitor. In some embodiments, the additional mTOR inhibitor inhibits mTOR by binding the catalytic active site of mTOR. Examples of such additional mTOR inhibitors include: dactolisib, 8-(6-methoxypyridin-3-yl)-3-methyl-1-(4-piperazin-1-yl-3-trifluoromethyl-phenyl)-1,3-dihydro-imidazo[4,5-c]quinolin-2-one (WO 2006/122806), vistusertib (AZD2014; WO 2009/153597); AZD8055 (WO 2009/153597; XL388 (U.S. Pat. App. Pub. 2010/0305093); sapanisertib (MLN0128; INK128; WO 2015/051043); DS3078; apitolisib (GDC0980; WO 2008/070740); omipalisib (GSK-2126458; WO 2008/14446); NVP-BGT226 (Chang, K. Y., et al., Clin. Cancer Res. 17(22): 7116-26 (2011)); voxtalisib (XL765; SAR245409; WO 2007/044813); PF04691502 (WO 2008/032162); gedatolisib (PF05212384; PKI-587; WO 2009/143313); SF1126 (WO 2004/089925); GSK1059615 (WO 2007/136940); BI-860585; OSI 027 (WO 2007/061737); VS 5584 (WO 2010/114484); CC-223 (WO 2010/062571); DCBCI-0901 (Lee, Y.E., et al., Mol. Canc. Thera. 12(11 Suppl): Abstract nr C270 (2013)):); LY3023414 (WO 2012/097039); P529 (WO 2007/133249); panulisib (P7170; WO 2012/007926); DS-7423 (Kashiyama, T., et al., PLoS One 9(2): e87220 (2014)); PWT33567 mesylate (VCD-597; WO 2010/110685); ME-344 (NV-128; Navarro, P., et al., Cell Rep. 15(12):2705-18 (2016)); ABTL0812 (WO 2010/106211); WYE-132; EXEL-3885 (Eur J Cancer Suppl. 6(12): Abst 322 (2008)); EXEL-4431 (Eur J Cancer Suppl. 6(12): Abst 322 (2008)); AR-mTOR-26 (101st Annu Meet Am Assoc Cancer Res (AACR) (April 17-21, Washington, D.C.) 2010, Abst 4484); NV-128 (A. B. Alvero et al., Mol Cancer Ther. 10(8): 1385-93 (2011)); salinomycin (VS-507; Gupta, P. B., et al., Cell 138(4): 645-59 (2009)); BN-107; BN-108; WAY-600; WYE-687; WYE-354 (Yu, K., et al., Cancer Res. 69(15): 6232-40 (2009)); Ku-063794 (Garcia-Martinez, J. M., et al., Biochem. J. 421(1): 29-42 (2009)); torkinib (PP242; Apsel, B., et al., Nat. Chem. Biol. 4(11): 691-99 (2008)); PP30; CZ415 (REF); INK1069; EXEL-2044; EXEL-7518; SB2158; SB2280; AR-mTOR-1 (Wallace, E. M., et al., Mol. Canc. Thera. 8(12 Suppl): Abst. B267 (2009)).

Reference to any particular additional mTOR inhibitor herein also comprises any pharmaceutically acceptable salts, stereoisomers, tautomers, solvates, hydrates and polymorphs thereof.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein (see also Luengo, J. I. etal., Chem. Biol., 2(7): 471-81 (1995); and Grinfeld, A. A. etal., Tet. Lett., 35(37): 6835-38 (1994)).

List of abbreviations used in the experimental section.
$CH_3CN$: acetonitrile
DCE: dichloroethane
DCM: dichloromethane
DIPEA: N,N-diisopropylethylamine
DMF: N,N-dimethylformamide
DMSO: dimethyl sulfoxide
ESI: electrospray ionization
EtOAc: ethyl acetate
EtOH: ethanol
h: hours
HBr: hydrogen bromide
HF: hydrogen fluoride
HND-8: acidic ion exchange resin (e.g., Amberlyst)
H2O: water
HPLC: high performance liquid chromatography
MeOH: methanol
min: minutes
mL: milliliters
mM: millimolar
mmol: millimoles
MS: mass spectrometry
$N_2$: nitrogen gas
$NaHCO_3$: sodium bicarbonate
NaI: sodium iodide
$NaN_3$: sodium azide
NaOH: sodium hydroxide
$Na_2SO_4$: sodium sulfate
$NH_4Cl$: ammonium chloride
NMR: Nuclear Magnetic Resonance
° C.: degrees Celsius prep-HPLC: preparative high performance liquid chromatography
PPh₃: triphenylphosphine
p-TsOH: para toluenesulfonic acid
rt: room temperature
TEA: triethylamine
TFA: trifluoracetic acid
THF: tetrahydrofuran

EXAMPLE 1

Synthesis of (21E,23E,25E,26E,34R,35S,36R,37R,39R,41S,44S,45R,46R,55S)-45,55-dihydroxy-43-[2-[2-(2-hydroxyethoxy)ethoxy]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-28, I-29 and I-30):

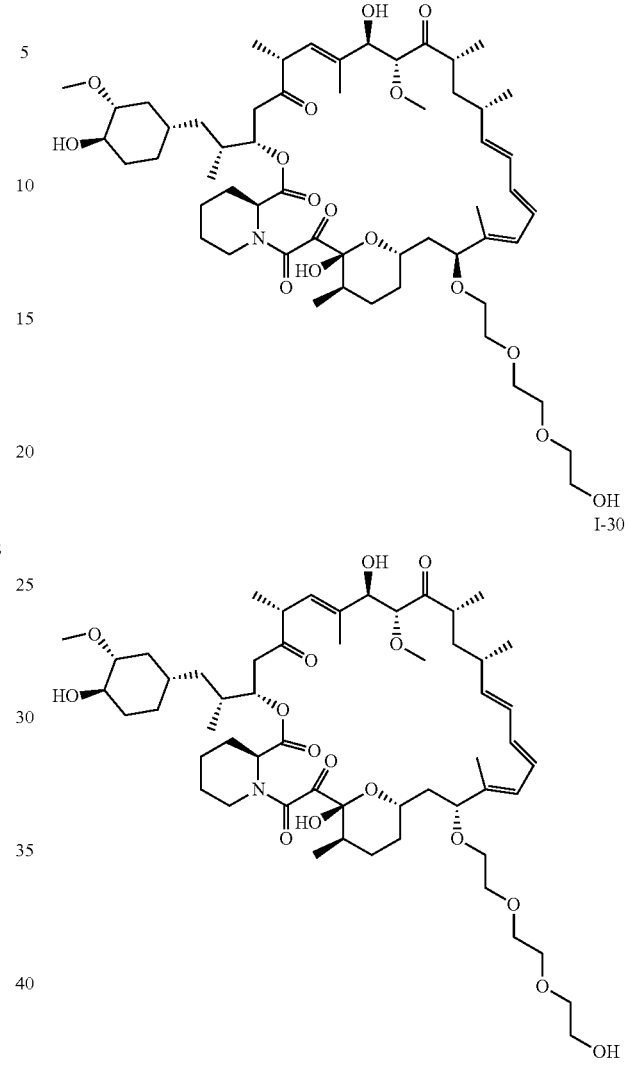

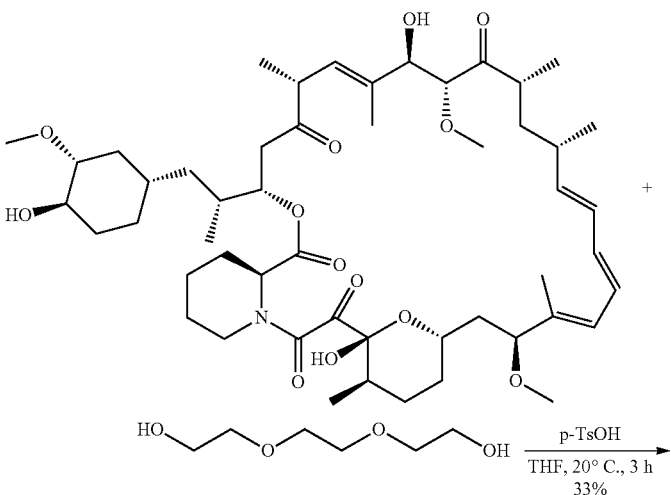

-continued
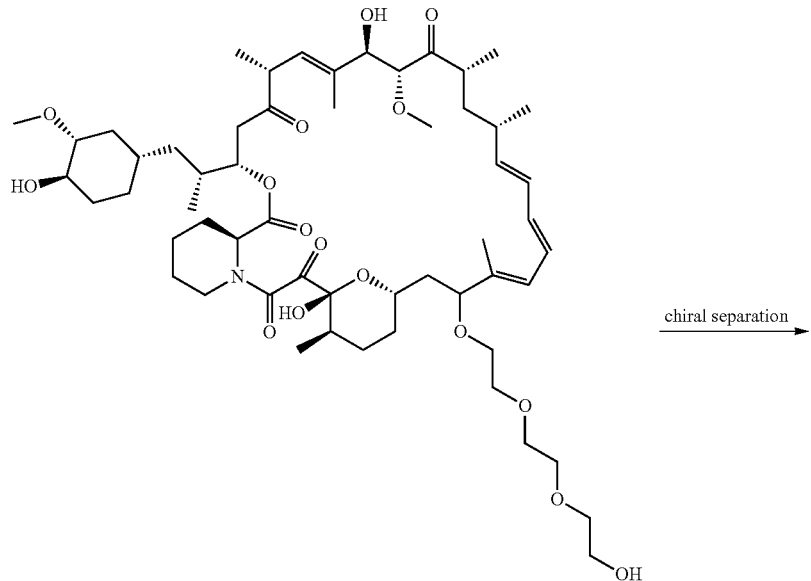
I-28
chiral separation →
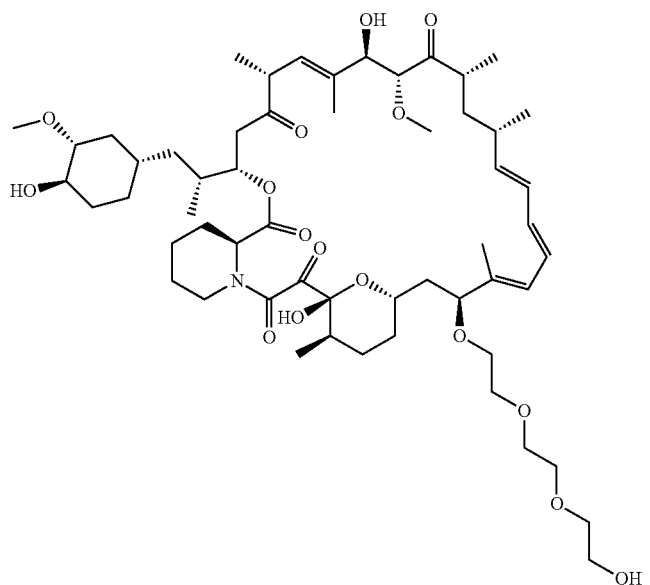
I-29

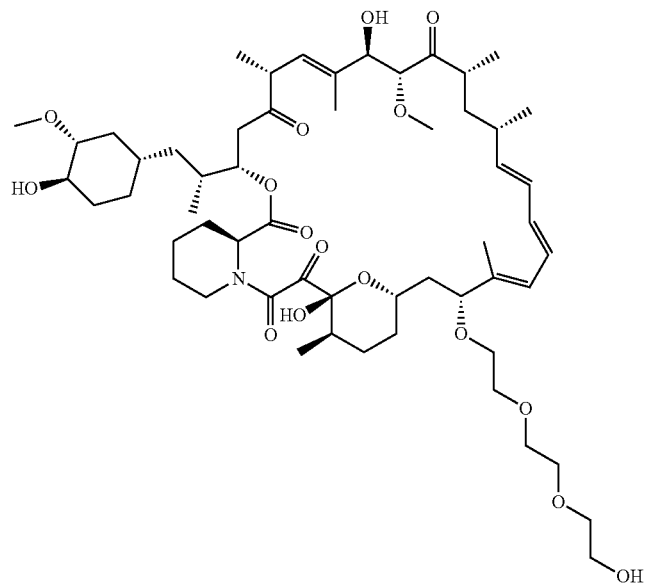

1-30

Procedures and Characterization:

2-[2-(2-hydroxyethoxy)ethoxy]ethanol (5 mL) was added to a solution of rapamycin (0.5 g, 0.547 mmol) and p-toluenesulfonic acid hydrate (0.52 g, 2.73 mmol) in THF (15 mL) at 25° C. The resulting mixture was stirred for 2 hours, then added to an ice cold saturated $NaHCO_3$ aqueous solution and extracted with EtOAc (30 mL× 3). The organic layers were combined then dried over $Na_2SO_4$, filtered, and concentrated in vacuo. The crude material was purified by reverse phase chromatography ($CH_3CN$/pure water: 7:3) to obtain (21E,23E,25E,26E,34R,35S,36R,37R,39R,41S,44S,45R,46R,55S)-45,55-dihydroxy-43-[2-[2-(2-hydroxyethoxy)ethoxy]ethoxy]-44-[(1 S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-28: 0.19 g, 33.7% yield) as a white solid. MS ($EI^+$, m/z): 1054.4 $[M+Na]^+$. 1.5 g of this material was sent for chiral separation which provided I-29 (0.6 g) and I-30 (0.2 g).

The chiral separation method:

Column: CHIRALPAK IC (IC00CD-TB016)

Column size: 0.46 cm I.D.×15 cm L

Mobile phase: Hexane/EtOH=60/40(V/V)

Flow rate: 1.0 ml/min

Wave length: UV 254 nm

Temperature: 35° C.

HPLC equipment: Shimadzu LC-20AD CP-HPLC-05

I-29: $^1$H NMR (500 MHz, $CDCl_3$) δ 6.41-6.20 (m, 2H), 6.13 (dd, J=15.0, 10.3 Hz, 1H), 5.92 (dd, J=32.7, 11.0 Hz, 1H), 5.51 (dd, J=15.1, 8.9 Hz, 1H), 5.41 (d, J=9.9 Hz, 1H), 5.27 (d, J=5.3 Hz, 1H), 5.13 (dd, J=26.5, 20.5 Hz, 1H), 4.85 (s, 1H), 4.19 (t, J=8.9 Hz, 1H), 3.92 (d, J=36.4 Hz, 1H), 3.80-3.51 (m, 12H), 3.50-3.24 (m, 12H), 2.87-2.51 (m, 6H), 2.29 (t, J=34.7 Hz, 2H), 2.12-1.87 (m, 5H), 1.84-1.66 (m, 13H), 1.53-1.15 (m, 9H), 1.15-0.77 (m, 18H), 0.65 (dt, J=20.2, 10.1 Hz, 1H).

EXAMPLE 2
Synthesis of (21E,23E,25E,26E,34R,35S,36R,37R, 39R,41S,44S,45R,46R,55S)-43-[2-[2-(2-aminoethoxy)ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-57-azatricyclohexatriaconta-21,23,25(47),26(48)-tetraene-49,50,51,52,53-pentone trifluoroacetic acid salt (I-39):
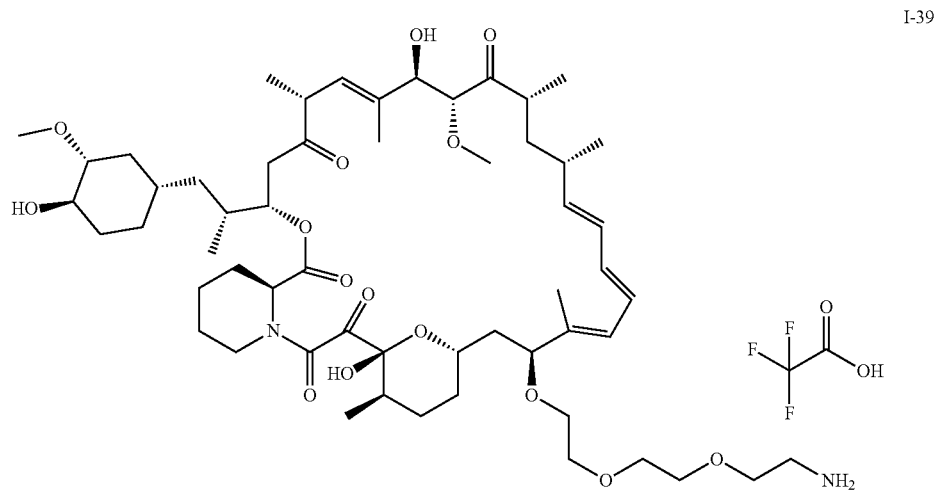
I-39
Synthetic Scheme:
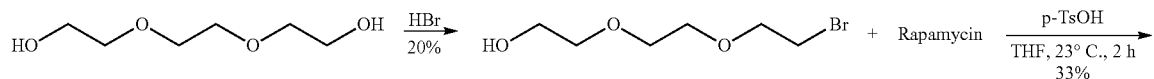
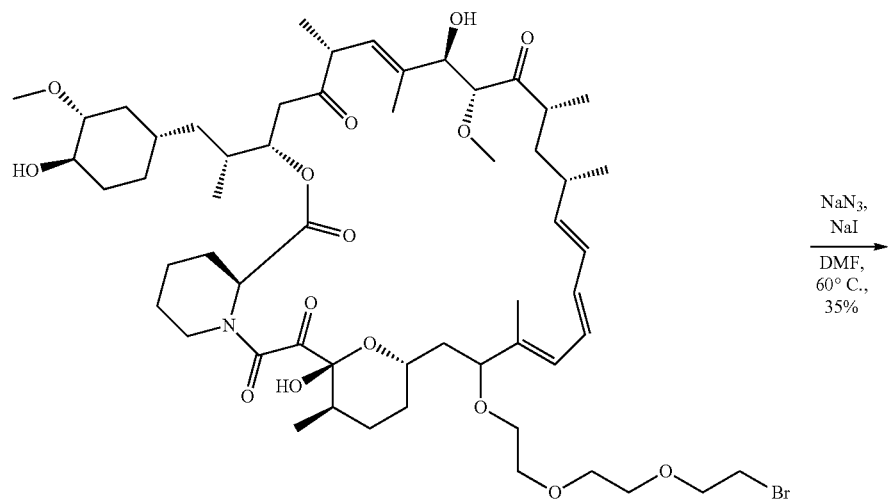

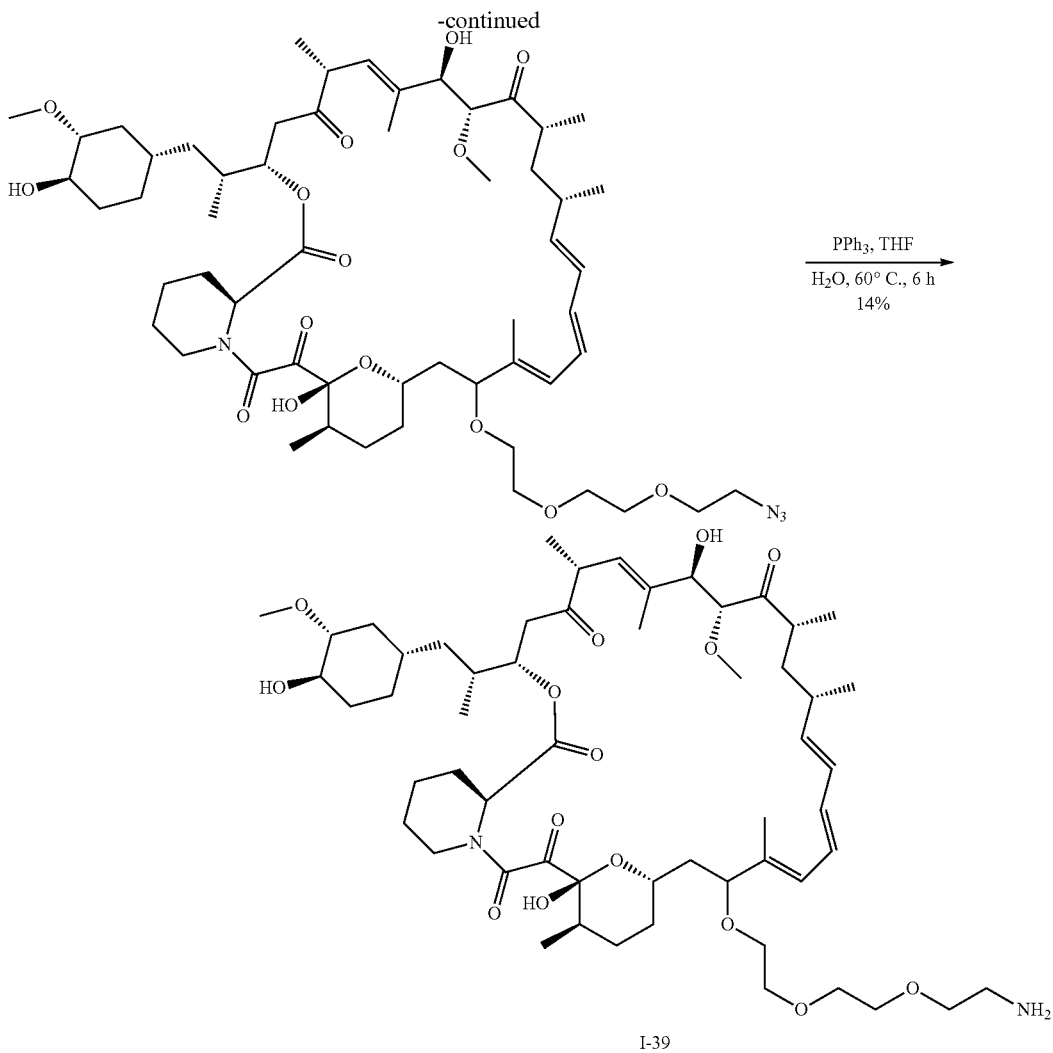

I-39

Procedures and Characterization:

Step 1: 2-(2-(2-bromoethoxy)ethoxy)ethanol:

Hydrogen bromide (86.21 g, 1.07 mmol, 115 mL) was added to a solution of 2-[2-(2-hydroxyethoxy)ethoxy]ethanol (100 g, 665.90 mmol) in toluene (1.15 L) and the resulting mixture was stirred at reflux for 18 hours, then the water layer was discarded. The organic layer was washed with aqueous NaOH solution, concentrated in vacuo, then purified by silica gel chromatography (MeOH:DCM=1:20) to obtain 2-[2-(2-bromoethoxy)ethoxy]ethanol (20 g, 14% yield) as a liquid. $^1$H NMR (400 MHz, CDCl$_3$) δ 3.83 (t, J=6.2 Hz, 2H), 3.77-3.72 (m, 2H), 3.69 (s, 4H), 3.64-3.61 (m, 2H), 3.49 (t, J=6.1 Hz, 2H), 2.51 (t, J=6.1 Hz, 1H).

Step 2: (21E,23E,25E,26E,34R,35S,36R,37R,39R,41S,44S,45R,46R,55S)-43-[2-[2-(2-bromoethoxy)ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-65,66-dioxa-56-azatricyclohexatriaconta-21,23,25(47),26(48)-tetraene-49,50,51,52,53-pentone:

2-[2-(2-bromoethoxy)ethoxy]ethanol (0.12 g, 0.547 mmol, 2 mL) was added to a solution of rapamycin (0.5 g, 0.547 mmol) and p-toluenesulfonic acid hydrate (0.5 g, 2.73 mmol) in THF (7 mL) at room temperature and the resulting mixture was stirred for 2 hours. Ice cold NaHCO$_3$ aqueous solution was then added and the mixture was extracted with EtOAc (30 mL×3). The organic phase was then dried over Na$_2$SO$_4$, filtered, and concentrated in vacuo. The resulting crude material was purified by reverse phase chromatography (CH$_3$CN/pure water=7:3) to obtain (21E,23E,25E,26E, 34R,35S,36R,37R, 39R,41S,44S,45R,46R,55S)-43-[2-[2-(2-bromoethoxy)ethoxy]ethoxy]-45,55-dihydroxy-44-[(1S)-2-[(1S, 3R,4R)-4-hydroxy-3-methoxy-cyclohexyl]-1-methyl-ethyl]-46-methoxy-34,35, 36,37,47,48-hexamethyl-65,66-dioxa-56-azatricyclohexatriaconta-21,23,25(47),26 (48)-tetraene-49,50,51,52,53-pentone (0.2 g, 33.4% yield, $^1$HNMR shows a rapamycin impurity) as a white solid. MS (EI$^+$, m/z): 1116.4 [M+Na]$^+$.

Step 3: (21E,23E,25E,26E,34R,35S,36R,37R,39R,41S,44S,45R,46R,55S)-43-[2-[2-(2-azidoethoxy)ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-68,69-dioxa-59-azatricyclohexatriaconta-21,23,25(47),26(48)-tetraene-49,50,51,52,53-pentone:

A solution of NaN$_3$ (1.07 g, 16.44 mmol), NaI (0.33 g, 2.19 mmol) and (21E,23E,25E,26E,34R,35S,36R,37R,39R, 41S,44S,45R,46R,55S)-43-[2-[2-(2-bromoethoxy) ethoxy]ethoxy]-45,55-dihydroxy-44-[(1S)-2-[(1S,3R,4R)-4-hydroxy-3-methoxy-cyclohexyl]-1-methyl-ethyl]-46- methoxy-34,35,36,37,47,48-hexamethyl-65,66-dioxa-56-azatricyclohexatriaconta-21,23,25(47),26(48)-tetraene-49,50,51,52,53-pentone (0.6 g, 0.548 mmol) in DMF (10 mL) was stirred at 60° C. for 1.5 hours. The reaction was then quenched by EtOAc (50 mL) and the mixture washed with $NH_4Cl$ aqueous solution (20 mL), dried over $Na_2SO_4$, filtered and concentrated in vacuo. The resulting crude material was purified by reverse phase chromatography ($CH_3CN$/pure water=4:1) to obtain (21E,23E,25E,26E,34R,35S,36R,37R,39R,41S,44S,45R,46R,55S)-43-[2-[2-(2-azidoethoxy) ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-68,69-dioxa-59-azatricyclohexatriaconta-21,23,25(47),26(48)-tetraene-49,50,51,52,53-pentone (0.3 g, 51.8% yield) as a light yellow solid. MS ($EI^+$, m/z): 1079.4$[M+Na]^+$.

Step 4: (21E,23E,25E,26E,34R,35S,36R,37R,39R,41S,44S,45R,46R,55S)-43-[2-[2-(2-aminoethoxy)ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-57-azatricyclohexatriaconta-21,23,25(47),26(48)-tetraene-49,50,51,52,53-pentone trifluoroacetic acid salt:

Triphenylphoshine (0.186 g, 0.7 mmol) was added slowly to a solution of (21E,23E,25E,26E,34R,35S,36R,37R,39R,41S,44S,45R,46R,55S)-43-[2-[2-(2-azidoethoxy) ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-68,69-dioxa-59-azatricyclohexatriaconta-21,23,25(47),26(48)-tetraene-49,50,51,52,53-pentone (0.25 g, 0.24 mmol) in THF (5 mL) triphenylphosphine. The resulting solution was stirred at 60° C. for 2 hours, and then 0.05 mL of water was added and the mixture stirred at room temperature for 6 hours, then concentrated. The resulting crude material was purified by reverse phase chromatography ($CH_3CN$/0.02% TFA in water (2:3) to obtain (21E,23E,25E,26E,34R,35S,36R,37R,39R,41S,44S,45R,46R,55S)-43-[2-[2-(2-aminoethoxy) ethoxy]ethoxy]-45,55-dihydroxy-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-57-azatricyclohexatriaconta-21,23,25(47),26(48)-tetraene-49,50,51,52,53 -pentone (I-39: 0.035 g, 14% yield) as a white solid. MS ($EI^+$, m/z): 1031.4$[M+H]^+$. $^1H$ NMR (500 MHz, DMSO-$d_6$) δ 7.82 (s, 3H), 6.42 (dd, J=33.7, 19.3 Hz, 2H), 6.25-6.09 (m, 2H), 5.46 (dd, J=14.7, 9.7 Hz, 1H), 5.28 (s, 1H), 5.08 (d, J=10.1 Hz, 1H), 5.00-4.92 (m, 1H), 4.08-3.92 (m, 2H), 3.78 (d, J=11.6 Hz, 1H), 3.63-3.38 (m, 16H), 3.36-3.08 (m, 12H), 2.99 (dd, J=22.3, 17.1 Hz, 2H), 2.87-2.73 (m, 2H), 2.37 (dd, J=17.9, 8.4 Hz, 1H), 2.30-1.75(m, 4H), 1.7-1.49 (m, 15H), 1.51-1.01 (m, 6H), 1.01-0.65 (m, 18H), 0.63-0.56 (m, 1H).

EXAMPLE 3

Synthesis of (21E,23E,25E,26E,36R,37S,38R,39R,41R,43S,46S,47R,48R,57S)-47,57-dihydroxy-45-[2-[2-[2-(2-hydroxyethoxy)ethoxy]ethoxy]ethoxy]-46-[(1S)-2-[(1S,3R,4R)-4-hydroxy-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-36):

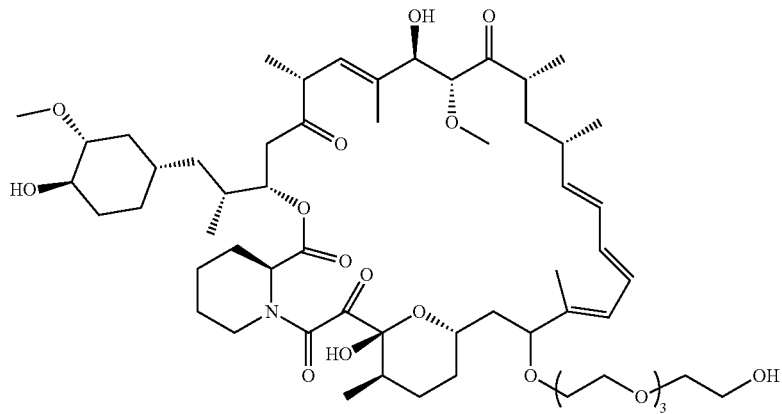

I-36

Synthetic Scheme:

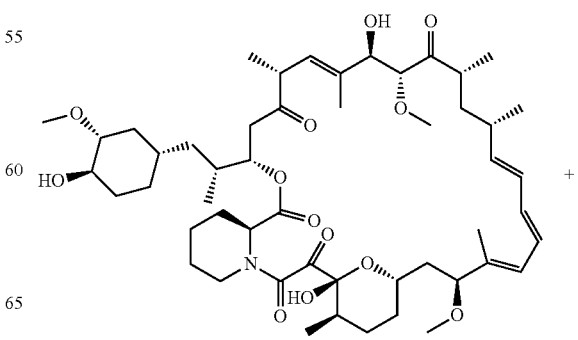

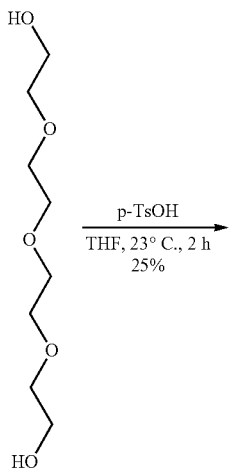

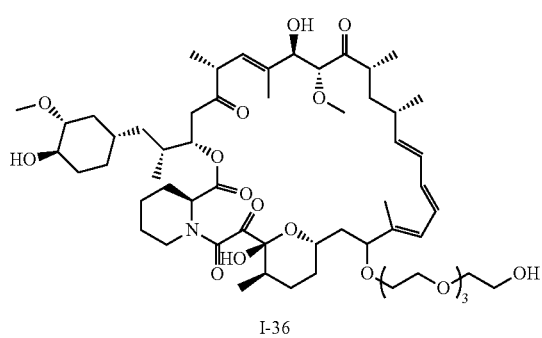

I-36

Procedures and Characterization:

2-[2-[2-(2-hydroxyethoxy)ethoxy]ethoxy]ethanol (1.06 g, 5.47 mmol, 5 mL) was added to a solution of rapamycin (0.5 g, 0.547 mmol) and p-toluenesulfonic acid hydrate (0.21 g, 1.09 mmol) in THF (15 mL) at room temperature. The reaction mixture was stirred at room temperature for 2 hours, then added to ice cold saturated NaHCO$_3$ aqueous solution and extracted with EtOAc (30 mL×3). The organic layers were the combined and dried over Na$_2$SO$_4$, filtered and concentrated. The crude was purified by reverse phase chromatography (CH$_3$CN/pure water=3:2) to obtain (21E, 23E,25E,26E,36R, 37S,38R,39R,41R,43S,46S,47R,48R, 57S)-47,57-dihydroxy-45-[2-[2-[2-(2-hydroxyethoxy) ethoxy]ethoxy]ethoxy]-46-[(1S)-2-[(1S,3R,4R)-4-hydroxy-3-methoxy-cyclohexyl]-1-methyl-ethyl]-48-methoxy-36,37, 38,39,49,50-hexamethyl-68,69-dioxa-58-azatricyclohexatriaconta-21,23,25(49),26(50)-tetraene-51,52,53,54,55-pentone (I-36: 0.15 g, 25.5% yield) as a white solid. MS (EI$^+$, m/z): 1098.4[M+H]$^+$. $^1$H NMR (500 MHz, CDCl$_3$) δ 6.40-5.92 (m, 4H), 5.73-5.35 (m, 3H), 5.25-5.05 (m, 2H), 4.31-4.12 (m, 1H), 3.97 (dd, J=25.7, 6.3 Hz, 1H), 3.87-3.53 (m, 15H), 3.52-3.17 (m, 11H), 2.99-2.46 (m, 6H), 2.36-1.93 (m, 9H), 1.90-1.54 (m, 13H), 1.52-1.17 (m, 9H), 1.15-0.81 (m, 18H), 0.68-0.58 (m, 1H).

EXAMPLE 4

Synthesis of (21E,23E,25E,26E,38R,39S,40R,41R, 43R,45S,47R,48S,49R,50R,59S)-49,59-dihydroxy-47-[2-[2-[2-[2-(2-hydroxyethoxy)ethoxy]ethoxy] ethoxy]ethoxy]-48-[(1S)-2-[(1S,3R,4R)-4-hydroxy-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone (I-35):

I-35

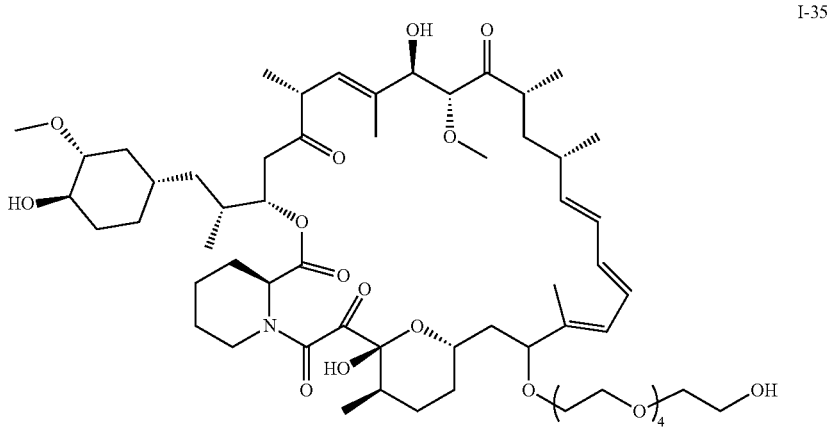

Synthetic Scheme:

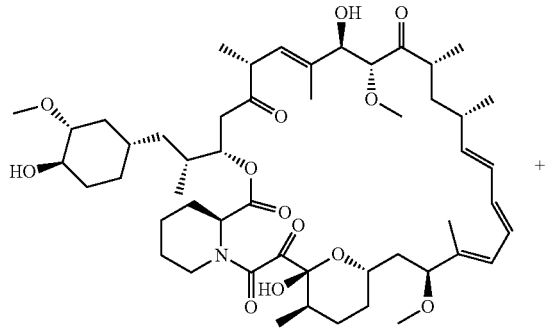

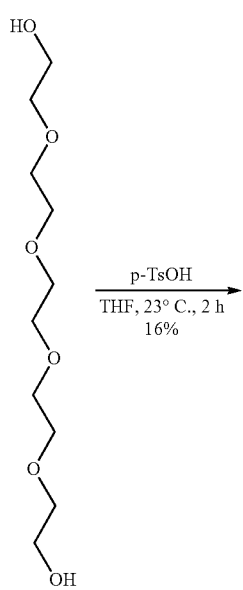

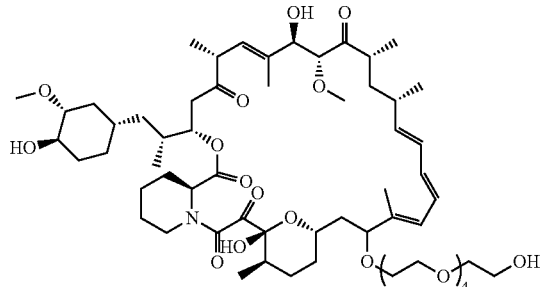

I-35

Procedures and Characterization:

2-[2-[2-[2-(2-hydroxyethoxy)ethoxy]ethoxy]ethoxy]ethanol (0.08 g, 0.33 mmol, 2 mL) was added to a solution of rapamycin (0.3 g, 0.328 mmol) and p-toluenesulfonic acid hydrate (0.31 g, 1.64 mmol) in THF (6 mL) at room temperature. The resulting mixture was stirred at room temperature for 2 hours, then added to ice cold saturated NaHCO$_3$ aqueous solution and extracted with EtOAc (20 mL×3). The organic layers were combined and then dried over Na$_2$SO$_4$, filtered, and concentrated in vacuo. The crude material was purified by reverse phase chromatography (CH$_3$CN/pure water: 3:2) to obtain (21E,23E,25E,26E,38R, 39S,40R,41R,43R,45S,47R,48S,49R,50R,59S)-49,59-dihydroxy-47-[2-[2-[2-[2-(2-hydroxyethoxy)ethoxy]ethoxy]ethoxy]ethoxy]-48-[(1S)-2-[(1S,3R,4R)-4-hydroxy-3-methoxy-cyclohexyl]-1-methyl-ethyl]-50-methoxy-38,39,40,41,51,52-hexamethyl -70,71-dioxa-60-azatricyclohexatriaconta-21,23,25(51),26(52)-tetraene-53,54,55,56,57-pentone (I-35: 0.06 g, 16.3% yield) as a white solid. MS (EI$^+$, m/z): 1042.4[M+Na]$^+$. $^1$H NMR (500 MHz, CDCl$_3$) δ 6.42-5.81 (m, 4H), 5.58-4.81 (m, 4H), 4.31-4.11 (m, 1H), 4.01-3.51 (m, 22H), 3.49-3.13 (m, 11H), 3.01-2.43 (m, 6H), 2.29 (t, J=30.6 Hz, 2H), 2.15-1.88 (m, 7H), 1.76-1.55 (m, 12H), 1.51-1.18 (m, 9H), 1.15-0.74 (m, 18H), 0.66 (dd, J=23.9, 12.0 Hz, 1H).

EXAMPLE 5

Synthesis of (21E,23E,25E,26E,30R,31S,32R,33R, 35R,37S,39S,40S,41R,42R,52S)-39-(2,3-dihydroxypropoxy)-41,52-dihydroxy-40-[(1S)-2-[(1S,3R,4R)-4-hydroxy-3-methoxy-cyclohexyl]-1-methyl-ethyl]-42-methoxy-30,31,32,33,43,44-hexamethyl-64,65-dioxa-53-azatricyclohexatriaconta-21,23,25(43),26(44)-tetraene-45,46,47,48,49-pentone (I-25):

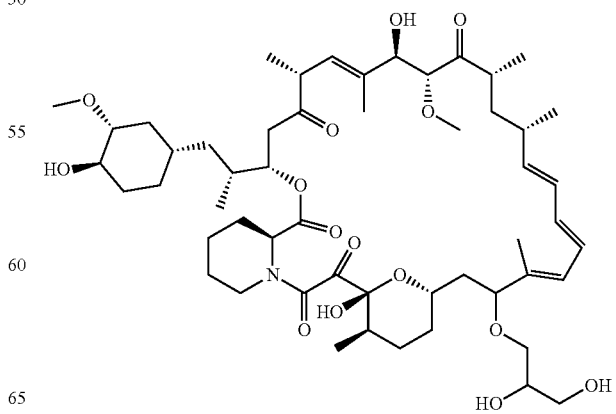

I-25

Synthetic Scheme:

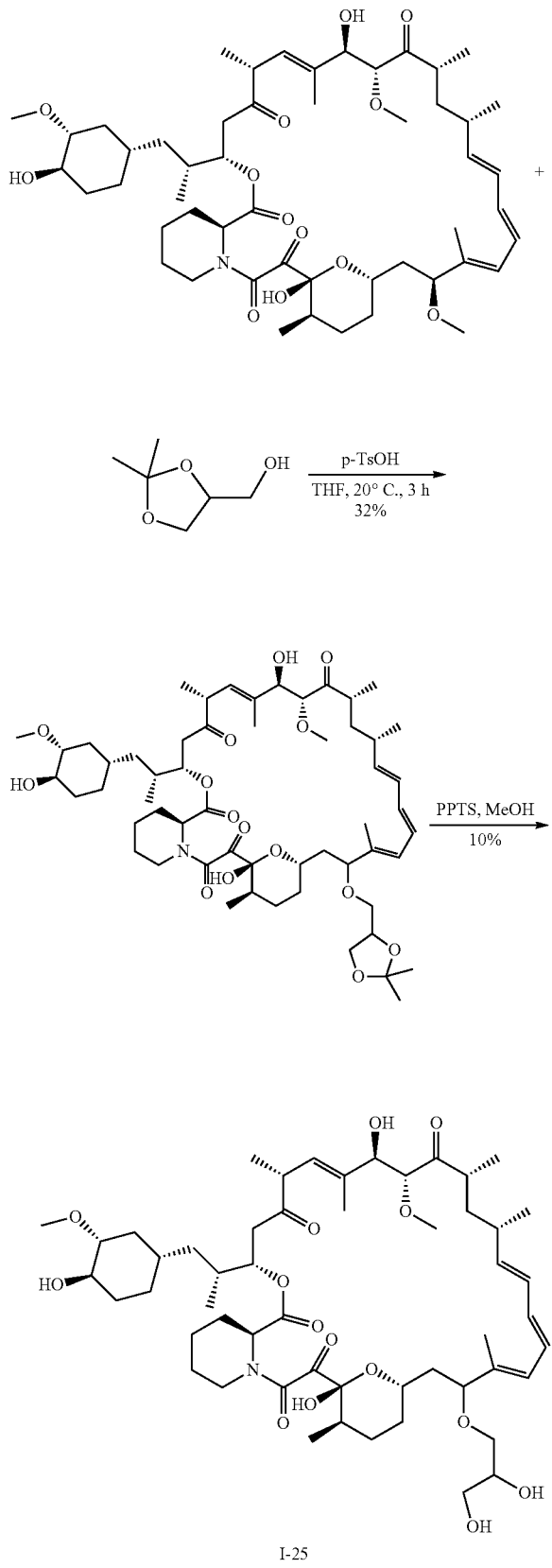

Procedures and Characterization:

Step 1: (24E,26E,28E,29E,32R,33S,34R,35R,37R,39S,41S,42S,44R,45R,55S)-41-[(2,2-dimethyl-1,3-dioxolan-4-yl)methoxy]-44,55-dihydroxy-42-[(1S)-2-[(1S,3R,4R)-4-hydroxy-3-methoxy-cyclohexyl]-1-methyl-ethyl]-45-methoxy-32,33,34,35,46,47-hexamethyl-66,67-dioxa-56-azatricyclohexatriaconta-24,26,28(46),29(47)-tetraene-48,49,50,51,52-pentone:

(2,2-dimethyl-1,3-dioxolan-4-yl)methanol (1 mL) was added to a solution of rapamycin (0.2 g, 0.22 mmol) and p-toluenesulfonic acid hydrate (0.1 g, 0.547 mmol) in THF (3 mL) at room temperature. The resulting mixture stirred at room temperature for 2 hours, then added to ice cold saturated NaHCO$_3$ aqueous solution and extracted with EtOAc (20 mL×2). The organic layers were combined and then dried over Na$_2$SO$_4$, filtered, and concentrated in vacuo. The crude was purified by reverse phase chromatography (CH$_3$CN/pure water: 7:3) to obtain (24E,26E,28E,29E,32R,33S,34R,35R,37R,39S,41S,42S,44R,45R,55S)-41-[(2,2-dimethyl-1,3-dioxolan-4-yl)methoxy]-44,55-dihydroxy-42-[(1S)-2-[(1S,3R,4R)-4-hydroxy-3-methoxy-cyclohexyl]-1-methyl-ethyl]-45-methoxy-32,33,34,35,46,47-hexamethyl-66,67-dioxa-56-azatricyclohexatriaconta-24,26,28(46),29(47)-tetraene-48,49,50,51,52-pentone (0.07 g, 32% yield) as a white solid. MS (EI$^+$, m/z): 1036.4[M+Na]$^+$.

Step 2: (21E,23E,25E,26E,30R,31S,32R,33R,35R,37S,39S,40S,41R,42R,52S)-39-(2,3-dihydroxypropoxy)-41,52-dihydroxy-40-[(1S)-2-[(1S,3R,4R)-4-hydroxy-3-methoxy-cyclohexyl]-1-methyl-ethyl]-42-methoxy-30,31,32,33,43,44-hexamethyl-64,65-dioxa-53-azatricyclohexatriaconta-21,23,25(43),26(44)-tetraene-45,46,47,48,49-pentone (I-25):

4-methylbenzenesulfonic acid·pyridine (0.037 g, 0.148 mmol) was added to a solution of (24E,26E,28E,29E,32R,33S,34R,35R,37R,39S,41S,42S,44R,45R,55S)-41-[(2,2-dimethyl-1,3 -dioxolan-4-yl)methoxy]-44,55-dihydroxy-42-[(1S)-2-[(1S,3R,4R)-4-hydroxy-3-methoxy-cyclohexyl]-1-methyl-ethyl]-45-methoxy-32,33,34,35,46,47-hexamethyl-66,67-dioxa-56-azatricyclohexatriaconta-24,26,28(46),29(47)-tetraene-48,49,50,51,52-pentone (0.05 g, 0.05 mmol) in MeOH (2 mL). The mixture was stirred at room temperature for 18 hours. After the evaporation of methanol, the residue was neutralized with saturated aqueous NaHCO$_3$. The mixture was then extracted with EtOAc (10 mL×3). The organic layers were combined, dried over Na$_2$SO$_4$, and concentrated with the resulting crude material purified by reverse phase chromatography (CH$_3$CN/pure water=1:1) to give (21E,23E,25E,26E,30R,31S,32R,33R,35R,37S,39S,40S,41R,42R,52S)-39-(2,3-dihydroxypropoxy)-41,52-dihydroxy-40-[(1S)-2-[(1S,3R,4R)-4-hydroxy-3-methoxy-cyclohexyl]-1-methyl-ethyl]-42-methoxy-30,31,32,33,43,44-hexamethyl-64,65-dioxa-53-azatricyclohexatriaconta-21,23,25(43),26(44)-tetraene-45,46,47,48,49-pentone (I-25: 0.005 g, 10% yield) as a white solid. MS (EI$^+$, m/z): 996.5[M+Na]$^+$. $^1$H NMR (500 MHz, CDCl$_3$) δ 6.21-5.97 (m, 4H), 5.77-4.78 (m, 5H), 4.53-4.12 (m, 2H), 4.05-3.11 (m, 19H), 3.07-2.88 (m, 2H), 2.65-2.5 (m, 4H), 2.39-1.91 (m, 7H), 1.89-1.69 (m, 12H), 1.52-1.20 (m, 9H), 1.17-0.76 (m, 18H), 0.73-0.61 (m, 1H).

EXAMPLE 6
Synthesis of (21E,23E,25E,26E,42R,43S,44R,45R, 47S,49S,51S,52S,53R,54R,63R)-53,63-dihydroxy-51-[2-[2-[2-[2-[2-[2-[2-(2-hydroxyethoxy)ethoxy]ethoxy]ethoxy]ethoxy]ethoxy]ethoxy]-52-[(1R)-2-[(1S,3R,4R)-4-hydroxy-3-methoxy-cyclohexyl]-1-methyl-ethyl]-54-methoxy-42,43,44, 45,55,56-hexamethyl-74,75-dioxa-64-azatricyclohexatriaconta-21,23,25(55),26(56)-tetraene-57,58,59,60,61-pentone (I-24):
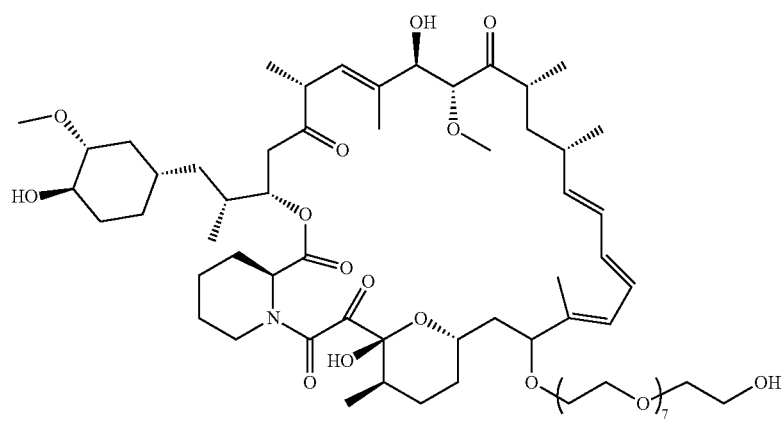
I-24
Synthetic Scheme:
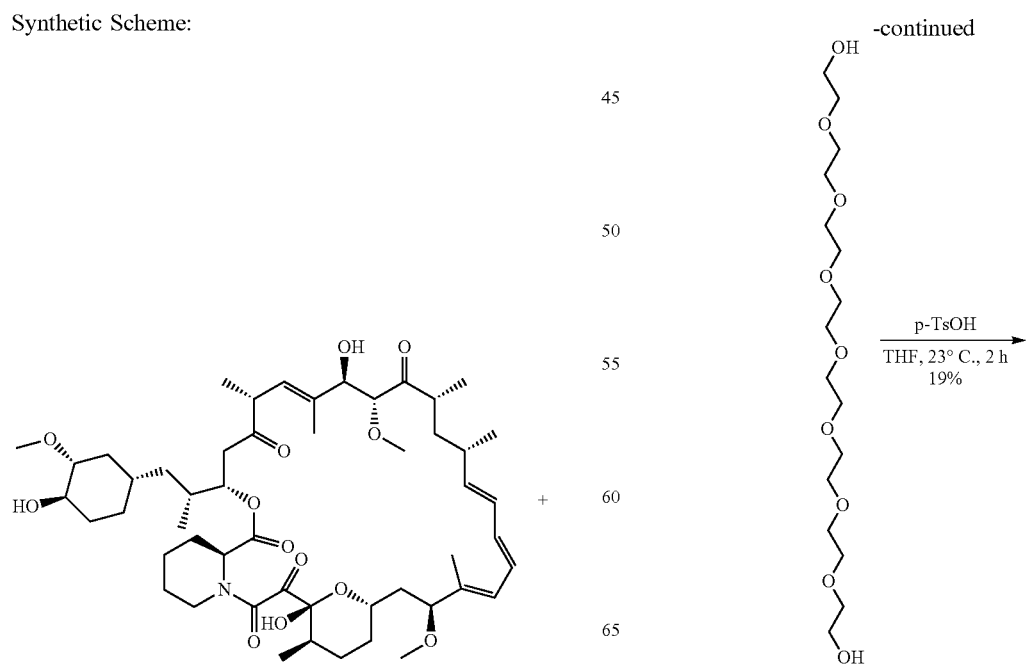

-continued

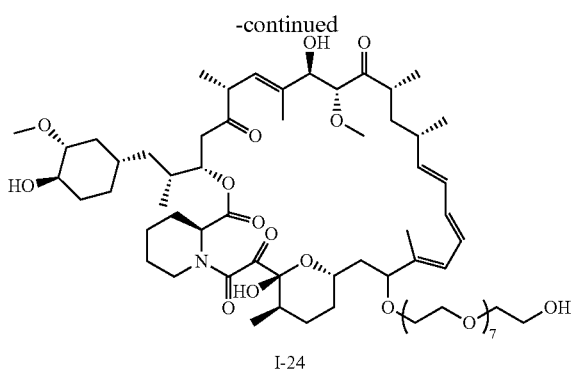

I-24

Procedures and Characterization:

A solution of rapamycin (0.5 g, 547 mmol) and 2-[2-[2-[2-[2-[2-[2-(2-hydroxyethoxy)ethoxy]ethoxy]ethoxy]ethoxy]ethoxy]ethanol (0.2 g, 0.547 mmol, 3 mL) and p-toluenesulfonic acid hydrate (0.52 g, 2.73 mmol) in THF (15 mL) was stirred at room temperature for 3 hours, then quenched with EtOAc (30 mL×3). The combined organic layers were washed with ice cold saturated NaHCO$_3$ solution and concentrated. The resulting crude material was purified by reverse phase chromatography (CH$_3$CN/pure water=7:3) to obtain (21E,23E,25E,26E,42R,43S,44R,45R,47S,49S,51S,52S,53R,54R,63R)-53,63-dihydroxy-51 -[2-[2-[2-[2-[2-[2-[2-(2-hydroxyethoxy)ethoxy]ethoxy]ethoxy]ethoxy]ethoxy]ethoxy]-52-[(1R)-2-[(1S, 3R,4R)-4-hydroxy-3-methoxy-cyclohexyl]-1-methyl-ethyl]-54-methoxy-42,43,44,45,55,56-hexamethyl-74,75-dioxa-64-azatricyclohexatriaconta-21,23,25(55),26(56)-tetraene-57,58,59,60,61-pentone (I-24: 0.13 g, 19%) as a white solid. MS (EI$^+$, m/z): 1275.6[M+Na]$^+$. $^1$H NMR (500 MHz, CDCl$_3$) δ 6.45-5.80 (m, 4H), 5.57-5.05 (m, 4H), 4.85-4.08 (m, 2H), 3.90-3.50 (m, 34H), 3.47-3.24 (m, 13H), 2.97-2.44 (m, 7H), 2.39-2.06 (m, 2H), 2.03-1.84 (m, 6H), 1.78-1.58 (m, 13H), 1.53-1.16 (m, 9H), 1.14-0.78 (m, 18H), 0.67-0.53 (m, 1H).

EXAMPLE 7

Synthesis of (21E,23E,25E,26E,34R,35S,36R,37R,38S,41S,43S,45R,46R,55R)-45,55-dihydroxy-42-[2-(2-hydroxyethoxy)ethoxy]-43-[(1R)-2-[(1S,2R,3R)-3-(2-hydroxyethoxy)-2-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-23):

I-23

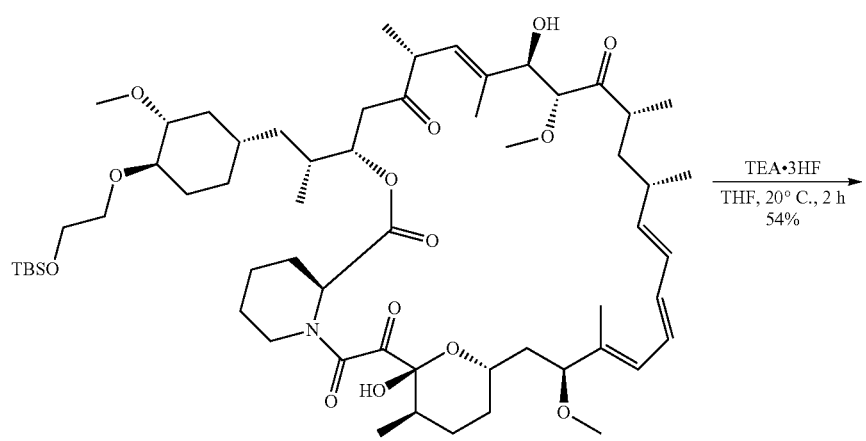

Synthetic Scheme:

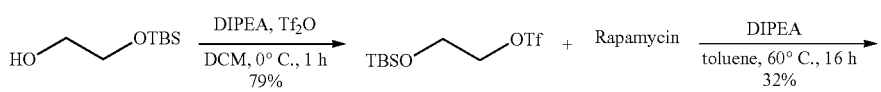

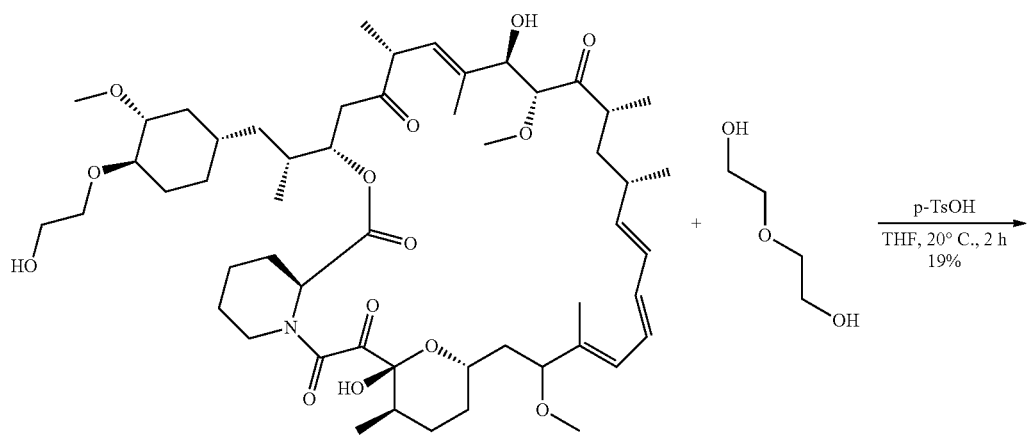

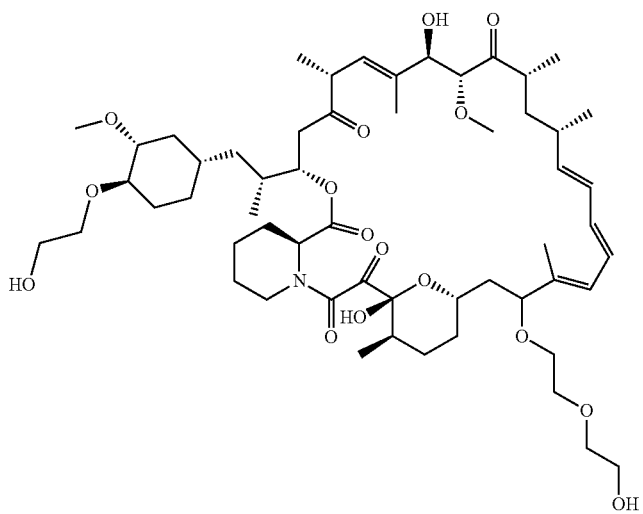

I-23

Procedures and Characterization:

Step 1: 2-[tert-butyl(dimethyl)silyl]oxyethyl trifluoromethanesulfonate:

A mixture of 2-[tert-butyl(dimethyl)silyl]oxyethanol (4 g, 22.69 mmol) and DIPEA (3.81 g, 29.49 mmol, 5.14 mL) in DCM (50 mL) was cooled to 0° C. under $N_2$, then trifluoromethylsulfonyl trifluoromethanesulfonate (7.04 g, 24.95 mmol) was added and the resulting mixture was stirred at 0° C. for 1 hour. The reaction was diluted with EtOAc (200 mL) then washed with saturated.NaHCO$_3$ (200 mL), water (200 mL), brine (200 mL), and then the organic layer was dried over $Na_2SO_4$, filtered, and concentrated in vacuo to afford 2-[tert-butyl(dimethyl)silyl]oxyethyl trifluoromethanesulfonate (5.5 g, 78.6% yield) as a brown oil. $^1$H NMR (500 MHz, CDCl$_3$) δ 4.50-4.42 (t, 2H), 3.85-3.80 (t, 2H), 0.84-0.78 (s, 9H), 0.00 (s, 6H).

Step 2: (27E,29E,31E,32E,36R,37S,38R,39R,40S,43S,44S,45S,47R,48R,57R)-45-[(1R)-2-[(1S,2R,3R)-3-[2-[tert-butyl(dimethyl)silyl]oxyethoxy]-2-methoxy-cyclohexyl]-1-methyl-ethyl]-47,57-dihydroxy-44,48-dimethoxy-36,37,38,39,49,50-hexamethyl-67,68-dioxa-59-azatricyclohexatriaconta-27,29,31(49),32(50)-tetraene-51,52,53,54,55-pentone:

Rapamycin (2 g, 2.19 mmol) and DIPEA (2.26 g, 17.50 mmol, 3.05 mL) were dissolved in toluene (60 mL) then heated to 60° C. 2-[tert-butyl(dimethyl)silyl]oxyethyl trifluoromethanesulfonate (5.40 g, 17.50 mmol)was then added under $N_2$, then stirred at 60° C. for 16 hours. The mixture was poured into ice cold saturated NaHCO$_3$ (100 mL) and then extracted with EtOAc (150 mL×3). The combined organic layers were washed with water and brine, then concentrated in vacuo. The residue was then purified by reverse phase chromatography (CH$_3$CN/pure water=4:1) to afford (27E,29E,31E,32E,36R,37S,38R,39R,40S,43S,44S,45S,47R,48R,57R)-45-[(1R)-2-[(1S,2R,3R)-3-[2-[tert-butyl(dimethyl)silyl]oxyethoxy]-2-methoxy-cyclohexyl]-1-methyl-ethyl]-47,57-dihydroxy-44,48-dimethoxy-36,37,38,39,49,50-hexamethyl-67,68-dioxa-59-azatricyclohexatriaconta-27,29,31(49),32(50)-tetraene-51,52,53,54,55-pentone (0.75 g, 32% yield) as a colorless oil. ESI-MS (EI$^+$, m/z): 1095.5 [M+Na]$^+$.

Step 3: (22E,24E,26E,27E,31R,32S,33R,34R,35S,38S,39S, 40S,42R,43R,52R)-42,52-dihydroxy-40-[(1R)-2-[(1S,2R, 3R)-3-(2-hydroxyethoxy)-2-methoxy-cyclohexyl]-1-methyl-ethyl]-39,43-dimethoxy-31,32,33,34,44,45-hexamethyl-62,63-dioxa-53-azatricyclohexatriaconta-22, 24,26(44),27(45)-tetraene-46,47,48,49,50-pentone:

A solution of TEA·3HF (4.65 g, 28.87 mmol) and (27E, 29E,31E,32E,36R,37S,38R,39R,40S,43S,44S,45S,47R, 48R,57R)-45-[(1R)-2-[(1S,2R,3R)-3-[2-[tert-butyl(dimethyl)silyl]ethoxy]-2-methoxy-cyclohexyl]-1-methyl-ethyl]-47,57-dihydroxy-44,48-dimethyl-36,37,38,39,49, 50-hexamethyl-67,68-dioxa-59-azatricyclohexatriaconta-27,29,31(49),32(50)-tetraene-51,52,53,54,55-pentone (3.05 g, 2.89 mmol) in THF (50 mL) was stirred at 20° C. for 2 hours. The mixture was poured into ice cold saturated NaHCO₃ (100 mL) then extracted with EtOAc (150 mL×3). The organic layers were combined and washed with water and brine, then concentrated in vacuo. The residue was purified by reverse phase chromatography (CH₃CN/pure water: 7:3) to afford (22E,24E,26E,27E,31R,32S,33R,34R, 35 S,38S,39S,40S,42R,43R,52R)-42,52-dihydroxy-40-[(1R)-2-[(1S,2R,3R)-3-(2-hydroxyethoxy)-2-methoxy-cyclohexyl]-1-methyl-ethyl]-39,43-dimethoxy-31,32,33,34, 44,45-hexamethyl-62,63-dioxa-53-azatricyclohexatriaconta-22,24,26(44),27(45)-tetraene-46, 47,48,49,50-pentone (1.5 g, 54% yield) as a white solid. ESI-MS (EI⁺, m/z): 980.5 [M+Na]⁺.

Step 4: (21E,23E,25E,26E,34R,35S,36R,37R,38S,41S,43S, 45R,46R,55R)-45,55-dihydroxy-42-[2-(2-hydroxyethoxy) ethoxy]-43-[(1R)-2-[(1S,2R,3R)-3-(2-hydroxyethoxy)-2-methoxy-cyclohexyl]-1-methyl-ethyl]-46-methoxy-34,35, 36,37,47,48-hexamethyl-66,67-dioxa-56-azatricyclohexatriaconta-21,23,25(47),26(48)-tetraene-49, 50,51,52,53-pentone (I-23):

A mixture of (22E,24E,26E,27E,31R,32S,33R,34R,35S, 38S,39S,40S,42R,43R, 52R)-42,52-dihydroxy-40-[(1R)-2-[(1S,2R,3R)-3-(2-hydroxyethoxy)-2-methoxy-cyclohexyl]-1-methyl-ethyl]-39,43-dimethoxy-31,32,33,34,44,45-hexamethyl-62,63-dioxa-53-azatricyclohexatriaconta-22, 24,26(44),27(45)-tetraene-46,47,48,49,50-pentone (0.5 g, 0.52 mmol), 2-(2-hydroxyethoxy)ethanol (2.77 g, 26.09 mmol) and p-toluenesulfonic acid hydrate (0.54 g, 3.13 mmol) in THF (6 mL) was stirred at 20° C. for 2 hours. The mixture was poured into ice cold saturated NaHCO₃ (30 mL) and extracted with EtOAc (50 mL×3). The organic layers were combined and then washed with water and brine, then concentrated in vacuo. The residue was purified by reverse phase chromatography (CH₃CN/pure water=1:1) to afford (21E,23E,25E,26E,34R,35S,36R,37R,38S,41S,43S,45R, 46R,55R)-45,55-dihydroxy-42-[2-(2-hydroxyethoxy) ethoxy]-43-[(1R)-2-[(1S,2R,3R)-3-(2-hydroxyethoxy)-2-methoxy-cyclohexyl]-1-methyl-ethyl]-46-methoxy-34,35, 36,37,47,48-hexamethyl-66,67-dioxa-56-azatricyclohexatriaconta-21,23,25(47),26(48)-tetraene-49, 50,51,52,53-pentone (I-23: 0.1 g, 19% yield) as a white solid. ESI-MS (EI⁺, m/z): 1054.4 [M+Na]⁺. ¹H NMR (500 MHz, CDCl₃) δ 6.63-5.86 (m, 4H), 5.70-5.00 (m, 4H), 4.87-4.15 (m, 2H), 4.02-3.54 (m, 14H), 3.50-3.26 (m, 11H), 3.24-3.02 (m, 3H), 2.76-2.46 (m, 3H), 2.38-1.86 (m, 8H), 1.84-1.54 (m, 14H), 1.47 (m, 3H), 1.25 (m, 6H), 1.00 (m, 16H), 0.69 (dt, J=34.1, 12.1 Hz, 1H).

EXAMPLE 8

Synthesis of (21E,23E,25E,26E,36R,37S,38R,39R, 40S,43S,45S,47R,48R,57R)-47,57-dihydroxy-44-[2-[2-(2-hydroxyethoxy)ethoxy]ethoxy]-45-[(1R)-2-[(1S,2R,3R)-3-(2-hydroxyethoxy)-2-methoxy-cyclohexyl]-1-methyl-ethyl]-48-methoxy-36,37,38, 39,49,50-hexamethyl-68,69-dioxa-58-azatricyclohexatriaconta-21,23,25(49),26(50)-tetraene-51,52,53,54,55-pentone (I-32):

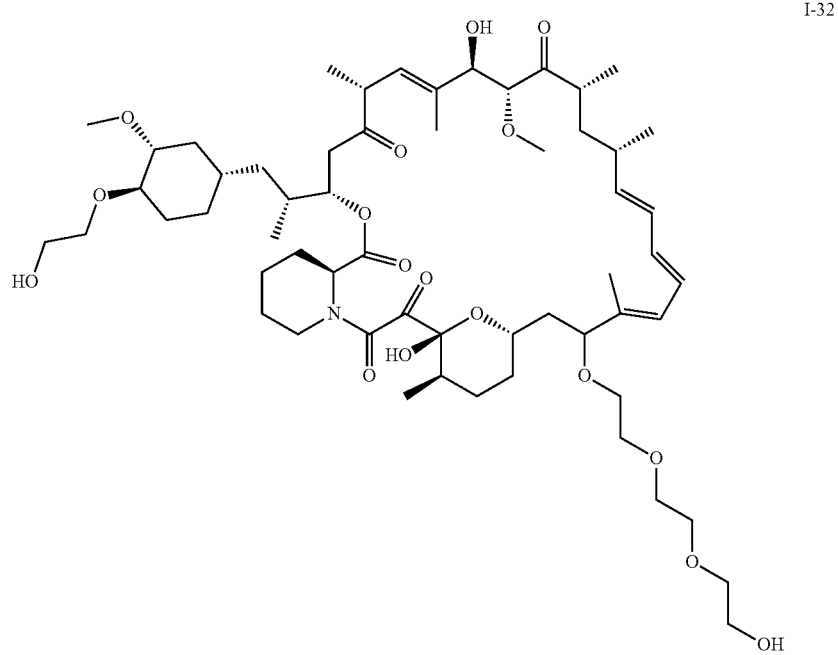 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCOCCO)C[C@@H]3CC[C@@H](C)[C@@](O)(O3)C(=O)C(=O)N3CCCC[C@H]3C(=O)O2)CC[C@H]1OCCO]

I-32

Synthetic Scheme:

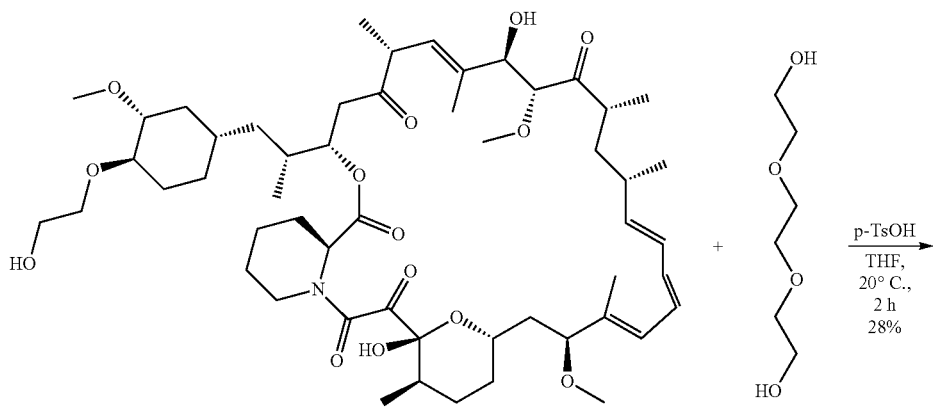

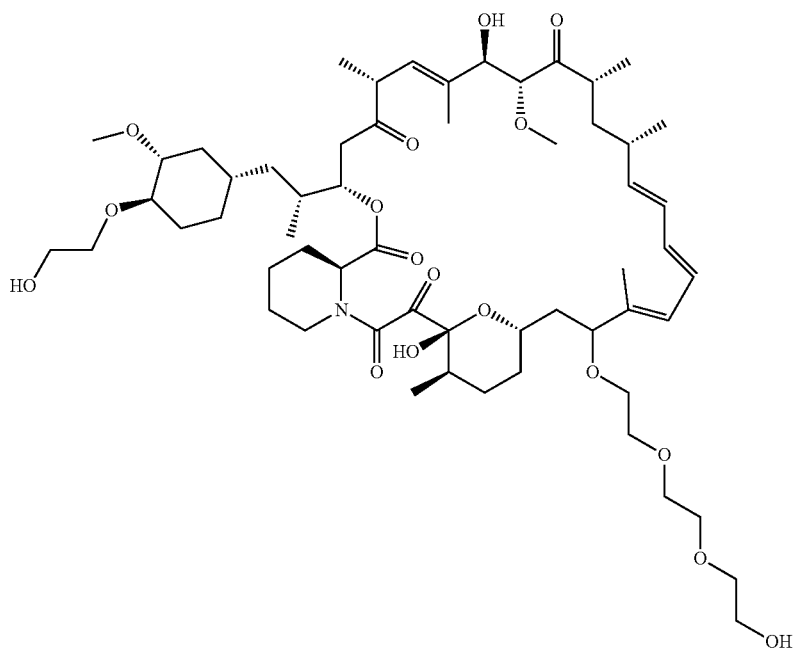

I-32

Procedures and Characterization:

A mixture of everolimus (3.92 g, 26.09 mmol) and p-toluenesulfonic acid hydrate (0.45 g, 2.61 mmol) in THF (10 mL) was stirred at 20° C. for 2 hours. The mixture was poured into ice cold saturated $NaHCO_3$ (30 mL) and extracted with EtOAc (50 mL×3). The organic layers were combined and then washed with water and brine, then concentrated in vacuo. The residue was purified by reversed phase chromatography ($CH_3CN$/pure water=1:1) to afford (21E,23E,25E,26E,36R,37S,38R,39R,40S,43S,45S,47R,48R,57R)-47,57-dihydroxy-44-[2-[2-(2-hydroxyethoxy)ethoxy]ethoxy]-45-[(1R)-2-[(1S,2R,3R)-3-(2-hydroxyethoxy)-2-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-32: 0.155 g, 28% yield) as a white solid. ESI-MS ($EI^+$, m/z): 1098.4 $[M+Na]^+$. $^1$H NMR (500 MHz, $CDCl_3$) δ 6.49-5.83 (m, 4H), 5.67-5.35 (m, 2H), 5.33-5.01 (m, 2H), 4.92-4.08 (m, 2H), 4.05-3.51 (m, 17H), 3.52-3.23 (m, 11H), 3.23-3.01 (m, 3H), 2.66 (m, 4H), 2.40-1.95 (m, 5H), 1.95-1.55 (m, 17H), 1.52-1.13 (m, 9H), 1.13-0.79 (m, 16H), 0.71 (dd, J=23.8, 11.9 Hz, 1H).

EXAMPLE 9
Synthesis of (21E,23E,25E,26E,38R,39S,40R,41R, 42S,45S,47S,49R,50R,59R)-49,59-dihydroxy-46-[2-[2-[2-(2-hydroxyethoxy)ethoxy]ethoxy]ethoxy]-47-[(1R)-2-[(1S,2R,3R)-3-(2-hydroxyethoxy)-2-methoxy-cyclohexyl]-1-methyl-ethyl]-50-methoxy-38,39,40,41,51,52-hexamethyl-70,71-dioxa-60-azatricyclohexatriaconta-21,23,25(51),26(52)-tetraene-53,54,55,56,57-pentone (I-22):
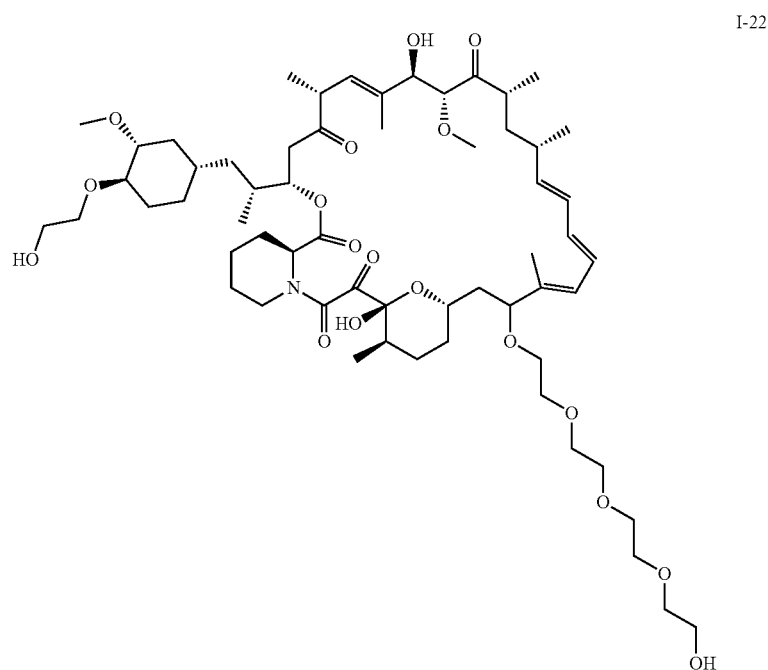 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCCOCCOCCO)C[C@@H]3CC[C@@H](C)[C@@](O)(O3)C(=O)C(=O)N3CCCC[C@H]3C(=O)O2)CC[C@H]1OCCO]
Synthetic Scheme:
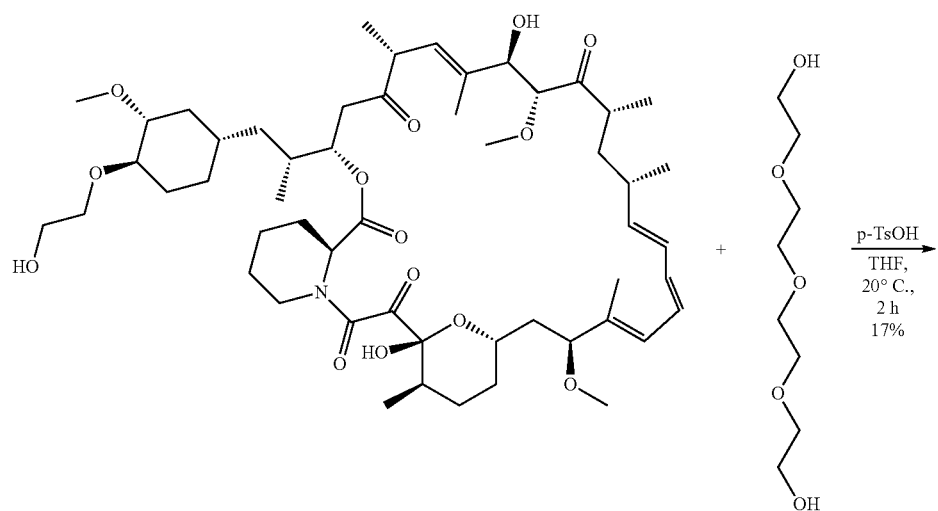

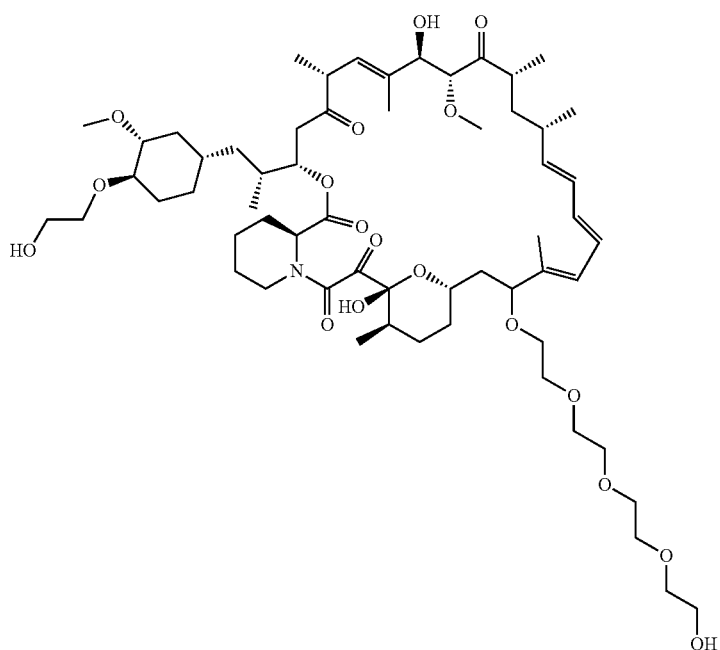

I-22

Procedures and Characterization:

A mixture of everolimus (0.5 g, 0.52 mmol), 2-[2-[2-(2-hydroxyethoxy)ethoxy]ethoxy]ethanol (2.03 g, 10.44 mmol) and p-toluenesulfonic acid hydrate (0.54 g, 3.13 mmol) in THF (6 mL) was stirred at 20° C. for 2 h. The mixture was poured into ice cold saturated $NaHCO_3$ (30 mL) and extracted with EtOAc (50 mL*3). The combined organic layers were washed with water, brine, then concentrated in vacuo. The residue was purified by reversed phase chromatography ($CH_3CN$/pure water=1:1) to afford (21E,23E,25E,26E,38R,39S,40R,41R,42S,45S,47S,49R,50R,59R)-49,59-dihydroxy-46-[2-[2-[2-(2-hydroxyethoxy)ethoxy]ethoxy]ethoxy]-47-[(1R)-2-[(1S,2R,3R)-3-(2-hydroxyethoxy)-2-methoxy-cyclohexyl]-1-methyl-ethyl]-50-methoxy-38,39,40,41,51,52-hexamethyl-70,71-dioxa-60-azatricyclohexatriaconta-21,23,25(51),26(52)-tetraene-53,54,55,56,57-pentone (I-22: 0.1 g, 17% yield) as a white solid. ESI-MS (EI$^+$, m/z): 1043.4 [M+Na]$^+$. $^1$H NMR (500 MHz, $CDCl_3$) δ 6.71-5.78 (m, 4H), 5.77-5.01 (m, 4H), 4.65-3.88 (m, 3H), 3.87-3.50 (m, 20H), 3.50-3.00 (m, 14H), 2.77-1.95 (m, 11H), 1.89-1.53 (m, 13H), 1.53-0.79 (m, 27H), 0.76-0.62 (m, 1H).

EXAMPLE 10

Synthesis of (22E,24E,26E,27E,35R,36S,37R,38R, 39S,42S,44S,46R,47R,56R)-46,56-dihydroxy-44-[(1R)-2-[(1S,2R,3R)-3-hydroxy-2-methoxy-cyclohexyl]-1-methyl-ethyl]-47-methoxy-43-[2-[2-(2-methoxyethoxy)ethoxy]ethoxy]-35,36,37,38,48,49-hexamethyl-66,67-dioxa-57-azatricyclohexatriaconta-22,24,26(48),27(49)-tetraene-50,51,52,53,54-pentone (I-27):

Synthetic Scheme:

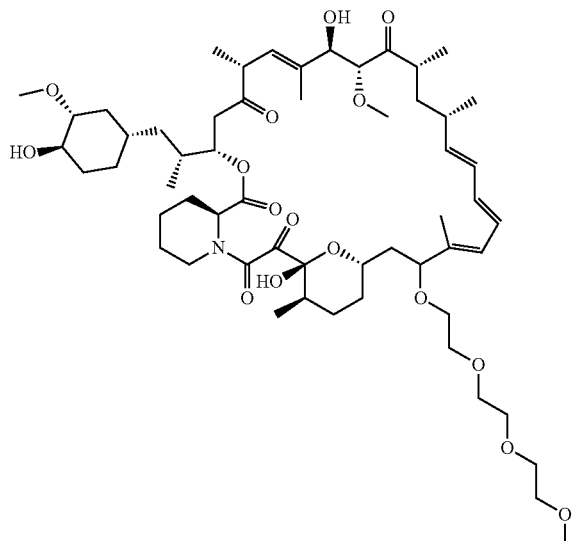

I-27

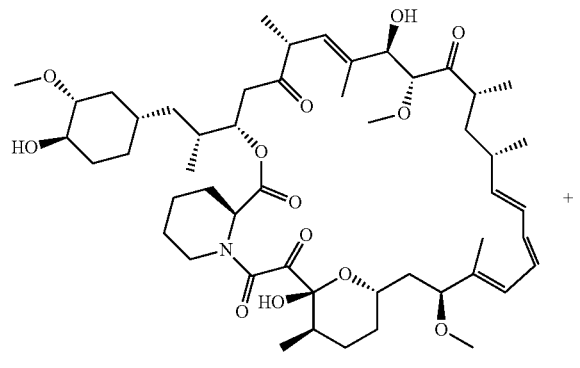

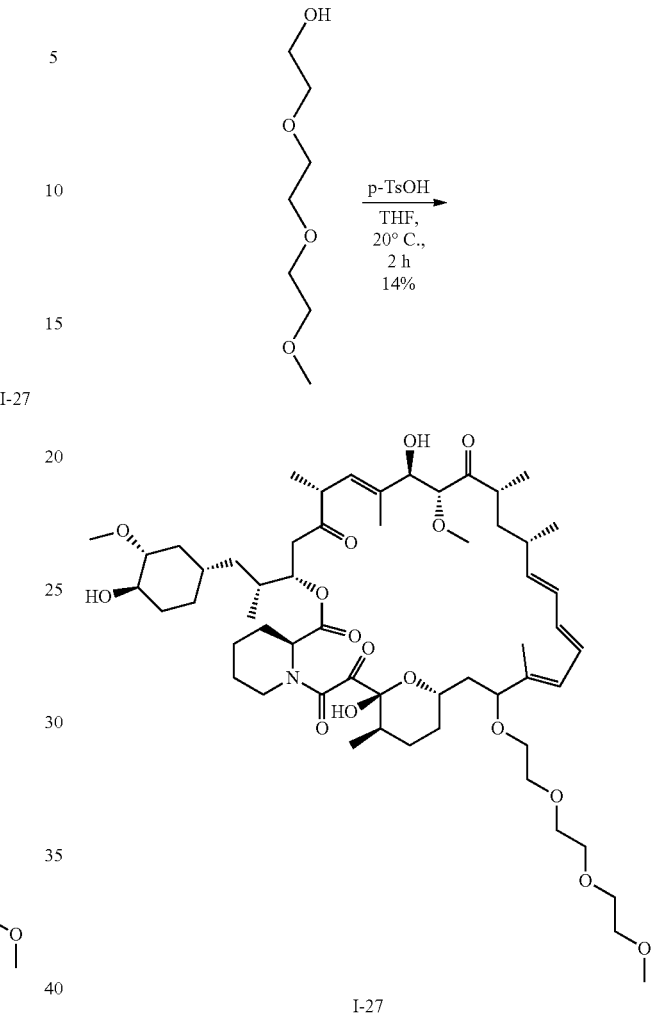

I-27

Procedures and Characterization:

A mixture of rapamycin (1 g, 1.09 mmol), 2-[2-(2-methoxyethoxy)ethoxy]ethanol (8.98 g, 54.69 mmol) and p-toluenesulfonic acid hydrate (0.94 g, 5.47 mmol) in THF (20 mL) was stirred at 20° C. for 2 hours. The mixture was poured into ice cold saturated $NaHCO_3$ (50 mL) and extracted with EtOAc (100 mL×3). The combined organic layers were washed with water, brine, then concentrated in vacuo. The residue was purified by reversed phase chromatography ($CH_3CN$/pure water=4:1) to afford (22E,24E,26E, 27E,35R,36S,37R,38R,39S,42S,44S,46R,47R,56R)-46,56-dihydroxy-44-[(1R)-2-[(1S,2R,3R)-3-hydroxy-2-methoxy-cyclohexyl]-1-methyl-ethyl]-47-methoxy-43-[2-[2-(2-methoxyethoxy)ethoxy]ethoxy]-35,36,37,38,48,49-hexamethyl-66,67-dioxa-57-azatricyclohexatriaconta-22, 24,26(48),27(49)-tetraene-50,51,52,53,54-pentone (I-27: 0.16 g, 14% yield) as a white solid. ESI-MS ($EI^+$, m/z): 1068.4 $[M+Na]^+$. $^1H$ NMR (500 MHz, $CDCl_3$) δ 6.50-5.81 (m, 4H), 5.73-5.05 (m, 4H), 4.85-3.98 (m, 3H), 3.90-3.10 (m, 27H), 3.02-2.24 (m, 7H), 1.98 (m, 6H), 1.82-1.55 (m, 13H), 1.54-1.16 (m, 9H), 1.16-0.78 (m, 17H), 0.75-0.59 (m, 1H).

EXAMPLE 11

Synthesis of (21E,23E,25E,26E,31R,32S,33R,34R, 35S,38S,40S,42R,43R,52R)-42,52-dihydroxy-40-[(1R)-2-[(1S,2R,3R)-3-hydroxy-2-methoxy-cyclohexyl]-1-methyl-ethyl]-39-(3-hydroxypropoxy)-43-methoxy-31,32,33,34,44,45-hexamethyl-63,64-dioxa-53-azatricyclohexatriaconta-21,23,25(44),26(45)-tetraene-46,47,48,49,50-pentone (I-34):

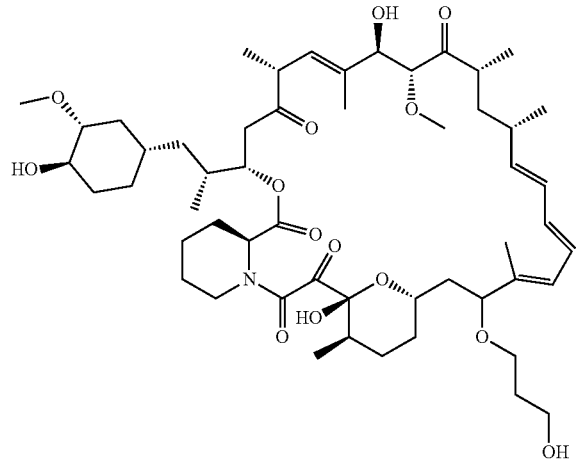

I-34

Synthetic Scheme:

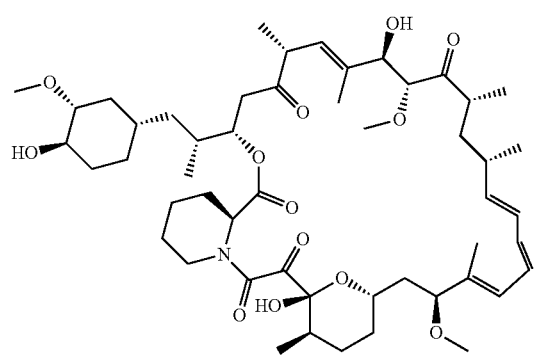

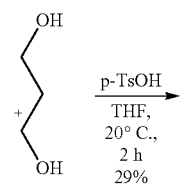

$\xrightarrow[\substack{20°\text{ C.,}\\2\text{ h}\\29\%}]{\substack{p\text{-TsOH}\\\text{THF,}}}$

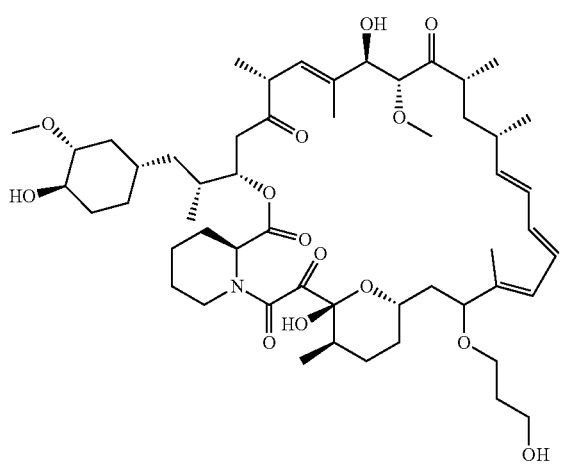

I-34

Procedures and Characterization:

A mixture of rapamycin (0.5 g, 0.55 mmol), propane-1,3-diol (13.13 g, 172.48 mmol, 12.5 mL), and p-toluenesulfonic acid hydrate (0.47 g, 2.74 mmol) in THF (37.5 mL) was stirred at 20° C. for 2 hours. The mixture was poured into ice cold saturated NaHCO$_3$ (100 mL) and extracted with EtOAc (100 mL×3). The organic layers were combined and washed with water and brine, then concentrated in vacuo. The residue was purified by reverse phase chromatography (CH$_3$CN/pure water=7:3) to afford (21E,23E,25E,26E,31R, 32S,33R,34R,35S,38S,40S,42R,43R,52R)-42,52-dihydroxy-40-[(1R)-2-[(1S,2R,3R)-3-hydroxy-2-methoxy-cyclohexyl]-1-methyl-ethyl]-39-(3-hydroxypropoxy)-43-methoxy-31,32, 33,34,44,45-hexamethyl-63,64-dioxa-53-azatricyclohexatriaconta-21,23,25(44),26(45)-tetraene-46, 47,48,49,50-pentone (0.15 g, 29% yield) as a white solid. ESI-MS (EI$^+$, m/z): 980.3 [M+Na]$^+$. $^1$H NMR (500 MHz, CDCl$_3$) δ 6.58-5.84 (m, 4H), 5.72-4.83 (m, 4H), 4.65-4.06 (m, 2H), 4.03-3.63 (m, 5H), 3.62-3.05 (m, 12H), 3.03-2.40 (m, 6H), 2.42-1.91 (m, 7H), 1.89-1.56 (m, 17H), 1.53-1.27 (m, 6H), 1.25-0.76 (m, 19H), 0.62 (m, 1H).

EXAMPLE 12

Synthesis of (21E,23E,25E,26E,30R,31S,32R,33R, 35R,37S,40S,41R,42R,51S)-41,51-dihydroxy-39-(2-hydroxyethoxy)-40-[(1S)-2-[(1S,3R,4R)-4-hydroxy-3-methoxy-cyclohexyl]-1-methyl-ethyl]-42-methoxy-30,31,32,33,43,44-hexamethyl-62,63-dioxa-52-azatricyclohexatriaconta-21,23,25(43),26(44)-tetraene-45,46,47,48,49-pentone (I-38):

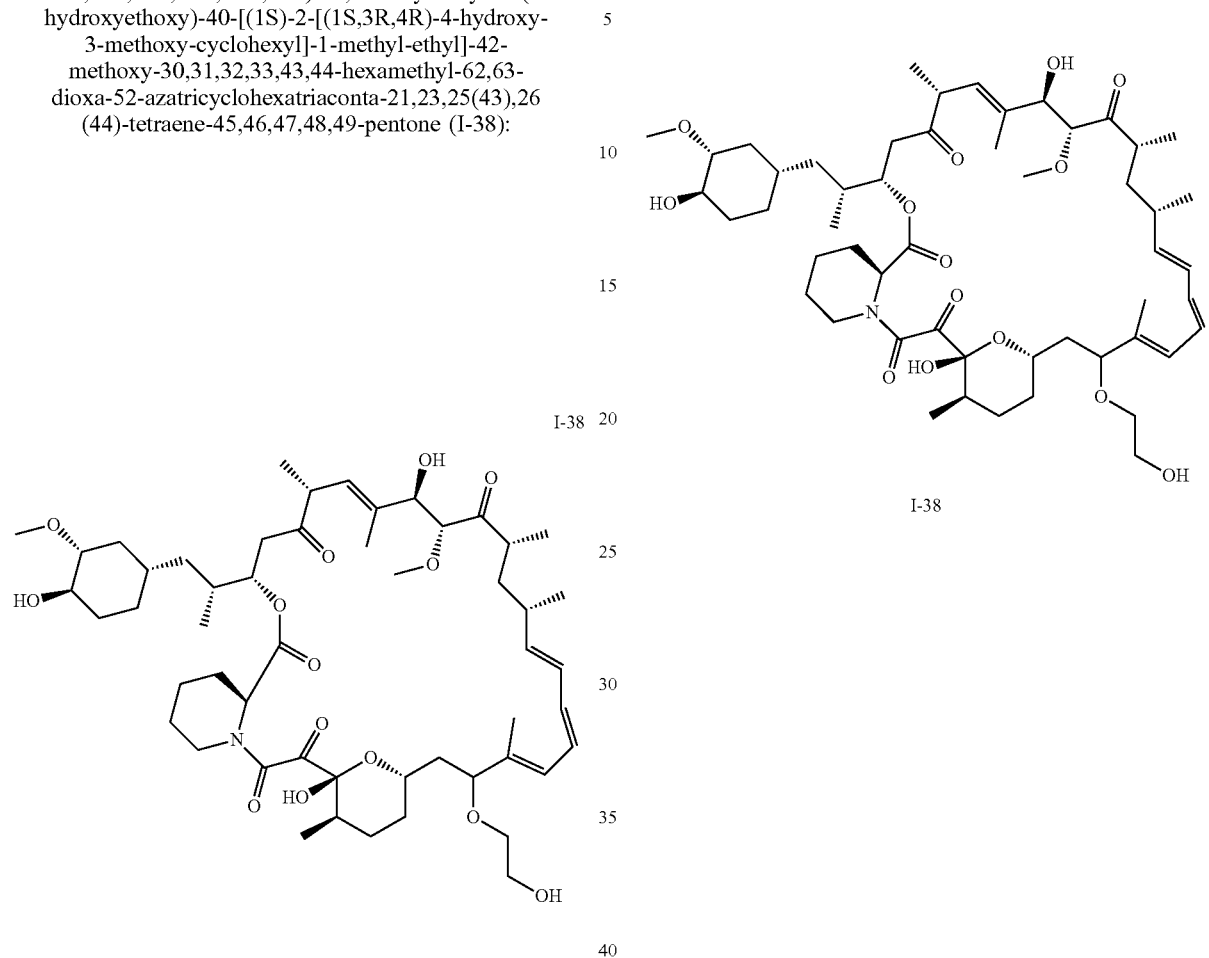

I-38

Synthetic Scheme:

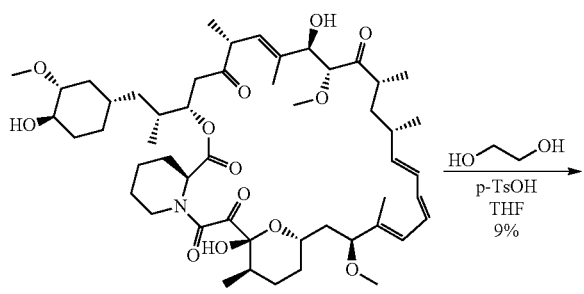

Procedures and Characterization:

p-toluenesulfonic acid hydrate (0.31 g, 1.64 mmol) was added to a mixture of rapamycin (0.5 g, 0.547 mmol) and ethylene glycol (3 mL) in THF (10 mL) at 10° C. The resulting mixture was stirred at 10° C. for 17 hours then the reaction mixture was diluted with EtOAc (100 mL) and adjusted to pH 9 using saturated aqueous NaHCO$_3$ solution (about 50 mL). The organic layer was concentrated in vacuo then the residue was purified by reverse phase chromatography (CH$_3$CN/pure water=5.5: 4.5). The solvent was then removed by lyophilization yielding (21E,23E,25E,26E,30R,31S,32R,33R,35R,37S,40S,41R,42R,51S)-41,51-dihydroxy-39-(2-hydroxyethoxy)-40-[(1S)-2-[(1S,3R,4R)-4-hydroxy-3-methoxy-cyclohexyl]-1-methyl-ethyl]-42-methoxy-30,31,32,33,43,44-hexamethyl-62,63-dioxa-52-azatricyclohexatriaconta-21,23,25(43),26(44)-tetraene-45,46,47,48,49-pentone (0.05 g, 9% yield) as a white solid. MS (EI$^+$, m/z): 966.3 [M+Na]$^+$. $^1$H NMR (500 MHz, CDCl$_3$) δ 6.47-5.91 (m, 4H), 5.60-5.13 (m, 4H), 4.85-3.92 (m, 3H), 3.88-3.68 (m, 4H), 3.60-3.53 (m, 1H), 3.46-3.29 (m, 10H), 3.25-3.19 (m, 1H), 2.97-2.84 (m, 2H), 2.76-2.53 (m, 4H), 2.35-1.83 (m, 8H), 1.80-1.64 (m, 12H), 1.53-1.16 (m, 9H), 1.14-0.82 (m, 18H), 0.67-0.57 (m, 1H).

EXAMPLE 13
Synthesis of (21E,23E,25E,26E,40R,41S,42R,43R, 45R,47S,50S,51R,52R,61S)-51,61-dihydroxy-49-[2-[2-[2-[2-[2-(2-hydroxyethoxy)ethoxy]ethoxy]ethoxy]ethoxy]ethoxy]-50-[(1S)-2-[(1S,3R,4R)-4-hydroxy-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-33):
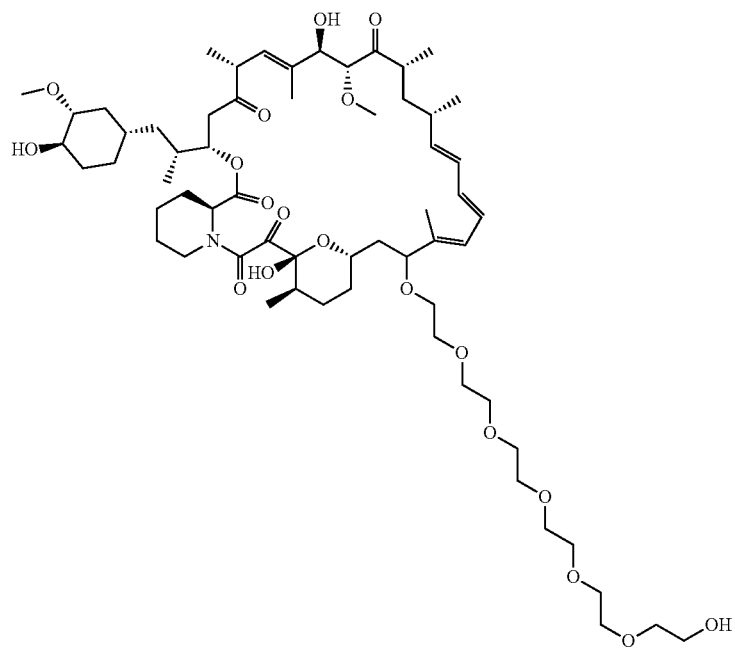
I-33
Synthetic Scheme:
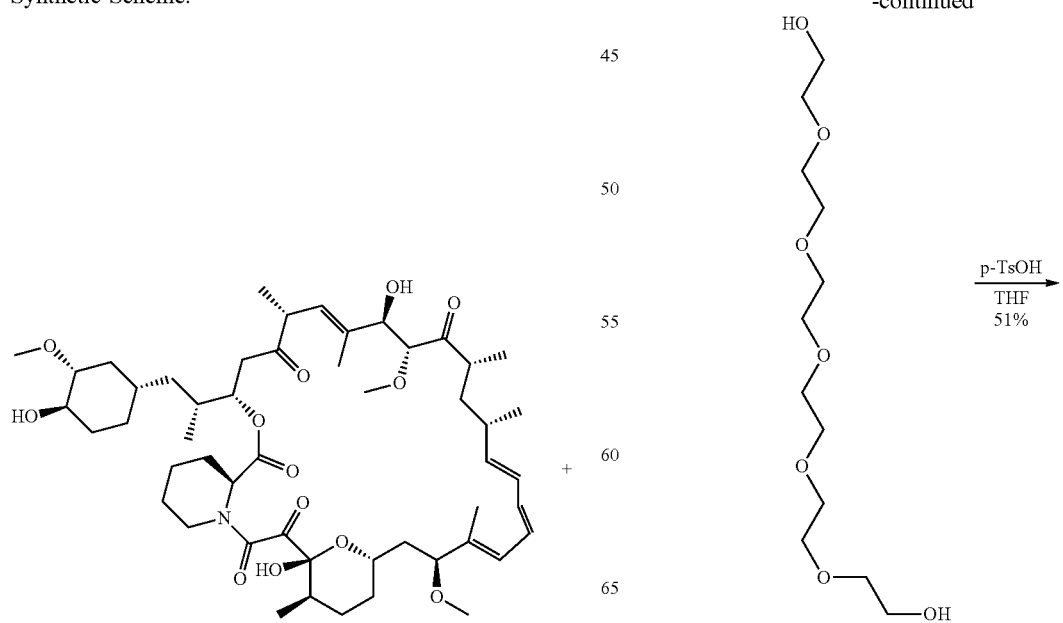

237

-continued

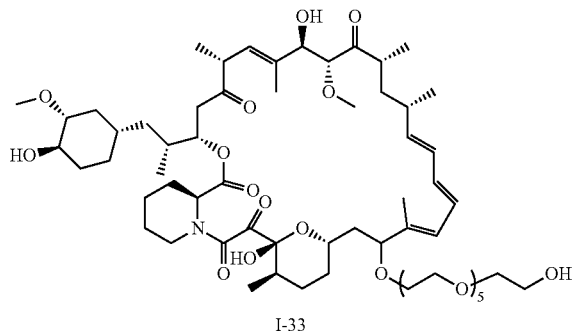

I-33

Procedures and Characterization:

p-toluenesulfonic acid hydrate (0.19 g, 1.02 mmol) was added to a mixture of rapamycin (0.31 g, 0.34 mmol) and hexaethylene glycol (2 mL) in THF (6 mL) at 15° C. The resulting mixture was stirred at 15° C. for 17 hours then the reaction mixture was diluted with EtOAc (200 mL) and adjusted to pH 9 using saturated aqueous NaHCO$_3$ solution (about 100 mL). The organic layer was concentrated in vacuo. The residue was purified by reverse phase chromatography (CH$_3$CN/pure water=3:2). The solvent was then removed by lyophilization. (21E,23E,25E,26E,40R,41S, 42R,43R,45R,47S,50S,51R,52R,61S)-51,61-dihydroxy-49-[2-[2-[2-[2-[2-(2-hydroxyethoxy)ethoxy]ethoxy]ethoxy]ethoxy]ethoxy]-50-[(1S)-2-[(1S,3R,4R)-4-hydroxy-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-33: 0.21 g, 51% yield) was obtained as a white solid. MS (EI$^+$, m/z): 1186.8 [M+Na]$^+$. $^1$H NMR (500 MHz, CDCl$_3$) δ 6.39-5.94 (m, 4H), 5.55-5.14 (m, 4H), 4.93-3.75 (m, 2H), 3.73-3.71 (m, 2H), 3.67-3.55 (m, 22H), 3.48-3.44 (m, 1H), 3.41-3.16 (m, 12H), 2.98-2.86 (m, 2H), 2.75-2.69 (m, 2H), 2.59-2.44 (m, 1H), 2.34-2.21 (m, 1H), 2.11-1.97 (m, 4H), 1.90 (s, 3H), 1.78-1.54 (m, 13H), 1.50-1.12 (m, 9H), 1.08-0.83 (m, 18H), 0.71-0.62 (m, 1H).

238

EXAMPLE 14

Synthesis of (21E,23E,25E,26E,32R,33S,34R,35R,37R,39S,42S,43R,44R,53S)-43,53-dihydroxy-41-[2-(2-hydroxyethoxy)ethoxy]-42-[(1S)-2-[(1S,3R,4R)-4-hydroxy-3-methoxy-cyclohexyl]-1-methyl-ethyl]-44-methoxy-32,33,34,35,45,46-hexamethyl-64,65-dioxa-54-azatricyclohexatriaconta-21,23,25(45),26(46)-tetraene-47,48,49,50,51-pentone (I-18):

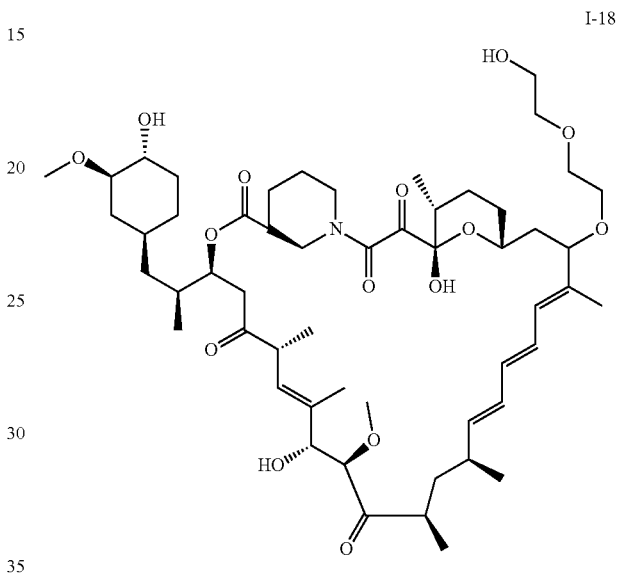

I-18

Synthetic Scheme:

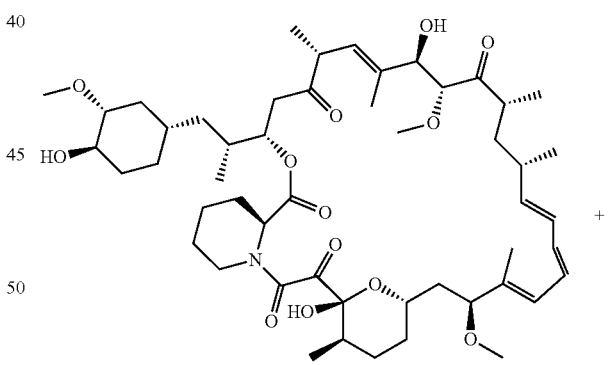

+

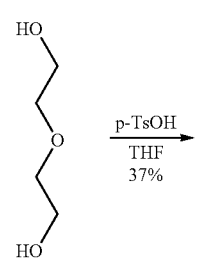

p-TsOH
THF
37%

239
-continued

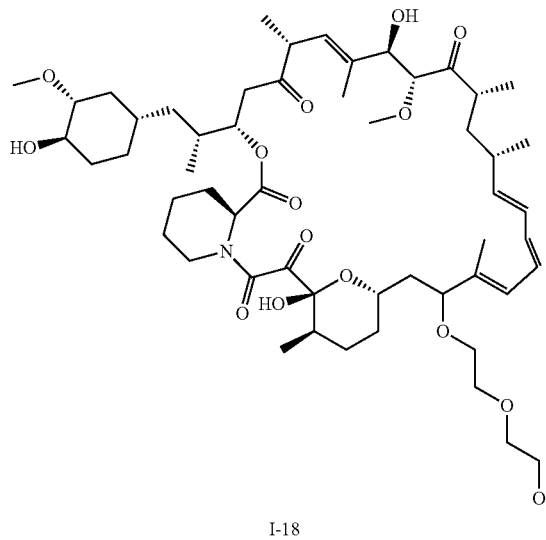

I-18

Procedures and Characterization:

p-toluenesulfonic acid hydrate (0.187 g, 0.98 mmol) was added to a mixture of rapamycin (0.3 g, 0.33 mmol) and diethylene glycol (2 mL) in THF (6 mL) at 10° C. The resulting mixture was stirred at 10° C. for 17 hours then the reaction mixture was diluted with EtOAc (100 mL) and adjusted to pH 9 using saturated aqueous NaHCO$_3$ solution (about 50 mL). The organic layer was concentrated under vacuum. The residue was purified by reverse phase (CH$_3$CN/pure water=3:2). The solvents were removed by lyophilization, yielding (21E,23E,25E,26E,32R,33S,34R, 35R,37R,39S,42S,43R,44R,53S)-43,53-dihydroxy-41-[2-(2-hydroxyethoxy)ethoxy]-42-[(1S)-2-[(1S,3R,4R)-4-hydroxy-3-methoxy-cyclohexyl]-1-methyl-ethyl]-44-methoxy-32,33,34,35,45,46-hexamethyl-64,65 -dioxa-54-azatricyclohexatriaconta-21,23,25(45),26(46)-tetraene-47,48,49,50,51-pentone (I-18: 0.126 g, 37% yield) as a white solid. MS (EI$^+$, m/z): 1010.7 [M+Na]$^+$. $^1$H NMR (500 MHz, CDCl$_3$) δ 6.40-5.95 (m, 4H), 5.55-5.14 (m, 4H), 4.85-4.17 (m, 2H), 4.05-3.57 (m, 10H), 3.53-3.15 (m, 12H), 2.97-2.89 (m, 2H), 2.76-2.48 (m, 4H), 2.36-1.84 (m, 7H), 1.79-1.56 (m, 14H), 1.49-1.14 (m, 9H), 1.10-0.81 (m, 18H), 0.70-0.61 (m, 1H).

240
EXAMPLE 15

Synthesis of (21E,23E,25E,26E,31R,32S,33R,34R, 36R,38S,41S,42R,43R,53S)-42,53-dihydroxy-40-[3-hydroxy-2-(hydroxymethyl)propoxy]-41-[(1S)-2-[(1S,3R,4R)-4-hydroxy-3-methoxy-cyclohexyl]-1-methyl-ethyl]-43-methoxy-31,32,33,34,44,45-hexamethyl-65,66-dioxa-54-azatricyclohexatriaconta-21,23,25(44),26(45)-tetraene-46,47,48,49,50-pentone (I-31):

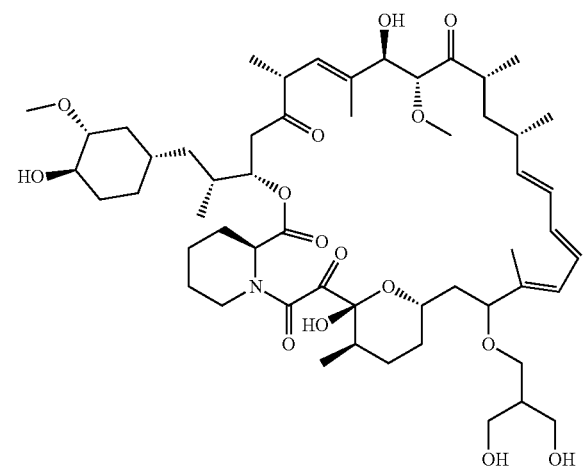

I-31

Synthetic Scheme:

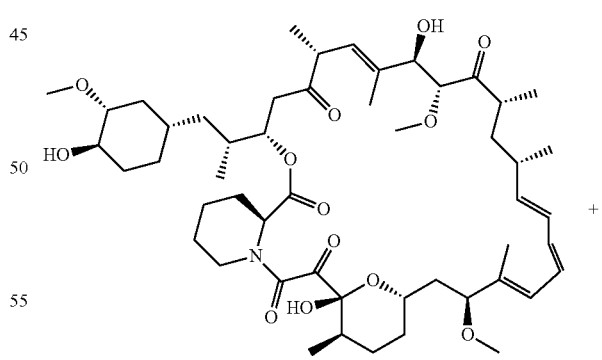

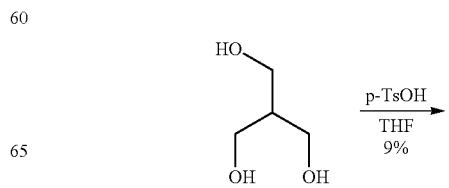

p-TsOH
THF
9%

EXAMPLE 16

Synthesis of (21E,23E,25E,26E,34R,35S,36R,37R, 39R,41S,44S,45R,46R,55S)-45,55-dihydroxy-43-[2-[2-(2-hydroxyethylsulfanyl)ethylsulfanyl]ethoxy]-44-[(1S)-2-[(1S,3R,4R)-4-hydroxy-3-methoxy-cyclohexyl]-1-methyl-ethyl]-46-methoxy-34,35,36, 37,47,48-hexamethyl-66,67-dioxa-56-azatricyclohexatriaconta-21,23,25(47),26(48)-tetraene-49,50,51,52,53-pentone (I-21):

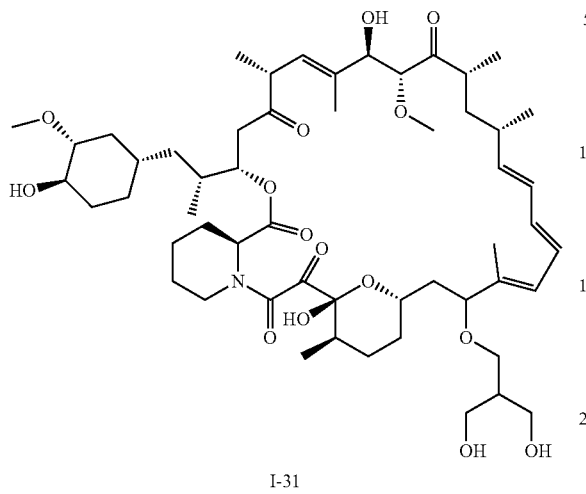

I-31

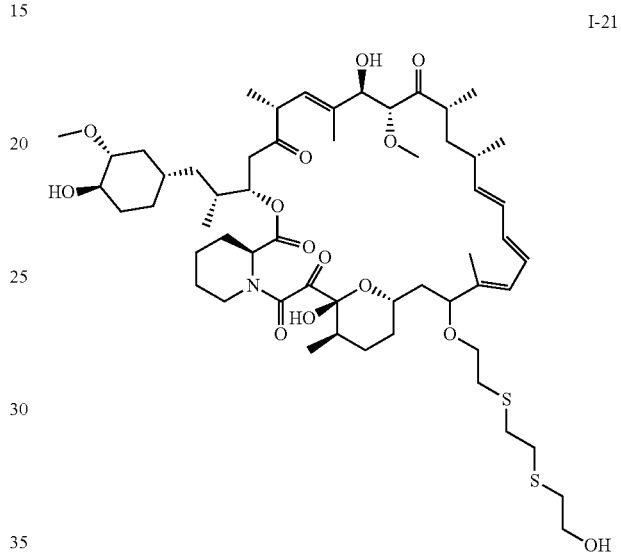

I-21

Synthetic Scheme:

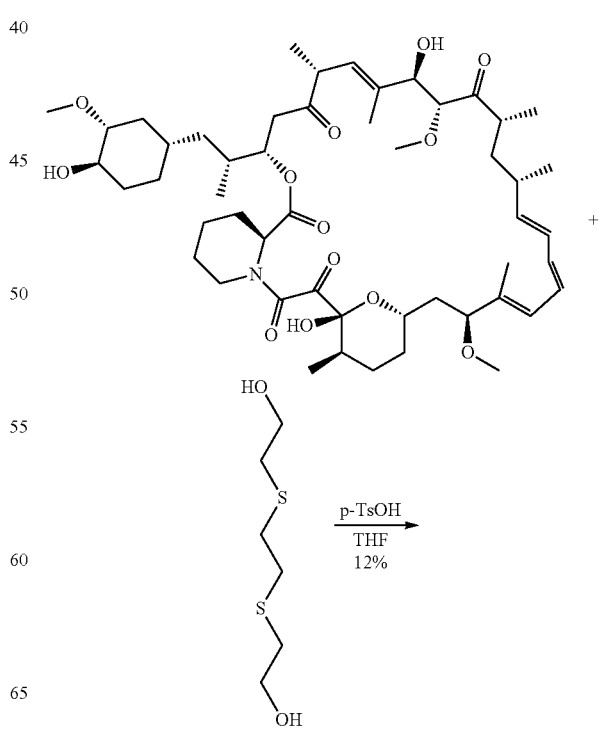

Procedures and Characterization:

p-toluenesulfonic acid hydrate (0.31 g, 1.64 mmol) was added to a mixture of rapamycin (0.5 g, 0.547 mmol) and 2-(hydroxymethyl) propane-1,3-diol (0.58 g, 5.47 mmol) in THF (10 mL) at 15° C. The resulting mixture was stirred at 15° C. for 17 hours then the reaction mixture was diluted with EtOAc (100 mL) and adjusted to pH 9 using saturated aqueous NaHCO$_3$ solution (about 50 mL). The organic layer was concentrated under vacuum. The residue was purified by reverse phase chromatography (CH$_3$CN/pure water=3:2). The solvent was removed by lyophilization, yielding (21E, 23E,25E,26E,31R,32S, 33R,34R,36R,38S,41S,42R,43R, 53S)-42,53-dihydroxy-40-[3-hydroxy-2-(hydroxymethyl) propoxy]-41-[(1S)-2-[(1S,3R,4R)-4-hydroxy -3-methoxy-cyclohexyl]-1-methyl-ethyl]-43-methoxy-31,32,33,34,44, 45-hexamethyl-65,66-dioxa-54-azatricyclohexatriaconta-21,23,25(44),26(45)-tetraene-46,47,48,49,50-pentone (I-31: 0.054 g, 9% yield) as a white solid. MS (EI$^+$, m/z): 1010.4 [M+Na]$^+$. $^1$H NMR (500 MHz, CDCl$_3$) δ 6.37-5.96 (m, 4H), 5.56-5.15 (m, 4H), 4.86-4.17 (m, 2H), 3.85-3.47 (m, 10H), 2.96-2.91 (m, 2H), 2.75-2.58 (m, 3H), 2.35-2.22 (m, 3H), 2.11-1.94 (m, 6H), 1.84-1.46 (m, 23H), 1.35-1.12 (m, 9H), 1.11-0.88 (m, 18H), 0.67-0.65 (m, 1H).

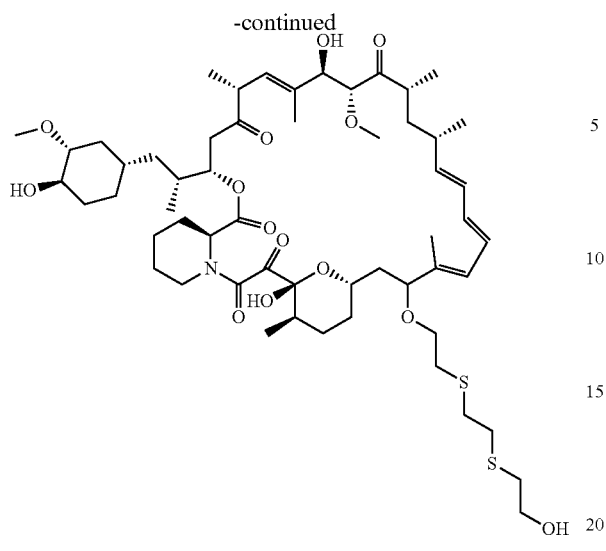

I-21

Procedures and Characterization:

p-toluenesulfonic acid hydrate (0.62 g, 3.28 mmol) was added to a mixture of rapamycin (1 g, 1.09 mmol) and 2-[2-(2-hydroxyethylsulfanyl)ethylsulfanyl]ethanol (1.99 g, 10.94 mmol) in THF (20 mL) at 15° C. The resulting mixture was stirred at 15° C. for 17 hours then the reaction mixture was diluted with EtOAc (100 mL) and adjusted to pH 9 using saturated aqueous NaHCO₃ solution (about 50 mL). The organic layer was concentrated under vacuum. The residue was purified by reverse phase chromatography (CH₃CN/pure water=3:2). The solvents were removed by lyophilization yielding (21E,23E,25E,26E,34R,35S,36R,37R,39R,41S,44S,45R,46R,55S)-45,55-dihydroxy-43-[2-[2-(2-hydroxyethylsulfanyl)ethylsulfanyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-21: 0.15 g, 0.133 mmol, 12% yield) as a yellow solid. MS (EI⁺, m/z): 1086.4 [M+Na]⁺. ¹H NMR (500 MHz, CDCl₃) δ 6.39-5.95 (m, 4H), 5.54-5.19 (m, 4H), 4.81-4.17 (m, 2H), 3.96-3.73 (m, 4H), 3.59-3.14 (m, 12H), 2.96-2.55 (m, 14H), 2.35-1.87 (m, 6H), 1.81-1.59 (m, 13H), 1.53-1.13 (m, 11H), 1.16-0.84 (m, 18H), 0.71-0.63 (m, 1H).

EXAMPLE 17

Synthesis of Synthesis of (21E,23E,25E,26E,42R,43S,44R,45R,47S,49S,51S,52S,53R,54R,63R)-53,63-dihydroxy-51-[2-[2-[2-[2-[2-[2-(2-hydroxyethoxy)ethoxy]ethoxy]ethoxy]ethoxy]ethoxy]-52-[(1R)-2-[(1S,3R,4R)-4-hydroxy-3-methoxy-cyclohexyl]-1-methyl-ethyl]-54-methoxy-42,43,44,45,55,56-hexamethyl-74,75-dioxa-64-azatricyclohexatriaconta-21,23,25(55),26(56)-tetraene-57,58,59,60,61-pentone (I-26):

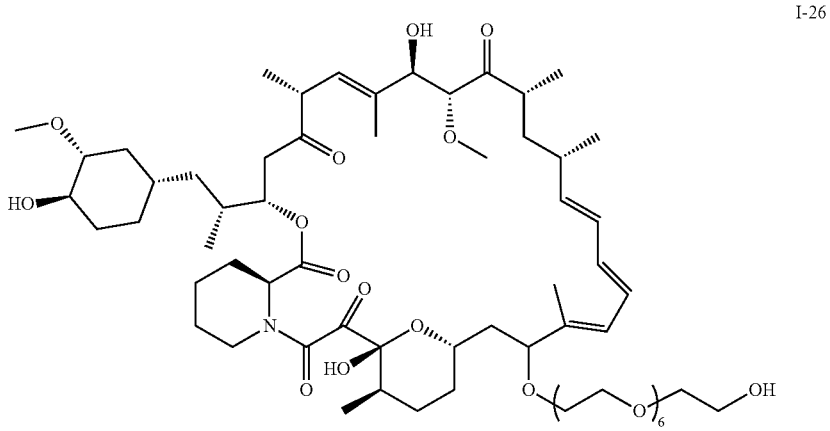

I-26

Synthetic Scheme:

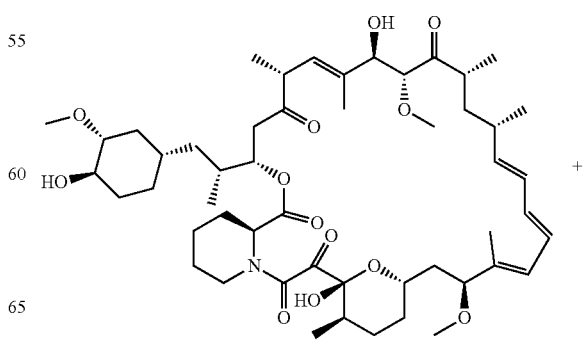

+

245
-continued

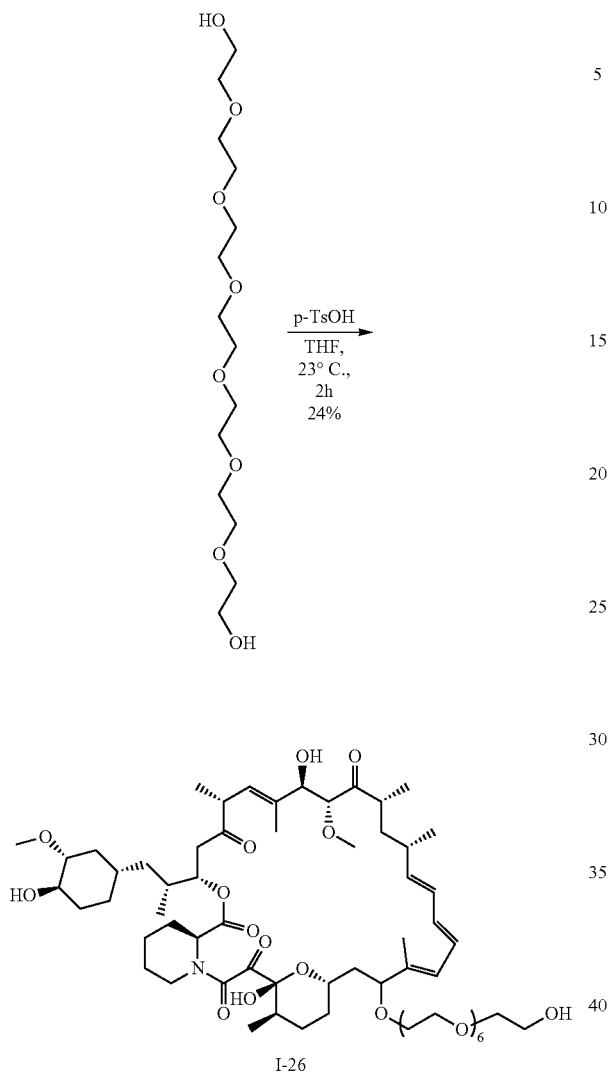

I-26

Procedures and Characterization:

p-toluenesulfonic acid hydrate (0.52 g, 2.73 mmol) was added slowly to a solution of rapamycin (0.5 g, 0.55 mmol) and 2-[2-[2-[2-[2-[2-(2-hydroxyethoxy)ethoxy]ethoxy]ethoxy]ethoxy]ethanol (3.57 g, 10.94 mmol) in THF (10 mL). The resultant solution was stirred at 20° C. for 17 hours and then concentrated. The residue was purified by reverse phase chromatography ($CH_3CN$/pure water=7:3) to obtain (21E,23E,25E,26E,42R,43S,44R,45R,47S,49S,51S, 52S,53R,54R,63R)-53,63-dihydroxy-51-[2-[2-[2-[2-[2-[2-(2-hydroxyethoxy)ethoxy]ethoxy]ethoxy]ethoxy]ethoxy]-52-[(1R)- 2-[(1S,3R,4R)-4-hydroxy-3-methoxy-cyclohexyl]-1-methyl-ethyl]-54-methoxy-42,43,44,45,55,56-hexamethyl-74,75-dioxa-64-azatricyclohexatriaconta-21,23,25(55),26(56)-tetraene-57, 58,59,60,61-pentone (I-26: 0.16 g, 24% yield) as a white solid. MS ($EI^+$, m/z): 1230.6[M+Na]$^+$. $^1$H NMR (500 MHz, $CDCl_3$) δ 6.46-5.74 (m, 4H), 5.61-4.74 (m, 4H), 4.05-4.5 (m, 2H), 4.02-3.51 (m, 35H), 3.43-3.16 (m, 14H), 2.99-2.42 (m, 8H), 2.4-1.6 (m, 7H), 1.61-1.1 (m, 12H), 1.13-0.79 (m, 18H), 0.74-0.61 (m, 1H).

246

EXAMPLE 19

Synthesis of (22E,24E,26E,27E,33R,34S,35R,36R, 38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[R-2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (I-119) and (22E, 24E,26E,27E,33R,34S,35R,36R,38S,40S,43S,44R, 45R,54R)-44,54-dihydroxy-43-[(1R)-2-[(1S,3R,4R)-4-hydroxy-3-methoxy-cyclohexyl]-1-methyl-ethyl]-45-methoxy-42-[S-2-(2-methoxyethoxy)ethoxy]-33, 34,35,36,46,47-hexamethyl-64,65-dioxa-55-azatricyclohexatriaconta-22,24,26(46),27(47)-tetraene-48,49,50,51,52-pentone (I-120):

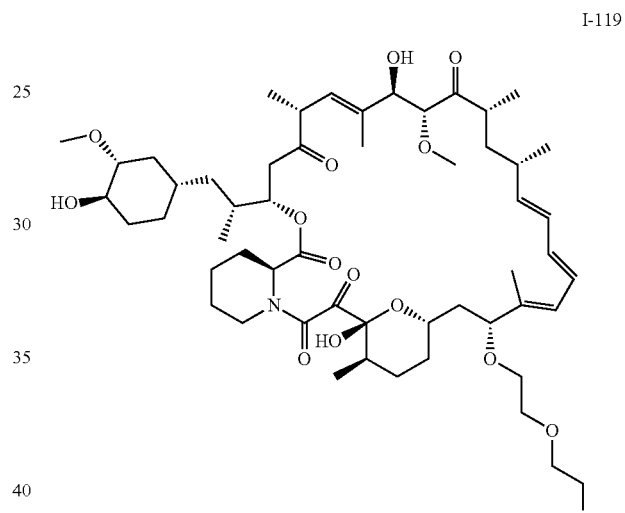

I-119

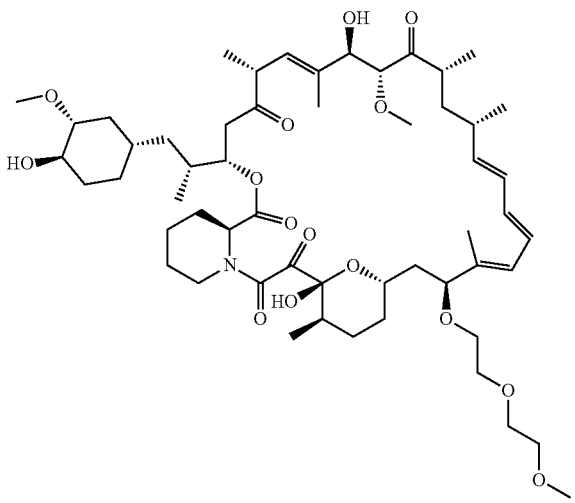

I-120

Synthetic Scheme:

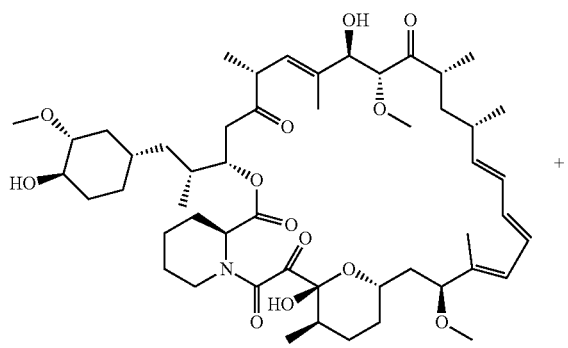

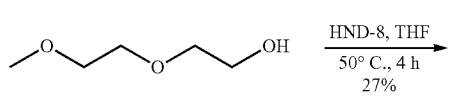

HND-8, THF
50° C., 4 h
27%

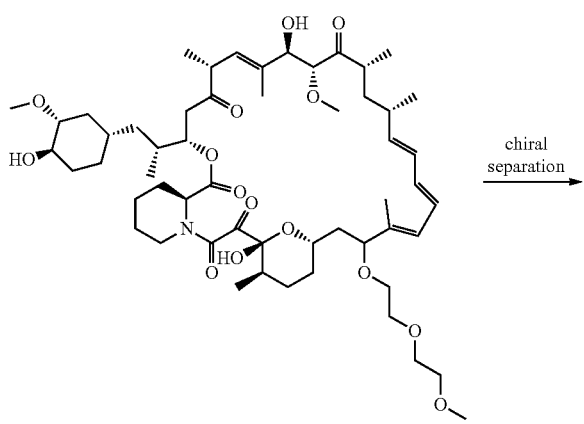

I-120

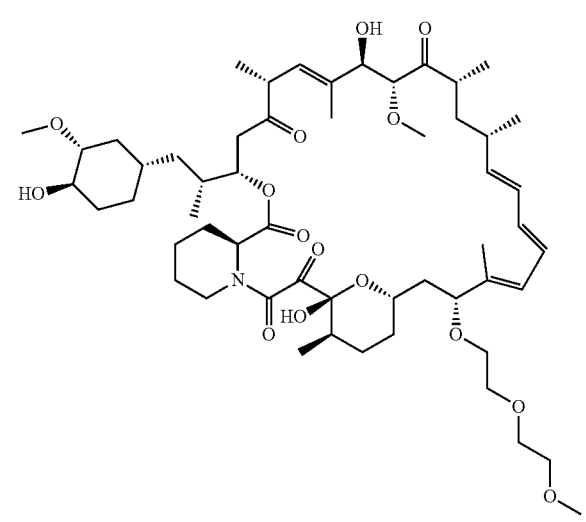

I-119

Procedures and Characterization:

Step 1: Synthesis of (22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone:

To a mixture of rapamycin (2 g, 2.19 mmol), 2-(2-methoxyethoxy)ethanol (4 mL) in THF (30 mL) was added HND-8 (240 mg, 2.19 mmol) and the reaction stirred at 50° C. for 4 h under $N_2$, then filtered and concentrated. The resulting crude product was purified via reverse phase chromatography (C18, $CH_3CN$: $H_2O$=3:1) to provide (22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (0.6 g, 27% yield) as a light yellow solid. ESI-MS (EI+, m/z): 1024.3 [M+Na]+. $^1$H NMR (400 MHz, $CDCl_3$) δ 6.56-5.82 (m, 4H), 5.47 (ddd, J=37.4, 17.7, 9.4 Hz, 2H), 5.31-5.06 (m, 2H), 4.82-4.50 (m, 1H), 4.32-3.94 (m, 2H), 3.92-3.71 (m, 2H), 3.70-3.44 (m, 8H), 3.43-3.26 (m, 12H), 3.20 (dd, J=27.0, 16.2 Hz, 1H), 3.00-2.22 (m, 7H), 2.18-1.56 (m, 19H), 1.54-1.25 (m, 7H), 1.24-0.81 (m, 19H), 0.67 (dd, J=23.8, 11.9 Hz, 1H).

Step 2: Synthesis of (22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-424R-2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (I-119) and (22E,24E,26E,27E,33R,

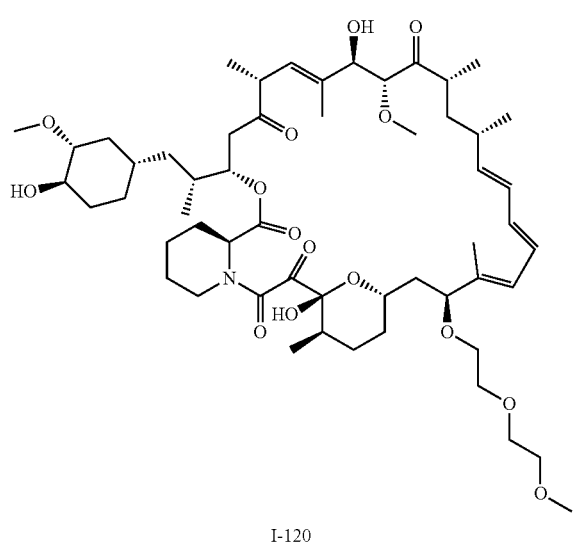

34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-424S-2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (I-120):

(22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (0.095 g, 0.095 mmol) was purified via prep chiral HPLC to provide (22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[R-2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (I-119: 13.2 mg, 14% yield) and (22E,24E,26E,27E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-42-[S-2-(2-methoxyethoxy)ethoxy]-33,34,35,36,46,47-hexamethyl-64,65-dioxa-55-azatricyclohexatriaconta-22,24,26(46),27(47)-tetraene-48,49,50,51,52-pentone (I-120: 18.1 mg, 19% yield), both as white solids.

The chiral separation method is listed below:

Instrument: Gilson-281

Column: CHIRALPAK IC 20×250 mm, 10 um (Daicel)

Column temperature: 35° C.

Mobile phase: n-Hexane:Ethanol=60:40

Flow rate: 50 ml/min

Detection wavelength: 214 nm

Cycle time: 18 min

Sample solution: 95 mg dissolved in 7 ml Methanol

Injection volume : 0.5 ml (loading: 7.1 mg/injection)

I-119: ESI-MS (EI$^+$, m/z): 1024.4 [M+Na]$^+$. $^1$H NMR (400 MHz, CDCl$_3$) δ 6.42-5.92 (m, 4H), 5.75-5.05 (m, 4H), 4.49 (s, 1H), 4.28 (s, 1H), 4.15 (d, J=10.9 Hz, 1H), 3.99 (t, J=13.3 Hz, 1H), 3.88-3.73 (m, 1H), 3.69-3.46 (m, 8H), 3.45-3.29 (m, 11H), 3.22 (dd, J=10.1, 6.5 Hz, 2H), 2.99-2.77 (m, 3H), 2.68 (dt, J=28.5, 11.1 Hz, 3H), 2.61-2.22 (m, 4H), 2.05 (ddd, J=21.5, 15.3, 7.5 Hz, 5H), 1.88-1.65 (m, 12H), 1.53-1.30 (m, 7H), 1.17-0.78 (m, 19H), 0.73-0.57 (m, 1H).

I-120: ESI-MS (EI$^+$, m/z): 1024.3 [M+Na]$^+$. $^1$H NMR (400 MHz, CDCl$_3$) δ 6.43-6.18 (m, 2H), 6.13 (dd, J=15.0, 10.0 Hz, 1H), 5.91 (dd, J=31.6, 10.6 Hz, 1H), 5.56-5.36 (m, 2H), 5.27 (d, J=4.9 Hz, 1H), 5.16 (dt, J=18.2, 9.1 Hz, 1H), 4.78 (s, 1H), 4.20 (dd, J=21.1, 11.1 Hz, 1H), 3.96-3.71 (m, 3H), 3.70-3.43 (m, 9H), 3.42-3.26 (m, 14H), 2.98-2.87 (m, 1H), 2.77-2.62 (m, 3H), 2.58 (dd, J=16.9, 6.3 Hz, 1H), 2.34 (d, J=13.4 Hz, 2H), 2.15-1.84 (m, 5H), 1.83-1.64 (m, 7H), 1.34 (dddd, J=22.7, 19.4, 18.1, 9.1 Hz, 12H), 1.16-0.80 (m, 19H), 0.66 (dt, J=16.8, 8.4 Hz, 1H).

EXAMPLE 20

Synthesis of (23E,25E,27E,28E,32R,33S,34R,35R,36S,39S,41S,45R,46R,55R)-45,55-dihydroxy-41-[(1R)-2-[(1S,2R,3R)-3-hydroxy-2-methoxy-cyclohexyl]-1-methyl-ethyl]-40-[[(2S,5S)-5-(hydroxymethyl)-1,4-dioxan-2-yl]methoxy]-46-methoxy-32,33,34,35,47,48-hexamethyl-68,69-dioxa-56-azatricyclohexatriaconta-23,25,27(47),28(48)-tetraene-49,50,51,52,53-pentone (I-118):

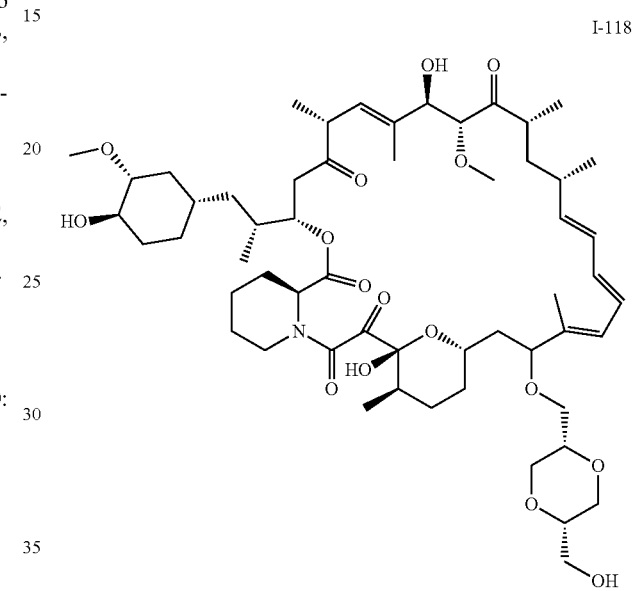

Synthetic Scheme:

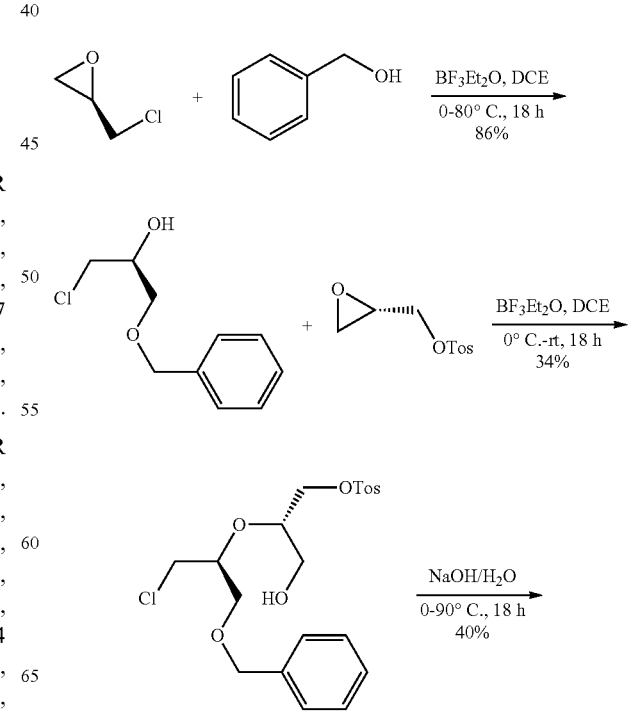

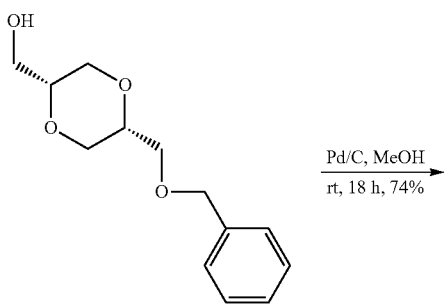

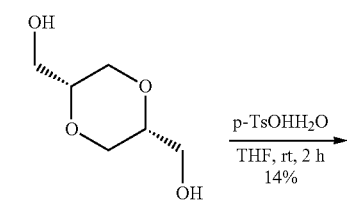

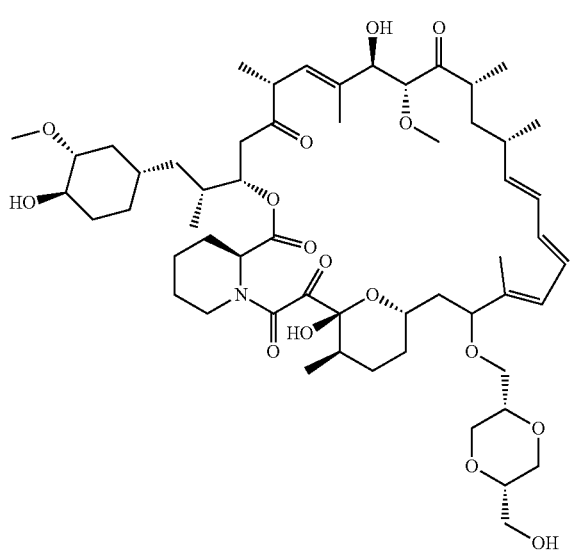

I-118

Procedures and Characterization:

Step 1: Synthesis of (S)-1-(benzyloxy)-3-chloropropan-2-ol:

A solution of (2R)-2-(chloromethyl)oxirane (1 g, 10.81 mmol) and phenylmethanol (2.34 g, 21.62 mmol) in DCE (10 mL) was stirred at rt for 1 h then cooled to 0° C., boron trifluoride etherate (76.7 mg, 0.54 mmol) was added slowly. The reaction mixture was allowed to warm to rt, stirred overnight then refluxed for 2 h. Upon cooling, the reaction mixture was diluted with 10% NaHCO$_3$ aqueous solution and extracted with EtOAc (100 mL×3). The combined organic layers were dried over anhydrous Na$_2$SO$_4$, filtered, and concentrated. The resulting residue was purified via silica gel chromatography (PE: EtOAc=10: 1) to provide the desired product (1.8 g, 86% yield) as a colorless oil. ESI-MS (EI$^+$, m/z): 218.1 [M+H$_2$O]$^+$. $^1$H NMR (500 MHz, CDCl$_3$) δ 7.36-7.27 (m, 5H), 4.64 (s, 2H), 3.99-3.95 (m, 1H), 3.64-3.55 (m, 4H), 2.75 (d, J=6.0 Hz, 1H).

Step 2: Synthesis of (S)-2-((S)-1-(benzyloxy)-3-chloropropan-2-yloxy)-3-hydroxypropyl 4-methylbenzenesulfonate:

A solution of (2S)-1-benzyloxy-3-chloro-propan-2-ol (6 g, 29.9 mmol) and [(2S)-oxiran-2-yl]methyl 4-methylbenzenesulfonate (6.83 g, 29.9 mmol) in DCE (100 mL) was stirred at rt for 1 h then cooled to 0° C. and boron trifluoride etherate (254.6 mg, 1.79 mmol) was added slowly. The reaction was warmed to rt, stirred at rt overnight, refluxed for 2 h then cooled to rt. EtOAc (100 mL) and water (50 mL) were added. The layers were separated and the aqueous layer further extracted with EtOAc (100 mL×2) The combined organic layers were then washed with water (2×50 mL) and brine (50 mL), dried over anhydrous Na$_2$SO$_4$, filtered and concentrated under vacuum. The resulting residue was purified by silica gel chromatography (8% EtOAc in PE) to afford [(2S)-2-[(1S)-1-(benzyloxymethyl)-2-chloroethoxy]-3-hydroxy-propyl]4-methylbenzenesulfonate (4.4 g, 34% yield) as a colorless oil. ESI-MS (EI$^+$, m/z): 429.1 [M+H]$^+$.

Step 3: Synthesis of ((2R,5R)-5-(benzyloxymethyl)-1,4-dioxan-2-yl)methanol:

A solution of [(2S)-2-[(1S)-1-(benzyloxymethyl)-2-chloro-ethoxy]-3-hydroxy-propyl] 4-methylbenzenesulfonate (0.78 g, 1.82 mmol), NaOH (0.22 g, 5.46 mmol) in H$_2$O (10 mL) was stirred at room temperature for 2.5 h, then heated at 90° C. for 4 h, cooled to rt and stirred overnight, then heated at 90° C. for another 2 h. The reaction mixture was acidified with 1N HCl aqueous solution and extracted with DCM (100 mL×3). The combined organic layers were washed with NaHCO$_3$ aqueous solution, dried over anhydrous Na$_2$SO$_4$, filtered and concentrated to obtain [(2R,5R)-5-(benzyloxymethyl)-1,4-dioxan-2-yl]methanol (4.4 g, 41% yield) as a colorless oil. This material was used without further purification. ESI-MS (EI$^+$, m/z): 239.1 [M+H]$^+$.

Step 4: Synthesis of ((2R,5R)-1,4-dioxane-2,5-diyl)dimethanol:

To a solution of [(2R,5R)-5-(benzyloxymethyl)-1,4-dioxan-2-yl]methanol (2.4 g, 10 mmol) in MeOH (30 mL) was added Pd/C (0.86 g). The mixture was allowed to stir at rt overnight under a hydrogen balloon then filtered through a short celite plug, washing with ethanol. The combined organic washes were concentrated under reduced pressure to provide (2R,5R)-1,4-dioxane-2,5-diyl)dimethanol (1.2 g, 74% yield) as an oil. ESI-MS (EI$^+$, m/z): 149.2 [M+H]$^+$.

Step 5: Synthesis of (23E,25E,27E,28E,32R,33S,34R,35R, 36S,39S,41S,45R,46R,55R)-45,55-dihydroxy-41-[(1R)-2-[(1S,2R,3R)-3-hydroxy-2-methoxy-cyclohexyl]-1-methyl-ethyl]-40-[[(2S,5S)-5-(hydroxymethyl)-1,4-dioxan-2-yl]methoxy]-46-methoxy-32,33,34,35,47,48-hexamethyl-68,69-dioxa-56-azatricyclohexatriaconta-23,25,27(47),28(48)-tetraene-49,50,51,52,53-pentone (I-118):

To a solution of rapamycin (0.5 g, 0.547 mmol) and 4-methylbenzenesulfonic acid hydrate (0.471 g, 2.73 mmol) in THF (15 mL) was added [(2R,5R)-5-(hydroxymethyl)-1,4-dioxan-2-yl]methanol (0.81 g, 5.47 mmol) at 25° C. After stirring at rt for 2 h, the reaction was quenched with cold NaHCO$_3$ aqueous solution and extracted with EtOAc (50 mL×2). The combined organic layere were then dried over anhydrous Na$_2$SO$_4$, filtered and concentrated. The residue was purified via reverse-phase chromatography (C18, CH$_3$CN:H$_2$O=65:35) followed via silica gel chromatography (hexane:DCM:EtOAc:MeOH=8:8:3:1) to obtain (23E, 25E,27E,28E,32R,33S,34R,35R,36S,39S,41S,45R,46R, 55R)-45,55-dihydroxy-41-[(1R)-2-[(1S,2R,3R)-3-hydroxy-2-methoxy-cyclohexyl]-1-methyl-ethyl]-40-[[(2S,5S)-5-(hydroxymethyl)-1,4-dioxan-2-yl]methoxy]-46-methoxy-32,33,34,35,47,48-hexamethyl-68,69-dioxa-56-azatricyclohexatriaconta-23,25,27(47),28(48)-tetraene-49,50,51,52,53-pentone (I-118: 80 mg, 14% yield) as a white solid. ESI-MS (EI$^+$, m/z): 1052.9 [M+Na]$^+$. $^1$H NMR (500 MHz, CDCl$_3$) δ 6.46-5.86 (m, 4H), 5.69-5.06 (m, 4H), 4.16 (ddd, J=56.1, 52.0, 39.5 Hz, 3H), 3.94-3.49 (m, 10H), 3.48-3.11 (m, 12H), 3.08-2.46 (m, 7H), 2.40-1.93 (m, 7H), 1.73 (dd, J=16.9, 10.5 Hz, 13H), 1.52-1.17 (m, 8H), 1.16-0.79 (m, 18H), 0.65 (d, J=17.5 Hz, 1H).

EXAMPLE 21

Synthesis of (21E,23E,25E,26E,34R,35S,36R,37R, 39S,41S,43R,44S,45R,46R,55R)-45,55-dihydroxy-43-[2-(2-hydroxyethoxy)ethoxy]-44-[(1R)-2-[(1S, 3R,4R)-4-(2-hydroxyethoxy)-3-methoxy-cyclohexyl]-1-methyl-ethyl]-46-methoxy-34,35,36, 37,47,48-hexamethyl-66,67-dioxa-56-azatricyclohexatriaconta-21,23,25(47),26(48)-tetraene-49,50,51,52,53-pentone (I-116) and (21E, 23E,25E,26E,34R,35S,36R,37R,39S,41S,43S,44S, 45R,46R, 55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-117):

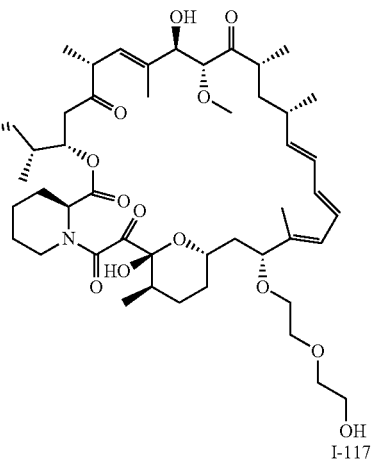
I-116

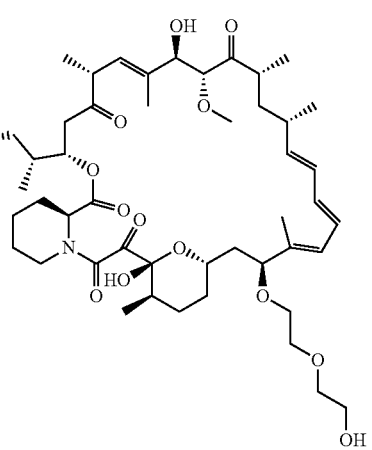
I-117

Synthetic Scheme:

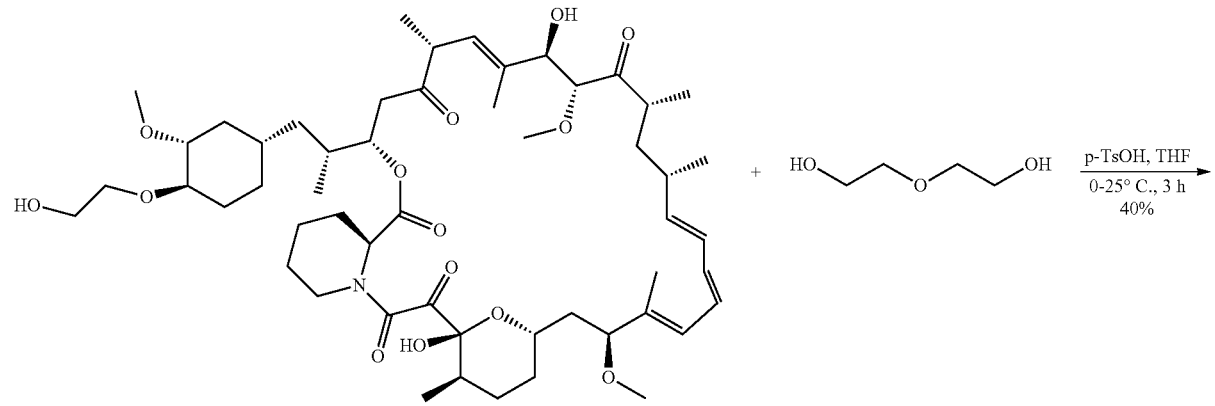

-continued
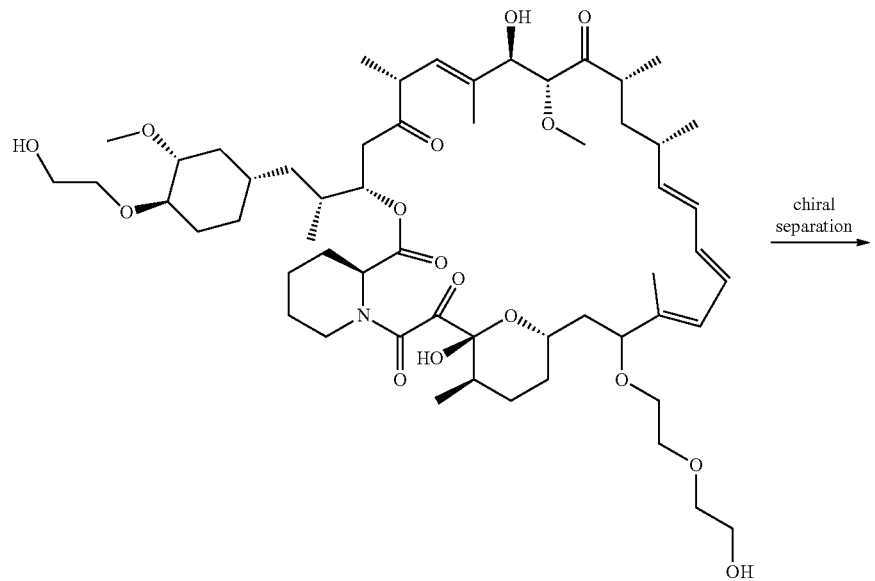
chiral separation →
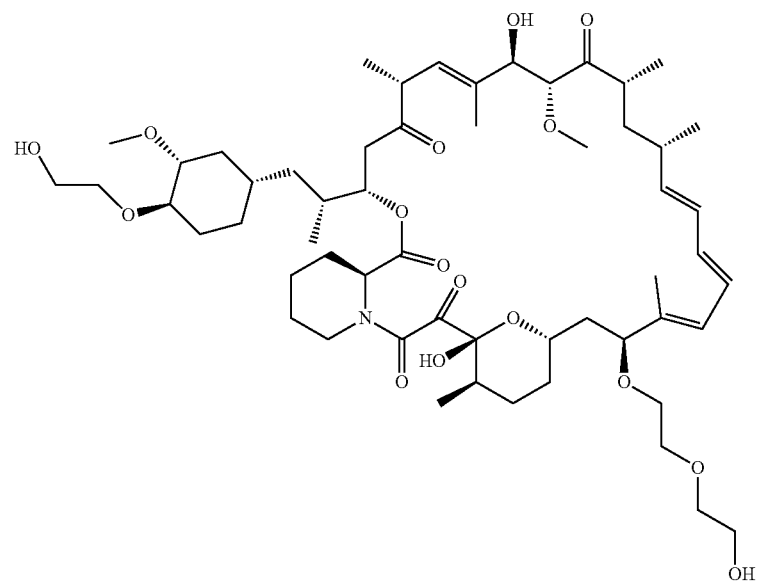
I-117

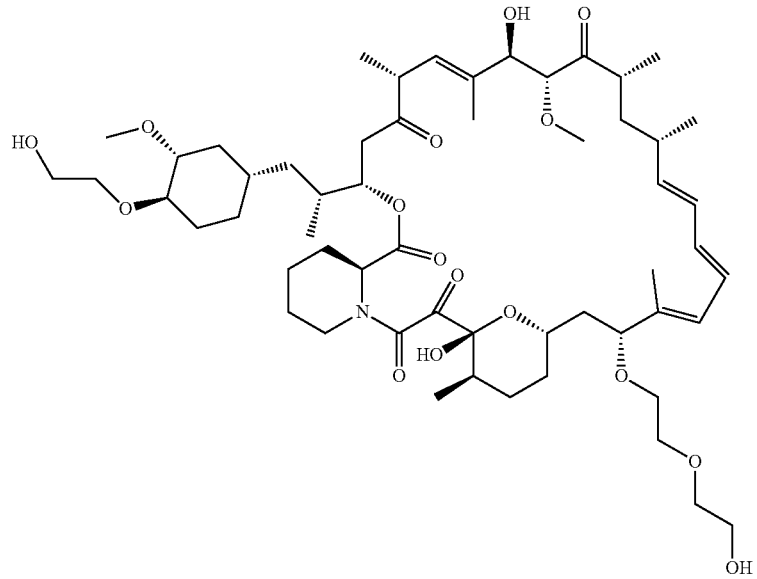

I-116

Procedures and Characterization:

Step 1: Synthesis of (21E,23E,25E,26E,34R,35S,36R,37R, 39S,41S,44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone:

A solution of everolimus (1 g, 1.04 mmol) in THF (15 mL) was degassed with N$_2$. p-toluenesulfonic acid (0.895 g, 5.20 mmol) was added at 0° C. followed by 2-(2-hydroxyethoxy)ethanol (2.8 mL). The resulting mixture was stirred at 0° C. for 0.5 h under N$_2$, then at 25° C. for 3 h. The reaction was poured into sat.NaHCO$_3$ (40 mL), extracted with EtOAc (30 mL), washed with water (30 mL×2) and brine (40 mL) then dried over anhydrous Na$_2$SO$_4$, filtered and concentrated. The resulting residue was purified by normal phase silica gel chromatography (MeOH: DCM=1: 15) then reverse-phase chromatography (C18, CH$_3$CN: H$_2$O=7: 3) to obtain (21E,23E,25E,26E,34R,35S,36R,37R, 39S,41S,44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49, 50,51,52,53-pentone (0.43 g, 40% yield) as a light yellow solid. ESI-MS (EI$^+$, m/z):1053.9 [M+Na]$^+$. $^1$H NMR (400 MHz, CDCl$_3$) δ 6.47-5.85 (m, 4H), 5.40 (ddd, J=99.7, 51.9, 29.1 Hz, 4H), 4.80 (d, J=22.0 Hz, 1H), 4.23 (d, J=42.5 Hz, 1H), 4.05-3.54 (m, 13H), 3.52-3.01 (m, 14H), 2.67 (ddd, J=46.8, 27.3, 6.8 Hz, 4H), 2.17 (dd, J=82.0, 45.9 Hz, 6H), 1.70 (dt, J=21.0, 15.8 Hz, 12H), 1.34 (dd, J=105.2, 26.3 Hz, 11H), 1.15-0.79 (m, 18H), 0.76-0.64 (m, 1H).

Step 2: Synthesis of (21E,23E,25E,26E,34R,35S,36R,3 7R,39S,41S,43R,44S,45R,46R,55R)-45,55-dihydroxy-43-[2-(2-hydroxyethoxy)ethoxy]-44-[(1R)-2-[(1S,3R,4R)-4-(2-hydroxyethoxy) -3-methoxy-cyclohexyl]-1-methyl-ethyl]-46-methoxy-34,35,36,3 7,47,48-hexamethyl-66,67-dioxa-56-azatricyclohexatriaconta-21,23,25(47),26(48)-tetraene-49,50,51,52,53-pentone (I-116) and (21E,23E,25E,26E, 34R,35S,36R,3 7R,39S,41S,43S,44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,3 7,47,48-hexamethyl-66,67-dioxa-56-azatricyclohexatriaconta-21, 23,25(47),26(48)-tetraene-49,50,51,52,53-pentone (I-117):

90 mg of (21E,23E,25E,26E,34R,35S,36R,37R,39S,41S, 44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49, 50,51,52,53-pentone was purified via prep chiral HPLC and the resulting epimers were obtained: (21E,23E,25E,26E, 34R,35S,36R,37R,39S,41S,43R,44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21, 23,25(47),26(48)-tetraene-49,50,51,52,53-pentone (I-116: 14 mg, 16% yield) and (21E,23E,25E,26E,34R,35S,36R, 37R,39S,41S,43S,44S,45R,46R,55R)-45,55-dihydroxy-43-[2-(2-hydroxyethoxy)ethoxy]-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-117: 15 mg, 17% yield), both as white solids.

The chiral separation method is listed below:
Column: CHIRALPAK IC
Column size: 5.0 cm I.D.×25 cm L
Solution concentration: 11.5 mg/ml
Injection: 10 ml
Mobile phase: Hexane/EtOH=50/50(V/V)
Flow rate: 60 ml/min
Wave length: UV 254 nm
Temperature: 35° C.

I-116: ESI-MS (EI+, m/z):1054.0 [M+Na]+. $^1$H NMR (500 MHz, CDCl$_3$) δ 6.42-5.90 (m, 4H), 5.79 (ddd, J=51.6, 30.9, 16.6 Hz, 1H), 5.54-5.08 (m, 4H), 5.03-4.88 (m, 1H), 4.74 (d, J=61.6 Hz, 1H), 4.28 (dd, J=57.6, 29.0 Hz, 2H), 3.99 (dd, J=26.5, 6.0 Hz, 1H), 3.89-3.55 (m, 12H), 3.54-2.96 (m, 15H), 2.87-2.47 (m, 4H), 2.38-1.92 (m, 8H), 1.86-1.67 (m, 11H), 1.51-1.30 (m, 6 H), 1.14-0.80 (m, 18H), 0.76-0.64 (m, 1H).

I-117: ESI-MS (EI+, m/z):1053.9 [M+Na]+. $^1$H NMR (500 MHz, CDCl$_3$) δ 6.41-6.22 (m, 2H), 6.13 (dd, J=15.1, 10.1 Hz, 1H), 5.94 (dd, J=22.3, 10.8 Hz, 1H), 5.52 (dt, J=18.4, 9.2 Hz, 1H), 5.41 (d, J=9.9 Hz, 1H), 5.27 (d, J=5.3 Hz, 1H), 5.12 (dt, J=46.3, 5.6 Hz, 1H), 4.83 (s, 1H), 4.23-4.14 (m, 1H), 3.91-3.52 (m, 15H), 3.49-3.25 (m, 12H), 3.23-3.03 (m, 3H), 2.94-2.80 (m, 1H), 2.65 (ddd, J=23.4, 16.9, 6.0 Hz, 3H), 2.39-2.15 (m, 2H), 2.16-1.85 (m, 5H), 1.82-1.64 (m, 10H), 1.47 (dd, J=26.8, 15.9 Hz, 5H), 1.38-1.16 (m, 6H), 1.10 (d, J=6.8 Hz, 3H), 1.07-1.03 (m, 3H), 1.00 (t, J=6.8 Hz, 3H), 0.94 (d, J=6.6 Hz, 3H), 0.88 (ddd, J=34.0, 16.9, 5.0 Hz, 6H), 0.71 (dd, J=23.9, 11.8 Hz, 1H).

EXAMPLE 22

Synthesis of (21E,23E,25E,26E,38R,39S,40R,41R, 43S,45S,47R,48S,49R,50R,59R)-49,59-dihydroxy-47-[2-[2-[2-(2-hydroxyethoxy)ethoxy]ethoxy] ethoxy]-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25 (51),26(52)-tetraene-53,54,55,56,57-pentone (I-114) and (21E,23E,25E,26E,38R,39S,40R,41R,43S,45S, 47S,48S,49R,50R,59R)-49,59-dihydroxy-47-[2-[2-[2-(2-hydroxyethoxy)ethoxy]ethoxy]-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26(52)-tetra-ene-53,54,55,56,57-pentone (I-115):

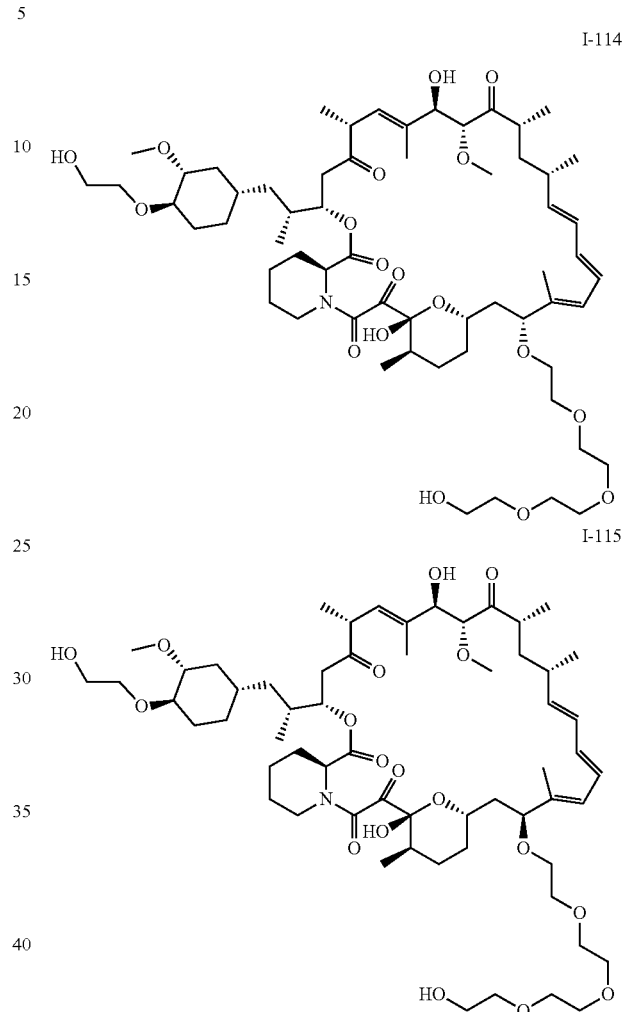

Synthetic Scheme:

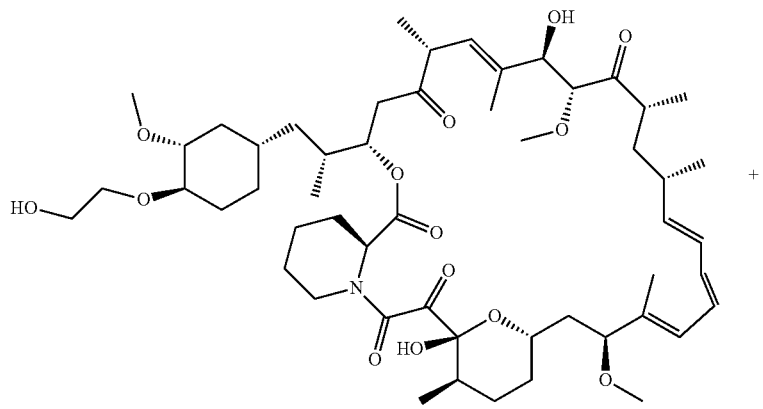

261
-continued
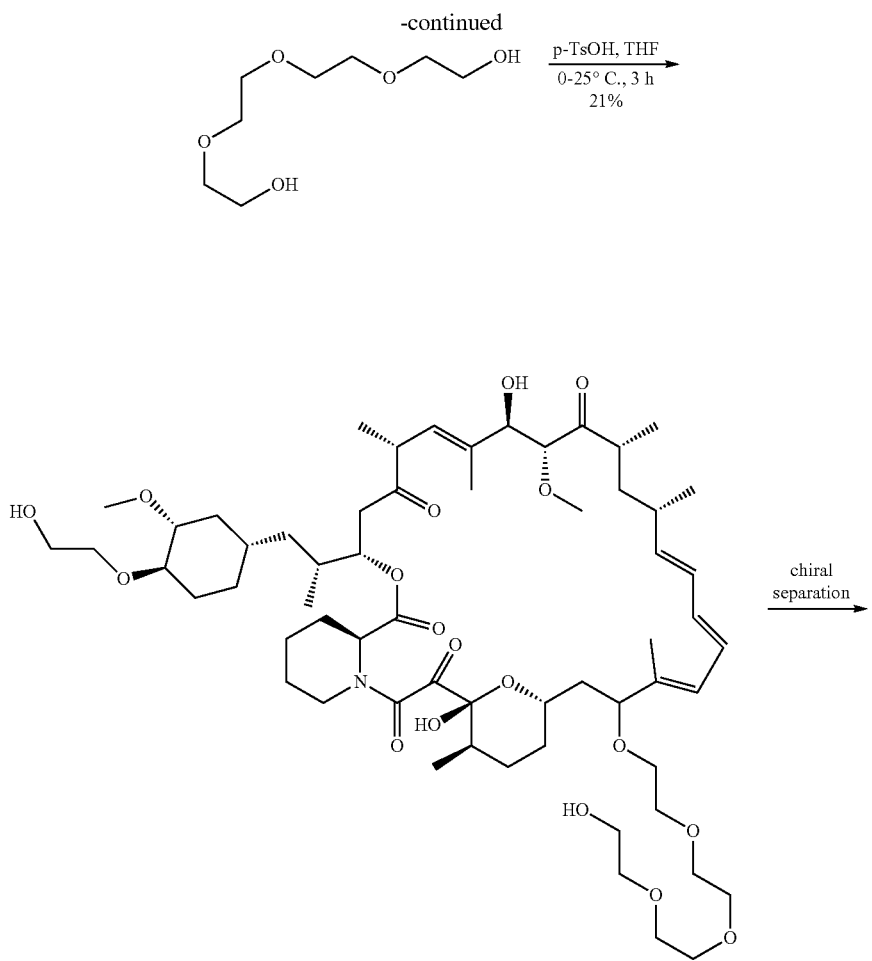
262
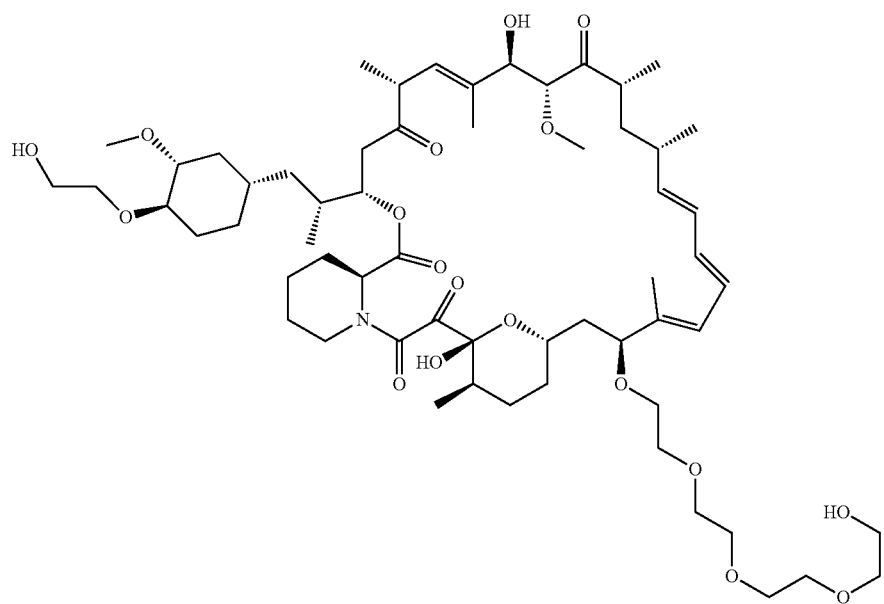
I-115

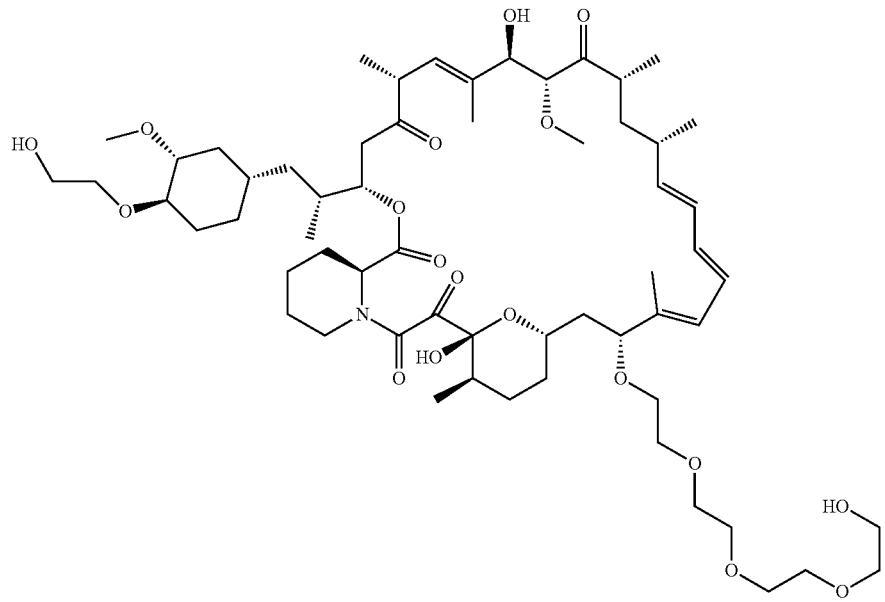

I-114

Procedures and Characterization:
Step 1: Synthesis of (21E,23E,25E,26E,38R,39S,40R,41R, 43S,45S,48S,49R,50R,59R)-49,59-dihydroxy-47-[2-[2-[2-(2-hydroxyethoxy)ethoxy]ethoxy]ethoxy]-48-[(1R)-2-[(1S, 3R,4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone:

A mixture of everolimus (1 g, 1.04 mmol), 2-[2-[2-(2-hydroxyethoxy)ethoxy]ethoxy]ethanol (4.05 g, 20.87 mmol) andp-toluenesulfonic acid (0.898 g, 5.22 mmol) in THF (20 mL) was stirred at 20° C. for 2 h. The mixture was then poured into cold sat.NaHCO$_3$ (30 mL), extracted with EtOAc (50 mL×3) and the combined organic layers washed with water and brine then dried over anhydrous Na$_2$SO$_4$, filtered and concentrated. The resulting residue was purified by reversed phase chromatography (C18, CH$_3$CN: H$_2$O=6: 4) to afford (21E,23E,25E,26E,38R,39S,40R,41R,43S,45S, 48S,49R,50R,59R)-49,59-dihydroxy-47-[2-[2-[2-(2-hydroxyethoxy)ethoxy]ethoxy]ethoxy]-48-[(1R)-2-[(1S,3R, 4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone (0.25 g, 21% yield) as white solid. ESI-MS (EI$^+$, m/z):1142.4 [M+Na]$^+$. $^1$H NMR (400 MHz, CDCl$_3$) δ 6.41-5.85 (m, 4H), 5.78 (s, 1H), 5.60-4.98 (m, 4H), 4.22 (t, J=27.1 Hz, 1H), 3.97 (dd, J=17.7, 6.4 Hz, 1H), 3.87-3.54 (m, 21H), 3.51-3.03 (m, 15H), 2.72-2.45 (m, 3H), 2.28 (s, 6H), 2.16-1.96 (m, 4H), 1.89-1.56 (m, 10H), 1.51-1.17 (m, 8H), 1.17-0.81 (m, 18H), 0.78-0.62 (m, 1H).

Step 2: Synthesis of (21E,23E,25E,26E,38R,39S,40R,41R, 43S,45S,47R,48S,49R,50R,59R)-49,59-dihydroxy-47-[2-[2-[2-[2-(2-hydroxyethoxy)ethoxy]ethoxy]ethoxy]-48-[(1R)-2-[(1S,3R,4R)-4-(2-hydroxyethoxy)-3-methoxy-cyclohexyl]-1-methyl-ethyl]-50-methoxy-38,39,40,41,51, 52-hexamethyl-70,71-dioxa-60-azatricyclohexatriaconta-21,23,25(51),26(52)-tetraene-53,54,55,56,57-pentone (I-114) and (21E,23E,25E,26E,38R,39S,40R,41R,43S,45S, 47S,48S,49R,50R,59R)-49,59-dihydroxy-47-[2-[2-[2-(2-hydroxyethoxy)ethoxy]ethoxy]-48-[(1R)-2-[(1S,3R, 4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone (I-115):

1.5 g of (21E,23E,25E,26E,38R,39S,40R,41R,43S,45S, 48S,49R,50R,59R)-49,59-dihydroxy-47-[2-[2-[2-(2-hydroxyethoxy)ethoxy]ethoxy]ethoxy]-48-[(1R)-2-[(1S,3R, 4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone was purified via prep chiral HPLC and the resulting epimers purified via silica gel chromatography (hexane:DCM:EtOAc:MeOH=8:8:3:1.2) to obtain (21E,23E,25E,26E,38R,39S,40R,41R,43S,45S, 47R,48S,49R,50R,59R)-49,59-dihydroxy-47-[2-[2-[2-(2-hydroxyethoxy)ethoxy]ethoxy]ethoxy]-48-[(1R)-2-[(1S,3R, 4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26 (52)-tetraene-53,54,55,56,57-pentone (I-114: 300 mg, 20% yield) and (21E,23E,25E,26E,38R,39S,40R,41R,43S,45S, 47S,48S,49R,50R,59R)-49,59-dihydroxy-47-[2-[2-[2-(2- hydroxyethoxy)ethoxy]ethoxy]ethoxy]-48-[(1R)-2-[(1S,3R,4R)-4-(2-hydroxyethoxy)-3-methoxy-cyclohexyl]-1-methyl-ethyl]-50-methoxy-38,39,40,41,51,52-hexamethyl-70,71-dioxa-60-azatricyclohexatriaconta-21,23,25(51),26(52)-tetraene-53,54,55,56,57-pentone (I-115: 563 mg, 38% yield) as a white solids.

Chiral analysis conditions:
Column: CHIRALPAK IC-3(IC30CE-NJ008)
Column size: 0.46 cm I.D.×15 cm L
Injection: 20.0 ul
Mobile phase: Hexane/EtOH=60/40(V/V)
Flow rate: 1.0 ml/min
Wave length: UV 254nm
Temperature: 35° C.
HPLC equipment: Shimadzu LC-20AT I-114: ESI-MS (EI$^+$, m/z):1142.5 [M+Na]$^+$. $^1$H NMR (500 MHz, CDCl$_3$) δ 6.42-5.91 (m, 4H), 5.60-5.08 (m, 4H), 4.19 (dd, J=43.8, 32.6 Hz, 1H), 3.96 (dd, J=27.1, 6.3 Hz, 1H), 3.85-3.54 (m, 21H), 3.53-3.01 (m, 12H), 2.93-2.80 (m, 1H), 2.75-2.45 (m, 3H), 2.30 (d, J=12.1 Hz, 1H), 2.03 (dd, J=37.0, 32.8 Hz, 13H), 1.84-1.69 (m, 12H), 1.50-1.18 (m, 5H), 1.16-0.82 (m, 18H), 0.71 (dt, J=23.8, 12.1 Hz, 1H).

I-115: ESI-MS (EI$^+$, m/z):1142.4 [M+Na]$^+$. $^1$H NMR (500 MHz, CDCl$_3$) δ 6.36 (dd, J=14.7, 10.9 Hz, 1H), 6.23 (dd, J=14.7, 10.6 Hz, 1H), 6.10 (dd, J=15.0, 10.5 Hz, 1H), 5.92 (dd, J=45.2, 10.5 Hz, 1H), 5.61 (s, 1H), 5.43 (dd, J=15.6, 9.6 Hz, 2H), 5.21 (d, J=5.4 Hz, 1H), 5.10 (dd, J=9.9, 5.9 Hz, 1H), 4.20 (d, J=4.5 Hz, 1H), 4.10-3.95 (m, 1H), 3.84 (d, J=5.0 Hz, 1H), 3.80-3.49 (m, 21H), 3.48-3.13 (m, 12H), 3.11-3.01 (m, 1H), 2.73-2.50 (m, 3H), 2.34-2.19 (m, 2H), 2.01 (ddd, J=62.0, 34.6, 28.2 Hz, 12H), 1.80-1.54 (m, 10H), 1.51-1.37 (m, 5H), 1.35-1.12 (m, 6H), 1.05 (dd, J=6.4, 5.0 Hz, 6H), 0.97 (d, J=6.5 Hz, 3H), 0.93 (d, J=6.6 Hz, 3H), 0.91-0.82 (m, 6H), 0.74-0.67 (m, 1H).

EXAMPLE 23

Synthesis of (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-(5-hydroxypentoxy)-45-methoxy-33,34,35,36,46,47-hexamethyl-65,66-dioxa-55-azatricyclohexatriaconta-21,23,25(46),26(47)-tetraene-48,49,50,51,52-pentone (I-113):

I-113

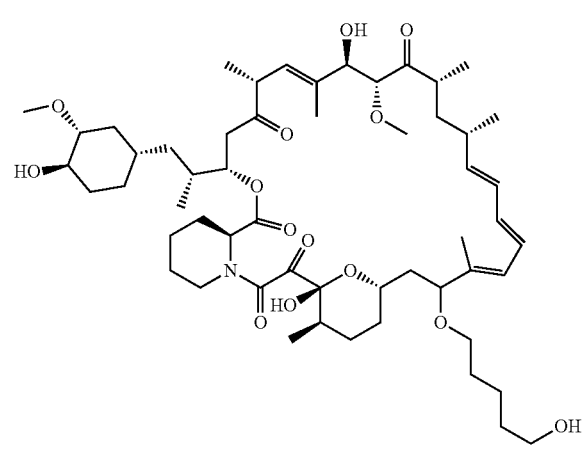

Synthetic Scheme:

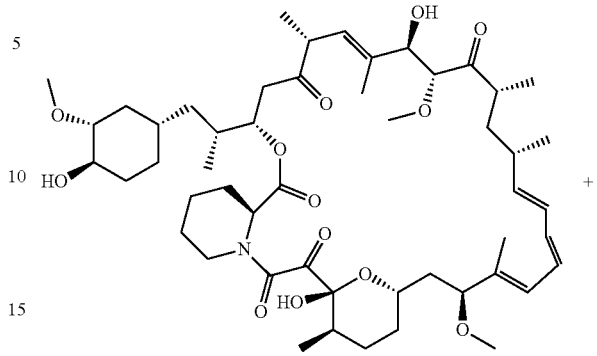

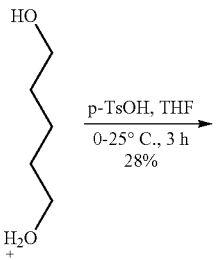

p-TsOH, THF
0-25° C., 3 h
28%

I-113

Procedures and Characterization:

Step 1: Synthesis of (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-(5-hydroxypentoxy)-45-methoxy-33,34,35,36,46, 47-hexamethyl-65,66-dioxa-55-azatricyclohexatriaconta-21,23,25(46),26(47)-tetraene-48,49,50,51,52-pentone (I-113):

To a solution of rapamycin (0.5 g, 0.547 mmol) in THF (10 mL) was added 4-methylbenzenesulfonic acid hydrate (0.52 g, 2.73 mmol) and pentane-1,5-diol (3 mL). The resulting solution was stirred at rt for 2 h then poured into cold NaHCO$_3$ aqueous solution and extracted with EtOAc. The organic layer was concentrated and purified by reverse-phase chromatography (C18, CH$_3$CN:H$_2$O from 10% to 72% yield) to afford (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-42-(5-hydroxypentoxy)-45-methoxy-33,34,35,36,46,47-hexamethyl-65,66-dioxa-55-azatricyclohexatriaconta-21,23,25(46),26(47)-tetraene-48,49,50,51,52-pentone (I-113: 150 mg, 28% yield) as a white solid. ESI-MS (EI$^+$, m/z):1008.0 [M+Na]$^+$. $^1$HNMR (500 MHz, CDCl$_3$) δ 6.42-5.82 (m, 4H), 5.58-5.37 (m, 2H), 5.32-5.02 (m, 2H), 4.78 (t, J=25.9 Hz, 1H), 4.31-4.08 (m, 1H), 4.00-3.53 (m, 5H), 3.53-3.05 (m, 12H), 2.99-2.80 (m, 2H), 2.77-2.51 (m, 3H), 2.48-2.23 (m, 2H), 2.15-1.89 (m, 4H), 1.89-1.16 (m, 32H), 1.15-0.78 (m, 18H), 0.65 (dt, J=24.1, 12.0 Hz, 1H).

EXAMPLE 24

Synthesis of (28E,30E,32E,33E,36R,37S,38R,39R,41S,43S,45R,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-111) and (28E,30E,32E,33E,36R,37S,38R,39R,41S,43S,45S,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-112):

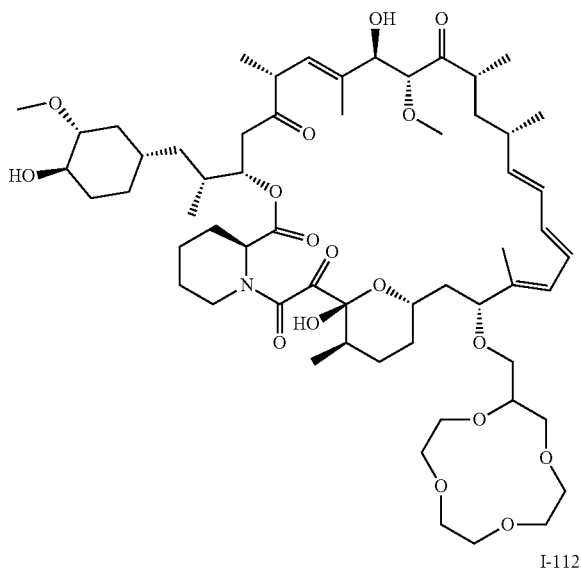

I-111

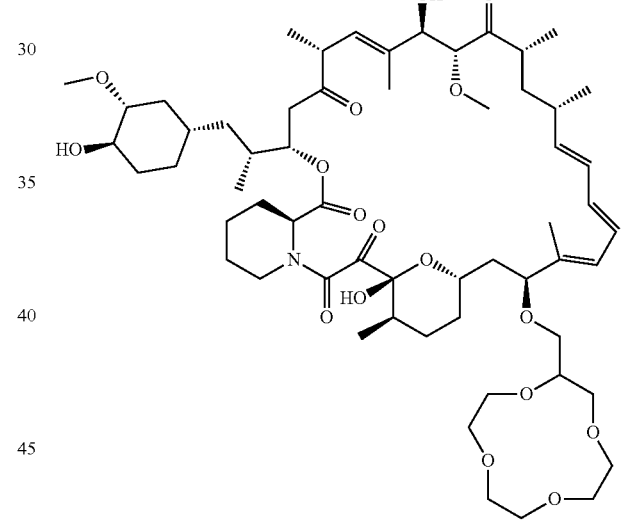

I-112

Synthetic Scheme:

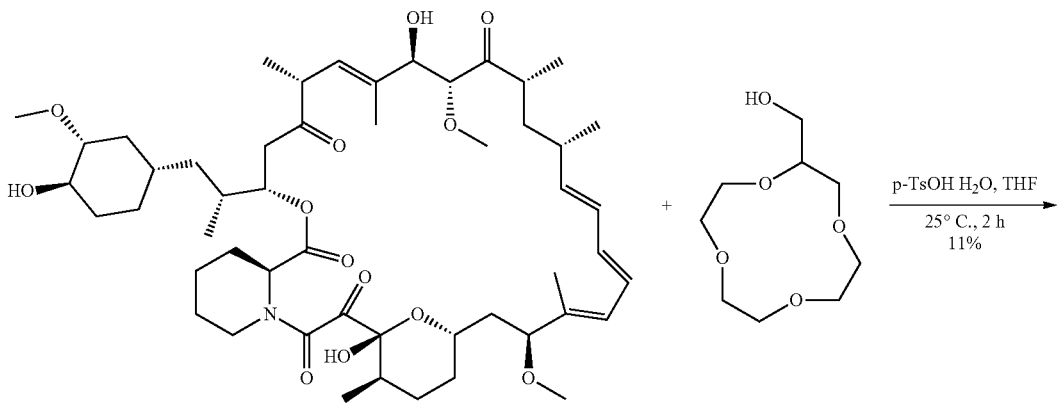

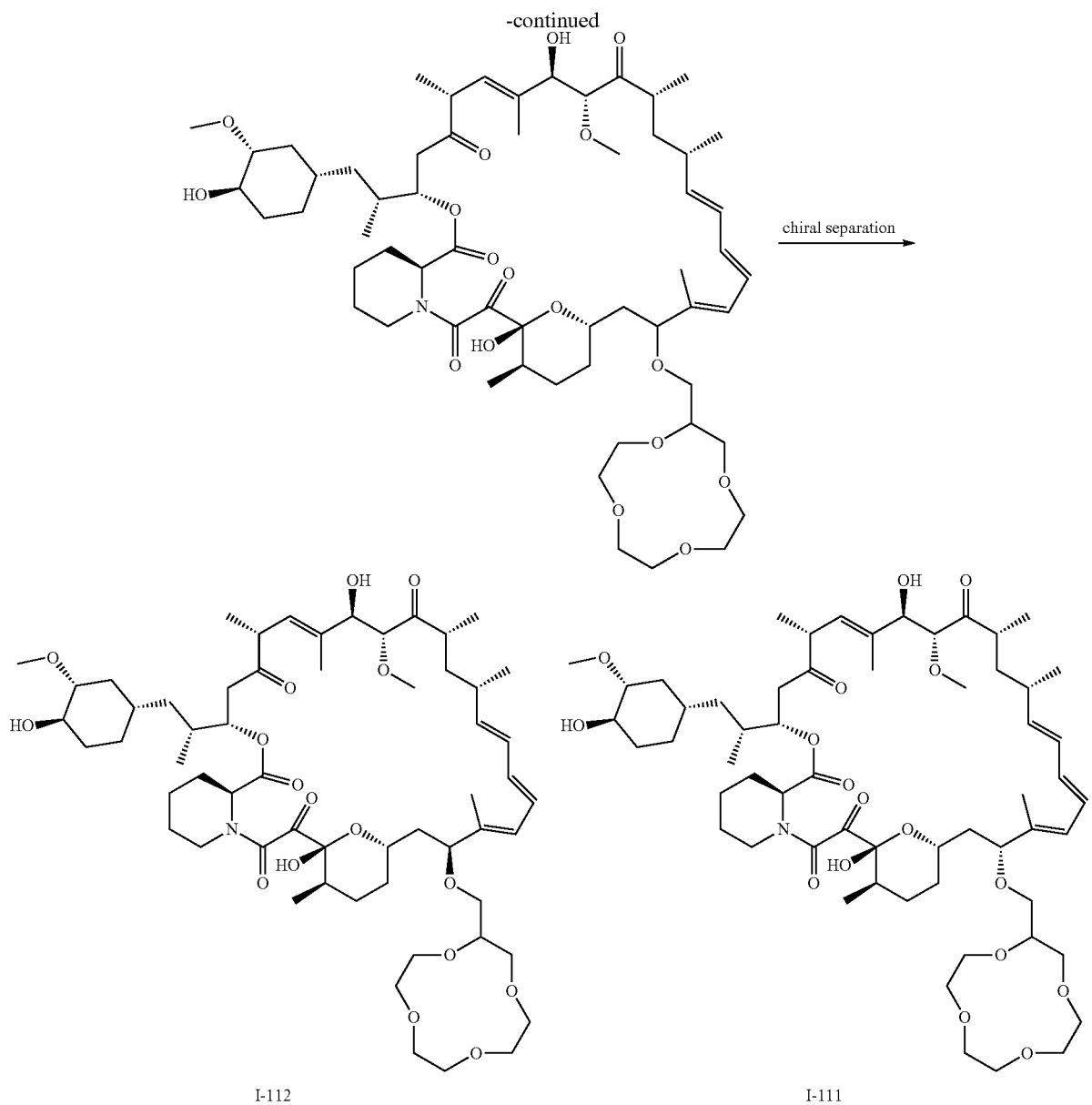

I-112      I-111

Procedures and Characterization:

Step 1: Synthesis of (28E,30E,32E,33E,36R,37S,38R,39R,41S,43S,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone:

To a solution of rapamycin (0.5 g, 0.547 mmol) and 4-methylbenzenesulfonic acid hydrate (0.471 g, 2.73 mmol) in THF (15 mL) was added 1,4,7,10-tetraoxacyclododec-2-ylmethanol (2.25 g, 10.9 mmol) at 25° C. The resulting mixture was stirred at rt for 2 h then poured into ice cold NaHCO$_3$ aqueous solution and extracted with EtOAc. The organic layer was then then dried over anhydrous Na$_2$SO$_4$, filtered and concentrated. The resulting residue was purified by reverse-phase chromatography (C18, CH$_3$CN:H$_2$O=7:3) to obtain (28E,30E,32E,33E,36R,37S,38R,39R,41S,43S,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (70 mg, 11% yield) as a white solid. ESI-MS (EI$^+$, m/z):1110.5 [M+Na]$^+$. $^1$H NMR (500 MHz, CDCl$_3$) δ 6.41-5.82 (m, 4H), 5.54-5.04 (m, 4H), 4.72 (d, J=22.1 Hz, 1H), 4.35-4.09 (m, 1H), 3.92-3.51 (m, 18H), 3.48-3.03 (m, 14H), 2.99-2.51 (m, 5H), 2.34 (d, J=13.4 Hz, 1H), 2.04 (d, J=62.6 Hz, 4H), 1.72 (ddd, J=43.8, 30.6, 28.9 Hz, 12H), 1.53-1.17 (m, 10H), 1.14-0.81 (m, 18H), 0.70-0.62 (m, 1H).

Step 2: Synthesis of (28E,30E,32E,33E,36R,37S,38R,39R,41S,43S,45S,46S,48R,49R,58R)-48,58-dihydroxy-46-[(1R)-2-1(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-112) and (28E,30E,32E, 33E,36R,37S,38R,39R,41S,43S,45R,46S,48R,49R,58R)-48,58-dihydroxy-46-[(1R)-2-1(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-111):

(28E,30E,32E,33E,36R,37S,38R,39R,41S,43S,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (170 mg) was purified via prep chiral HPLC and the resulting epimers purified via silica gel chromatography (hexane:DCM:EtOAc:MeOH=3:3:1:0.5) to obtain (28E,30E,32E,33E,36R,37S,38R,39R,41S,43S,45S,46R,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-112: 55 mg, 32% yield) and (28E,30E,32E,33E,36R,37S,38R,39R,41S,43S,45R,46S,48R,49R,58R)-48,58-dihydroxy-46-[(1R)-2-[(1S,3R,4R)-4-hydroxy-3-methoxy-cyclohexyl]-1-methyl-ethyl]-49-methoxy-36,37,38,39,50,51-hexamethyl-45-(1,4,7,10-tetraoxacyclododec-2-ylmethoxy)-72,73-dioxa-59-azatricyclohexatriaconta-28,30,32(50),33(51)-tetraene-52,53,54,55,56-pentone (I-111: 11 mg, 6% yield), both as white solids.

Chiral analysis method:
Column: CHIRALPAK IC(IC00CE-OL002)
Column size: 0.46 cm I.D.×25 cm L
Injection: 100.0 ul
Mobile phase: Hexane/EtOH=60/40 (V/V)
Flow rate: 1.0 ml/min
Wave length: UV 254 nm
Temperature: 35° C.
HPLC equipment: Shimadzu LC-20AT CP-HPLC-06

I-112: ESI-MS (E+, m/z):1109.9 [M+Na]+. $^1$H NMR (500 MHz, CDCl$_3$) δ 6.40-6.03 (m, 3H), 5.90 (dd, J=37.1, 9.8 Hz, 1H), 5.54-5.06 (m, 4H), 4.71 (d, J=22.4 Hz, 1H), 4.20 (t, J=20.9 Hz, 1H), 3.93-3.52 (m, 17H), 3.50-3.24 (m, 11H), 3.14-3.02 (m, 1H), 2.93 (dt, J=31.2, 12.0 Hz, 1H), 2.63 (tdd, J=17.0, 14.2, 5.5 Hz, 3H), 2.37-2.18 (m, 2H), 1.94 (ddd, J=31.3, 24.3, 22.1 Hz, 5H), 1.71 (dt, J=22.5, 10.1 Hz, 11H), 1.51-1.17 (m, 13H), 1.15-0.81 (m, 18H), 0.67 (dd, J=23.7, 11.9 Hz, 1H).

I-111: $^1$H NMR (500 MHz, CDCl$_3$) δ 6.46-5.78 (m, 4H), 5.75-5.14 (m, 4H), 4.58 (d, J=31.9 Hz, 1H), 4.21 (d, J=66.8 Hz, 1H), 3.87-3.47 (m, 16H), 3.43-3.14 (m, 10H), 2.94 (s, 1H), 2.80-2.54 (m, 3H), 2.26 (ddd, J=110.3, 80.5, 42.6 Hz, 6H), 1.81-1.49 (m, 18H), 1.46-1.25 (m, 10H), 1.18-0.77 (m, 18H), 0.72-0.61 (m, 1H).

EXAMPLE 25

Synthesis of (21E,23E,25E,26E,36R,37S,38R,39R,41S,43S,45R,46S,47R,48R,57R)-47,57-dihydroxy-45-[2-[2-(2-hydroxyethoxy)ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-109) and (21E,23E,25E,26E,36R,37S,38R,39R,41S,43S,45S,46S,47R,48R,57R)-47,57-dihydroxy-45-[2-[2-(2-hydroxyethoxy)ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-110):

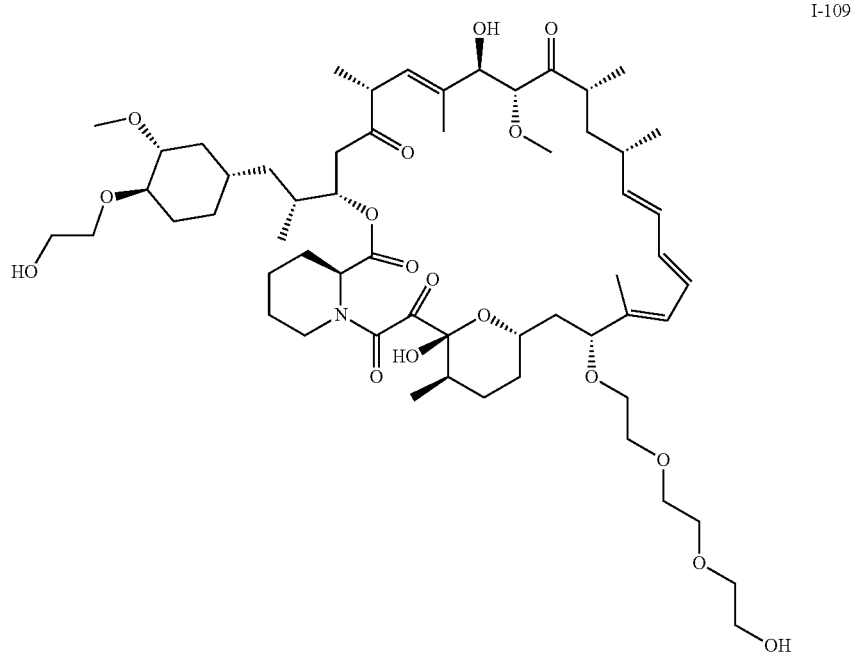

I-109

I-110
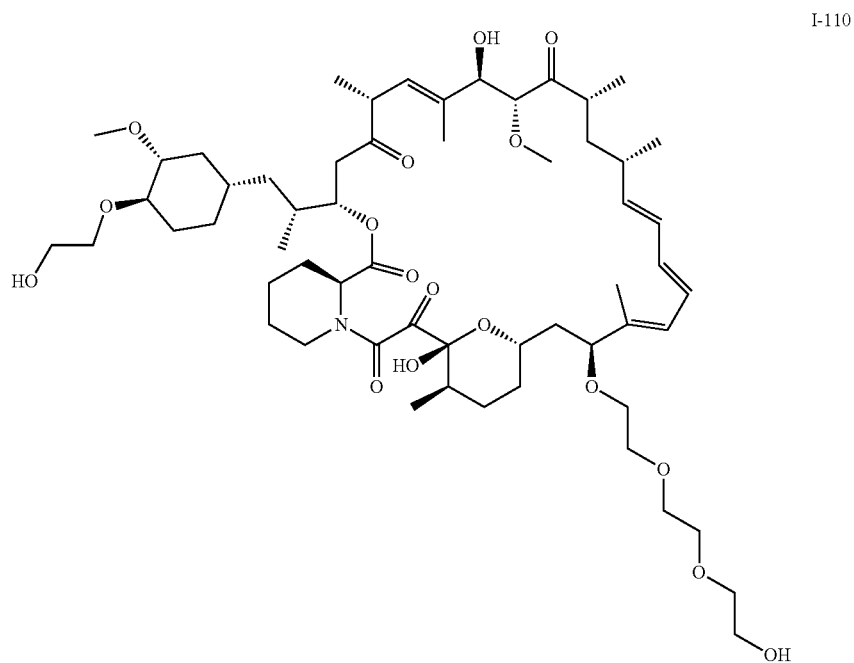
Synthetic Scheme:
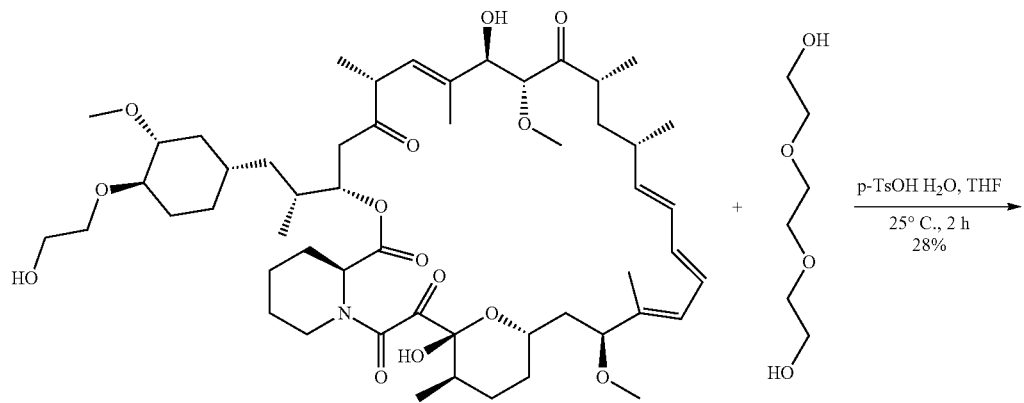

-continued
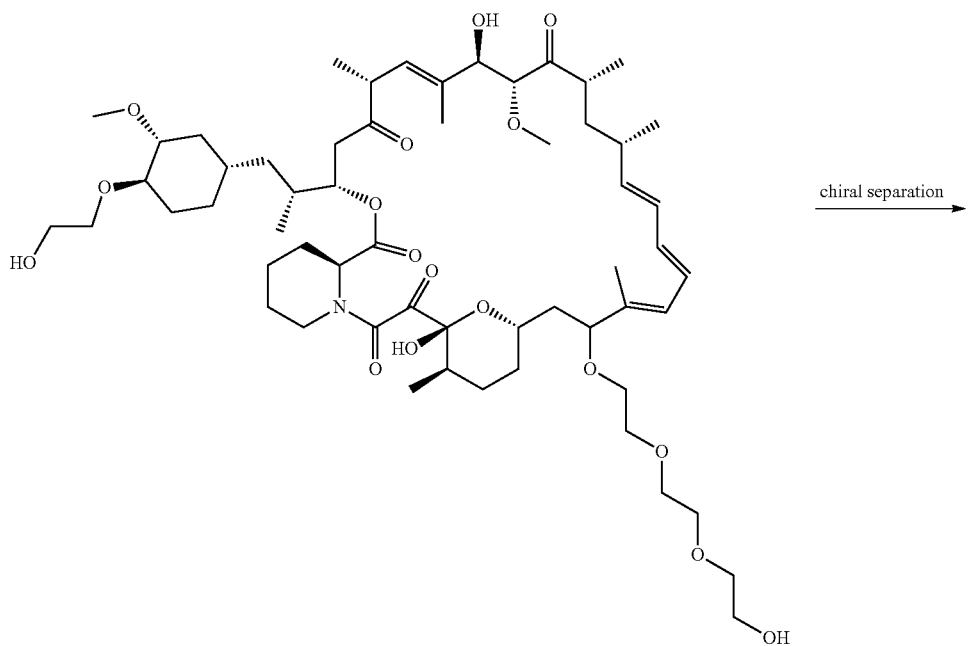
chiral separation
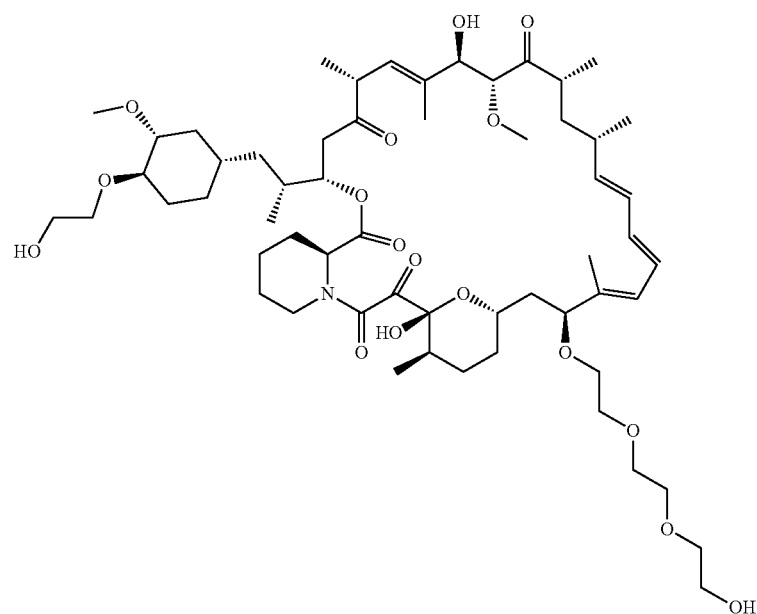
I-110

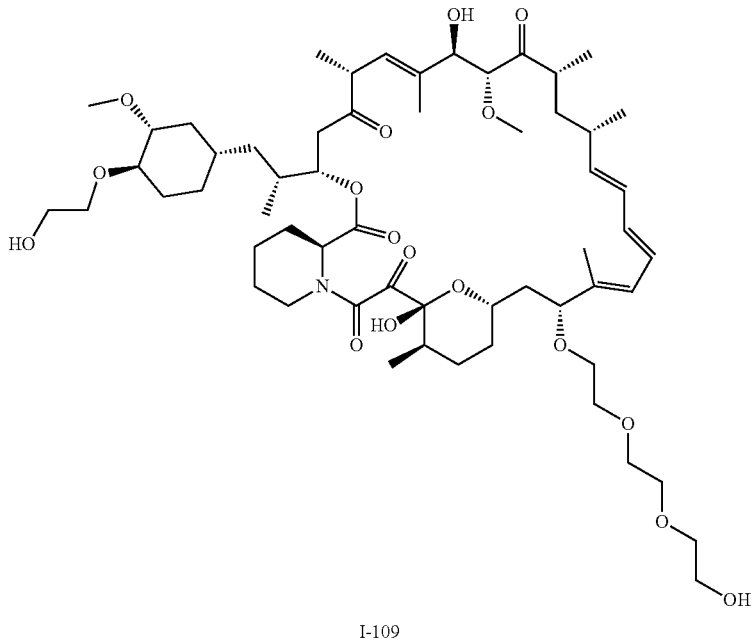 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOCCOCCO)C[C@@H]3CC[C@@H](C)[C@@](O)(O3)C(=O)C(=O)N3CCCC[C@H]3C(=O)O2)CC[C@H]1OCCO]

I-109

Procedures and Characterization:

Step 1: Synthesis of (21E,23E,25E,26E,36R,37S,38R,39R, 41S,43S,46S,47R,48R,57R)-47,57-dihydroxy-45-[2-[2-(2-hydroxyethoxy)ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone:

A mixture of everolimus (0.5 g, 0.522 mmol), 2-[2-(2-hydroxyethoxy)ethoxy]ethanol (3.92 g, 26.09 mmol) and p-toluenesulfonic acid monohydrate (0.45 g, 2.61 mmol) in THF (10 mL) was stirred at 20° C. for 2 h. The mixture was then poured into ice cold sat. NaHCO$_3$ (30 mL) and extracted with EtOAc (50 mL×3). The combined organic layers were washed with water and brine then dried over anhydrous Na$_2$SO$_4$, filtered and concentrated. The reslting residue was purified via reverse phase chromatography (C18, CH$_3$CN:H$_2$O=6.5: 3.5) to afford (21E,23E,25E,26E, 36R,37S,38R,39R,41S,43S,46S,47R,48R,57R)-47,57-dihydroxy-45-[2-[2-(2-hydroxyethoxy)ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49, 50-hexamethyl-68,69-dioxa-58-azatricyclohexatriaconta-21,23,25(49),26(50)-tetraene-51,52,53,54,55-pentone (0.155 g, 28%) as white solid. ESI-MS (EI$^+$, m/z):1098.4 [M+Na]$^+$. $^1$H NMR (500 MHz, CDCl$_3$) δ 6.42-5.87 (m, 4H), 5.63-5.34 (m, 2H), 5.32-5.00 (m, 2H), 4.85 (s, 1H), 4.35-4.09 (m, 1H), 4.05-3.49 (m, 18H), 3.49-3.01 (m, 14H), 2.66 (dddd, J=31.3, 24.8, 21.2, 13.0 Hz, 4H), 2.33 (d, J=12.0 Hz, 2H), 2.06 (dd, J=39.9, 10.6 Hz, 3H), 1.77-1.53 (m, 13H), 1.51-1.14 (m, 10H), 1.14-0.81 (m, 18H), 0.71 (dd, J=23.8, 11.9 Hz, 1H).

Step 2: Synthesis of (21E,23E,25E,26E,36R,37S,38R,39R, 41S,43S,45S,46S,47R,48R,57R)-47,57-dihydroxy-45-[2-[2-(2-hydroxyethoxy)ethoxy]ethoxy]-46-[(1R)-2-[(1S,3R, 4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26 (50)-tetraene-51,52,53,54,55-pentone (I-110) and (21E,23E, 25E,26E,36R,37S,38R,39R,41S,43S,45R,46S,47R,48R, 57R)-47,57-dihydroxy-45-[2-[2-(2-hydroxyethoxy)ethoxy] ethoxy]-46-[(1R)-2-[(1S,3R,4R)-4-(2-hydroxyethoxy)-3-methoxy-cyclohexyl]-1-methyl-ethyl]-48-methoxy-36,37, 38,39,49,50-hexamethyl-68,69-dioxa-58-azatricyclohexatriaconta-21,23,25(49),26(50)-tetraene-51, 52,53,54,55-pentone (I-109):

170 mg of (21E,23E,25E,26E,36R,37S,38R,39R,41S, 43S,46S,47R,48R,57R)-47,57-dihydroxy-45-[2-[2-(2-hydroxyethoxy)ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone purified via prep chiral HPLC and the resulting epimers purified via silica gel chromatography (hexane:DCM:EtOAc:MeOH=3:3:1:0.8) to obtain (21E, 23E,25E,26E,36R,37S,38R,39R,41S,43 S,45S,46S,47R, 48R,57R)-47,57-dihydroxy-45-[2-[2-(2-hydroxyethoxy) ethoxy]ethoxy]-46-[(1R)-2-[(1S,3R,4R)-4-(2-hydroxyethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-110: 37 mg, 21% yield) and (21E, 23E,25E,26E,36R,37S,38R,39R,41S,43S,45R,46S,47R, 48R,57R)-47,57-dihydroxy-45-[2-[2-(2-hydroxyethoxy)

ethoxy]ethoxy]-46-[(1R)-2-[(1S,3R,4R)-4-(2-hydroxy-ethoxy)-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-109: 33 mg, 19% yield), both as white solids.

Chiral analysis method:
Column: CHIRALPAK IC(IC00CE-OL002)
Column size: 0.46 cm I.D.×25 cm L
Injection: 30.0 ul
Mobile phase: Hexane/EtOH=60/40(V/V)
Flow rate: 1.0 ml/min
Wave length: UV 254 nm
Temperature: 35 oC
HPLC equipment: Shimadzu LC-20AT CP-HPLC-06

I-110: ESI-MS (EI$^+$, m/z):1098.0 [M+Na]$^+$. $^1$H NMR (500 MHz, CDCl$_3$) δ 6.41-6.18 (m, 2H), 6.12 (dd, J=15.0, 10.3 Hz, 1H), 5.93 (dd, J=33.7, 10.6 Hz, 1H), 5.47 (ddd, J=33.0, 20.8, 9.5 Hz, 2H), 5.26 (d, J=5.6 Hz, 1H), 5.13 (dt, J=21.8, 10.8 Hz, 1H), 4.88 (s, 1H), 4.19 (t, J=9.3 Hz, 1H), 3.94-3.52 (m, 19H), 3.49-3.25 (m, 12H), 3.24-3.02 (m, 3H), 2.76 (ddd, J=26.2, 16.6, 10.3 Hz, 3H), 2.57 (dd, J=17.0, 6.3 Hz, 1H), 2.29 (t, J=26.2 Hz, 2H), 2.16-1.85 (m, 6H), 1.74-1.53 (m, 10H), 1.53-1.16 (m, 9H), 1.15-1.01 (m, 8H), 1.01-0.82 (m, 10H), 0.71 (dd, J=23.9, 12.0 Hz, 1H).

I-109: ESI-MS (EI$^+$, m/z):1098.0 [M+Na]$^+$. $^1$H NMR (500 MHz, CDCl$_3$) δ 6.43-5.90 (m, 4H), 5.62-5.02 (m, 5H), 4.24 (d, J=63.6 Hz, 1H), 3.97 (dd, J=21.5, 6.8 Hz, 1H), 3.86-3.50 (m, 18H), 3.45-3.01 (m, 14H), 2.73-2.46 (m, 3H), 2.39-1.94 (m, 6H), 1.91-1.69 (m, 10H), 1.50-1.31 (m, 12H), 1.16-0.85 (m, 18H), 0.69 (d, J=11.7 Hz, 1H).

EXAMPLE 26

Synthesis of (30E,32E,34E,35E,38R,39S,40R,41R,43S,45S,47R,48S,50R,51R,60R)-50,60-dihydroxy-48-R1R)-2-[(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone (I-107): (30E,32E,34E,35E,38R,39S,40R,41R,43S,45S,47S,48S,50R,51R,60R)-50,60-dihydroxy-48-[(1R)-2-[(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone (I-108):

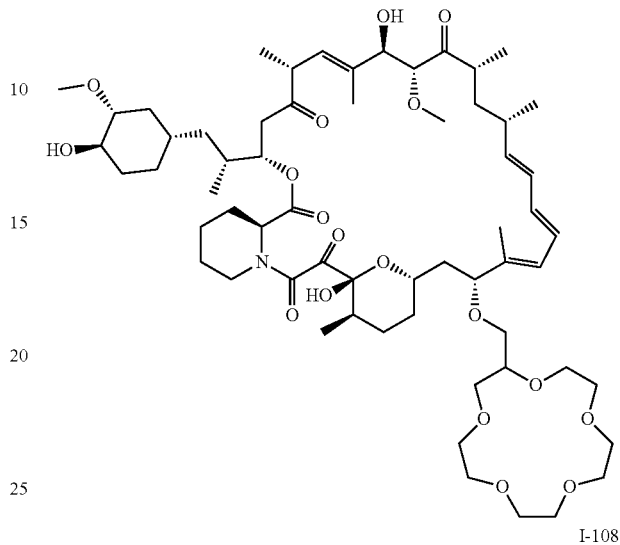

I-107

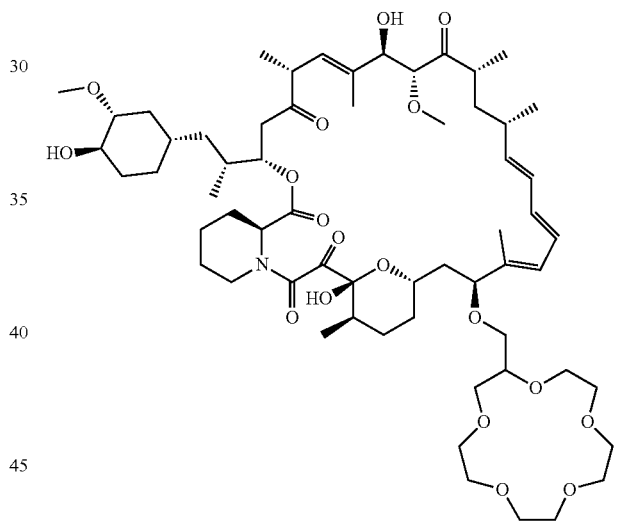

I-108

Synthetic Scheme:

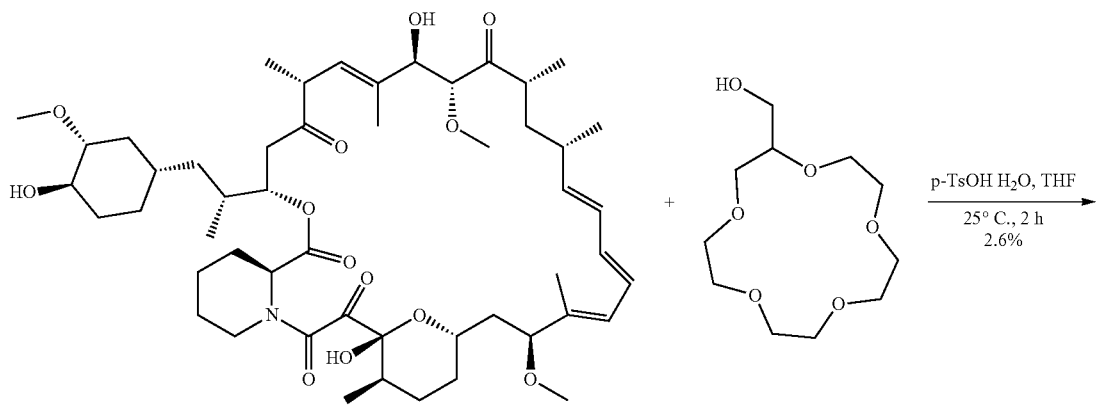

-continued

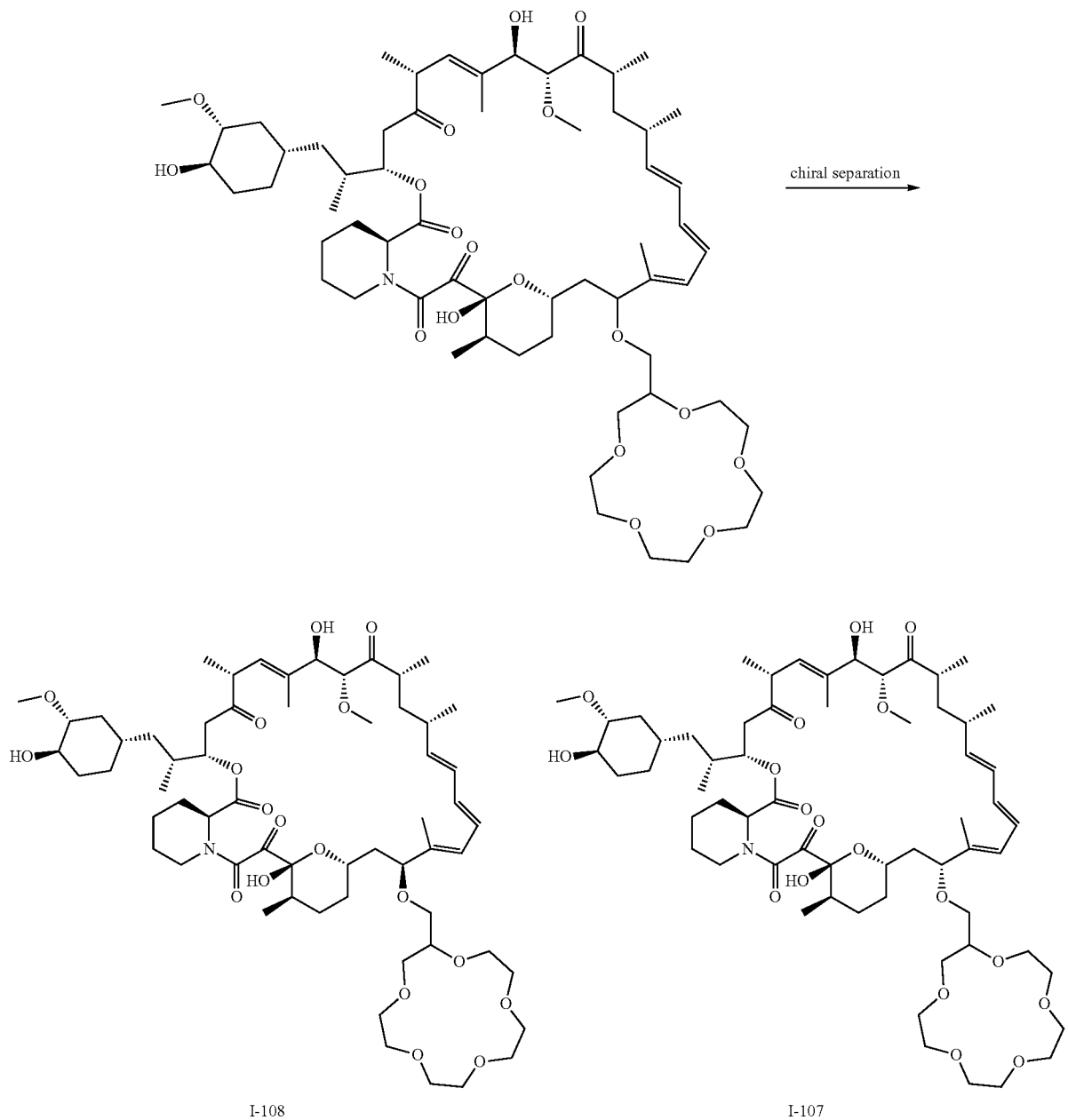

I-108  I-107

Procedures and Characterization:
Step 1: Synthesis of (30E,32E,34E,35E,38R,39S,40R,41R, 43S,45S,48S,50R,51R,60R)-50,60-dihydroxy-48-[(1R)-2-[(1S,3R,4R)-4-hydroxy-3-methoxy-cyclohexyl]-1-methyl-ethyl]-51-methoxy-38,39,40,41,52,53-hexamethyl-4 7-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone:

A solution of rapamycin (2 g, 2.19 mmol), 1,4,7,10,13-pentaoxacyclopentadec-2-ylmethanol (3.83 g, 15.31 mmol) and p-toluenesulfonic acid monohydrate (1.88 g, 10.94 mmol) in THF (10 mL) was stirred at 20° C. for 2 h. The mixture was then poured into ice cold sat.NaHCO₃ (50 mL) and extracted with EtOAc (100 mL×3). The combined organic layers were washed with water and brine, then dried in vacuo and the resulting residue purified via reverse phase chromatography (C18, CH₃CN:H₂O=8:2) to afford (30E, 32E,34E,35E,38R,39S,40R,41R,43S,45S,48S,50R,51R, 60R)-50,60-dihydroxy-48-[(1R)-2-[(1S,3R,4R)-4-hydroxy-3-methoxy-cyclohexyl]-1-methyl-ethyl]-51-methoxy-38,39, 40,41,52,53-hexamethyl-47-(1,4,7,10,13-pentaoxacyclopentadec-2-ylmethoxy)-75,76-dioxa-61-azatricyclohexatriaconta-30,32,34(52),35(53)-tetraene-54, 55,56,57,58-pentone (80 mg, 2.6% yield) as a white solid. ESI-MS (EI⁺, m/z):1154.0 [M+Na]⁺. ¹H NMR (500 MHz, CDCl₃) δ 6.16 (tdt, J=40.0, 33.8, 20.7 Hz, 4H), 5.54-5.03

(m, 4H), 4.21 (t, J=22.5 Hz, 1H), 3.90-3.46 (m, 22H), 3.44-3.04 (m, 12H), 2.74 (dddd, J=27.8, 22.2, 13.7, 4.7 Hz, 5H), 2.37-1.56 (m, 22H), 1.50-1.16 (m, 8H), 1.13-0.81 (m, 18H), 0.67 (dd, J=23.8, 11.9 Hz, 1H).

Step 2: Synthesis of (30E,32E,34E,35E,38R,39S,40R,41R, 43S,45S,47S,48S,50R,51R,60R)-50,60-dihydroxy-48-[(1R)-2-1(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone (I-108) and (30E,32E,34E,35E,38R,39S,40R,41R,43S,45S,47R,48S,50R,51R,60R)-50,60-dihydroxy-48-[(1R)-2-1(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone (I-107):

130 mg of (30E,32E,34E,35E,38R,39S,40R,41R,43S,45S,48S,50R,51R,60R)-50,60-dihydroxy-48-[(1R)-2-[(1S,3R,4R)-4-hydroxy-3-methoxy-cyclohexyl]-1-methyl-ethyl]-51-methoxy-38,39,40,41,52,53 -hexamethyl-47-(1,4,7,10,13-pentaoxacyclopentadec-2-ylmethoxy)-75,76-dioxa-61-azatricyclohexatriaconta-30,32,34(52),35(53)-tetraene-54,55,56,57,58-pentone was purified via prep chiral HPLC and the resulting epimers purified via silica gel chromatography (hexane:DCM:EtOAc:MeOH=3:3:1:0.5) to obtain (30E,32E,34E,35E,38R,39S,40R,41R,43 S,45 S,47S,48S, 50R,51R,60R)-50,60-dihydroxy-48-[(1R)-2-[(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35 (53)-tetraene-54,55,56,57,58-pentone (I-108: 18 mg, 13% yield) and (30E,32E,34E,35E,38R,39S,40R,41R,43S,45S,47R,48S,50R, 51R,60R)-50,60-dihydroxy-48-[(1R)-2-[(1S,3R,4R)-4-hydroxy-3-methoxy-cyclohexyl]-1-methyl-ethyl]-51-methoxy-38,39,40,41,52,53-hexamethyl-47-(1,4,7,10,13-pentaoxacyclopentadec-2-ylmethoxy)-75,76-dioxa-61-azatricyclohexatriaconta-30,32,34(52),35 (53)-tetraene-54, 55,56,57,58-pentone (I-107: 16 mg, 12% yield), both as white solids.

Chiral analysis method:
Column: CHIRALPAK IC(IC00CE-OL002)
Column size: 0.46 cm I.D.×25 cm L
Injection: 100.0 ul
Mobile phase: Hexane/EtOH=60/40(V/V)
Flow rate: 1.0 ml/min
Wave length: UV 254 nm
Temperature: 35 oC
HPLC equipment: Shimadzu LC-20AT CP-HPLC-06

I-108: ESI-MS (EI$^+$, m/z):1153.9 [M+Na]$^+$. $^1$H NMR (500 MHz, CDCl$_3$) δ 6.31 (dt, J=25.1, 14.5 Hz, 2H), 6.17-6.08 (m, 1H), 5.95 (s, 1H), 5.55-5.37 (m, 2H), 5.26 (s, 1H), 5.16 (d, J=4.4 Hz, 1H), 4.71 (d, J=28.0 Hz, 1H), 4.19 (s, 1H), 3.93-3.48 (m, 25H), 3.44-3.26 (m, 12H), 3.20-3.03 (m, 1H), 2.94 (dd, J=16.5, 7.7 Hz, 1H), 2.70 (dd, J=17.9, 12.1 Hz, 3H), 2.56 (d, J=17.0 Hz, 1H), 2.33 (d, J=12.0 Hz, 2H), 2.13-1.84 (m, 5H), 1.81-1.67 (m, 8H), 1.50-1.17 (m, 8H), 1.14-0.81 (m, 20H), 0.67 (dd, J=23.8, 11.9 Hz, 1H).

I-107: ESI-MS (EI$^+$, m/z):1153.9 [M+Na]$^+$. $^1$H NMR (500 MHz, CDCl$_3$) δ 6.40-5.95 (m, 4H), 5.58-5.11 (m, 4H), 4.30-4.12 (m, 1H), 3.88-3.51 (m, 25H), 3.42-3.12 (m, 12H), 2.99-2.53 (m, 5H), 2.50-1.90 (m, 5H), 1.83-1.65 (m, 14H), 1.44-1.30 (m, 8H), 1.12-0.76 (m, 18H), 0.74-0.62 (m, 1H).

EXAMPLE 27

Synthesis of (21E,23E,25E,26E,31R,32S,33R,34R, 36S,38S,41S,42R,43R,52R)-40-[bis(hydroxymethyl) phosphorylmethoxy]-42,52-dihydroxy-41-R1R)-2-[(1S,3R,4R)-4-hydroxy-3-methoxy-cyclohexyl]-1-methyl-ethyl]-43-methoxy-31,32,33,34,44,45-hexamethyl-65,66-dioxa-53-azatricyclohexatriaconta-21,23,25(44),26(45)-tetraene-46,47,48,49,50-pentone (I-106):

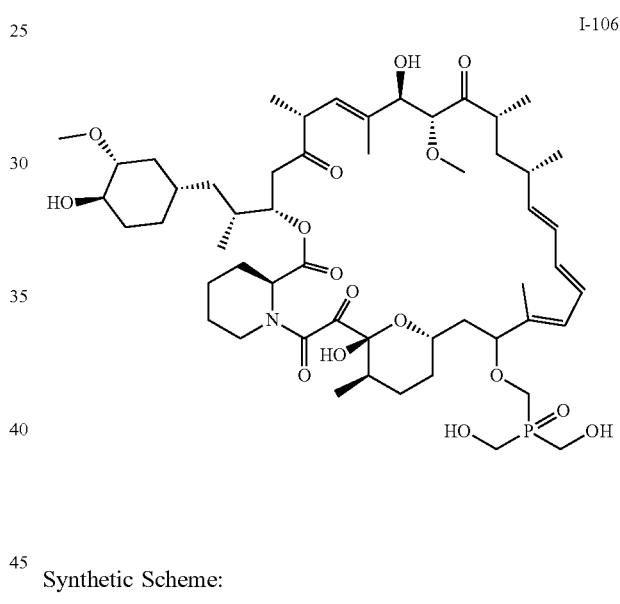

I-106

Synthetic Scheme:

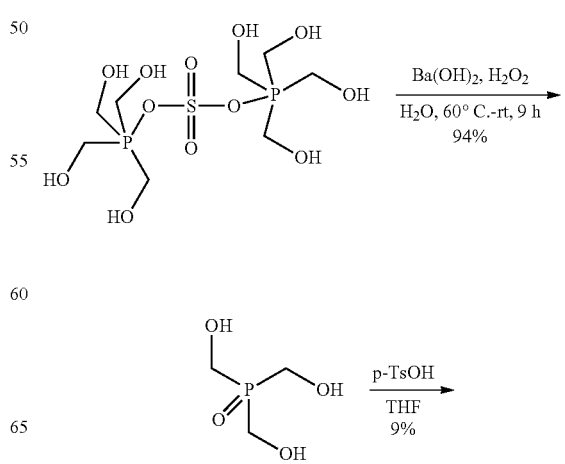

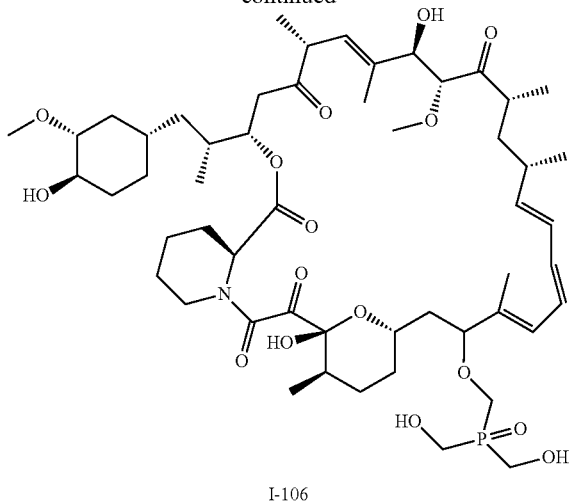

I-106

Procedures and Characterization:
Step 1: Synthesis of Bis(hydroxymethyl)phosphorylmethanol:

Ba(OH)$_2$ (8.43 g, 49.23 mmol) was dissolved in 50 mL of distilled water at 60° C. Tetrakis(hydroxymethyl)phosphonium sulfate (20 g, 49.23 mmol) was added dropwise to the solution which was then stirred at 60° C. for 4 h. After the BaSO$_4$ was removed via centrifugation, hydrogen peroxide (30% solution, 98.45 mmol) was added slowly and the resulting reaction stirred at room temperature for 5 h. The mixture was washed with chloroform then the desired product obtained by removing the water under reduced pressure (6.5 g, 94% yield) as an oil. ESI-MS (EI$^+$, m/z):141.1 [M+H]$^+$. $^1$HNMR (500 MHz, DMSO-d$_6$): δ 5.35 (bs, 3H), 3.97 (s, 6H).

Step 2: Synthesis of (21E,23E,25E,26E,31R,32S,33R,34R,36S,38S,41S,42R,43R,52R)-40-[bis(hydroxymethyl)phosphorylmethoxy]-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-65,66-dioxa-53-azatricyclohexatriaconta-21,23,25(44),26(45)-tetraene-46,47,48,49,50-pentone (I-106):

A mixture of rapamycin (0.5 g, 0.547 mmol), bis(hydroxymethyl)phosphorylmethanol (0.766 g, 5.47 mmol) and 4-methylbenzenesulfonic acid hydrate (0.52 g, 2.73 mmol) in THF (20 mL) was stirred at 25° C. for 4h. EtOAc (100 mL) and water (50 mL) were added. The aqueous layer was extracted with EtOAc (100 mL×2) and the combined organic layers washed with water (2×50 mL) and brine (50 mL) then dried over anhydrous Na$_2$SO$_4$, filtered and concentrated. The resulting residue was purified via reverse phase chromatography (C18, CH$_3$CN:H$_2$O=7:3) to afford (21E,23E,25E,26E,31R,32S,33R,34R,36S,38S,41S,42R,43R,52R)-40-[bis(hydroxymethyl) phosphorylmethoxy]-42,52-dihydroxy-41-[(1R)-2-[(1S,3R,4R)-4-hydroxy-3-methoxy-cyclohexyl]-1-methyl-ethyl]-43-methoxy-31,32,33,34,44,45-hexamethyl-65,66-dioxa-53-azatricyclohexatriaconta-21,23,25(44),26(45)-tetraene-46,47,48,49,50-pentone (I-106: 50 mg, 9% yield) as a white solid. ESI-MS (EI$^+$, m/z):1043.9 [M+Na]$^+$. $^1$H NMR (500 MHz, CDCl$_3$) δ 6.47-5.91 (m, 4H), 5.58-5.08 (m, 4H), 4.51-3.63 (m, 12H), 3.59-3.16 (m, 14H), 2.80 (d, J=138.1 Hz, 6H), 2.38-1.91 (m, 8H), 1.50-0.77 (m, 35H), 0.67 (d, J=9.0 Hz, 1H).

EXAMPLE 28

Synthesis of (22E,24E,26E,27E,35R,36S,37R,38R,40S,42S,44R,45S,46R,47R,56R)-46,56-dihydroxy-45-[(1R)-2-1(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38,48,49-hexamethyl-66,67-dioxa-57-azatricyclohexatriaconta-22,24,26(48),27(49)-tetraene-50,51,52,53,54-pentone (I-104) and (22E,24E,26E,27E,35R,36S,37R,38R,40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38,48,49-hexamethyl-66,67-dioxa-57-azatricyclohexatriaconta-22,24,26(48),27(49)-tetraene-50,51,52,53,54-pentone (I-105):

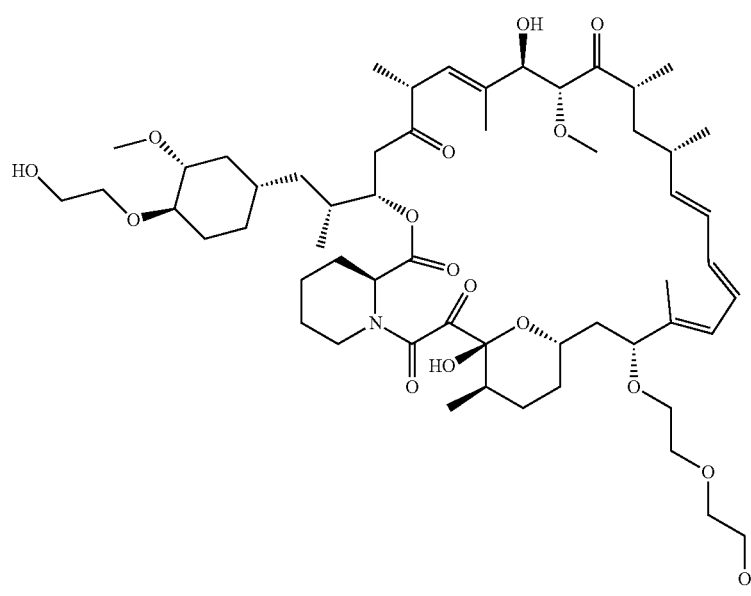

I-104

I-105
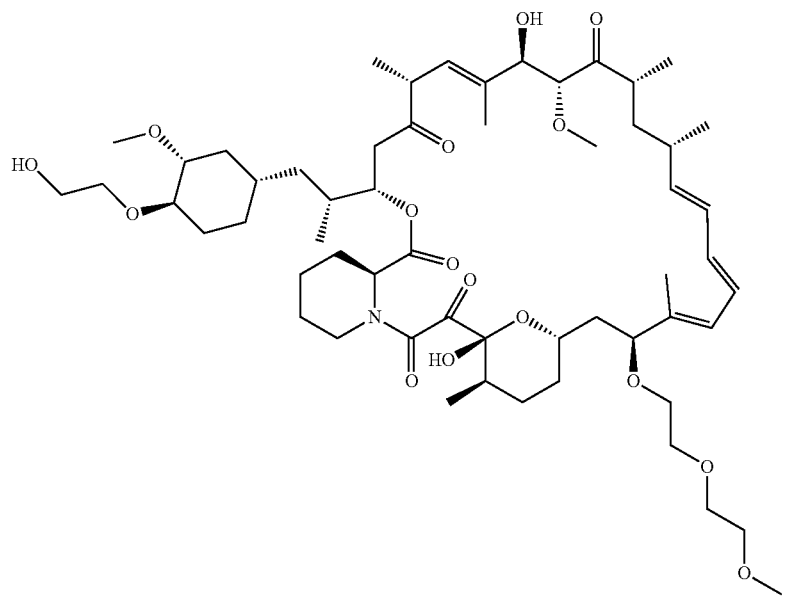
Synthetic Scheme:
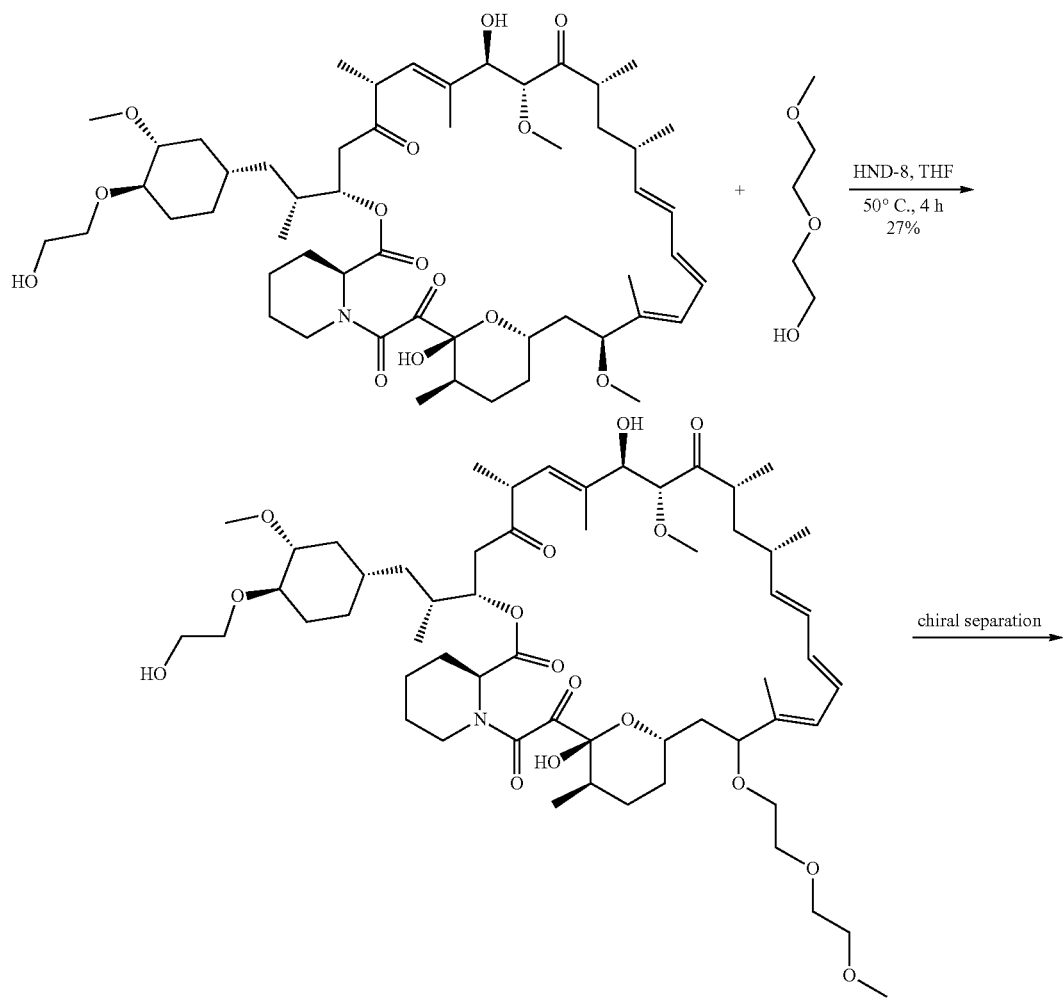

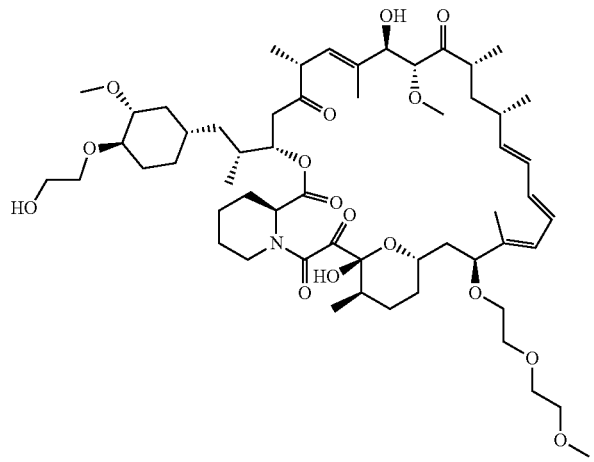

I-105

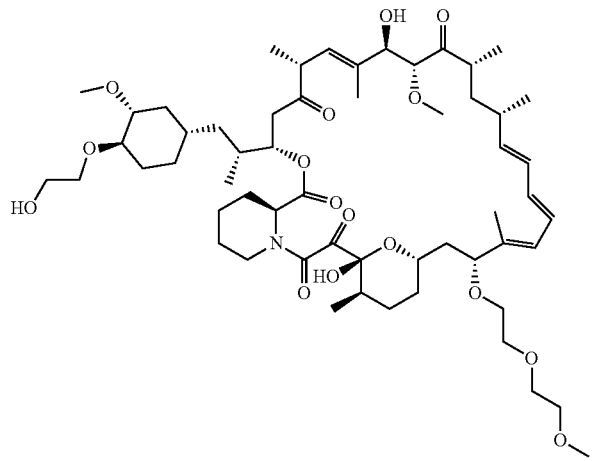

I-104

Procedures and Characterization:
Step 1: Synthesis of (22E,24E,26E,27E,35R,36S,37R,38R, 40S,42S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy) ethoxy]-35,36,37,38,48,49-hexamethyl-66,67-dioxa-57-azatricyclohexatriaconta-22,24,26(48),27(49)-tetraene-50, 51,52,53,54-pentone:

A mixture of everolimus (5 g, 5.22 mmol) and 2-(2-methoxyethoxy)ethanol (15 mL) in THF (80 mL) was degassed with $N_2$ then heated at 50° C. HND-8 (600 mg) was added and the resulting mixture stirred at 50° C. for 4 h under $N_2$ then filtered and diluted with EtOAc. After concentration, the residue was purified by reverse phase chromatography (C18, $CH_3CN$: $H_2O$ from 0%-100% yield) to afford (22E,24E,26E,27E,35R,36S,37R,38R,40S,42S, 45S,46R,47R,56R)-46,56-dihydroxy-45-[(1R)-2-[(1S,3R, 4R)-4-(2-hydroxyethoxy)-3-methoxy-cyclohexyl]-1-methyl-ethyl]-47-methoxy-44-[2-(2-methoxyethoxy) ethoxy]-35,36,37,38,48,49-hexamethyl-66,67-dioxa-57-azatricyclohexatriaconta-22,24,26(48),27(49)-tetraene-50, 51,52,53,54-pentone (1.5 g, 27% yield) as a white solid. ESI-MS (EI$^+$, m/z):1068.4 [M+Na]$^+$. $^1$H NMR (400 MHz, CDCl$_3$) δ 6.40-5.85 (m, 4H), 5.56-5.36 (m, 2H), 5.21 (ddd, J=16.0, 11.7, 5.6 Hz, 2H), 4.21 (dd, J=25.8, 15.5 Hz, 2H), 3.94-3.26 (m, 28H), 3.25-3.02 (m, 4H), 2.76-2.40 (m, 3H), 2.34 (d, J=13.3 Hz, 2H), 2.19-2.06 (m, 2H), 2.01-1.67 (m, 13H), 1.54-1.30 (m, 7H), 1.15-0.81 (m, 18H), 0.72 (dd, J=23.1, 11.7 Hz, 1H).

Step 2: Synthesis of (22E,24E,26E,27E,35R,36S,37R,38R, 40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38,48,49-hexamethyl-66,67-dioxa-57-azatricyclohexatriaconta-22,24,26(48),27(49)-tetraene-50, 51,52,53,54-pentone (I-105) and (22E,24E,26E, 27E,35R,36S,37R,38R,40S,42S,44R,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-4442-(2-methoxyethoxy)ethoxy]-35,36,37,38, 48,49-hexamethyl-66,67-dioxa-57-azatricyclohexatriaconta-22,24,26(48),27(49)-tetraene-50, 51,52,53,54-pentone (I-104):

120 mg of (22E,24E,26E,27E,35R,36S,37R,38R,40S, 42S,45S,46R,47R,56R)-46,56-dihydroxy-45-[(1R)-2-[(1S, 3R,4R)-4-(2-hydroxyethoxy)-3-methoxy-cyclohexyl]-1-methyl-ethyl]-47-methoxy-44-[2-(2-methoxyethoxy) ethoxy]-35,36,37,38,48,49-hexamethyl-66,67-dioxa-57-azatricyclohexatriaconta-22,24,26(48),27(49)-tetraene-50, 51,52,53,54-pentone was purified via prep chiral HPLC to obtain (22E,24E,26E,27E,35R,36S,37R,38R,40S,42S,44S, 45S,46R,47R,56R)-46,56-dihydroxy-45-[(1R)-2-[(1S,3R, 4R)-4-(2-hydroxyethoxy)-3-methoxy-cyclohexyl]-1-methyl-ethyl]-47-methoxy-44-[2-(2-methoxyethoxy) ethoxy]-35,36,37,38,48,49-hexamethyl-66,67-dioxa-57-azatricyclohexatriaconta-22,24,26(48),27(49)-tetraene-50, 51,52,53,54-pentone (I-105: 17 mg, 20% yield) and (22E, 24E,26E,27E,35R,36S,37R,38R,40S,42S,44R,45S,46R, 47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38, 48,49-hexamethyl-66,67-dioxa-57-azatricyclohexatriaconta-22,24,26(48),27(49)-tetraene-50, 51,52,53,54-pentone (I-104: 15 mg, 16% yield), both as white solids.

Chiral separation method:

Column CHIRALPAK IC

Column size: 2.5 cm I.D.×25 cm L, 10 μm

Sample solution: 14 mg/ml in Mobile phase

Injection: 15 ml

Mobile phase: Hexane/EtOH=50/50(V/V)

Flow rate: 60 ml/min

Wave length: UV 254 nm

Temperature: 35° C.

I-105: ESI-MS (EI+, m/z):1068.4 [M+Na]+. ¹H NMR (400 MHz, CDCl₃) δ 6.42-6.19 (m, 2H), 6.13 (dd, J=15.1, 10.0 Hz, 1H), 5.91 (dd, J=33.0, 10.5 Hz, 1H), 5.56-5.38 (m, 2H), 5.27 (d, J=5.0 Hz, 1H), 5.15 (dt, J=15.2, 7.6 Hz, 1H), 4.76 (s, 1H), 4.18 (d, J=5.6 Hz, 1H), 3.93-3.25 (m, 30H), 3.24-3.03 (m, 3H), 2.72 (dd, J=16.7, 5.6 Hz, 2H), 2.57 (dd, J=16.8, 6.5 Hz, 1H), 2.34 (d,J=13.9 Hz, 2H), 2.13-1.84 (m, 6H), 1.82-1.67 (m, 7H), 1.47 (dd, J=24.1, 16.7 Hz, 4H), 1.25 (ddd, J=24.1, 20.2, 10.0 Hz, 7H), 1.14-0.81 (m, 18H), 0.72 (dd, J=23.9, 12.1 Hz, 1H).

I-104: ESI-MS (EI+, m/z):1068.4 [M+Na]+. ¹H NMR (400 MHz, CDCl₃) δ 6.19 (m, 4H), 5.56-5.36 (m, 2H), 5.28-5.07 (m, 2H), 4.83 (d, J=4.9 Hz, 4H), 4.28 (s, 1H), 4.21-4.09 (m, 1H), 4.04-3.51 (m, 15H), 3.46-3.29 (m, 11H), 3.27-2.91 (m, 5H), 2.76-2.42 (m, 3H), 2.31 (d, J=11.3 Hz, 2H), 2.18-1.70 (m, 13H), 1.53-1.19 (m, 8H), 1.16-0.84 (m, 18H), 0.76-0.60 (m, 1H).

EXAMPLE 29

Synthesis of (21E,23E,25E,26E,34R,35S,36R,37R, 39S,41S,43S,44S,45R,46R,55R)-45,55-dihydroxy-43-[2-[2-(2-hydroxyethylsulfonyl)ethylsulfonyl]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49,50,51,52,53-pentone (I-95) and (21E,23E,25E,26E,34R,35S,36R,37R,39R,41S,44S,45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36, 37,47,48-hexamethyl-70,71-dioxa-56-azatricyclohexatriaconta-21,23,25(47),26(48)-tetraene-49,50, 51,52,53-pentone (I-102):

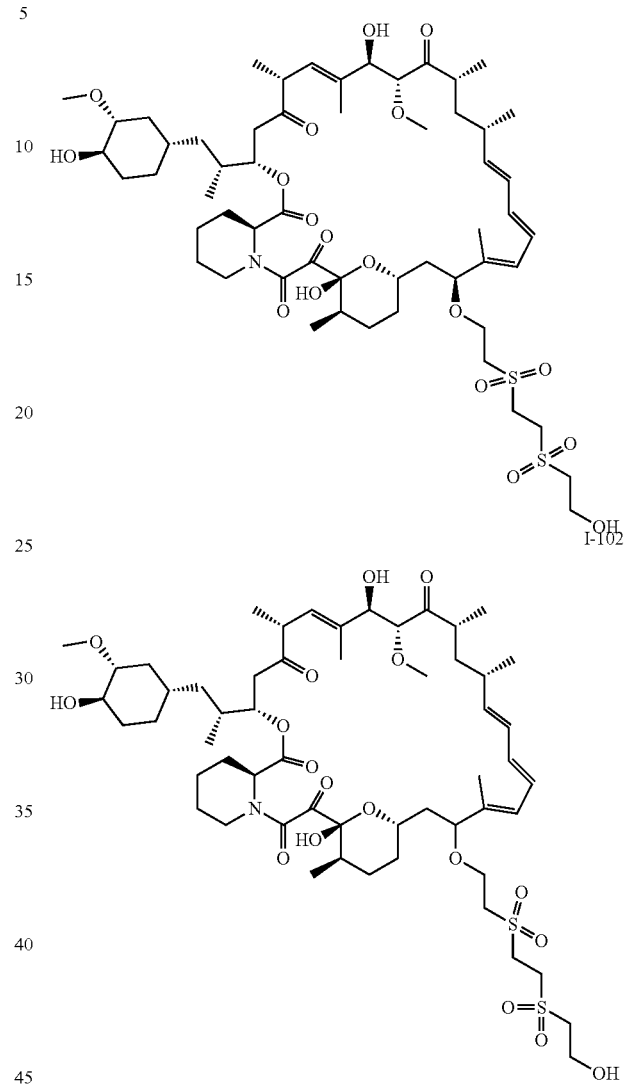

Synthetic Scheme:

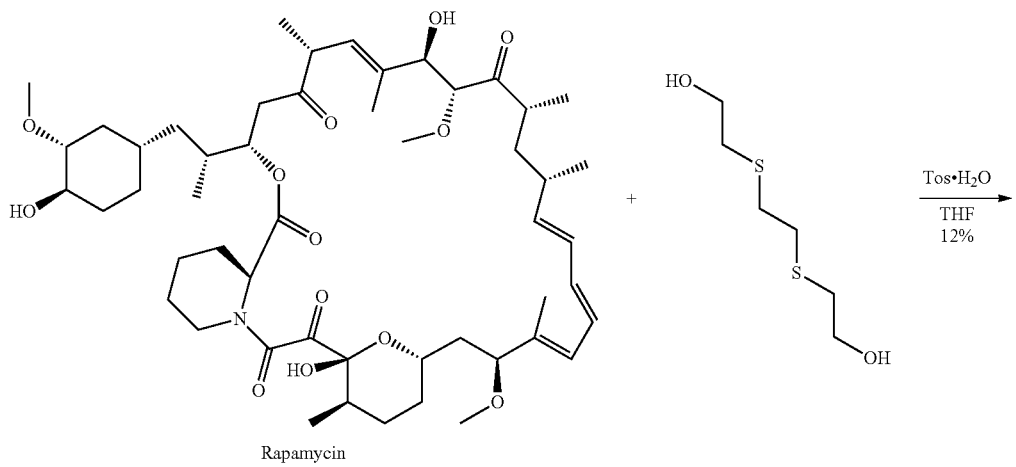

-continued
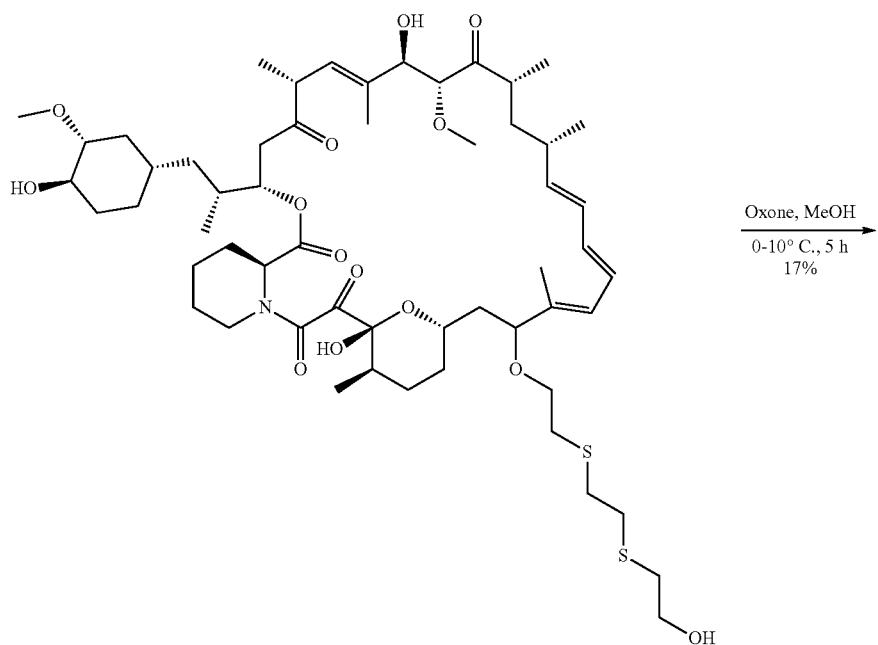
Oxone, MeOH
0-10° C., 5 h
17%
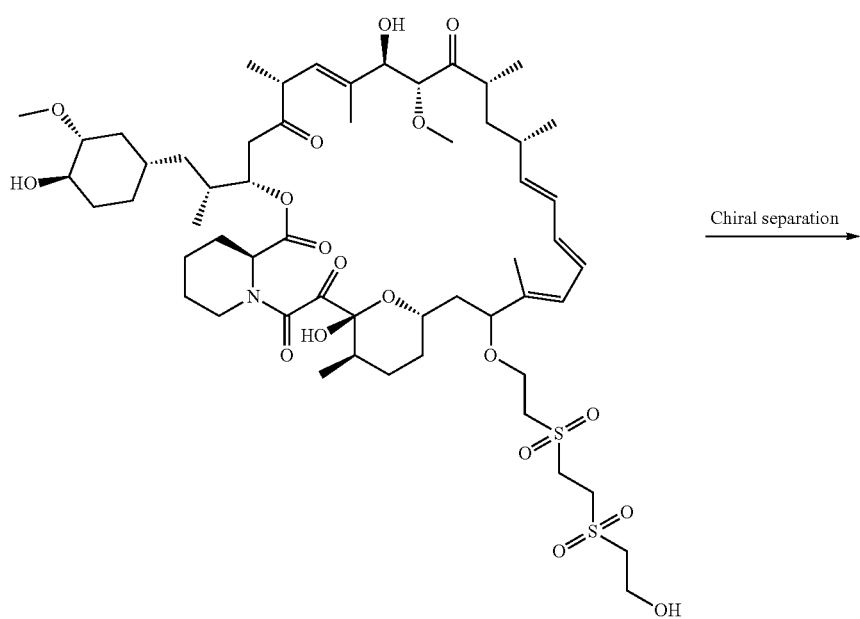
I-102
Chiral separation -continued

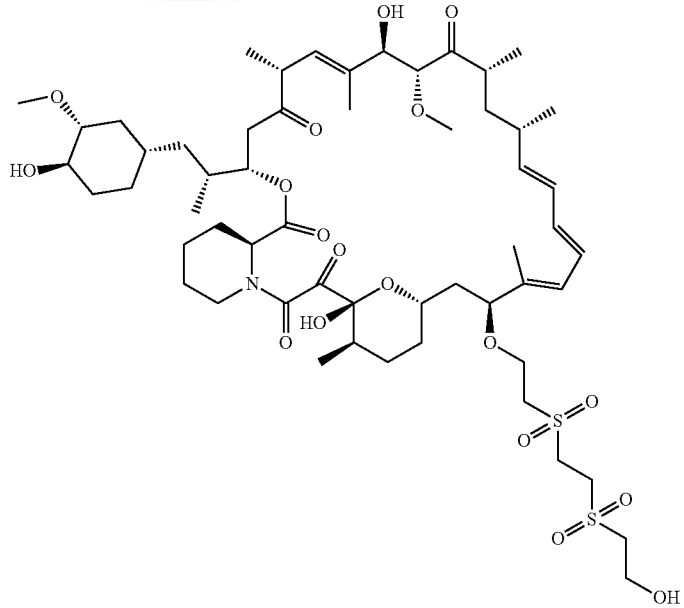

I-95

Procedures and Characterization:

Step 1: Synthesis of (21E,23E,25E,26E,34R,35S,36R,37R, 39R,41S,44S,45R,46R,55S)-45,55-dihydroxy-43-[2-[2-(2-hydroxyethylsulfanyl)ethylsulfanyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone:

To a mixture of rapamycin (1 g, 1.09 mmol), 2-[2-(2-hydroxyethylsulfanyl)ethylsulfanyl]ethanol (2 g, 10.94 mmol) in THF (20 mL) was added 4-methylbenzenesulfonic acid monohydrate (0.62 g, 3.28 mmol) at 15° C. The resulting mixture was stirred at 15° C. for 17 h then diluted with EtOAc (100 mL) and adjusted to pH 9 using saturated aqueous NaHCO$_3$ solution (about 50 mL). The organic layer was then concentrated and the residue purified by reverse phase chromatography (C18, CH$_3$CN:H$_2$O=6:4) to provide (21E,23E,25E,26E,34R,35S,36R,37R,39R,41S,44S,45R, 46R,55S)-45,55-dihydroxy-43-[2-[2-(2-hydroxy ethylsulfanyl)ethylsulfanyl] ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49, 50,51,52,53-pentone (150 mg, 12% yield) as a yellow solid. ESI-MS (EI$^+$, m/z):1086.4 [M+Na]$^+$. $^1$H NMR (500 MHz, CDCl$_3$) δ 6.39-5.95 (m, 4H), 5.54-5.19 (m, 4H), 4.81-4.17 (m, 2H), 3.96-3.73 (m, 4H), 3.59-3.14 (m, 12H), 2.96-2.55 (m, 14H), 2.35-1.87 (m, 6H), 1.81-1.59 (m, 13H), 1.53-1.13 (m, 11H), 1.16-0.84 (m, 18H), 0.71-0.63 (m, 1H).

Step 2: Synthesis of (21E,23E,25E,26E,34R,35S,36R,37R, 39R,41S,44S,45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49,50,51,52,53-pentone (I-102):

To a solution of (21E,23E,25E,26E,34R,35S,36R,37R, 39R,41S,44S,45R,46R,55S)-45,55-dihydroxy-43-[2-[2-(2-hydroxyethylsulfanyl)ethylsulfanyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (170 mg, 0.16 mmol) in methanol (8 mL) was added Oxone (393 mg, 0.64 mmol) at 0° C. The resulting mixture was allowed to warm to 10° C. and stirred for 5 h. The reaction was filtered then purified via reverse phase chromatography (C18, using a 5-60% acetonitrile-water) to afford (21E,23E,25E,26E,34R,35 S,36R,37R, 39R,41S,44S,45R,46R,55S)-45,55-dihydroxy-43-[2-[2-(2-hydroxyethylsulfonyl)ethylsulfonyl]ethoxy]-44-[(1S)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49,50,51,52,53-pentone (I-102, 30 mg, 17% yield) as a white solid. ESI-MS (EI$^+$, m/z):1150.8 [M+Na]$^+$. $^1$H NMR (500 MHz, CDCl$_3$) δ 6.40-5.90 (m, 4H), 5.57-5.08 (m, 5H), 4.14 (s, 4H), 3.68 (tdd, J=37.6, 33.2, 11.6 Hz, 11H), 3.48-3.13 (m, 20H), 2.95 (s, 2H), 2.68 (dd, J=36.4, 30.5 Hz, 5H), 2.37-1.70 (m, 12H), 1.31 (dd, J=78.6, 46.8 Hz, 7H), 1.13-0.81 (m, 18H), 0.67 (d, J=11.9 Hz, 1H).

Step 3: Synthesis of (21E,23E,25E,26E,34R,35S,36R,37R, 39S,41S,43S,44S,45R,46R,55R)-45,55-dihydroxy-43-[2-[2-(2-hydroxyethylsulfonyl)ethylsulfonyl]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26 (48)-tetraene-49,50,51,52,53-pentone (I-95):

90 mg of (21E,23E,25E,26E,34R,35S,36R,37R,39R,41S, 44S,45R,46R,55S)-45,55-dihydroxy-43-[2-[2-(2-hydroxy-ethylsulfonyl)ethylsulfonyl]ethoxy]-44-[(1S)-2-[(1S,3R, 4R)-4-hydroxy-3-methoxy-cyclohexyl]-1-methyl-ethyl]-46-methoxy-34,35,36,37,47,48-hexamethyl-70,71-dioxa-56-azatricyclohexatriaconta-21,23,25(47),26(48)-tetraene-49, 50,51,52,53-pentone was purified via prep chiral HPLC to provide (21E,23E,25E,26E,34R,35S,36R,37R,39S,41S, 43S,44S,45R,46R,55R)-45,55-dihydroxy-43-[2-[2-(2-hydroxyethylsulfonyl)ethylsulfonyl]ethoxy]-44-[(1R)-2-[(1S, 3R,4R)-4-hydroxy-3-methoxy-cyclohexyl]-1-methylethyl]-46-methoxy-34,35,36,37,47,48-hexamethyl-70,71-dioxa-56-azatricyclohexatriaconta-21,23,25(47),26(48)-tetraene-49,50,51,52,53-pentone (I-95: 15 mg, 16% yield) as a white solid.

Chiral analysis method:
Column: CHIRALPAK IC(IC00CD-NA012)
Column size: 0.46 cm I.D.×15 cm L
Injection: 10.0 ul
Mobile phase: EtOH=100%
Flow rate: 0.5 ml/min
Wave length: UV 254 nm
Temperature: 35° C.
HPLC equipment: Shimadzu LC-20AD CP-HPLC-06

I-95: ESI-MS (EI$^+$, m/z):1150.3 [M+Na]$^+$. $^1$HNMR (400 MHz, CDCl$_3$) δ 6.32 (td, J=24.8, 14.8 Hz, 2H), 6.13 (dd, J=14.9, 9.9 Hz, 1H), 5.98 (dd, J=22.1, 10.3 Hz, 1H), 5.56-5.31 (m, 2H), 5.26 (d, J=5.4 Hz, 1H), 5.14 (d, J=4.1 Hz, 1H), 4.86 (s, 1H), 4.16 (dd, J=11.9, 5.5 Hz, 3H), 3.92-3.49 (m, 11H), 3.44-3.17 (m, 15H), 2.93 (dd, J=14.1, 5.5 Hz, 1H), 2.78-2.50 (m, 5H), 2.36-2.17 (m, 2H), 2.01 (ddd, J=21.5, 18.0, 9.0 Hz, 5H), 1.84-1.65 (m, 11H), 1.49-1.16 (m, 12H), 1.14-0.82 (m, 14H), 0.66 (dd, J=23.8, 12.0 Hz, 1H).

EXAMPLE 29

Synthesis of 3-[2,2-bis(2-cyanoethoxymethyl)-3-[[(21E,23E,25E,26E,41R,42S,43R,44R,46S,48S,51S,52R,53R,62R)-52,62-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-67-azatricyclohexatriaconta-21,23,25(54),26(55)-tetraen-50-yl]oxy]propoxy]propanenitrile (I-101):

I-101

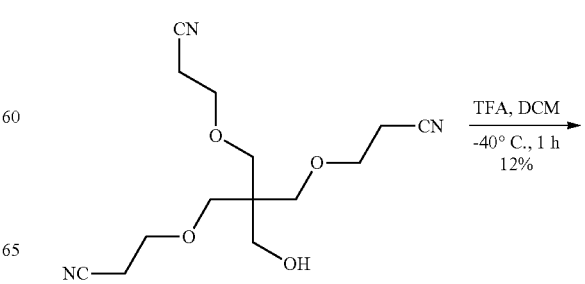

Synthetic Scheme:

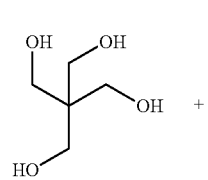

+

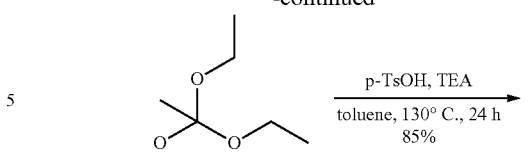

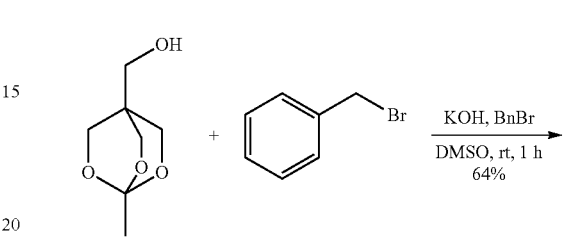

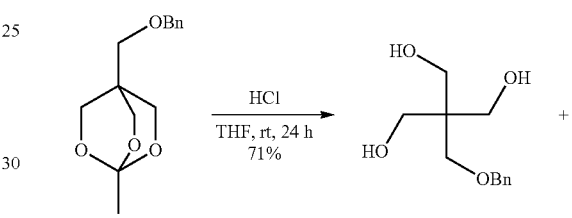

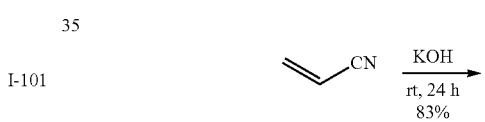

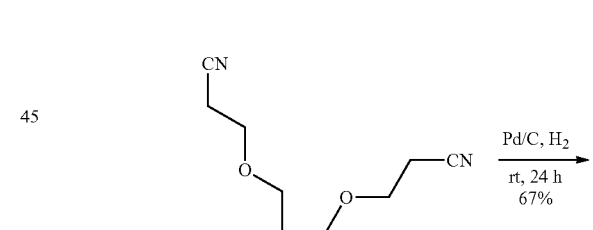

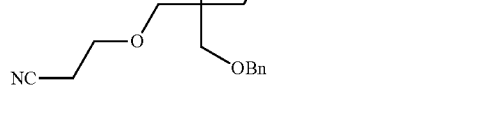

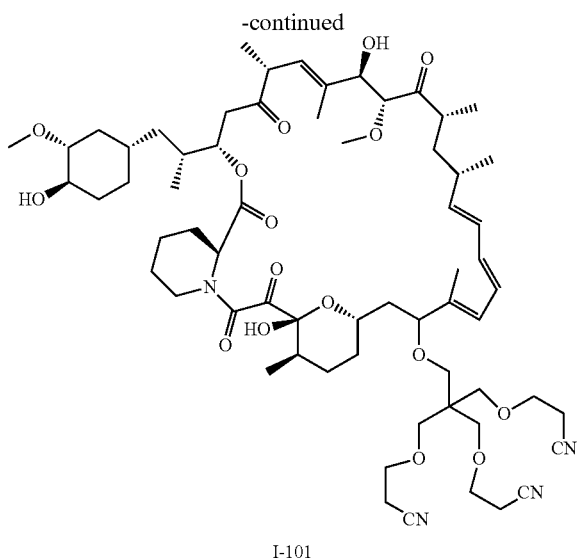

I-101

Procedures and Characterization:
Step 1: Synthesis of (1-methyl-2,6,7-trioxabicyclo[2.2.2]octan-4-yl)methanol:

To a solution of 2,2-bis(hydroxymethyl)propane-1,3-diol (20 g, 146.9 mmol) and 4-methylbenzenesulfonic acid (0.25 g, 1.47 mmol) in toluene (200 mL) was added 1,1,1-triethoxyethane (27 mL, 146.9 mmol) at reflux. The reaction was then stirred at 130° C. until the solution became clear, a few drops of TEA were added and the reaction filtered while still hot. The filtrate was cooled then concentrated to provide (1-methyl-2,6,7-trioxabicyclo[2.2.2]octan-4-yl)methanol (20 g, 85% yield) as colorless crystals. $^1$HNMR (500 MHz, DMSO-$d_6$): δ 4.79 (t, J=5.3 Hz, 1H), 3.85 (s, 6H), 3.22 (d, J=5.3 Hz, 2H), 1.29 (s, 3H).

Step 2: Synthesis of 4-(benzyloxymethyl)-1-methyl-2,6,7-trioxabicyclo[2.2.2]octane:

Solid (1-methyl-2,6,7-trioxabicyclo[2.2.2]octan-4-yl)methanol (1.5 g, 9.37 mmol) was added to a stirred suspension of finely powered KOH (2.47 g, 44 mmol) and BnBr (1.86 g, 10.86 mmol) in DMSO (5 mL). The resulting solution was stirred at rt for 1 h then poured into ice water and extracted with EtOAc, dried, filtered and concentrated. The residue was purified via silical gel chromatography (EtOAc:PE=1:10) to afford 4-(benzyloxymethyl)-1-methyl-2,6,7-trioxabicyclo[2.2.2]octane (1.5 g, 64% yield) as a light yellow solid. ESI-MS (EI$^+$, m/z):251.1 [M+H]$^{+1}$H NMR (500 MHz, CDCl$_3$) δ 7.36-7.25 (m, 5H), 4.45 (s, 2H), 4.01 (s, 6H), 3.19 (s, 2H), 1.45 (s, 3H).

Step 3: Synthesis of 2-(benzyloxymethyl)-2-(hydroxymethyl)propane-1,3-diol:

A solution of 4-(benzyloxymethyl)-1-methyl-2,6,7-trioxabicyclo[2.2.2]octane (2 g, 8 mmol) and hydrogen chloride (2 mL, 2M in water) in THF (20 mL) was stirred at rt overnight then concentrated and purified by reverse phase chromatography (C18, CH$_3$CN:H$_2$O=1:3) to provide 2-(benzyloxymethyl)-2-(hydroxymethyl)propane-1,3-diol (1.3 g, 72% yield) as a thick yellow oil. ESI-MS (EI$^+$, m/z): 227.1 [M+H]$^+$. $^1$H NMR (500 MHz, CDCl$_3$) δ 7.36-7.26 (m, 5H), 4.48 (s, 2H), 3.68 (s, 6H), 3.46 (s, 2H), 3.40 (bs, 3H).

Step 4: Synthesis of 3-[2-(benzyloxymethyl)-3-(2-cyanoethoxy)-2-(2-cyanoethoxymethyl) propoxy]propanenitrile:

To a mixture of 2-(benzyloxymethyl)-2-(hydroxymethyl)propane-1,3-diol (4.9 g, 21.66 mmol) and KOH (98 mg, 1.75 mmol) was slowly added acrylonitrile (11.49 g, 216.56 mmol), ensuring that the internal reaction temperature did not exceed 30° C. The mixture was then stirred overnight at room temperature, neutralized with 1 N HCl aqueous solution and extracted with EtOAc (200 mL). The combined organic layers were washed twice with water, dried over anhydrous Na$_2$SO$_4$, filtered and concentrated to obtain 3-[2-(benzyloxymethyl)-3-(2-cyanoethoxy)-2-(2-cyanoethoxymethyl)propoxy]propanenitrile (7 g, 84% yield) as a yellow solid. ESI-MS (EI$^+$, m/z): 386.3 [M+H]$^+$.

Step 5: Synthesis of 3-[2,2-bis(2-cyanoethoxymethyl)-3-hydroxy-propoxy]propanenitrile:

To a solution of 3-[2-(benzyloxymethyl)-3-(2-cyanoethoxy)-2-(2-cyanoethoxymethyl)propoxy]propanenitrile (5 g, 12.97 mmol) in MeOH (50 mL) was added Pd/C (1.59 g). The mixture was stirred at room temperature overnight under a balloon of hydrogen then filtered through a pad of celite and washed with ethanol. The resulting solution was concentrated to provide 3-[2,2-bis(2-cyanoethoxymethyl)-3-hydroxy-propoxy]propanenitrile (2.6 g, 68% yield) as a colorless oil. ESI-MS (EI$^+$, m/z): 296.2 [M+H]$^+$.

Step 6: Synthesis of 3-[2,2-bis(2-cyanoethoxymethyl)-3-[[(21E,23E,25E,26E,41R,42S,43R,44R,46S,48S,51S,52R,53R,62R)-52,62-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-67-azatricyclohexatriaconta-21,23,25(54),26(55)-tetraen-50-yl]oxy]propoxy]propanenitrile (I-101):

To a solution of rapamycin (0.5 g, 0.547 mmol) in DCM (30 mL) was added 2,2,2-trifluoroacetic acid (2.4 mL) at −40° C. The reaction was stirred at −40° C. for 10 min, then 3-[2,2-bis(2-cyanoethoxymethyl)-3-hydroxy-propoxy]propanenitrile (0.48 g, 1.64 mmol) was added. After stirring for a further 1h, the reaction was diluted with DCM (3 ml) and poured into a cold NaHCO$_3$ aqueous solution. The organic layer was washed with water and brine, dried over Na$_2$SO$_4$, filtered and concentrated. The residue was purified by reverse phase chromatography (C18, CH$_3$CN:H$_2$O=8:2) to provide 3-[2,2-bis(2-cyanoethoxymethyl)-3-[[(21E,23E,25E,26E,41R,42S,43R,44R,46S,48S,51S,52R,53R,62R)-52,62-dihydroxy-51-[(1R)-2-[(1S,3R,4R)-4-hydroxy-3-methoxy-cyclohexyl]-1-methyl-ethyl]-53-methoxy-41,42,43,44,54,55-hexamethyl-56,57,58,59,60-pentaoxo-76,77-dioxa-67-azatricyclohexatriaconta-21,23,25(54),26(55)-tetraen-50-yl]oxy]propoxy]propanenitrile (I-101: 80 mg, 12% yield) as a white solid. ESI-MS (EI$^+$, m/z): 1198.8 [M+Na]$^+$. $^1$H NMR (500 MHz, CDCl$_3$) δ 6.42-5.87 (m, 4H), 5.35 (ddd, J=120.9, 41.2, 32.5 Hz, 4H), 4.24 (dd, J=29.5, 16.4 Hz, 2H), 3.98 (d, J=4.2 Hz, 1H), 3.87-3.60 (m, 7H), 3.56-3.01 (m, 18H), 2.88 (d, J=59.1 Hz, 2H), 2.74-2.42 (m, 9H), 2.34 (s, 2H), 2.23-1.84 (m, 5H), 1.82-1.65 (m, 13H), 1.53-1.22 (m, 10H), 1.16-0.84 (m, 18H), 0.72-0.61 (m, 1H).

EXAMPLE 30

Synthesis of (21E,23E,25E,26E,37R,38S,39R,40R, 42S,44S,47S,48R,49R,59R)-48,59-dihydroxy-46-[2-[3-(2-hydroxyethoxy)-2-(2-hydroxyethoxymethyl) propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26 (51)-tetraene-52,53,54,55,56-pentone (I-100) and (21E,23E,25E,26E,37R,38S,39R,40R,42S,44S,46R, 47S,48R,49R,59R)-48,59-dihydroxy-46-[2-[3-(2-hydroxyethoxy)-2-(2-hydroxyethoxymethyl) propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26 (51)-tetraene-52,53,54,55,56-pentone (I-64) and (21E,23E,25E,26E,37R,38S,39R,40R,42S,44S,46S, 47S,48R,49R,59R)-48,59-dihydroxy-46-[2-[3-(2-hydroxyethoxy)-2-(2-hydroxyethoxymethyl) propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26 (51)-tetraene-52,53,54,55,56-pentone (I-65):

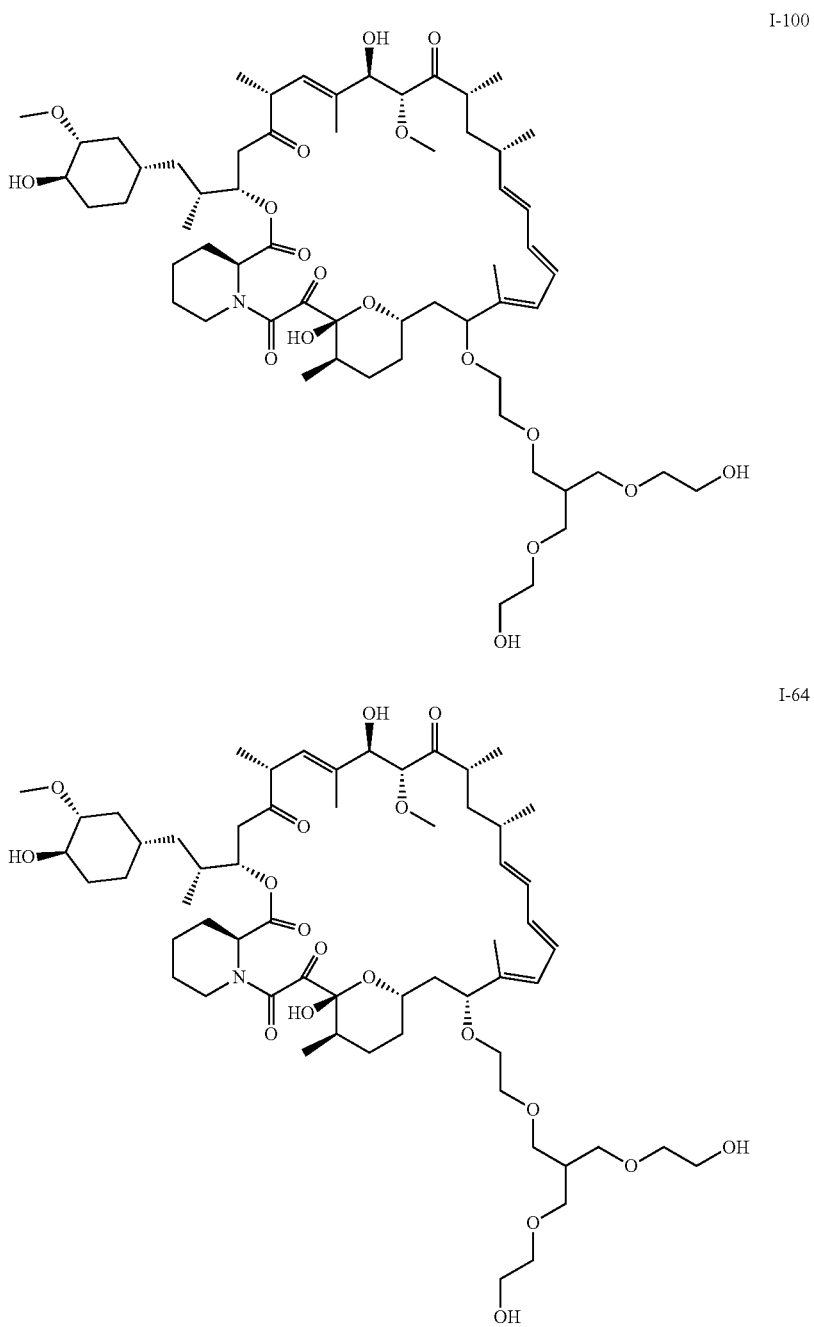 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)C(OCCOCC(COCCO)COCCO)C[C@@H]3CC[C@@H](C)[C@@](O)(O3)C(=O)C(=O)N3CCCC[C@H]3C(=O)O2)CC[C@H]1O ; CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@H](OCCOCC(COCCO)COCCO)C[C@@H]3CC[C@@H](C)[C@@](O)(O3)C(=O)C(=O)N3CCCC[C@H]3C(=O)O2)CC[C@H]1O]

-continued
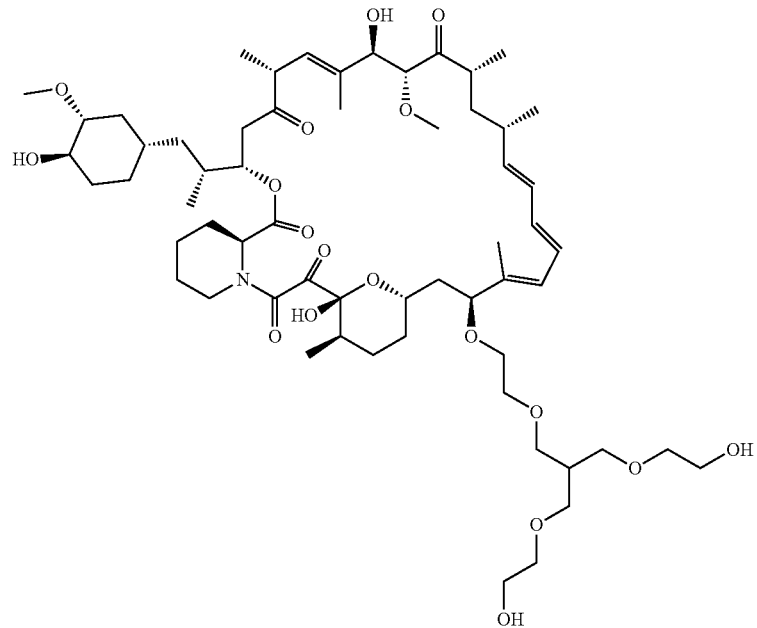
I-65
Synthetic Scheme:
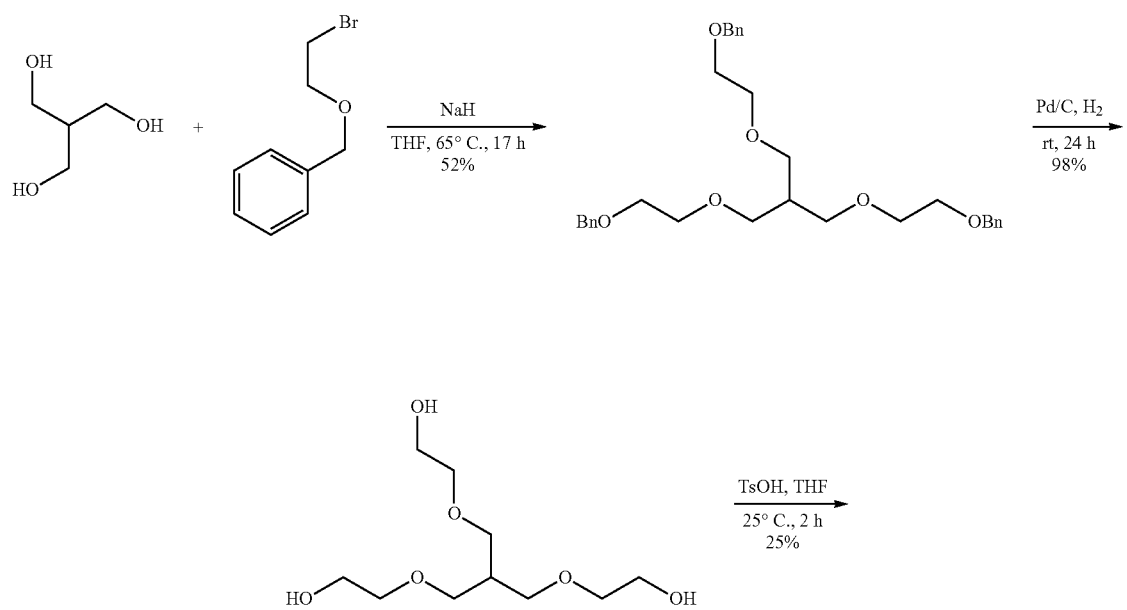

-continued
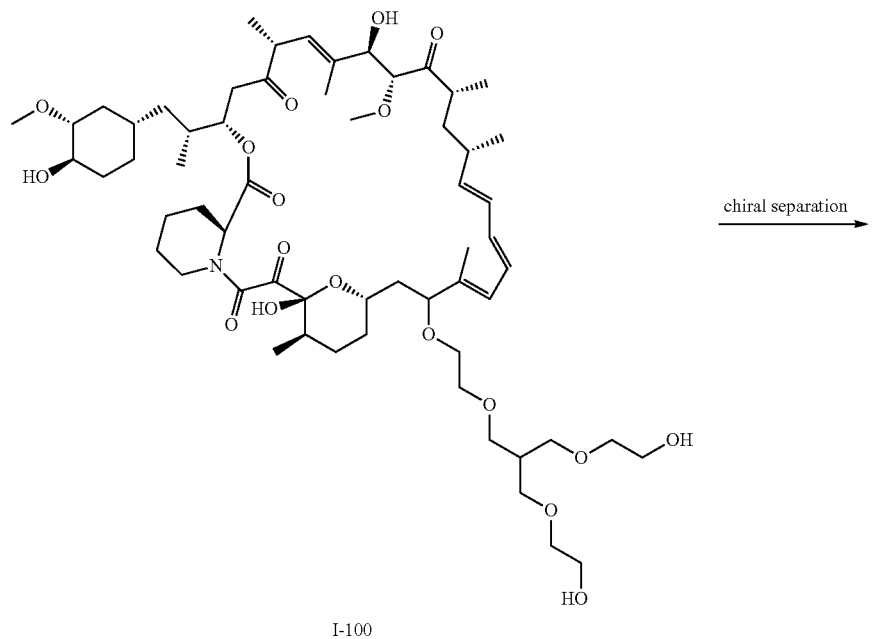
I-100
chiral separation →
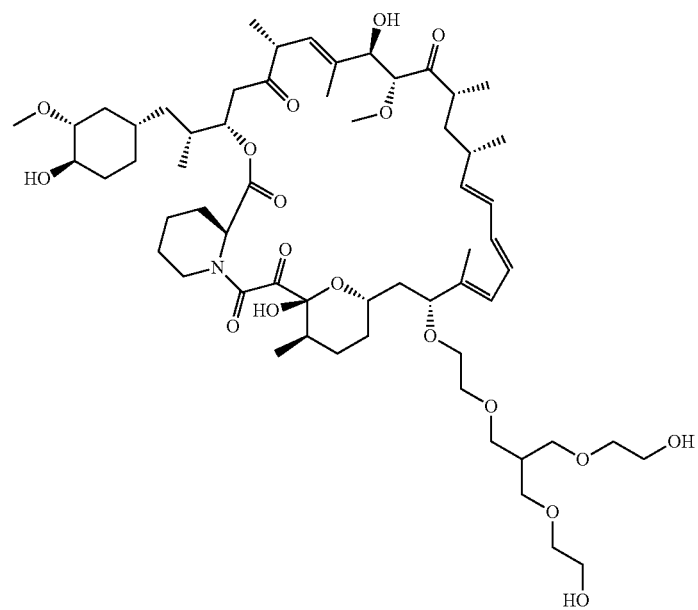
+
I-64

-continued

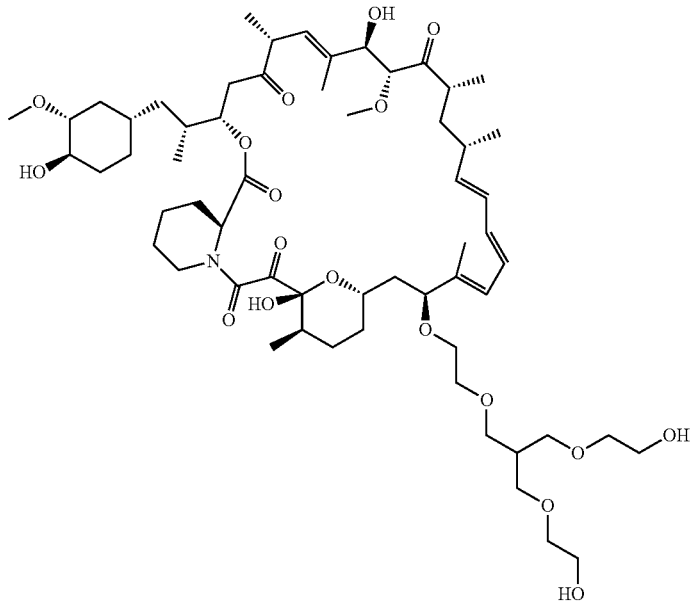

I-65

Procedures and Characterization:

Step 1: Synthesis of 7-[2-(benzyloxy)ethoxy)methyl)-1,13-diphenyl-2,5,9,12-tetraoxatridecane:

To a solution of 2-(hydroxymethyl)propane-1,3-diol (2 g, 18.85 mmol) in THF (30 mL) at 0° C. was added sodium hydride (9.05 g, 376.93 mmol). and the reaction heated to 50° C. for 1 h then cooled to rt. 2-bromoethoxymethylbenzene (40.54 g, 188.47 mmol) was then added and the mixture heated to 65° C. for 17 h. The reaction was quenched with ice-water (50 mL), then this was extracted with EtOAc (50 mL× 2). The combined organicc layers were washed with brine (100 mL), dried, filtered, concentrated and then purified by silica gel chromatography (PE:E-tOAc=20:1) to afford 2-[3-(2-benzyloxyethoxy)-2-(2-benzyloxyethoxymethyl)propoxy]ethoxymethylbenzene (5 g, 52% yield) as a colorless liquid. ESI-MS (EI+, m/z): 509.0 [M+H]+.

Step 2: Synthesis of 2,2'-(2-[2-hydroxyethoxy)methyl)propane-1,3-diyl)bis(oxy)diethanol:

To a solution of 2-[3-(2-benzyloxyethoxy)-2-(2-benzyloxyethoxymethyl)propoxy]ethoxymethylbenzene (2 g, 3.93 mmol) in MeOH (20 mL) was added Pd/C (2.41 g). The mixture was stirred at room temperature overnight under a balloon of hydrogen. The reaction mixture was then filtered through a pad of celite and which was then washed with ethanol. The resulting solution was concentrated under reduced pressure to provide 2,2'-((2-((2-hydroxyethoxy)methyl)propane-1,3-diyl)bis(oxy))bis(ethan-1-ol) (0.92 g, 98% yield). $^1$HNMR (500 MHz, CDCl$_3$) δ 3.65 (dd, J=5.7, 3.4 Hz, 6H), 3.53-3.48 (m, 12H), 2.22-2.14 (m, 1H).

Step 3: Synthesis of (21E,23E,25E,26E,37R,38S,39R,40R,42S,44S,47S,48R,49R,59R)-48,59-dihydroxy-46-[2-[3-(2-hydroxyethoxy)-2-(2-hydroxyethoxymethyl)propoxy]ethoxy]-47-[(1R)-2-[(1S,3R,4R)-4-hydroxy-3-methoxy-cyclohexyl]-1-methyl-ethyl]-49-methoxy-37,38,39,40,50, 51-hexamethyl-71,72-dioxa-60-azatricyclohexatriaconta-21,23,25(50),26(51)-tetraene-52,53,54,55,56-pentone (I-100):

To a solution of rapamycin (0.5 g, 0.547 mmol) and 4-methylbenzenesulfonic acid (0.47 g, 2.73 mmol) in THF (10 mL) was added 2-[3-(2-hydroxyethoxy)-2-(2-hydroxyethoxymethyl)propoxy]ethanol (1.3 g, 5.47 mmol). The mixture was stirred at 25° C. for 2 h then poured into ice-cold NaHCO$_3$ aqueous solution and extracted with EtOAc. The organic layer was dried, filtered and concentrated. The residue was purified by reverse phase chromatography (C18, CH$_3$CN: H$_2$O: 7:3) followed by silica gel chromatography (DCM:MeOH=15:1) to provide (21E,23E, 25E,26E,37R,38S,39R,40R,42S,44S,47S,48R,49R,59R)-48,59-dihydroxy-46-[2-[3-(2-hydroxyethoxy)-2-(2-hydroxyethoxymethyl)propoxy]ethoxy]-47-[(1R)-2-[(1S,3R, 4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26(51)-tetraene-52, 53,54,55,56-pentone (I-100, 150 mg, 25% yield) as a white solid. ESI-MS (EI+, m/z): 1142.0 [M+Na]+. $^1$H NMR (500 MHz, CDCl$_3$) δ 6.21 (dddd, J=32.0, 27.8, 21.3, 10.2 Hz, 3H), 6.05-5.84 (m, 1H), 5.57-5.36 (m, 2H), 5.29-4.97 (m, 2H), 4.83 (s, 1H), 4.20 (dd, J=36.3, 30.2 Hz, 1H), 4.01-3.66 (m, 6H), 3.62-3.22 (m, 29H), 3.00-2.43 (m, 9H), 2.36-1.85 (m, 9H), 1.77-1.51 (m, 6H), 1.52-1.17 (m, 9H), 1.16-0.79 (m, 18H), 0.65 (dt, J=21.9, 11.0 Hz, 1H).

Step 4: Synthesis of (21E,23E,25E,26E,37R,38S,39R,40R, 42S,44S,46S,47S,48R,49R,59R)-48,59-dihydroxy-46-[2-[3-(2-hydroxyethoxy)-2-(2-hydroxyethoxymethy0propoxy] ethoxy]-47-[(1R)-2-[(1S,3R,4R)-4-hydroxy-3-methoxy-cyclohexyl]-1-methyl-ethyl]-49-methoxy-37,38,39,40,50, 51-hexamethyl-71,72-dioxa-60-azatricyclohexatriaconta-21,23,25(50),26(51)-tetraene-52,53,54,55,56-pentone (I-65) and (21E,23E,25E,26E,37R,38S,39R,40R,42S,44S,46R, 47S,48R,49R,59R)-48,59-dihydroxy-46-[2-[3-(2-hydroxy-ethoxy)-2-(2-hydroxyethoxymethyl)propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26(51)-tetraene-52,53,54,55,56-pentone (I-64):

140 mg of (21E,23E,25E,26E,37R,38S,39R,40R,42S,44S,47S,48R,49R,59R)-48,59-dihydroxy-46-[2-[3-(2-hydroxyethoxy)-2-(2-hydroxyethoxymethyl)propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26(51)-tetraene-52,53,54,55,56-pentone was purified via prep chiral HPLC and the resulting epimers purified via silica gel chromatography (hexane:DCM:EtOAc:MeOH=3:3:1:1) to obtain (21E,23E,25E,26E,37R,38S,39R,40R,42S,44S,46S,47S,48R,49R,59R)-48,59-dihydroxy-46-[2-[3-(2-hydroxyethoxy)-2-(2-hydroxyethoxymethyl)propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26(51)-tetraene-52,53,54,55,56-pentone (I-65: 35.2 mg, 25% yield) and (21E,23E,25E,26E,37R,38S,39R,40R,42S,44S,46R,47S,48R,49R,59R)-48,59-dihydroxy-46-[2-[3-(2-hydroxy-ethoxy)-2-(2-hydroxyethoxymethyl)propoxy]ethoxy]-47-[(1R)-2-[(1S,3R,4R)-4-hydroxy-3-methoxy-cyclohexyl]-1-methyl-ethyl]-49-methoxy-37,38,39,40,50,51-hexamethyl-71,72-dioxa-60-azatricyclohexatriaconta-21,23,25(50),26(51)-tetraene-52,53,54,55,56-pentone (I-64:16 mg, 11% yield), both as white solids.

Chiral separation method:
Column: CHIRALPAK IC
Column size: 2.5 cm I.D.×25 cm L
Solution concentration: 1.4 mg/ml
Injection: 7 ml
Mobile phase: Hexane/EtOH=60/40(V/V)
Flow rate: 30 ml/min
Wave length: UV 254 nm
Temperature: 35° C.

I-65: ESI-MS (EI$^+$, m/z): 1142.4 [M+Na]$^+$. $^1$H NMR (400 MHz, CDCl$_3$) δ 6.42-6.18 (m, 2H), 6.13 (dd, J=14.9, 10.1 Hz, 1H), 5.93 (dd, J=23.9, 11.0 Hz, 1H), 5.54-4.89 (m, 6H), 4.80 (s, 1H), 4.18 (d, J=6.0 Hz, 1H), 3.90 (s, 1H), 3.80-3.66 (m, 5H), 3.63-3.48 (m, 11H), 3.47-3.21 (m, 11H), 2.99-2.47 (m, 6H), 2.38-2.15 (m, 3H), 2.14-1.85 (m, 5H), 1.84-1.64 (m, 12H), 1.46 (dd, J=28.7, 18.7 Hz, 5H), 1.35-1.15 (m, 7H), 1.15-0.81 (m, 18H), 0.66 (dd, J=23.7, 11.8 Hz, 1H).

I-64: ESI-MS (EI$^+$, m/z): 1142.4 [M+Na]$^+$. $^1$H NMR (400 MHz, CDCl$_3$) δ 6.34-5.86 (m, 4H), 5.41 (ddd, J=54.0, 26.4, 18.2 Hz, 2H), 5.16 (dd, J=9.6, 5.0 Hz, 2H), 4.88 (s, 1H), 4.20 (d, J=11.0 Hz, 1H), 4.14-4.02 (m, 1H), 3.93 (d, J=3.9 Hz, 1H), 3.87-3.72 (m, 1H), 3.64 (d, J=4.4 Hz, 4H), 3.57-3.36 (m, 14H), 3.36-3.22 (m, 8H), 3.21-3.11 (m, 1H), 2.92-2.33 (m, 8H), 2.32-2.11 (m, 3H), 2.11-1.85 (m, 5H), 1.82-1.63 (m, 11H), 1.48-1.25 (m, 9H), 1.09-0.72 (m, 18H), 0.66-0.50 (m, 1H).

EXAMPLE 31

Synthesis of (21E,23E,25E,26E,48R,49S,50R,51R,53S,55S,58S,59R,60R,69R)-59,69-dihydroxy-57-[2-[2-[2-[2-[2-[2-[2-[2-(2-hydroxyethoxy)ethoxy]ethoxy]ethoxy]ethoxy]ethoxy]ethoxy]ethoxy]ethoxy]-58-[(1R)-2-[(1S,3R,4R)-4-hydroxy-3-methoxy-cyclohexyl]-1-methyl-ethyl]-60-methoxy-48,49,50,51,61,62-hexamethyl-80,81-dioxa-70-azatricyclohexatriaconta-21,23,25(61),26(62)-tetraene-63,64,65,66,67-pentone (I-98):

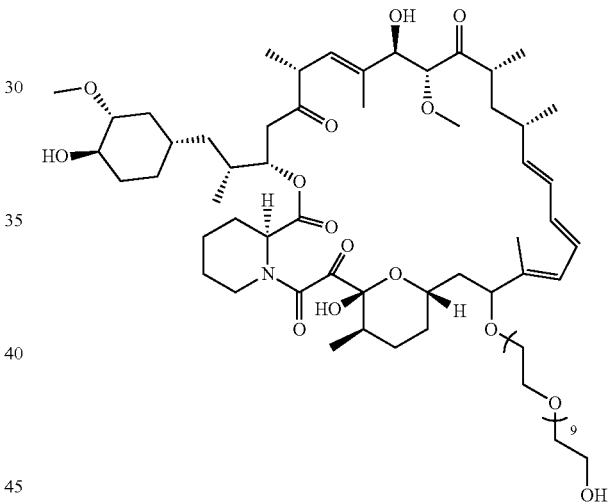

Synthetic Scheme:

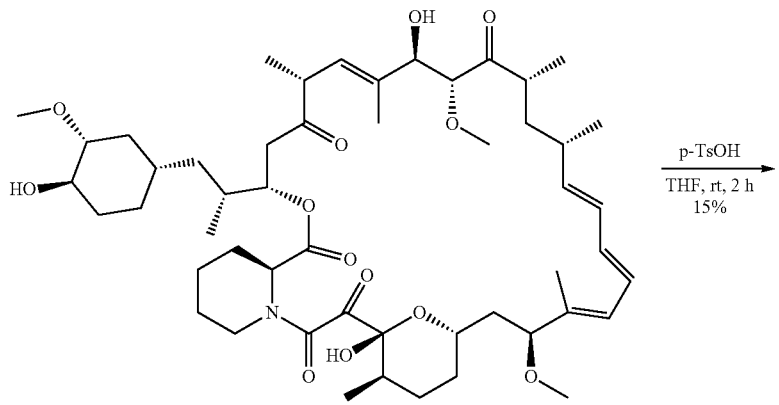

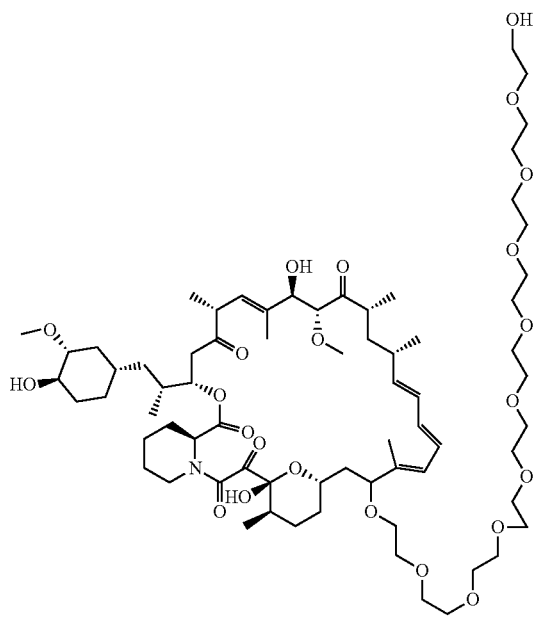

I-98

Procedures and Characterization:
Step 1: Synthesis of (21E,23E,25E,26E,48R,49S,50R,51R,53S,55S,58S,59R,60R,69R)-59,69-dihydroxy-57-[2-[2-[2-[2-[2-[2-[2-[2-[2-(2-hydroxyethoxy)ethoxy]ethoxy]ethoxy]ethoxy]ethoxy]ethoxy]ethoxy]ethoxy]-58-[(1R)-2-[(1S,3R,4R)-4-hydroxy-3-methoxy-cyclohexyl]-1-methyl-ethyl]-60-methoxy-48,49,50,51,61,62-hexamethyl-80,81-dioxa-70-azatricyclohexatriaconta-21,23,25(61),26(62)-tetraene-63,64,65,66,67-pentone (I-98):

To a solution of rapamycin (0.5 g, 0.547 mmol) and 4-methylbenzenesulfonic acid (0.47 g, 2.73 mmol) in THF (15 mL) was added 2-[2-[2-[2-[2-[2-[2-[2-[2-(2-hydroxyethoxy)ethoxy]ethoxy]ethoxy]ethoxy]ethoxy]ethoxy]ethoxy]ethoxy]ethanol (2.51 g, 5.47 mmol) and the mixture stirred at 25° C. for 2 h. The reaction was then poured into a cold aqueous $NaHCO_3$ solution which was then extracted with EtOAc. The organic layer was then dried over $Na_2SO_4$, filtered and concentrated. The residue was purified by reverse phase chromatography ($CH_3CN$:pure water=7:3) to provide (21E,23E,25E,26E,48R,49S,50R, 51R,53S,55S, 58S,59R,60R,69R)-59,69-dihydroxy-57-[2-[2-[2-[2-[2-[2-[2-[2-[2-(2-hydroxyethoxy)ethoxy]ethoxy]ethoxy]ethoxy] ethoxy]ethoxy]ethoxy]ethoxy]-58-[(1R)-2-[(1S,3R, 4R)-4-hydroxy-3-methoxy-cyclohexyl]-1-methyl-ethyl]-60-methoxy-48,49,50,51,61,62-hexamethyl-80,81-dioxa-70-azatricyclohexatriaconta-21,23,25(61),26(62)-tetraene-63, 64,65,66,67-pentone (I-98: 115 mg, 15% yield) as a thick oil. ESI-MS ($EI^+$, m/z): 1362.9 $[M+Na]^+$. $^1H$ NMR (500 MHz, $CDCl_3$) δ 6.40-5.83 (m, 4H), 5.55-5.35 (m, 2H), 5.32-5.03 (m, 2H), 4.31-4.10 (m, 1H), 3.93 (dd, J=70.7, 6.3 Hz, 1H), 3.78-3.15 (m, 53H), 2.97-2.41 (m, 5H), 2.32 (s, 2H), 2.15-1.55 (m, 18H), 1.52-1.16 (m, 10H), 1.14-0.81 (m, 18H), 0.73-0.58 (m, 1H).

EXAMPLE 32

Synthesis of 2-[[(22E,24E,26E,27E,33R,34S,35R, 36R,38S,40S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-81) and 2-[[(22E,24E,26E, 27E,33R,34S,35R,36R,38S,40S,42R,43S,44R,45R, 55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-74) and 2-[[(22E,24E,26E,27E,33R,34S,35R,36R,38S, 40S,42S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-75):

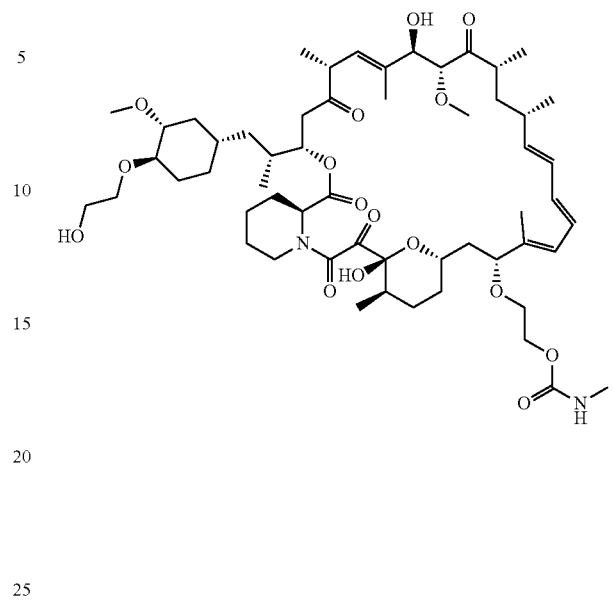

I-74

I-81

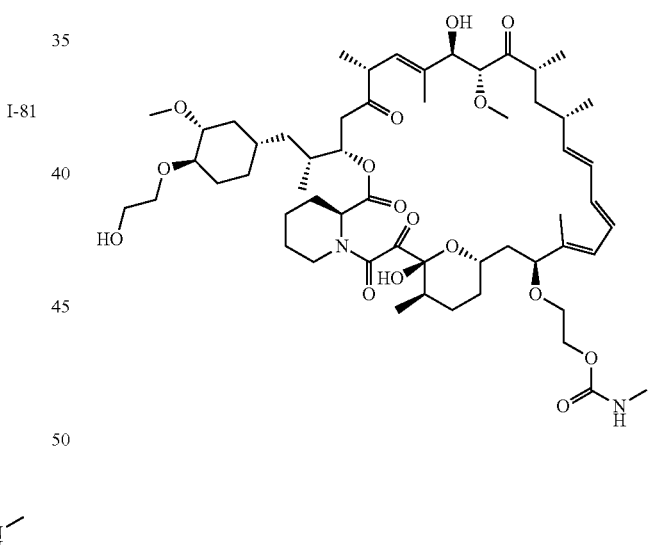

I-75

Synthetic Scheme:

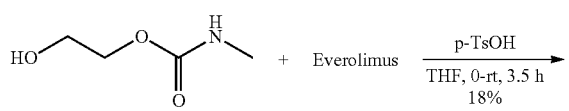

-continued
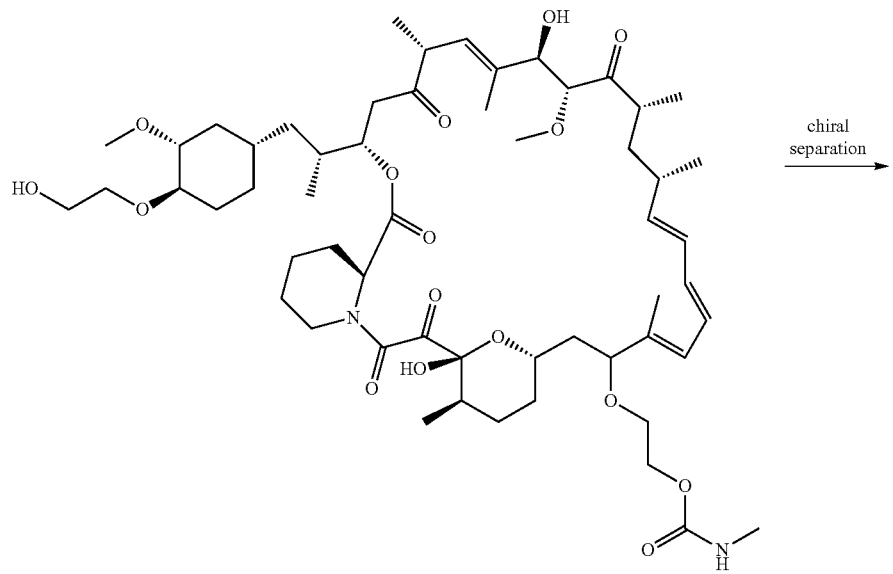
I-81
→ chiral separation
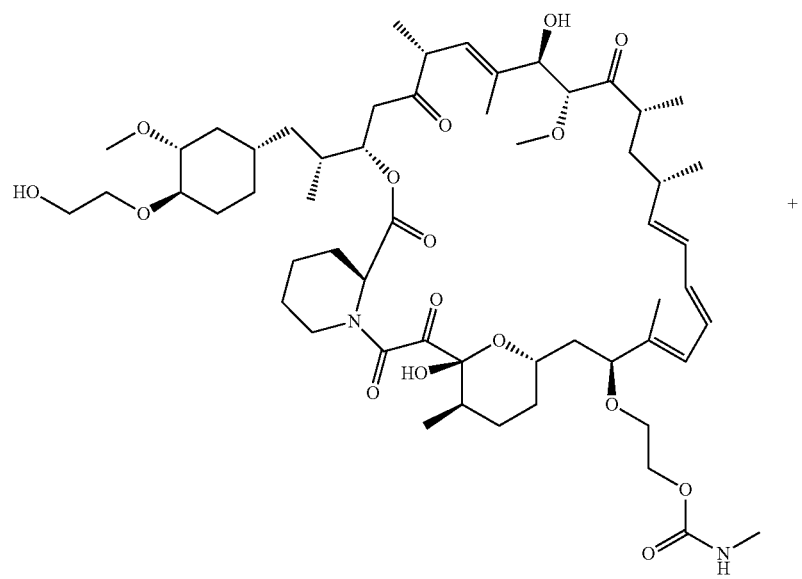
I-75
+

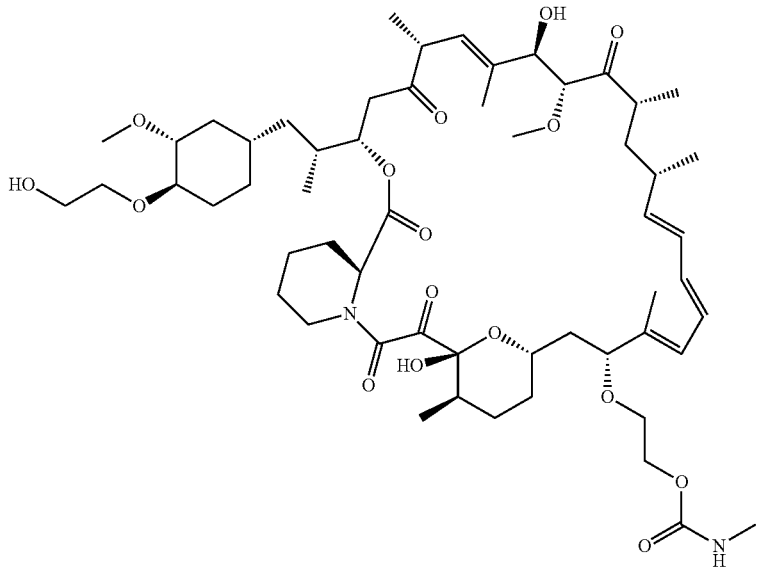

I-74

Procedures and Characterization:
Step 1: Synthesis of 2-[[(22E,24E,26E,27E,33R,34S,35R, 36R,38S,40S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-81):

To a degassed solution of everolimus (0.5 g, 0.52 mmol) in THF (10 mL) at 0° C., was added p-toluenesulfonic acid (0.45 g, 2.61 mmol) and 2-hydroxyethyl N-methylcarbamate (2.80 mL). The resulting mixture was stirred at 0° C. for 0.5 h under $N_2$, then warmed 23° C. and stirred for 3 h. The mixture was poured into sat.NaHCO$_3$ (40 mL) which was extracted with EtOAc (30 mL). The organic layer was washed with water (30 mL× 2), brine (40 mL), dried over anhydrous Na$_2$SO$_4$, filtered, and concentrated. The residue was purified by silica gel chromatography (DCM: MeOH=10:1) then additionally purified via reverse phase chromatography (C18, CH$_3$CN:H$_2$O=7:3) to provide 2-[[(22E,24E,26E,27E,33R,34S,35R,36R,38S,40S,43S, 44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49, 50,51,52-pentaoxo-67,68-dioxa-57-azatricyclohexatriaconta-22,24,26(46),27(47)-tetraen-42-yl]oxy]ethyl N-methylcarbamate (I-81: 100 mg, 18% yield) as a white solid. ESI-MS (EI$^+$, m/z): 1067.4 [M+Na]$^+$. $^1$H NMR (400 MHz, CDCl$_3$) δ 6.50-5.91 (m, 4H), 5.58-4.97 (m, 4H), 4.70 (s, 1H), 4.51 (d, J=40.4 Hz, 1H), 4.33-4.02 (m, 3H), 3.93-3.62 (m, 6H), 3.61-3.00 (m, 13H), 2.86-2.46 (m, 6H), 2.40-2.22 (m, 2H), 2.18-1.69 (m, 22H), 1.58-1.25 (m, 7H), 1.24-0.79 (m, 18H), 0.79-0.62 (m, 1H).

Step 2: Synthesis of 2-[[(22E,24E,26E,27E,33R,34S,35R, 36R,38S,40S,42S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-75) and 2-[[(22E,24E, 26E,27E,33R,34S,35R,36R,38S,40S,42R,43S,44R,45R, 55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51, 52-pentaoxo-67,68-dioxa-57-azatricyclohexatriaconta-22, 24,26(46),27(47)-tetraen-42-yl]oxy]ethyl N-methylcarbamate (I-74):

120 mg of 2-[[(22E,24E,26E,27E,33R,34S,35R,36R,38S, 40S,43S,44R,45R,55R)-44,55-dihydroxy-43-[(1R)-2-[(1S, 3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate was purified via prep chiral HPLC and the resulting epimers purified via silica gel chromatography (hexane:DCM:EtOAc:MeOH=3:3:1:0.6) to provide 2-[[(22E,24E,26E,27E,33R,34S,35R,36R,38S, 40S,42S,43S,44R,45R,55R)-44,55-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42- yl]oxy]ethyl N-methylcarbamate (I-75: 18 mg, 15% yield) and 2-[[(22E,24E,26E,27E,33R,34S,35R,36R,38S,40S, 42R,43S,44R,45R,55R)-44,55-dihydroxy-43-[(1R)-2-[(1S, 3R,4R)-4-(2-hydroxyethoxy)-3-methoxy-cyclohexyl]-1-methyl-ethyl]-45-methoxy-33,34,35,36,46,47-hexamethyl-48,49,50,51,52-pentaoxo-67,68-dioxa-57-azatricyclohexatriaconta-22,24,26(46),27(47)-tetraen-42-yl]oxy]ethyl N-methylcarbamate (I-74: 20 mg, 16% yield), both as white solids.

Chiral separation method:

Column CHIRALPAK IC

Column size 5.0 cm I.D.×25 cm L

Solution concentration: 2.4 mg/ml

Injection 8 ml

Mobile phase Hexane/EtOH=60/40(V/V)

Flow rate 30 ml/min

Wave length UV 254 nm

Temperature 35° C.

I-75: ESI-MS (EI$^+$, m/z): 1067.3 [M+Na]$^+$. $^1$H NMR (400 MHz, CDCl$_3$) δ 6.33 (dt, J=24.4, 14.6 Hz, 2H), 6.13 (dd, J=15.0, 9.9 Hz, 1H), 5.93 (dd, J=24.5, 10.6 Hz, 1H), 5.52 (dd, J=15.0, 8.8 Hz, 1H), 5.41 (d, J=10.2 Hz, 1H), 5.35 (t, J=4.7 Hz, 1H), 5.27 (d, J=5.3 Hz, 1H), 5.16 (d, J=4.9 Hz, 1H), 4.75 (s, 1H), 4.29-4.07 (m, 3H), 3.93-3.63 (m, 6H), 3.62-3.47 (m, 3H), 3.46-3.25 (m, 11H), 3.23-3.01 (m, 3H), 2.79 (d, J=4.9 Hz, 3H), 2.74-2.62 (m, 2H), 2.57 (dd, J=16.5, 6.4 Hz, 1H), 2.34 (d, J=12.7 Hz, 2H), 2.25-2.19 (m, 1H), 2.08 (s, 1H), 1.93 (dd, J=30.0, 22.7 Hz, 5H), 1.83-1.65 (m, 7H), 1.55-1.42 (m, 5H), 1.28 (s, 6H), 1.15-0.83 (m, 18H), 0.72 (dd, J=23.6, 12.0 Hz, 1H).

I-74: ESI-MS (EI$^+$, m/z): 1067.4 [M+Na]$^+$. $^1$H NMR (400 MHz, CDCl$_3$) δ 6.50-5.95 (m, 4H), 5.60-4.96 (m, 5H), 4.59-3.96 (m, 4H), 3.95-3.66 (m, 6H), 3.64-2.97 (m, 15H), 2.95-2.65 (m, 6H), 2.59 (d, J=11.0 Hz, 1H), 2.51-1.95 (m, 5H), 1.78 (q, J=6.8 Hz, 12H), 1.55-1.29 (m, 11H), 1.15-0.83 (m, 18H), 0.69 (dd, J=23.6, 11.5 Hz, 1H).

EXAMPLE 33

Synthesis of (21E,23E,25E,26E,30R,31S,32R,33R, 35S,37S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43, 44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-63) and (21E, 23E,25E,26E,30R,31S,32R,33R,35S,37S,39R,40S, 41R,42R,55R)-41,55-dihydroxy-40-[(1R)-2-[(1S,3R, 4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25 (43),26(44)-tetraene-45,46,47,48,49-pentone (I-57) and (21E,23E,25E,26E,30R,31S,32R,33R,35S,37S, 39S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-58):

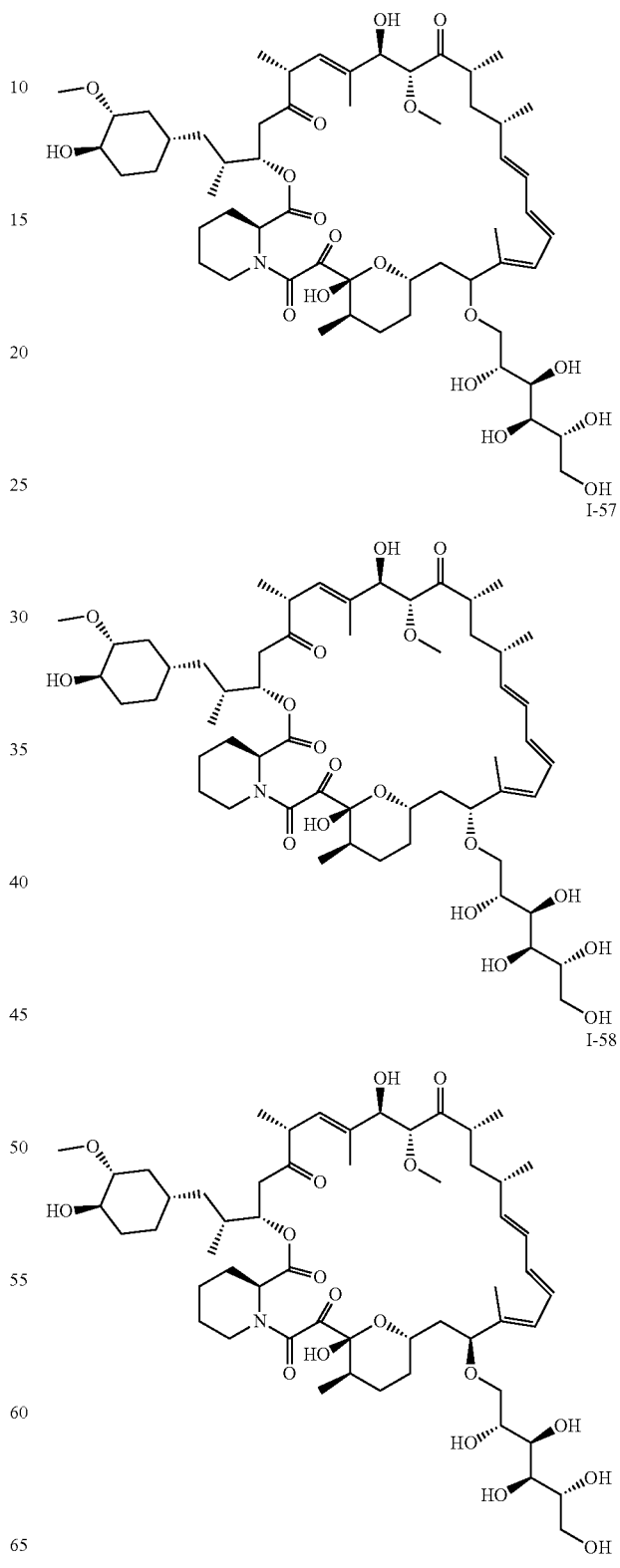

Synthetic Scheme:
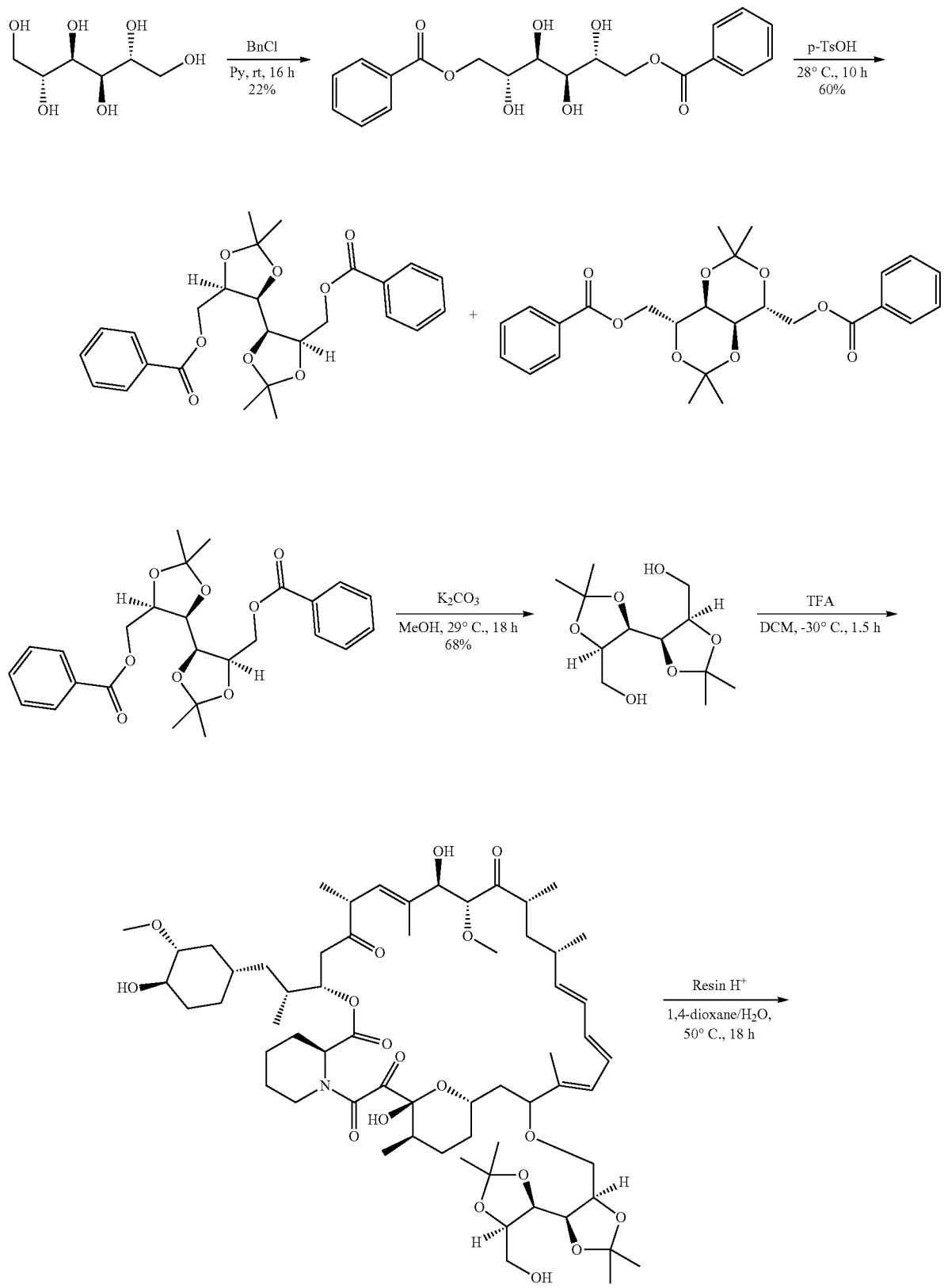

-continued

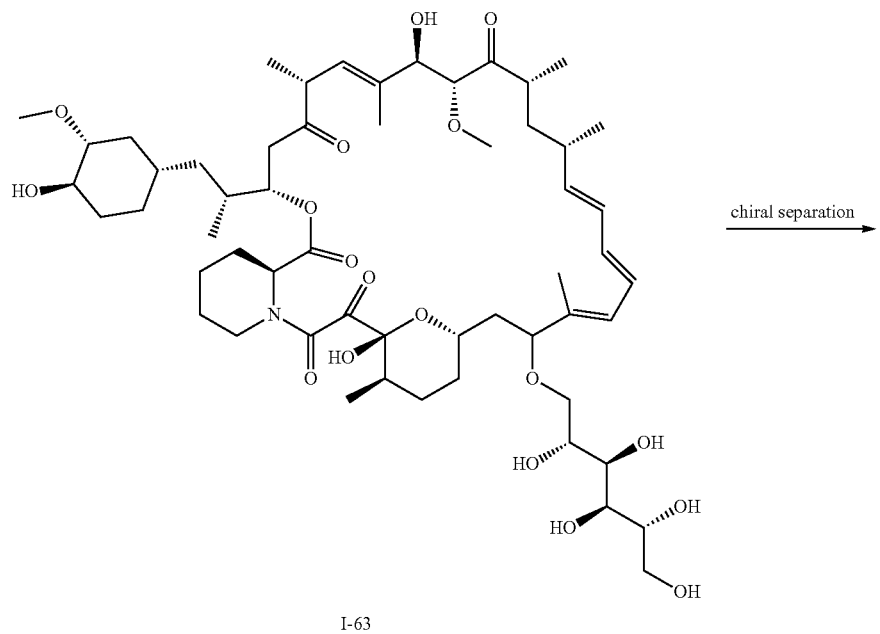

I-63

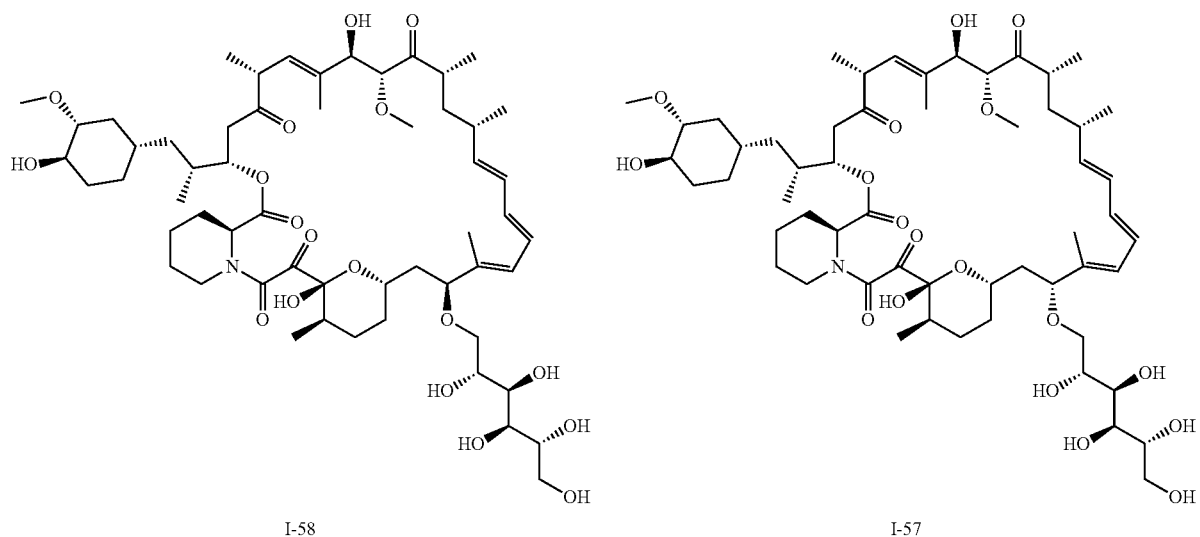

I-58  I-57

Procedures and Characterization:

Step 1: Synthesis of (2R,3R,4R,5R)-2,3,4,5-tetrahydroxy-hexane-1,6-diyl dibenzoate:

To a solution of (2R,3R,4R,5R)-hexane-1,2,3,4,5,6-hexaol (10.0 g, 54.89 mmol, 1.0 eq) in pyridine (25.39 g, 548.9 mmol, 10.0 eq) at 0° C. was added benzyl chloride (7.72 g, 54.89 mmol, 1.0 eq). The reaction mixture was then stirred at room temperature for 16 h, diluted with $H_2O$ (200 mL) and extracted with DCM (150 mL×3). The combined organic layers were washed with brine (100 mL), dried over $Na_2SO_4$, filtered, concentrated, and purified by reverse-phase chromatography ($CH_3CN:H_2O$=40%~60% yield) to afford (2R,3R,4R,5R)-2,3,4,5-tetrahydroxyhexane-1,6-diyl dibenzoate (4.7 g, 22% yield) as a white solid. ESI-MS (EI[+], m/z): 391.1 [M+H][+]. $^1$HNMR (400 MHz, DMSO-$d_6$) δ 8.07-8.00 (m, 4H), 7.66 (t, J=7.4 Hz, 2H), 7.54 (t, J=7.7 Hz, 4H), 5.09 (d, J=6.1 Hz, 2H), 4.60-4.48 (m, 4H), 4.28 (dd, J=11.2, 6.2 Hz, 2H), 3.87 (dt, J=6.1, 5.3 Hz, 2H), 3.77 (t, J=8.6 Hz, 2H).

Step 2: Synthesis of ((4R,4'R,5R,5'R)-2,2,2',2'-tetramethyl-4,4'-bi(1,3-dioxolane)-5,5'-diyl)bis(methylene) dibenzoate and ((4R,4aR,8R,8aR)-2,2,6,6-tetramethyltetrahydro-[1,3]dioxino[5,4-d][1,3]dioxine-4,8-diyl)bis(methylene) dibenzoate:

A solution of [(2R,3R,4R,5R)-6-benzoyloxy-2,3,4,5-tetrahydroxy-hexyl] benzoate (5 g, 12.81 mmol) and p-TsOH (1.22 g, 6.40 mmol) in 2,2-dimethoxypropane (50 mL) was stirred at 28° C. for 10 h. The resulting mixture was extracted with EtOAc (100 mL×3). The combined organic layers were dried over anhydrous $Na_2SO_4$, filtered and concentrated. The residue was purified by silica gel chromatography (EtOAc:PE=1:10 to 1:2) to provide both [(4R,5R)-5-[(4R,5R)-5-(benzoyloxymethyl)-2,2-dimethyl-1,3-dioxolan-4-yl]-2,2-dimethyl-1,3-dioxolan-4-yl]methyl benzoate (2.4 g, 40% yield) and [(4R,4aR,8R,8aR)-4-(benzoyloxymethyl)-2,2,6,6-tetramethyl-4,4a,8,8a-tetrahydro-[1,3]dioxino[5,4-d][1,3]dioxin-8-yl]methyl benzoate 1.2 g, 20% yield) as white solids. ESI-MS (EI$^+$, m/z): 493.2 [M+Na]$^+$.

[(4R,5R)-5-[(4R,5R)-5-(benzoyloxymethyl)-2,2-dimethyl-1,3-dioxolan-4-yl]-2,2-dimethyl-1,3-dioxolan-4-yl]methyl benzoate: $^1$HNMR (400 MHz, DMSO-$d_6$): δ 7.98 (dd, J=11.6, 4.5 Hz, 4H), 7.67 (dd, J=11.7, 4.3 Hz, 2H), 7.55 (t, J=7.7 Hz, 4H), 4.42-4.33 (m, 4H), 4.08-3.94 (m, 4H), 1.33 (s, 6H), 1.26 (s, 6H). $^{13}$C NMR (101 MHz, DMSO-$d_6$) δ 165.52, 133.44, 129.47, 129.15, 128.78, 100.61, 67.89, 67.60, 64.25, 24.24, 23.45.

[(4R,4aR,8R,8aR)-4-(benzoyloxymethyl)-2,2,6,6-tetramethyl-4,4a,8,8a-tetrahydro-[1,3]dioxino[5,4-d][1,3]dioxin-8-yl]methyl benzoate: $^1$HNMR (400 MHz, DMSO-$d_6$): δ 8.03-7.92 (m, 4H), 7.67 (dd, J=10.6, 4.3 Hz, 2H), 7.54 (t, J=7.7 Hz, 4H), 4.57 (dd, J=11.1, 5.9 Hz, 2H), 4.53-4.44 (m, 4H), 4.39 (dd, J=11.5, 7.3 Hz, 2H), 1.43 (s, 6H), 1.29 (s, 6H). $^{13}$C NMR (101 MHz, DMSO-$d_6$) δ 165.45, 133.42, 129.52, 129.17, 128.75, 108.39, 74.49, 73.77, 64.17, 27.04, 25.27.

Step 3: Synthesis of ((4R,4'R,5R,5'R)-2,2,2',2'-tetramethyl-4,4'-bi(1,3-dioxolane)-5,5'-diyl)dimethanol:

A mixture of [(4R,5R)-5-[(4R,5R)-5-(benzoyloxymethyl)-2,2-dimethyl-1,3-dioxolan-4-yl]-2,2-dimethyl-1,3-dioxolan-4-yl]methyl benzoate (8.5 g, 18.07 mmol) and $K_2CO_3$ (7.48 g, 54.20 mmol) in THF (25 mL) and $CH_3OH$ (25 mL) was stirred at 29° C. for 18 h. The reaction was concentrated and then purified via silica gel chromatography (EtOAc/PE=1:1) to afford [(4R,5R)-5-[(4R,5R)-5-(hydroxymethyl)-2,2-dimethyl-1,3-dioxolan-4-yl]-2,2-dimethyl-1,3-dioxolan-4-yl]methanol (3.2 g, 68% yield) as a white solid. ESI-MS (EI$^+$, m/z): 285.1 [M+Na]$^+$. $^1$H NMR (400 MHz, DMSO-$d_6$): δ 4.73 (t, J=5.8 Hz, 2H), 3.71 (t, J=5.6 Hz, 2H), 3.55-3.35 (m, 6H), 1.29 (s, 6H), 1.23 (s, 6H).

Step 4: Synthesis of (25E,27E,29E,30E,34R,35S,36R,37R,39S,41S,44S,49R,50R,61R)-49,61-dihydroxy-44-[(1R)-2-[(1S,3R,4R)-4-hydroxy-3-methoxy-cyclohexyl]-1-methyl-ethyl]-43-[[(4R,5R)-5-[(4R,5R)-5-(hydroxymethyl)-2,2-dimethyl-1,3-dioxolan-2,2-dimethyl-1,3-dioxolan-4-yl]methoxy]-50-methoxy-34,35,36,37,51,52-hexamethyl-72,73-dioxa-62-azatricyclohexatriaconta-25,27,29(51),30(52)-tetraene-53,54,55,56,57-pentone:

To a solution of rapamycin (0.5 g, 0.547 mol) in DCM (16 mL) was added 2,2,2-trifluoroacetic acid (1.2 mL) at −40° C. After stirring for 10 minutes R4R,5R)-5-[(4R,5R)-5-(hydroxymethyl)-2,2-dimethyl-1,3-dioxolan-4-yl]-2,2-dimethyl-1,3-dioxolan-4-yl]methanol (0.43 g, 1.64 mmol) was added and the reaction was stirred at −30° C. for 1.5 h, then diluted with DCM (10 mL) and poured into a cold aqueous $NaHCO_3$ solution. The organic layer was washed with water and brine, dried over anhydrous $Na_2SO_4$, filtered and concentrated. The resulting residue was purified via reverse phase chromatography (C18, $CH_3CN/H_2O$=7:3) to provide (25E,27E,29E,30E,34R,35S,36R,37R,39S,41S,44S,49R,50R,61R)-49,61-dihydroxy-44-[(1R)-2-[(1S,3R,4R)-4-hydroxy-3-methoxy-cyclohexyl]-1-methyl-ethyl]-43-[[(4R,5R)-5-[(4R,5R)-5-(hydroxymethyl)-2,2-dimethyl-1,3-dioxolan-4-yl]-2,2-dimethyl-1,3-dioxolan-4-yl]methoxy]-50-methoxy-34,35,36,37,51,52-hexamethyl-72,73-dioxa-62-azatricyclohexatriaconta-25,27,29(51),30(52)-tetraene-53,54,55,56,57-pentone (150 mg, 24% yield) as a white solid. ESI-MS (EI$^+$, m/z): 1166.4 [M+Na]$^+$. $^1$HNMR (400 MHz, CDCl$_3$) δ 6.52-5.69 (m, 4H), 5.48-5.10 (m, 4H), 4.51 (d, J=40.1 Hz, 1H), 4.23 (s, 1H), 3.94 (dd, J=26.3, 5.8 Hz, 4H), 3.52-3.12 (m, 13H), 2.98-2.45 (m, 8H), 2.41-2.17 (m, 2H), 2.00 (s, 3H), 1.76 (dt, J=29.0, 14.4 Hz, 15H), 1.50-1.31 (m, 24H), 1.14-0.77 (m, 18H), 0.62 (d, J=12.1 Hz, 1H).

Step 5: Synthesis of (21E,23E,25E,26E,30R,31S,32R,33R,35S,37S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-63):

To a solution of (25E,27E,29E,30E,34R,35S,36R,37R,39S,41S,44S,49R,50R,61R)-49,61-dihydroxy-44-[(1R)-2-[(1S,3R,4R)-4-hydroxy-3-methoxy-cyclohexyl]-1-methyl-ethyl]-43-[[(4R,5R)-5-[(4R,5R)-5 -(hydroxymethyl)-2,2-dimethyl-1,3-dioxolan-4-yl]-2,2-dimethyl-1,3-dioxolan-4-yl]methoxy]-50-methoxy-34,35,36,37,51,52-hexamethyl-72,73-dioxa-62-azatricyclohexatriaconta-25,27,29(51),30(52)-tetraene-53,54,55,56,57-pentone (500 mg, 0.437 mmol) in 1,4-dioxane (6 mL) and $H_2O$ (6 mL) was added Dowex 50W-X8 (1.0 g) and the resulting mixture stirred at 50° C. for 24 h, then filtered and purified by reverse phase chromatography (C18, $CH_3CN:H_2O$=4:6) to provide (21E,23E,25E,26E,30R,31S,32R,33R,35S,37S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-63: 70 mg, 15% yield) as a white solid. ESI-MS (EI$^+$, m/z): 1086.4 [M+Na]$^+$. $^1$H NMR (400 MHz, CDCl$_3$) δ 6.51-5.91 (m, 4H), 5.61-4.98 (m, 5H), 4.24 (d, J=22.2 Hz, 1H), 3.78 (dd, J=34.1, 28.6 Hz, 9H), 3.59-3.17 (m, 19H), 3.00-2.49 (m, 5H), 2.38-2.22 (m, 1H), 2.05 (d, J=33.7 Hz, 3H), 1.82-1.68 (m, 11H), 1.29 (ddd, J=46.4, 34.9, 8.8 Hz, 12H), 1.09-0.77 (m, 18H), 0.70-0.56 (m, 1H).

Step 6: Synthesis of (21E,23E,25E,26E,30R,31S,32R,33R,35S,37S,39S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxyl]-70,71-dioxa-56-azatricyclohexatriaconta-21,23,25(43),26(44)-tetraene-45,46,47,48,49-pentone (I-58) and (21E,23E,25E,26E,30R,31S,32R,33R,35S,37S,39R,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-57):

90 mg of (21E,23E,25E,26E,30R,31S,32R,33R,35S,37S,40S,41R,42R,55R)-41,55 -dihydroxy-40-[(1R)-2-[(1S,3R, 4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone was purified via prep chiral HPLC and the resulting epimers purified via silica gel chromatography (hexane:DCM:EtOAc:MeOH=3:3:1:1) to provide (21E,23E,25E,26E,30R,31S,32R,33R,35S,37S,39S,40S,41R,42R,55R)-41,55-dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-58: 15 mg, 17%) and (21E,23E,25E,26E,30R,31S,32R,33R,35S,37S,39R,40S,41R,42R,55R)-41,55 -dihydroxy-40-[(1R)-2-[(1S,3R,4R)-4-hydroxy-3-methoxy-cyclohexyl]-1-methyl-ethyl]-42-methoxy-30,31,32,33,43,44-hexamethyl-39-[(2R,3R,4R,5R)-2,3,4,5,6-pentahydroxyhexoxy]-70,71-dioxa-56-azatricyclohexatriaconta-21,23,25(43),26(44)-tetraene-45,46,47,48,49-pentone (I-57: 8 mg, 9% yield), both as white solids.

Chiral analysis method:
Column: CHIRALPAK IC-3(IC30CE-NJ008)
Column size: 0.46 cm I.D.×25 cm L
Injection: 50.0 ul
Mobile phase: Hexane/EtOH=50/50(V/V)
Flow rate: 0.8 ml/min
Wave length: UV 254 nm
Temperature: 35 oC
HPLC equipment: Shimadzu LC-20AT CP-HPLC-06

I-58: ESI-MS (EI$^+$, m/z): 1086.3 [M+Na]$^+$. $^1$H NMR (400 MHz, CDCl$_3$) δ 6.45-5.93 (m, 4H), 5.59-4.88 (m, 5H), 4.23 (d, J=26.4 Hz, 1H), 4.00-3.48 (m, 14H), 3.46-3.23 (m, 11H), 2.93 (d, J=6.8 Hz, 2H), 2.79-2.49 (m, 3H), 2.38-1.84 (m, 8H), 1.66 (t, J=14.8 Hz, 9H), 1.50-1.17 (m, 11H), 1.16-0.79 (m, 18H), 0.64 (dd, J=23.7, 11.8 Hz, 1H).

I-57: ESI-MS (EI$^+$, m/z): 1086.3 [M+Na]$^+$. $^1$H NMR (400 MHz, CDCl$_3$) δ 6.49-5.98 (m, 4H), 5.52-5.11 (m, 5H), 4.32-4.23 (m, 1H), 4.08-3.11 (m, 14H), 3.05-2.43 (m, 9H), 2.37-1.95 (m, 8H), 1.91-1.53 (m, 17H), 1.46-0.54 (m, 30H).

EXAMPLE 34

Synthesis of (21E,23E,25E,26E,40R,41S,42R,43R,45S,47S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy) ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-78) and (21E,23E,25E,26E,40R,41S,42R,43R,45S,47S,49R,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-72) and (21E,23E,25E,26E,40R,41S,42R,43R,45S,47S,49S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-73):

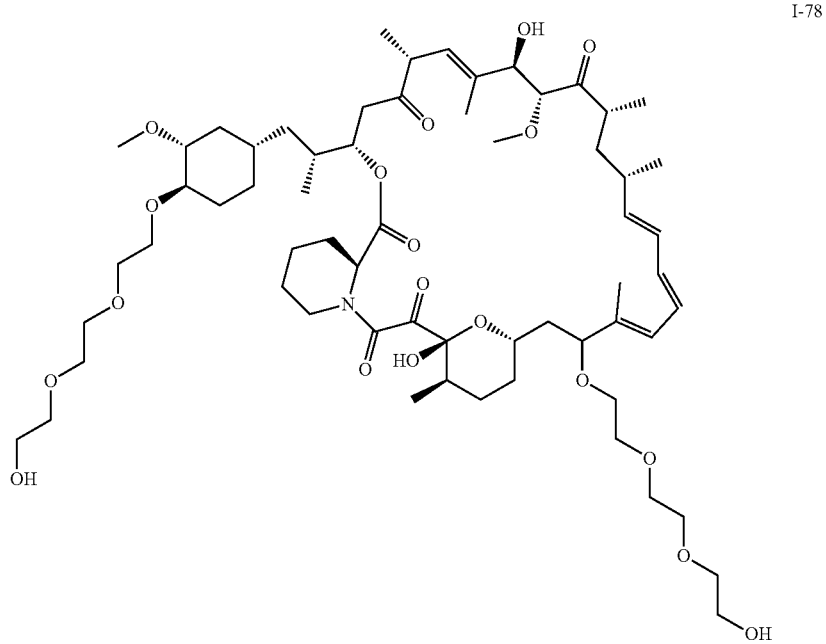 [SMILES: CO[C@@H]1C[C@H](C[C@@H](C)[C@@H]2CC(=O)[C@H](C)/C=C(\C)[C@@H](O)[C@@H](OC)C(=O)[C@H](C)C[C@H](C)/C=C/C=C/C=C(\C)[C@@H](OCCOCCOCCO)C[C@@H]3CC[C@@H](C)[C@@](O)(O3)C(=O)C(=O)N3CCCC[C@H]3C(=O)O2)CC[C@H]1OCCOCCOCCO]

I-78

-continued
I-72
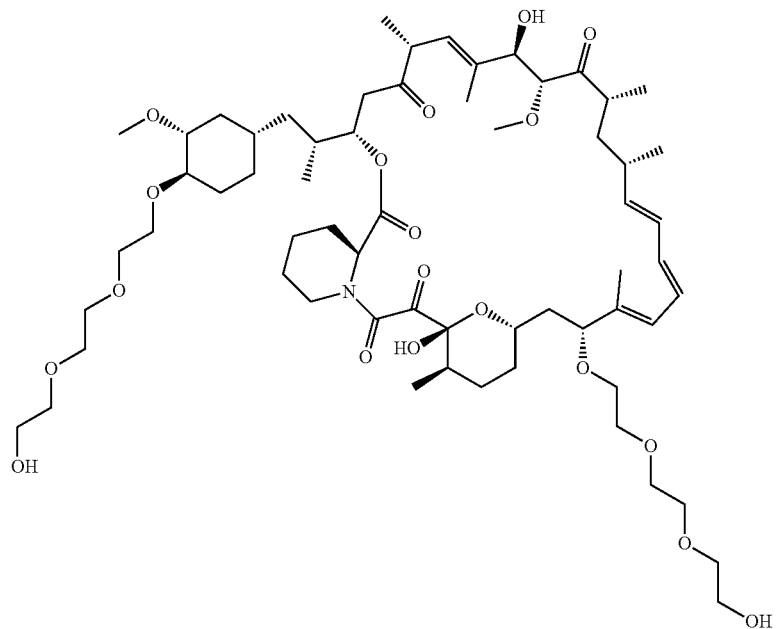
I-73
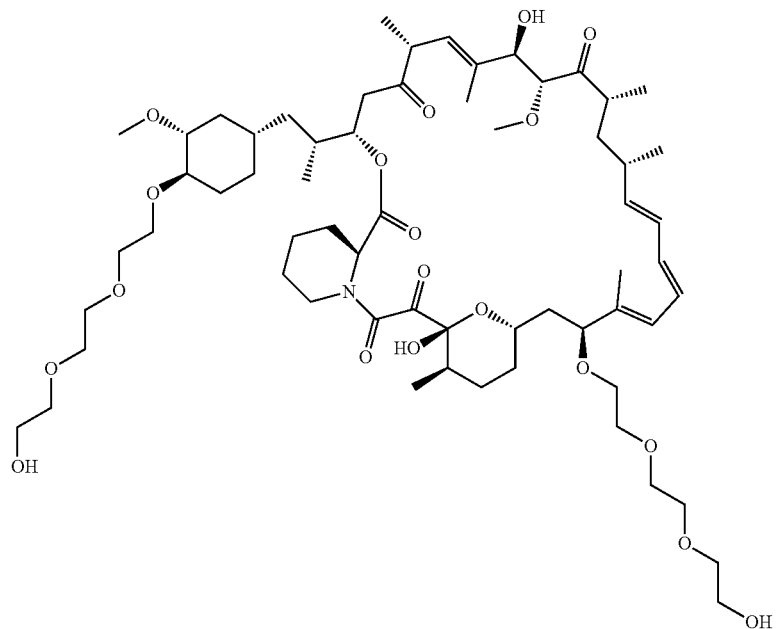
Synthetic Scheme:
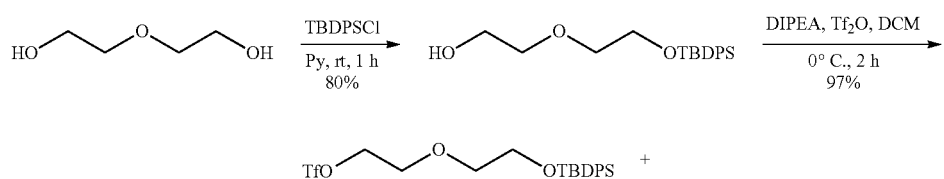

-continued
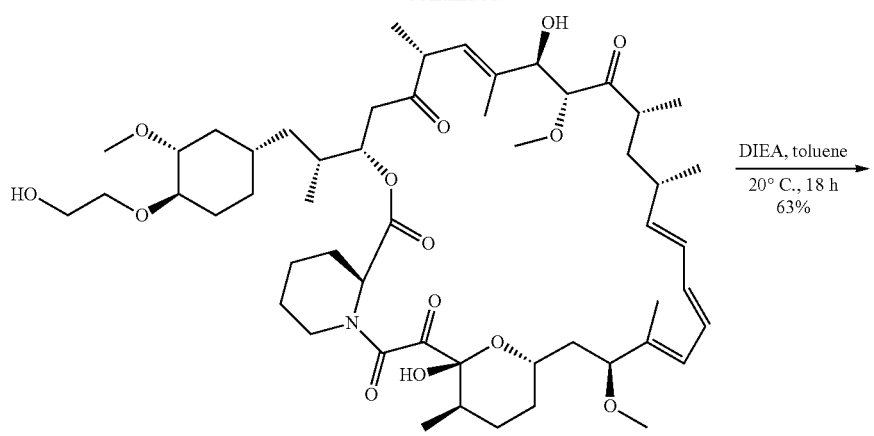
DIEA, toluene
20° C., 18 h
63%
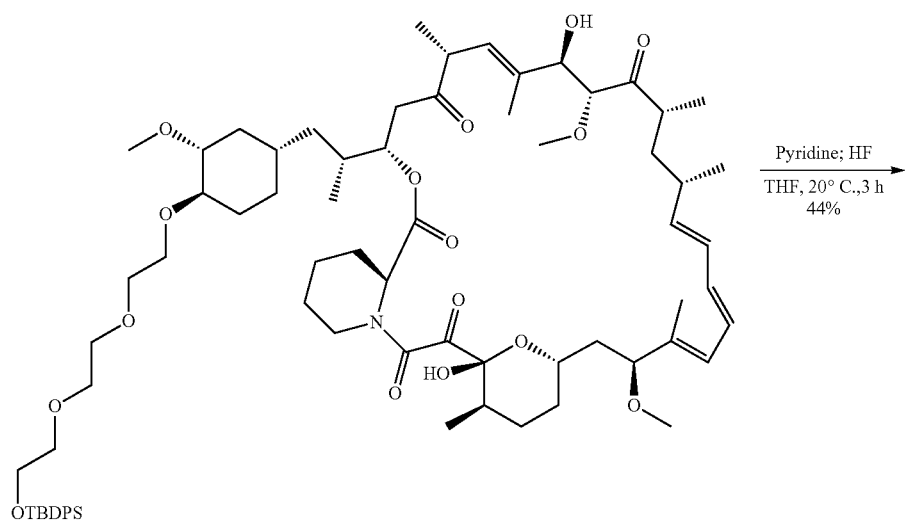
Pyridine; HF
THF, 20° C., 3 h
44%
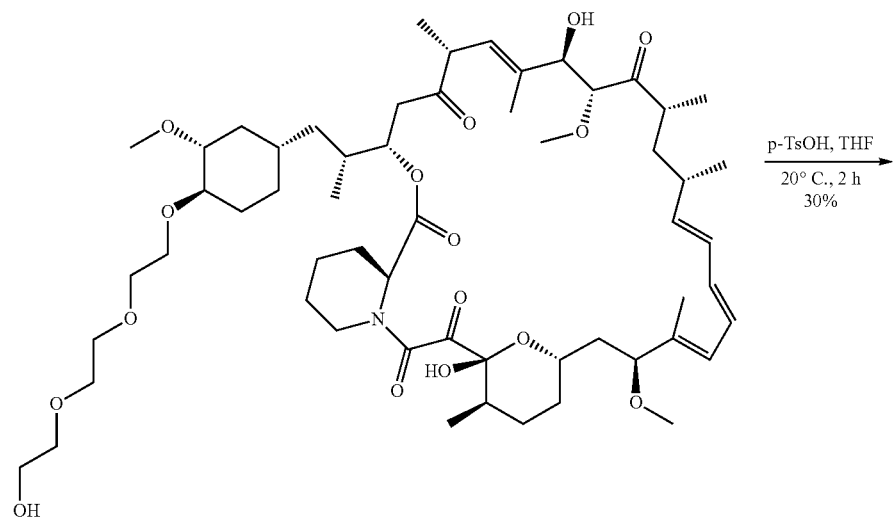
p-TsOH, THF
20° C., 2 h
30%

-continued
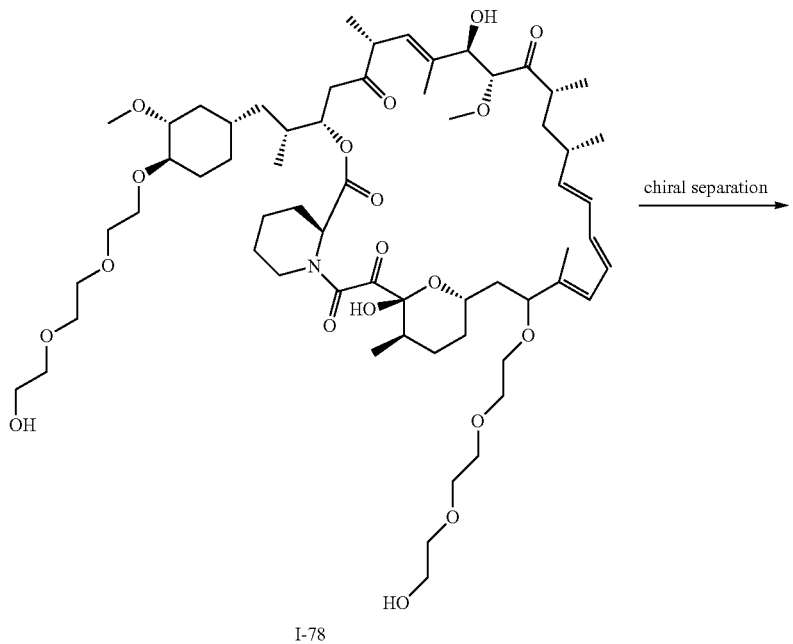
I-78
chiral separation →
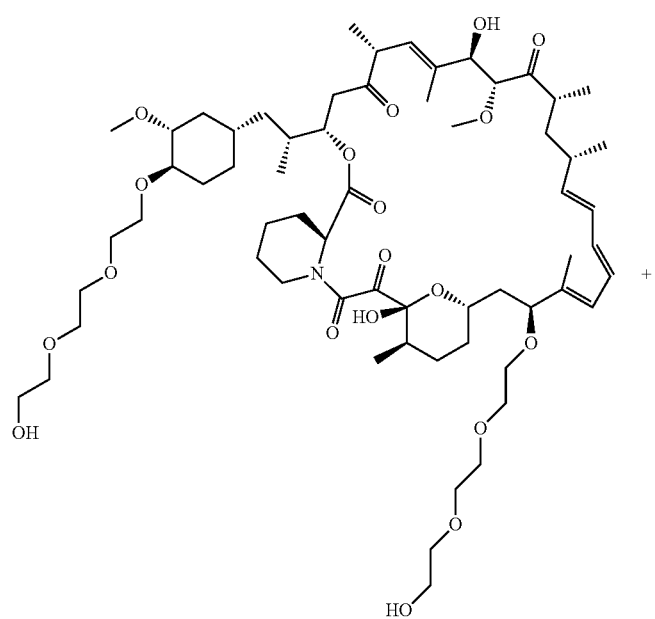
I-73
+

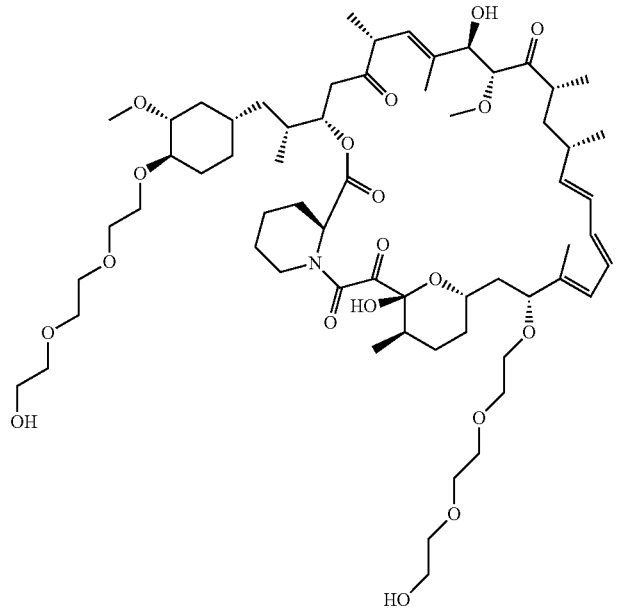

I-72

Procedures and Characterization:
Step 1: Synthesis of 2-[2-[tert-butyl(diphenyl)silyl]oxyethoxy]ethanol:
To a solution of 2-(2-hydroxyethoxy)ethanol (50 g, 471.2 mmol) in pyridine (49.6 mL) at 0° C. was added tert-butyl-chloro-diphenyl-silane (30 g, 109.2 mmol). The resulting solution was stirred at rt for 1 h then poured into water (300 mL) and extracted with EtOAc (300 mL×3). The combined organic layers were dried over anhydrous $Na_2SO_4$, filtered, and concentrated. The resulting residue was purified by silica gel chromatography (EtOAc:PE=1:8) to provide 2-[2-[tert-butyl(diphenyl)silyl]oxyethoxy]ethanol (29.9 g, 80% yield) as a colorless oil. ESI-MS (EI$^+$, m/z): 367.2 [M+Na]$^+$. $^1$H NMR (400 MHz, CDCl$_3$) δ 7.74-7.64 (m, 4H), 7.46-7.33 (m, 6H), 3.81 (t, J=5.2 Hz, 2H), 3.73-3.66 (m, 2H), 3.63-3.54 (m, 4H), 2.32 (d, J=3.5 Hz, 1H), 1.06 (s, 9H).
Step 2: Synthesis of 2-[2-[tert-butyl(diphenyl)silyl]oxyethoxy]ethyl trifluoromethanesulfonate:
To a solution of 2-[2-[tert-butyl(diphenyl)silyl]oxyethoxy]ethanol (7.6 g, 22 mmol) and DIPEA (5.76 mL) in DCM (50 mL) at 0° C., under $N_2$, was added trifluoromethylsulfonyl 1,1-difluoroethanesulfonate (3.92 mL) The mixture was then diluted with DCM (150 mL), washed with saturated NaHCO$_3$ (150 mL), water (150 mL) and brine (150 mL). The organic layer was then dried over anhydrous $Na_2SO_4$, filtered and concentrated under vacuum to provide 2-[2-[tert-butyl(diphenyl)silyl]oxyethoxy]ethyl trifluoromethanesulfonate (10.21 g, 97% yield) as a brown oil which was used without any further purification. $^1$H NMR (400 MHz, CDCl$_3$) δ 7.69-7.66 (m, 4H), 7.43-7.36 (m, 6H), 4.58 (t, J=4.8 Hz, 2H), 3.83-3.80 (m, 4H), 3.64-3.61 (t, J=5.6 Hz, 2H), 1.05 (s, 9H).
Step 3: Synthesis of (35E,37E,39E,40E,50R,51S,52R,53R,55S,57S,59S,60S,61R,62R,71R)-60-[(1R)-2-[(1S,3R,4R)-4-[2-[2-[2-[tert-butyl(diphenyl)silyl]oxyethoxy]ethoxy]ethoxy]-3-methoxy-cyclohexyl]-1-methyl-ethyl)-61,71-dihydroxy-59,62-dimethoxy-50,51,52,53,63,64-hexamethyl-81,82-dioxa-73-azatricyclohexatriaconta-35,37,39(63),40(64)-tetraene-65,66,67,68,69-pentone:
A mixture of everolimus (2 g, 2.09 mmol), 2-[2-[tert-butyl(diphenyl)silyl]oxyethoxy]ethyl trifluoromethanesulfonate (9.95 g, 20.87 mmol) and N-ethyl-N-isopropyl-propan-2-amine (5.82 mL) in toluene (50 mL) was stirred at 60° C. for 18 h then poured into ice cold sat.NaHCO$_3$ (60 mL). The reaction mixture was extracted with EtOAc (40 mL) and the organic layer washed with water (50 mL×3) and brine (50 mL) then dried over anhydrous $Na_2SO_4$, filtered and concentrated. The residue was purified by silica gel chromatography (PE:EA=5:1 to 3:1) to provide (35E,37E,39E,40E,50R,51S,52R,53R,55S,57S,59S,60S,61R,62R,71R)-60-[(1R)-2-[(1S,3R,4R)-4-[2-[2-[2-[tert-butyl(diphenyl)silyl]oxyethoxy]ethoxy]ethoxy]-3-methoxy-cyclohexyl]-1-methyl-ethyl]-61,71-dihydroxy-59,62-dimethoxy-50,51,52,53,63,64-hexamethyl-81,82-dioxa-73-azatricyclohexatriaconta-35,37,39(63),40(64)-tetraene-65,66,67,68,69-pentone (1.7 g, 63% yield) as yellow solid. ESI-MS (EI$^+$, m/z): 1307.5 [M+Na]$^+$.
Step 4: Synthesis of (22E,24E,26E,27E,35R,36S,37R,38R,40S,42S,44S,45S,46R,47R,56R)-46,56-dihydroxy-45-[(1R)-2-[(1S,3R,4R)-4-[2-[2-(2-hydroxyethoxy)ethoxy]ethoxy]-3-methoxy-cyclohexyl]-1-methyl-ethyl]-44,47-dimethoxy-35,36,37,38,48,49-hexamethyl-66,67-dioxa-57-azatricyclohexatriaconta-22,24,26(48),27(49)-tetraene-50,51,52,53,54-pentone:
To a solution of (35E,37E,39E,40E,50R,51S,52R,53R,55S,57S,59S,60S,61R,62R,71R)-60-[(1R)-2-[(1S,3R,4R)-4-[2-[2-[2-[tert-butyl(diphenyl)silyl]oxyethoxy]ethoxy]

ethoxy]-3-methoxy-cyclohexyl]-1-methyl-ethyl]-61,71-dihydroxy-59,62-dimethoxy-50,51,52,53,63,64-hexamethyl-81,82-dioxa-73-azatricyclohexatriaconta-35,37,39(63),40(64)-tetraene-65,66,67,68,69-pentone (322 mg, 0.251 mmol) in THF (10 mL) was added HF pyridine (248.5 mg, 2.51 mmol). The resulting solution was stirred at rt for 3 h, then poured into saturated aqueous NaHCO₃ and extracted with EtOAc. The organic layer was concentrated and purified via silica gel chromatography (acetone:PE=1:3) to provide (22E,24E,26E,27E,35R,36S,37R,38R,40S,42S,44S,45S,46R,47R,56R)-46,56-dihydroxy-45-[(1R)-2-[(1S,3R,4R)-4-[2-[2-(2-hydroxyethoxy)ethoxy]ethoxy]-3-methoxy-cyclohexyl]-1-methyl-ethyl]-44,47-dimethoxy-35,36,37,38,48,49-hexamethyl-66,67-dioxa-57-azatricyclohexatriaconta-22,24,26(48),27(49)-tetraene-50,51,52,53,54-pentone (114 mg, 44% yield) as light yellow solid. ESI-MS (EI⁺, m/z): 1069.3 [M+Na]⁺.

Step 5: Synthesis of (21E,23E,25E,26E,40R,41S,42R,43R,45S,47S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-78):

A mixture of (22E,24E,26E,27E,35R,36S,37R,38R,40S,42S,44S,45S,46R,47R,56R)-46,56-dihydroxy-45-[(1R)-2-[(1S,3R,4R)-4-[2-[2-(2-hydroxyethoxy)ethoxy]ethoxy]-3-methoxy-cyclohexyl]-1-methyl-ethyl]-44,47-dimethoxy-35,36,37,38,48,49-hexamethyl-66,67-dioxa-57-azatricyclohexatriaconta-22,24,26(48),27(49)-tetraene-50,51,52,53,54-pentone (0.95 g, 0.908 mmol), 2-[2-(2-hydroxyethoxy)ethoxy]ethanol (2 mL) and p-toluenesulfonic acid (0.78 g, 4.54 mmol) in THF (20 mL) was stirred at 20° C. for 2 h. The reaction was poured into ice-cold saturated aqueous NaHCO₃ (30 mL) and extracted with EtOAc (50 mL×3). The combined organic layers were washed with water and brine, then concentrated and purified via reverse-phase chromatography (C18, CH₃CN:H₂O=6.5:1) to provide (21E,23E,25E,26E,40R,41S,42R,43R,45S,47S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-78: 0.317 g, 30% yield) as a white solid. ESI-MS (EI m/z): 1186.4 [M+Na]⁺. ¹H NMR (400 MHz, CDCl₃) δ 6.39-5.95 (m, 4H), 5.59-5.34 (m, 2H), 5.26-5.09 (m, 2H), 4.81 (s, 1H), 4.29-4.15 (m, 1H), 4.00-3.49 (m, 28H), 3.48-3.34 (m, 9H), 3.16-3.0 (m, 4H), 2.80-2.52 (m, 3H), 2.34-2.20 (m, 2H), 2.07-1.88 (m, 4H), 1.79-1.72 (m, 5H), 1.66(s, 3H), 1.51-1.38 (m, 4H), 1.37-1.22 (m, 7H), 1.21-0.84 (m, 20H), 0.76-0.64 (m, 1H).

Step 6: Synthesis of (21E,23E,25E,26E,40R,41S,42R,43R,45S,47S,49S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-73) and (21E,23E,25E,26E,40R,41S,42R,43R,45S,47S,49R,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-72):

330 mg of (21E,23E,25E,26E,40R,41S,42R,43R,45S,47S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone was purified via prep chiral HPLC and the resulting epimers purified via silica gel chromatography (hexane:DCM:EtOAc:MeOH=3:3:1:1) to provide (21E,23E,25E,26E,40R,41S,42R,43R,45S,47S,49S,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-73: 77 mg, 23% yield) and (21E,23E,25E,26E,40R,41S,42R,43R,45S,47S,49R,50S,51R,52R,61R)-51,61-dihydroxy-49-[2-[2-(2-hydroxyethoxy)ethoxy]ethoxy]-50-[(1R)-2-[(1S,3R,4R)-4-[2-[2-(2-hydroxyethoxy)ethoxy]ethoxy]-3-methoxy-cyclohexyl]-1-methyl-ethyl]-52-methoxy-40,41,42,43,53,54-hexamethyl-72,73-dioxa-62-azatricyclohexatriaconta-21,23,25(53),26(54)-tetraene-55,56,57,58,59-pentone (I-72: 50 mg, 15% yield), both as white solids.

Chiral separation method:

Column: CHIRALPAK IC

Column size: 2.5 cm I.D.×25 cm L

Solution concentration: 6.5 mg/ml

Injection: 7 ml

Mobile phase: Hexane/EtOH=60/40 (V/V)

Flow rate: 40 ml/min

Wave length: UV 254 nm

Temperature: 35° C.

I-73: ESI-MS (EI⁺, m/z): 1186.6 [M+Na]⁺. ¹H NMR (400 MHz, CDCl₃) δ 6.42-6.06 (m, 3H), 5.92 (dd, J=29.5, 10.8 Hz, 1H), 5.55-5.37 (m, 2H), 5.26 (d, J=5.2 Hz, 1H), 5.14 (d, J=4.3 Hz, 1H), 4.80 (s, 1H), 4.23 (d, J=24.9 Hz, 1H), 3.90 (s, 1H), 3.81-3.22 (m, 36H), 3.19-2.99 (m, 3H), 2.78-2.48 (m, 3H), 2.33 (d, J=12.4 Hz, 2H), 2.10-1.87 (m, 5H), 1.76-1.55 (m, 13H), 1.46 (s, 4H), 1.39-1.18 (m, 5H), 1.15-0.81 (m, 18H), 0.71 (dd, J=23.5, 11.7 Hz, 1H).

I-72: ¹H NMR (400 MHz, CDCl₃) δ 6.42-5.92 (m, 4H), 5.61-5.04 (m, 5H), 4.24 (d, J=53.9 Hz, 2H), 3.99 (dd, J=13.8, 6.9 Hz, 1H), 3.83-2.90 (m, 36H), 2.75-2.46 (m, 3H), 2.16 (ddd, J=109.4, 53.2, 24.9 Hz, 7H), 1.86-1.69 (m, 7H), 1.52-1.16 (m, 17H), 1.15-0.80 (m, 18H), 0.66 (dd, J=23.9, 11.6 Hz, 1H).

EXAMPLE 35
Synthesis of (21E,23E,25E,26E,33R,34S,35R,36R, 38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46, 47-hexamethyl-42-[2-[2-(2,2,2-trifluoroethoxy) ethoxy]ethoxy]-65,66-dioxa-56-azatricyclohexatriaconta-21,23,25(46),26(47)-tetraene-48,49,50,51,52-pentone (I-91):
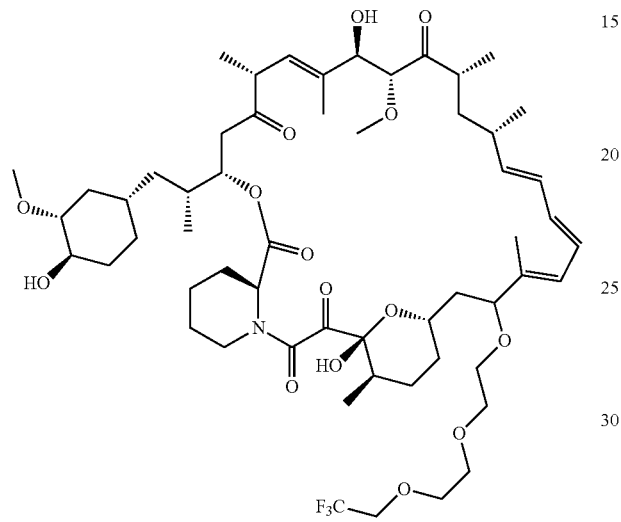
Synthetic Scheme:
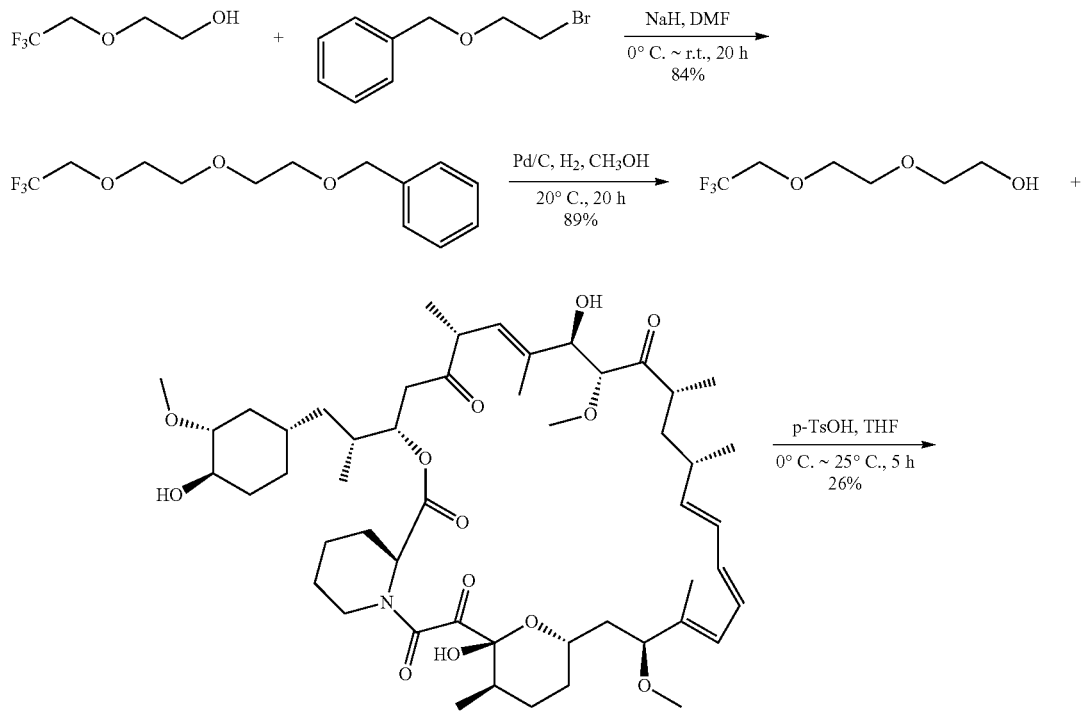

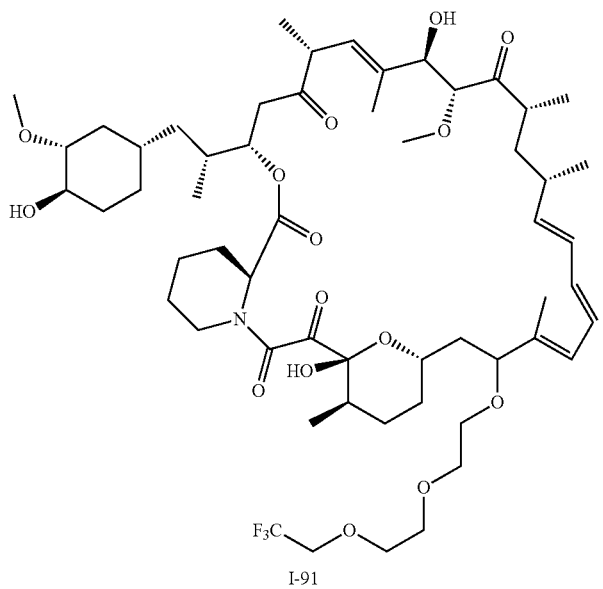

I-91

Procedures and Characterization:

Step 1: Synthesis of 2-[2-(2,2,2-trifluoroethoxy)ethoxy]ethoxymethylbenzene:

To a slurry of sodium hydride (12.49 g, 520.5 mmol) in DMF (150 mL) was added 2-(2,2,2-trifluoroethoxy)ethanol (5 g, 34.7 mmol) in DMF (10 mL) under $N_2$ atmosphere at 0° C. The mixture was stirred for 1 h then 2-bromoethoxymethylbenzene (18.66 g, 86.75 mmol) was added dropwise. The mixture was stirred at room temperature for 20 h then quenched with water (50 mL) and extracted with EtOAc (80 mL). The organic layer was washed with water (50 mL×3), brine (50 mL), dried over anhydrous $Na_2SO_4$, filtered, and concentrated. The residue was purified via silica gel chromatography (PE:EA=25:1 to 20:1) to provide 2-[2-(2,2,2-trifluoroethoxy)ethoxy]ethoxymethylbenzene (8.1 g, 84% yield) as a colorless liquid. $^1$H NMR (400 MHz, $CDCl_3$): δ 7.37-7.26 (m, 5H), 4.57 (s, 2H), 3.90 (q, J=8.8 Hz, 2H), 3.79 (dd, J=5.6, 3.5 Hz, 2H), 3.71-3.61 (m, 6H).

Step 2: Synthesis of 2-[2-(2,2,2-trifluoroethoxy)ethoxy]:

To a solution of 2-[2-(2,2,2-trifluoroethoxy)ethoxy]ethoxymethylbenzene (0.5 g, 1.8 mmol) in $CH_3OH$ (10 mL) was added Pd/C (0.43 g) and the reaction stirred under $H_2$ atmosphere at room temperature (20° C.) for 20 h. The Pd/C was removed via filtration and the resulting filtrate concentrated and purified by silica gel chromatography (DCM:$CH_3OH$=50:1) to provide 2-[2-(2,2,2-trifluoroethoxy)ethoxy]ethanol (0.30 g, 89% yield) as colorless oil. $^1$H NMR (400 MHz, $CDCl_3$) δ 3.91 (q, J=8.7 Hz, 2H), 3.80 (dd, J=5.6, 3.4 Hz, 2H), 3.75 (d, J=4.0 Hz, 2H), 3.70 (dd, J=5.5, 3.5 Hz, 2H), 3.62 (dd, J=5.2, 3.9 Hz, 2H), 2.23 (t, J=5.7 Hz, 1H (OH)). $^{19}$F NMR (376 MHz, $CDCl_3$, (trifluoromethylbenzene as standard) δ-74.33 (t, J=8.8 Hz).

Step 3: Synthesis of (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone:

To a degassed solution of (22E,24E,26E,27E,29R,30S,31R,32R,34S,36S,38S,39S,40R, 41R,50R)-40,50-dihydroxy-39-[(1R)-2-[(1S,3R,4R)-4-hydroxy-3-methoxy-cyclohexyl]-1-methyl-ethyl]-38,41-dimethoxy-29,30,31,32,42,43-hexamethyl-60,61-dioxa-51-azatricyclohexatriaconta-22,24,26(42),27(43)-tetraene-44,45,46,47,48-pentone (0.1 g, 0.11 mmol) in THF (5 mL) at 0° C. was added p-toluenesulfonic acid (94 mg, 0.547 mmol) and 2-[2-(2,2,2-trifluoroethoxy)ethoxy]ethanol (0.2 g, 1.09 mmol). The resulting mixture was stirred at 23° C. for 5 h under $N_2$ then poured into sat.$NaHCO_3$ (40 mL) then extracted with EtOAc (30 mL). The organic layer was washed with water (30 mL×2), brine (20 mL), dried over anhydrous $Na_2SO_4$, filtered, and concentrated. The residue was purified by reverse phase chromatography ($C_{18}$, $CH_3CN$:$H_2O$=0% to 65% yield) to provide (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-91: 30 mg, 26% yield) as a white solid. ESI-MS (EI$^+$, m/z): 1093.5 [M+Na]$^+$. $^1$H NMR (400 MHz, $CDCl_3$) δ 6.38-5.90 (m, 4H), 5.46-5.05 (m, 4H), 4.5-4.4 (m, 1H), 4.21-4.11 (m, 2H), 3.91-3.52 (m, 6H), 3.34-3.25 (m, 8H), 3.07 (s, 1H), 2.84-2.59 (m, 5H), 2.31-1.91 (m, 6H), 1.77-1.54 (m, 22H), 1.43-1.19 (m, 10H), 1.04-0.80 (m, 16H), 0.60 (q, J=12 Hz, 1H).

EXAMPLE 36

Synthesis of (23E,25E,27E,28E,36R,37S,38R,39R, 41S,43S,46S,47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy) cyclohexyl]-1-methyl-ethyl]-36,37,38,39,49,50-hexamethyl-66,67-dioxa-58-azatricyclohexatriaconta-23,25,27(49),28(50)-tetraene-51,52,53,54,55-pentone (I-92) and (23E, 25E,27E,28E,36R,37S,38R,39R,41S,43S,45S,46S, 47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy)cyclohexyl]-1-methyl-ethyl]-36,37,38,39,49,50-hexamethyl-66,67-dioxa-58-azatricyclohexatriaconta-23,25,27(49),28 (50)-tetraene-51,52,53,54,55-pentone (I-90) and (23E,25E,27E,28E,36R,37S,38R,39R,41S,43S,45R, 46S,47R,48R,57R)-47,57-dihydroxy-48-methoxy-45-[2-(2-methoxyethoxy)ethoxy]-46-[(1R)-2-[(1S, 3R,4R)-3-methoxy-4-(2-methoxyethoxy) cyclohexyl]-1-methyl-ethyl]-36,37,38,39,49,50-hexamethyl-66,67-dioxa-58-azatricyclohexatriaconta-23,25,27(49),28(50)-tetraene-51,52,53,54,55-pentone (I-89):

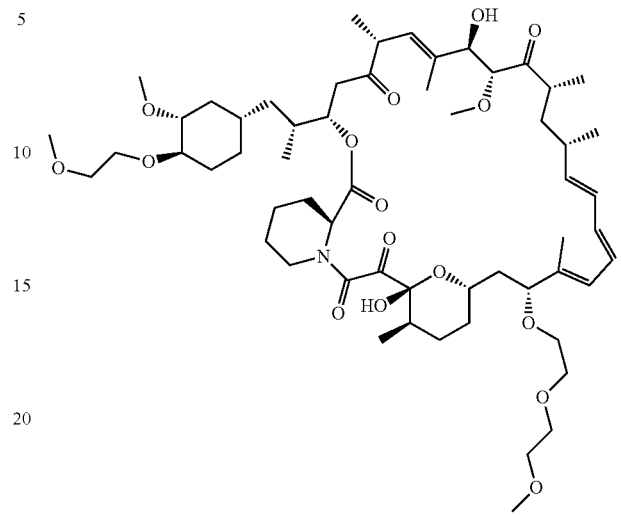

I-89

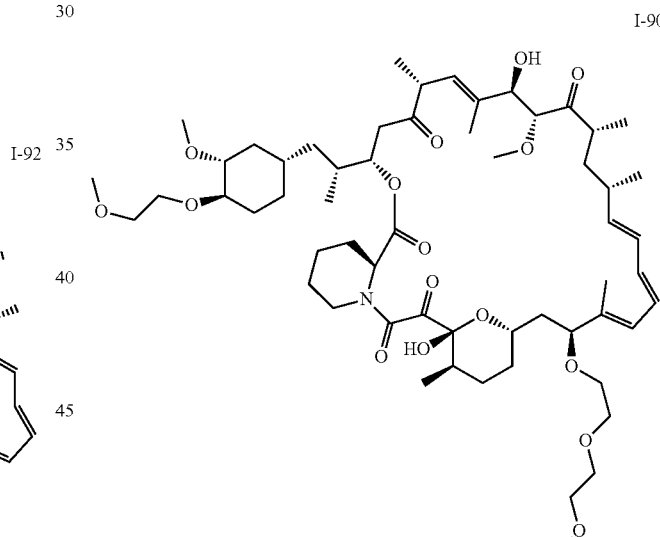

I-90

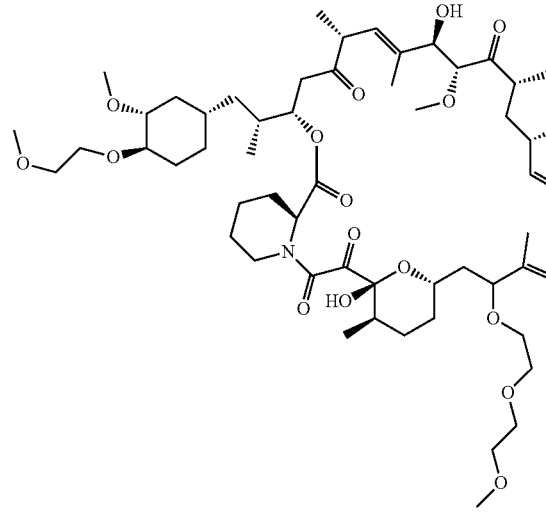

I-92

Synthetic Scheme:

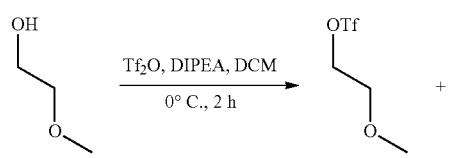

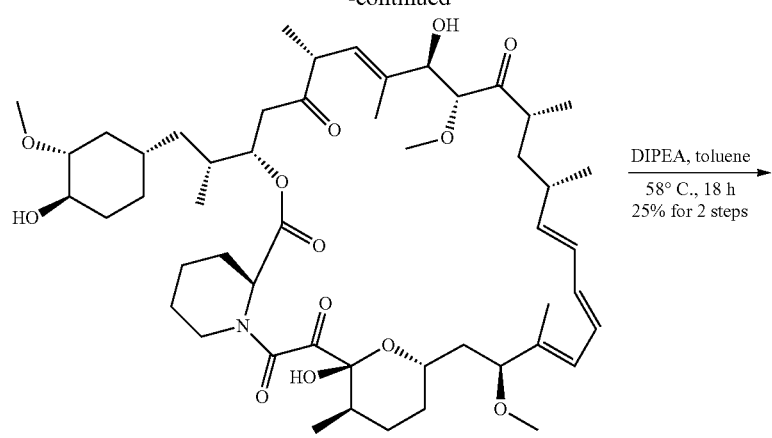
DIPEA, toluene
58° C., 18 h
25% for 2 steps
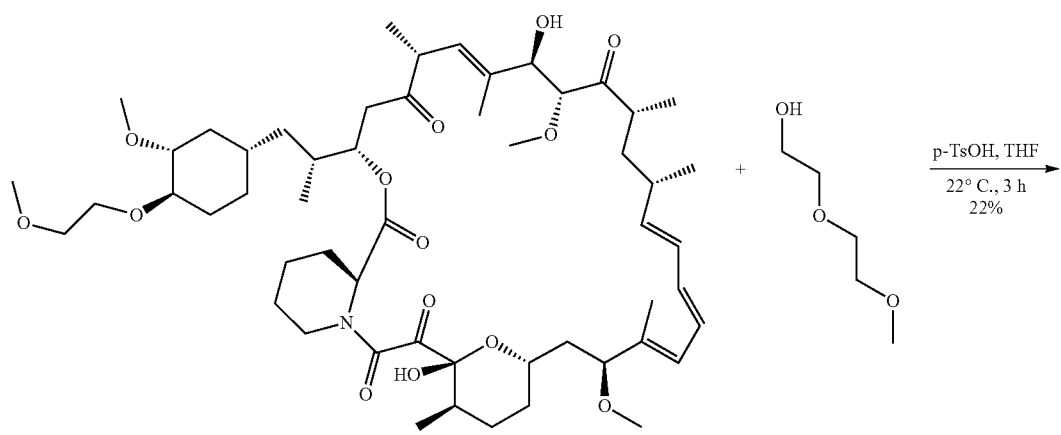
p-TsOH, THF
22° C., 3 h
22%
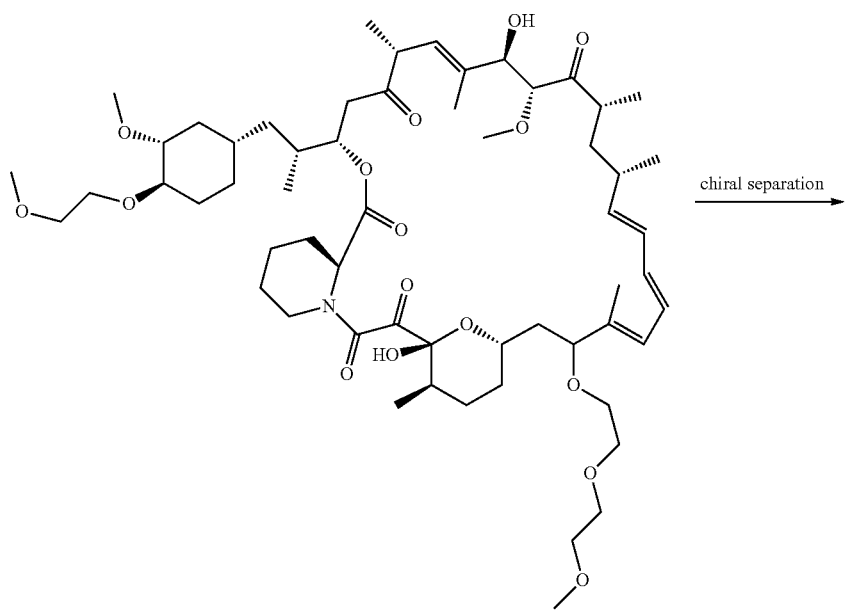
chiral separation
I-92

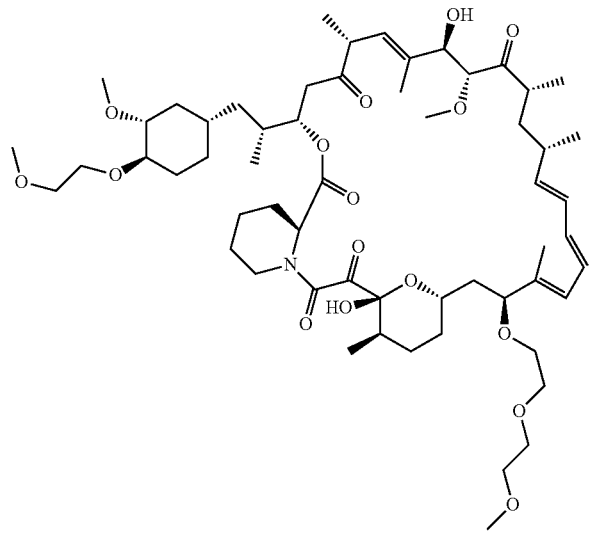

I-90

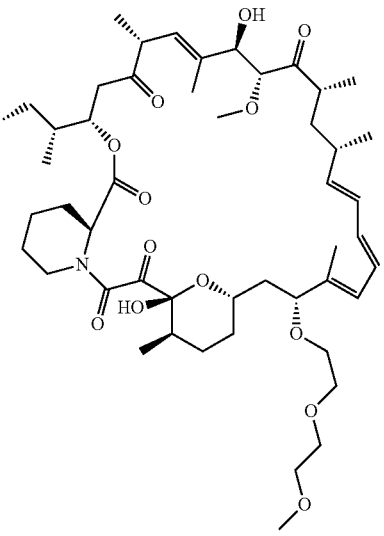

I-89

Procedures and Characterization:

Step 1: Synthesis of 2-methoxyethyl trifluoromethanesulfonate:

A solution of 2-methoxyethanol (3 g, 39.42 mmol) and DIPEA (10.30 mL, 59.14 mmol) in DCM (60 mL) was cooled to 0° C. under $N_2$, and trifluoromethanesufonic anhydride (7.28 mL, 43.37 mmol,) added dropwise. The mixture was stirred at 0° C. for 2 h then diluted with DCM (50 mL). The organic layer was washed with sat. $NaHCO_3$ (50 mL), water (50 mL), brine (50 mL), then dried over anhydrous $Na_2SO_4$, filtrated, and concentrated under vacuum to afford 2-methoxyethyl trifluoromethanesulfonate as brown oil. This was used in the next step without further purification. $^1H$ NMR (400 MHz, $CDCl_3$) δ 4.62-4.58 (t, J=4.4 Hz 2H), 3.70-3.65 (t, J=4.4 Hz, 2H), 3.39 (s, 3H).

Step 2: Synthesis of (23E,25E,27E,28E,32R,33S,34R,35R,37S,39S,41S,42S,43R,44R,53R)-43,53-dihydroxy-41,44-dimethoxy-42-[(1R)-2-[(1S,3R,4R)-3-methoxy-4-(2-methoxyethoxy)cyclohexyl]-1-methyl-ethyl]-32,33,34,35,45,46-hexamethyl-62,63-dioxa-54-azatricyclohexatriaconta-23,25,27(45),28(46)-tetraene-47,48,49,50,51-pentone:

A mixture of rapamycin (2 g, 2.19 mmol), 2-methoxyethyl trifluoromethanesulfonate and N-ethyl-N-isopropylpropan-2-amine (6.48 mL, 37.19 mmol) in toluene (60 mL) was stirred at 58° C. for 18 h then diluted with EtOAc (100 mL), poured into ice-cold Sat. $NaHCO_3$ (150 mL), washed with ice-cold water twice (250 mL), brine (200 mL), dried over anhydrous $Na_2SO_4$, filtered and concentrated. The crude was purified via silica gel chromatography (acetone:PE=1:6) to provide (23E,25E,27E,28E,32R,33S,34R,35R,37S,39S,41S,42S,43R,44R,53R)-43,53-dihydroxy-41,44-dimethoxy-42-[(1R)-2-[(1S,3R,4R)-3-methoxy-4-(2-methoxyethoxy)cyclohexyl]-1-methyl-ethyl]-32,33,34,35,45,46-hexamethyl-62,63-dioxa-54-azatricyclohexatriaconta-23,25,27(45),28(46)-tetraene-47,48,49,50,51-pentone (0.53 g, 25% yield) as a light brown solid. ESI-MS ($EI^+$, m/z): 994.5 $[M+Na]^+$. $^1H$ NMR (400 MHz, $CDCl_3$) δ 6.42-6.11 (m, 3H), 5.96 (m, 1H), 5.58-5.40 (m, 2H), 5.29-5.14 (m, 2H), 4.80 (s, 1H), 4.18 (m, 1H), 3.75-3.64 (m, 5H), 5.59-3.50 (m, 3H), 3.46-3.43 (m, 4H), 3.38-3.30 (m, 6H), 3.17-3.05 (m, 4H), 2.80-2.56 (m, 3H), 2.06-1.92 (m, 4H), 1.86-1.75 (m, 6H), 1.69-1.59 (m, 10H), 1.51-1.42 (m, 5H), 1.31-1.15 (m, 8H), 1.11-1.04 (m, 6H), 1.00-0.83 (m, 10H), 0.72 (q, J=12 Hz, 1H).

Step 3: Synthesis of (23E,25E,27E,28E,36R,37S,38R,39R,41S,43S,46S,47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy)cyclohexyl]-1-methyl-ethyl]-36,37,38,39,49,50-hexamethyl-66,67-dioxa-58-azatricyclohexatriaconta-23,25,27(49),28(50)-tetraene-51,52,53,54,55-pentone (I-92):

A solution of (23E,25E,27E,28E,32R,33S,34R,35R,37S,39S,41S,42S,43R, 44R,53R)-43,53-dihydroxy-41,44-dimethoxy-42-[(1R)-2-[(1S,3R,4R)-3-methoxy-4-(2-methoxyethoxy)cyclohexyl]-1-methyl-ethyl]-32,33,34,35,45,46-hexamethyl-62,63-dioxa-54-azatricyclohexatriaconta-23,25,27(45),28(46)-tetraene-47,48,49,50,51-pentone (0.45 g, 0.463 mmol) in THF (25 mL) was degassed with $N_2$, 4-methylbenzenesulfonic acid (0.4 g, 2.31 mmol) was added at 0° C., followed by 2-(2-methoxyethoxy)ethanol (4 mL). The resulting mixture was stirred at 0° C. for 0.5 h under $N_2$, then at 25° C. for 3 h. The mixture was poured into ice-cold sat. $NaHCO_3$ (50 mL), extracted with EtOAc (80 mL×2), the organic layer was washed with water (100 mL), brine (100 mL) and concentrated under vacuum. The residue was purified via reverse phase chromatography (C18, CH₃CN: H₂O from 10%~75% yield) to afford (23E,25E,27E,28E, 36R,37S,38R,39R,41S,43S,46S,47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy) cyclohexyl]-1-methyl-ethyl]-36,37,38,39,49,50-hexamethyl-66,67-dioxa-58-azatricyclohexatriaconta-23,25,27 (49),28(50)-tetraene-51,52,53,54,55-pentone (I-92: 0.11 g 22% yield) as a white solid. ESI-MS (EI⁺, m/z): 1082.5 [M+Na]⁺. ¹H NMR (400 MHz, CDCl₃) 6.32-5.99 (m, 3H), 5.89-5.78 (m, 1H), 5.48-5.07 (m, 4H), 4.70-4.51 (m, 1H), 4.20-4.10 (m, 1H), 3.83-3.76 (m, 1H), 3.73-3.62 (m, 3H), 3.57-5.43 (m, 8H), 3.41-3.37 (m, 4H), 3.35-3.21 (m, 12H), 3.14-3.97 (m, 3H), 2.68-2.45 (m, 3H), 2.24 (m, 2H), 1.99-1.81 (m, 4H), 1.68-1.52 (m, 15H), 1.44-1.34 (m, 4H), 1.26-1.14 (m, 5H), 1.05-0.94 (m, 8H), 0.92-0.77 (m, 10H), 0.65 (q, J=12Hz, 1H).

Step 4: Synthesis of (23E,25E,27E,28E,36R,37S,38R,39R, 41S,43S,45S,46S,47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy)cyclohexyl]-1-methyl-ethyl]-36,37,38,39,49,50-hexamethyl-66,67-dioxa-58-azatricyclohexatriaconta-23,25,27(49),28(50)-tetraene-51,52,53,54,55-pentone (I-90) and (23E,25E,27E, 28E,36R,37S,38R,39R,41S,43S,45R,46S,47R,48R,57R)-47,57-dihydroxy-48-methoxy-45-[2-[2-methoxyethoxy) ethoxy]-46-[(1R)-2-[(1S,3R,4R)-3-methoxy-4-(2-methoxyethoxy)cyclohexyl]-1-methyl-ethyl]-36,37,38,39, 49,50-hexamethyl-66,67-dioxa-58-azatricyclohexatriaconta-23,25,27(49),28(50)-tetraene-51, 52,53,54,55-pentone (I-89):

1.16 g of (23E,25E,27E,28E,36R,37S,38R,39R,41S,43S, 46S,47R,48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy) cyclohexyl]-1-methyl-ethyl]-36,37,38,39,49,50-hexamethyl-66,67-dioxa-58-azatricyclohexatriaconta-23,25,27(49),28(50)-tetraene-51, 52,53,54,55-pentone was purified via prep chiral HPLC and the resulting epimers purified via silica gel chromatography (hexane: DCM:EtOAc:MeOH=3:3:1:0.3) to obtain (23E, 25E,27E,28E,36R,37S,38R,39R,41S,43S,45S,46S,47R, 48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy)cyclohexyl]-1-methyl-ethyl]-36,37,38,39, 49,50-hexamethyl-66,67-dioxa-58-azatricyclohexatriaconta-23,25,27(49),28(50)-tetraene-51, 52,53,54,55-pentone (I-90: 340 mg, 28% yield) and (23E, 25E,27E,28E,36R,37S,38R,39R,41S,43S,45R,46S,47R, 48R,57R)-47,57-dihydroxy-48-methoxy-45-[2-(2-methoxyethoxy)ethoxy]-46-[(1R)-2-[(1S,3R,4R)-3-methoxy-4-(2-methoxyethoxy)cyclohexyl]-1-methyl-ethyl]-36,37,38,39,49,50-hexamethyl-66,67-dioxa-58-azatricyclohexatriaconta-23,25,27(49),28(50)-tetraene-51, 52,53,54,55-pentone (I-89: 135 mg, 11% yield), both as white solids.

Chiral separation method:
Column: CHIRALPAK IC
Column size: 2.5 cm I.D.×25 cm L
Solution concentration: 2.5 mg/ml
Injection: 3 ml
Mobile phase: Hexane/EtOH=60/40 (V/V)
Flow rate: 30 ml/min
Wave length: UV 254 nm
Temperature: 35° C.

I-90: ESI-MS (EI⁺, m/z): 1082.4 [M+Na]⁺. ¹H NMR (400 MHz, CDCl₃) δ 6.40-6.22 (m, 2H), 6.14 (dt, J=15.0, 9.8 Hz, 1H), 5.90 (dd, J=32.4, 10.7 Hz, 1H), 5.56-5.32 (m, 2H), 5.27 (d, J=5.0 Hz, 1H), 5.16 (d, J=4.2 Hz, 1H), 4.77 (s, 1H), 4.18 (d, J=5.9 Hz, 1H), 3.87 (s, 1H), 3.80-3.24 (m, 29H), 3.22-3.01 (m, 3H), 2.72 (dd, J=16.9, 5.8 Hz, 2H), 2.57 (dd, J=16.8, 6.4 Hz, 1H), 2.30 (t, J=21.1 Hz, 2H), 1.93 (ddd, J=26.1, 21.2, 9.8 Hz, 6H), 1.82-1.64 (m, 8H), 1.50 (dd, J=22.1, 10.9 Hz, 6H), 1.37-1.15 (m, 6H), 1.15-0.82 (m, 18H), 0.71 (q, J=8.0, 20.0 Hz, 1H).

I-89: ESI-MS (EI⁺, m/z): 1082.4 [M+Na]⁺. ¹H NMR (400 MHz, CDCl₃) δ 6.41-5.93 (m, 4H), 5.59-5.37 (m, 2H), 5.20 (dd, J=23.8, 19.2 Hz, 2H), 4.55 (d, J=10.4 Hz, 1H), 4.28 (s, 1H), 4.15 (d, J=10.2 Hz, 1H), 4.00 (d, J=3.7 Hz, 1H), 3.91-3.27 (m, 28H), 3.27-2.85 (m, 5H), 2.76-2.24 (m, 5H), 2.18-1.55 (m, 14H), 1.54-1.20 (m, 10H), 1.16-0.82 (m, 18H), 0.75-0.61 (m, 1H).

EXAMPLE 37

Synthesis of (21E,23E,25E,26E,35R,36S,37R,38R, 40S,42S,45S,46R,47R,56R)-46,56-dihydroxy-45-[(1R)-2-1(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-86) and (21E, 23E,25E,26E,35R,36S,37R,38R,40S,42S,44S,45S, 46R,47R,56R)-46,56-dihydroxy-45-[(1R)-2-[(1S,3R, 4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy] ethoxy]-67,68-dioxa-58-azatricyclohexatriaconta-21, 23,25(48),26(49)-tetraene-50,51,52,53,54-pentone (I-85):

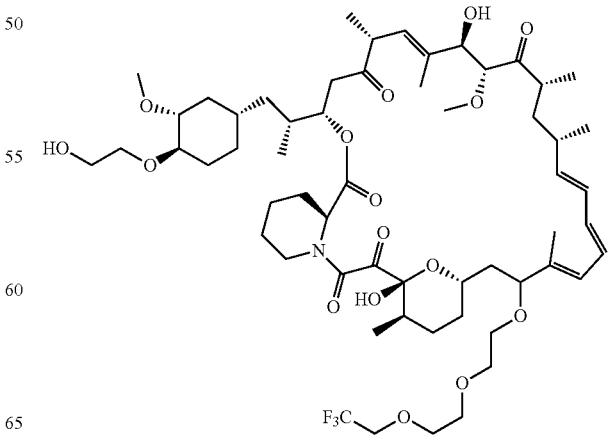

I-86

351
-continued
352
-continued
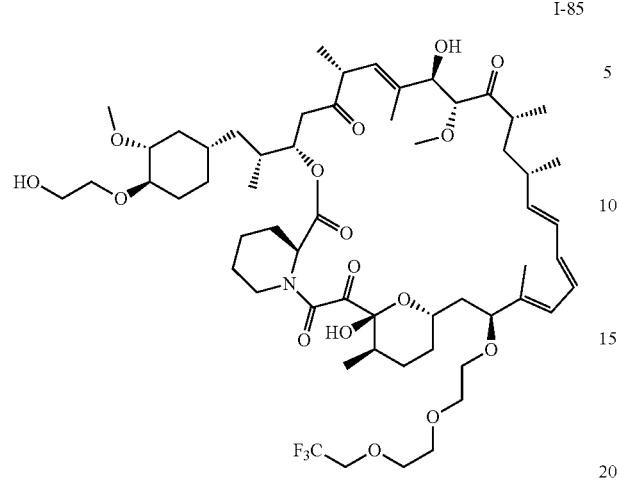
I-85
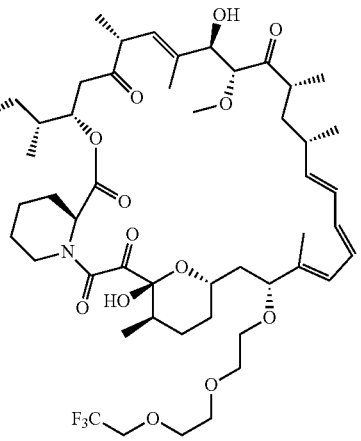
I-124
Synthetic Scheme:
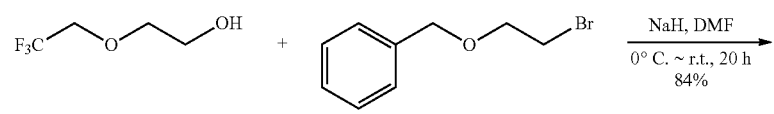
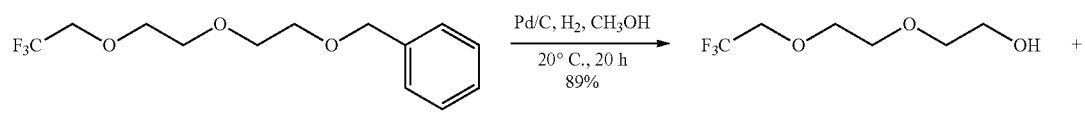
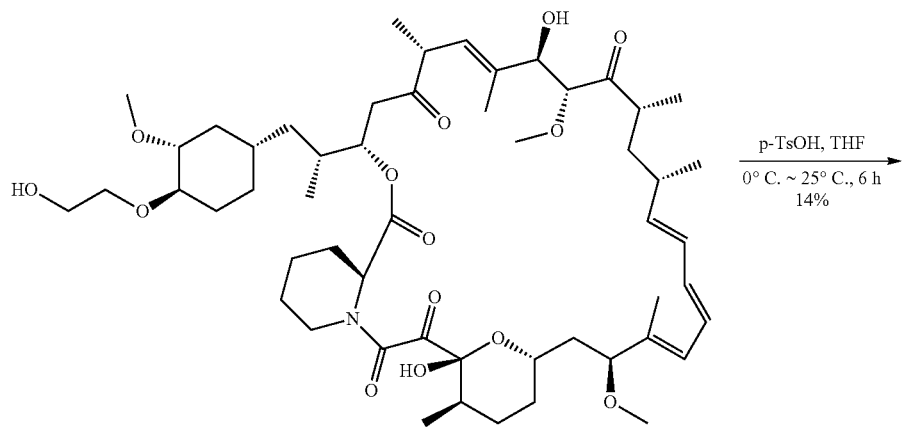

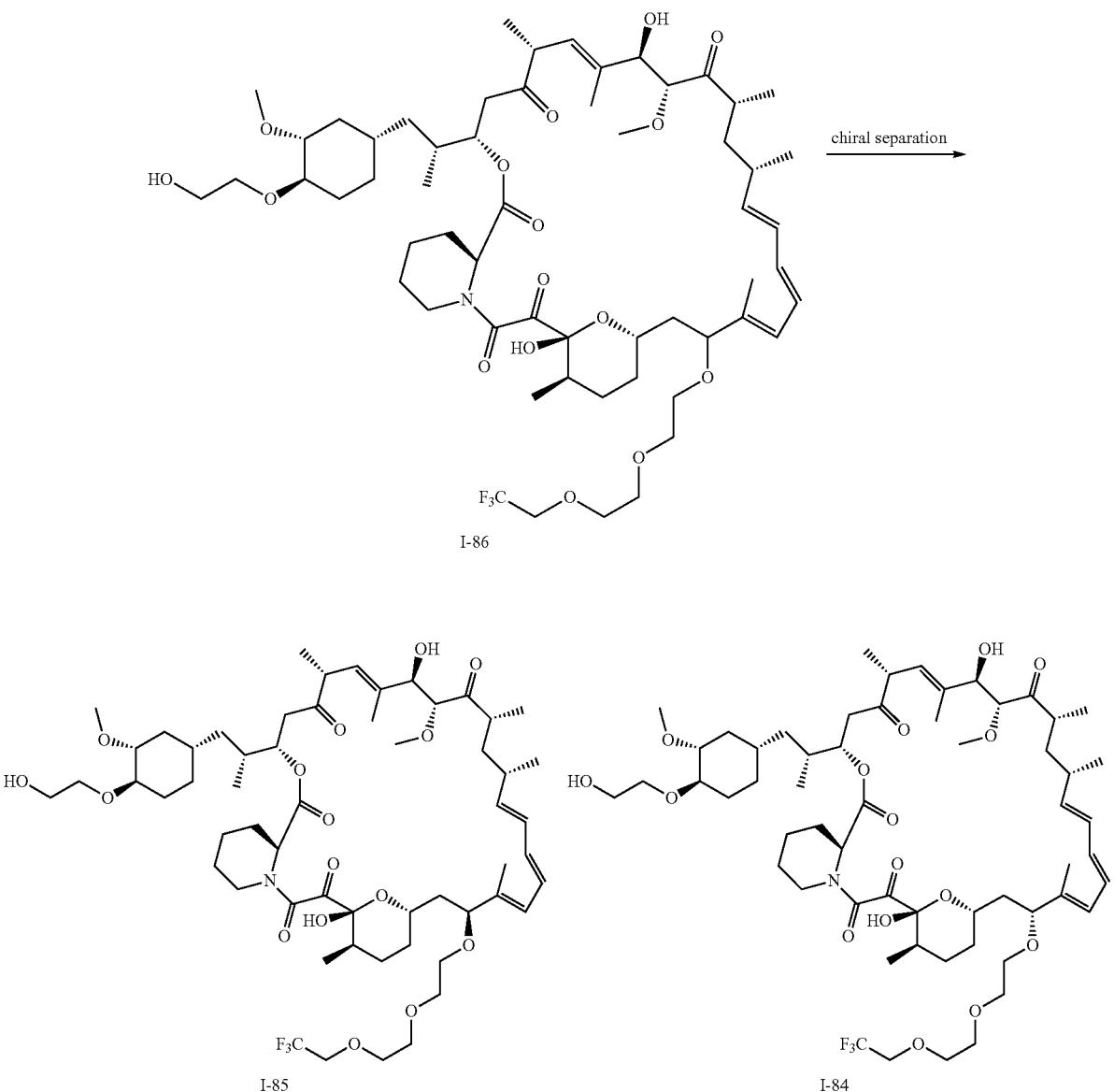

Procedures and Characterization:
Step 1: Synthesis of 2-[2-(2,2,2-trifluoroethoxy)ethoxy] ethoxymethylbenzene:

To a slurry of sodium hydride (12.49 g, 520.5 mmol) in DMF (150 mL) was added 2-(2,2,2-trifluoroethoxy)ethanol (5 g, 34.7 mmol) in DMF (10 mL) under $N_2$ at 0° C. The mixture was stirred at for 0° C. 1 h, then 2-bromoethoxymethylbenzene (18.66 g, 86.75 mmol) was added dropwise and the reaction stirred at room temperature for 20 h. The mixture was quenched by water (50 mL) and extracted with EtOAc (80 mL). The organic layer was washed with water (50 mL×3), brine (50 mL), dried over anhydrous $Na_2SO_4$, filtered and concentrated. The residue was purified via silica gel chromatography (PE:EtOAc=25:1 to 20:1) to obtain 2-[2-(2,2,2-trifluoroethoxy)ethoxy]ethoxymethylbenzene (8.1 g, 83.9% yield) as colorless liquid. NMR (400 MHz, CDCl$_3$): δ 7.37-7.26 (m, 5H), 4.57 (s, 2H), 3.90 (q, J=8.8 Hz, 2H), 3.79 (dd, J=5.6, 3.5 Hz, 2H), 3.71-3.61 (m, 6H).

Step 2: Synthesis of 2-[2-(2,2,2-trifluoroethoxy)ethoxy]:

To a solution of 2-[2-(2,2,2-trifluoroethoxy)ethoxy] ethoxymethylbenzene (0.5 g, 1.80 mmol) in CH$_3$OH (10 mL) was added Pd/C (436.45 mg). This mixture was then stirred under H$_2$ atmosphere at room temperature for 20 h, filtered and the filtrate concentrated and purified via silica gel chromatography (DCM: CH$_3$OH=50: 1) to obtain 2-[2-(2,2,2-trifluoroethoxy)ethoxy]ethanol (0.30 g, 89% yield) as colorless oil. $^1$H NMR (400 MHz, CDCl$_3$) δ 3.91 (q, J=8.7 Hz, 2H), 3.80 (dd, J=5.6, 3.4 Hz, 2H), 3.75 (d, J=4.0 Hz, 2H), 3.70 (dd, J=5.5, 3.5 Hz, 2H), 3.62 (dd, J=5.2, 3.9 Hz, 2H), 2.23 (t, J=5.7 Hz, 1H (OH)). $^{19}$F NMR (376 MHz, CDCl$_3$, (trifluoromethyl)benzene as standard) δ −74.33 (t, J=8.8 Hz).

Step 3: Synthesis of (21E,23E,25E,26E,35R,36S,37R,38R,40S,42S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy) ethoxy]ethoxy]-67,68-dioxa-58-azatricyclohexatriaconta-21,23,25(48),26(49)-tetraene-50,51,52,53,54-pentone (I-86):

A solution of everolimus (0.5 g, 0.52 mmol) in THF (5 mL) was degassed, p-toluenesulfonic acid (0.45 g, 2.61 mmol) was added at 0° C. followed by 2-[2-(2,2,2-trifluoroethoxy)ethoxy]ethanol (0.98 g, 5.22 mmol). The resulting mixture was stirred at 0° C. for 0.5 h under $N_2$, then at 23° C. for 6 h, poured into sat.NaHCO$_3$ (40 mL) and extracted with EtOAc (30 mL). The organic layer was washed with water (30 mL× 2), brine (40 mL), dried over anhydrous Na$_2$SO$_4$, filtered, and concentrated under reduced pressure. The residue was purified by reverse phase chromatography (C18, CH$_3$CN:H$_2$O from 0% to 70% yield) to provide (21E,23E,25E,26E,35R,36S,37R,38R,40S,42S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-86: 0.08 g, 14% yield) as a white solid. ESI-MS (EI$^+$, m/z): 1136.5 [M+Na]$^+$. $^1$H NMR (400 MHz, CDCl$_3$): δ 6.44-5.88 (m, 4H), 5.73-5.06 (m, 4H), 4.52-4.32 (m, 1H), 4.22-4.12 (m, 1H), 3.91-3.81 (m, 2H), 3.71-3.51 (m, 6H), 3.42-3.21 (m, 16H), 3.13-2.98 (m, 4H), 2.63-2.42 (m, 4H), 2.32-2.14 (m, 2H), 2.05-1.93 (m, 3H), 1.86-1.55 (m, 16H), 1.44-1.35 (m, 4H), 1.24-1.15 (m, 5H), 1.06-0.78 (m, 17H), 0.65-0.51 (m, 1H).

Step 4: Synthesis of (21E,23E,25E,26E,35R,36S,37R,38R,40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-85):

100 mg of (21E,23E,25E,26E,35R,36S,37R,38R,40S,42S,45S, 46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy) ethoxy]ethoxy]-67,68-dioxa-58-azatricyclohexatriaconta-21,23,25(48),26(49)-tetraene-50,51,52,53,54-pentone was purified via prep chiral HPLC which provided (21E,23E,25E,26E,35R,36S,37R,38R,40S,42S,44S,45S,46R,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-44-[2-[2-(2,2,2-trifluoroethoxy)ethoxy]ethoxy]-67,68-dioxa-58-azatricyclohexatriaconta-21,23,25(48),26(49)-tetraene-50,51,52,53,54-pentone (I-85: 14.3 mg, 14.3% yield) as a white solid.

Chiral separation method:
Column: CHIRALPAK IC
Column size: 5.0 cm I.D.×25 cm L
Solution concentration: 2.4 mg/ml
Injection: 5 ml
Mobile phase: Hexane/EtOH=70/30(V/V)
Flow rate: 30 ml/min
Wave length: UV 254 nm
Temperature: 35° C.

I-85: ESI-MS (EI$^+$, m/z): 1136.4 [M+Na]$^+$. $^1$H NMR (400 MHz, CDCl$_3$) δ 6.42-6.06 (m, 3H), 5.92 (dd, J=30.3, 10.3 Hz, 1H), 5.56-5.06 (m, 5H), 4.74 (s, 1H), 4.18 (d, J=5.7 Hz, 1H), 3.94-3.83 (m, 2H), 3.82-3.51 (m, 12H), 3.49-3.25 (m, 11H), 3.22-3.03 (m, 2H), 2.72 (dd, J=16.6, 5.5 Hz, 2H), 2.57 (dd, J=17.0, 6.5 Hz, 1H), 2.34 (d, J=12.4 Hz, 2H), 2.25-2.18 (m, 1H), 2.13-1.85 (m, 5H), 1.69 (dd, J=35.2, 8.9 Hz, 10H), 1.47 (dd, J=20.5, 13.6 Hz, 5H), 1.26 (s, 7H), 1.15-0.81 (m, 18H), 0.71 (dd, J=23.9, 12.0 Hz, 1H).

EXAMPLE 38

Synthesis of (21E,23E,25E,26E,33R,34S,35R,36R,38S,40S,43S,44R,45R,54R)-44,54-dihydroxy-43-[(1R)-2-1(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-91) and (21E,23E,25E,26E,33R,34S,35R,36R,38S,40S,42S,43S,44R,45R,54R)-44,54-dihydroxy-43-[(1R)-2-1(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-85) and (21E,23E,25E,26E,33R,34S,35R,36R,38S,40S,42R,43S,44R,45R,54R)-44,54-dihydroxy-43-[(1R)-2-1(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone:

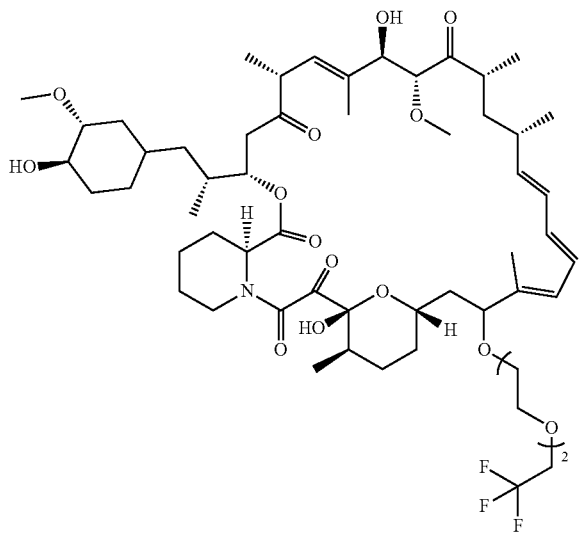

I-91

357
-continued
I-125
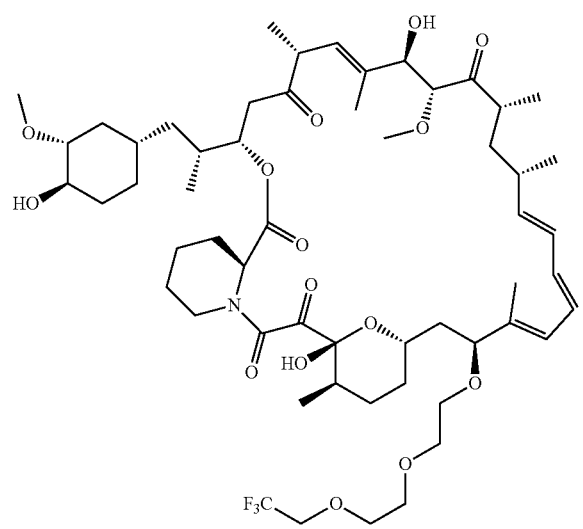
358
-continued
I-126
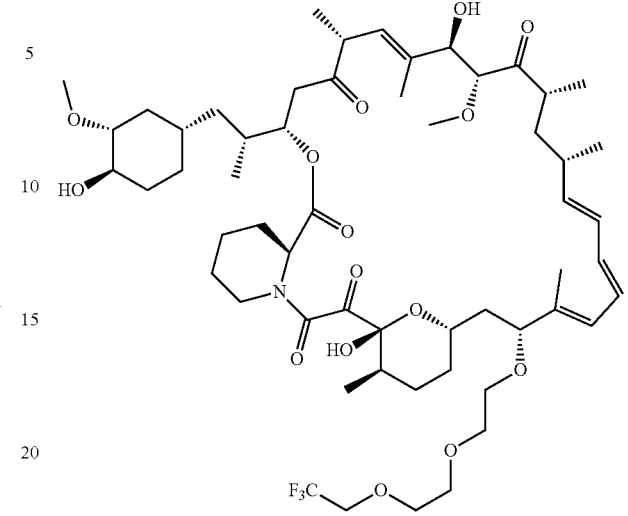
Synthetic Scheme:
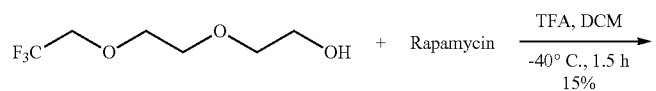
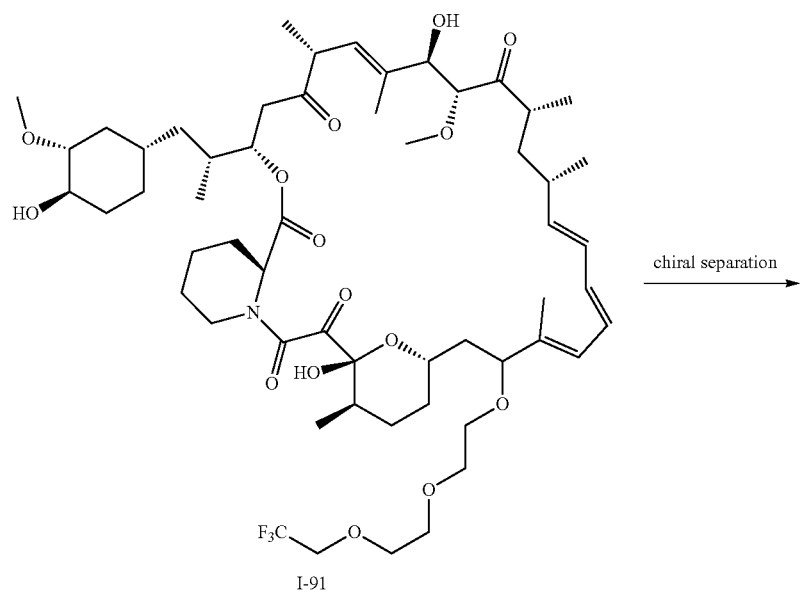
I-91

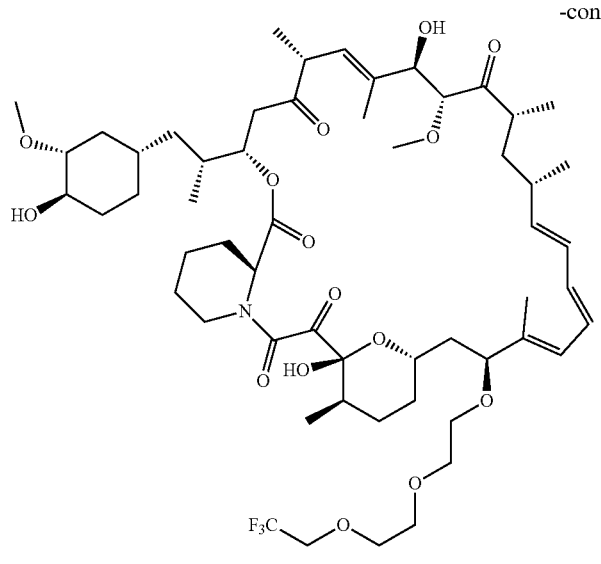

I-125

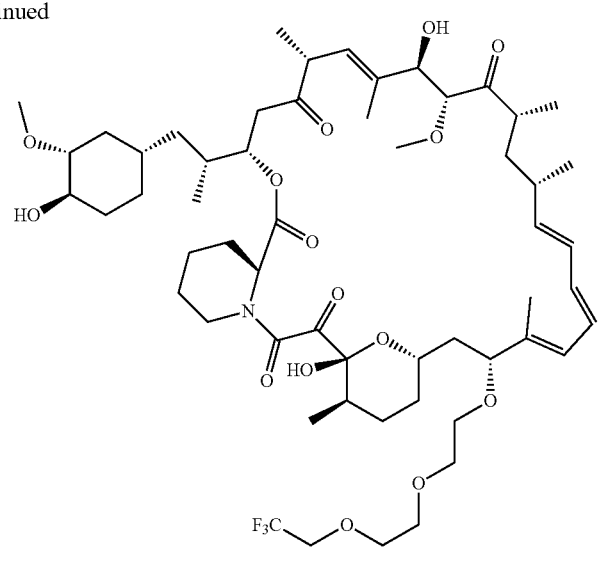

I-126

Procedures and Characterization:

Step 1: Synthesis of 2-[2-(2,2,2-trifluoroethoxy)ethoxy]ethanol:

2-[2-(2,2,2-trifluoroethoxy)ethoxy]ethanol was same as Example 37.

Step 2: Synthesis of (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-91):

A solution of rapamycin (0.5 g, 0.547 mmol) in DCM (20 mL) was degassed at −40° C., and trifluoroacetic acid (1.67 mL) was added. After stirring for 10 min. 2-[2-(2,2,2-trifluoroethoxy)ethoxy]ethanol (0.2 g, 1.09 mmol) was added. The mixture was stirred at −40° C. for a further 40 min. then poured into ice cold NaHCO₃ (aq. 60 mL), washed with water (20 mL), brine (20 mL), dried over MgSO₄, filtered and concentrated. The residue was purified by reverse phase chromatography (C18, CH₃CN:H₂O=65:35) to provide (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-91: 85 mg, 15% yield) as a white solid. ESI-MS (EI⁺, m/z): 1092.4 [M+Na]⁺. ¹H NMR (400 MHz, CDCl₃) δ 6.45-5.76 (m, 4H), 5.40 (ddd, J=24.9, 15.2, 8.0 Hz, 2H), 5.25-4.99 (m, 2H), 4.57-4.01 (m, 3H), 3.98-3.45 (m, 7H), 3.43-2.99 (m, 11H), 2.95-2.37 (m, 6H), 2.26 (d, J=13.9 Hz, 2H), 2.08-1.76 (m, 6H), 1.75-1.52 (m, 14 H) 1.48-1.10 (m, 10H), 1.07-0.74 (m, 18H), 0.60 (dd, J=23.5, 12.0 Hz, 1H).

Step 3: Synthesis of (21E,23E,25E,26E,33R,34S,35R,36R,38S,40S,42R,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-126):

159 mg of (21E,23E,25E,26E,33R,34S,35R,36R,38S,40S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone was purified via prep chiral HPLC to provide (21E,23E,25E,26E,33R,34S,35R,36R,38S,40S,42S,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-125: 48.5 mg, 30% yield) and (21E,23E,25E,26E,33R,34S,35R,36R,38S,40S,42R,43S,44R,45R,54R)-44,54-dihydroxy-43-[(1R)-2-[(1S,3R,4R)-4-hydroxy-3-methoxy-cyclohexyl]-1-methyl-ethyl]-45-methoxy-33,34,35,36,46,47-hexamethyl-42-[2-[2-(2,2,2-trifluoroethoxy)ethoxy]ethoxy]-65,66-dioxa-56-azatricyclohexatriaconta-21,23,25(46),26(47)-tetraene-48,49,50,51,52-pentone (I-126:43 mg, 27% yield) as a white solid.

Chiral separation method:
Column: CHIRALPAK IC
Column size: 5.0 cm I.D.×25 cm L
Solution concentration: 3.0 mg/ml
Injection: 3 ml
Mobile phase: Hexane/EtOH=70/30(V/V)
Flow rate: 30 ml/min
Wave length: UV 254 nm
Temperature: 35° C.

I-125: ESI-MS (EI⁺, m/z): 1092.4 [M+Na]⁺. ¹H NMR (400 MHz, CDCl₃) δ 6.36-6.13 (m, 2H), 6.06 (dd, J=15.0, 10.0 Hz, 1H), 5.85 (dd, J=29.4, 10.8 Hz, 1H), 5.49-5.37 (m, 1H), 5.33 (d, J=10.0 Hz, 1H), 5.20 (d, J=4.6 Hz, 1H), 5.08 (t, J=11.7 Hz, 1H), 4.68 (s, 1H), 4.11 (d, J=5.8 Hz, 1H), 3.94-3.64 (m, 7H), 3.63-3.46 (m, 5H), 3.42-3.18 (m, 12H), 2.93-2.79 (m, 2H), 2.71-2.43 (m, 4H), 2.27 (d, J=11.8 Hz, 2H), 2.08-1.85 (m, 6H), 1.83-1.61 (m, 11H), 1.48-1.21 (m, 8H), 1.08-0.74 (m, 18H), 0.65-0.54 (m, 1H).

I-126: ESI-MS (Er, m/z): 1092.4 [M+Na]⁺. ¹H NMR (400 MHz, CDCl₃) δ 6.41-6.07 (m, 3H), 6.00-5.81 (m, 1H), 5.56-5.05 (m, 4H), 4.75 (s, 1H), 4.18 (d, J=5.8 Hz, 1H), 3.98-3.52 (m, 11H), 3.50-3.22 (m, 12H), 2.95 (d, J=8.6 Hz, 1H), 2.77-2.50 (m, 4H), 2.38-2.16 (m, 2H), 2.12-1.83 (m, 5H), 1.69 (dd, J=39.3, 11.0 Hz, 12H), 1.49-1.17 (m, 11H), 1.15-0.80 (m, 18H), 0.74-0.60 (m, 1H).

EXAMPLE 39

Synthesis of (21E,23E,25E,26E,34R,35S,36R,37R, 39S,41S,44S,45R,46R,55R)-45,55-dihydroxy-44-[(1R)-2-1(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49,50,51,52,53-pentone (I-88) and (21E, 23E,25E,26E,34R,35S,36R,37R,39S,41S,43R,44S, 45R,46R,55R)-45,55-dihydroxy-44-[(1R)-2-1(1S, 3R,4R)-4-(2-hydroxyethoxy)-3-methoxy-cyclohexyl]-1-methyl-ethyl]-46-methoxy-34,35,36, 37,47,48-hexamethyl-43-[2-[2-(trifluoromethoxy) ethoxy]ethoxy]-66,67-dioxa-57-azatricyclohexatriaconta-21,23,25(47),26(48)-tetraene-49,50,51,52,53-pentone (I-82) and (21E, 23E,25E,26E,34R,35S,36R,37R,39S,41S,43S,44S, 45R,46R,55R)-45,55-dihydroxy-44-[(1R)-2-[(1S,3R, 4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy] ethoxy]-66,67-dioxa-57-azatricyclohexatriaconta-21, 23,25(47),26(48)-tetraene-49,50,51,52,53-pentone (I-83):

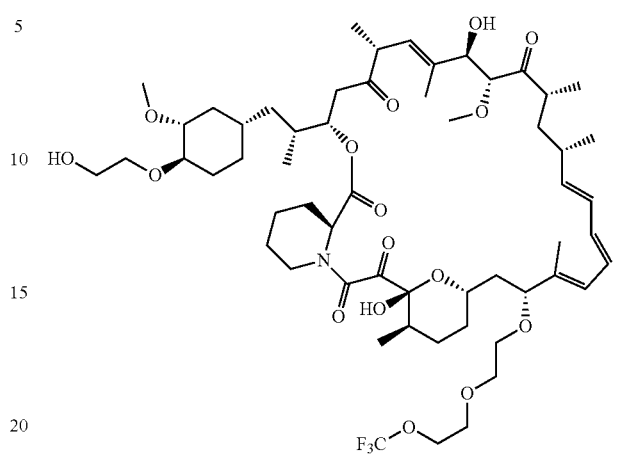

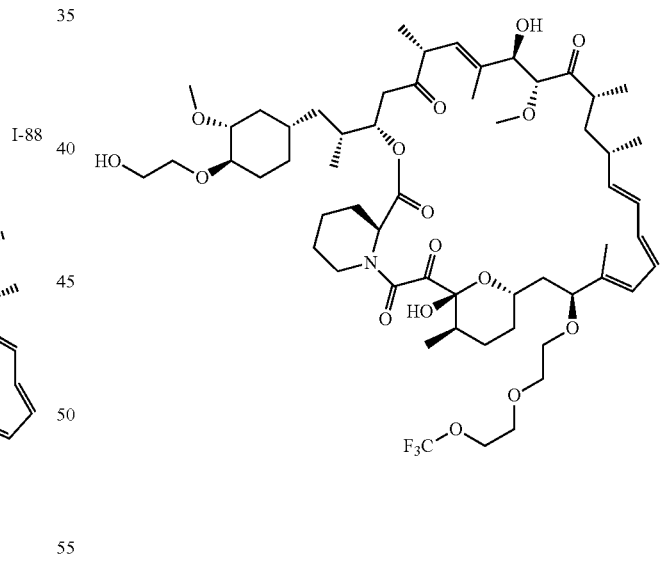

Synthetic Scheme:

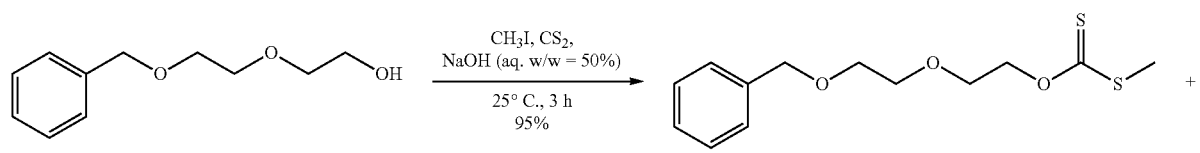

363
364
-continued
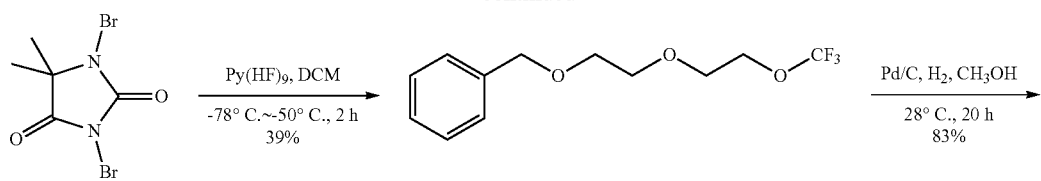
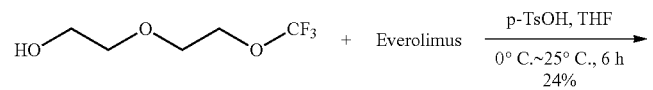
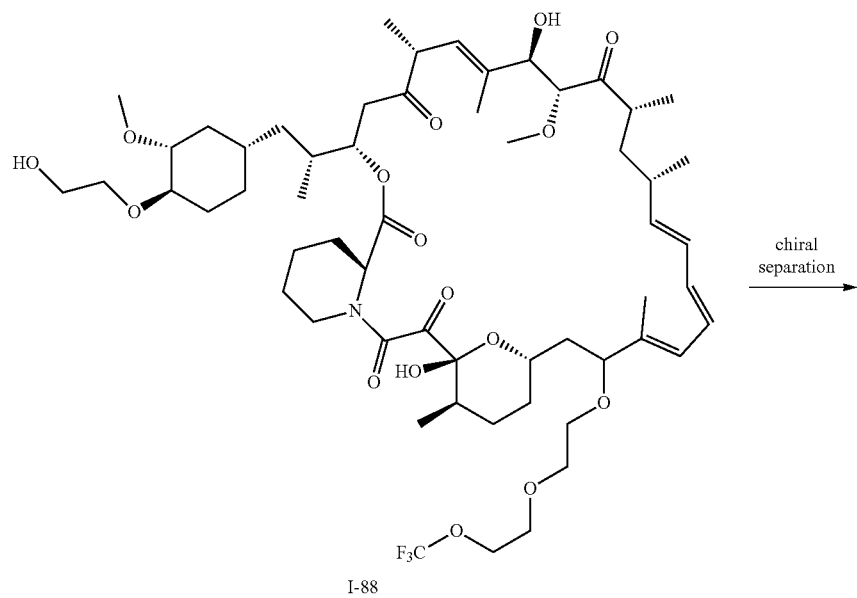
I-88
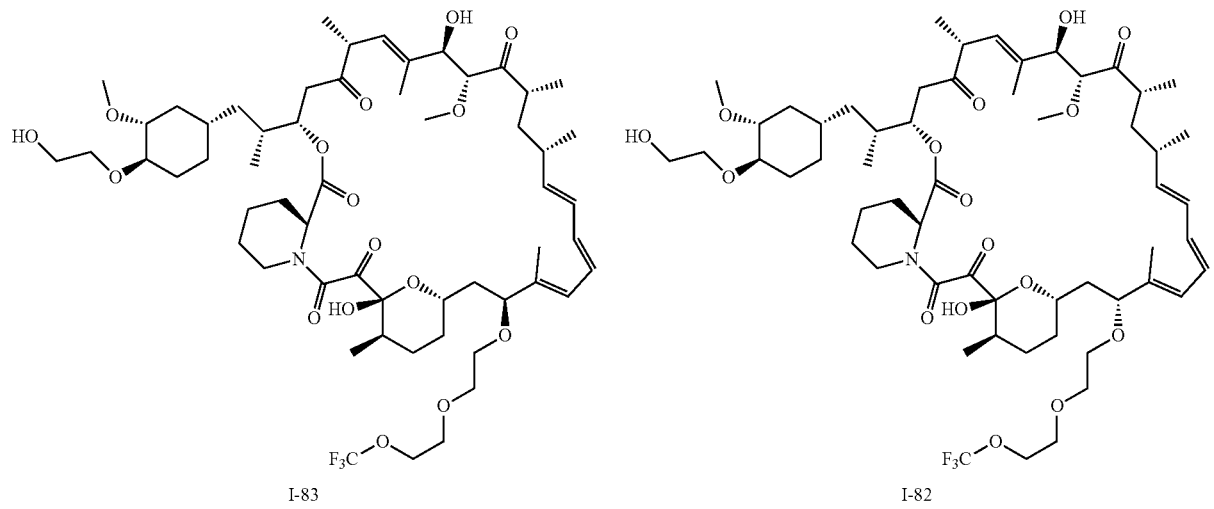
I-83
I-82

Procedures and Characterization:
Step 1: Synthesis of O-[2-(2-benzyloxyethoxy)ethyl]methylsulfanylmethanethioate:

A two-necked 1000 mL round-bottom flask equipped with a magnetic stir bar was charged with 2-(2-benzyloxyethoxy) ethanol (12 g, 61.2 mmol) and benzyl(triethyl)ammonium chloride (1.0 g, 4.87 mmol). A 50% aqueous solution of sodium hydroxide (141 mL) was added via a dropping funnel. After the mixture was stirred for 10 min, $CS_2$ (141 mL, 2.34 mol) was added dropwise, followed by iodomethane (22.0 g, 154 mmol). The mixture was stirred for 3 h at room temperature. Water (100 mL) was added. The organic layer was removed, and the aqueous phase was extracted with $CH_2Cl_2$ (100 mL×3). The combined organic layers were washed with brine (2×100 mL), dried over $MgSO_4$, filtered and concentrated. The residue was purified via silica gel chromatography (EtOAc:PE=1:3) to obtain O-[2-(2-benzyloxyethoxy)ethyl]methylsulfanylmethanethioate (16.8 g, 95% yield) as a yellow oil. ESI-MS (EI$^+$, m/z): 308.9 [M+Na]$^+$. $^1$H NMR (500 MHz, DMSO-d$_6$) δ 7.32 (dt, J=18.3, 6.8 Hz, 5H), 4.74-4.62 (m, 2H), 4.50 (s, 2H), 3.85-3.72 (m, 2H), 3.60 (ddd, J=8.7, 6.2, 3.6 Hz, 4H), 2.56 (s, 3H).

Step 2: Synthesis of 2-[2-(trifluoromethoxy)ethoxy] ethoxymethylbenzene:

To a suspension of 1,3-dibromo-5,5-dimethyl-imidazolidine-2,4-dione (29.95 g, 104.75 mmol) in DCM (150 mL) was added (HF)$_9$/Py pyridinium poly (hydrogen fluoride) (49.36 mL, 209.49 mmol,) and O-[2-(2-benzyloxyethoxy) ethyl]methylsulfanylmethanethioate (10 g, 34.92 mmol) at −78° C., and the mixture was stirred at −50° C. for 2 h. The mixture was poured into an aqueous solution of $NaHCO_3$ and $NaHSO_3$, dried over anhydrous $Na_2SO_4$, filtered, and concentrated, then purified via silica gel chromatography (PE:EtOAc=25:1) to provide the crude product. Then the crude was further purified via silica gel chromatography (PE:E0Ac=100:1 to 50:1 to 40:1) to obtain 2-[2-(trifluoromethoxy)ethoxy]ethoxymethylbenzene (3.6 g, 39% yield) as colorless liquid. ESI-MS (EI$^+$, m/z): 287.1 [M+Na]$^+$. $^1$H NMR (400 MHz, CDCl$_3$) δ 7.37-7.22 (m, 5H), 4.57 (s, 2H), 4.10 (t, J=4.8 Hz, 2H), 3.75 (t, J=4.8 Hz, 2H), 3.72-3.62 (m, 4H).

Step 3: Synthesis of 2-[2-(trifluoromethoxy)ethoxy]ethanol:

To a solution of 2[2-(trifluoromethoxy)ethoxy]ethoxymethylbenzene (3.4 g, 12.87 mmol) in $CH_3OH$ (60 mL) was added Pd/C (3.13 g). This mixture was then stirred under $H_2$ atmosphere at room temperature for 20 h, filtered, concentrated then purified by silica gel chromatography (DCM:$CH_3OH$=50: 1) to provide 2-[2-(trifluoromethoxy)ethoxy] ethanol (1.87 g, 83% yield) as colorless liquid. $^1$H NMR (400 MHz, CDCl$_3$) δ 4.11-4.03 (m, 2H), 3.69 (dt, J=4.4, 2.3 Hz, 4H), 3.61-3.54 (m, 2H), 2.75 (t, J=5.9 Hz, 1H). $^{19}$F NMR (376 MHz, CDCl$_3$) δ −61.11 (s).

Step 4: Synthesis of (21E,23E,25E,26E,34R,35S,36R,37R, 39S,41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49,50,51,52,53-pentone (I-88):

To a degassed solution of everolimus (0.5 g, 0.52 mmol) in THF (30 mL) was added p-toluenesulfonic acid (0.45 g, 2.61 mmol) at 0° C. followed by 2-[2-(trifluoromethoxy) ethoxy]ethanol (0.91 g, 5.22 mmol). The resulting mixture was stirred at 0° C. for 0.5 h under N$_2$, then at 23° C. for 6 h. The reaction was poured into sat.NaHCO$_3$ (40 mL) and extracted with EtOAc (30 mL). The organic layer was washed with water (30 mL×2), brine (20 mL), dried over anhydrous Na$_2$SO$_4$, filtered, and concentrated under reduced pressure at room temperature. The residue was purified by reverse phase chromatography (C18, CH$_3$CN: H$_2$O=0% to 70% yield) to provide (21E,23E,25E,26E,34R,35S,36R, 37R,39S, 41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49,50,51,52,53-pentone (I-88: 141 mg, 24% yield) as a white solid. ESI-MS (EI$^+$, m/z): 1122.3 [M+Na]$^+$. $^1$H NMR (400 MHz, CDCl$_3$) δ 6.39-5.88 (m, 4H), 5.73-5.05 (m, 5H), 4.52-3.83(m, 5H), 3.70-3.50 (m, 6H), 3.43-3.21 (m, 8H), 3.12-2.93 (m, 4H), 2.80-2.44 (m, 4H), 2.31-2.16 (m, 4H), 2.05-1.59 (m, 20H), 1.43-1.34 (m, 4H), 1.21-1.09 (m, 6H), 1.01-0.78 (m, 17H), 0.62-0.51 (m, 1H).

Step 5: Synthesis of (21E,23E,25E,26E,34R,35S,36R,37R, 39S,41S,43S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy) ethoxy]ethoxy]-66,67-dioxa-57-azatricyclohexatriaconta-21,23,25(47),26(48)-tetraene-49,50,51,52,53-pentone (I-83) and (21E,23E,25E,26E,34R,35S,36R,37R,39S,41S,43R,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49, 50,51,52,53-pentone (I-82):

130 mg of (21E,23E,25E,26E,34R,35S,36R,37R,39S, 41S,44S,45R,46R,55R)-45,55-dihydroxy-44-[(1R)-2-[(1S, 3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy) ethoxy]ethoxy]-66,67-dioxa-57-azatricyclohexatriaconta-21,23,25(47),26(48)-tetraene-49,50,51,52,53-pentone was purified via prep chiral HPLC to provide (21E,23E,25E,26E,34R,35S,36R,37R,39S,41S, 43R,44S,45R,46R,55R)-45,55-dihydroxy-44-[(1R)-2-[(1S, 3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49,50,51,52,53-pentone (I-82: 19 mg, 14.6% yield) and (21E,23E,25E,26E,34R,35S,36R,37R,39S,41S,43S,44S, 45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(trifluoromethoxy)ethoxy]ethoxy]-66,67-dioxa-57-azatricyclohexatriaconta-21,23,25(47),26(48)-tetraene-49,50,51,52,53-pentone (I-83: 12 mg, 9.2% yield), both as white solids.

Chiral analysis method:
Column: CHIRALPAK IC(IC00CE-OL002)
Column size: 0.46 cm I.D.×25 cm L
Injection: 40.0 ul
Mobile phase: Hexane/EtOH=60/40(V/V)
Flow rate: 1.0 ml/min
Wave length: UV 254 nm
Temperature: 35° C.
HPLC equipment: Shimadzu LC-20AT CP-HPLC-07

I-82: ESI-MS (EI$^+$, m/z): 1122.4 [M+Na]$^+$. $^1$H NMR (500 MHz, CDCl$_3$) δ 6.43-5.83 (m, 4H), 5.57-5.13 (m, 5H), 4.31-4.04 (m, 3H), 3.91-3.53 (m, 11H), 3.49-3.00 (m, 19H), 2.76-2.52 (m, 3H), 2.25 (dd, J=34.2, 26.6 Hz, 3H), 2.12-1.96

(m, 5H), 1.75 (dd, J=35.2, 24.7 Hz, 8H), 1.52-1.34 (m, 8H), 1.15-0.79 (m, 18H), 0.72 (d, J=12.1 Hz, 1H).

I-83: ESI-MS (EI+, m/z): 1122.4 [M+Na]+.1H NMR (500 MHz, CDCl3) δ 6.54-6.41 (m, 1H), 6.18 (tdd, J=29.7, 22.4, 12.7 Hz, 3H), 5.82-5.68 (m, 1H), 5.46-5.30 (m, 2H), 5.19 (dd, J=25.5, 20.6 Hz, 2H), 4.62-4.40 (m, 1H), 4.21 (d, J=18.4 Hz, 1H), 3.94 (dd, J=34.8, 4.5 Hz, 1H), 3.83-3.62 (m, 4H), 3.59 (d, J=3.3 Hz, 1H), 3.50-2.95 (m, 13H), 2.62 (dt, J=55.5, 38.6 Hz, 2H), 2.42-2.17 (m, 3H), 2.16-1.57 (m, 24H), 1.54-1.27 (m, 10H), 1.12-0.80 (m, 18H), 0.71-0.62 (m, 1H).

EXAMPLE 40

Synthesis of (21E,23E,25E,26E,34R,35S,36R,37R, 39S,41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-87) and (21E, 23E,25E,26E,34R,35S,36R,37R,39S,41S,43R,44S, 45R,46R,55R)-45,55-dihydroxy-44-[(1R)-2-R1S,3R, 4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy) ethoxy]ethoxy]-67,68-dioxa-58-azatricyclohexatriaconta-21,23,25(47),26(48)-tetraene-49,50,51,52,53-pentone (I-79) and (21E, 23E,25E,26E,34R,35S,36R,37R,39S,41S,43S,44S, 45R,46R,55R)-45,55-dihydroxy-44-[(1R)-2-R1S,3R, 4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy) ethoxy]ethoxy]-67,68-dioxa-58-azatricyclohexatriaconta-21,23,25(47),26(48)-tetraene-49,50,51,52,53-pentone (I-80):

I-87

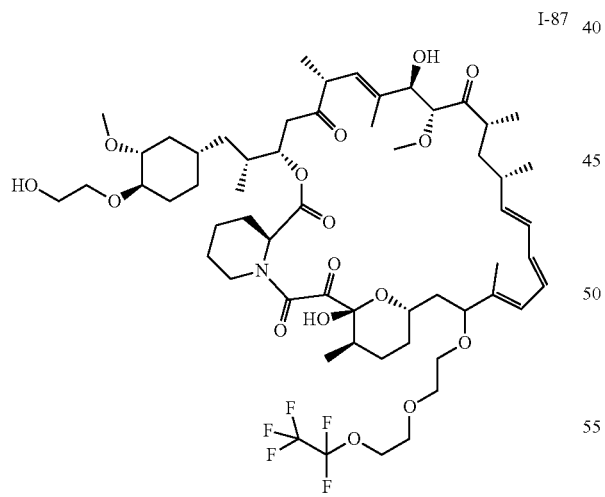

I-79

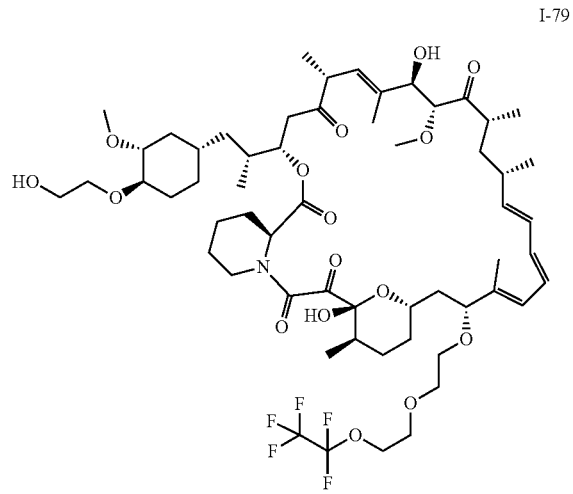

I-80

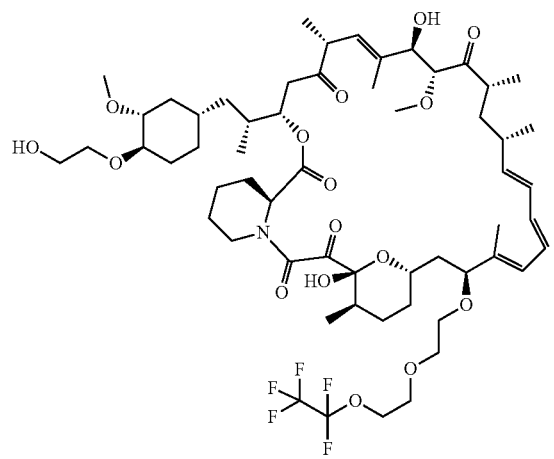

Synthetic Scheme:

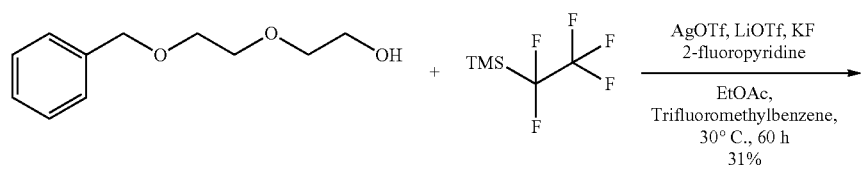

-continued
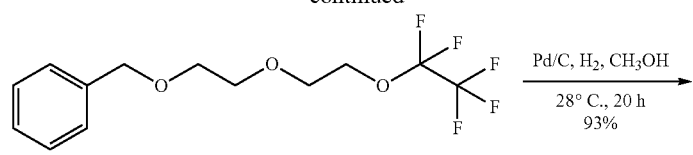
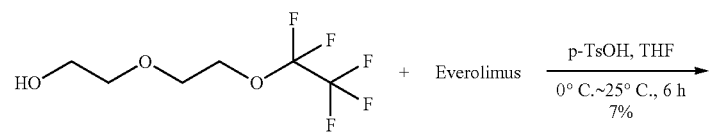
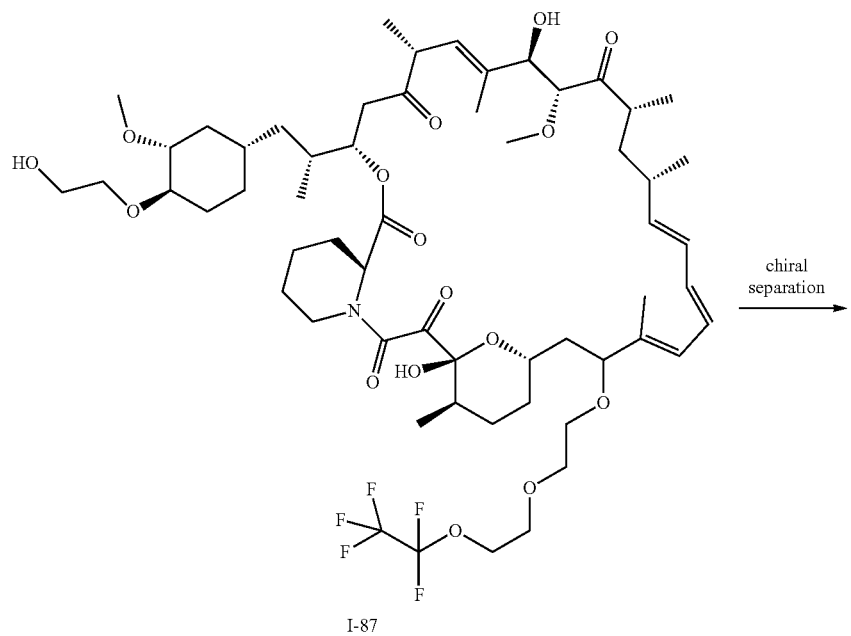
I-87
chiral separation →
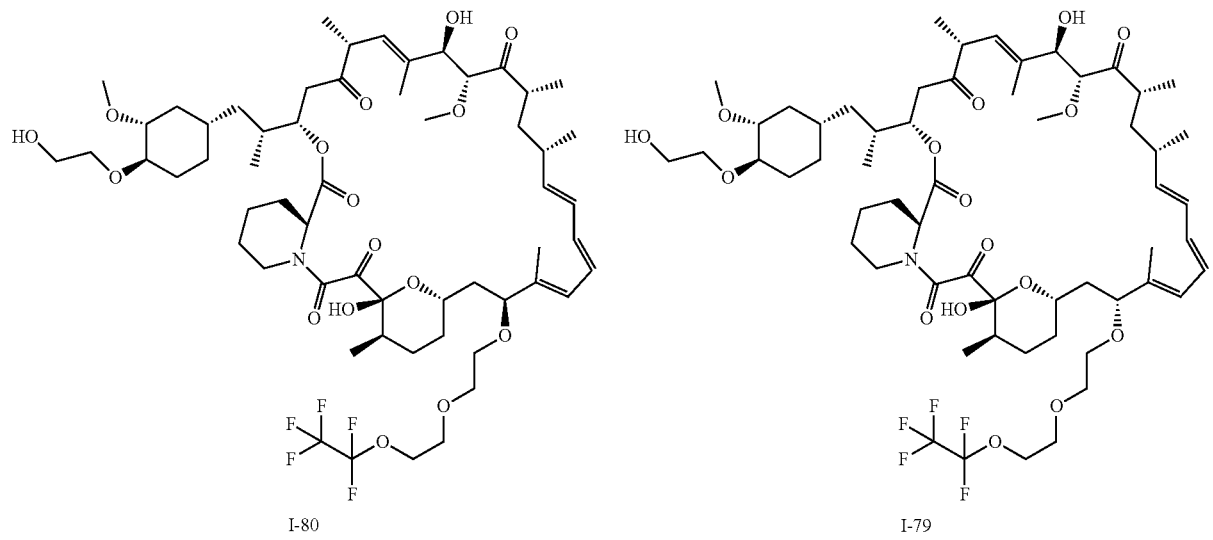
I-80          I-79

Procedures and Characterization:

Step 1: Synthesis of 2-[2-(1,1,2,2,2-pentafluoroethoxy)ethoxy]ethoxymethylbenzene:

Under a nitrogen atmosphere, silver trifluoromethane sulfonate (19.64 g, 76.44 mmol), lithium trifluoromethane sulfonate (3.97 g, 25.48 mmol), 1-(chloromethyl)-4-fluoro-1,4-diazoniabicyclo[2.2.2]octane bis(tetrafluoroborate) (18.05 g, 50.96 mmol) and potassium fluoride (5.92 g, 101.92 mmol) were mixed. 2-(2-benzyloxyethoxy)ethanol (5 g, 25.48 mmol), trimethyl(1,1,2,2,2-pentafluoroethyl)silane (14.69 g, 76.44 mmol), EtOAc (20 mL), trifluoromethylbenzene (20 mL), and 2-fluoropyridine (7.42 g, 76.44 mmol) were then added under $N_2$ atmosphere in this order. The reaction mixture was stirred under $N_2$ atmosphere for 60 h at 30° C. then filtered through a plug of silica (eluting with EtOAc). The filtrate was collected and concentrated. The residue was purified via silica gel chromatography (PE:EtOAc=25:1) to obtain 2-[2-(1,1,2,2,2-pentafluoroethoxy)ethoxy]ethoxymethylbenzene (2.5 g, 31% yield) as a light yellow liquid. $^1$H NMR (400 MHz, CDCl$_3$) δ 7.36-7.24 (m, 5H), 4.56 (s, 2H), 4.17-4.11 (m, 2H), 3.76-3.72 (m, 2H), 3.71-3.65 (m, 2H), 3.65-3.60 (m, 2H). $^{19}$F NMR (376 MHz, CDCl$_3$) δ −90.77 (s), −86.02 (s).

Step 2: Synthesis of 2-[2-(1,1,2,2,2-pentafluoroethoxy)ethoxy]ethanol:

To a solution of 2-[2-(1,1,2,2,2-pentafluoroethoxy)ethoxy]ethoxymethylbenzene (0.757 g, 2.41 mmol) in CH$_3$OH (10 mL) was added Pd/C (0.58 g). The mixture was stirred under H$_2$ atmosphere at room temperature for 20 h then filtered and concentrated. The residue was purified by silica gel chromatography (DCM:CH$_3$OH=50:1) to obtain 2-[2-(1,1,2,2,2-pentafluoroethoxy)ethoxy]ethanol (0.5 g, 93% yield) as a colorless liquid. $^1$H NMR (400 MHz, CDCl$_3$) δ 4.13-4.06 (m, 2H), 3.69 (dd, J=5.4, 4.1 Hz, 4H), 3.54 (dd, J=5.2, 3.9 Hz, 2H), 2.47 (s, 1H). $^{19}$F NMR (376 MHz, CDCl$_3$) δ −86.21 (d, J=1.2 Hz), −90.98 (d, J=1.2 Hz).

Step 3: Synthesis of (21E,23E,25E,26E,34R,35S,36R,37R,39S,41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-87):

To a solution of everolimus (0.5 g, 0.52 mmol) in THF (10 mL) was added p-toluenesulfonic acid (0.45 g, 2.61 mmol) at 0° C., followed by 2-[2-(1,1,2,2,2-pentafluoroethoxy)ethoxy]ethanol (0.58 g, 2.61 mmol). The resulting mixture was stirred at 0° C. for 0.5 h under N$_2$, then at 22° C. for 6 h, poured into sat. NaHCO$_3$ (40 mL) and extracted with EtOAc (30 mL). The organic layer was washed with water (30 mL×2), brine (20 mL), dried over anhydrous Na$_2$SO$_4$, filtered and concentrated under reduced pressure at room temperature. The residue was purified by reverse phase chromatography (C18, CH$_3$CN: H$_2$O 0% to 70% yield) to provide (21E,23E,25E,26E, 34R,35S,36R,37R,39S,41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53 -pentone (I-87: 40 mg, 7% yield) as a white solid. ESI-MS (EI$^+$, m/z): 1172.3 [M+Na]$^+$. $^1$H NMR (400 MHz, CDCl$_3$) 6.45-5.95 (m, 4H), 5.79-5.13 (m, 5H), 4.59-4.17 (m, 3H), 3.98-3.59 (m, 8H), 3.50-3.28 (m, 10H), 3.20-3.00 (m, 5H), 2.89-2.49 (m, 4H), 2.37-2.22 (m, 4H), 2.10-1.61 (m, 20H), 1.51-1.23 (m, 8H), 1.06-0.85 (m, 16H), 0.71-0.63 (m, 1H).

Step 4: Synthesis of (21E,23E,25E,26E,34R,35S,36R,37R,39S,41S,43S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-80) and (21E,23E,25E,26E,34R,35S,36R,37R,39S,41S,43R,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-79):

95 mg of (21E,23E,25E,26E,34R,35S,36R,37R,39S,41S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone was sent for chiral separation to obtain (21E,23E,25E,26E,34R,35S,36R,37R,39S,41S,43S,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-80: 7.2 mg, 7.5% yield) and (21E,23E,25E,26E,34R,35S,36R,37R,39S,41S,43R,44S,45R,46R,55R)-45,55-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-43-[2-[2-(1,1,2,2,2-pentafluoroethoxy)ethoxy]ethoxy]-67,68-dioxa-58-azatricyclohexatriaconta-21,23,25(47),26(48)-tetraene-49,50,51,52,53-pentone (I-79: 5.1 mg, 5.3% yield) as a white solid.

Chiral separation method:

Column: CHIRALPAK IC

Column size: 5.0 cm I.D.×25 cm L

Solution concentration: 0.79 mg/ml

Injection: 5 ml

Mobile phase: Hexane/EtOH=70/30(V/V)

Flow rate: 30 ml/min

Wave length: UV 254 nm

Temperature: 35° C.

I-80: ESI-MS (EI$^+$, m/z): 1150.3 [M+H]$^+$. $^1$H NMR (400 MHz, CDCl$_3$) δ 6.42-5.80 (m, 4H), 5.58-5.05 (m, 5H), 4.74 (s, 1H), 4.24-4.08 (m, 3H), 3.92-3.51 (m, 10H), 3.48-3.24 (m, 12H), 3.13 (ddd, J=24.2, 17.1, 11.3 Hz, 3H), 2.64 (ddd, J=23.4, 16.8, 6.0 Hz, 3H), 2.42-2.15 (m, 3H), 2.14-1.88 (m, 6H), 1.84-1.64 (m, 14H), 1.54-1.39 (m, 5H), 1.17-0.81 (m, 18H), 0.71 (dd, J=23.8, 12.1 Hz, 1H).

I-79: ESI-MS (EI$^+$, m/z): 1172.3 [M+Na]$^+$. $^1$H NMR (400 MHz, CDCl$_3$) δ 6.42-5.90 (m, 4H), 5.54-5.03 (m, 6H), 4.31-3.96 (m, 5H), 3.88-3.01 (m, 22H), 2.94-2.37 (m, 5H), 2.39-1.94 (m, 7H), 1.68 (dd, J=28.2, 19.2 Hz, 8H), 1.52-1.31 (m, 6H), 1.14-1.00 (m, 6H), 0.97-0.62 (m, 19H).

EXAMPLE 41

Synthesis of (21E,23E,25E,26E,36R,37S,38R,39R, 41S,43S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-76) and (21E, 23E,25E,26E,36R,37S,38R,39R,41S,43S,45S,46S, 47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-66) and (21E, 23E,25E,26E,36R,37S,38R,39R,41S,43S,45S,46S, 47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-67):

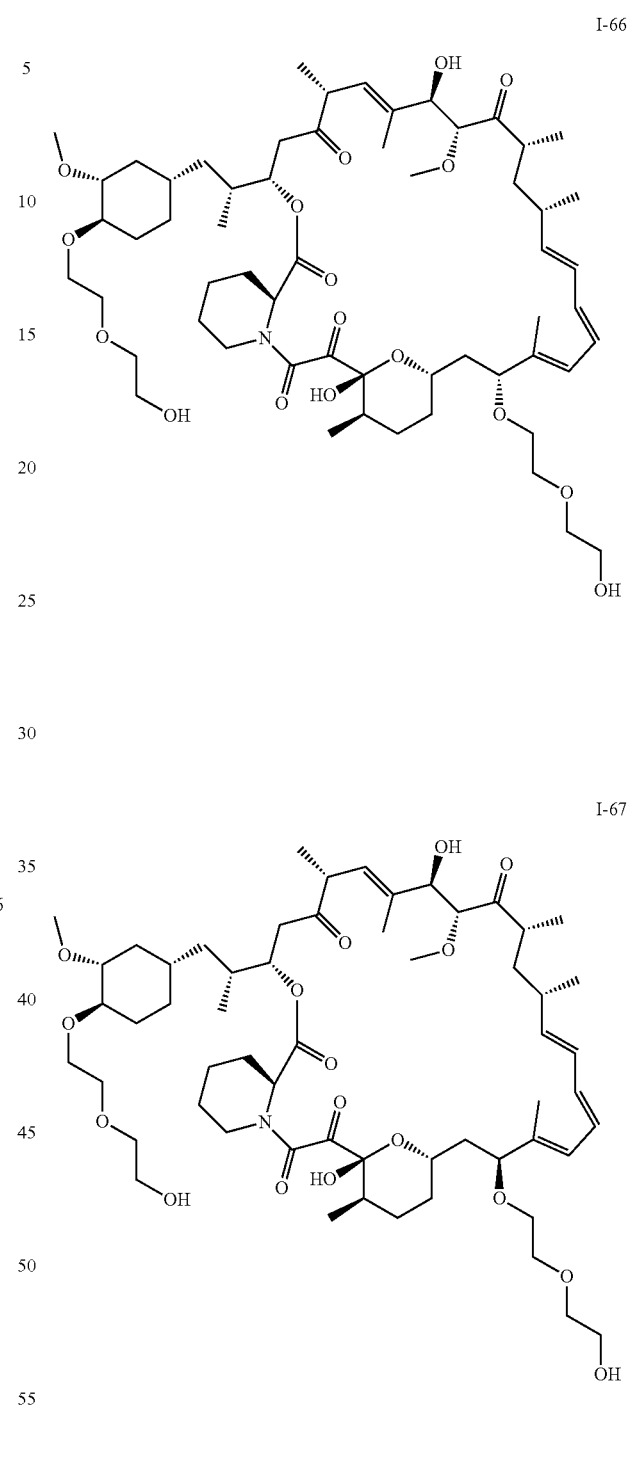

Synthetic Scheme:

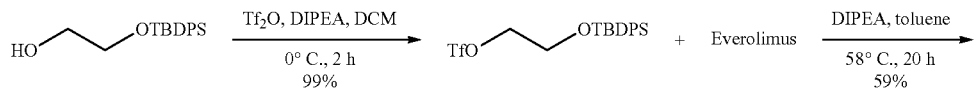

-continued
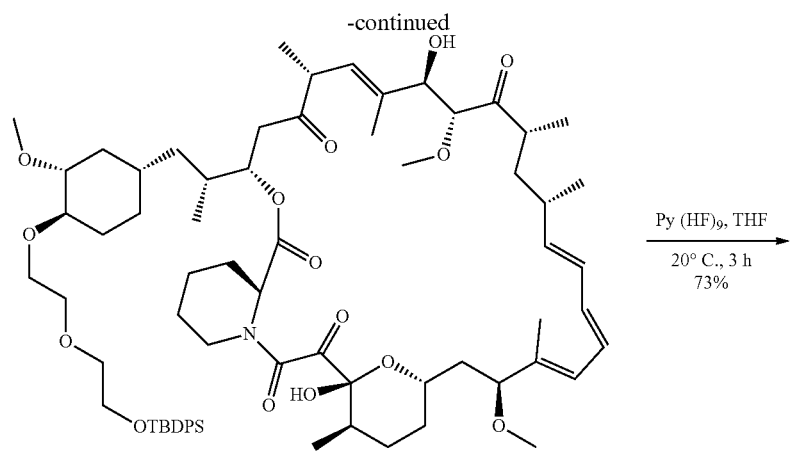
Py (HF)$_9$, THF
20° C., 3 h
73%
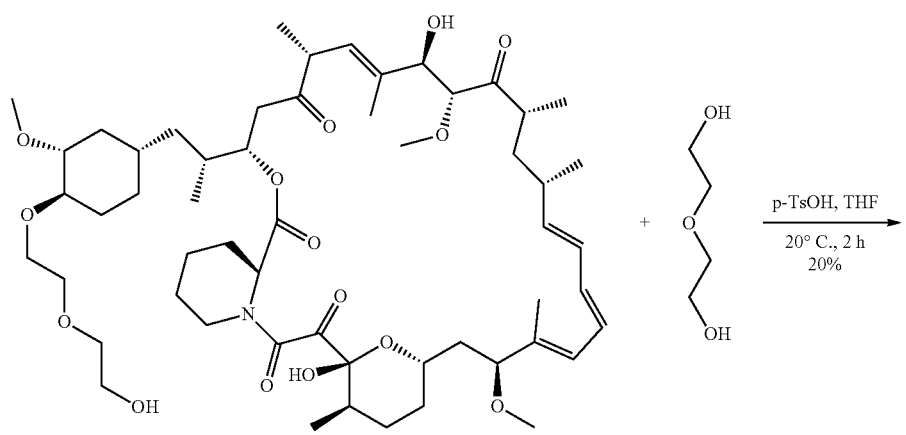
p-TsOH, THF
20° C., 2 h
20%
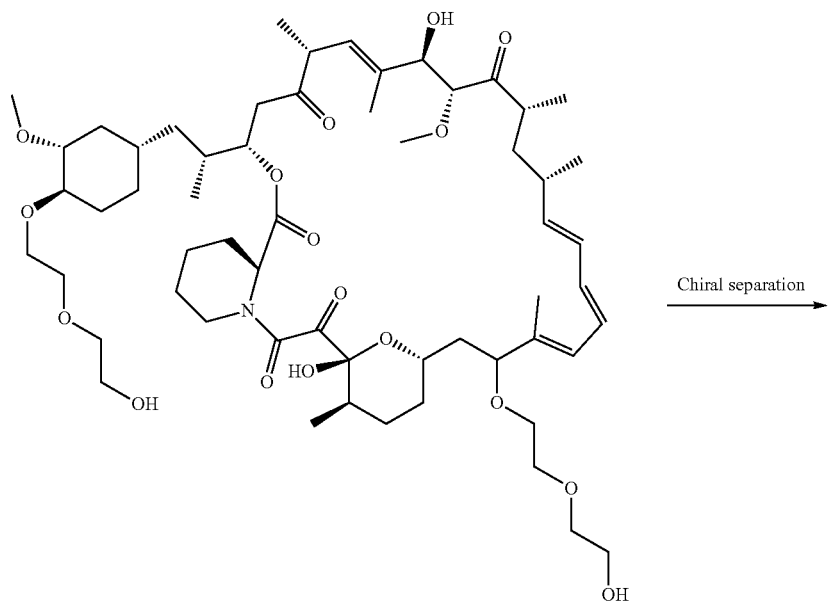
Chiral separation
I-76

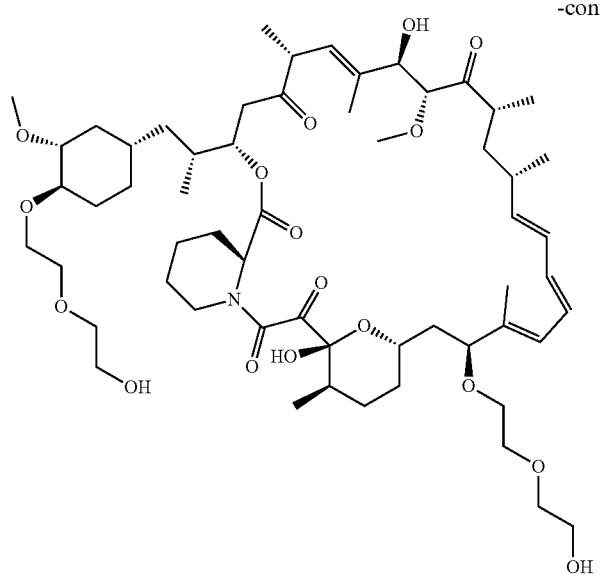

I-67

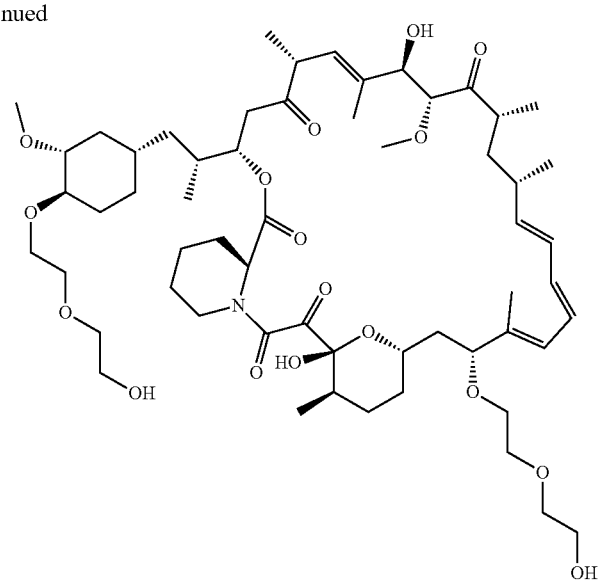

I-66

Procedures and Characterization:
Step 1: Synthesis of 2-[tert-butyl(diphenyl)silyl]oxyethyl trifluoromethanesulfonate:

A solution of 2-[tert-butyl(diphenyl)silyl]oxyethanol (4.3 g, 14.31 mmol) and DIPEA (2.77 g, 21.47 mmol) in DCM (40 mL) was cooled to 0° C. under $N_2$ and trifluoromethanesulfonic anhydride (4.44 g, 15.74 mmol) added dropwise. The mixture was stirred at 0° C. for 2 h then diluted with DCM (50 mL), washed with sat. $NaHCO_3$ (50 mL), water (50 mL×3), and brine (50 mL). The the organic layer was then dried over $MgSO_4$, filtered, and concentrated under vacuum to afford 2-[tert-butyl(diphenyl)silyl]oxyethyl trifluoromethanesulfonate (6.19 g, 99% yield) as a brown oil. This was used in the next step without any further purification. $^1$H NMR (400 MHz, $CDCl_3$) δ 7.66 (dd, J=7.9, 1.5 Hz, 4H), 7.45-7.38 (m, 6H), 4.56 (t, J=4.4 Hz, 2H), 3.91 (t, J=4.4 Hz, 2H).

Step 2: Synthesis of (35E,37E,39E,40E,48R,49S,50R,51R,53S,55S,57S,58S,59R,60R,69R)- 58-[(1R)-2-[(1S,3R,4R)-4-[2-[2-[tert-butyl(diphenyl)silyl]oxyethoxy]ethoxy]-3-methoxy-cyclohexyl]-1-methyl-ethyl]-59, 69-dihydroxy-57,60-dimethoxy-48,49,50,51,61,62-hexamethyl-79,80-dioxa-71-azatricyclohexatriaconta-35,37,39(61),40(62)-tetraene-63,64,65,66,67-pentone:

A solution of everolimus (1.5 g, 1.57 mmol), 2-[tert-butyl(diphenyl)silyl]oxyethyl trifluoromethanesulfonate and DIPEA (3.27 mL, 18.78 mmol) in toluene (20 mL) was stirred at 45° C. for 18 h. The mixture was then poured into ice cold sat. $NaHCO_3$ (50 mL), washed with ice-water twice (60 mL), brine (50 mL), dried over anhydrous $Na_2SO_4$, filtered, and concentrated. The mixture was purified via silica gel chromatography (PE:EtOAc=5:1 to 2:1, then PE:acetone=4:1) to obtain (35E,37E,39E,40E,48R,49S,50R,51R,53S,55S,57S,58S,59R,60R,69R)-58-[(1R)-2-[(1S,3R,4R)-4-[2-[2-[tert-butyl(diphenyl)silyl]oxyethoxy]ethoxy]-3-methoxy-cyclohexyl]-1-methyl-ethyl]-59,69-dihydroxy-57,60-dimethoxy-48,49,50,51,61,62-hexamethyl-79,80-dioxa-71-azatricyclohexatriaconta-35,37,39(61),40(62)-tetraene-63,64,65,66,67-pentone (1.15 g, 59% yield) as a brown solid. ESI-MS (EI$^+$, m/z): 1263.4 [M+Na]$^+$. $^1$H NMR (400 MHz, $CDCl_3$) δ 7.62-7.60 (m, 4H), 7.35-7.28 (m, 6H), 6.35-5.80 (m, 4H), 5.51-5.09 (m, 4H), 4.75 (s, 1H), 4.37-4.02 (m, 2H), 3.87-3.49 (m, 11H), 3.37-3.26 (m, 8H), 3.10-2.96 (m, 5H), 2.76-2.48 (m, 3H), 2.28-2.21 (m, 2H), 1.98-1.90 (m, 3H), 1.67-1.39 (m, 18H), 1.26-1.08 (m, 7H), 1.04-0.76 (m, 26H), 0.64 (q, J=11.2 Hz, 1H).

Step 3: Synthesis of (22E,24E,26E,27E,33R,34S,35R,36R,38S,40S,42S,43S,44R,45R,54R)-44,54-dihydroxy-43-[(1R)-2-[(1S,3R,4R)-4-[2-(2-hydroxyethoxy)ethoxy]-3-methoxy-cyclohexyl]-1-methyl-ethyl]-42,45-dimethoxy-33,34,35,36,46,47-hexamethyl-64,65-dioxa-55-azatricyclohexatriaconta-22,24,26(46),27(47)-tetraene-48,49,50,51,52-pentone:

(35E,37E,39E,40E,48R,49S,50R,51R,53S,55S,57S,58S,59R,60R,69R)-58-[(1R)-2-[(1S,3R,4R)-4-[2-[2-[tert-butyl(diphenyl)silyl]oxyethoxy]ethoxy]-3-methoxy-cyclohexyl]-1-methyl-ethyl]-59,69-dihydroxy-57,60-dimethoxy-48,49,50,51,61,62-hexamethyl-79,80-dioxa-71-azatricyclohexatriaconta-35,37,39(61),40(62)-tetraene-63,64,65,66,67-pentone (1.15 g, 0.93 mmol) was dissolved in THF (10 mL). Pyridinium hydrofluoride (0.437 mL, 1.85 mmol,) was added and the mixture stirred for 3 h at room temperature. The mixture was diluted with EtOAc (30 mL), washed with sat. $NaHCO_3$ (aq., 40 mL×2) until pH 10, then washed with water until neutral, brine (40 mL), dried over anhydrous $Na_2SO_4$, filtered, and concentrated. The residue was purified via silica gel chromatography (PE:acetone=4:1 to 2:1) to obtain (22E,24E,26E,27E,33R,34S,35R,36R,38S,40S,42S,43S,44R,45R,54R)-44,54-dihydroxy-43-[(1R)-2-[(1S,3R,4R)-4-[2-(2-hydroxyethoxy)ethoxy]-3-methoxy-cyclohexyl]-1-methyl-ethyl]-42,45-dimethoxy-33,34,35,36,46,47-hexamethyl-64,65-dioxa-55-azatricyclohexatriaconta-22,24,26(46),27(47)-tetraene-48,49,50,51,52-pentone (680 mg, 73% yield) as a white solid. ESI-MS (EI$^+$, m/z): 1024.3 [M+Na]$^+$. $^1$H NMR (400 MHz, $CDCl_3$) 6.35-5.80 (m, 4H), 5.51-5.09 (m, 4H), 4.75 (s, 1H), 4.37-4.02 (m, 2H), 3.87-3.49 (m, 11H), 3.37-3.26 (m, 8H), 3.10-2.96 (m, 5H), 2.76-2.48 (m, 3H), 2.28-2.21 (m, 2H), 1.98-1.90 (m, 3H), 1.67-1.39 (m, 18H), 1.26-1.08 (m, 7H), 1.04-0.76 (m, 17H), 0.64 (q, J=11.2Hz, 1H).

Step 4: Synthesis of (21E,23E,25E,26E,36R,37S,38R,39R,41S,43S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-76):

To a solution of (22E,24E,26E,27E,33R,34S,35R,36R,38S,40S,42S,43S,44R, 45R,54R)-44,54-dihydroxy-43-[(1R)-2-[(1S,3R,4R)-4-[2-(2-hydroxyethoxy)ethoxy]-3-methoxy-cyclohexyl]-1-methyl-ethyl]-42,45-dimethoxy-33,34,35,36,46,47-hexamethyl-64,65-dioxa-55-azatricyclohexatriaconta-22,24,26(46),27(47)-tetraene-48,49,50,51,52-pentone (0.65 g, 0.65 mmol) in THF (6 mL) under $N_2$ at 0° C. was added p-TsOH (0.56 g, 3.24 mmol) followed by 2-(2-hydroxyethoxy)ethanol (1.38 g, 12.97 mmol). The resulting mixture was stirred at 0° C. for 10 min, then at 20° C. for 2 h. The mixture was poured into sat.$NaHCO_3$ (40 mL) and extracted with EtOAc (30 mL). The organic layer was washed with water (30 mL×2), brine (40 mL), dried over anhydrous $Na_2SO_4$, filtered and concentrated under reduced pressure at room temperature. The residue was purified via silica gel chromatography (PE:EtOAc=50% to 100% EtOAc, then to DCM:$CH_3OH$=95:5 to 90:10) then purified by reverse-phase chromatography (C18, $CH_3CN$:$H_2O$=50: 50) to provide (21E,23E,25E,26E,36R,37S,38R,39R,41S,43S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-76: 140 mg, 20% yield) as a white solid. ESI-MS ($EI^+$, m/z): 1098.5 $[M+Na]^+$. $^1$H NMR (400 MHz, $CDCl_3$) δ 6.31-5.80 (m, 4H), 5.46-4.74 (m, 5H), 4.21-4.11 (m, 2H), 3.68-3.56 (m, 18H), 3.4-3.14 (m, 12H), 3.03-2.97 (m, 2H), 2.68-2.39 (m, 5H), 2.28-2.25 (d, 2H), 1.73-1.55 (m, 18H), 1.40-1.14 (m, 8H), 1.03-0.79 (m, 16H), 0.64 (q, J=11.2 Hz, 1H).

Step 5: Synthesis of (21E,23E,25E,26E,36R,37S,38R,39R,41S,43S,45S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-67) and (21E,23E,25E,26E,36R,37S,38R,39R,41S,43S,45S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-66):

140 mg of (21E,23E,25E,26E,36R,37S,38R,39R,41S,43S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone purified via prep chiral HPLC and the resulting epimers repurified via silica gel chromatography (hexane:DCM:EtOAc:MeOH=3:3:1:1) to provide (21E,23E,25E,26E,36R,37S,38R,39R,41S,43S,45S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-67: 25.3 mg, 18.1% yield) and (21E,23E,25E,26E,36R,37S,38R,39R,41S,43S,45S,46S,47R,48R,57R)-47,57-dihydroxy-45-[2-(2-hydroxyethoxy)ethoxy]-46-[(1R)-2-[(1S,3R,4R)-4-[2-(2-hydroxyethoxy)ethoxy]-3-methoxy-cyclohexyl]-1-methyl-ethyl]-48-methoxy-36,37,38,39,49,50-hexamethyl-68,69-dioxa-58-azatricyclohexatriaconta-21,23,25(49),26(50)-tetraene-51,52,53,54,55-pentone (I-66: 34 mg, 24.3% yield), both as white solids.

Chiral analysis method:
Column: CHIRALPAK IC(IC00CD-OL002)
Column size: 0.46 cm I.D.×25 cm L
Injection: 100.0 ul
Mobile phase: Hexane/EtOH=60/40(V/V)
Flow rate: 1.0 ml/min
Wave length: UV 254 nm
Temperature: 35° C.
HPLC equipment: Shimadzu LC-20AD CP-HPLC-08

I-67: ESI-MS ($EI^+$, m/z): 1098.4 $[M+Na]^+$. $^1$H NMR (400 MHz, $CDCl_3$) δ 6.49-6.19 (m, 2H), 6.13 (dd, J=15.0, 9.8 Hz, 1H), 5.94 (dd, J=24.3, 10.5 Hz, 1H), 5.58-5.45 (m, 1H), 5.41 (d, J=9.8 Hz, 1H), 5.37-5.24 (m, 1H), 5.13 (t, J=10.8 Hz, 1H), 4.80 (s, 1H), 4.19 (t, J=8.7 Hz, 1H), 3.92-3.52 (m, 16H), 3.51-3.25 (m, 11H), 3.25-2.99 (m, 3H), 2.72 (dd, J=16.9, 5.6 Hz, 2H), 2.57 (dd, J=16.8, 6.3 Hz, 1H), 2.39-2.18 (m, 2H), 1.95 (ddd, J=29.6, 22.0, 10.2 Hz, 6H), 1.83-1.40 (m, 15H), 1.37-1.16 (m, 8H), 1.15-0.82 (m, 18H), 0.71 (dd, J=24.0, 12.0 Hz, 1H).

I-66: ESI-MS ($EI^+$, m/z): 1098.4 $[M+Na]^+$. $^1$H NMR (400 MHz, $CDCl_3$) δ 6.45-5.92 (m, 4H), 5.52-4.75 (m, 5H), 4.31-3.92 (m, 3H), 3.88-3.54 (m, 16H), 3.51-3.13 (m, 13H), 3.07 (s, 2H), 2.87-2.42 (m, 4H), 2.38-1.55 (m, 12H), 1.51-1.29 (m, 15H), 1.13-0.72 (m, 18H), 0.69-0.58 (m, 1H).

EXAMPLE 42

Synthesis of (22E,24E,26E,27E,34R,35S,36R,37R,39S,41S,43S,44S,45R,46R,55R)-43-hexoxy-45,55-dihydroxy-44-[(1R)-2-[(1S,3R,4R)-4-hydroxy-3-methoxy-cyclohexyl]-1-methyl-ethyl]-46-methoxy-34,35,36,37,47,48-hexamethyl-65,66-dioxa-56-azatricyclohexatriaconta-22,24,26(47),27(48)-tetraene-49,50,51,52,53-pentone (I-103):

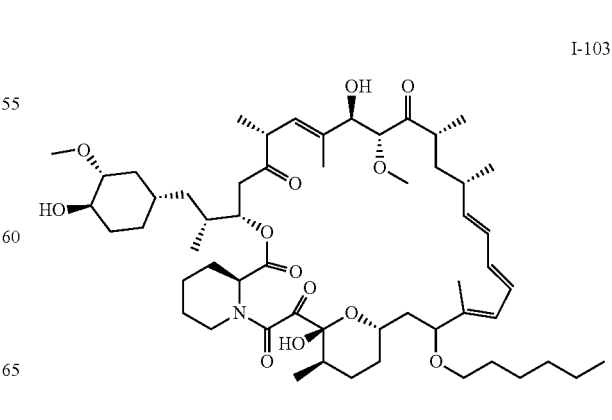

I-103

Synthetic Scheme:

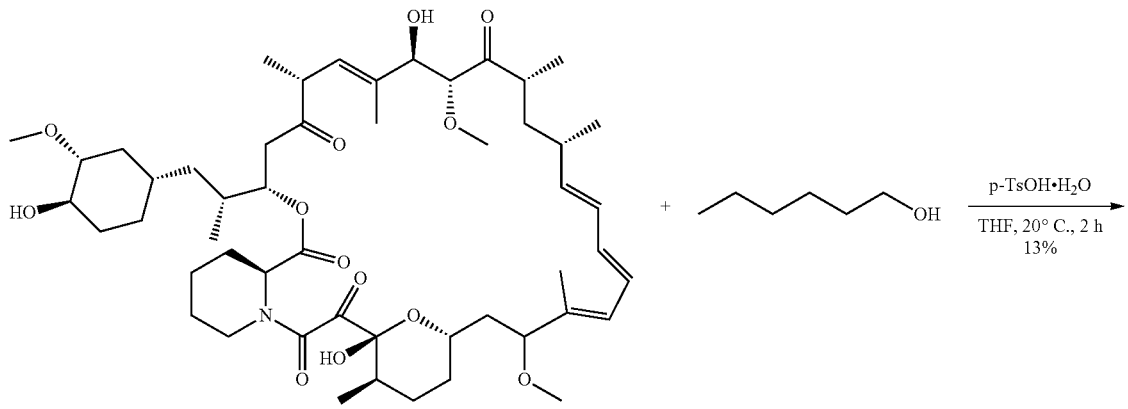

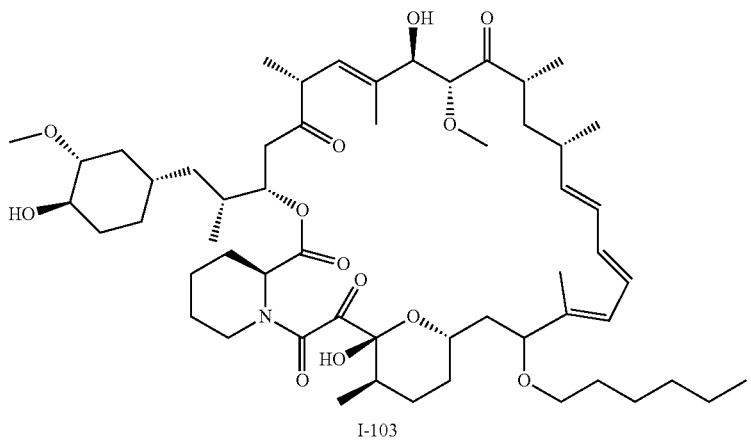

I-103

Procedures and Characterization:
Step 1: Synthesis of (22E,24E,26E,27E,34R,35S,36R,37R, 39S,41S,43S,44S,45R,46R,55R)-43-hexoxy-45,55-dihydroxy-44-[(1R)-2-[(1S,3R,4R)-4-hydroxy-3-methoxy-cyclohexyl]-1-methyl-ethyl]-46-methoxy-34,35,36,37,47,48-hexamethyl-65,66-dioxa-56-azatricyclohexatriaconta-22,24,26(47),27(48)-tetraene-49,50,51,52,53-pentone (I-103):

To a solution of rapamycin (0.5 g, 0.547 mmol) and hexan-1-ol (56 mg, 0.547 mmol) in THF (10 mL) was added 4-methylbenzenesulfonic acid hydrate (0.52 g, 2.73 mmol) slowly. The resulting solution was stirred at 20° C. for 2 h under $N_2$, then the mixture was poured into ice cold aq. $NaHCO_3$ and extracted with EtOAc (30 mL). The organic layer was dried, filtered and concentrated. The residue was then purified via reverse phase chromatography (C18, $CH_3CN:H_2O=78:22$ to afford (22E,24E,26E,27E,34R,35S, 36R,37R,39S,41S,43S,44S,45R,46R,55R)-43-hexoxy-45, 55-dihydroxy-44-[(1R)-2-[(1S,3R,4R)-4-hydroxy-3-methoxy-cyclohexyl]-1-methyl-ethyl]-46-methoxy-34,35, 36,37,47,48-hexamethyl-65,66-dioxa-56-azatricyclohexatriaconta-22,24,26(47),27(48)-tetraene-49, 50,51,52,53-pentone (I-103: 72 mg, 13% yield) as a white solid. ESI-MS (EI$^+$, m/z): 1006.0 [M+Na]$^+$. $^1$H NMR(500 MHz, CDCl$_3$) δ 6.44-5.85 (m, 4H), 5.60-5.07 (m, 4H), 4.77 (s, 1H), 4.29-3.98 (m, 2H), 3.76-3.67 (m, 1H), 3.46-3.28 (m, 10H), 3.23-3.03 (m, 2H), 3.02-2.77 (m, 2H), 2.69 (m, 3H), 2.36 (d, J=32.6 Hz, 2H), 2.17-1.90 (m, 4H), 1.66-1.44 (m, 22H), 1.35-1.21 (m, 11H), 1.17-0.84 (m, 22H), 0.72-0.65 (m, 1H).

EXAMPLE 43
Synthesis of (21E,23E,25E,26E,44R,45S,46R,47R, 49S,51S,54S,55R,56R,65R)-55,65-dihydroxy-53-[2-[2-[2-[2-[2-[2-(2-hydroxyethoxy)ethoxy]ethoxy]ethoxy]ethoxy]ethoxy]-54-[(1R)-2-[(1S,3R,4R)-4-(2-hydroxyethoxy)-3-methoxy-cyclohexyl]-1-methyl-ethyl]-56-methoxy-44,45,46,47,57,58-hexamethyl-76,77-dioxa-66-azatricyclohexatriaconta-21,23,25(57),26(58)-tetraene-59,60,61,62,63-pentone (I-99):
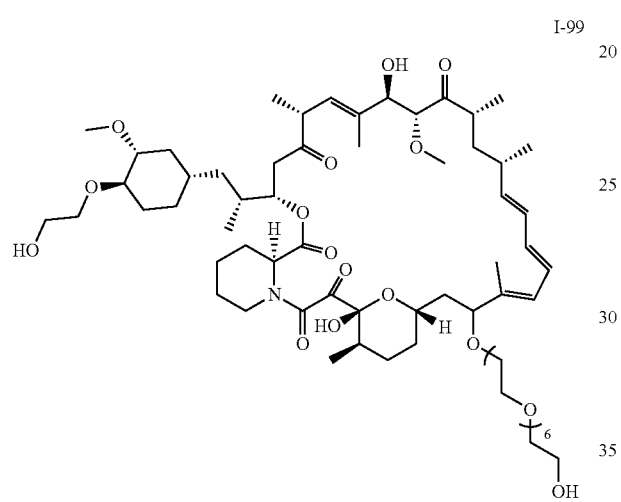
Synthetic Scheme:
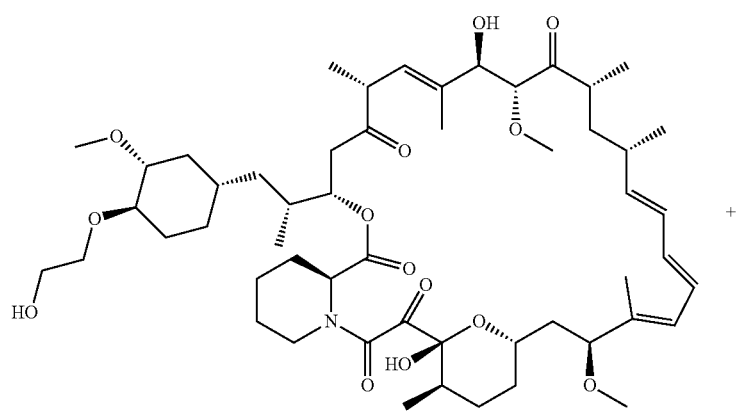

-continued

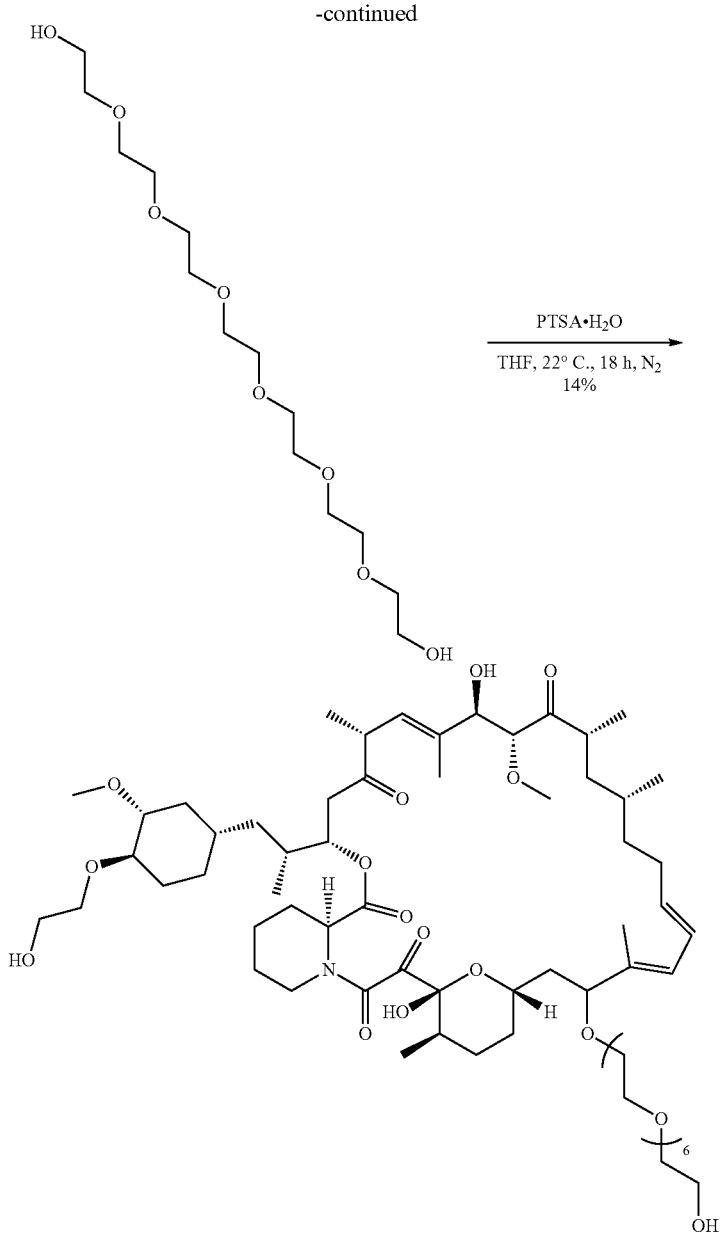

I-99

Procedures and Characterization:
Step 1: Synthesis of (21E,23E,25E,26E,44R,45S,46R,47R, 49S,51S,54S,55R,56R,65R)-55,65-dihydroxy-53-[2-[2-[2-[2-[2-[2-(2-hydroxyethoxy)ethoxy]ethoxy]ethoxy]ethoxy]ethoxy]-54-[(1R)-2-[(1S,3R,4R)-4-(2-hydroxyethoxy)-3-methoxy-cyclohexyl]-1-methyl-ethyl-[56-methoxy-44,45,46,47,57,58-hexamethyl-76,77-dioxa-66-azatricyclohexatriaconta-21,23,25(57),26(58)-tetraene-59,60,61,62,63-pentone (I-99):

To a solution of everolimus (0.5 g, 0.52 mmol) and 2-[2-[2-[2-[2-[2-(2-hydroxyethoxy)ethoxy]ethoxy]ethoxy]ethoxy]ethanol (3.41 g, 10.44 mmol) in THF (15 mL) was added 4-methylbenzenesulfonic acid hydrate (0.52 g, 2.73 mmol) slowly. The resulting mixture was stirred at 22° C. for 18 h under $N_2$ then quenched with aq. $NaHCO_3$ (30 mL) and extracted with EtOAc (60 mL×3). The combined organic layers were washed with water (50 mL), brine (50 mL), dried over anhydrous $Na_2SO_4$, filtered, and concentrated under vacuum. The residue was purified by reverse phase chromatography (C18, $CH_3CN$:$H_2O$=70:30) to afford (21E,23E,25E,26E,44R,45S,46R,47R,49S,51S,54S,55R, 56R,65R)-55,65-dihydroxy-53 -[2-[2-[2-[2-[2-[2-(2-hydroxyethoxy)ethoxy]ethoxy]ethoxy]ethoxy]ethoxy]-54-[(1R)-2-[(1S,3R,4R)-4-(2-hydroxyethoxy)-3-methoxy-cyclohexyl]-1-methyl-ethyl]-56-methoxy-44,45, 46,47,57,58-hexamethyl-76,77-dioxa-66-azatricyclohexatriaconta-21,23,25(57),26(58)-tetraene-59, 60,61,62,63-pentone (I-99: 93 mg, 14% yield) as a white solid. ESI-MS (EI+, m/z): 1274.9 [M+Na]+. $^1$H NMR (500 MHz, $CDCl_3$) δ 6.42-5.82 (m, 4H), 5.64-5.06 (m, 4H), 4.81 (s, 1H), 4.30-4.08 (m, 1H), 3.81-3.53 (m, 35H), 3.46-3.26 (m, 12H), 3.22-3.05 (m, 4H), 2.76-2.65 (m, 2H), 2.39-2.22

(m, 2H), 2.14-1.97 (m, 3H), 1.75-1.55 (m, 13H), 1.52-1.39 (m, 4H), 1.30-1.13 (m, 6H), 1.08-0.82 (m, 17H), 0.76-0.65 (m, 1H).

EXAMPLE 44

Synthesis of (21E,23E,25E,26E,46R,47S,48R,49R, 51S,53S,56S,57R,58R,67R)-57,67-dihydroxy-55-[2-[2-[2-[2-[2-[2-[2-[2-(2-hydroxyethoxy)ethoxy]ethoxy]ethoxy]ethoxy]ethoxy]ethoxy]ethoxy]-56-[(1R)-2-[(1S,3R,4R)-4-hydroxy-3-methoxy-cyclohexyl]-1-methyl-ethyl]-58-methoxy-46,47,48,49,59,60-hexamethyl-78,79-dioxa-68-azatricyclohexatriaconta-21,23,25(59),26(60)-tetraene-61,62,63,64,65-pentone (I-97):

I-97

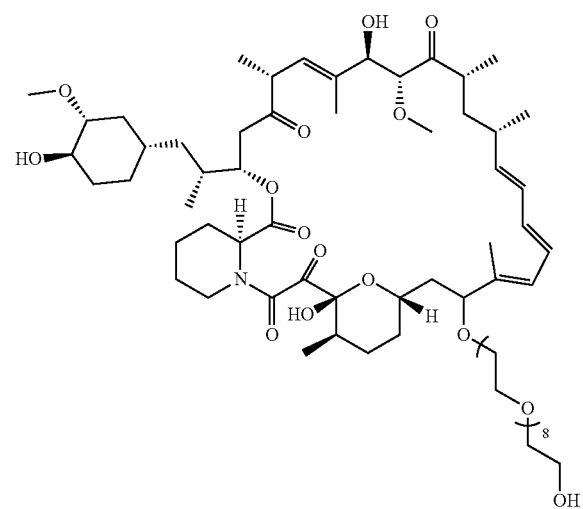

Synthetic Scheme:

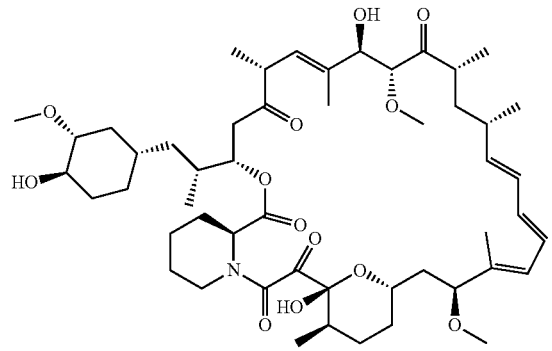

+

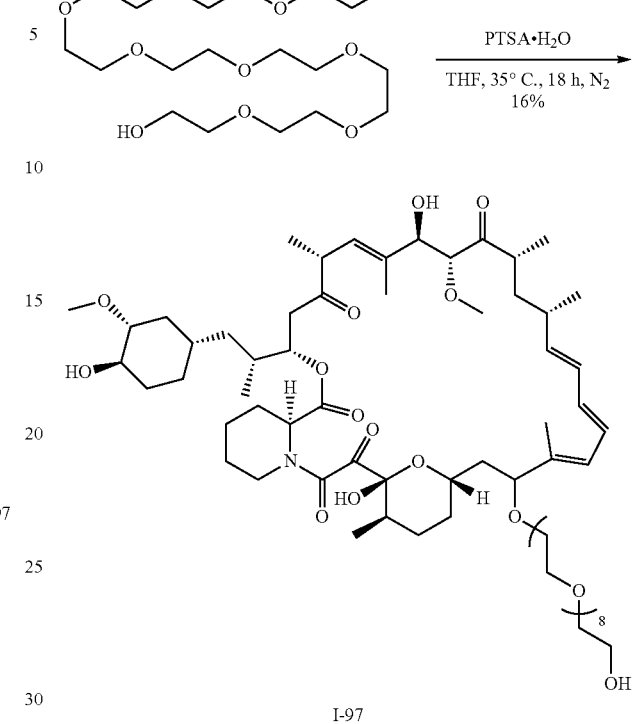

I-97

Procedures and Characterization:

Step 1: Synthesis of (21E,23E,25E,26E,46R,47S,48R,49R, 51S,53S,56S,57R,58R,67R)-57,67-dihydroxy-55-[2-[2-[2-[2-[2-[2-[2-[2-(2-hydroxyethoxy)ethoxy]ethoxy]ethoxy]ethoxy]ethoxy]ethoxy]ethoxy]-56-[(1R)-2-[(1S,3R,4R)-4-hydroxy-3-methoxy-cyclohexyl]-1-methyl-ethyl]-58-methoxy-46,47,48,49,59,60-hexamethyl-78,79-dioxa-68-azatricyclohexatriaconta-21,23,25(59),26(60)-tetraene-61,62,63,64,65-pentone (I-97):

To a solution of rapamycin (0.5 g, 0.547 mmol) in THF (15 mL) was added 4-methylbenzenesulfonic acid (0.47 g, 2.73 mmol) and nonaethylene glycol (2.27 g, 5.47 mmol) at 10° C. The reaction was stirred at 30° C. for 18 h under $N_2$ then quenched with aq. NaHCO$_3$ and extracted with EtOAc (60 mL×3). The combined organic layers were washed with water (50 mL), brine (50 mL), dried over anhydrous Na$_2$SO$_4$, filtered and concentrated. The residue was purified by reverse phase chromatography (C18, CH$_3$CN:H$_2$O=63:37) to provide (21E,23E,25E,26E,46R,47S,48R,49R,51S, 53S,56S,57R,58R,67R)-57,67-dihydroxy-55-[2-[2-[2-[2-[2-[2-[2-[2-(2-hydroxyethoxy)ethoxy]ethoxy]ethoxy]ethoxy]ethoxy]ethoxy]ethoxy]-56-[(1R)-2-[(1S,3R,4R)-4-hydroxy-3-methoxy-cyclohexyl]-1-methyl-ethyl]-58-methoxy-46,47,48,49,59,60-hexamethyl-78,79-dioxa-68-azatricyclohexatriaconta- 21,23,25(59),26(60)-tetraene-61,62,63,64,65-pentone (I-97: 111 mg, 16% yield) as a white solid. ESI-MS (EI$^+$, m/z): 1318.9 [M+Na]$^+$. $^1$H NMR (500 MHz, CDCl$_3$) δ 6.50-5.79 (m, 4H), 5.64-5.06 (m, 4H), 4.89 (d, J=53.5 Hz, 1H), 4.51-3.94 (m, 2H), 3.75-3.18 (m, 46H), 3.02-2.86 (m, 2H), 2.82-2.61 (m, 3H), 2.39-2.18 (m, 2H), 2.20-1.91 (m, 6H), 1.78-1.54 (m, 16H), 1.51-1.19 (m, 11H), 1.09-0.82 (m, 17H), 0.74-0.62 (m, 1H).

EXAMPLE 45
Synthesis of (21E,23E,25E,26E,50R,51S,52R,53R, 55S,57S,60S,61R,62R,71R)-61,71-dihydroxy-59-[2-[2-[2-[2-[2-[2-[2-[2-[2-(2-hydroxyethoxy)ethoxy]ethoxy]ethoxy]ethoxy]ethoxy]ethoxy]ethoxy]ethoxy]ethoxy]-60-[(1R)-2-[(1S,3R,4R)-4-hydroxy-3-methoxy-cyclohexyl]-1-methyl-ethyl]-62-methoxy-50,51,52,53,63,64-hexamethyl-82,83-dioxa-72-azatricyclohexatriaconta-21,23,25(63),26(64)-tetraene-65,66,67,68,69-pentone (I-96):
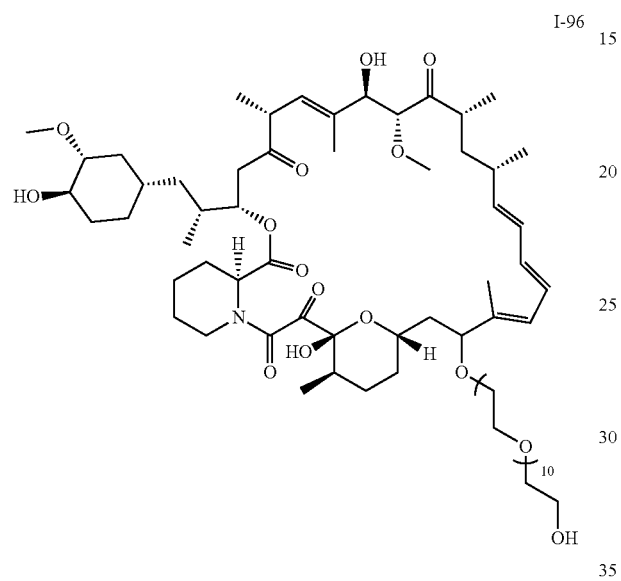
Synthetic Scheme:
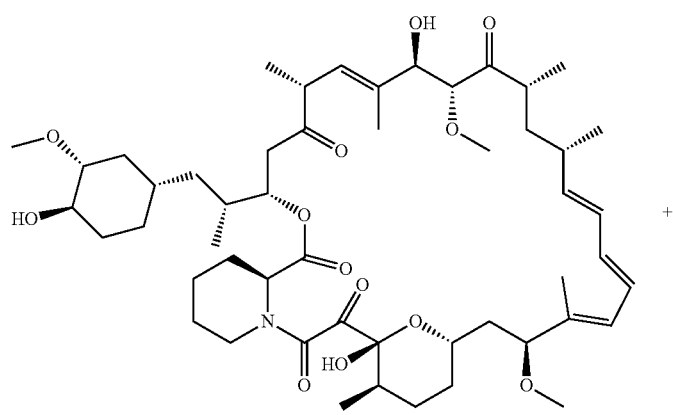
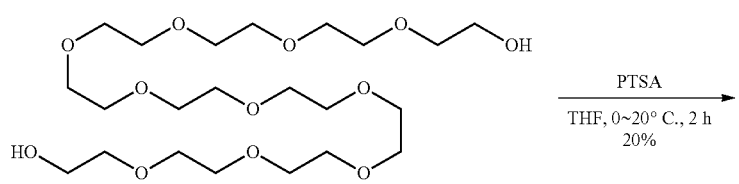

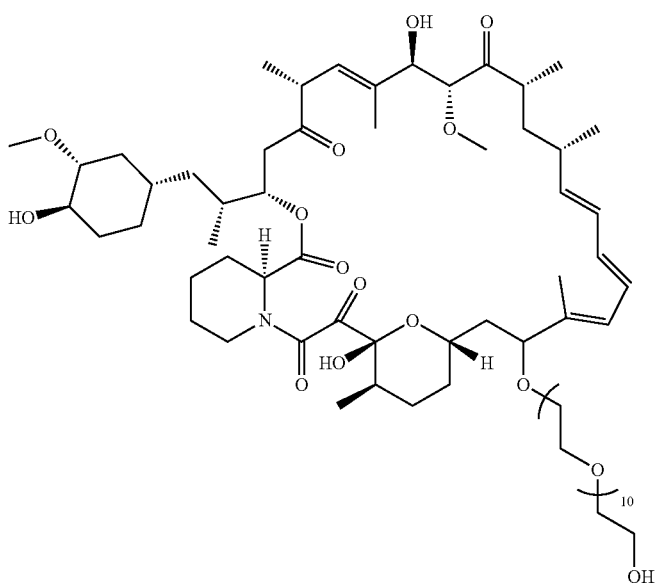

I-96

Procedures and Characterization:
Step 1: Synthesis of (21E,23E,25E,26E,50R,51S,52R,53R, 55S,57S,60S,61R,62R,71R)-61,71-dihydroxy-59-[2-[2-[2-[2-[2-[2-[2-[2-[2-[2-(2-hydroxyethoxy)ethoxy]ethoxy]ethoxy]ethoxy]ethoxy]ethoxy]ethoxy]ethoxy]ethoxy]-60-[(1R)-2-[(1S,3R,4R)-4-hydroxy-3-methoxy-cyclohexyl]-1-methyl-ethyl]-62-methoxy-50,51,52,53,63,64-hexamethyl-82,83-dioxa-72-azatricyclohexatriaconta-21,23,25(63),26(64)-tetraene-65,66,67,68,69-pentone (I-96):

To a solution of rapamycin (0.2 g, 0.22 mmol) and 4-methylbenzenesulfonic acid (0.19 g, 1.09 mmol) in THF (6 mL) was added 2-[2-[2-[2-[2-[2-[2-[2-[2-[2-(2-hydroxyethoxy)ethoxy]ethoxy]ethoxy]ethoxy]ethoxy]ethoxy]ethoxy]ethoxy]ethoxy] ethanol (1.10 g, 2.19 mmol) at 0° C. and the reaction was stirred at 20° C. for 2 h then poured into sat. NaHCO$_3$ (30 mL) and extracted with EtOAc (40 mL×3). The combined organic layers were washed with water (40 mL), brine (40 mL), dried over anhydrous Na$_2$SO$_4$, filtered and concentrated. The residue was purified by reverse phase chromatography (C18, CH$_3$CN: H$_2$O=51:49) to obtain (21E, 23E,25E,26E,50R,51S,52R,53R,55S,57S,60S,61R,62R, 71R)-61,71-dihydroxy-59-[2-[2-[2-[2-[2-[2-[2-[2-[2-[2-(2-hydroxyethoxy)ethoxy]ethoxy]ethoxy]ethoxy]ethoxy] ethoxy]ethoxy]ethoxy]ethoxy]ethoxy]-60-[(1R)-2-[(1S,3R, 4R)-4-hydroxy-3-methoxy-cyclohexyl]-1-methyl-ethyl]-62-methoxy-50, 51,52, 53,63,64-hexamethyl-82,83-dioxa-72-azatricyclohexatriaconta-21,23,25(63),26(64)-tetraene-65, 66,67,68,69-pentone (I-96: 61 mg, 20% yield) as a colorless oil. ESI-MS (EI$^+$, m/z): 1408.0 [M+Na]$^+$. $^1$H NMR (500 MHz, CDCl$_3$) δ 6.41-5.84 (m, 4H), 5.61-5.08 (m, 4H), 4.79 (s, 1H), 4.32-4.05 (m, 1H), 3.89-3.46 (m, 44H), 3.46-3.16 (m, 12H), 2.98-2.50 (m, 7H), 2.32 (s, 2H), 2.15-1.89 (m, 4H), 1.82-1.68 (m, 8H), 1.56-1.16 (m, 14H), 1.12-0.82 (m, 18H), 0.74-0.56 (m, 1H).

EXAMPLE 46

Synthesis of (21E,23E,25E,26E,33R,34S,35R,36R, 38S,40S,43S,44R,45R,54R)-44,54-dihydroxy-43-[(1R)-2-1(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy)ethoxy]-65,66-dioxa-56-azatricyclohexatriaconta-21,23,25(46),26(47)-tetraene-48,49,50,51,52-pentone (I-77) and (21E, 23E,25E,26E,33R,34S,35R,36R,38S,40S,42S,43S, 44R,45R,54R)-44,54-dihydroxy-43-[(1R)-2-1(1S, 3R,4R)-4-(2-hydroxyethoxy)-3-methoxy-cyclohexyl]-1-methyl-ethyl]-45-methoxy-33,34,35, 36,46,47-hexamethyl-42-[2-(2,2,2-trifluoroethoxy) ethoxy]-65,66-dioxa-56-azatricyclohexatriaconta-21, 23,25(46),26(47)-tetraene-48,49,50,51,52-pentone and (21E,23E,25E,26E,33R,34S,35R,36R,38S,40S, 42S,43R,44R,45R,54R)-44,54-dihydroxy-43-[(1R)-2-1(1S,3R,4R)-4-(2-hydroxyethoxy)-3-methoxy-cyclohexyl]-1-methyl-ethyl]-45-methoxy-33,34,35, 36,46,47-hexamethyl-42-[2-(2,2,2-trifluoroethoxy) ethoxy]-65,66-dioxa-56-azatricyclohexatriaconta-21, 23,25(46),26(47)-tetraene-48,49,50,51,52-pentone:

I-77

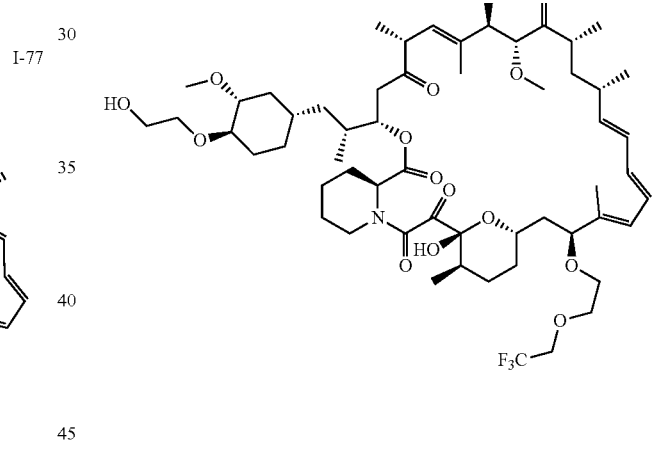

I-70

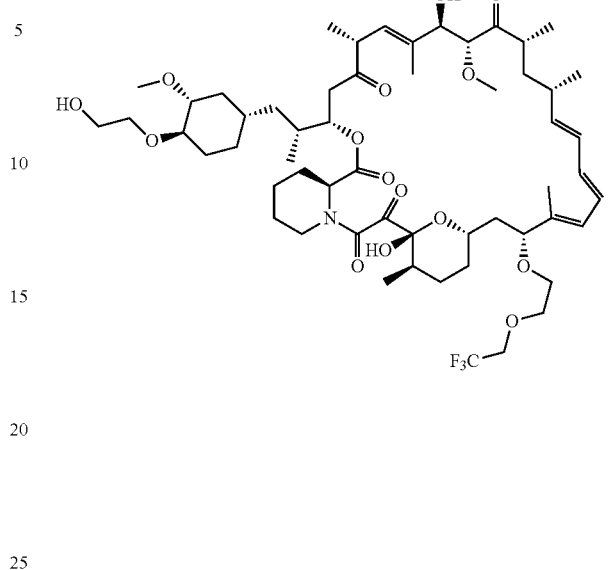

I-71

Synthetic Scheme:

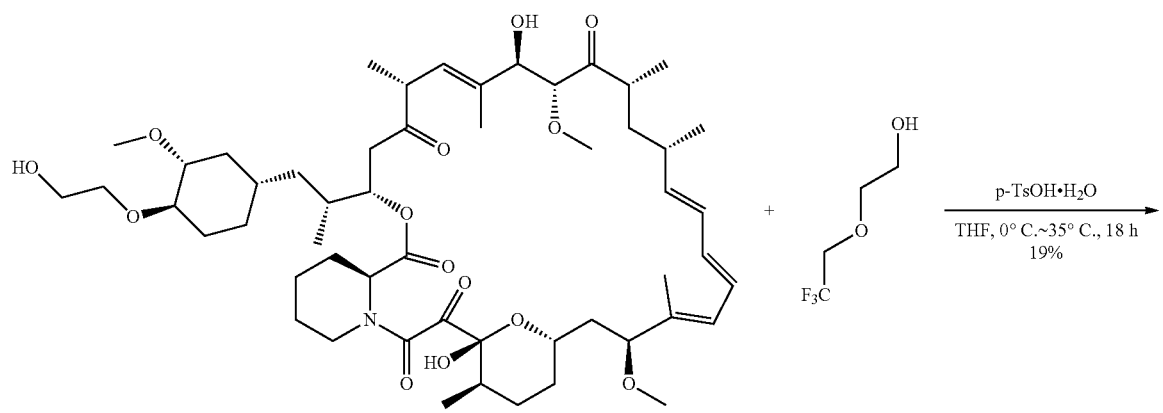

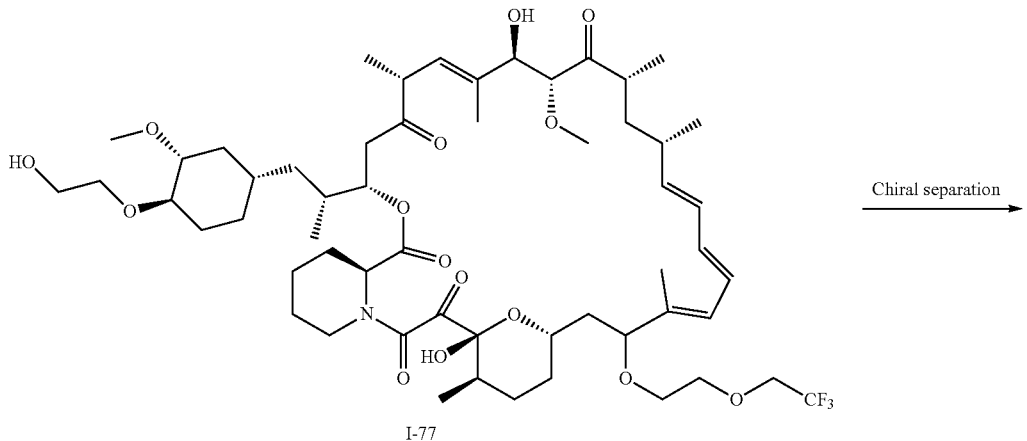

I-77

Chiral separation →

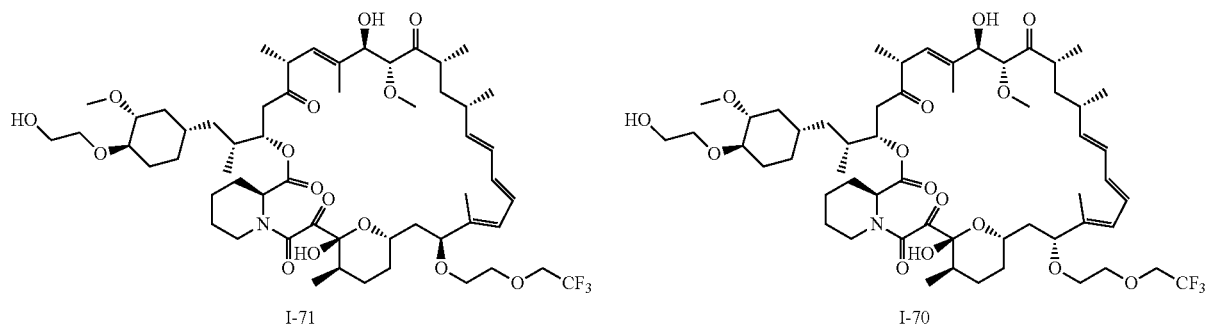

I-71      I-70

Procedures and Characterization:

Step 1: Synthesis of (21E,23E,25E,26E,33R,34S,35R,36R, 38S,40S,43S,44R,45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy) ethoxy]-65,66-dioxa-56-azatricyclohexatriaconta-21,23,25(46),26(47)-tetraene-48,49,50,51,52-pentone (I-77):

A solution of rapamycin (0.3 g, 0.313 mmol) and 2-(2,2,2-trifluoroethoxy)ethanol (0.9 g, 6.26 mmol) in THF (9 mL) was cooled to 0° C. and p-TsOH (0.27 g, 1.57 mmol) was added. The resulting mixture was stirried at 35° C. for 5 h under $N_2$ then poured into ice cold $NaHCO_3$ and extracted with EtOAc (40 mL×3). The combined organic layers were washed with water (30 mL), brine (30 mL), dried, filtered, and concentrated. The residue was purified via reverse phase chromatography (C18, $CH_3CN$:$H_2O$=57:43) to provide (21E,23E,25E,26E,33R,34S,35R,36R,38S,40S,43S,44R, 45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy)ethoxy]-65,66-dioxa-56-azatricyclohexatriaconta-21,23,25(46),26(47)-tetraene-48, 49,50,51,52-pentone (I-77: 0.063 g, 19% yield) as a white solid. ESI-MS (EI$^+$, m/z): 1092.3 [M+Na]$^+$. $^1$H NMR (400 MHz, CDCl$_3$) δ 6.55-5.88 (m, 4H), 5.72-5.03 (m, 4H), 4.78 (s, 1H), 4.63-4.34 (m, 1H), 4.32-4.09 (m, 1H), 4.00-2.81 (m, 21H), 2.77-2.43 (m, 3H), 2.41-2.17 (m, 2H), 2.18-1.93 (m, 3H), 1.93-1.54 (m, 18H), 1.54-1.14 (m, 10H), 1.13-0.79 (m, 16H), 0.78-0.63 (m, 1H).

Step 2: Synthesis of (21E,23E,25E,26E,33R,34S,35R,36R, 38S,40S,42S,43S,44R,45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy) ethoxy]-65,66-dioxa-56-azatricyclohexatriaconta-21,23,25(46),26(47)-tetraene-48,49,50,51,52-pentone (I-71) and (21E,23E,25E, 26E,33R,34S,35R,36R,38S,40S,42S,43R,44R,45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy)ethoxy]-65,66-dioxa-56-azatricyclohexatriaconta-21,23,25(46),26(47)-tetraene-48, 49,50,51,52-pentone (I-70):

100 mg of (21E,23E,25E,26E,33R,34S,35R,36R,38S, 40S,43S,44R,45R,54R)-44,54-dihydroxy-43-[(1R)-2-[(1S, 3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy) ethoxy]-65,66-dioxa-56-azatricyclohexatriaconta-21,23,25(46),26(47)-tetraene-48, 49,50,51,52-pentone was purified via prep chiral HPLC and the resulting epimers purified via silica gel chromatography (hexane:DCM:EtOAc:MeOH=3:3:1:0.3) to provide (21E, 23E,25E,26E,33R,34S,35R,36R,38S,40S,42S,43S,44R, 45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy)ethoxy]-65,66-dioxa-56-azatricyclohexatriaconta-21,23,25(46),26(47)-tetraene-48, 49,50,51,52-pentone (I-71: 16 mg, 16% yield) and (21E, 23E,25E,26E,33R,34S,35R,36R,38S,40S,42S,43R,44R, 45R,54R)-44,54-dihydroxy-43-[(1R)-2-[(1S,3R,4R)-4-(2-hydroxyethoxy)-3-methoxy-cyclohexyl]-1-methyl-ethyl]-45-methoxy-33,34,35,36,46,47-hexamethyl-42-[2-(2,2,2-trifluoroethoxy)ethoxy]-65,66-dioxa-56-azatricyclohexatriaconta-21,23,25(46),26(47)-tetraene-48, 49,50,51,52-pentone (I-70: 8 mg, 8% yield) as a white solid.

Chiral separation method:

Column: CHIRALPAK IC

Column size: 2.5 cm I.D.×25 cm L

Solution concentration: 2.0 mg/ml

Injection: 7 ml

Mobile phase: Hexane/EtOH=70/30(V/V)

Flow rate: 40 ml/min

Wave length: UV 254 nm

Temperature: 35° C.

I-71: ESI-MS (EI$^+$, m/z): 1092.4 [M+Na]$^+$. $^1$H NMR (400 MHz, CDCl$_3$) δ 6.41-6.20 (m, 2H), 6.13 (dd, J=15.1, 9.7 Hz, 1H), 5.93 (dd, J=22.9, 10.3 Hz, 1H), 5.58-5.45 (m, 1H), 5.41 (d, J=9.8 Hz, 1H), 5.27 (d, J=5.2 Hz, 1H), 5.19-5.03 (m, 1H), 4.78 (s, 1H), 4.19 (dd, J=13.9, 5.9 Hz, 1H), 3.95-3.63 (m, 10H), 3.63-3.53 (m, 2H), 3.52-3.25 (m, 11H), 3.24-3.01 (m, 3H), 2.72 (dd, J=16.8, 5.8 Hz, 2H), 2.58 (dd, J=16.8, 6.3 Hz, 1H), 2.31 (t, J=23.5 Hz, 2H), 2.15-1.40 (m, 18H), 1.27 (ddd, J=32.5, 16.2, 6.3 Hz, 8H), 1.15-0.81 (m, 18H), 0.70 (dt, J=17.8, 9.0 Hz, 1H).

I-70: ESI-MS (EI$^+$, m/z): 1092.4 [M+Na]$^+$. $^1$H NMR (400 MHz, CDCl$_3$) δ 6.43-5.90 (m, 4H), 5.56-5.08 (m, 5H), 4.33-3.99 (m, 3H), 3.95-3.63 (m, 8H), 3.62-3.02 (m, 18H), 2.89-1.97 (m, 12H), 1.76 (dd, J=31.4, 24.8 Hz, 8H), 1.40 (ddd, J=39.2, 29.5, 12.0 Hz, 9H), 1.14-0.79 (m, 18H), 0.76-0.61 (m, 1H).

EXAMPLE 47

Synthesis of 4-[[(23E,25E,27E,28E,35R,36S,37R, 38R,40S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy[-N,N-dimethyl-butanamide (I-69) and 4-[[(23E,25E,27E, 28E,35R,36S,37R,38R,40S,42S,44R,45S,46R,47R, 57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-61) and 4-[[(23E,25E,27E,28E,35R,36S,37R,38R,40S, 42S,44S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-62):

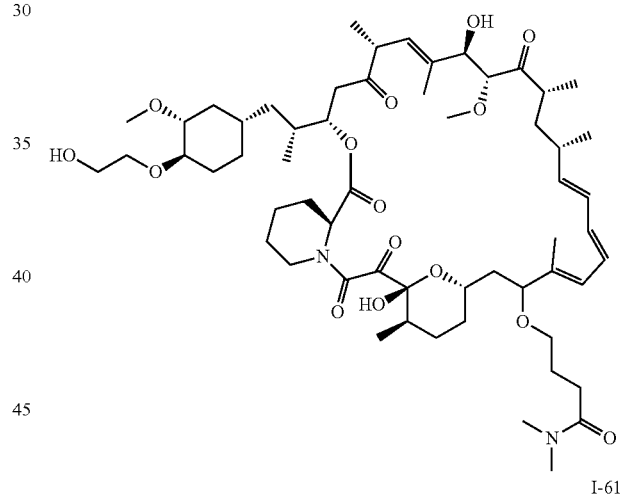

I-69

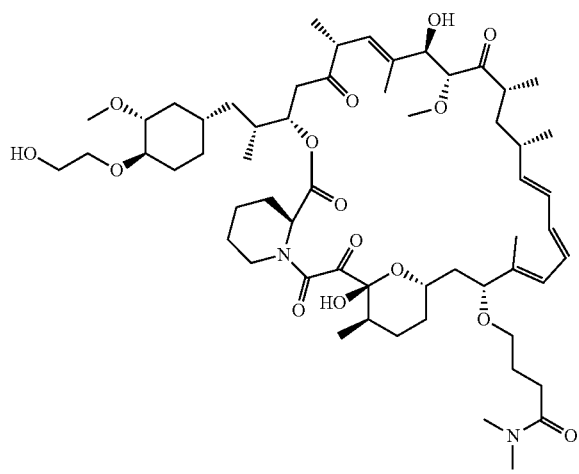

I-61

I-62
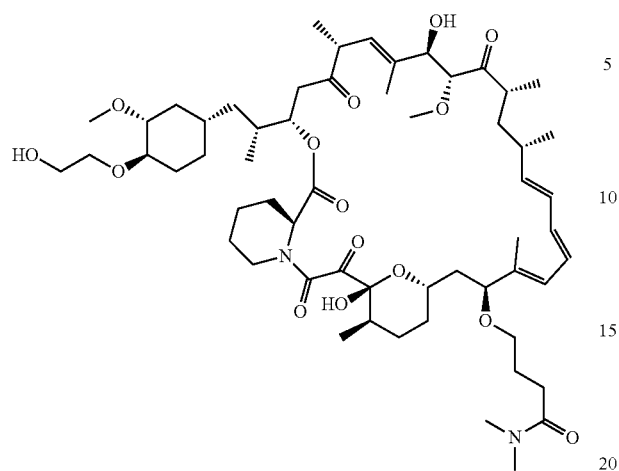
Synthetic Scheme:
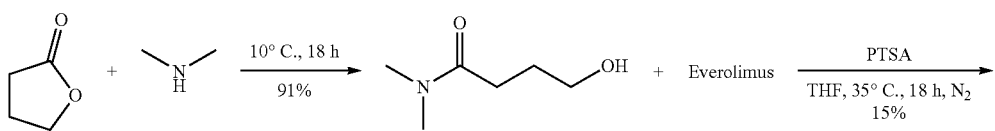
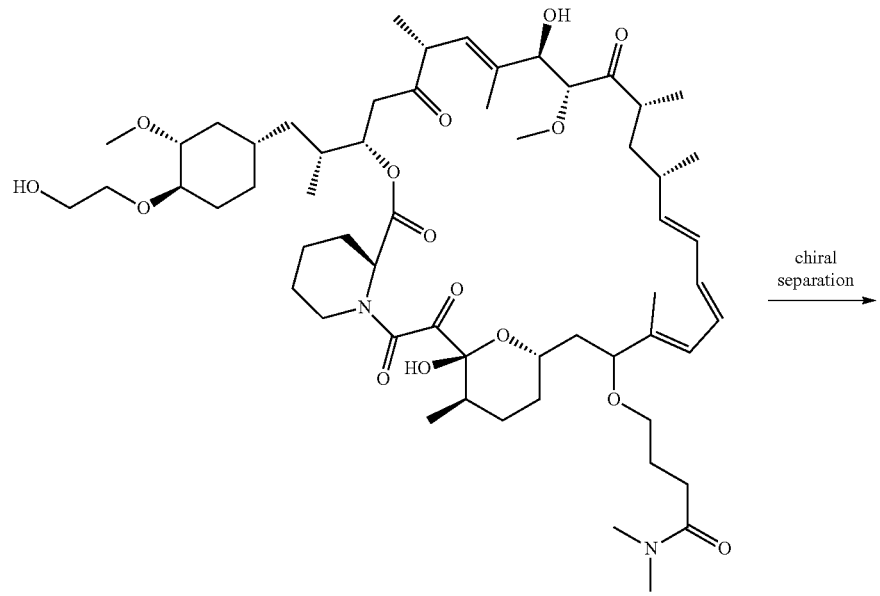
I-69

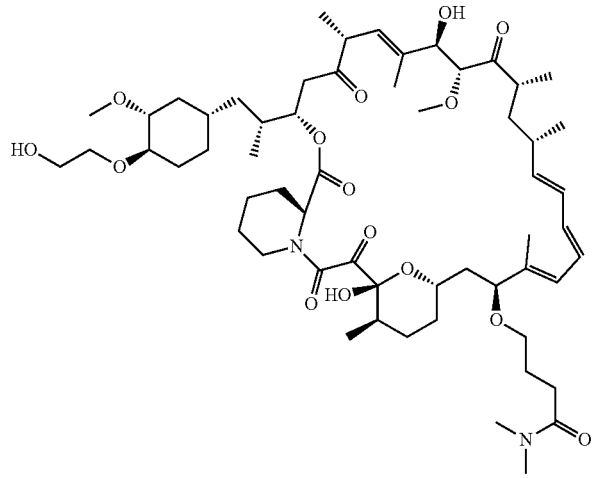

I-62

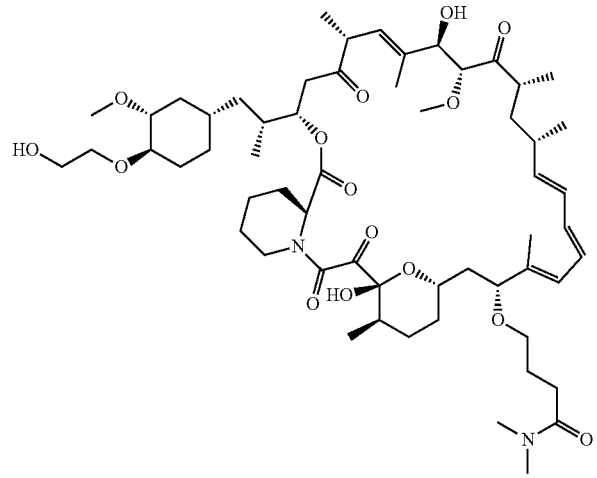

I-61

Procedures and Characterization:

Step 1: Synthesis of 4-hydroxy-N,N-dimethylbutanamide:

A mixture of tetrahydrofuran-2-one (5 g, 58.1 mmol) and N-methylmethanamine (43.64 g, 290.4 mmol, 90 mL) was stirred at 10° C. for 18 h, the solvent was removed, and then lyophilized to afford 4-hydroxy-N,N-dimethyl-butanamide (6.9 g, 91% yield) as a colorless oil. ESI-MS (EI$^+$, m/z): 132.3 [M+H]$^+$. $^1$H NMR (400 MHz, CDCl$_3$) δ 3.67 (t, J=5.8 Hz, 2H), 3.04 (s, 3H), 2.96 (s, 3H), 2.49 (t, J=6.9 Hz, 2H), 1.94-1.84 (m, 2H).

Step 2: Synthesis of 4-[[(23E,25E,27E,28E,35R,36S,37R, 38R,40S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-69):

To a solution of everolimus (0.3 g, 0.313 mmol) in THF (9 mL) at 0° C. under N$_2$ was added p-toluenesulfonic acid (0.27 g, 1.57 mmol) and 4-hydroxy-N,N-dimethyl-butanamide (0.82 g, 6.26 mmol). The mixture was warmed to 35° C. and stirred for 18 h then poured into ice cold NaHCO$_3$ and extracted with EtOAc (20 mL×3). The combined organic layers were washed with water (30 mL), brine (30 mL), dried over anhydrous Na$_2$SO$_4$, filtered, and concentrated. The residue was purified by reverse phase chromatography (C18, CH$_3$CN:H$_2$O=55:45) to provide 4-[[(23E,25E,27E, 28E,35R,36S,37R,38R,40S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36, 37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-69: 0.05 g, 15% yield) as a white solid. ESI-MS (EI$^+$, m/z): 1079.4 [M+Na]$^+$. $^1$H NMR (400 MHz, CDCl$_3$) δ 6.52-5.78 (m, 4H), 5.67-5.05 (m, 4H), 4.75 (s, 1H), 4.48-4.09 (m, 2H), 4.04-3.51 (m, 7H), 3.52-3.12 (m, 12H), 3.12-2.88 (m, 7H), 2.82-2.27 (m, 6H), 2.22-1.53 (m, 23H), 1.54-1.13 (m, 10H), 1.12-0.80 (m, 15H), 0.79-0.61 (m, 1H).

Step 3: Synthesis of 4-[[(23E,25E,27E,28E,35R,36S,37R, 38R,40S,42S,44S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-62) and 4-[[(23E,25E, 27E,28E,35R,36S,37R,38R,40S,42S,44R,45S,46R,47R, 57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53, 54-pentaoxo-69,70-dioxa-58-azatricyclohexatriaconta-23, 25,27(48),28(49)-tetraen-44-yl]oxy]-N,N-dimethyl-butanamide (I-61):

120 mg of 4-[[(23E,25E,27E,28E,35R,36S,37R,38R,40S, 42S,45S,46R,47R,57R)-46,57-dihydroxy-45-[(1R)-2-[(1S, 3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide was purified via prep chiral HPLC to provide 4-[[(23E,25E,27E,28E,35R,36S, 37R,38R,40S,42S,44S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-62: 34.3 mg, 29% yield) and 4-[[(23E,25E,27E,28E,35R,36S,37R,38R,40S,42S,44R,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-61: 24.2 mg, 20% yield), both as white solids.

Chiral separation method:
Column: CHIRALPAK IC
Column size: 5.0 cm I.D.×25 cm L
Solution concentration: 1 mg/ml
Injection: 5 ml
Mobile phase: EtOH=100%
Flow rate: 50 ml/min
Wave length: UV 254 nm
Temperature: 35° C.

I-62: ESI-MS (EI$^+$, m/z): 1079.4 [M+Na]$^+$. $^1$H NMR (400 MHz, CDCl$_3$) δ 6.30 (tt, J=34.4, 17.0 Hz, 2H), 6.13 (dd, J=14.9, 10.0 Hz, 1H), 5.91 (dd, J=28.8, 10.6 Hz, 1H), 5.51 (dd, J=15.0, 8.9 Hz, 1H), 5.45-5.37 (m, 1H), 5.27 (d, J=5.4 Hz, 1H), 5.17 (d, J=4.4 Hz, 1H), 4.75 (s, 1H), 4.19 (d, J=4.9 Hz, 1H), 3.88 (s, 1H), 3.82-3.64 (m, 5H), 3.62-3.52 (m, 2H), 3.47-3.25 (m, 11H), 3.24-3.14 (m, 2H), 3.10 (d, J=7.0 Hz, 1H), 3.01 (s, 3H), 2.94 (s, 3H), 2.71 (dd, J=16.7, 5.7 Hz, 2H), 2.55 (dd, J=16.8, 6.6 Hz, 1H), 2.44-2.25 (m, 4H), 2.14-1.63 (m, 17H), 1.33 (ddd, J=40.8, 27.4, 12.3 Hz, 11H), 1.14-0.83 (m, 18H), 0.71 (dd, J=23.8, 11.9 Hz, 1H).

I-61: ESI-MS (EI$^+$, m/z): 1079.3 [M+Na]$^+$. $^1$H NMR (400 MHz, CDCl$_3$) δ 6.43-5.88 (m, 4H), 5.65-5.08 (m, 5H), 4.33-4.08 (m, 2H), 3.94-3.52 (m, 6H), 3.49-3.31 (m, 8H), 3.30-3.12 (m, 8H), 3.09-2.81 (m, 8H), 2.75-2.26 (m, 6H), 2.10 (d, J=63.9 Hz, 3H), 1.88-1.65 (m, 14H), 1.35 (dt, J=49.7, 11.3 Hz, 9H), 1.18-0.81 (m, 18H), 0.77-0.60 (m, 1H).

EXAMPLE 48

Synthesis of 4-[[(23E,25E,27E,28E,35R,36S,37R,38R,40S,42S,45S,46R,47R,57R)-46,57-dihydroxy-45-[(1R)-2-[(1S,3R,4R)-4-(2-hydroxyethoxy)-3-methoxy-cyclohexyl]-1-methyl-ethyl]-47-methoxy-35,36,37,38,48,49-hexamethyl-50,51,52,53,54-pentaoxo-69,70-dioxa-58-azatricyclohexatriaconta-23,25,27(48),28(49)-tetraen-44-yl]oxy]-N,N-dimethyl-butanamide (I-68) and 4-[[(22E,24E,26E,27E,34R,35S,36R,37R,39S,41S,43R,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-59) and 4-[[(22E,24E,26E,27E,34R,35S,36R,37R,39S,41S,43S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-60):

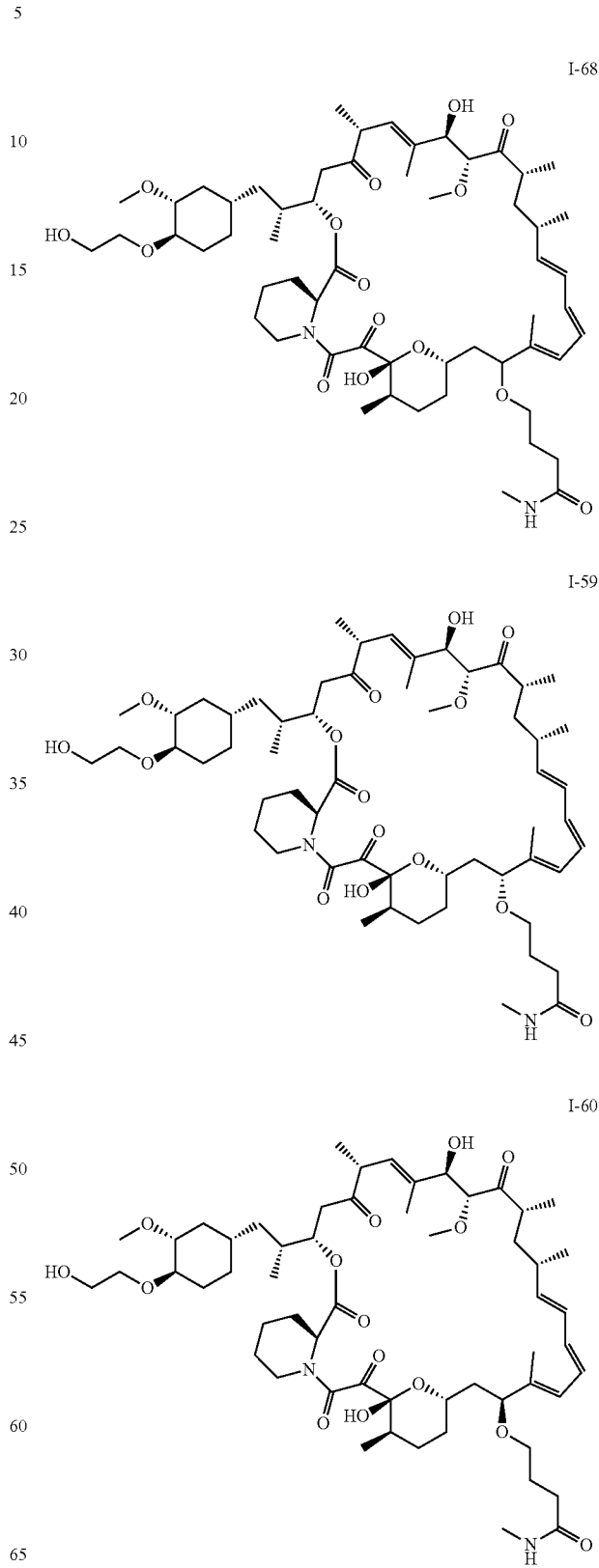

Synthetic Scheme:

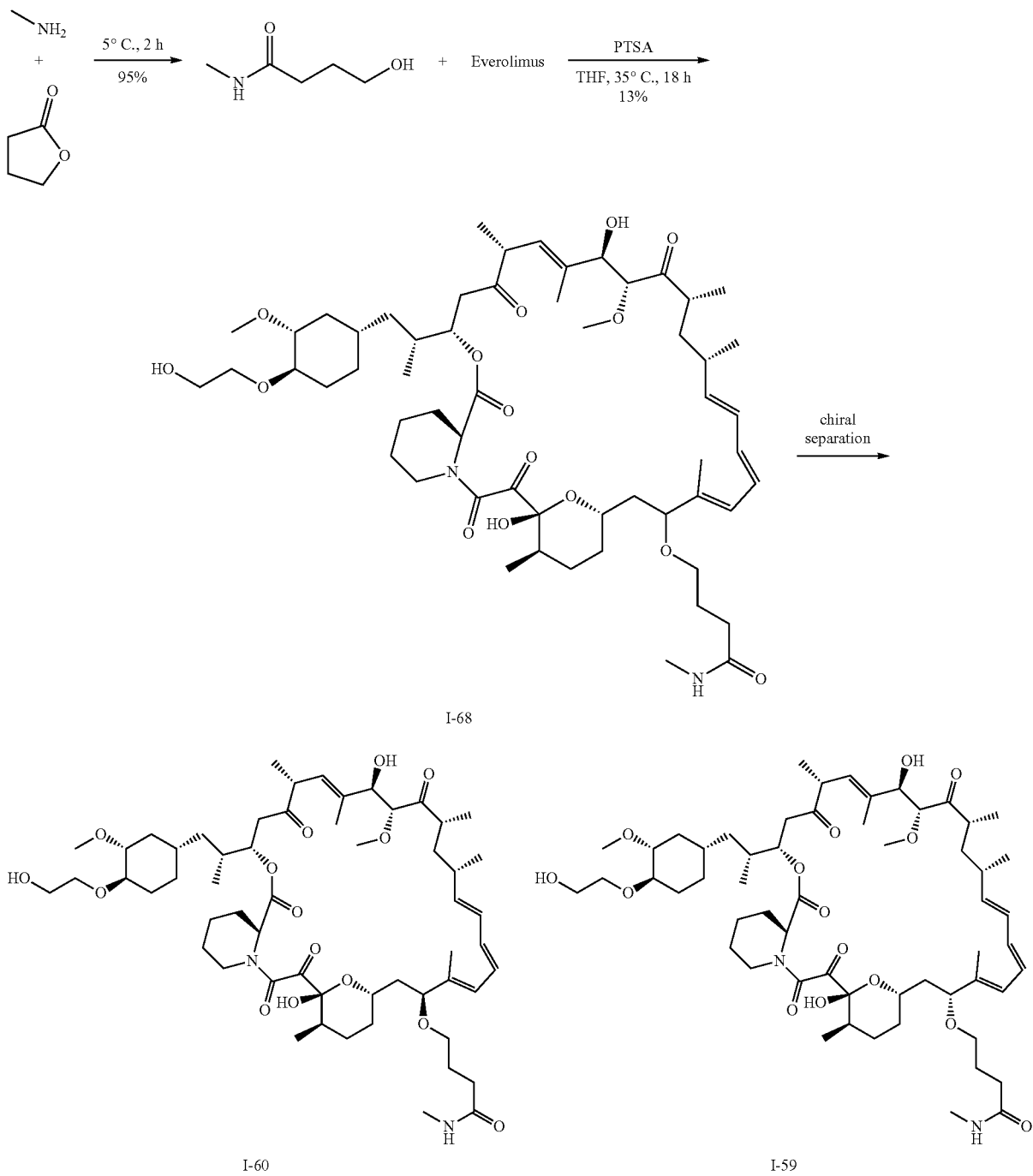

Procedures and Characterization:

Step 1: Synthesis of 4-hydroxy-N,N-dimethylbutanamide:

To a solution of methylamine (5.41 g, 174.24 mmol) in water (30 mL) was added tetrahydrofuran-2-one (5 g, 58.08 mmol) dropwise at 0° C. The mixture was stirred at 5° C. for 2 h then concentrated and lyophilized to afford 4-hydroxy-N-methyl-butanamide (6.5 g, 95.5% yield) as a thick liquid. ESI-MS (EI$^+$, m/z): 118.3 [M+H]$^+$. $^1$H NMR (400 MHz, CDCl$_3$) δ 6.02 (s, 1H), 3.69 (t, J=5.7 Hz, 2H), 2.81 (d, J=4.8 Hz, 3H), 2.36 (t, J=6.8 Hz, 2H), 1.88 (dt, J=12.2, 6.1 Hz, 2H).

Step 2: Synthesis of 4-[[(22E,24E,26E,27E,34R,35S,36R, 37R,39S,41S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58- azatricyclohexatriaconta-22,24,26(47),27(48)-tetraen-43-yl]oxy]-N-methyl-butanamide (I-68):

A solution of everolimus (1 g, 1.04 mmol) and 4-hydroxy-N-methyl-butanamide (2.45 g, 20.87 mmol) in THF (30 mL) was cooled to 0° C. under $N_2$ and p-toluenesulfonic acid (0.9 g, 5.22 mmol) added. The reaction was warmed to 35° C. and stirred for 18 h then poured into sat. $NaHCO_3$ (150 mL) and extracted with EtOAc (100 mL×3). The combined organic layers were washed with water (80 mL), brine (80 mL), dried over anhydrous $Na_2SO_4$, filtered and concentrated. The residue was purified by reverse phase chromatography (C18, 80 g, $CH_3CN:H_2O=37:33$) to provide 4-[[(22E,24E,26E,27E,34R,35S,36R,37R,39S,41S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-68: 0.14 g, 13% yield) as a white solid. ESI-MS (EI$^+$, m/z): 1065.3 [M+Na]$^+$. $^1$H NMR (400 MHz, CDCl$_3$) δ 6.50-5.85 (m, 4H), 5.78-4.96 (m, 5H), 4.78 (s, 1H), 4.33-4.03 (m, 2H), 3.98-3.64 (m, 5H), 3.63-3.49 (m, 2H), 3.49-2.90 (m, 13H), 2.90-2.48 (m, 6H), 2.41-1.94 (m, 7H), 1.93-1.54 (m, 18H), 1.53-1.11 (m, 10H), 1.11-0.80 (m, 16H), 0.78-0.54 (m, 1H).

Step 3: Synthesis of 4-[[(22E,24E,26E,27E,34R,35S,36R,37R,39S,41S,43S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-60) and 4-[[(22E,24E,26E,27E,34R,35S,36R,37R,39S,41S,43R,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-59):

130 mg of 4-[[(22E,24E,26E,27E,34R,35S,36R,37R,39S,41S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide was purified via prep chiral HPLC and the resulting epimers purified via silica gel chromatography (hexane:DCM:EtOAc:MeOH=3:3:1:0.8) to provide 4-[[(22E,24E,26E,27E,34R,35S,36R,37R,39S,41S,43S,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-60: mg, 19% yield) and 4-[[(22E,24E,26E,27E,34R,35S,36R,37R,39S,41S,43R,44S,45R,46R,56R)-45,56-dihydroxy-44-[(1R)-2-[(1S,3R,4R)-4-(2-hydroxyethoxy)-3-methoxy-cyclohexyl]-1-methyl-ethyl]-46-methoxy-34,35,36,37,47,48-hexamethyl-49,50,51,52,53-pentaoxo-68,69-dioxa-58-azatricyclohexatriaconta-22,24,26(47),27(48)-tetraen-43-yl]oxy]-N-methyl-butanamide (I-59: 36 mg, 27% yield), both as white solids.

Chiral analysis method:
Column: CHIRALPAK IC-3(IC30CE-NJ008)
Column size: 0.46 cm I.D.×25 cm L
Injection: 50.0 ul
Mobile phase: Hexane/EtOH=50/50(V/V)
Flow rate: 1.0 ml/min
Wave length: UV 254 nm
Temperature: 35° C.
HPLC equipment: Shimadzu LC-20AT CP-HPLC-06

I-60: ESI-MS (EI$^+$, m/z): 1065.4 [M+Na]$^+$. $^1$H NMR (400 MHz, CDCl$_3$) δ 6.32 (ddd, J=31.4, 14.8, 10.2 Hz, 2H), 6.13 (dd, J=15.1, 9.9 Hz, 1H), 6.00-5.85 (m, 1H), 5.69 (s, 1H), 5.51 (dd, J=14.9, 9.0 Hz, 1H), 5.41 (d, J=9.9 Hz, 1H), 5.27 (d, J=5.7 Hz, 1H), 5.13 (dt, J=48.5, 24.3 Hz, 1H), 4.77 (s, 1H), 4.18 (d, J=5.7 Hz, 1H), 3.92-3.63 (m, 6H), 3.61-3.50 (m, 2H), 3.46-3.25 (m, 10H), 3.22-3.00 (m, 3H), 2.79 (dd, J=4.8, 2.2 Hz, 3H), 2.72 (dd, J=16.9, 5.5 Hz, 2H), 2.55 (dd, J=16.8, 6.5 Hz, 1H), 2.38-2.14 (m, 4H), 2.12-1.91 (m, 4H), 1.89-1.62 (m, 15H), 1.52-1.11 (m, 13H), 1.10-1.01 (m, 6H), 1.00-0.81 (m, 9H), 0.71 (dd, J=23.6, 12.1 Hz, 1H).

I-59: ESI-MS (EI$^+$, m/z): 1065.4 [M+Na]$^+$. $^1$H NMR (400 MHz, CDCl$_3$) δ 6.37-5.81 (m, 4H), 5.66 (d, J=15.6 Hz, 1H), 5.60-4.89 (m, 4H), 4.16 (ddd, J=31.9, 15.6, 5.8 Hz, 2H), 3.93-3.42 (m, 8H), 3.38-2.95 (m, 12H), 2.89-2.39 (m, 7H), 2.37-1.89 (m, 9H), 1.83-1.60 (m, 13H), 1.45-1.05 (m, 11H), 1.03-0.73 (m, 18H), 0.62 (dd, J=23.9, 12.1 Hz, 1H).

EXAMPLE 49

Synthesis of (21E,23E,25E,26E,34R,35S,36R,37R,39S,41S,44S,45R,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-28):

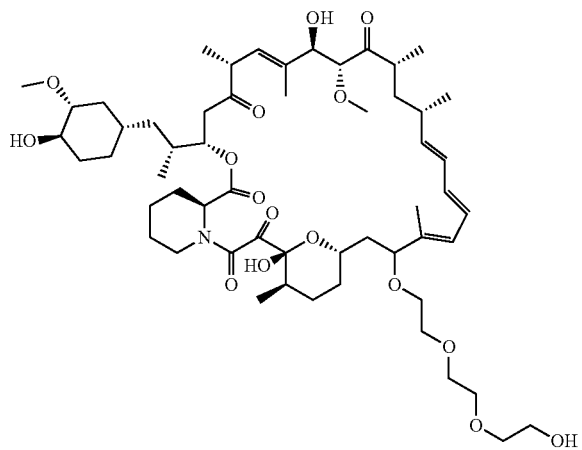

I-28

Synthetic Scheme:

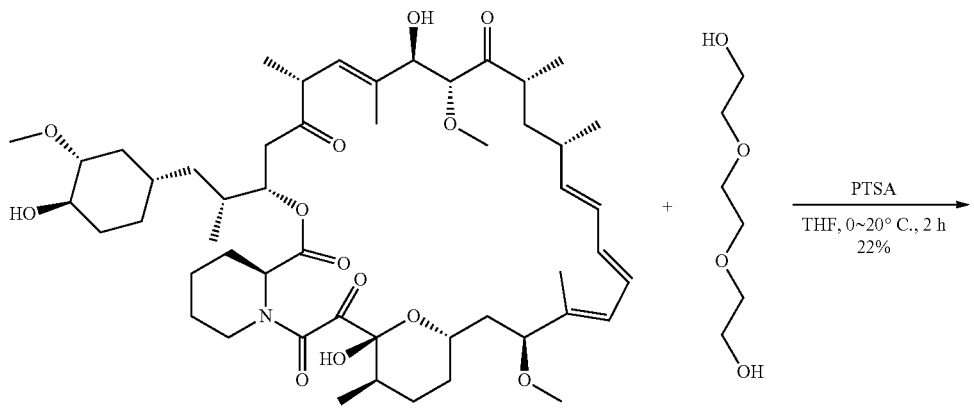

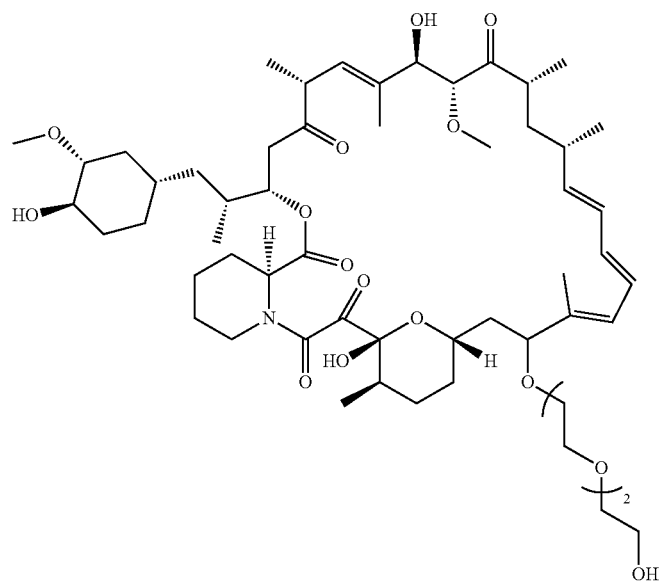

I-28

Procedures and Characterization:
Step 1: Synthesis of (21E,23E,25E,26E,34R,35S,36R,37R,39S,41S,44S,45R,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-28):

To a solution of rapamycin (0.5 g, 0.547 mmol) in THF (10 mL) at 20° C. under $N_2$ was added 4-methylbenzenesulfonic acid hydrate (0.52 g, 2.73 mmol) slowly and 2-[2-(2-hydroxyethoxy)ethoxy]ethanol (1.72 g, 11.49 mmol, 3 mL). The resulting solution was stirred for 2 h then poured into sat. $NaHCO_3$ (80 mL) and extracted with EtOAc (60 mL×3). The combined organic layers were washed with water (60 mL), brine (60 mL), dried over anhydrous $Na_2SO_4$, filtered and concentrated. The residue was purified by reverse phase chromatography (C-18, $CH_3CN:H_2O$=75:25) to provide (21E,23E,25E,26E,34R,35S,36R,37R,39S,41S,44S,45R,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53 -pentone (I-28: 125 mg, 22% yield) as a white solid. ESI-MS (EI$^+$, m/z): 1054.5 [M+Na]$^+$. $^1$H NMR (500 MHz, $CDCl_3$) δ 6.44-5.87 (m, 4H), 5.52-5.12 (m, 4H), 4.90 (s, 1H), 4.34-4.11 (m, 1H), 4.05-3.83 (m, 1H), 3.80-3.53 (m, 13H), 3.50-3.22 (m, 12H), 3.01-2.49 (m, 6H), 2.39-1.87 (m, 6H), 1.82-1.68 (m, 8H), 1.44-1.15 (m, 13H), 1.11-0.85 (m, 18H), 0.71-0.57 (m, 1H).

EXAMPLE 50
Synthesis of (21E,23E,25E,26E,34R,35S,36R,37R, 39S,41S,43R,44S,45R,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36, 37,47,48-hexamethyl-66,67-dioxa-56-azatricyclo-hexatriaconta-21,23,25(47),26(48)-tetraene-49,50, 51,52,53-pentone (I-30):
I-30
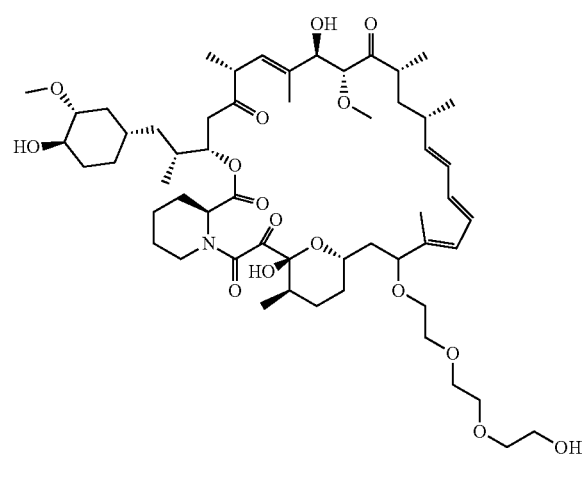
Synthetic Scheme:
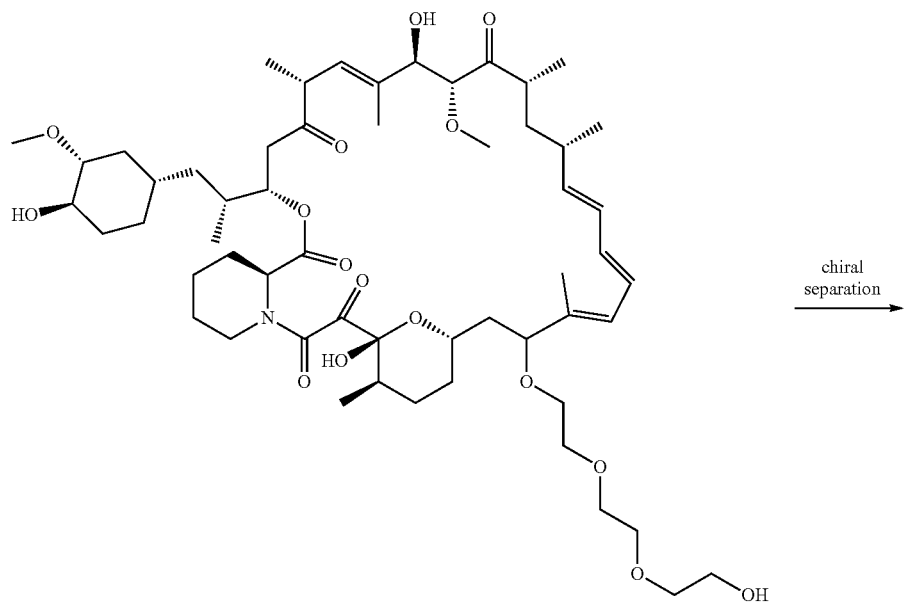
chiral separation

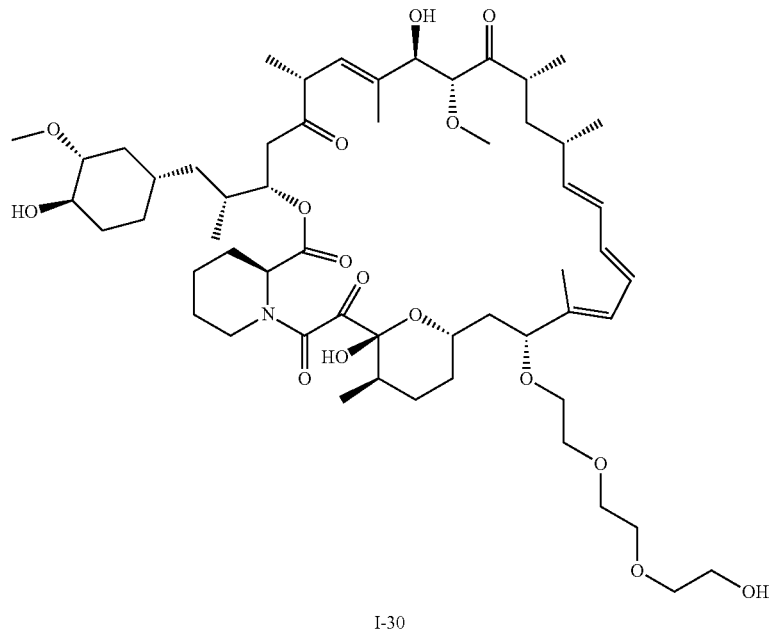

I-30

Procedures and Characterization:

Step 1: Synthesis of (21E,23E,25E,26E,34R,35S,36R,37R, 39S,41S,43R,44S,45R,46R,55R)-45,55-dihydroxy-43-[2-[2-[2-hydroxyethoxy)ethoxy]ethoxy]-44-[(1R)-2-[(1S,3R, 4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49, 50,51,52,53-pentone (I-30):

7.0 g of the epimeric mixture (Example 49; I-28) was purified via prep chiral HPLC to obtain (21E,23E,25E,26E, 34R,35S,36R,37R,39S,41S,43R,44S,45R,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26 (48)-tetraene-49,50,51,52,53-pentone (I-30: 1.113 g, 16% yield) as a white solid. ESI-MS (EI+, m/z): 1054.4 [M+Na]+. 
$^1$H NMR (500 MHz, CDCl$_3$) δ 6.41-5.92 (m, 4H), 5.63 (ddd, J=23.1, 15.1, 8.2 Hz, 1H), 5.47 (dd, J=29.9, 10.3 Hz, 1H), 5.30-5.00 (m, 2H), 4.33-4.12 (m, 2H), 3.97 (dd, J=18.9, 6.6 Hz, 1H), 3.86-3.48 (m, 14H), 3.44-3.22 (m, 10H), 2.97-2.88 (m, 1H), 2.82 (s, 1H), 2.74-2.46 (m, 3H), 2.30 (d, J=14.3 Hz, 2H), 2.21-1.91 (m, 5H), 1.86-1.57 (m, 11H), 1.50-1.22 (m, 12H), 1.16-0.81 (m, 18H), 0.66 (dt, J=23.8, 11.7 Hz, 1H).

EXAMPLE 51

Synthesis of (22E,24E,26E,27E,35R,36S,37R,38R, 40S,42S,45S,46S,47R,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38,48,49-hexamethyl-66,67-dioxa-57-azatricyclohexatriaconta-22,24,26(48),27(49)-tetraene-50,51,52,53,54-pentone (I-121):

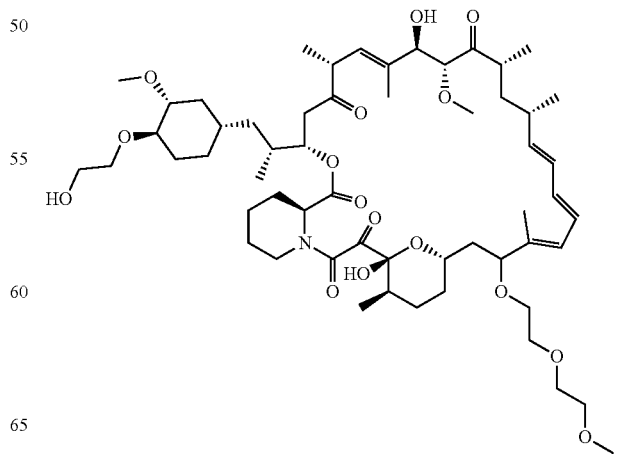

I-121

Synthetic Scheme:
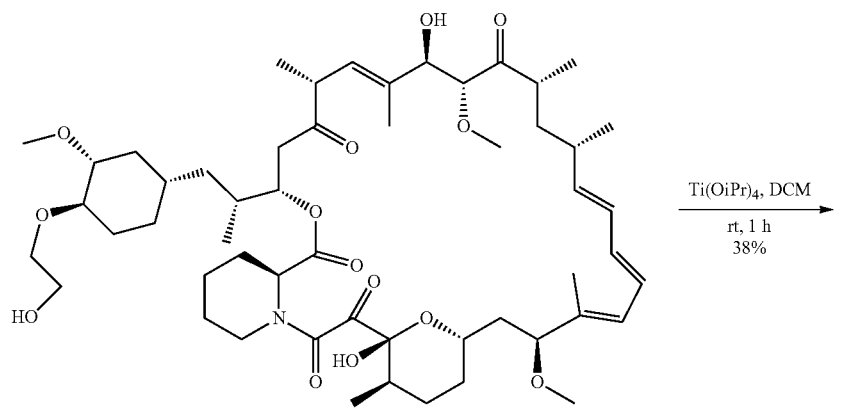
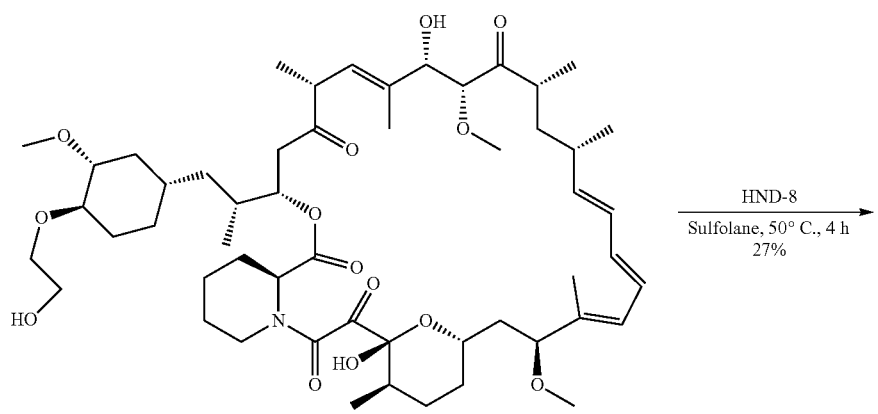
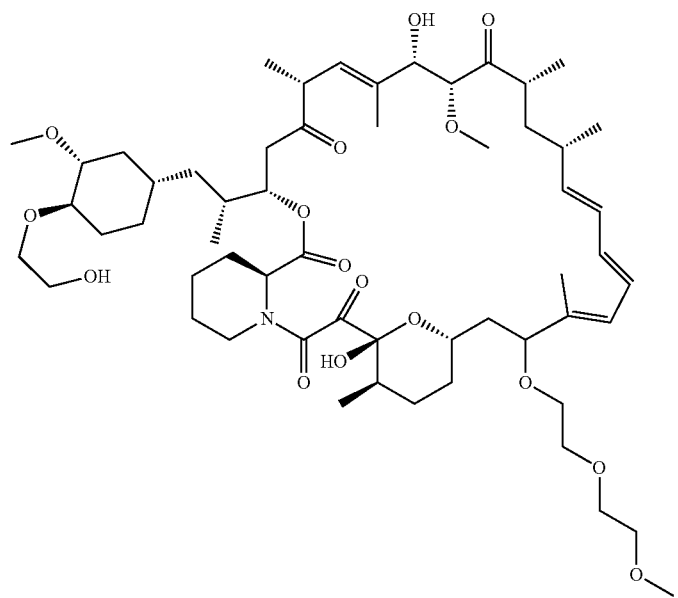
I-121

Procedures and Characterization:

Step 1: Synthesis of (22E,24E,26E,27E,31R,32S,33R,34R, 36S,38S,40S,41S,42S,43R,52R)-42,52-dihydroxy-41-[(1R)-2-[(1S,3R,4R)-4-(2-hydroxyethoxy)-3-methoxy-cyclohexyl]-1-methyl-ethyl]-40,43-dimethoxy-31,32,33,34, 44,45-hexamethyl-62,63-dioxa-53-azatricyclohexatriaconta-22,24,26(44),27(45)-tetraene-46, 47,48,49,50-pentone:

To a solution of everolimus (1 g, 1.04 mmol) in DCM (50 mL) was added Ti(OiPr)$_4$ (0.89 g, 3.13 mmol) dropwise at rt. The reaction mixture turned pale yellow. After 30 min, the solution was poured into a separatory funnel containing a heterogeneous mixture of 1N HCl (50 mL) and EtOAc(50 mL). The organic layer was sequentially washed with saturated aqueous NaHCO$_3$ (30 mL), H$_2$O (50 mL), brine (50 mL), dried over anhydrous Na$_2$SO$_4$, filtered and concentrated under vacuum. The residue was purified by silica gel chromatography (hexane: acetone=2:1) to obtain (22E,24E, 26E,27E,31R,32S,33R,34R,36S,38S,40S,41S,42S,43R, 52R)-42,52-dihydroxy-41-[(1R)-2-[(1S,3R,4R)-4-(2-hydroxyethoxy)-3-methoxy-cyclohexyl]-1-methyl-ethyl]-40, 43 -dimethoxy-31,32,33,34,44,45 -hexamethyl-62,63-dioxa-53-azatricyclohexatriaconta-22,24,26(44),27(45)-tetraene-46,47,48,49,50-pentone (380 mg, 38% yield) as a light yellow solid. $^1$H NMR (400 MHz, DMSO-d$_6$) δ 6.44 (dt, J=13.9, 10.3 Hz, 2H), 6.33-6.06 (m, 3H), 5.54-4.85 (m, 5H), 4.48 (t, J=5.3 Hz, 1H), 4.10-3.91 (m, 2H), 3.89-3.79 (m, 1H), 3.62 (d, J=11.5 Hz, 1H), 3.54-3.41 (m, 5H), 3.38-3.28 (m, 8H), 3.19 (dt, J=11.9, 7.6 Hz, 4H), 3.10-2.92 (m, 6H), 2.71 (t, J=14.8 Hz, 1H), 2.43-1.78 (m, 6H), 1.75-1.44 (m, 10H), 1.38-0.90 (m, 14H), 0.89-0.67 (m, 13H), 0.66-0.56 (m, 1H).

Step 2: Synthesis of (22E,24E,26E,27E,35R,36S,37R,38R, 40S,42S,45S,56R)-46,56-dihydroxy-45-[(1R)-2-[(1S,3R, 4R)-4-(2-hydroxyethoxy)-3-methoxy-cyclohexyl]-1-methyl-ethyl]-47-methoxy-44-[2-(2-methoxyethoxy) ethoxy]-35,36,37,38,48,49-hexamethyl-66,67-dioxa-57-azatricyclohexatriaconta-22,24,26(48),27(49)-tetraene-50, 51,52,53,54-pentone (I-121):

To a solution of 28-epi-everolimus (0.2 g, 0.208 mmol) and 2-(2-methoxyethoxy)ethanol (0.99 mL, 8.35 mmol) in sulfolane (5 mL) was added HND-8 (35 mg) at 50° C. under N$_2$. The resulting solution was stirred at 50° C. for 4 h, filtered and diluted with water (30 mL) and EtOAc (30 mL). The organic layer was washed with water (10 mL×3), brine (20 mL), dried over anhydrous Na$_2$SO$_4$, filtered and concentrated. The residue was purified via reverse-phase chromatography (C18, CH$_3$CN: H$_2$O=6.5: 3.5) to provide (22E, 24E,26E,27E,35R,36S,37R,38R,40S,42S,45S,56R)-46,56-dihydroxy-45-[(1R)-2-[(1S,3R,4R)-4-(2-hydroxyethoxy)-3-methoxy-cyclohexyl]-1-methyl-ethyl]-47-methoxy-44-[2-(2-methoxyethoxy)ethoxy]-35,36,37,38,48,49-hexamethyl-66,67-dioxa-57-azatricyclohexatriaconta-22,24,26(48),27 (49)-tetraene-50,51,52,53,54-pentone (I-121: 60 mg, 27% yield) as a white solid. ESI-MS (EI$^+$, m/z): 1068.1 [M+Na]$^+$. $^1$H NMR (500 MHz, DMSO-d$_6$) δ 6.57-6.35 (m, 2H), 6.31-5.88 (m, 3H), 5.61-5.38 (m, 1H), 5.28-4.82 (m, 4H), 4.47 (t J=5.3 Hz, 1H), 3.98 (dd, J=40.4, 6.9 Hz, 2H), 3.88-3.73 (m, 2H), 3.59-3.40 (m, 12H), 3.30 (dd, J=12.1, 8.2 Hz, 4H), 3.26-3.14 (m, 8H), 3.08-2.92 (m, 3H), 2.85-2.62 (m, 2H), 2.43-2.22 (m, 2H), 2.19-1.82 (m, 6H), 1.79-1.45 (m, 9H), 1.32 (dd, J=58.1, 21.2 Hz, 5H), 1.19-0.92 (m, 10H), 0.90-0.57 (m, 15H).

EXAMPLE 52

Synthesis of (21E,23E,25E,26E,34R,35S,36R,37R, 39S,41S,44S,45S,46R,55R)-45,55-dihydroxy-43-[2-[2-(2-hydroxyethoxy)ethoxy]ethoxy]-44-[(1R)-2-1 (1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-127) and (21E, 23E,25E,26E,34R,35S,36R,37R,39S,41S,43S,44S, 45S,46R,55R)-45,55-dihydroxy-43-[2-[2-(2-hydroxyethoxy)ethoxy]ethoxy]-44-[(1R)-2-1(1S,3R, 4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25 (47),26(48)-tetraene-49,50,51,52,53-pentone (I-128) and (21E,23E,25E,26E,34R,35S,36R,37R,39S,41S, 43R,44S,45S,46R,55R)-45,55-dihydroxy-43-[2-[2-(2-hydroxyethoxy)ethoxy]ethoxy]-44-[(1R)-2-1(1S, 3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-129):

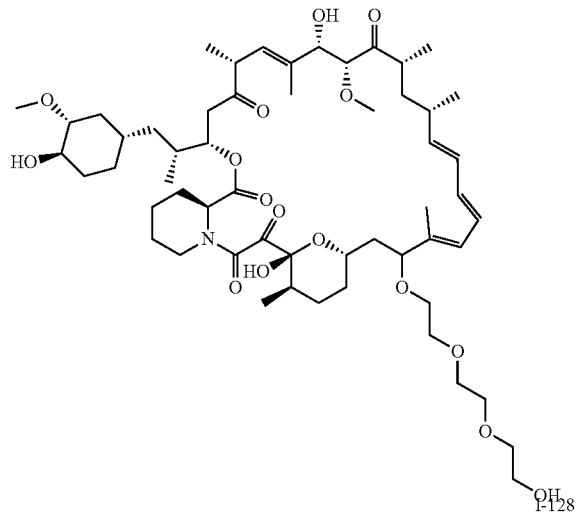

I-127

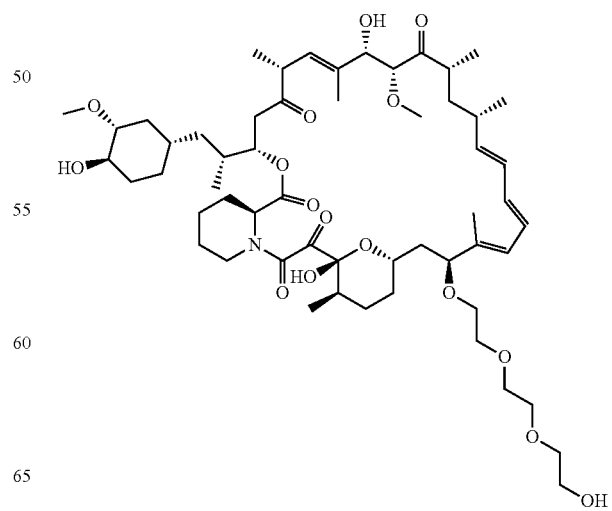

I-128

-continued
I-129
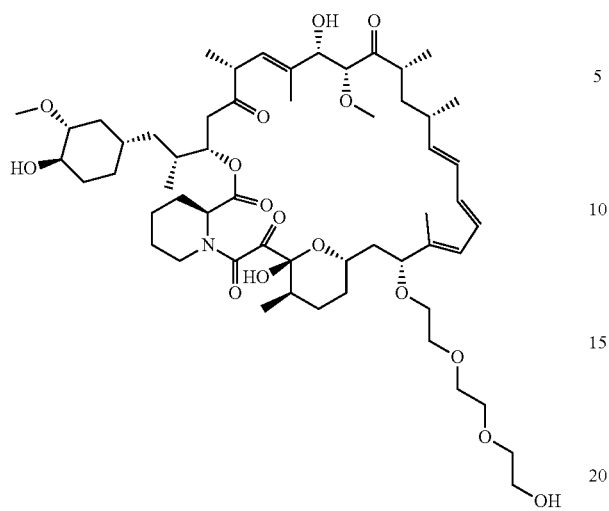
Synthetic scheme:
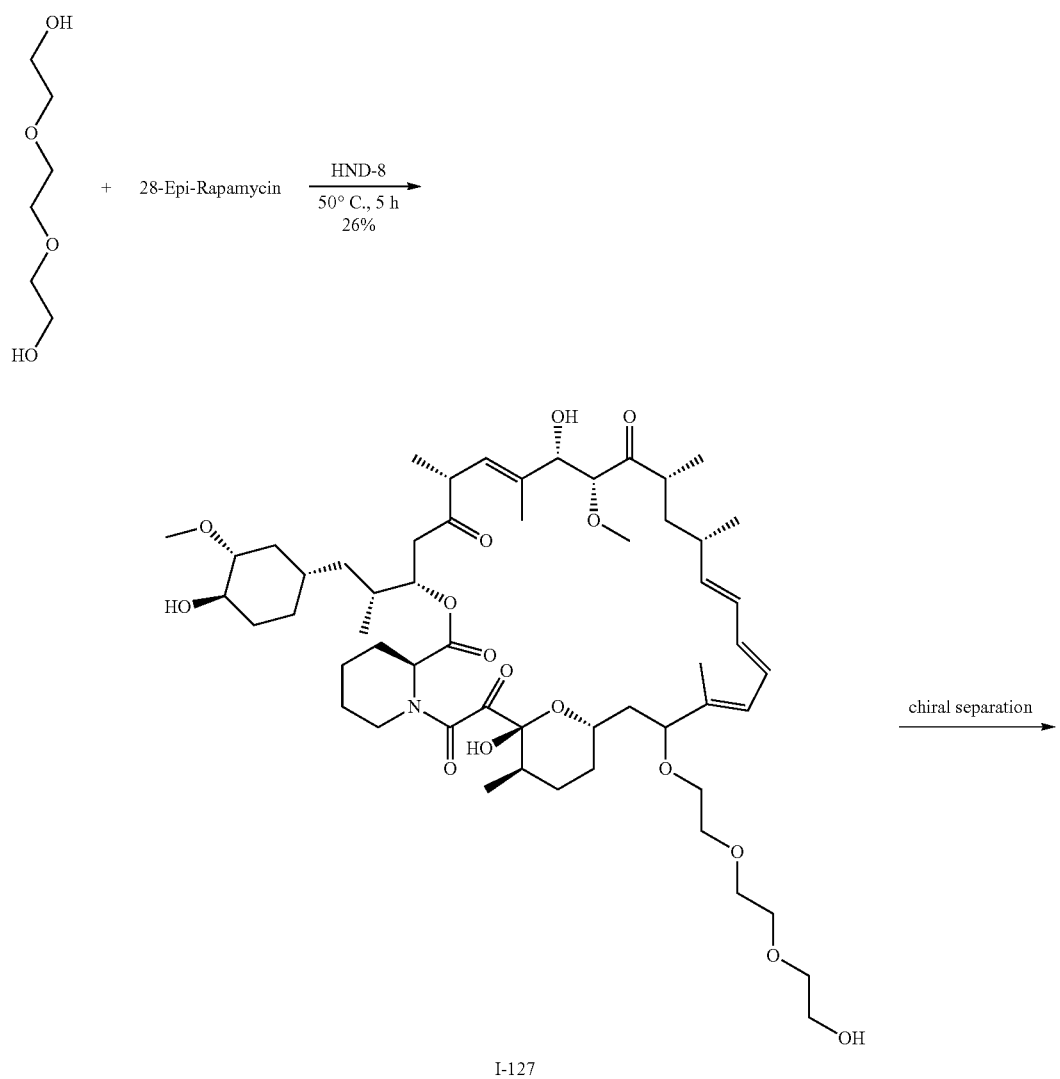

421

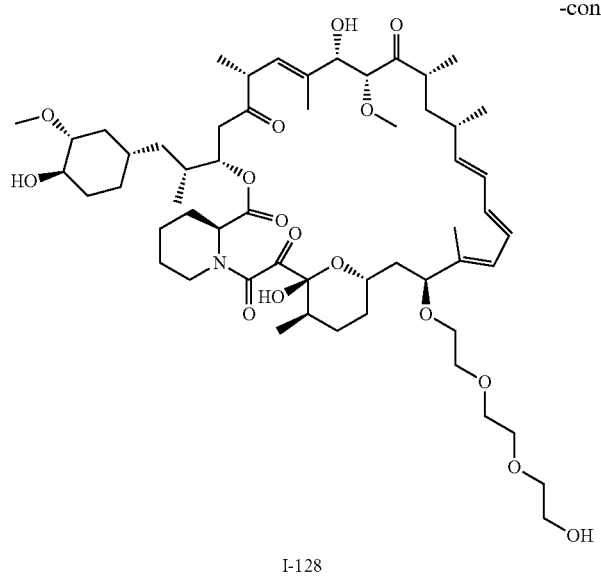

I-128

422
-continued

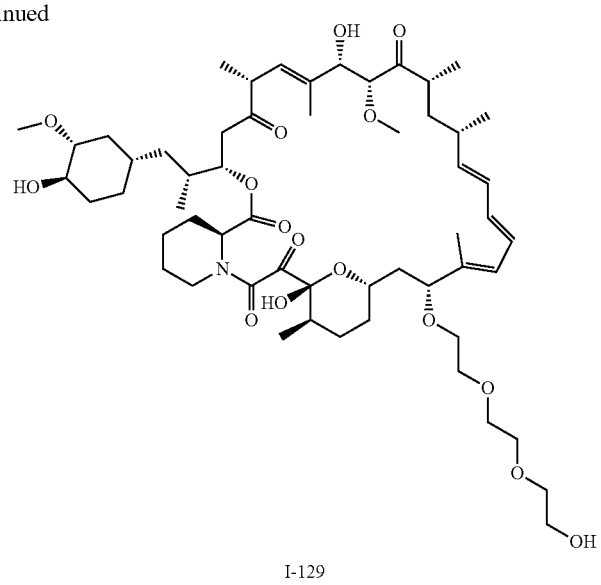

I-129

Procedures and Characterization:
Step 1: Synthesis of (21E,23E,25E,26E,34R,35S,36R,37R,39S,41S,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-127):

To a solution of 28-epi-rapamycin (0.2 g, 0.22 mmol; see Example 52) and 2-[2-(2-hydroxyethoxy)ethoxy]ethanol (0.436 mL, 3.28 mmol) in sulfolane (5 mL) was added HND-8 (30 mg) and the mixture stirred at 50° C. for 5 h. Upon cooling, the reaction was diluted with EtOAc (50 mL), filtered, washed with water (50 mL× 3) and brine(50 mL), dried over anhydrous $Na_2SO_4$, filtered and concentrated. The residue was purified by reverse phase chromatography (C18, $CH_3CN:H_2O$ from 0 to 70% yield) to provide (21E,23E,25E,26E,34R,35S,36R,37R,39S,41S,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-127: 60 mg, 26% yield) as a light yellow solid. ESI-MS (EI$^+$, m/z): 1054.4 [M+Na]$^+$. $^1$H NMR (400 MHz, DMSO-$d_6$) δ 6.61-6.32 (m, 2H), 6.30-5.98 (m, 3H), 5.65-5.38 (m, 1H), 5.28-4.89 (m, 4H), 4.68-4.53 (m, 2H), 4.11-3.91 (m, 2H), 3.89-3.71 (m, 2H), 3.54-3.44 (m, 9H), 3.44-3.40 (m, 3H), 3.31-3.28 (m, 4H), 3.27-3.11 (m, 6H), 2.86-2.66 (m, 3H), 2.20-1.82 (m, 7H), 1.80-1.58 (m, 13H), 1.42-1.06 (m, 9H), 1.05-0.68 (m, 18H), 0.56 (dd, J=23.8, 12.0 Hz, 1H).
Step 2: Synthesis of (21E,23E,25E,26E,34R,35S,36R,37R,39S,41S,43S,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-128) and (21E,23E,25E,26E,34R,35S,36R,37R,39S,41S,43R,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-129):

130 mg of (21E,23E,25E,26E,34R,35S,36R,37R,39S,41S,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone was purified via prep chiral HPLC and the resulting epimers purified via silica gel chromatography (hexane:DCM:EtOAc:MeOH=3:3:1:0 to 3:3:1:0.8) to provide (21E,23E,25E,26E,34R,35S,36R,37R,39S,41S,43S,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-128: 28 mg, 21.5% yield) and (21E,23E,25E,26E,34R,35S,36R,37R,39S,41S,43R,44S,45S,46R,55R)-45,55-dihydroxy-43-[2-[2-(2-hydroxyethoxy)ethoxy]ethoxy]-44-[(1R)-2-[(1S,3R,4R)-4-hydroxy-3-methoxy-cyclohexyl]-1-methyl-ethyl]-46-methoxy-34,35,36,37,47,48-hexamethyl-66,67-dioxa-56-azatricyclohexatriaconta-21,23,25(47),26(48)-tetraene-49,50,51,52,53-pentone (I-129: 22 mg, 16.9% yield), both as white solids.

Chiral separation method:
Column: CHIRALPAK IC(IC00CE-WF029)
Column size: 0.46 cm I.D. ×25 cm L
Injection: 10.0 ul
Mobile phase: Hexane/EtOH=60/40(V/V)
Flow rate: 1.0 ml/min
Wave length: UV 254 nm
Temperature: 35° C.
HPLC equipment: Shimadzu LC-20AT CP-HPLC-09
I-128: ESI-MS (EI$^+$, m/z): 1054.2 [M+Na]$^+$. $^1$H NMR (500 MHz, CDCl$_3$) δ 6.56-6.22 (m, 2H), 6.14 (dd, J=15.0, 10.3 Hz, 1H), 6.00 (dd, J=17.9, 11.0 Hz, 1H), 5.61-5.46 (m, 1H), 5.46-5.32 (m, 1H), 5.29-5.12 (m, 2H), 4.70 (s, 1H), 4.15-4.04 (m, 1H), 3.99-3.88 (m, 1H), 3.86-3.52 (m, 13H), 3.51-3.25 (m, 11H), 3.01-2.60 (m, 5H), 2.52 (dd, J=16.7, 7.1

Hz, 2H), 2.39-1.87 (m, 7H), 1.74 (dt, J=13.3, 8.7 Hz, 8H), 1.63-1.16 (m, 13H), 1.14-0.78 (m, 18H), 0.67 (dd, J=23.8, 12.0 Hz, 1H).

I-129: ESI-MS (EI+, m/z): 1054.1 [M+Na]$^+$. $^1$H NMR (500 MHz, CDCl$_3$) δ 6.46-5.89 (m, 4H), 5.60-4.93 (m, 5H), 4.15 (dd, J=50.5, 20.8 Hz, 2H), 3.97-3.15 (m, 25H), 3.06-2.43 (m, 8H), 2.39-1.69 (m, 16H), 1.54-1.19 (m, 10H), 1.13-0.79 (m, 18H), 0.66 (dd, J=23.6, 11.7 Hz, 1H).

EXAMPLE 53

AlphaLISA Ultra pS6K1 Assay

Assay Protocol
1. Seed MCF-7 cells in Corning 3701 plate and incubate for 20~24 hour. 12,000~16,000 cells will be seeded in 36 μL medium per well.
2. Change the culture medium with fresh medium and incubate for another 2 hours.
3. Add 12 μL (4X) compounds into the cell plate by HAMILTON. Final DMSO concentration is 0.5%. Incubate for 90 minutes.
4. Aspirate 38 μL by HAMILTON, 10 μL rest per well.
5. Add 10 μL 2X lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 μL lysate to assay plate (Optiplate-384).
7. Add 5 μL acceptor beads into assay plate and incubation for 2 hours
8. Add 5 μL donor beads and incubation for 2 hours
9. Count the plate by EnSpire Multimode Plate Reader

TABLE 2

Key Reagents/Supplies

| Reagents/materials | Vendor | Cat. No. | Lot. No. |
|---|---|---|---|
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| Rapamycin | SELLECK | S1039 | 08 |
| OptiPlate-384, White Opaque 384-well MicroPlate | PerkinElmer | 6007299 | 8210-14501 |
| AlphaLISA SureFire Ultra p-p70 S6 Kinase (Thr389) Assay Kit | PerkinElmer | ALSU-PP70-A10K | U0381 |

EXAMPLE 54

AlphaLISA Ultra pAKT Assay

Assay Protocol:
1. MCF-7 cells in Corning 3701 plate and incubate for 20~24 hour. 16,000~20,000 cells will be seeded in 36 μL medium per well.
2. Change the culture medium with fresh medium and incubate for another 90 minutes.
3. Add 12 μL (4X) compounds into the cell plate by HAMILTON. Final DMSO concentration is 0.5%. Incubate for 2 hours.
4. Aspirate 38 μL by HAMILTON, 10 μL rest per well.
5. Add 10 μL 2X lysis buffer using HAMILTON; total volume in wells is 20 μL. Allow cells to shake for 30 min. Cover plate by plastic foil and store plate at −80° C. up to analysis.
6. Thaw cell lysate at RT and transfer 10 ul lysate to assay plate (Optiplate-384).
7. Add 5 μL acceptor beads into assay plate and incubation for 2 hours
8. Add 5 μL donor beads and incubation for 2 hours
9. Count the plate by EnSpire Multimode Plate Reader

TABLE 3

Key Reagents/Supplies

| Reagents/materials | Vendor | Cat. No. | Lot. No. |
|---|---|---|---|
| MCF-7 | ATCC | HTB-22 | 5105360 |
| DMEM | Invitrogen | 12430-054 | 1677193 |
| FBS | Invitrogen | 10099-141 | 1660516 |
| 0.25% Trypsin-EDTA | Invitrogen | 25200-072 | 1638603 |
| 384 well plate, tissue culture treated | Corning | CLS3701 | 29214010 |
| Corning 384 well storage plates | Corning | CLS3656 | 29514036 |
| Torin1 | Selleck | S2827 | 01 |
| Rapamycin | SELLECK | S1039 | 08 |
| OptiPlate-384, White Opaque 384-well MicroPlate | PerkinElmer | 6007299 | 8210-14501 |
| AlphaLISA SureFire Ultra p-Akt 1/2/3 (Ser473) Assay Kits | PerkinElmer | ALSU-PAKT-B10K | U0329 |

EXAMPLE 55

Western Blot Based pS6K1 and pAKT Assay at 24 and 48 Hour Timepoints

Assay Protocol
1. Seed six well plate with 500,000 PC3 cells per well and incubate for 20~24 hour.
2. Add compounds into the cell plate. Incubate for 24 to 48 hours.
4. Plate is placed on ice and the media is removed via aspiration. The wells are washed with 1 mL of 1× PBS and then fully aspirated.
5. 110 μL of 1% Triton Lysis Buffer is added and each well is scraped vigorously.
6. Cell homogenates are transferred to 1.5 mL eppendorf tubes on ice and spun down at 4° C. for 10 minutes at 10,000 rpm.
7. Protein concentration of resulting cell lysates were quantified utilizing a Bradford assay and the samples run analyzed via Western blot on 4-12% Bis/Tris gels with 1× MES buffer.
8. The gels were transferred onto membranes at 50V for 100 minutes, blocked with Odyssey Blocking buffer for 30 minutes then incubated overnight with primary antibody (pS6K1 T389 Rabbit or pAkt S473 Rabbit) overnight at 4° C. on a rotator.
9. The membranes were washed 3X with TBS-T with a 5 minute incubation between each wash then incubated with secondary antibody (LiCor IRDye 800 Donkey Anti Rabbit) for at least 30 minutes.
10. The membranes were washed 3X with TBS-T with a 5 minute incubation between each wash.

11. The gels were then incubated for 5 minutes with PBS at room temperature then imaged using a Li-Cor.

Figure 1:
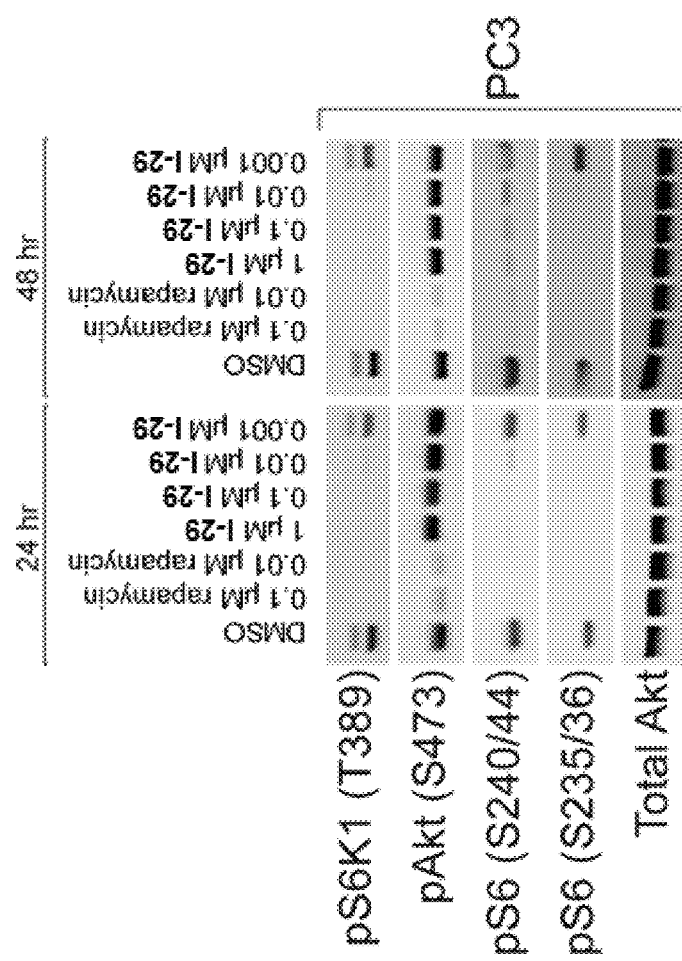
FIG. 1 shows a comparison between two Western blots performed after treating PC3 cells with rapamycin or a compound of the present invention (I-29) for 24 and 48 hours. Staining indicates strong inhibition of the mTORC1 pathway for both rapamycin and I-29 at both time points. In contrast, the mTORC2 pathway, while inhibited by rapamycin at both 24 and 48 hours, is not inhibited by I-29, as demonstrated by the lack of Akt phosphorylation inhibition.
Figure 2:
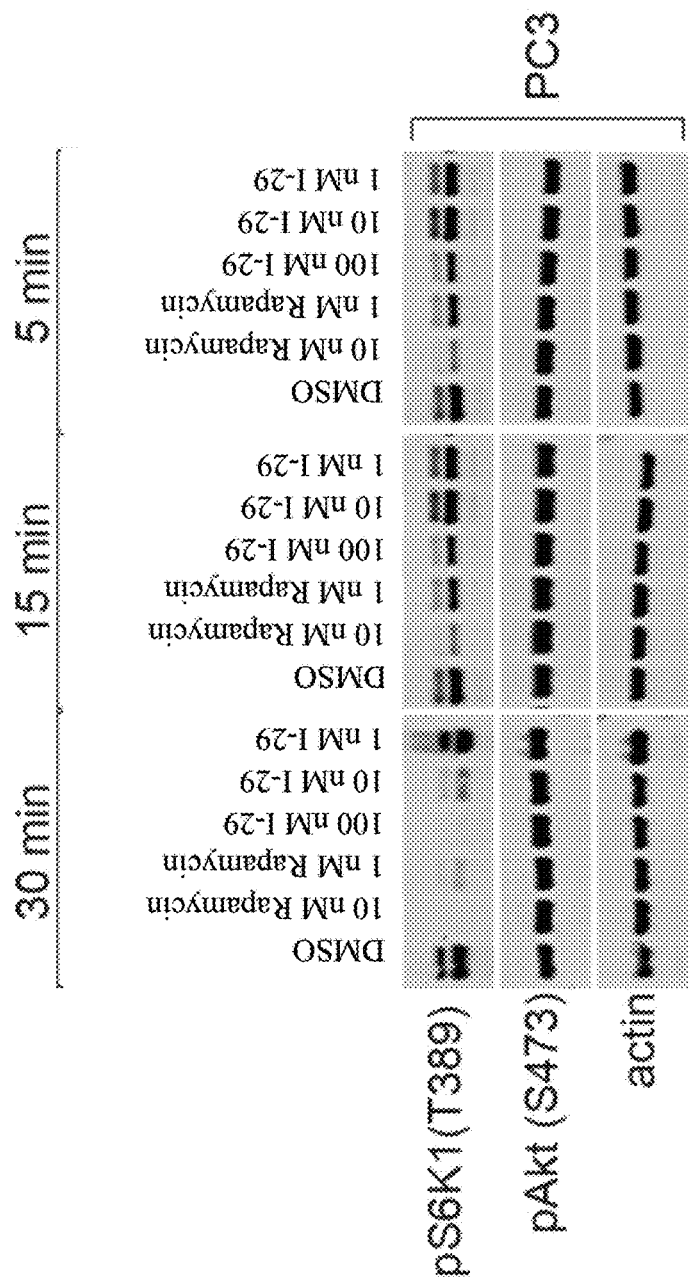
FIG. 2 shows a comparison among three Western blots performed after treating PC3 cells with rapamycin or a compound of the present invention I-29 for 30, 15, or 5 minutes. Staining indicates a time dependent inhibition of the mTORC1 pathway for both rapamycin and I-29.
Figure 3:
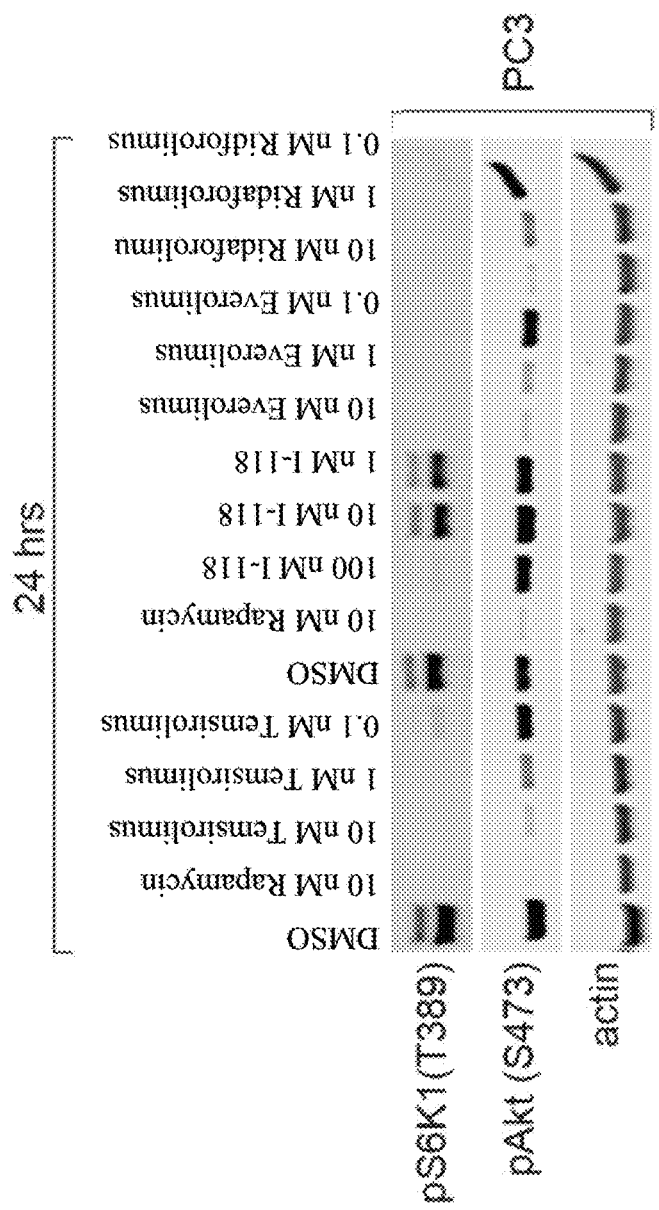
FIG. 3 shows a Western blot performed after treating PC3 cells with rapamycin, temsirolimus, everolimus, ridaforolimus, or a compound of the present invention (I-118) for 24 hrs. Staining indicates strong inhibition of the mTORC1 pathway for all compounds, and moderate concentration dependent inhibition of mTORC1 by I-118. Significantly, rapamycin, temsirolimus, everolimus, and ridaforolimus show a dose dependent inhibition of the mTORC2 pathway, while I-118 does not inhibit the mTORC2 pathway, as demonstrated by the lack of Akt phosphorylation inhibition.
Figure 4:
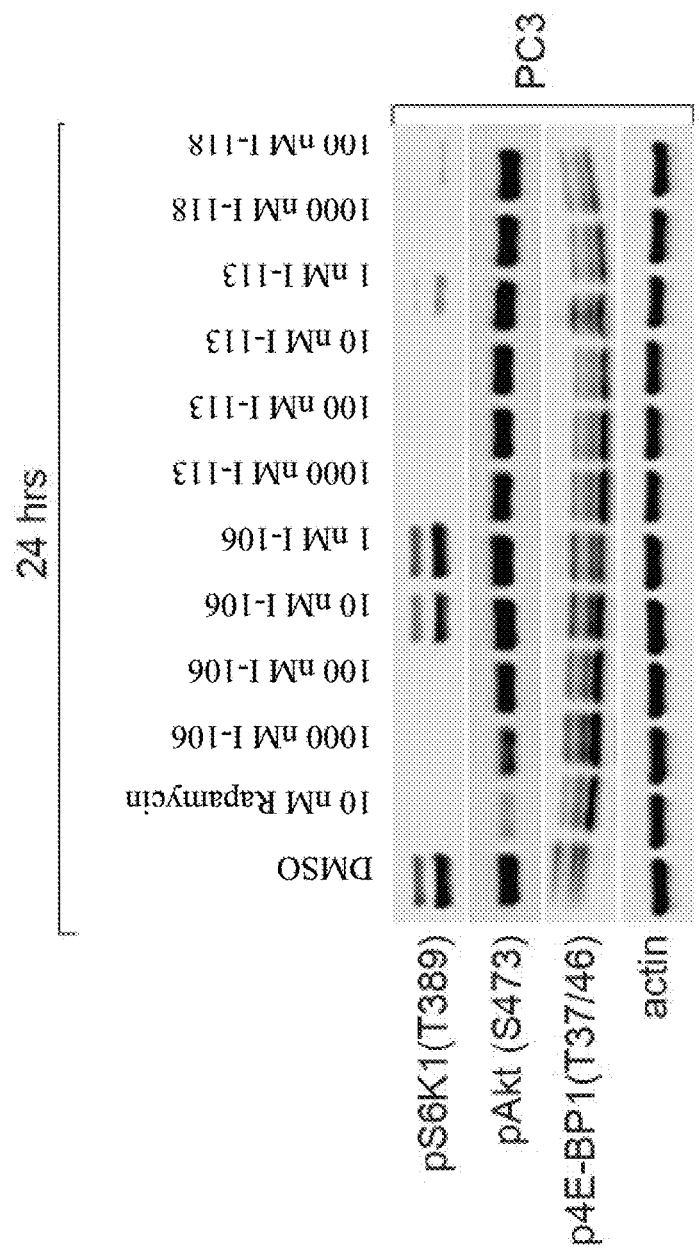
FIG. 4 shows a Western blot performed after treating PC3 cells with rapamycin or compounds of the present invention (I-106, I-113, and I-118) for 24 hours. Staining indicates strong inhibition of the mTORC1 pathway for each compound tested and no inhibition of 4E-BP1 phosphorylation. Significantly, the compounds of the present invention do not inhibit mTORC2, as demonstrated by the lack of Akt phosphorylation inhibition.
Figure 5:
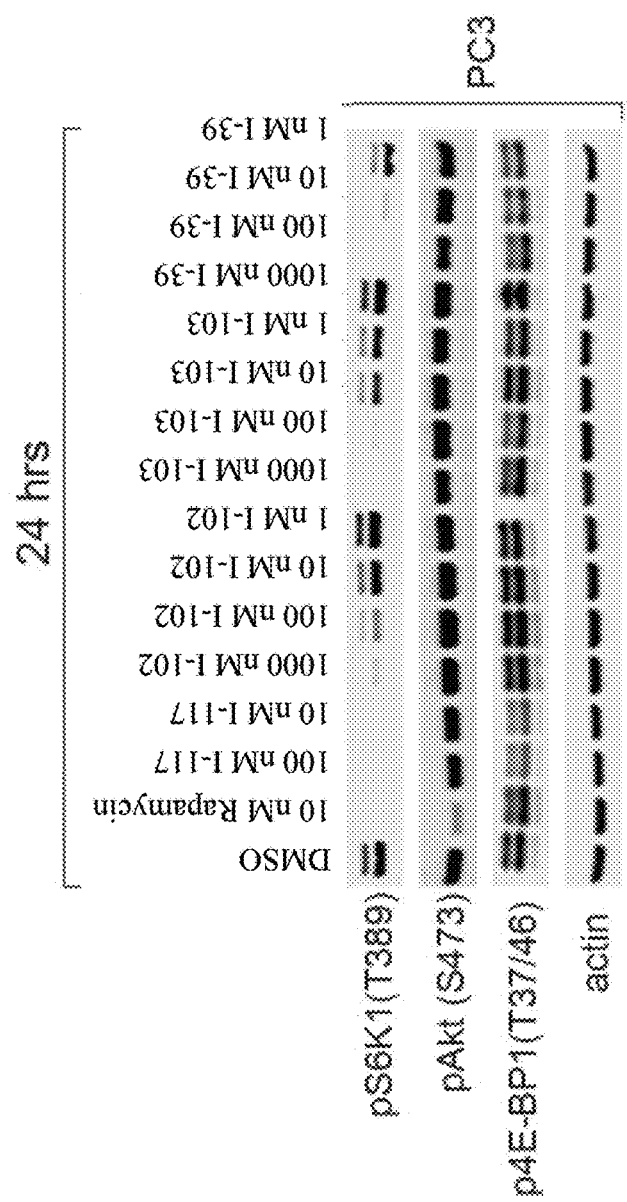
FIG. 5 shows a Western blot performed after treating PC3 cells with rapamycin or compounds of the present invention (I-117, I-102, I-103, and I-39) for 24 hours. Staining indicates strong inhibition of the mTORC1 pathway for each compound tested and no inhibition of 4E-BP1 phosphorylation. Significantly, the compounds of the present invention do not inhibit mTORC2, as demonstrated by the lack of Akt phosphorylation inhibition.
Figure 6:
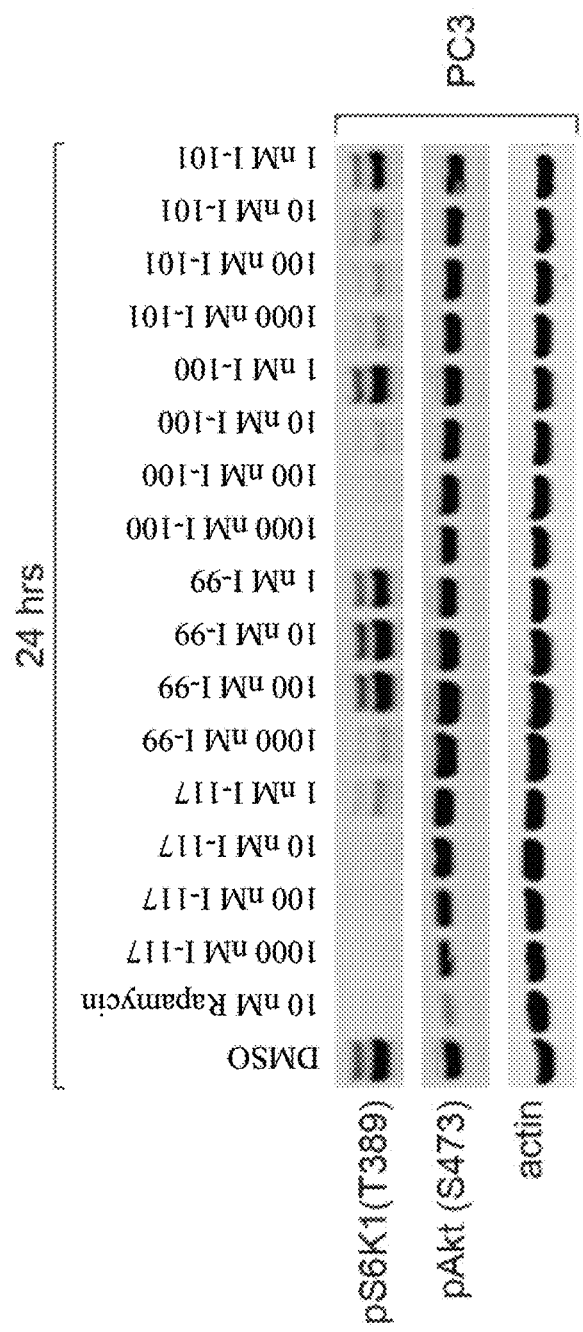
FIG. 6 shows a Western blot performed after treating PC3 cells with rapamycin or compounds of the present invention (I-117, I-99, I-100, and I-101) for 24 hours. Staining indicates strong inhibition of the mTORC1 pathway for rapamycin I-117, I-100, and I-101, and an appreciable concentration dependent inhibition of the mTORC1 pathway for I-99. Significantly, the compounds of the present invention do not inhibit mTORC2, as demonstrated by the lack of Akt phosphorylation inhibition.
Figure 7:
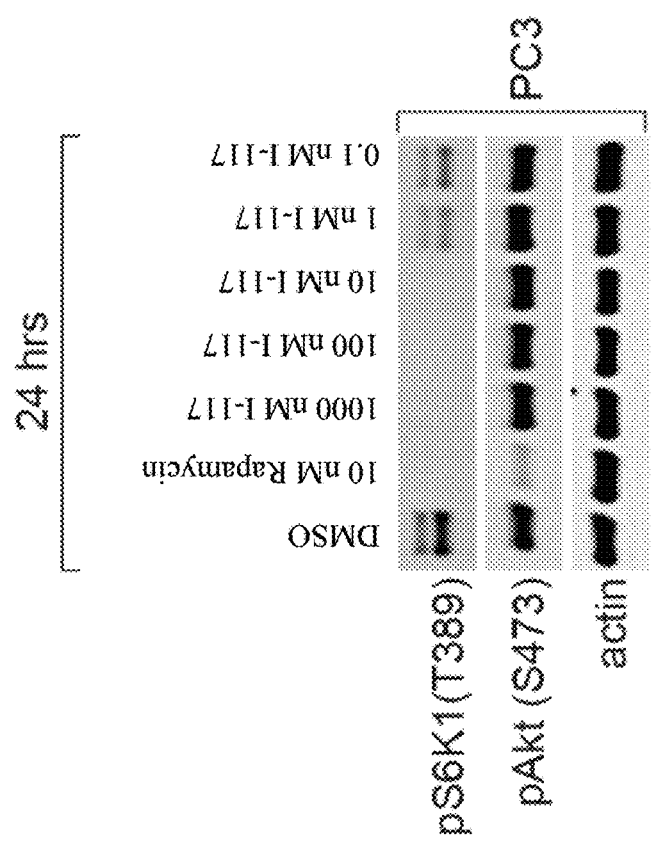
FIG. 7 shows a Western blot performed after treating PC3 cells with rapamycin or a compound of the present invention (I-117) for 24. Staining indicates strong inhibition of the mTOCR1 pathway by both compounds tested. Significantly, the compound of the present invention does not inhibit mTORC2, as demonstrated by the lack of Akt phosphorylation inhibition.
Figure 8:
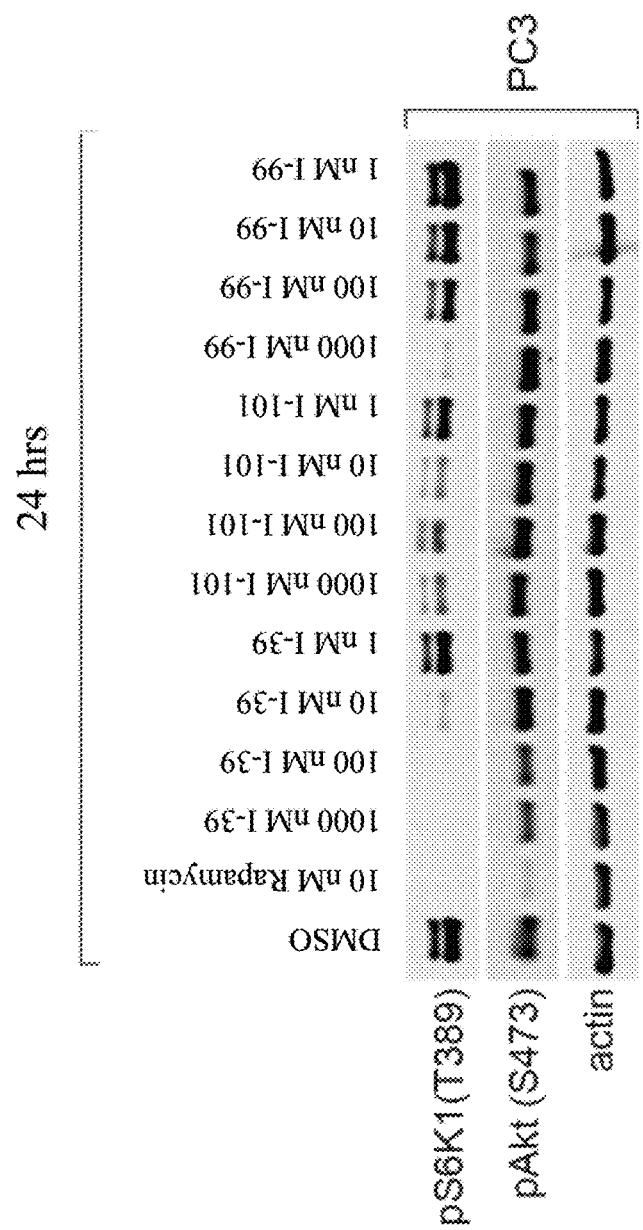
FIG. 8 shows a Western blot performed after treating PC3 cells with rapamycin or compounds of the present invention (I-39, I-101, and I-99) for 24 hours. Staining indicates strong inhibition of the mTORC1 pathway for rapamycin and I-39, and an appreciable concentration dependent inhibition of the mTORC1 pathway for I-101 and I-99. Significantly, the compounds of the present invention do not inhibit mTORC2, as demonstrated by the lack of Akt phosphorylation inhibition.
Figure 9:
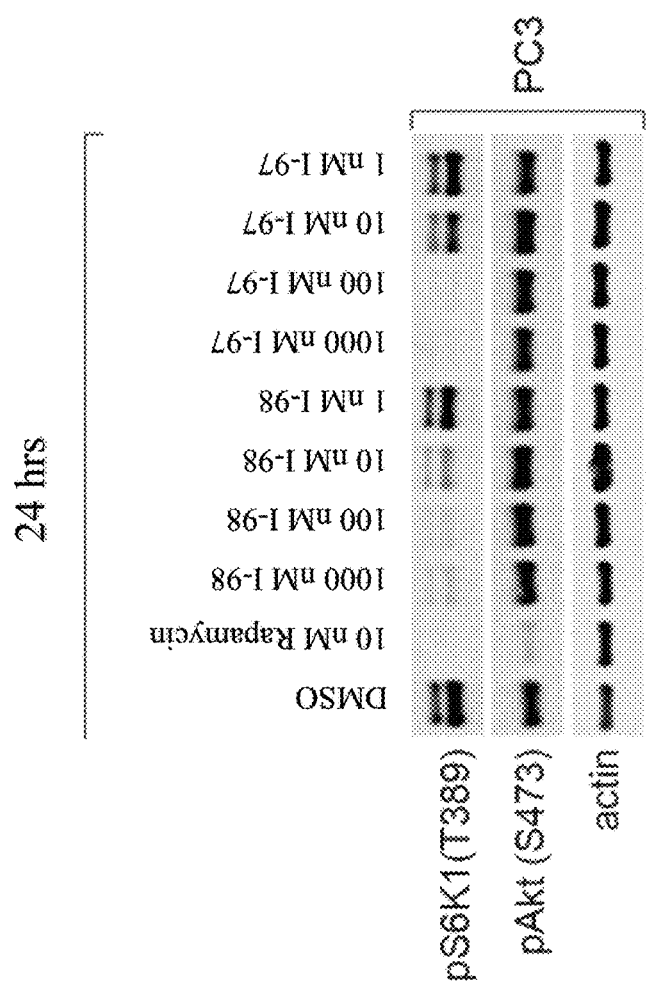
FIG. 9 shows a Western blot performed after treating PC3 cells with rapamycin or compounds of the present invention (I-98 and I-97) for 24 hours. Staining indicates strong inhibition of the mTORC1 pathway for rapamycin and I-98, and a moderate concentration dependent inhibition of the mTORC1 pathway for I-101 and I-99. Significantly, the compounds of the present invention do not inhibit mTORC2, as demonstrated by the lack of Akt phosphorylation inhibition.
Figure 10:
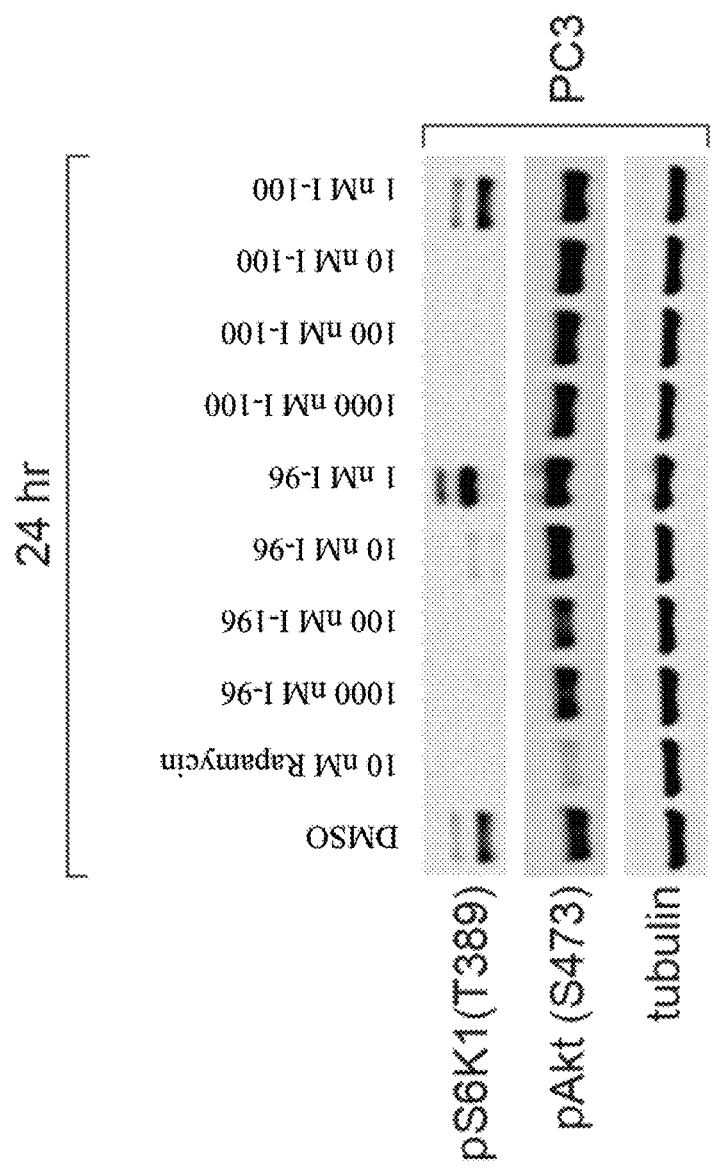
FIG. 10 shows a Western blot performed after treating PC3 cells with rapamycin or compounds of the present invention (I-96 and I-100) for 24 hours. Staining indicates strong inhibition of the mTORC1 pathway for all compounds tested. Significantly, the compounds of the present invention do not inhibit mTORC2, as demonstrated by the lack of Akt phosphorylation inhibition.
Figure 11:
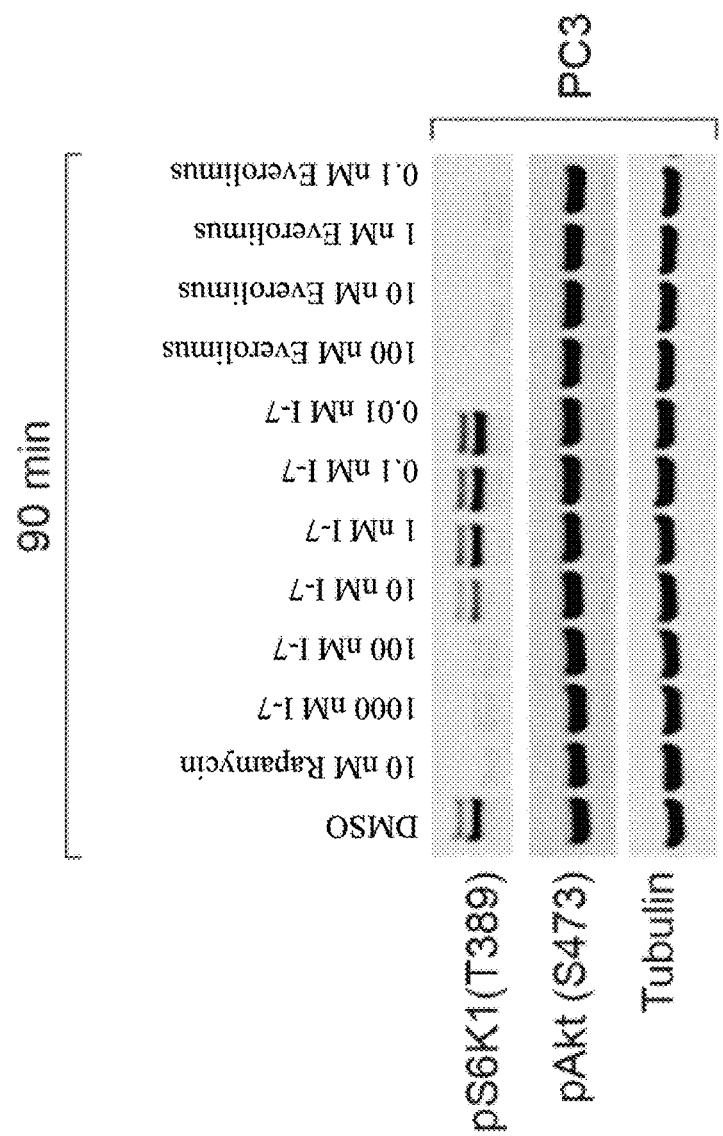
FIG. 11 shows a Western blot performed after treating PC3 cells with rapamycin, everolimus, or a compound of the present invention (I-7) for 90 minutes. Staining indicates strong inhibition of the mTORC1 pathway for rapamycin and everolimus, and a moderate concentration dependent inhibition of the mTORC1 pathway for I-7. Significantly, the compound of the present invention does not inhibit mTORC2, as demonstrated by the lack of Akt phosphorylation inhibition.
Figure 12:
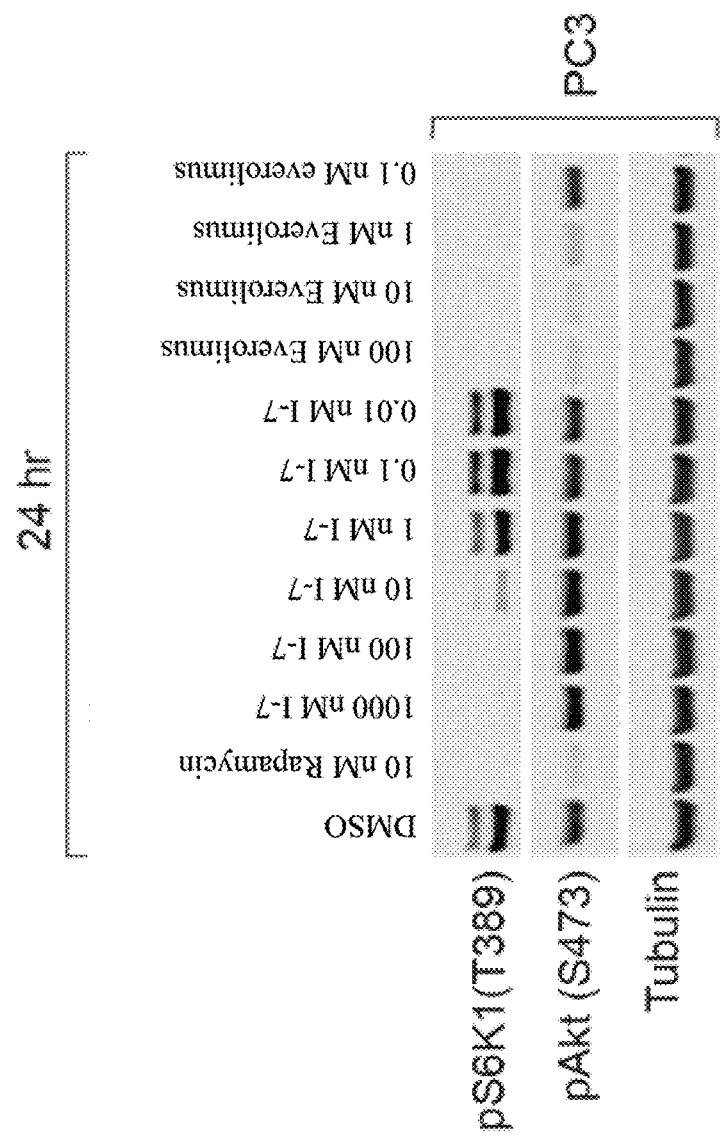
FIG. 12 shows a Western blot performed after treating PC3 cells with rapamycin, everolimus, or a compound of the present invention (I-7) for 24 hours. Staining indicates strong inhibition of the mTORC1 pathway for rapamycin and everolimus, and a moderate concentration dependent inhibition of the mTORC1 pathway for I-7. Significantly, the compound of the present invention does not inhibit mTORC2, as demonstrated by the lack of Akt phosphorylation inhibition.
Figure 13:
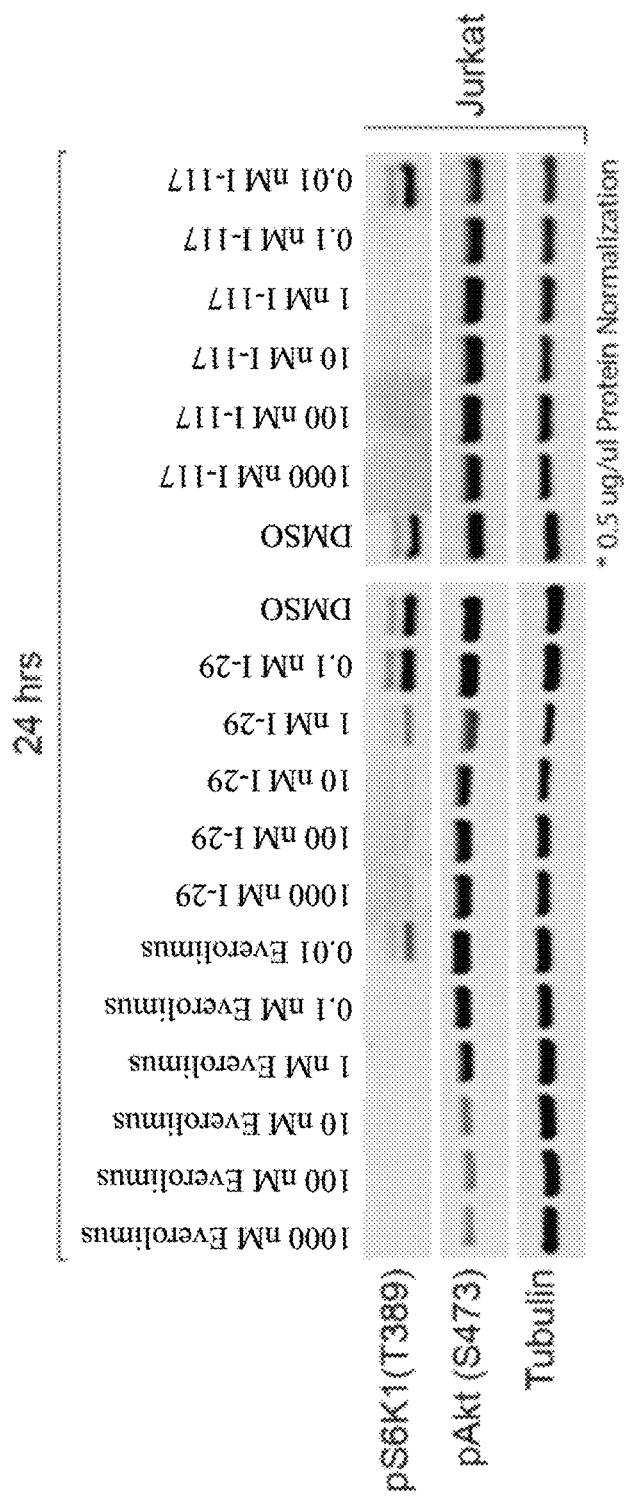
FIG. 13 shows two Western blots performed after treating Jurkat cells with everolimus or compounds of the present invention (I-29 and I-117) for 24 hrs. Staining indicates strong inhibition of the mTORC1 pathway for all compounds tested. Significantly, the compounds of the present invention do not inhibit mTORC2, as demonstrated by the lack of Akt phosphorylation inhibition.
Figure 14:
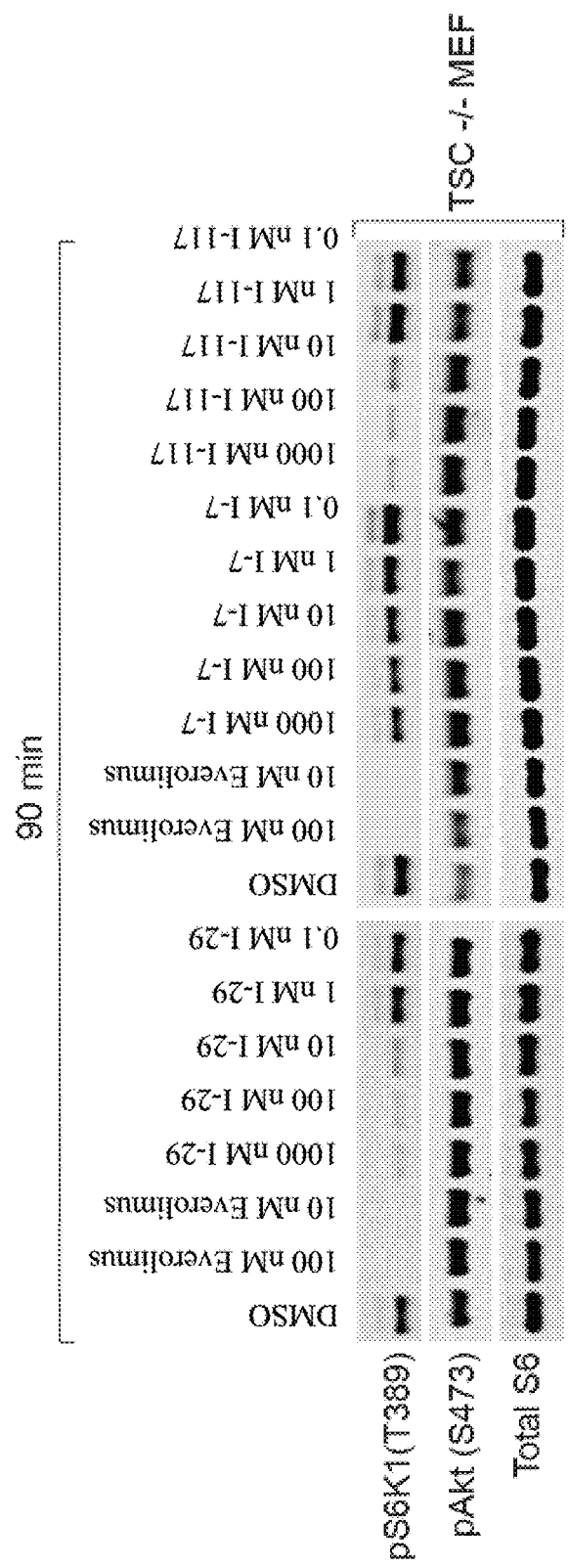
FIG. 14 shows two Western blots performed after treating tuberous sclerosis (TSC2) negative (TSC −/−) MEF cells with everolimus or compounds of the present invention (I-29, I-7, and I-117) for 90 minutes. Staining indicates strong inhibition of the mTORC1 pathway for everolimus, I-29, and I-117, and appreciable concentration dependent inhibition of the mTORC1 pathway for I-7. Significantly, the compounds of the present invention do not inhibit mTORC2, as demonstrated by the lack of Akt phosphorylation inhibition.
Figure 15:
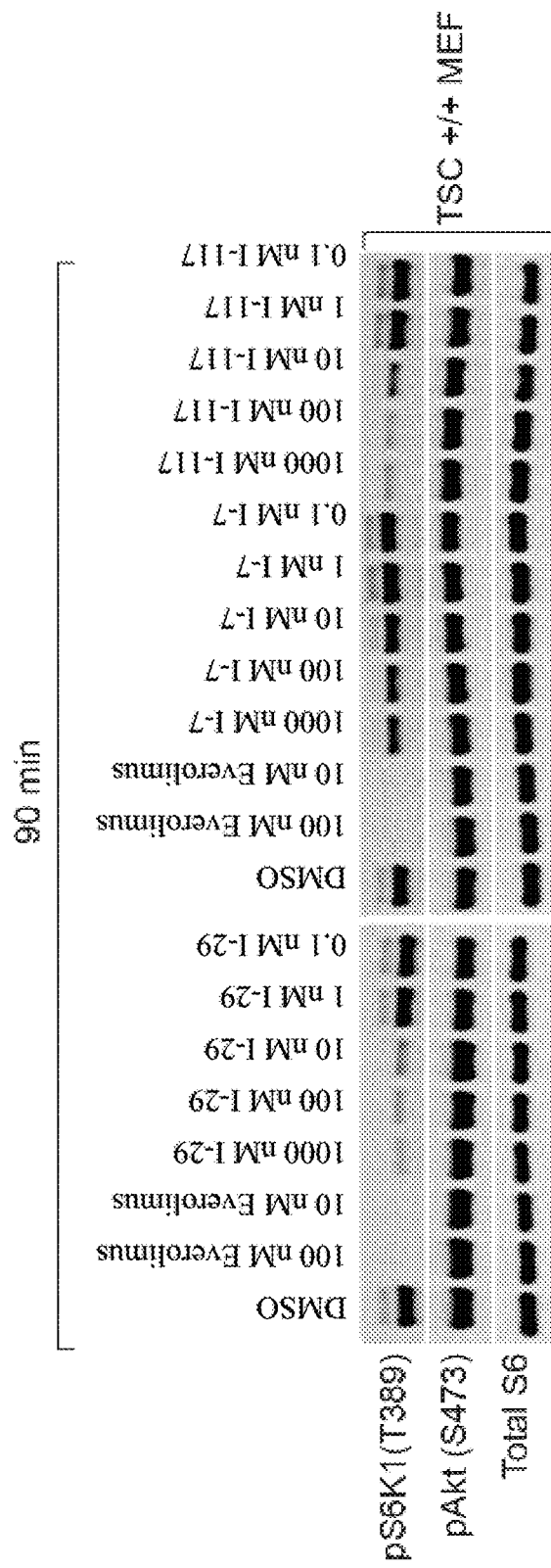
FIG. 15 shows two Western blots performed after treating tuberous sclerosis 2 (TSC2) positive (TSC +/+) MEF cells with everolimus or compounds of the present invention (I-29, I-7, and I-117) for 90 minutes. Staining indicates strong inhibition of the mTORC1 pathway for everolimus and I-29, moderate concentration dependent inhibition of the mTORC1 pathway for I-117, and appreciable concentration dependent inhibition of the mTORC1 pathway for I-7. Significantly, the compounds of the present invention do not inhibit mTORC2, as demonstrated by the lack of Akt phosphorylation inhibition.
Figure 16:
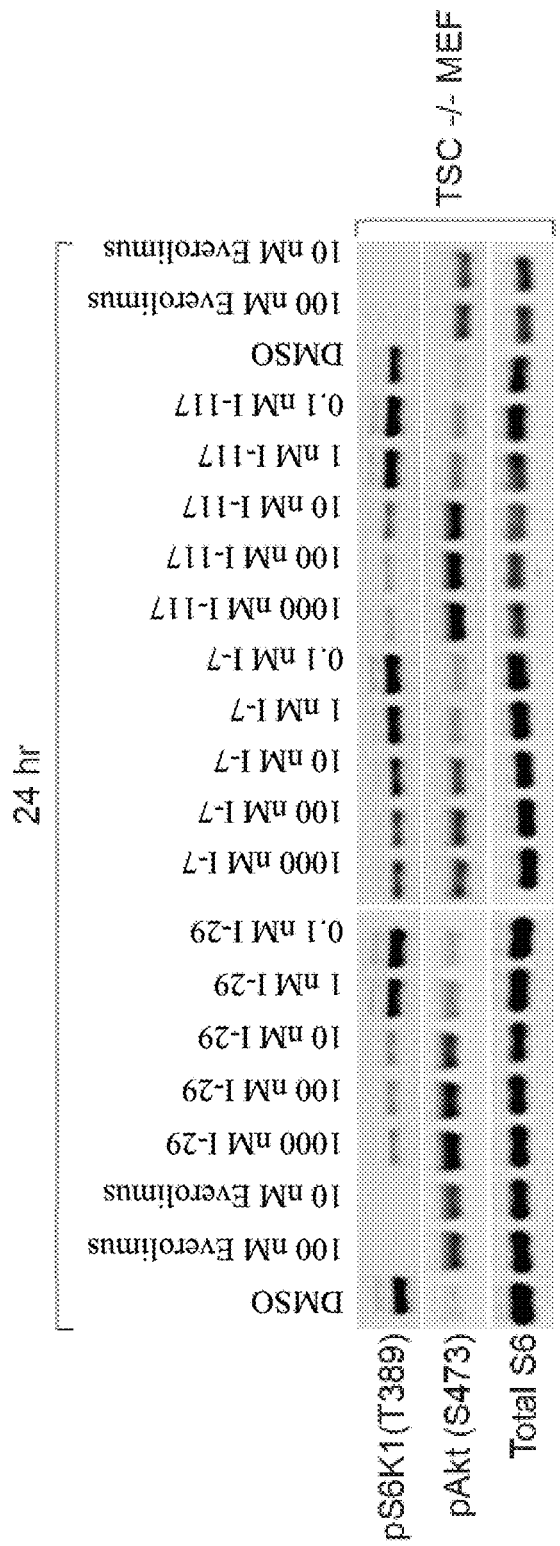
FIG. 16 shows two Western blots performed after treating TSC −/− MEF cells with everolimus or compounds of the present invention (I-29, I-7, and I-117) for 24 hours. Staining indicates strong inhibition of the mTORC1 pathway for everolimus, I-29, and I-117, and an appreciable concentration dependent inhibition of the mTORC1 pathway for I-7. Significantly, the compounds of the present invention do not inhibit mTORC2, as demonstrated by the lack of Akt phosphorylation inhibition.
Figure 17:
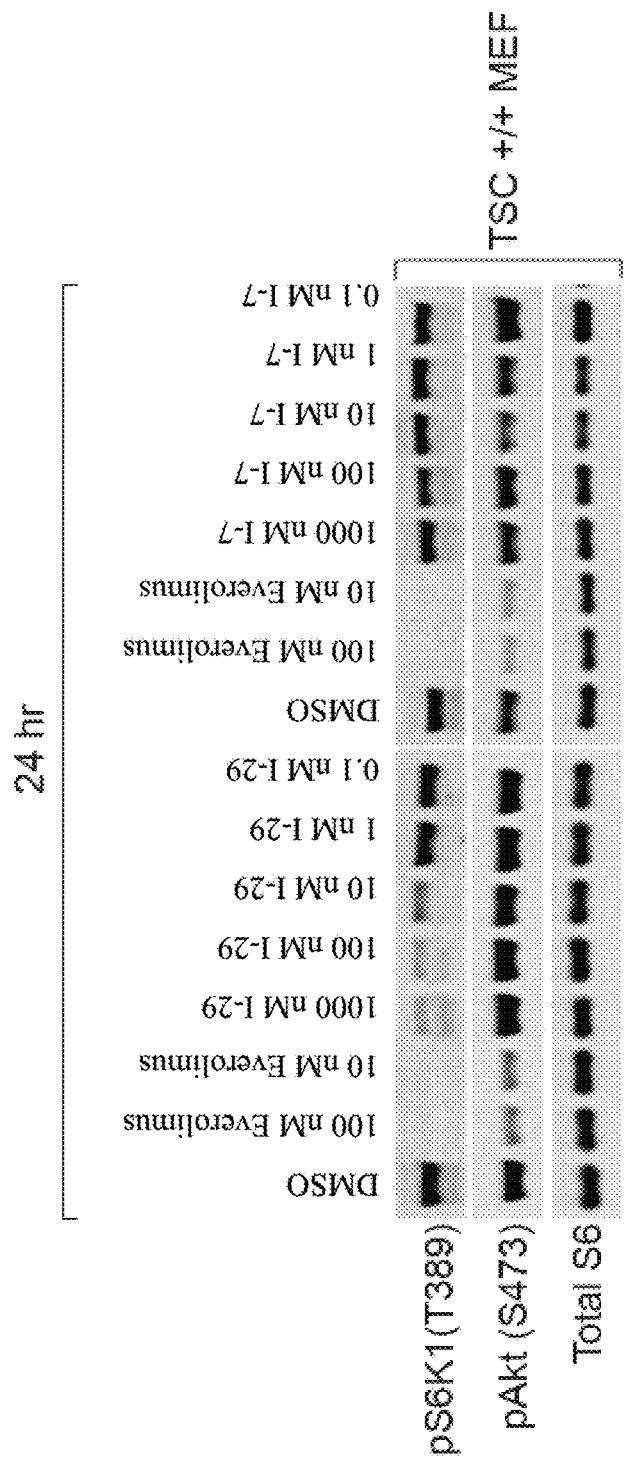
FIG. 17 shows two Western blots performed after treating TSC +/+ MEF cells with everolimus or compounds of the present invention (I-29 and I-7) for 24 hours. Staining indicates strong inhibition of the mTORC1 pathway for everolimus, a moderate concentration dependent inhibition of the mTORC1 pathway for I-29, and a modest concentration dependent inhibition of the mTORC1 pathway for I-7.

Results for a representative Western blot are summarized in FIG. 1. PC3 cells were treated with rapamycin (0.1 μM and 0.01 μM) or I-29 (1 μM, 0.1 μM, 0.01 μM, and 0.001 μM) for 24 and 48 hours. Blots clearly demonstrate a significant reduction in pS6K1 for both rapamycin and I-29 at both 24 and 48 hours, indicating inhibition of the mTORC1 pathway. Importantly, I-29 did not reduce the levels of pAkt at 24 or 48 hours. In contrast, rapamycin exhibited inhibition of S6K1 phosphorylation ($S^{473}$) at both 24 and 48 hours, indicative of mTORC2 pathway inhibition.

Results for additional representative Western blots, and the compounds evaluated therein, are summarized in FIG. 2 through FIG. 42. The methods employed were substantially similar to those described above. Compounds were evaluated in PC3 cells, Jurkat cells, wild-type mouse embryotic fibroblast (MEF) cells, tuberous sclerosis 2 (TSC2) negative (TSC −/−) MEF cells, and tuberous sclerosis 2 (TSC2) positive (TSC +/+) MEF cells. Cells were incubated with compounds of the present invention for various time periods (e.g., 5 minutes, 15 minutes, 30 minutes, 90 minutes, 24 hours, or 48 hours), and evaluated according to known methodologies, such as those herein described.

Table 4 shows the inhibitory activity ($IC_{50}$) of selected compounds of this invention in the pS6K1 and pAKT assays, and their solubility in 100 mM phosphate buffer (pH 7.4). The compound numbers correspond to the compound numbers in Table 1.

Compounds of the present invention that selectively inhibit mTORC1 over mTORC2—and retain selectivity for at least 24 hours—are indicated by "YES" in the "mTORC1 selective @ 24 hrs" column of Table 4. Compounds that are not selective at the 24 hrs mark are indicated by "NO" in the "mTORC1 selective @24 hrs" column of Table 4. Compounds that partially retain selectivity for mTORC1 inhibition over mTORC2 are indicated by "Partial" in the "mTORC1 selective @24 hrs" column of Table 4. "N/A" stands for "not assayed."

Compounds denoted "+" exhibit solubilities less than 30 μM (x<30 μM). Compounds denoted "++" exhibit solubitilies greater then or equal to 30 μM and less than 60 μM (30 μM≤x<60 μM). Compounds denoted "+++" exhibit solubiltites greater than or equal to 60 μM (60 μM≤x).

Compounds denoted "A" exhibited an $IC_{50}$ lower than 0.1 nM (x<0.1 nM). Compounds denoted "B" exhibited an $IC_{50}$ greater than or equal to 0.1 nM and less than 1 nM (0.1 nM≤x<1.0 nM). Compounds denoted "C" exhibited an $IC_{50}$ greater than or equal to 1.0 nM and less than 10 nM (1.0 nM≤x<10 nM). Compounds denoted "D" exhibited an $IC_{50}$ greater than or equal to 10 nM and les than 100 nM (10 nM≤x<100 nM). Compounds denoted "E" exhibited an $IC_{50}$ greater than or equal to 100 nM (100 nM≤x).

TABLE 4

Assay Data for Exemplary Compounds

| Compound Number | pS6K1 in MCF7 @ 90 min: $IC_{50}$ | pAKT in MCF7 @ 90 min: $IC_{50}$ | mTORC1 selective @ 24 hrs | Aqueous Solubility at pH 7.4 (μM) |
|---|---|---|---|---|
| I-1 | B | E | YES | ++ |
| I-2 | B | E | YES | ++ |
| I-3 | B | E | YES | ++ |
| I-4 | B | N/A | YES | N/A |
| I-5 | N/A | N/A | YES | N/A |
| I-6 | C | E | YES | N/A |
| I-7 | N/A | N/A | YES | N/A |
| I-8 | C | N/A | YES | N/A |
| I-9 | N/A | N/A | YES | N/A |
| I-10 | A | E | YES | N/A |
| I-11 | C | E | YES | N/A |
| I-12 | N/A | N/A | YES | N/A |
| I-13 | C | N/A | YES | N/A |
| I-14 | N/A | N/A | YES | N/A |
| I-15 | C | E | YES | ++ |
| I-16 | B | E | YES | ++ |
| I-17 | B | E | YES | ++ |
| I-19 | A | E | YES | ++ |
| I-20 | B | E | YES | ++ |
| I-21 | A | E | YES | + |
| I-22 | B | E | YES | N/A |
| I-23 | A | E | YES | N/A |
| I-24 | A | E | YES | + |
| I-25 | B | E | YES | N/A |
| I-26 | B | E | YES | +++ |
| I-27 | B | E | YES | ++ |
| I-30 | B | E | YES | +++ |
| I-31 | B | E | YES | +++ |
| I-32 | B | E | YES | +++ |
| I-33 | C | E | YES | +++ |
| I-34 | B | E | NO | ++ |
| I-35 | B | E | YES | +++ |
| I-36 | C | E | YES | +++ |
| I-37 | C | E | YES | ++ |
| I-38 | A | E | NO | ++ |
| I-39 | C | E | YES | N/A |
| I-29 | A | E | YES | ++ |
| I-57 | A | N/A | YES | N/A |
| I-58 | B | N/A | YES | N/A |
| I-59 | E | N/A | YES | N/A |
| I-60 | C | N/A | YES | N/A |
| I-61 | C | N/A | YES | N/A |
| I-62 | C | N/A | YES | N/A |
| I-63 | E | N/A | YES | N/A |
| I-64 | C | N/A | YES | N/A |
| I-65 | B | N/A | YES | N/A |
| I-66 | C | N/A | YES | N/A |
| I-67 | B | N/A | YES | N/A |
| I-68 | C | N/A | YES | N/A |
| I-69 | B | N/A | YES | N/A |
| I-70 | C | N/A | YES | N/A |
| I-71 | B | N/A | YES | N/A |
| I-72 | C | N/A | YES | N/A |
| I-73 | C | N/A | YES | N/A |
| I-74 | B | N/A | NO | N/A |
| I-75 | A | N/A | YES | N/A |
| I-76 | C | N/A | YES | N/A |
| I-77 | A | N/A | YES | N/A |
| I-78 | C | N/A | YES | N/A |
| I-79 | C | N/A | YES | N/A |
| I-80 | B | N/A | YES | N/A |
| I-81 | C | N/A | YES | N/A |
| I-82 | B | N/A | YES | N/A |
| I-83 | N/A | N/A | YES | N/A |
| I-84 | B | N/A | YES | N/A |
| I-85 | N/A | N/A | YES | N/A |
| I-86 | A | N/A | YES | N/A |
| I-87 | A | N/A | YES | N/A |
| I-88 | A | N/A | YES | N/A |
| I-89 | C | N/A | YES | N/A |
| I-90 | | N/A | YES | N/A |
| I-91 | A | N/A | YES | N/A |
| I-92 | B | N/A | YES | N/A |
| I-95 | N/A | N/A | YES | N/A |
| I-96 | B | N/A | YES | N/A |
| I-97 | C | N/A | YES | N/A |

TABLE 4-continued

Assay Data for Exemplary Compounds

| Compound Number | pS6K1 in MCF7 @ 90 min: $IC_{50}$ | pAKT in MCF7 @ 90 min: $IC_{50}$ | mTORC1 selective @ 24 hrs | Aqueous Solubility at pH 7.4 (μM) |
|---|---|---|---|---|
| I-98 | C | N/A | YES | N/A |
| I-99 | B | N/A | YES | N/A |
| I-100 | C | N/A | YES | N/A |
| I-101 | B | N/A | YES | N/A |
| I-102 | D | N/A | YES | N/A |
| I-103 | B | N/A | YES | N/A |
| I-104 | B | N/A | YES | N/A |
| I-105 | A | N/A | YES | N/A |
| I-106 | B | N/A | YES | N/A |
| I-107 | E | N/A | YES | N/A |
| I-108 | B | N/A | YES | N/A |
| I-109 | C | N/A | YES | N/A |
| I-110 | B | N/A | YES | N/A |
| I-111 | C | N/A | YES | N/A |
| I-112 | B | N/A | YES | N/A |
| I-113 | B | N/A | YES | N/A |
| I-114 | C | N/A | YES | N/A |
| I-115 | B | N/A | YES | N/A |
| I-116 | B | N/A | YES | N/A |
| I-117 | A | N/A | YES | N/A |
| I-118 | C | N/A | YES | N/A |
| I-119 | A | N/A | YES | N/A |
| I-120 | A | N/A | YES | N/A |

EXAMPLE 56

Pharmacokinetic Properties

The pharmacokinetic properties of compounds of the present invention were evaluated in C57B1/6 mice and compared with rapamycin. Animals were fasted overnight prior to administration of I-29 or rapamycin (1 mg/kg IV, 10 mg/kg PO, or 2 mg/kg IP). Animals were bled at time intervals for upto 48 hours following administration of compounds. Whole blood from each mouse was indivisually collected in polypropylene tubes and immediately centrifuged. Alloquates of the separated plasma were promptly prepared for HPCL analysis. The results of the pharmacokinetics studies are summarized in Table 5. Compound I-29 shows improved oral bioavailability compared to rapamycin, as well as lower clearance, longer half life, increased Cmax, and increased AUC as compared to rapamycin.

TABLE 5

Comparison of mouse pharmacokinetic properties of rapamycin and I-29

| | | I-29 | Rapamycin |
|---|---|---|---|
| 1 mg/kg IV | CL (L/hr/Kg) | 0.054 | 0.276 |
| | $V_{ss}$ (L/Kg) | 0.863 | 1.73 |
| | Terminal $T_{1/2}$ (h) | 14.7 | 8.35 |
| | $AUC_{last}$ (h · ng/mL) | 17591 | 3616 |
| | $AUC_{INF}$ (h · ng/mL) | 18393 | 3627 |
| | $MRT_{INF}$ (h) | 15.9 | 6.27 |
| 10 mg/kg PO | $T_{max}$ (h) | 0.25 | 3 |
| | $C_{max}$ (ng/mL) | 3287 | 52.8 |
| | Terminal $T_{1/2}$ (h) | 11 | N/A |
| | $AUC_{last}$ (h · ng/mL) | 31236 | 292 |
| | $AUC_{INF}$ (h · ng/mL) | 31726 | N/A |
| | F (%) | 17.2 | 0.8 |
| 2 mg/kg IP | $T_{max}$ (h) | 0.25 | 0.25 |
| | $C_{max}$ (ng/mL) | 2590 | 614 |
| | Terminal $T_{1/2}$ (h) | 12.6 | 4.8 |
| | $AUC_{last}$ (h · ng/mL) | 16607 | 2481 |
| | $AUC_{INF}$ (h · ng/mL) | 16937 | 2544 |
| | F (%) | 46 | 35.1 |

EXAMPLE 57

Assessment of Effect of Chronic Treatment with I-29 on Glucose Tolerance and Insulin Sensitivity in Lean C57B1/6 Mice C57B1/6 mice (n=12; 8 weeks of age) were randomized and baseline measurements (weight, fasting glucose, and fasting insulin) were measured four (4) days prior to the administration of compounds or vehicle. Animals were then treated with I-29 (10 mg/kg PO), rapamycin (10 mg/kg IP) or vehicle (PO or IP) for 19 days. On day 7 and 14 animals were weighed and fed glucose and fed insulin levels were evaluated. Animals were fasted overnight on day 14 and on day 15 fasting insulin and an intraperitoneal glucose tolerance test (ipGTT) were evaluated. On day 19 animals were sacrificed one (1) hour after compound or vehicle administration. Tissues were harvested for evaluating compound levels and pharmacodynamics. The time course of the study is summarized in FIG. 43.

The results of the ipGTT are summarized in FIG. 44 and FIG. 45. Briefly, chronic rapamycin treatment for 15 days induced glucose intolerance in C57B1/6 mice, as demonstrated by the elevated glucose levels compared to Vh R. In comparison, I-29 did not induce glucose intolerance.

EXAMPLE 58

Assessment of Effect of I-29, I-117 and Everolimus in the Acute Kidney Disease/Chronic Kidney Disease (AKI/CKD) Mouse Model C57B1/6 mice (n=15; male; 10 weeks of age) were randomized. Following 7 days of acclimation, IR or sham surgery was performed. Mice were allowed to recover for one (1) day and beginning on day 2 animals receiving the IR surgery were administered vehicle, everolimus (10 mg/kg PO), I-29 (10 mg/kg PO), or I-117 (10 mg/kg PO). On day 9 uninephrectomy (Unx) or sham surgery was performed. On day 29 animals were sacrificed.

Kidney histology was evaluated by PAS, Masson's trichrome staining or Sirius red. Results for Sirus red staining are summarized in FIG. 46 and FIG. 47. Briefly, I-29 showed a significant reducing in kidney fibrosis as compared to vehicle.

Kidney tissue mRNA was analysis for inflammatory and fibrotic markers (qPCR for TGFβ, collegen I, collagen III, CCCTC-binding factor (CTCF), fibronectin (FN), and alpha-smooth muscle actin (α-SMA)).

Immunohistochemistry was evaluated for collagen I, collagen IV, α-SMA, 4-hydroxynonenal (4-HNE), and F4/80 macrophage.

Plasma was evaluated for compound levels and kidney tissue was evaluated for pharmacodynamics.

Results for the expression of fibrosis markers and macrophage infiltration in the kidneys is summarized in FIG. 48 to FIG. 51. Briefly, I-29 significantly reduced the expression of collagen I, collagen III, and fibronectin mRNA. Further, I-29 significantly decreased infiltration of macrophage into the kidney.

EXAMPLE 59

Assessment of Effect on IFN-γ Production in Allogenic Mixed Lymphocyte Reaction

The effect of rapamycin, everolimus, I-29, and I-117 on IFN-γ production was evaluated in an allogenic mixed lymphocyte reaction (E.g., Eleftheriadis, T. et al., Int. J. Mol. Med., 37(5): 1412-20 (2016) https://doi.org/10.3892/ijmm.2016.2547). $IC_{50}$ values are summarized in Table 6, below, and FIG. 52. Briefly, I-29 and I-117 did not inhibit IFN-γ production, whereas rapamycin and everolimus significantly inhibited IFN-γ production.

TABLE 6

| | IFN-γ Inhibition | | | |
|---|---|---|---|---|
| | Rapamycin | Everolimus | I-29 | I-117 |
| $IC_{50}$s (nM) | 2.4 | 15.2 | >3000 | >3000 |

We claim:
1. A compound of Formula II:

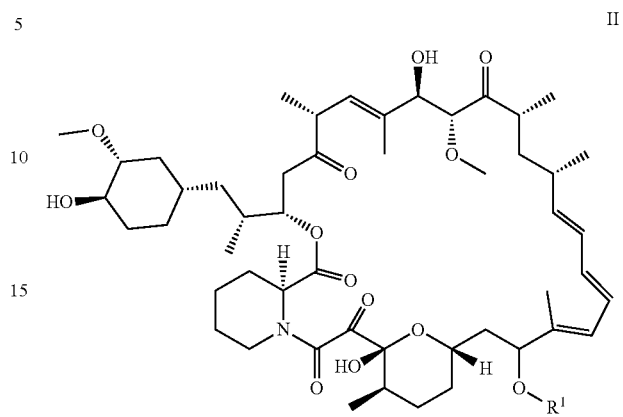

or a pharmaceutically acceptable salt thereof, wherein:
$R^1$ is selected from

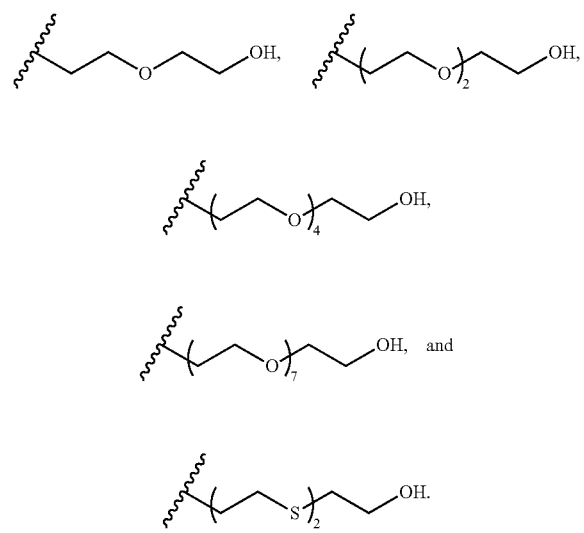

2. The compound according to claim 1, wherein said compound is selected from:

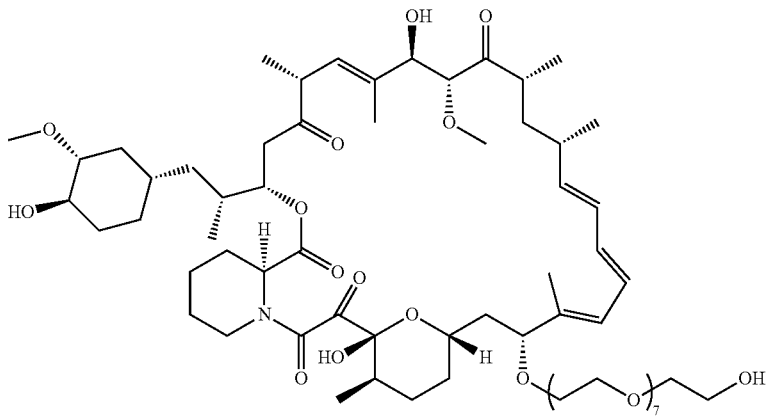

I-8

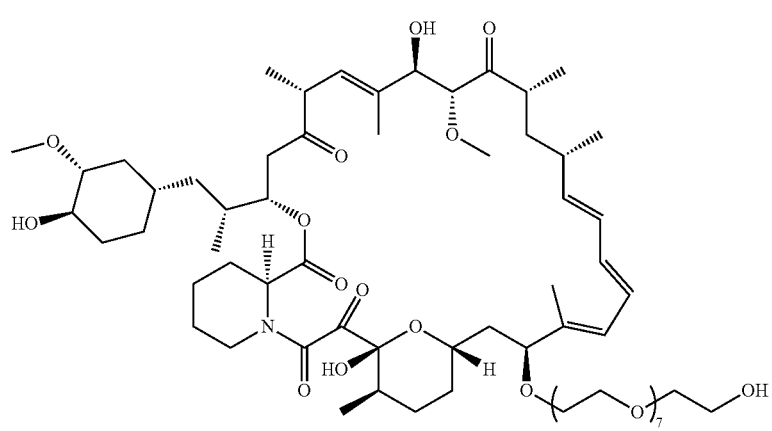
I-9
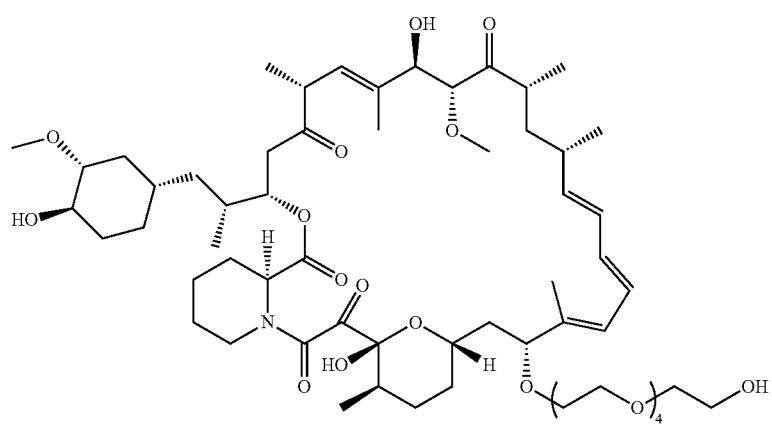
I-13
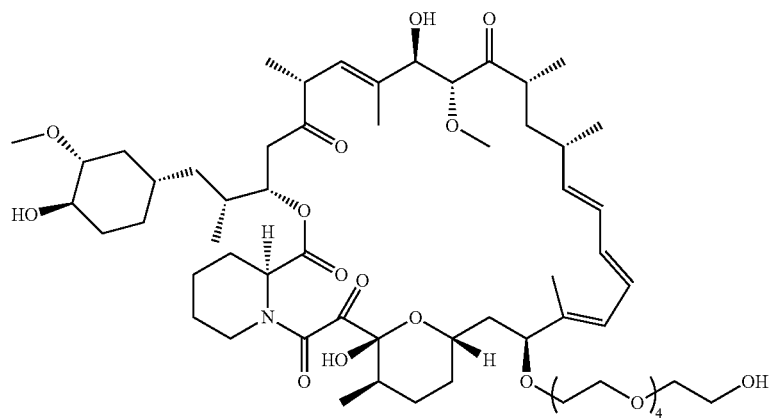
I-14

I-18
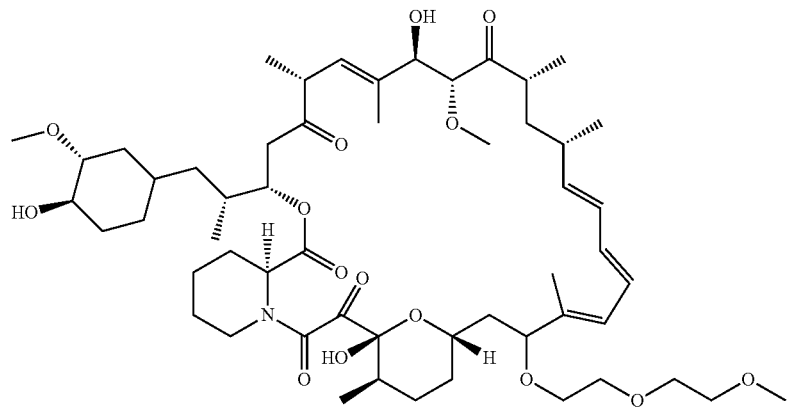
I-19
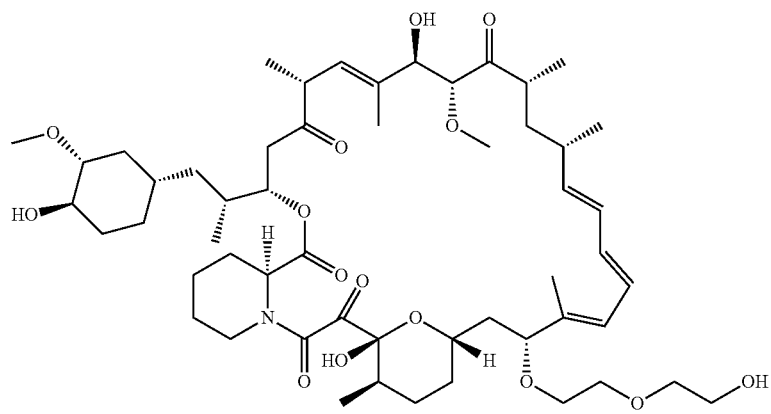
I-20
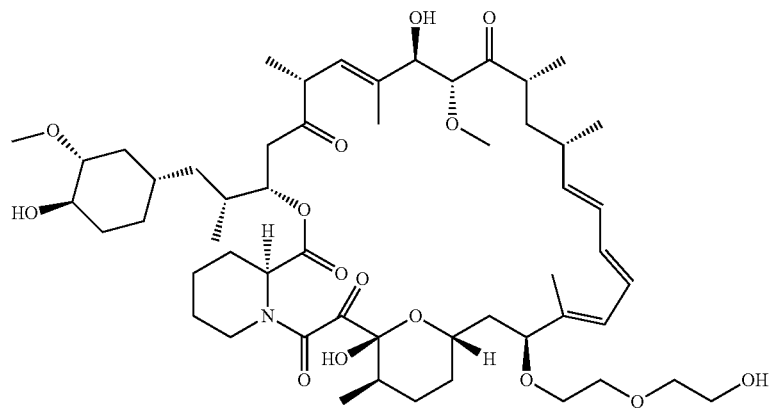
I-21
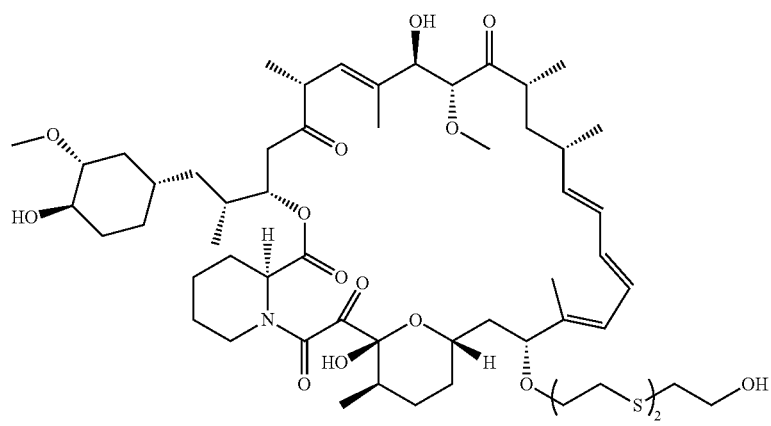

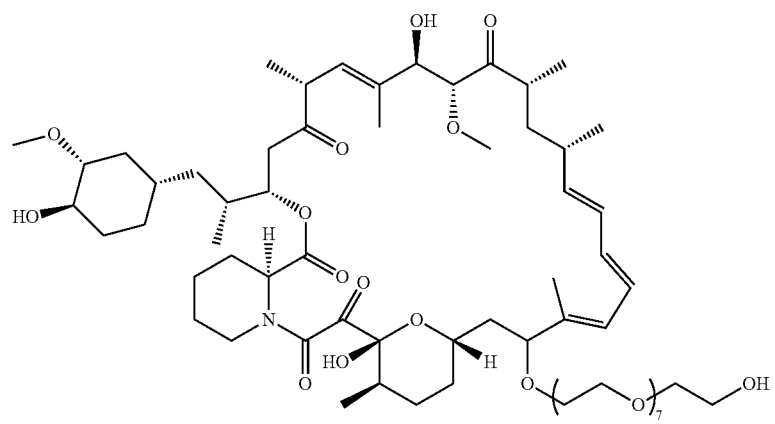
I-24
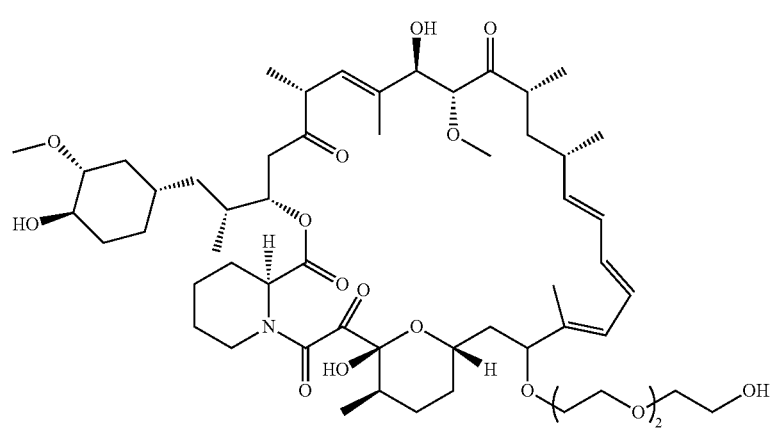
I-28
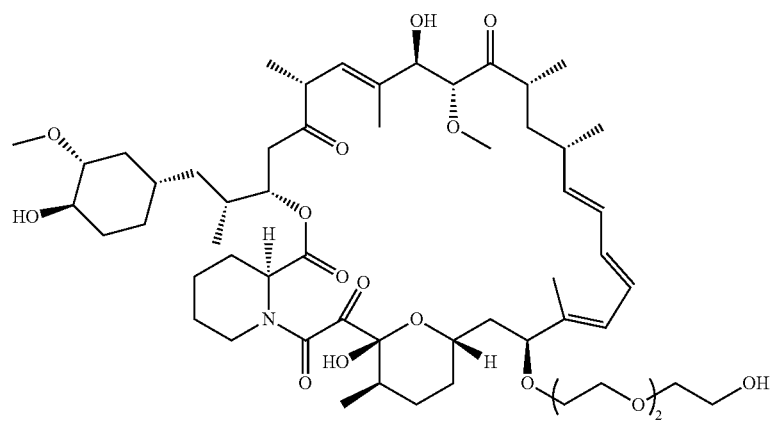
I-29

-continued
I-30
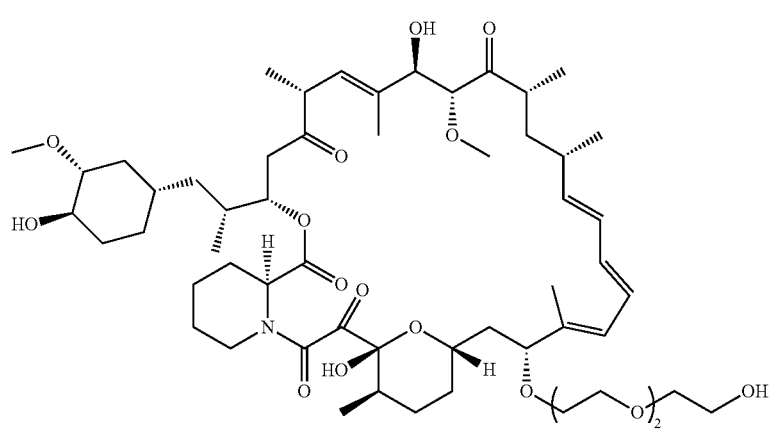
I-35
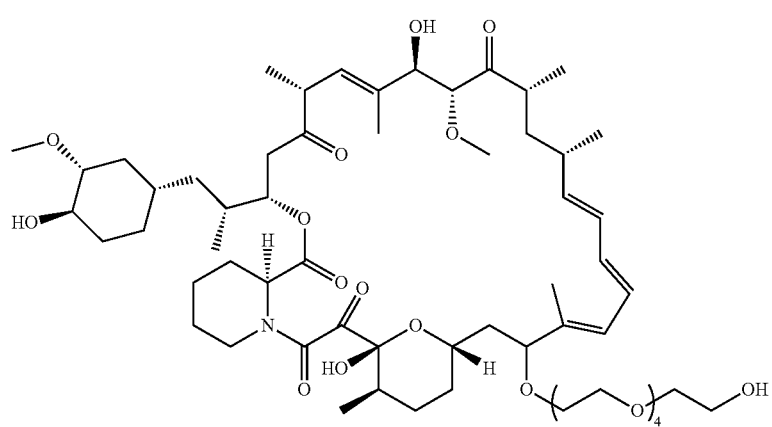
I-37
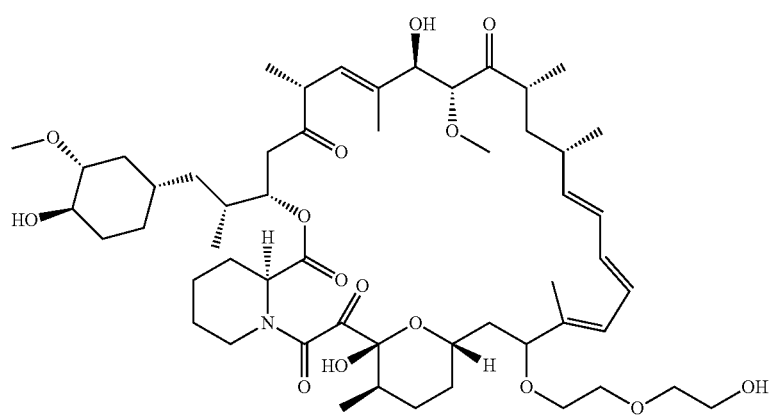
or pharmaceutically acceptable salt thereof.
3. A pharmaceutically acceptable composition comprising a compound of claim 1, and a pharmaceutically acceptable carrier, adjuvant, or vehicle.
4. A pharmaceutically acceptable composition comprising a compound of claim 2, and a pharmaceutically acceptable carrier, adjuvant, or vehicle.
* * * * *